United States Patent
Linz et al.

(10) Patent No.: US 6,420,430 B1
(45) Date of Patent: Jul. 16, 2002

(54) USE OF INHIBITORS OF THE SODIUM-HYDROGEN EXCHANGER FOR PREPARING A MEDICAMENT FOR PREVENTING AGE-RELATED DISORDERS, AND FOR PROLONGING LIFE

(75) Inventors: Wolfgang Linz, Mainz; Hans-Jochen Lang, Hofheim; Bela Kelety, Frankfurt am Main; Peter Schmid, Waldbrunn-Lahr, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/469,299

(22) Filed: Dec. 22, 1999

(30) Foreign Application Priority Data

Dec. 23, 1998 (DE) ......................................... 198 59 727

(51) Int. Cl.[7] ..................... A61K 31/155; A61K 31/477; A61K 31/425; A61K 31/42; A61K 31/415

(52) U.S. Cl. ..................... 514/634; 514/307; 514/365; 514/367; 514/374; 514/394; 514/412; 514/415; 514/438; 514/461

(58) Field of Search ............................... 514/634, 307, 514/365, 367, 374, 394, 412, 415, 438, 461

(56) References Cited

U.S. PATENT DOCUMENTS

| | | | |
|---|---|---|---|
| 5,591,754 A | 1/1997 | Lang et al. | 514/331 |
| 5,696,167 A | 12/1997 | Gericke et al. | 514/618 |
| 5,739,142 A | 4/1998 | Gericke et al. | 514/275 |
| 5,747,541 A | 5/1998 | Weichert et al. | 514/622 |
| 5,753,680 A | 5/1998 | Gericke et al. | 514/331 |
| 5,856,344 A | 1/1999 | Kleemann et al. | 514/346 |

FOREIGN PATENT DOCUMENTS

| | | |
|---|---|---|
| CA | 2130703 | 2/1995 |
| CA | 2206198 | 11/1997 |
| DE | 195 02 895 A1 | 1/1995 |
| DE | 197 34 693 A1 | 8/1997 |
| EP | 0 589 336 A1 | 3/1994 |
| EP | 590455 * | 4/1994 |
| EP | 0 640 587 A1 | 3/1995 |
| EP | 0 669 666 A1 | 8/1995 |
| EP | 0 765 867 A1 | 9/1995 |
| EP | 0 723 963 A1 | 1/1996 |
| EP | 0 738 712 A1 | 4/1996 |
| EP | 0 774 459 A1 | 11/1996 |
| EP | 0 810 207 A1 | 5/1997 |
| EP | 0 937 459 A2 | 1/1999 |
| WO | WO 97/46226 | 12/1997 |
| WO | WO 98/55475 | 12/1998 |
| WO | WO 99/33460 | 7/1999 |

OTHER PUBLICATIONS

Linz, W., et al. "Long–term ACE Inhibition Doubles Lifespan of Hypertensive Rats", Circulation, vol. 96, No. 9, pp. 3164–3172, (1997).

Protective Effects of HOE642, A Selective Sodium–Hydrogen Exchange Subtype 1 Inhibitor, on Cardiac Ischaemia and Reperfusion, Wolfgang Scholz, et al., XP 000602918, Cardiovascular Research 29:260–268 (1995).

2–Methyl–5–(methylsulfonyl)benzoyl)guanidine NA+/H+ Antiporter Inhibitors, Manfred Baurngarth, et al., XP 000914594, J. Med Chem 40, pp. 2017–2034 (1997).

Hydrogen Peroxide Induced Impairment of Post–Ischemic Ventricular Function is Prevented by the Sodium–Hydrogen Exchange Inhibitor HOE 642 (Cariporide), Mary Lee Myers, et al., XP 00020530, Cardiovascular Research 40 pp. 290–296 (1998).

Dose–Dependent Reduction of Myocardial Infarct Mass in Rabbits by the NHE–1 Inhibitor Cariporide (HOE 642), W. Linz, et al., XP 000920536, Clin. and Exper. Hypertension, 20(7), pp. 733–749 (1998).

(List continued on next page.)

Primary Examiner—Kevin E. Weddington
(74) Attorney, Agent, or Firm—Finnegan, Henderson, Farabow, Garrett & Dunner, L.L.P.

(57) ABSTRACT

Inhibitors of the cellular sodium-hydrogen exchanger are employed for preparing a medicament for preventing age-related functional disorders and dysfuntional changes of organs of the body and for preventing age-related diorders and for prolonging life while maintaining an improved quality of life. Typical representatives of NHE inhibitors are cariporide

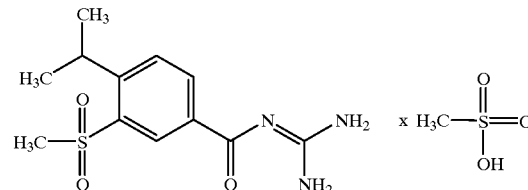

and eniporide

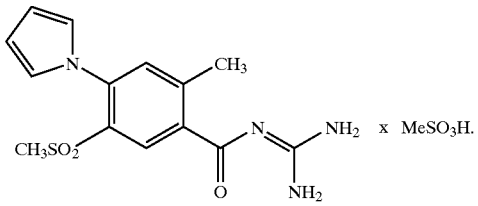

11 Claims, No Drawings

OTHER PUBLICATIONS

A New Sodium/Hydrogen Exchange Inhibitor, EMD 85131, Limits Infarct Size in Dogs When Administered Before or After Coronary Artery Occlusion, Richard J. Gumina, et al., XP 000920539, *The Journal of Pharmacology and Experimental Therapeutics*, 286 pp. 175–183, (1998).

Cariporide Mesilate, XP 000920592, *Drugs of the Future* 22(11) pp. 1197–1200 (1997).

Infarct Size Limitation by a New Na+–H+ Exchange Inhibitor, Hoe 642: Difference From Preconditioning in the Role of Protein Kinase C, Tetsuji Miura et al., XP 000920593, *JACC* 29(3), 693–701 (1997).

Effect of Sodium–Hydrogen Exchange Inhibition on Functional and Metabolic Impairment Produced by Oxidative Stress in the Isolated Rat Heart, A. N. Ehsanual Hoque, et al. XP 000920595, *Can. J. Physiol. Pharmacol.* 75 pp. 326–334 (1997).

Sodium Ion/Hydrogen Ion Exchange Inhibition: A New Pharmacologic Approach to Myocardial Ischemia and Reperfusion Injury, Josh Levitsky et al., XP 000920868, *Theapeutic Review, J Clin Pharmacol* 38 pp. 887–897 (1998).

EMD 96785: A Potent Cardioprotective Na+/H+–Exchange (NHE) Inhibitor, N. Beier, et al., XP 000920869, *Preclinical CV Research* 567 (1996).

XP 002141063 pp. 47–49 (1998).

Disorders Common Only in the Elderly, XP 002141064, Special Subjects, p. 2392 (1987).

Geriatric Medicine, XP 002141065 pp. 2503–2506 (1999).

Abstracts XP 002141068, *JACC* p. 268A (1998).

Bicyclic Acylguainidine Na+/H+ Antiporter Inhibitors, Manfred Baumgarth et al., XP 000914595, *J. Med. Chem.* 41, pp. 3736–3747 (1998).

* cited by examiner

USE OF INHIBITORS OF THE SODIUM-HYDROGEN EXCHANGER FOR PREPARING A MEDICAMENT FOR PREVENTING AGE-RELATED DISORDERS, AND FOR PROLONGING LIFE

The use of inhibitors of the sodium-hydrogen exchanger for preparing a medicament for preventing age-related organ dysfunction and age-related disorders, and for prolonging life.

The invention describes the use of inhibitors of the cellular sodium-hydrogen exchanger in human and veterinary medicine for preventing age-related functional disturbances and dysfunctional changes of body organs and for preventing age-related disorders, and for prolonging life while preserving an improved quality of life.

Within the last years, inhibitors of the sodium-hydrogen exchanger (NHE) have been characterized in numerous preclinical studies as substances which, in cases of hypoperfusion of the heart, are suitable in a superior manner for protecting the heart tissue at risk from the acute onset of the ischemia event from destruction. The protection of heart tissue by NHE inhibitors embraces all types of damage caused by the hypoperfusion, from cardiac arrhythmia to hypercontraction of the heart muscle and temporary loss of function to necrosis of heart tissue and associated permanent damage.

The mechanism of action of the NHE inhibitors, which is important in acute ischemic events, consists in that they reduce the increased influx of sodium ions which takes place in acute hypoperfused tissue by activation of NHE owing to intracellular acidification. This delays the situation of a sodium overload of the tissue. Since in heart tissue sodium and calcium ion transport are coupled with each other, this prevents the life-threatening calcium overload of the heart cells.

In the same manner as at the heart, most of the patents cited here also describe protection of the central nervous system under the influence of NHE inhibitors, and such active compounds protect the CNS similarly to the heart against acute ischemic states. These states are caused by an acute hypoperfusion and thus by insufficient supply of nutrients, oxygen, minerals, etc. Such ischemic damage of the CNS is particularly pronounced in the case of central infarcts, such as stroke.

Consequently, in accordance with expectations, in the case of normal healthy perfusion it was of course not possible to observe any protective effects of NHE inhibitors against these acute events, since there was no acute onset of ischemic tissue damage of the heart or the CNS.

Thus, it was surprising that NHE inhibitors, in addition to the protective effects against acute ischemic events and the subsequent likewise acutely stressing reperfusion events, also have direct therapeutically utilizable effects against disorders and disturbances of the entire organism of mammals which are connected with the manifestations of the chronic aging process and which are independent of acute states of hypoperfusion and which occur under normal non-ischemic conditions. These pathological age-related manifestations such as diseases, infirmity and death, which occur during the long period of aging and which are now accessible to treatment with NHE inhibitors are disorders and disturbances which are caused mainly by age-related changes of vital organs and their function and which become more and more important in the aging organism. NHE inhibitors such as, for example, cariporide act on such age-related disorders and disturbances of organs and their functions by a cascade of primary and secondary mechanisms whose mechanism has not yet been elucidated completely. It was therefore not possible to expect or predict a life-prolonging and antiaging effect for the NHE inhibitors, not to mention that such pronounced and strong effects have, according to our knowledge, not yet been shown in a comparable manner for any of the classes of active compounds known to date. It is true that recently a life-prolonging effect of ACE inhibitors, in particular under ramipril treatment, has been reported (Linz W, Jessen T, Becker RHA, Schölkens BA, Wiemer G. Long-term ACE inhibition doubles lifespan of hypertensive rats. Circulation. 1997; 96: 3164–3172). However, this life-prolonging effect only relates to hypertensive rats and organisms which, owing to their high blood pressure, have a reduced life expectancy compared with normotensive rats and organisms, respectively. Thus, the life-prolonging effect of ACE inhibitors relates only to animals suffering from high blood pressure and can, in the best case, only achieve the lifespan of a normotensive organism. Since at least a considerable part of the activity of the ACE inhibitors is caused by their hypotensive effect on individuals suffering from high blood pressure, the lack of a life-prolonging effect of ACE inhibitors on normotensive individuals came as no surprise. Likewise, ACE inhibitors did not show to a comparable extent an inhibiting action on age-related organ damage or the onset of cancer induced by the aging process.

Disorders associated with an age-related functional disturbance or with age-related manifestations of wear and tear of organs are, for example, the insufficient responsiveness and reactivity of the blood vessels to contraction and relaxation reactions. This age-related decrease of vessel reactivity on constrictory and relaxing stimuli, which are an essential process of the cardiovascular system and thus of life and health, can be eliminated or reduced significantly by NHE inhibitors. An important function and a measure for the maintenance of vessel reactivity is the blockage or delay of age-related progressive endothelial dysfunction which can be eliminated by NHE inhibitors in a highly significant manner.

An example of another measurement which characterizes the aging process is the reduction of the contractility of the heart and the decreased adaptation of the heart to a required pumping performance of the heart. This reduced ability of the heart to perform, as a consequence of the aging process, is in most cases associated with heart dysfunction caused, inter alia, by incorporation of connective tissue into heart tissue. This incorporation of connective tissue is characterized by an increase in the weight of the heart, by an increased heart size and by impaired heart function. It was surprising that such an aging of the organ's heart could be inhibited almost completely.

Whereas the earlier patents and patent applications claimed the treatment of various forms of cancerous diseases which have already become manifest, it was now extremely surprising that it is not only possible to treat a manifest cancerous disorder by inhibition of proliferation, but that it was also possible to prevent and delay in a highly significant manner the age-related frequency of the occurrence of cancer by using NHE inhibitors. Particularly noteworthy is the finding that age-related disorders of all organs and not only of certain forms of cancer can be prevented, or delayed in a highly significant manner.

What is found now is not only a delay of the onset of age-related disorders of all organs examined, including heart, vessels, liver, etc., delayed in a highly significant manner for more than the statistical norm, and a highly significant delay of age-related cancer. Rather, life is surprisingly prolonged to an extent which hitherto has not been achieved by any other group of medicaments or any natural substances.

This unique effect of the NHE inhibitors makes it also possible, in addition to using the active compound on its own in humans and animals, to combine these NHE inhibitors with other gerontologically applied principles of action, measures, substances and natural substances which are based on a different mechanism of action. Such classes of active compounds used in gerontological therapy are: in particular vitamins and antioxidants. Since there is a correlation between caloric stress or food intake and the aging process, a combination with dietary measures, for example with appetite suppressants, is possible. Also feasible is a combination with hypotensive medicaments, such as ACE inhibitors, angiotensin receptor antagonists, diuretics, $Ca^{2+}$ antagonists, etc., or with medicaments which have a normalizing action on the metabolism, such as cholesterol-lowering substances.

Studies

The effect of a life-long treatment of young normotensive Wistar-Kyoto rats (WKY rats) with the sodium-hydrogen exchanger ("NHE") inhibitor cariporide was investigated. In addition to the primary end point, the lifespan, surrogate parameters were studied and measured, for example the hypertrophy of the left ventricle of the heart, heart function, metabolism and endothelial function. In addition, organs, such as heart, kidneys, skeletal muscles and eyes, were examined histomorphologically.

Methods and Results

Ninety one-month-old WKY rats were randomized into two groups of placebo-treated (n=45) and cariporide-treated (n=45) rats. Cariporide was administered via the feed (active compound content 0.3%).

Cariporide is the compound

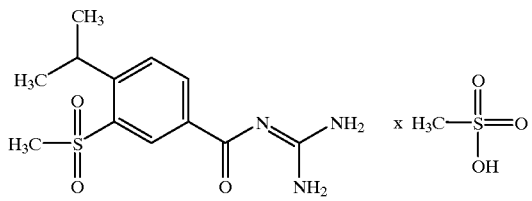

(see U.S. Pat. No. 5,292,755)

The surrogate parameters were determined after 30 months, at which time about 80% of the placebo group had already died. The life-long treatment with cariporide prolonged the life of the animals from 30 to 39 months. This prolongation of life correlated with a delayed onset of age-related cancer. Age-related hypertrophy of the heart, which occurred in placebo-treated animals, was prevented by cariporide. A significantly improved heart function in comparison with the placebo hearts was achieved by cariporide. The NHE inhibitor also improved age-related endothelial dysfunction significantly. Age-related morphological organ changes, such as the incorporation of connective tissue into the aging heart muscle, age-related tubulo-interstitial lesions of the kidney, muscular dystrophy and retina atrophy were reduced drastically or prevented completely by cariporide.

Result

The life-long treatment of normotensive WKY rats with the NHE inhibitor cariporide prolonged the lifespan of the animals from 30 to 39 months. This extension of the lifespan correlated with a prevention of age-related hypertrophy of the left ventricle, of cardiac and vascular dysfunction and of age-related changes of vital organs. In addition, the onset of all forms of age-related cancer was delayed significantly.

Methods

Animals

Male WKY rats were purchased from Møllegrad Denmark. The animals (3 per cage) were kept under standardized conditions with respect to temperature, atmospheric humidity and light. The rats had free access to a standard diet (Altromin® maintenance diet 1320, sodium content 0.2%) and received drinking water ad libitum. All experiments were carried out in accordance with the German Law on the Protection of Animals.

Study Design

Ninety one-month-old animals were randomized into two groups of in each case 45 animals. After randomization, placebo and cariporide were administered to the rats via the drinking water and the feed, respectively, a proportion of 0.3% of the feed ensuring complete blockage of the NHE for 24 hours.

At intervals of 3 months, the body weight was determined and the blood pressure was measured using the tail plethysmography method. Events of death were registered after they had occurred.

Interim Analysis

The interim analysis was carried out after 80% of the placebo-treated animals had died; this was the case after 30 months. 10 animals of each group were selected at random and anesthetized (hexobarbital, 80 $mg\cdot kg^{-1}$, i.p.). Blood samples were then taken, and the thoracic aortae and the hearts were prepared and biochemically and/or functionally examined (Linz et al., 1997).

Examination of the Function of the Isolated Heart

In accordance with the method described by Langendorff, the hearts were perfused with an oxygen-saturated (95% $O_2$, –5% $CO_2$), non-circulating Krebs-Henseleit solution of the following composition (mmol/l): NaCl, 118; KCl, 4.7; $CaCl_2$, 2.5; $MgSO_4$, 1.6; $NaHCO_3$, 24.9; $KH_2PO_4$, 1.2; glucose, 5.5; Na-pyruvate, 2.0, using a perfusion pressure of 60 mm Hg. The pressure in the left ventricle and the pulse frequency of the heart were measured using a balloon catheter. The coronary blood flow was determined using an electromagnetic flow gage. After a washing phase of 5 minutes, 1 ml of the coronary effluent was taken off for measuring the lactate concentrations and the lactate dehydrogenase and creatine kinase activities. The weights of the entire heart and the weights of the left and the right ventricle were then determined. The left ventricle was fixed in 10% strength neutral buffered formalin solution and embedded in paraffin for light-microscopic examination.

Vessel Function on Isolated Rings of the Thoracic Aorta

The aorta was introduced into Tyrode's solution and freed from the surrounding fatty tissue. Segments of 2 mm were then sliced into rings, and these rings were introduced in a temperature-controlled (37° C.) organ bath (10 ml) with Tyrode's solution (composition in mol/l: NaCl 136.9; $NaHCO_3$ 11.9; KCl 2.7; $CaCl_2$ 0.5; $MgCl_2$ 2.0; $NaHPO_4$ 0.4; glucose 5.5; pH=7.4), and 95% $O_2$/5% $CO_2$ was bubbled through the solution. Each ring was mounted vertically between two fine steel clamps. The upper clamp was connected to a force sensor. The force signal was recorded using a computer-assisted biosignal analyzer. The aorta rings were suspended using a passive tension of 4.9 mN. After an adaptation period of one hour, the rings were contracted using potassium chloride (20 mmol/l). After a plateau had been reached, increasing concentrations of acetylcholine of $10^{-8}$, $10^{-7}$, $10^{-6}$ and $10^{-5}$ mol/l were added to the bath, triggering an endothelium dependent relaxation.

Statistical Analysis

All data are stated as mean±standard deviations. The survival data were analyzed in accordance with Kaplan-Meier, followed by a Mantel-Cox log-rank test. Furthermore, variance analysis (ANOVA) followed by a Student-Newman-Keuls test were employed. Null hypotheses were rejected at p<0.05.

Results

The body weight increased from 72±3 g (1 month old) to 517±19 g (30 months old) in the placebo-treated animals and to 519±20 g in the cariporide-treated animals. In the placebo-treated WKY rats, the systolic blood pressure of 119±4 mm Hg (mean of all animals at the age of 1 month) remained almost unchanged up to the age of 30 months, 120±3 mm Hg. NHE inhibition with cariporide did not result in any significant change of the blood pressure in WKY rats (121±2 mm Hg).

Cumulative Survival Rate

Age-related, the placebo-treated WKY rats began to die after about 19 months, and they had all died after the experiment had lasted 30 months. In contrast, the maximum lifespan of the animals was extended by cariporide treatment to 39 months, corresponding to a life extension of 30% (Table 1).

TABLE 1

Survival rate in percent

| Months | Placebo | Cariporide |
|---|---|---|
| 19 | 95 | 100 |
| 20 | 92 | 100 |
| 21 | 86 | 100 |
| 22 | 75 | 100 |
| 23 | 70 | 97 |
| 24 | 69 | 97 |
| 25 | 65 | 97 |
| 26 | 55 | 97 |
| 27 | 50 | 97 |
| 28 | 45 | 97 |
| 29 | 30 | 92 |
| 30 | 25 | 89 |
| 31 | 10 | 80 |
| 32 | — | 75 |
| 33 | — | 67 |
| 34 | — | 59 |
| 35 | — | 49 |
| 36 | — | 38 |
| 37 | — | 28 |
| 38 | — | 17 |
| 39 | — | 10 |

Interim Analysis of the Study after 30 Months

Due to the cariporide treatment, the weight of the left and right ventricle of the heart were significantly reduced (Table 2).

TABLE 2

Heart weight

|  | Heart (total) | Left ventricle | Right ventricle |
|---|---|---|---|
| Placebo | 407 ± 12 | 360 ± 16 | 47 ± 2 |
| Cariporide | 235 ± 10* | 193 ± 8* | 36 ± 2* |

(mg/100 g of body weight,
n = 10/group,
*p < 0.05 vs placebo)

At 332±6 mg/100 mg of body weight, the weights of the kidneys of the two groups did not show any significant difference between the groups, whereas the weights of the spleens of the animals which had been treated with cariporide were significantly below those of the placebo-treated group of WKY rats (303±12 versus 255±13 mg/100 g of BW; p<0.05).

Isolated Heart Preparations

Hearts of cariporide-treated WKY rats showed a significant increase in the pressure of the left ventricle and the contractile force ($dP/dt_{max}$) of the left ventricle, compared with hearts of placebo-treated WKY rats. Here, the pulse frequency of the hearts was unchanged, whereas the coronary blood flow under cariporide was significantly higher than that in placebo-treated rats (Table 3).

In the hearts of normotensive WKY rats, the long-term treatment with cariporide resulted in a reduction of the activities of cytosolic enzymes (creatine kinase, lactate dehydrogenase) and in a reduced release of lactate into the coronary effluvium. This surprising finding demonstrates the considerably worse metabolic situation of the aged rats without cariporide (Table 3).

TABLE 3

Function and metabolism in the isolated working heart

|  | Placebo | Cariporide |
|---|---|---|
| LVP (mm Hg) | 91.9 ± 4.1 | 111.5 ± 3.9* |
| dP/dtmax (mm Hg/s) | 3490 ± 128 | 4432 ± 121* |
| HR (beats/min) | 180 ± 8 | 182 ± 7 |
| CF (ml/min/g) | 24.1 ± 0.5 | 34.6 ± 0.7* |
| CK (mU/min/g heart wwt) | 0.77 ± 0.08 | 0.20 ± 0.02* |
| LDH (mU/min/g heart wwt) | 0.94 ± 0.11 | 0.42 ± 0.02* |
| Lactate ($\mu$mol/min/g heart wwt) | 14.3 ± 1.3 | 2.5 ± 0.13* |

LVP: pressure in the left ventricle;
dp/dtmax: constriction rate of the left ventricle;
CF: coronary flow;
CK: creatine kinase in the coronary effluent;
LDH: lactate dehydrogenase in the coronary effluent;
wwt: wet weight.
*p < .05 versus Placebo,
n = 10 per group.

Isolated Thoracic Aorta

The endothelium-dependent relaxation of aorta strips pre-contracted with potassium chloride was examined. Here, aorta strips of the 30-month-old placebo-treated WKY rats showed the known deterioration of the endothelium-dependent relaxation which is reduced in an age-related manner.

In the 30-month-old WKY rats which had been treated with cariporide, relaxation was significantly better (Table 4).

TABLE 4

Vessel function on the aorta (relaxation in %)

| ACh (mol/l) | Placebo | Cariporide |
|---|---|---|
| $10^{-8}$ | 4 ± 1 | 5 ± 2 |
| $10^{-7}$ | 29 ± 4 | 50 ± 6* |
| $10^{-6}$ | 65 ± 7 | 85 ± 8* |
| $10^{-5}$ | 75 ± 6 | 95 ± 10 |

ACh: acetylcholine,
n = 10/group,
*p < 0.05 versus placebo

Histomorphological Results

Cariporide drastically reduced typically age-related histomorphological organ changes, such as the incorporation of connective tissue into the heart muscle, muscular dystrophy, tubulointerstitial damage of the kidney and retina atrophy. In addition, the livers of these rats were unchanged, compared with control animals.

SUMMARY OF THE RESULTS

The present results demonstrate that, by preventive therapy with an NHE1-blocker and in particular with cariporide, it is possible to suppress the most frequent age-related causes of death and to inhibit the genesis of age-related organ damage.

The compounds described in the publications below are suitable for the uses according to the invention:

I. (HOE 89/F 288-U.S. Pat. No. 5,292,755)

a) benzoylguanidines of the formula I

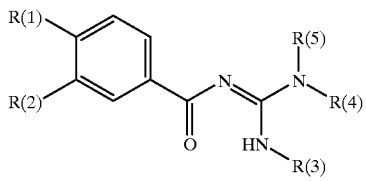

I in which:
R(1) or R(2) is R(6)—S(O)$_n$— or R(7)R(8)N—O$_2$S—;
and the other substituent R(1) or R(2) in each case is H, F, Cl, Br, (C$_1$–C$_4$)-alkyl, (C$_1$–C$_4$)-alkoxy or phenoxy, which is unsubstituted or substituted by 1–3 substituents selected from the group consisting of fluorine, chlorine, methyl and methoxy;
or the other substituent R(1) or R(2) in each case is R(6)—S(O)$_n$ or R(7)R(8)N—;
n is zero, 1 or 2;
R(6) is (C$_1$–C$_6$)-alkyl, (C$_5$–C$_7$)-cycloalkyl, cyclopentylmethyl, cyclohexylmethyl or phenyl, which is unsubstituted or substituted by 1–3 substituents selected from the group consisting of fluorine, chlorine, methyl and methoxy;
R(7) and R(8) identically or differently are H or (C$_1$–C$_6$)-alkyl; or
R(7) is phenyl-(CH$_2$)$_m$;
m is 1–4; or
R(7) is phenyl, which is unsubstituted or substituted by 1–2 substituents selected from the group consisting of fluorine, chlorine, methyl and methoxy; or
R(7) and R(8) together are a straight-chain or branched (C$_4$–C$_7$)-chain, where the chain can additionally be interrupted by O, S or NR(9);
R(9) is H or methyl; or
R(7) and R(8) together with the nitrogen atom to which they are bonded, are a dihydroindole, tetrahydroquinoline or tetrahydroisoquinoline system;
R(3), R(4) and R(5) independently of one another are H or (C$_1$–C$_2$)-alkyl, or
R(3) and R(4) together are a (C$_2$–C$_4$)-alkylene chain; or
R(4) and R(5) together are a (C$_4$–C$_7$)-alkylene chain;

and their pharmaceutically tolerable salts;

(HOE 92/F 34-U.S. Pat. No. 5,373,924)

b) benzoylguanidines of the formula I

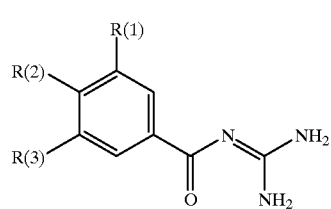

(I)

in which:
R(1) is R(4)—SO$_m$ or R(5)R(6)N—SO$_2$—;
m is zero, 1 or 2;
R(4) and R(5) are C$_1$–C$_8$-alkyl, C$_3$–C$_6$-alkenyl or —C$_n$H$_{2n}$—R(7);
n is zero, 1, 2, 3 or 4;
R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);
R(8) and R(9) are H or C$_1$–C$_4$-alkyl; or
R(5) is H;
R(6) is H or C$_1$–C$_4$-alkyl, or
R(5) and R(6) together are 4 or 5 methylene groups, of which one CH$_2$ group can be replaced by an O, S, NH, N—CH$_3$ or N-benzyl;
R(2) is hydrogen, F, Cl, Br, (C$_1$–C$_4$)-alkyl-, O—(CH$_2$)$_m$C$_p$F$_{2p+1}$ or —X—R(10);
m is zero or 1;
is 1, 2 or 3;
X is O, S or NR(11);
R(10) is H, C$_1$–C$_6$-alkyl, C$_5$–C$_7$-cycloalkyl, cyclohexylmethyl, cyclopentylmethyl or —C$_n$H$_{2n}$—R(12);
n is zero, 1, 2, 3 or 4;
R(12) is phenyl, which is unsubstituted or substituted by 1–3 substituents selected from the group consisting of F, Cl, CF$_3$, methyl, methoxy and NR(8)R(9);
R(8) and R(9) are H or C$_1$–C$_4$-alkyl;
R(11) is hydrogen or C$_1$–C$_3$-alkyl; or
R(10) and R(11) together are 4 or 5 methylene groups, of which one CH$_2$ group can be replaced by O, S, NH, N—CH$_3$ or N-benzyl;
R(3) is defined as R(1), or is C$_1$–C$_6$-alkyl, nitro, cyano, trifluoromethyl, F, Cl, Br, I or —X—R(10);
X is O, S or NR(11);
R(10) is H, C$_1$–C$_6$-alkyl, C$_5$–C$_7$-cycloalkyl, cyclohexylmethyl, cyclopentylmethyl or —C$_n$H$_{2n}$—R(12);
n is zero to 4;
R(12) is phenyl, which is unsubstituted or substituted by 1–3 substituents selected from the group consisting of F, Cl, CF$_3$, methyl, methoxy und NR(8)R(9);
R(8) and R(9) are H or C$_1$–C$_4$-alkyl;
R(11) is C$_1$–C$_3$-alkyl, or
R(10) and R(11) together are 4 or 5 methylene groups, of which one CH$_2$ group can be replaced by O, S, NH, N—CH$_3$ or N-benzyl;
and their pharmaceutically tolerable salts;
(HOE 92/F 035-EP-A 556 673)

c) ortho-substituted benzoylguanidines of the formula I

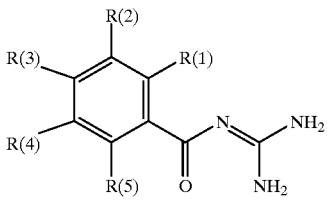

in which:
R(1) is F, Cl, Br, I, $C_1$–$C_6$-alkyl or —X—R(6);
  X is O, S, N R(7) or Y—ZO;
  Y is O or NR(7);
  Z is C or SO;
  R(6) is H, $C_1$–$C_6$-alkyl, $C_5$–$C_7$-cycloalkyl, cyclohexylmethyl, cyclopentylmethyl, —(CH$_2$)$_m$C$_p$F$_{2p+1}$ or —C$_n$H$_{2n}$—R(8);
  m is zero or 1;
  p is 1–3;
  n is zero to 4;
    R(8) is phenyl, which is unsubstituted or substituted by 1–3 substituents selected from the group consisting of the groups F, Cl, CF$_3$, methyl, methoxy and NR(9)R(10);
      R(9) and R(10) are H or $C_1$–$C_4$-alkyl;
  R(7) is H or $C_1$–$C_3$-alkyl; or
  R(6) and R(7) together are 4 or 5 methylene groups, of which one CH$_2$ group can be replaced by O, S, NH, N—CH$_3$ or N-benzyl;
R(3) is H or —X—R(6);
  X is O, S, NR(7) or Y—ZO;
  R(7) is H or $C_1$–$C_3$-alkyl;
  Y is O or NR(7);
    where Y is bonded to the phenyl radical of the formula I,
  Z is C or SO;
  R(6) is H, $C_1$–$C_6$-alkyl, $C_5$–$C_7$-cycloalkyl, cyclohexylmethyl, cyclopentylmethyl, —(CH$_2$)$_m$C$_p$F$_{2p+1}$ or —C$_n$H$_{2n}$—R(8);
  m is zero or 1;
  p is 1–3;
  n is zero to 4;
    R(8) is phenyl, which is unsubstituted or substituted by 1–3 substituents selected from the group consisting of F, Cl, CF$_3$, methyl, methoxy and NR(9)R(10);
      R(9) and R(10) are H or $C_1$–$C_4$-alkyl; or
  R(6) and R(7) together are 4 or 5 methylene groups, of which one CH$_2$ group can be replaced by O, S, NH, N—CH$_3$ or N-benzyl;
R(2) and R(4) identically or differently are R(11)—SO$_q$— or R(12)R(13)N—SO$_2$—;
  q is zero –2;
  R(11) is $C_1$–$C_4$-alkyl, which is unsubstituted or carries phenyl as a substituent, where phenyl is unsubstituted or substituted by 1–3 substituents selected from the group consisting of F, Cl, CF$_3$, methyl, methoxy and NR(9)R(10);
    R(9) and R(10) are H or $C_1$–$C_4$-alkyl;
  R(12) and R(13) are defined as R(6) and R(7); or
one of the two radicals R(2) or R(4) is hydrogen or is defined as R(1);

R(5) is H, methyl, F, Cl or methoxy, and their pharmaceutically tolerable salts;
(HOE 92/F 036-U.S. Pat. No. 5,364,868)
d) benzoylguanidine of the formula I

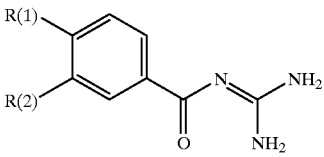

in which:
R(1) or R(2) is an amino group —NR(3)R(4);
  R(3) and R(4) identically or differently are H, $C_1$—$C_6$-alkyl or $C_3$–$C_7$-cycloalkyl; or
  R(3) is phenyl-(CH$_2$)$_p$—;
    p is 0, 1, 2, 3 or 4; or
  R(3) is phenyl, where the phenyl in each case is unsubstituted or carries one to two substituents selected from the group consisting of fluorine, chlorine, methyl and methoxy; or
  R(3) and R(4) together can be a straight-chain or branched $C_4$–$C_7$-methylene chain, where one —CH$_2$— member of the methylene chain can be replaced by oxygen, S or NR(5);
    R(5) is H or lower alkyl;
  the other substituent R(1) or R(2) in each case is H, F, Cl, $C_1$–$C_4$-alkyl, $C_1$–$C_4$-alkoxy, CF$_3$, $C_mF_{2m+1}$—CH$_2$—, benzyl or phenoxy, where the respective phenyl radical is unsubstituted or carries one to two substituents selected from the group consisting of methyl, methoxy, fluorine and chlorine;
  m is 1, 2 or 3;
and their pharmaceutically tolerable salts;
(92/F 197 K-NZ 248 013)
e) benzoylguanidines of the formula I

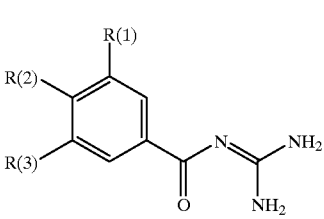

in which:
R(1) is R(4)—SO$_m$ or R(5)R(6)N—SO$_2$—;
  m is zero, 1 or 2;
  R(4) and R(5) are $C_1$–$C_8$-alkyl, $C_3$–$C_6$-alkenyl or —C$_n$H$_{2n}$—R(7);
    n is zero,1, 2, 3 or 4;
    R(7) is $C_5$–$C_7$-cycloalkyl or phenyl, which is unsubstituted or substituted by 1–3 substituents selected from the group consisting of F, Cl, CF$_3$, methyl, methoxy and NR(8)R(9);
      R(8) and R(9) are H or $C_1$–$C_4$-alkyl; or
  R(5) is H;
  R(6) is H or $C_1$–$C_4$-alkyl; or
  R(5) and R(6) together are 4 or 5 methylene groups, of which one CH$_2$ group can be replaced by an O, S, NH, N—CH$_3$ or N-benzyl;
R(2) is hydrogen, straight-chain or branched ($C_5$–$C_8$)-alkyl, —CR(13)=CHR(12) or —C≡CR(12);

R(12) is phenyl, which is unsubstituted or substituted by 1–3 substituents selected from the group consisting of F, Cl, CF$_3$, methyl, methoxy and NR(14)R(15);
  R(14) and R(15) are H or (C$_1$–C$_4$)-alkyl; or
R(12) is (C$_1$–C$_9$)-heteroaryl, which is unsubstituted or substituted as phenyl, or
R(12) is (C$_1$–C$_6$)-alkyl, which is unsubstituted or substituted by 1–3 OH, or
R(12) is (C$_3$–C$_9$)-cycloalkyl;
R(13) is hydrogen or methyl, or
R(12) is (C$_3$–C$_8$)-cycloalkyl, (C$_3$–C$_8$)-cycloalkyl-(C$_1$–C$_4$)-alkyl, phenyl, C$_6$H$_5$—(C$_1$–C$_4$)-alkyl, naphthyl, biphenylyl, 1,1-diphenyl-(C$_1$–C$_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2);
and where the aromatic substituents R(2) and R(3) are unsubstituted or substituted by 1–3 substituents from the groups F, Cl, CF$_3$, (C$_1$–C$_4$)-alkyl or -alkoxy, or NR(10)R(11) with R(10) and R(11) being H or (C$_1$–C$_4$)-alkyl; and their pharmaceutically tolerable salts;
(HOE 92/F 303 K-EP-A 589 336, NZ 248 703)

f) benzoylguanidines of the formula I

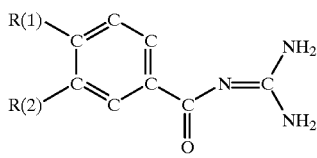

in which:
R(1) or R(2) is R(3)—S(O)$_n$— or R(4)R(5)N—SO$_2$—
the other substituent R(1) or R(2) in each case is H, OH, F, Cl, Br, I, C$_1$–C$_4$-alkyl, C$_1$–C$_4$-alkoxy, benzyloxy or phenoxy, which is unsubstituted or carries one to three substituents selected from the group consisting of fluorine, chlorine, methyl, methoxy, hydroxyl or benzyloxy,
R(3)—S(O)$_n$, —NR(4)R(5) or 3,4-dehydropiperidine
  R(3) is C$_1$–C$_6$-alkyl, C$_5$–C$_7$-cycloalkyl, cyclopentylmethyl, cyclohexylmethyl or phenyl, which is unsubstituted or carries one to three substituents selected from the group consisting of fluorine, chlorine, methyl and methoxy;
  R(4) and R(5) identically or differently, are H or C$_1$–C$_6$-alkyl; or
  R(4) is phenyl-(CH$_2$)$_m$—;
  m is 1, 2, 3 or 4; or
  R(4) is phenyl, which is unsubstituted or carries one to two substituents selected from the group consisting of fluorine, chlorine, methyl and methoxy; or
  R(4) and R(5) together are a straight-chain or branched C$_4$–C$_7$-chain, where the chain can additionally be interrupted by O, S or NR(6),
  R(6) is H or methyl; or
  R(4) and R(5) together with the nitrogen atom to which they are bonded, are a dihydroindole, tetrahydroquinoline or tetrahydroisoquinoline system;
  n is zero, 1 or 2;

and their pharmaceutically tolerable salts;
(92/F 304-U.S. Pat. No. 5,416,094)

g) isoquinolines of the formula I

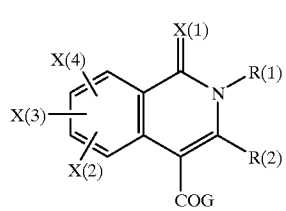

in which:
R(1) is hydrogen, alkyl, cycloalkyl, arylalkyl, alkenyl, substituted aminoalkyl or an aryl or heteroaryl ring;
  where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl,
R(2) is hydrogen, halogen, alkyl or aryl;
  which is unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl,
G is —N═C{[NR(3)R(4)][N(R5)R(6)]}
X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;
X(1) is hydrogen, oxygen, sulfur or NR(7);
  R(7) is hydrogen, alkyl, cycloalkyl, arylalkyl, alkenyl, substituted aminoalkyl or an aryl or a heteroaryl ring;
    which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;
  in which substituents each alkyl chain or alkenyl chain can be interrupted by oxygen, sulfur or NR(8);
  R(8) is hydrogen, alkyl, cycloalkyl, arylalkyl, alkenyl, substituted aminoalkyl or an aryl or heteroaryl ring,
    which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;

and their pharmaceutically acceptable salts;
(92/F 404-EP 602 522, NZ 250 438)

h) compounds of the formula I

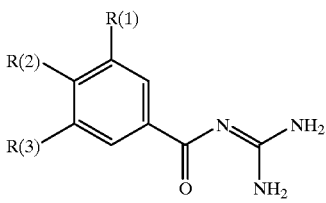

(I)

in which:
R(1) is hydrogen, F, Cl, Br, I, —NO$_2$, —C≡N, —CF$_3$, R(4)—SO$_m$ or R(5)R(6)N—SO$_2$—;
m is zero, 1 or 2;
R(4) and R(5) are (C$_1$–C$_8$)-alkyl, (C$_3$–C$_6$)-alkenyl, —C$_n$H$_{2n}$—R(7) or CF$_3$;
n is zero, 1, 2, 3 or 4;
R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);
R(8) and R(9) are H or C$_1$–C$_4$-alkyl; or
R(5) is H;
R(6) is H or (C$_1$–C$_4$)-alkyl; or
R(5) and R(6) together are 4 or 5 methylene groups, of which one CH$_2$ group can be replaced by oxygen, S, NH, N—CH$_3$ or N-benzyl;
R(2) is —SR(10), —OR(10), —NHR(10), —NR(10)R(11), —CHR(10)R(12), —[CR(12)R(13)OR(13')], —{C—[CH$_2$—OR(13')]R(12)(R(13)} or —[CR(18)R(17)]$_p$—(CO)—[CR(19)R(20)]$_q$—R(14); R(10) and R(11) identically or differently are —[CHR(16)]$_s$—(CH$_2$)$_p$—(CHOH)$_q$—(CH$_2$)$_r$—(CHOH)$_t$—R(21) or —(CH$_2$)$_p$—O—(CH$_2$—CH$_2$O)$_q$—R(21), R(21) is hydrogen, methyl, p, q, r identically or differently are zero, 1, 2, 3 or 4;
s is zero or 1;
t is 1, 2, 3 or 4;
R(12) and R(13) identically or differently are hydrogen, (C$_1$–C$_6$)-alkyl or, together with the carbon atom carrying them, are a (C$_3$–C$_8$)-cycloalkyl,
R(13') is hydrogen or (C$_1$–C$_4$)-alkyl;
R(14) is H, (C$_1$–C$_6$)-alkyl, (C$_3$–C$_8$)-cycloalkyl or —C$_a$H$_{2a}$—R(15);
a is zero, 1, 2, 3 or 4;
R(15) is phenyl, which is unsubstituted or substituted by 1–3 substituents selected from the group consisting of F, Cl, CF$_3$, methyl, methoxy and NR(8)R(9);
R(8) and R(9) are H or (C$_1$–C$_4$)-alkyl; or
R(15) is (C$_1$–C$_9$)-heteroaryl, which is unsubstituted or substituted as phenyl, or
R(15) is (C$_1$–C$_6$)-alkyl, which is unsubstituted or substituted by 1–3 OH;
R(16), R(17), R(18), R(19) and R(20) are hydrogen or (C$_1$–C$_3$)-alkyl;
R(3) is defined as R(1), or
R(3) is (C$_1$–C$_6$)-alkyl or —X—R(22);

X is oxygen, S or NR(16);
R(16) is H or (C$_1$–C$_3$)-alkyl; or
R(22) and R(16) together are 4 or 5 methylene groups, of which one CH$_2$ group can be replaced by oxygen, S, NH, N—CH$_3$ or N-benzyl;
R(22) is defined as R(14);
and their pharmaceutically tolerable salts;
(HOE 92/F 405-EP 602 523, NZ 250 437)
i) benzoylguanidines of the formula I

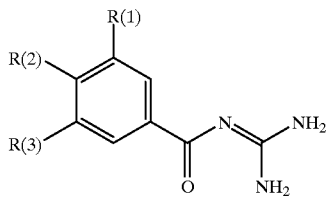

(I)

in which:
R(1) is hydrogen, F, Cl, Br, I, —NO$_2$, —C≡N, R(16)—C$_p$H$_{2p}$—O$_q$, R(4)—SO$_m$ or R(5)R(6)N—SO$_2$—;
m is zero, 1 or 2;
p is zero or 1;
q is zero, 1, 2 or 3;
R(16) is C$_r$F$_{2r+1}$;
r is 1, 2 or 3;
R(4) and R(5) are (C$_1$–C$_8$)-alkyl, (C$_3$–C$_6$)-alkenyl, —C$_n$H$_{2n}$—R(7) or CF$_3$;
n is zero, 1, 2, 3 or 4;
R(7) is (C$_3$–C$_7$)-cycloalkyl or phenyl, which is not substituted or is substituted by 1–3 substituents selected from the group consisting F, Cl, CF$_3$, methyl, methoxy and NR(8)R(9);
R(8) and R(9) are H or C$_1$–C$_4$-alkyl; or
R(5) is H;
R(6) is H or (C$_1$–C$_4$)-alkyl; or
R(5) and R(6) together are 4 or 5 methylene groups, of which one CH$_2$ group can be replaced by oxygen, S, NH, N—CH$_3$ or N-benzyl,
R(2) is (C$_1$–C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino; or
R(2) is —SR(10), —OR(10), —NR(10)R(11), —CR(10)R(11)R(12);
R(10) is —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
a is zero, 1 or 2;
R(11) and R(12) independently of one another are defined as R(10) or are hydrogen or (C$_1$–C$_4$)-alkyl;
R(3) is defined as R(1), or is (C$_1$–C$_6$)-alkyl or —X—R(13);
X is oxygen, S, or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);
b is zero, 1, 2, 3 or 4; or
R(13) and R(14) together are 4 or 5 methylene groups, of which one CH$_2$ group can be replaced by oxygen, S, NH, N—CH$_3$ or N-benzyl;

R(15) is phenyl, which is unsubstituted or substituted by 1–3 substituents selected from the group consisting of F, Cl, CF$_3$, methyl, methoxy and NR(8)R(9);

R(8) and R(9) are H or (C$_1$–C$_4$)-alkyl;

and their pharmaceutically tolerable salts;

(HOE 92/F 411-NZ 250 450, EP 603 650)

k) benzoylguanidines of the formula I

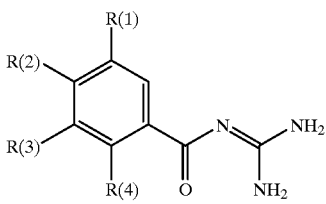

in which:

one of the substituents R(1), R(2), R(3) or R(4):
is an amino group —NR(5)[C$_n$H$_{2n}$—R(6)];
R(5) is hydrogen or C$_{(1-6)}$-alkyl;
n is zero, 1, 2, 3 or 4;
R(6) is H or C$_{(1-4)}$-alkyl;
in which one CH$_2$ group can be replaced by 1 sulfur atom or a group NR(7);
R(7) is hydrogen, methyl or ethyl; or
R(6) is C$_{(3-8)}$-cycloalkyl or phenyl, which is unsubstituted or carries 1, 2 or 3 substituents selected from the group consisting of F, Cl, Br, methyl, methoxy, —NR(8)R(9);
R(8) and R(9) are H, methyl or ethyl; or
R(5) and R(6) together with the nitrogen atom are a 5-, 6- or 7-membered ring, in which 1 carbon atom can be replaced by oxygen, S or NR(10);
R(10) is H, C$_{(1-3)}$-alkyl or benzyl;

and the other substituents R(1), R(2), R(3), R(4) in each case are:
hydrogen, F, Cl, Br, I, CN, CF$_3$, NO$_2$, CF$_3$—O—, C$_m$F$_{2m+1}$—CH$_2$—O— or R(11)—C$_q$H$_{2q}$—X$_p$—;
m is 1, 2 or 3;
q is zero, 1, 2, 3 or 4;
p is zero or 1;
X is oxygen or NR(12);
R(12) is H or C$_{1-3}$-alkyl;
R(11) is hydrogen, C$_{(1-6)}$-alkyl, C$_{(3-8)}$-cycloalkyl or phenyl, which is unsubstituted or substituted by 1, 2 or 3 substituents selected from the group consisting of F, Cl, CH$_3$, CH$_3$—O— and NR(13)R(14);
R(13), R(14) are H, methyl or ethyl;
and their pharmaceutically tolerable salts;

(HOE 92/F 422-EP 604 852)

l) benzoylguanidines of the formula I

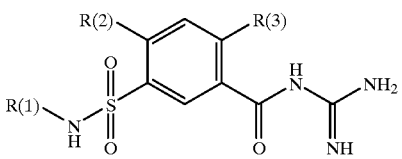

in which

R(1) is R(4)R(5)N—C(X)—;
X is oxygen, S or N—R(6);
R(4) and R(5) identically or differently, are H, (C$_1$–C$_8$)-alkyl, (C$_3$–C$_6$)-alkenyl or —C$_n$H$_{2n}$—R(7);

n is zero, 1, 2, 3 or 4;
R(7) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(4) and R(5) together are 4 or 5 methylene groups, of which one CH$_2$ group can be replaced by oxygen, S, NH, N—CH$_3$ or N-benzyl; R(6) is defined as R(4) or is amidine;

R(2) is H, F, Cl, Br, I, (C$_1$–C$_8$)-alkyl, 1-alkenyl or 1-alkynyl, (C$_3$–C$_8$)-cycloalkyl, (C$_3$–C$_8$)-cycloalkyl-(C$_1$–C$_4$)-alkyl, phenyl, C$_6$H$_5$-(C$_1$–C$_4$)-alkyl, naphthyl, biphenylyl, 1,1-diphenyl-(C$_1$–C$_4$)-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);

W is oxygen, S or NR(9);
R(8) is H, (C$_1$–C$_6$)-alkyl, (C$_5$–C$_7$)-cycloalkyl, cyclohexylmethyl, cyclopentylmethyl, —(CH$_2$)$_m$C$_p$F$_{2p+1}$ or —C$_q$H$_{2q}$—R(10);
m is zero or 1;
p is 1, 2 or 3;
q is zero, 1, 2, 3 or 4;
R(10) is phenyl, which is unsubstituted or substituted by 1–3 substituents selected from the group consisting of F, Cl, CF$_3$, methyl, methoxy and NR(11)R(12);
R(11) and R(12) are H or (C$_1$–C$_4$)-alkyl;
R(9) is H or (C$_1$–C$_3$)-alkyl; or
R(8) and R(9) together are 4 or 5 methylene groups, of which one CH$_2$ group can be replaced by oxygen, S, NH, N—CH$_3$ or N-benzyl;
R(3) is H, F, Cl, Br, I, (C$_1$–C$_6$)-alkyl or —W—R(8) as defined for R(2), and their pharmaceutically acceptable salts;

(93/F 054-NZ 250 919, EP-A 612 723)

m) benzoylguanidines of the formula I

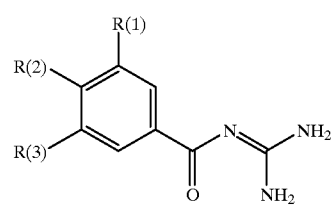

in which:

R(1), R(2), R(3)
are hydrogen, F, Cl, Br, I or (C$_1$–C$_{12}$)-alkyl;
one of the substituents R(1), R(2) or R(3) is N$_3$, CN, OH or (C$_1$–C$_{10}$)-alkyloxy, if at least one of the remaining substituents R(1), R(2) or R(3) is a sufficiently lipophilic alkyl radical having 3 to 12 carbon atoms; or
one of the substituents R(1), R(2) or R(3) is R(4)—C$_n$H$_{2n}$—O$_m$—;
m is zero or 1;
n is zero, 1, 2 or 3;
R(4) is C$_p$F$_{2p+1}$;
p is 1, 2 or 3, if n is zero or 1; or
R(4) is (C$_3$–C$_{12}$)-cycloalkyl, phenyl, pyridyl, quinolyl or isoquinolyl, where the aromatic and heteroaromatic ring systems are unsubstituted or substituted by a substituent selected from the group consisting of F, Cl, CF$_3$, methyl, methoxy and NR(5)R(6);

R(5) and R(6) are hydrogen or (C$_1$–C$_4$)-alkyl;
or one of the substituents R(1), R(2) or R(3) is —C≡CR(5) or —C[R(6)]=CR(5);
R(5) is phenyl, which is unsubstituted or substituted by 1–3 substituents selected from the group consisting of F, Cl, CF$_3$, methyl, methoxy, hydroxyl, amino, methylamino and dimethylamino,
(C$_1$–C$_9$)-heteroaryl, which is unsubstituted or substituted as phenyl, or
R(5) is (C$_1$–C$_6$)-alkyl, which is unsubstituted or substituted by 1–3 OH; or
R(5) is (C$_3$–C$_8$)-cycloalkyl,
R(6) is hydrogen or methyl;
and their pharmacologically acceptable salts
(93/F 153-EP-A 627 413, NZ 260 660)
o) benzoylguanidines of the formula I

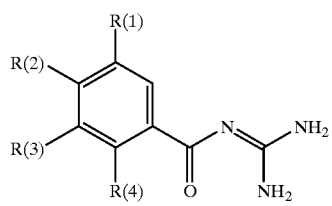
(I)

in which:
R(1) is hydrogen, F, Cl, Br, I, —NO$_2$, —C≡N, X$_o$—(CH$_2$)$_p$—(CF2)$_q$—CF$_3$, R(5)—SO$_m$, R(6)—CO— or R(6)R(7)N—SO$_2$—, where
X is oxygen, S or NR(14);
m is zero, 1 or 2;
o is zero or 1;
p is zero, 1 or 2;
q is zero, 1, 2, 3, 4, 5 or 6;
R(5) and R(6) are (C$_1$–C$_8$)-alkyl, (C$_3$–C$_6$)-alkenyl, —C$_n$H$_{2n}$—R(8) or CF$_3$;
n is zero, 1, 2, 3 or 4;
R(8) is (C$_3$–C$_7$)-cycloalkyl or phenyl, which is not substituted or is substituted by 1–3 substituents selected from the group consisting of F, Cl, CF$_3$, methyl, methoxy and NR(9)R(10);
R(9) and R(10) are H or C$_1$–C$_4$-alkyl; or
R(6) is H;
R(7) is H or (C$_1$–C$_4$)-alkyl; or
R(6) and R(7) together are 4 or 5 methylene groups, of which one CH$_2$ group can be replaced by oxygen, S, NH, N—CH$_3$ or N-benzyl;

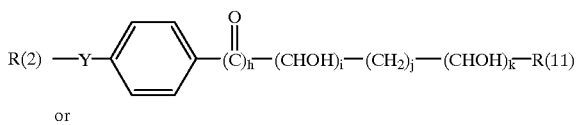

or

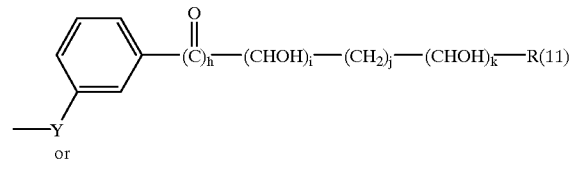

or

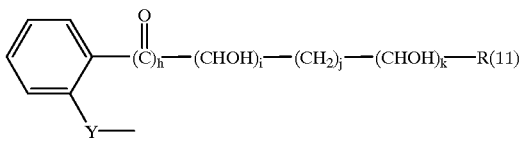

Y is oxygen, —S— or —NR(12)—;
R(11) and R(12) are hydrogen or (C$_1$–C$_3$)-alkyl;
h is zero or 1;
i, j and k independently are zero, 1, 2, 3 or 4;
but where h, i and k are not simultaneously zero,
R(3) is defined as R(1), or is (C$_1$–C$_6$)-alkyl or —X—R(13);
X is oxygen, S or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);
b is zero, 1, 2, 3 or 4; or
R(13) and R(14) together are 4 or 5 methylene groups, where one CH$_2$ group can be replaced by oxygen, S, NH, N—CH$_3$ or N-benzyl;
R(15) is phenyl, which is unsubstituted or substituted by 1–3 substituents selected from the group consisting of F, Cl, CF$_3$, methyl, methoxy and NR(9)R(10);
R(9) and R(10) are H or (C$_1$–C$_4$)-alkyl;
R(4) is hydrogen, —OR(16) or —NR(16)R(17);
R(16) and R(17) independently are hydrogen or (C$_1$–C$_3$)-alkyl;
and their pharmaceutically tolerable salts;
(HOE 93/F 154-EP-A 628 543, NZ 260 681)
p) benzoylguanidines of the formula I

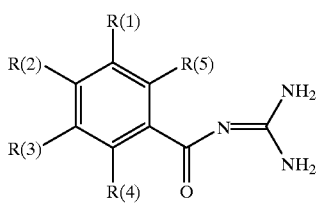
I in which:
R(1) is R(6)—CO or R(7)R(8)N—CO;
R(6) is (C$_1$–C$_8$)-alkyl, (C$_1$–C$_8$)-perfluoroalkyl, (C$_3$–C$_8$)-alkenyl or —C$_n$H$_{2n}$—R(9);
n is zero, 1, 2, 3 or 4;
R(9) is (C$_3$–C$_9$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);
R(10) and R(11) are H, (C$_1$–C$_4$)-alkyl or (C$_1$–C$_4$)-perfluoroalkyl;
R(7) is H, (C$_1$–C$_8$)-alkyl, (C$_1$–C$_8$)-perfluoroalkyl, (C$_3$–C$_8$)-alkenyl or —C$_n$H$_{2n}$—R(1 2);
n is zero, 1, 2, 3 or 4;
R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl;

R(8) is H, $(C_1-C_4)$-alkyl or $(C_1-C_4)$-perfluoroalkyl; or
R(7) and R(8) together are 4 or 5 methylene groups, of which one $CH_2$ group can be replaced by oxygen, S, NH, N—$CH_3$ or N-benzyl;

R(2) is defined as R(1), or is H, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}R(15)$;
n is zero, 1, 2, 3 or 4;
R(15) is $(C_3-C_9)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
  R(16) and R(17) are H, $(C_1-C_4)$-alkyl or $(C_1-C_4)$-perfluoroalkyl; or R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(2) is SR(18), —OR(18), —NR(18)R(19), —CR(18)R(19)R(20);
R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(19) and R(20) independently of one another are defined as R(18) or are hydrogen, $(C_1-C_4)$-alkyl or $(C_1-C_4)$-perfluoroalkyl; or R(2) is R(21)—$SO_m$ or R(22)R(23)N—$SO_2$—;
m is 1 or 2;
R(21) is $(C_1-C_8)$-alkyl, $(C_1-C_8)$-perfluoroalkyl, $(C_3-C_8)$-alkenyl, —$C_nH_{2n}$—R(24),
n is zero, 1, 2, 3 or 4;
R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
  R(27) and R(28) are H, $(C_1-C_4)$-alkyl or $(C_1-C_4)$-perfluoroalkyl;
R(22) is H, $(C_1-C_8)$-alkyl, $(C_1-C_8)$-perfluoroalkyl, $(C_3-C_8)$-alkenyl, —$C_nH_{2n}$—R(29);
n is zero, 1, 2, 3 or 4;
R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
  R(30) and R(31) are H, $(C_1-C_4)$-alkyl or $(C_1-C_4)$-perfluoroalkyl;
R(23) is H, $(C_1-C_4)$-alkyl or $(C_1-C_4)$-perfluoroalkyl; or
R(22) and R(23) together are 4 or 5 methylene groups, of which one $CH_2$ group can be replaced by oxygen, S, NH, N—$CH_3$ or N-benzyl; or R(2) is R(33)X—;
X is oxygen, S, NR(34), (D=O)A—, NR(34)C=MN$^{(*)}$R(35)—;
M is oxygen or S;
A is oxygen or NR(34);
D is C or SO;
R(33) is $(C_1-C_8)$-alkyl, $(C_3-C_8)$-alkenyl, $(CH_2)_bC_dF_{2d+1}$, —$C_nH_{2n}$—R(36),
b is zero or 1;
d is 1, 2, 3, 4, 5, 6 or 7;
n is zero, 1, 2, 3 or 4;
R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
  R(37) and R(38) are H, $(C_1-C_4)$-alkyl or $(C_1-C_4)$-perfluoroalkyl;
R(34) is H, $(C_1-C_4)$-alkyl or $(C_1-C_4)$-perfluoroalkyl;
R(35) is defined as R(33); or
R(33) and R(34) together are 4 or 5 methylene groups, of which one $CH_2$ group can be replaced by oxygen, S, NH, N—$CH_3$ or N-benzyl;
where A and N$^{(*)}$ are bonded to the phenyl nucleus of the benzoylguanidine parent structure; or R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR(49)R(50)]$_v$—R(44);
R(40), R(41) identically or differently are —$(CH_2)_p$—$(CHOH)_q$—$(H_2)_r$—$(CHOH)_t$—R(51) or —$(CH_2)_p$—O—$(CH_2$—$CH_2O)_q$—R(51); R(51) is hydrogen or methyl;
u is 1, 2, 3 or 4;
v is zero, 1, 2, 3 or 4;
p, q, r identically or differently are zero, 1, 2, 3 or 4;
t is 1, 2, 3 or 4;
R(42) and R(43) identically or differently are hydrogen or $(C_1-C_6)$-alkyl; or
R(42) and R(43) together with the carbon atom carrying them form a $(C_3-C_8)$-cycloalkyl;
R(44) is H, $(C_1-C_6)$-alkyl, $(C_3-C_8)$-cycloalkyl or —$C_eH_{2e}$—R(45);
e is zero, 1, 2, 3 or 4;
R(45) is phenyl, which is unsubstituted or substituted by 1–3 substituents from the group consisting of F, Cl, $CF_3$, methyl, methoxy and NR(52)R(53);
  R(52) and R(53) are H or $(C_1-C_4)$-alkyl, or
R(45) is $(C_1-C_9)$-heteroaryl, which is unsubstituted or substituted as phenyl; or
R(45) is $(C_1-C_6)$-alkyl, which is unsubstituted or substituted by 1–3 OH;
R(46), R(47), R(48), R(49) and R(50) are hydrogen or methyl; or R(2) is R(55)—NH—$SO_2$—;
R(55) is R(56)R(57)N—(C=Y)—;
Y is oxygen, S or N—R(58);
R(56) and R(57) identically or differently are H, $(C_1-C_8)$-alkyl, $(C_3-C_6)$-alkenyl or —$C_fH_{2f}$—R(59);
f is zero, 1, 2, 3 or 4;
R(59) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or
R(56) and R(57) together are 4 or 5 methylene groups, of which one $CH_2$ group can be replaced by oxygen, S, NH, N—$CH_3$ or N-benzyl;
R(58) is defined as R(56) or is amidine;
R(3), R(4) and R(5) independently of one another are defined as R(1) or R(2);
and their pharmaceutically tolerable salts;
(HOE 93/F 220-EP-A 640 593, NZ 264 117)

q) benzoylguanidines of the formula I

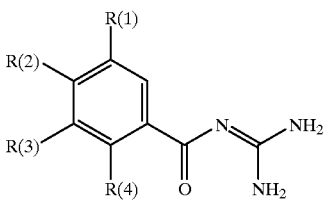

in which:

R(1) is hydrogen, F, Cl, Br, I, —NO$_2$, —C N, —X$_o$—(CH$_2$)$_p$—(CF$_2$)$_q$—CF$_3$, R(5)—SO$_m$—, R(6)—CO—, R(6)R(7)N—CO— or R(6)R(7)N—SO$_2$—;

X is oxygen, —S— or NR(14);

m is zero, 1 or 2;

o is zero or 1;

p is zero, 1 or 2;

q is zero, 1, 2, 3, 4, 5 or 6;

R(5) and R(6) are (C$_1$–C$_8$)-alkyl, (C$_3$–C$_6$)-alkenyl, —C$_n$H$_{2n}$—R(8) or CF$_3$;

n is zero, 1, 2, 3 or 4;

R(8) is (C$_3$–C$_7$)-cycloalkyl, phenyl, which is not substituted or is substituted by 1 to 3 substituents selected from the group consisting of F, Cl, CF$_3$, methyl, methoxy and NR(9)R(1 0);

R(9) and R(10) are H or (C$_1$–C$_4$)-alkyl; or

R(6) is hydrogen;

R(7) is hydrogen or (C$_1$–C$_4$)-alkyl; or

R(6) and R(7) together are 4 or 5 methylene groups, of which one CH$_2$ group can be replaced by oxygen, S, NH, N—CH$_3$ or N-benzyl;

 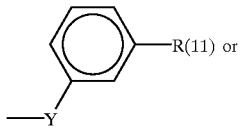

R(2)

R(11) is (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino and benzyl;

Y is oxygen, —S— or NR(12);

R(12) is H or (C$_1$–C$_4$)-alkyl;

R(3) is defined as R(1); or

R(3) is (C$_1$–C$_6$)-alkyl or —X—R(13);

X is oxygen, —S— or NR(14);

R(14) is H or (C$_1$–C$_3$)-alkyl;

R(13) is H, (C$_1$–C$_6$)-alkyl, (C$_3$–C$_8$)-cycloalkyl or —C$_b$H$_{2b}$—R(15);

b is zero, 1, 2, 3 or 4; or

R(13) and R(14) together are 4 or 5 methylene groups, of which one CH$_2$ group can be replaced by oxygen, S, NH, N—CH$_3$ or N-benzyl;

R(15) is phenyl, which is unsubstituted or substituted by 1–3 substituents selected from the group consisting of F, Cl, CF$_3$, methyl, methoxy and NR(9)R(10);

R)9) and R(10) are H or (C$_1$–C$_4$)-alkyl;

R(4) is hydrogen, —OR(16), —NR(16)R(17) or C$_r$F$_{2r+1}$;

R(16) and R(17) independently are hydrogen or (C$_1$–C$_3$)-alkyl;

r is 1, 2, 3 or 4;

and their pharmaceutically tolerable salts;

(HOE 93/F 223 K-EP 639 573, NZ 264 130)

r) benzo-fused 5-membered ring heterocycles of the formula I

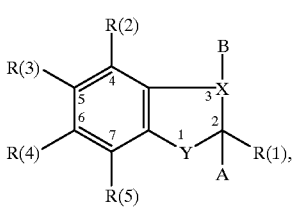

in which:

X is N or CR(6);

N is oxygen, S or NR(7);

A, B together are a bond or

A, B are both hydrogen, if X is CR(6) and Y is NR(7) simultaneously; one of the substituents R(1) to R(6) is a —CO—N═C(NH$_2$)$_2$ group; the other substituents R(1) to R(6) in each case are hydrogen, F, Cl, Br, I or (C$_1$–C$_6$)-alkyl;

up to two of the other substituents R(1) to R(6) are CN, NO$_2$, N$_3$, (C$_1$–C$_4$)-alkyloxy or CF$_3$;

up to one of the other substituents is R(8)—C$_n$H$_{2n}$—Z—;

n is zero to 10; where the alkylene chain —C$_n$H$_{2n}$— is straight-chain or branched and where one carbon atom can be replaced by an oxygen or sulfur atom or by a nitrogen atom;

R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH═CH—, and in which one methylene group can be replaced by an oxygen or sulfur atom or by a nitrogen atom; or R(8) is phenyl, which is unsubstituted or substituted by 1 to 3 substituents selected from the group consisting of F, Cl, Br, I, CF$_3$, CH$_3$—S(O)$_s$— or R(9)—W$_y$—;

s is zero, 1 or 2;

R(9) is H, methyl, ethyl,

W is oxygen or NR(10);

R(10) is H or methyl;

y is zero or 1; or

R(8) is C$_m$F$_{2m+1}$;

m is 1 to 3; or

R(8) is 1- or 2-naphthyl, pyridyl, quinolyl or isoquinolyl;

Z is —CO—, —CH$_2$— or —[CR(11)(OH)]$_q$—;

q is 1, 2 or 3;

R(11) is H or methyl; or

Z is oxygen or —NR(12)—;

R(12) is H or methyl; or

Z is —S(O)S—;
s is zero, 1 or 2; or
Z is —SO$_2$—NR(13)—;
R(13) is H or (C$_1$-C$_4$)-alkyl;
R(7) is hydrogen, (C$_1$-C$_{10}$)-alkyl, (C$_2$-C$_{10}$)-alkenyl or R(8)—C$_n$H$_{2n}$—;
and their pharmaceutically tolerable salts;
(HOE 93/F 236-EP-A 638 548, NZ 264 216)
s) benzoylguanidines of the formula I

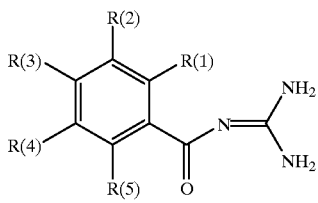

(I)

in which:
R(1), R(3) or R(4) is —NR(6) C=X NR(7)R(8);
X is oxygen or S;
R(6) is hydrogen, (C$_1$-C$_8$)-alkyl, (C$_1$-C$_8$)-perfluoroalkyl, (C$_3$-C$_8$)-alkenyl or —C$_n$H$_{2n}$—R(9);
n is zero, 1, 2, 3 or 4;
R(9) is (C$_3$-C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(10)R(11);
R(10) and R(11) are H, (C$_1$-C$_4$)-alkyl or (C$_1$-C$_4$)-perfluoroalkyl;
R(7) is hydrogen, (C$_1$-C$_8$)-alkyl, (C$_1$-C$_8$)-perfluoroalkyl, (C$_3$-C$_8$)-alkenyl or —C$_o$H$_{2o}$—R (12);
o is zero, 1, 2, 3 or 4;
R(12) is (C$_3$-C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(13)R(14);
R(13) and R(14) are H, (C$_1$-C$_4$)-alkyl or (C$_1$-C$_4$)-perfluoroalkyl;
R(8) is defined as R(7); or
R(7) and R(8) together are 4 or 5 methylene groups, of which one CH$_2$ group can be replaced by oxygen, S, NH, N—CH$_3$ or N-benzyl;
the remaining substituents R(2), R(3), R(4), R(5) or R(1), R(2), R(4), R(5) or R(1), R(2), R(3), R(5) in each case independently of one another are hydrogen, F, Cl, Br, I, —O$_{ta}$(C$_1$-C$_8$)-alkyl, —O$_{tb}$(C$_3$-C$_8$)-alkenyl, —O$_{tc}$(CH$_2$)$_b$C$_d$F$_{2d+1}$, —O$_{td}$C$_p$H$_{2p}$R(18), or up to 2 groups CN, NO$_2$, NR(16)R(17),
b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;
R(18) is (C$_3$-C$_8$)-cycloalkyl, phenyl, biphenylyl or naphthyl,
where the aromatics are not substituted or are substituted by 1–3 substituents selected from the group consisting of F, CG, CF$_3$, methyl, methoxy and NR(19)R(20);
R(19) and R(20) are hydrogen or (C$_1$-C$_4$)-alkyl or (C$_1$-C$_4$)-perfluoroalkyl;
R(16) is hydrogen, (C$_1$-C$_8$)-alkyl, (C$_1$-C$_8$)-perfluoroalkyl, (C$_3$-C$_8$)-alkenyl, —C$_q$H$_{2q}$—R(21),
q is zero, 1, 2, 3 or 4;
R(21) is (C$_3$-C$_8$)-cycloalkyl, phenyl, biphenylyl or naphthyl,
where the aromatics are not substituted or are substituted by 1–3 substituents from the group F, Cl, CF$_3$, methyl, methoxy or NR(22)R(23),
R(22) and R(23) are hydrogen, (C$_1$-C$_4$)-alkyl or (C$_1$-C$_4$)-perfluoroalkyl;
R(17) is hydrogen, (C$_1$-C$_8$)-alkyl, (C$_1$-C$_8$)-perfluoroalkyl, (C$_3$-C$_8$)-alkenyl, -C$_r$H$_{2r}$—R(24);
r is zero, 1, 2, 3 or 4;
R(24) is (C$_3$-C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(25)R(26);
R(25) and R(26) are hydrogen, (C$_1$-C$_4$)-alkyl or (C$_1$-C$_4$)-perfluoroalkyl; or
R(16) and R(17) together are 4 or 5 methylene groups, of which one CH$_2$ group can be replaced by oxygen, S, NH, N—CH$_3$ or N-benzyl;
and their pharmaceutically tolerable salts;
(HOE 93/F 249-EP-A 640 587, NZ 264 282)
t) diacyl-substituted guanidines of the formula I

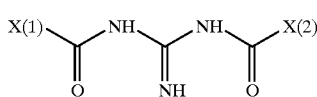

I in which:
X(1) and X(2) are

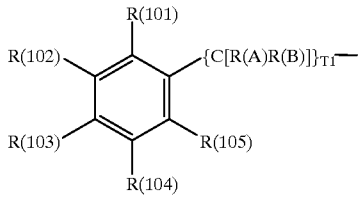

T1 is zero, 1, 2, 3 or 4;
R(A) and R(B) independently are hydrogen, F, Cl, Br, I, CN, OR(106), (C$_1$-C$_8$)-alkyl, (C$_3$-C$_8$)-cycloalkyl, O$_{zk}$(CH$_2$)$_{zl}$C$_{zm}$F$_{2zm+1}$, NR(107)R(108), phenyl or benzyl,
where the aromatics are not substituted or are substituted by 1–3 substituents selected from the group consisting of F, Cl, CF$_3$, methyl, methoxy and NR(109)R(110);
R(109) and R(110) are hydrogen, (C$_1$-C$_4$)-alkyl or (C$_1$-C$_4$)-perfluoroalkyl;
zl is zero, 1, 2, 3 or 4;
zk is zero or 1;
zm is 1, 2, 3, 4, 5, 6, 7 or 8;
R(106) is hydrogen, (C$_1$—C$_8$)-alkyl, (C$_1$-C$_8$)-perfluoroalkyl, (C$_3$-C$_8$)-alkenyl, (C$_3$-C$_8$)-cycloalkyl, phenyl or benzyl,
where the aromatics are not substituted or are substituted by 1–3 substituents selected from the group consisting of F, Cl, CF$_3$, methyl, methoxy and NR(111)R(112);
R(111) and R(112) are hydrogen, (C$_1$-C$_4$)-alkyl or (C$_1$-C$_4$)-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl; or X(1) and X(2) are

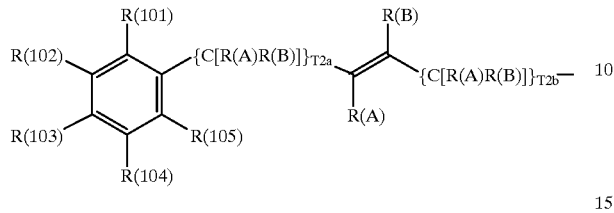

T2a and T2b independently of one another are zero, 1 or 2;

where the double bond can have the (E)- or (Z)-configuration; or

X(1) and X(2) are

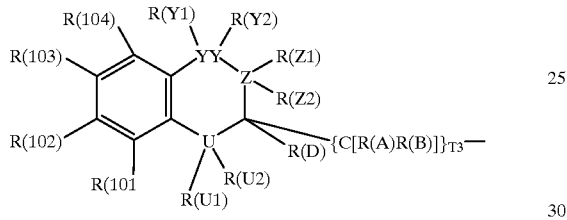

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;

zla is zero, 1, 2, 3 or 4;

zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as R(114); or

R(115) and R(116) together are 4 or 5 methylene groups, of which one $CH_2$ group can be replaced by oxygen, S, NH, N—$CH_3$ or N-benzyl;

but where the constitution of U being nitrogen (N), YY being nitrogen (N) and Z being carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—, where the perfluoroalkyl group is straight-chain or branched, X is oxygen, S or NR(114a);

R(114a) is H or $(C_1-C_3)$-alkyl;

zoa is zero or 1;

zbm is zero, 1 or 2;

zpa is zero, 1, 2, 3 or 4;

zqa is 1, 2, 3, 4, 5, 6, 7 or 8;

R(110a), R(110b), R(111a) and R(112a) independently are $(C_1-C_8)$-alkyl, $(C_3-C_8)$-alkenyl, —$C_{zn}H_{2zn}$—R(115a) or $(C_1-C_8)$-perfluoroalkyl;

zn is zero, 1, 2, 3 or 4;

R(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);

R(116a) and R(117a) are hydrogen, $(C_1-C_4)$-perfluoroalkyl or $(C_1-C_4)$-alkyl; or R(110b), R(111a) and R(112a) are hydrogen;

R(110c) and R(113a) independently are hydrogen, $(C_1-C_4)$-perfluoroalkyl or $(C_1-C_4)$-alkyl; or R(110b) and R(110c) and R(112a) and R(113a) together are 4 or 5 methylene groups, of which one $CH_2$ group can be replaced by oxygen, sulfur, NH, N—$CH_3$ or N-benzyl; or R(101), R(102), R(103), R(104), R(105) independently of one another are $(C_1-C_8)$-alkyl, —$C_{zal}H_{2zal}$R(118a) or $(C_3-C_8)$-alkenyl, zal is zero, 1, 2, 3 or 4;

R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(119b);

R(119a) and R(119b) are hydrogen, $(C_1-C_4)$-alkyl or $(C_1-C_4)$-perfluoroalkyl; or R(101), R(102), R(103), R(104), R(105) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino; or R(101), R(102), R(103), R(104), R(105) independently of one another are —C≡C—R(193);

R(1 93) is phenyl which is not substituted or is substituted by 1–3 substituents from the group consisting of F, Cl, $CF_3$, methyl, methoxy or NR(194)R(195);

R(194) and R(195) are hydrogen or $CH_3$; or

R(101), R(102), R(103), R(104), R(105) independently of one another are

—Y-para-$C_6H_4$—$(CO)_{zh}$—$(CHOH)_{zi}$—$(CH_2)_{zj}$—$(CHOH)_{zk}$—R(123),

—Y-meta-$C_6H_4$—$(CO)_{zad}$—$(CHOH)_{zae}$—$(CH_2)_{zaf}$—$(CHOH)_{zag}$—R(124) or —Y-ortho-$C_6H_4$—$(CO)_{zah}$—$(CHOH)_{zao}$—$(CH_2)_{zap}$—$(CHOH)_{zak}$—R(125);

Y is oxygen, —S— or —NR(122d)—;

zh, zad, zah independently are zero or 1;

zi, zj, zk, zae, zaf, zag, zao, zap and zak independently are zero, 1, 2, 3 or 4;

but where in each case zh, zi and zk are not simultaneously zero, zad, zae and zag are not simultaneously zero, and zah, zao and zak are not simultaneously zero, R(123), R(124), R(125) and R(122d) independently are hydrogen or $(C_1-C_3)$-alkyl; or R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1-C_9)$-heteroaryl, which is unsubstituted or substituted by 1–3 substituents from the group consisting of F, Cl, $CF_3$, $CH_3$, methoxy, hydroxyl, amino, methylamino and dimethylamino;

zab is zero, 1 or 2;

R(132), R(134) and R(135) independently of one another are defined as R(129) or are hydrogen, $(C_1-C_4)$-alkyl or $(C_1-C_4)$-perfluoroalkyl; or R(101), R(102), R(103), R(104) and R(105) independently of one another are —W-para-$(C_6H_4)$—R(196), —W-meta-$(C_6H_4)$—R(197) or —W-ortho-$(C_6H_4)$—R(198);

R(196), R(197) and R(198) independently are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;

W is oxygen, S or NR(136)—;

R(136) is hydrogen or $(C_1-C_4)$-alkyl; or

R(101), R(102), R(103), R(104) and R(105) independently of one another are R(146)X(1a)—;

X(1a) is oxygen, S, NR(147), (D=O)A—, NR(148)C=$MN^{(*)}$R(149)—;

M is oxygen or sulfur;

A is oxygen or NR(150);

D is C or SO;

R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);

zbz is zero or 1;

zdz is 1, 2, 3, 4, 5, 6 or 7;

zxa is zero, 1, 2, 3 or 4;

R(151) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);

R(152) and R(153) are hydrogen, $(C_1-C_4)$-alkyl or $(C_1-C_4)$-perfluoroalkyl;

R(147), R(148) and R(150) independently are hydrogen, $(C_1-C_4)$-alkyl, $(C_1-C_4)$-perfluoroalkyl;

R(149) is defined as R(146), or

R(146) and R(147), or R(146) and R(148) together are 4 or 5 methylene groups, of which one $CH_2$ group can be replaced by oxygen, sulfur, NH, N—$CH_3$ or N-benzyl where A and $N^{(*)}$ are bonded to the phenyl nucleus of the alkanoyl parent structure; or R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —[CR(159)R(160)]_{zu}—(C=O)—[CR(161)R(162)]_{zv}—R(163);

R(164), R(165), R(166), R(167), R(169) identically or differently are —$(CH_2)_{zy}$—$(CHOH)_{zz}$—$(CH_2)_{zaa}$—$(CHOH)_{zt}$—R(171) or —$(CH_2)_{zab}$—O—$(CH_2$—$CH_2O)_{zac}$—R(172);

R(171) and R(172) are hydrogen or methyl;

zu is 1, 2, 3 or 4;

zv is zero, 1, 2, 3 or 4;

zy, zz, zaa, zab, zac identically or differently are zero, 1, 2, 3 or 4;

zt is 1, 2, 3 or 4;

R(168), R(170), R(154), R(155) identically or differently are hydrogen or $(C_1-C_6)$-alkyl, or R(169) and R(170), or R(154) and R(155) together with the carbon atom carrying them are a $(C_3-C_8)$-cycloalkyl;

R(163) is hydrogen, $(C_1-C_6)$-alkyl, $(C_3-C_8)$-cycloalkyl or —$C_{zeb}H_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, $CF_3$, methyl, methoxy and NR(174)R(175);

R(174) and R(175) are hydrogen or $(C_1-C_4)$-alkyl; or

R(156), R(157) and R(173) independently are $(C_1-C_9)$-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—$SO_2$—;

R(176) is R(177)R(178)N—(C=Y')-;

Y' is oxygen, S or N—R(179);

R(177) and R(178) identically or differently are hydrogen, $(C_1-C_8)$-alkyl, $(C_3-C_6)$-alkenyl or —$C_{zfa}H_{2zfa}$—R(180);

zfa is zero, 1, 2, 3 or 4;

R(180) is $(C_5-C_7)$-cycloalkyl or phenyl, which is unsubstituted or substituted by 1–3 substituents selected from the group consisting of F, Cl, $CF_3$, methoxy or $(C_1-C_4)$-alkyl; or R(177) and R(178) together are 4 or 5 methylene groups, of which one $CH_2$ group can be replaced by oxygen, sulfur, NH, N—$CH_3$ or N-benzyl;

R(179) is defined as R(177) or is amidine, or

R(101), R(102), R(103), R(104), R(105) independently of one another are NR(184a)R(185), OR(184b), SR(184c) or —$C_{znx}H_{2znx}$—R(184d);

znx is zero, 1, 2, 3 or 4;

R(184d) is $(C_3-C_7)$-cycloalkyl or phenyl, which is not substituted or is substituted by 1–3 substituents from the group consisting of F, Cl, $CF_3$, methyl, methoxy and NR(116k)R(117k);

R(116k) and R(117k) are hydrogen or $C_1-C_4$-alkyl;

R(184a), R(184b), R(184c), R(185) independently of one another are hydrogen, $(C_1-C_8)$-alkyl, $(C_1-C_8)$-perfluoroalkyl or $(CH_2)_{zao}$—R(184g);

zao is zero, 1, 2, 3 or 4;

184g is $(C_3-C_7)$-cycloalkyl or phenyl, which is not substituted or is substituted by 1–3 substituents from the group consisting of F, Cl, $CF_3$, methyl, methoxy and NR(184u)R(184v);
R(184u) and R(184v) are hydrogen or $C_1-C_4$-alkyl; or
R(184a) and R(185) together are 4 or 5 methylene groups, of which one $CH_2$ group can be replaced by oxygen, sulfur, NH, N—$CH_3$ or N-benzyl;

and their pharmaceutically tolerable salts;
(HOE 93/F 254-EP-A 640 588, NZ 264 307)

u) benzoylguanidines of the formula I

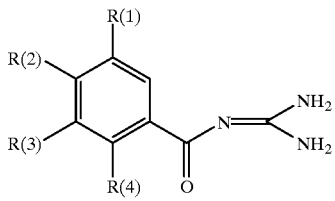

in which:

R(1) is H, F, Cl, Br, I, CN, $NO_2$, $(C_1-C_8)$-alkyl, $(C_3-C_8)$-cycloalkyl or
$X_a$—$(CH_2)_b$—$(CF_2)_c$—$CF_3$;
X is oxygen, S or NR(5);
a is zero or 1;
b is zero, 1 or 2;
c is zero, 1, 2 or 3;
R(5) is H, $(C_1-C_4)$-alkyl or —$C_dH_{2d}R(6)$;
d is zero, 1, 2, 3 or 4;
R(6) is $(C_3-C_8)$-cycloalkyl, phenyl, biphenylyl or naphthyl,
where the aromatics are not substituted or are substituted by 1 to 3 substituents selected from the group consisting of F, Cl, $CF_3$, methyl, methoxy and NR(7)R(8);
R(7) and R(8) independently are H or $(C_1-C_4)$-alkyl; or R(1) is -SR(10), —OR(10) or —CR(10)R(11)R(12);
R(10) is —$C_fH_{2f}$—$(C_3-C_8)$-cycloalkyl, —$(C_1-C_9)$-heteroaryl or phenyl,
where the aromatic systems are unsubstituted or substituted by 1 to 3 substituents selected from the group consisting of F, Cl, $CF_3$, $CH_3$, methoxy, hydroxyl, amino, methylamino and dimethylamino;
f is zero, 1 or 2;
R(11) and R(12) independently of one another are defined as R(10) or are hydrogen or $(C_1-C_4)$-alkyl; or R(1) is phenyl, naphthyl, biphenylyl or $(C_1-C_9)$-heteroaryl, the latter linked via C or N, and which are unsubstituted or substituted by 1 to 3 substituents selected from the group consisting of F, Cl, $CF_3$, $CH_3$, methoxy, hydroxyl, amino, methylamino and dimethylamino; or R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$;
R(13) and R(14) identically or differently are —$(CH_2)_g$—$(CHOH)_h$—$(CH_2)_i$—$(CHOH)_j$—R(17),
R(17) is hydrogen or methyl;

—$(CH_2)_g$—O—$(CH_2-CH_2O)_h$—R(24),
g,h,i identically or differently are zero, 1, 2, 3 or 4;
j is 1, 2, 3 or 4;
R(15) and R(16) identically or differently are hydrogen, $(C_1-C_6)$-alkyl or together with the carbon atom carrying them are a $(C_3-C_8)$-cycloalkyl;
R(18) is phenyl, which is unsubstituted or substituted by 1 to 3 substituents selected from the group consisting of F, Cl, $CF_3$, methyl, methoxy and NR(25)R(26);
R(25) and R(26) are H or $(C_1-C_4)$-alkyl; or
R(18) is $(C_1-C_9)$-heteroaryl, which is unsubstituted or substituted as phenyl; or
R(18) is $(C_1-C_6)$-alkyl, which is unsubstituted or substituted by 1 to 3 OH; or
R(18) is $(C_3-C_8)$-cycloalkyl;
R(19), R(20), R(21), R(22) and R(23) are hydrogen or methyl;
k is zero, 1, 2, 3 or 4;
l is zero, 1, 2, 3 or 4;
R(24) is H, $(C_1-C_6)$-alkyl, $(C_3-C_8)$-cycloalkyl or —$C_mH_{2m}$—R(18);
m is 1, 2, 3 or 4;
R(2) and R(3) independently of one another are defined as R(1);
R(4) is $(C_1-C_3)$-alkyl, F, Cl, Br, I, CN or —$(CH_2)_n$—$(CF_2)_o$—$CF_3$;
n is zero or 1;
o is zero, 1 or 2;

and their pharmaceutically tolerable salts;
(HOE 93/F 436-EP-A 659 748), NZ 270 264)

v) acylguanidines of the formula I

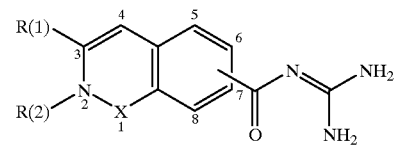

in which:

X is carbonyl, sulfonyl,
R(1) is H, $(C_1-C_8)$-alkyl, unsubstituted or substituted by hydroxyl,
$(C_3-C_8)$-cycloalkyl, phenyl, which is unsubstituted or substituted by 1–3 substituents from the group F, Cl, $CF_3$, $CH_3$, methoxy, hydroxyl, amino, methylamino or dimethylamino,
R(2) is H, $(C_1-C_4)$-alkyl, and their pharmaceutically tolerable salts;
(HOE 94/F 014 K-EP-A 666 252, NZ 270 370)

w) phenyl-substituted alkylcarboxylic acid guanidides, carrying perfluoroalkyl groups, of the formula I

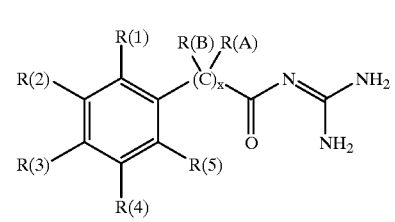

in which:

R(A) is hydrogen, F, Cl, Br, I, CN, OR(6), $(C_1-C_8)$-alkyl, $(C_3-C_8)$-cycloalkyl, $O_r(CH_2)_aC_bF_{2b+1}$ or NR(7)R(8);

r is zero or 1;
a is zero, 1, 2, 3 or 4;
b is 1, 2, 3, 4, 5, 6, 7 or 8;
R(6) is hydrogen, $(C_1-C_8)$-alkyl, $(C_3-C_8)$-alkenyl, $(C_3-C_8)$-cycloalkyl, phenyl or benzyl,
  where the aromatics are not substituted or are substituted by 1–3 substituents selected from the group consisting of F, Cl, $CF_3$, methyl, methoxy and NR(9)R(10);
  R(9) and R(10) are H, $(C_1-C_4)$-alkyl or $(C_1-C_4)$-perfluoroalkyl;
R(7) and R(8) independently of one another are defined as R(6);
R(B) independently is defined as R(A);
X is 1, 2 or 3;
R(1) is hydrogen, $(C_1-C_8)$-alkyl, $(C_3-C_8)$-cycloalkyl, $-O_t(CH_2)_dC_eF_{2e+1}$, F, Cl, Br, I or CN;
t is zero or 1;
d is zero, 1, 2, 3 or 4;
e is 1, 2, 3, 4, 5, 6, 7 or 8;
R(2), R(3), R(4) and R(5) independently of one another are defined as R(1);
but with the condition that at least one of the substituents R(1), R(2), R(3), R(4), R(5), R(A) and R(B) is an $-O_t CH_2)_d C_e F_{2e+1}$ or an $O_r(CH_2)_a C_b F_{2b+1}$ group,
and their pharmaceutically tolerable salts;
(HOE 94/F 094-EP-A 676 395, NZ 270 894)

x) heteroaroylguanidines of the formula I

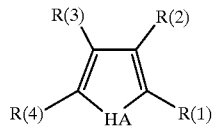

I in which:
HA is $SO_m$, O or NR(5);
  m is zero, 1 or 2;
  R(5) is hydrogen, $(C_1-C_8)$-alkyl or $-C_{am}H_{2am}R(81)$;
  am is zero, 1 or 2;
    R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);
      R(82) and R(83) are H or $CH_3$; or
    R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
one of the two substituents R(1) and R(2) is $-CO-N=C(NH_2)_2$;
and the other in each case is hydrogen, F, Cl, Br, I, $(C_1-C_3)$-alkyl, $-OR(6)$, $C_rF_{2r+1}$, $-CO-N=C(NH_2)_2$ or $-NR(6)R(7)$;
  R(6) and R(7) independently are hydrogen or $(C_1-C_3)$-alkyl;
  r is 1, 2, 3 or 4;
R(3) and R(4) independently of one another are hydrogen, F, Cl, Br, I, $-C\equiv N$, $X-(CH_2)_p-(C_q-F_{2q+1})$, $R(8)-SO_{bm}$, $R(9)R(10)N-CO$, $R(11)-CO-$ or $R(12)R(13)N-SO_2-$, where the perfluoroalkyl group is straight-chain or branched, X is oxygen, S or NR(14);
  R(14) is H or $(C_1-C_3)$-alkyl;
  bm is zero, 1 or 2;
  p is zero, 1 or 2;
  q is zero, 1, 2, 3, 4, 5 or 6;
  R(8), R(9), R(11) and R(12) independently are $(C_1-C_8)$-alkyl, $(C_3-C_6)$-alkenyl, $-C_nH_{2n}-R(15)$, $CF_3$;
    n is zero, 1, 2, 3 or 4;
    R(15) is $(C_3-C_7)$-cycloalkyl or phenyl, which is not substituted or is substituted by 1–3 substituents selected from the group consisting of F, Cl, $CF_3$, methyl, methoxy or NR(16)R(17);
      R(16) and R(17) are H or $C_1-C_4$-alkyl; or
  R(9), R(11) and R(12) are H;
  R(10) and R(13) independently are H or $(C_1-C_4)$-alkyl; or
  R(9) and R(10), and R(12) and R(13) together are 4 or 5 methylene groups, of which one $CH_2$ group can be replaced by oxygen, S, NH, N—$CH_3$ or N-benzyl, or
R(3) and R(4) independently of one another are $(C_1-C_8)$-alkyl or $-C_{a1}H_{2a1}R(18)$;
  a1 is zero, 1 or 2;
  R(18) is $(C_3-C_8)$-cycloalkyl or phenyl;
    which is not substituted or is substituted by 1–3 substituents selected from the group consisting of F, Cl, $CF_3$, methyl, methoxy and NR(19)R(20);
    R(19) and R(20) are H or $CH_3$; or
R(3) and R(4) independently of one another are $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(3) and R(4) independently of one another are

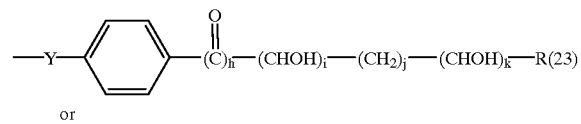

or

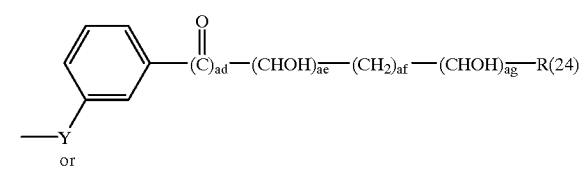

or

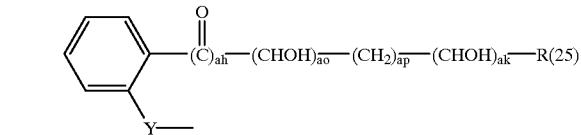

Y is oxygen, $-S-$ or $-NR(22)-$;
h, ad, ah independently are zero or 1;
i, j, k, ae, af, ag, ao, ap and ak independently are zero, 1, 2, 3, 4, but where in each case
  h, i and k are not simultaneously zero,
  ad, ae and ag are not simultaneously zero, and
  ah, ao and ak are not simultaneously zero,
R(23), R(24), R(25) and R(22) independently are hydrogen or $(C_1-C_3)$-alkyl; or
R(3) and R(4) independently of one another are hydrogen, F, Cl, Br, I, CN, $(C_1-C_8)$-alkyl, $(C_1-C_8)$-perfluoroalkyl, $(C_3-C_8)$-alkenyl or $-C_gH_{2g}R(26)$;

g is zero, 1, 2, 3 or 4;

R(26) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, $(C_1-C_4)$-alkyl or $(C_1-C_4)$-perfluoroalkyl; or

R(3) and R(4) independently of one another are SR(29), —OR(30), —NR(31)R(32) or —CR(33)R(34)R(35);

R(29), R(30), R(31) and R(33) independently are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl; or R(3) and R(4) independently of one another are

[structures: —W—C$_6$H$_4$—R(96), C$_6$H$_4$(—W)(—R(97)), C$_6$H$_4$(W—)(—R(98))]

R(96), R(97) and R(98) independently are $(C_1-C_9)$-heteroaryl, which is linked via C or N and which is unsubstituted or substituted by 1 to 3 substituents selected from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl; or

R(3) and R(4) independently of one another are R($^{37}$)—$SO_{cm}$ or R(38)R(39)N—$SO_2$—;

cm is 1 or 2;

R(37) is $(C_1-C_8)$-alkyl, $(C_1-C_8)$-perfluoroalkyl, $(C_3-C_8)$-alkenyl or —$C_sH_{2s}$R(40);

s is zero, 1, 2, 3 or 4;

R(40) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(41)R(42);

R(41) and R(42) are H, $(C_1-C_4)$-alkyl or $(C_1-C_4)$-perfluoroalkyl;

R(38) is H, $(C_1-C_8)$-alkyl, $(C_1-C_8)$-perfluoroalkyl, $(C_3-C_8)$-alkenyl or —$C_wH_{2w}$—R(43);

w is zero, 1, 2, 3 or 4;

R(43) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(44)R(45);

R(44) and R(45) are H, $(C_1-C_4)$-alkyl or $(C_1-C_4)$-perfluoroalkyl;

R(39) is H, $(C_1-C_4)$-alkyl or $(C_1-C_4)$-perfluoroalkyl; or

R(38) and R(39) together are 4 or 5 methylene groups, of which one $CH_2$ group can be replaced by oxygen, S, NH, N—$CH_3$ or N-benzyl; or R(3) and R(4) independently of one another are R(46)X(1)—;

X(1) is oxygen, S, NR(47), (D=O)A—, NR(48)C=MN$^{(*)}$R(49)-,

M is oxygen or S;

A is oxygen or NR(50);

D is C or SO;

R(46) is $(C_1-C_8)$-alkyl, $(C_3-C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are H, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46); or

R(46) and R(47), or R(46) and R(48) together are 4 or 5 methylene groups, of which one $CH_2$ group can be replaced by oxygen, S, NH, N—$CH_3$ or N-benzl, where A and $N^{(*)}$ are bonded to the phenyl nucleus of the benzoylguanidine parent structure; or R(3) and R(4) independently of one another are —SR(64), —OR(65), —NHR(66), —NR(67)R(68), —CHR(69)R(70), —C(OH)R(54)R(55), —C≡CR(56), —CR(58)=CHR(57), —[CR(59)R(60)]$_u$—(CO)—[CR(61)R(62)]$_v$—R(63); R(64), R(65), R(66), R(67) and R(69) identically or differently are —$(CH_2)_y$(CHOH)$_z$—$(CH_2)_{aa}$—$(CH_{20}H)_t$—R(71) or —$(CH_2)_{ab}$—O—$(CH_2$—$CH_2O)_{ac}$—R(72), R(71) and R(72) are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen, $(C_1-C_6)$-alkyl; or R(69) and R(70), or R(54) and R(55) together with the carbon atom carrying them are a $(C_3-C_8)$-cycloalkyl;

R(63) is H, $(C_1-C_6)$-alkyl, $(C_3-C_8)$-cycloalkyl or —$C_eH_{2e}$—R(73);

e is zero, 1, 2, 3 or 4;

R(56), R(57) and R(73) independently are phenyl, which is unsubstituted or substituted by 1–3 substituents selected from the group consisting of F, Cl, $CF_3$, methyl, methoxy and NR(74)R(75);

R(74) and R(75) are H or $(C_1-C_4)$-alkyl; or

R(56), R(57) and R(73) independently are $(C_1-C_9)$-heteroaryl, which is unsubstituted or substitued as phenyl;

R(58), R(59), R(60), R(61) and R(62) are hydrogen or methyl, or

R(3) and R(4) independently of one another are R(76)—NH—$SO_2$—;

R(76) is R(77)R(78)N—(C=Y')—;

Y' is oxygen, S or N—R(79);

R(77) and R(78) identically or differently are H, $(C_1-C_8)$-alkyl, $(C_3-C_6)$-alkenyl, —$C_fH_{2f}$—R(80);

f is zero, 1, 2, 3 or 4;

R(80) is $(C_5-C_7)$-cycloalkyl or phenyl, which is unsubstituted or substituted by 1–3 substituents selected from the group consisting of F, Cl, CF$_3$, methoxy and (C$_1$–C$_4$)-alkyl; or R(77) and R(78) together are 4 or 5 methylene groups, of which one CH$_2$ group can be replaced by oxygen, S, NH, N—CH$_3$ or N-benzyl, R(79) is defined as R(77) or is amidine; or R(3) and R(4) independently of one another are NR(84)R(85);

R(84) and R(85) independently of one another are H, (C$_1$–C$_4$)-alkyl, or together are 4 or 5 methylene groups, of which one CH$_2$ group can be replaced by oxygen, S, NH, N—CH$_3$ or N-benzyl; or of which one or two CH$_2$ groups can be replaced by CH—C$_{dm}$H$_{2dm+1}$, and their pharmaceutically tolerable salts;
(HOE 94/F 123-EP-A 682 017, NZ 272 058)

y) bicyclic heteroaroylguanidines of the formula I

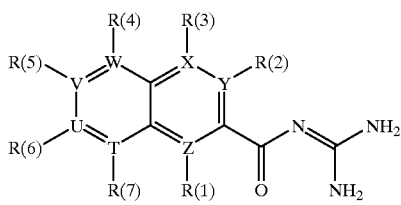

in which:

T, U, V, W, X, Y and Z independently of one another are nitrogen or carbon;
  but with the restriction that X and Z are not simultaneously nitrogen,
  and that T, U, V, W, X, Y and Z carry no substituents if they are nitrogen,
  and that no more than four of them are simultaneously nitrogen, R(1) and R(2) independently of one another are hydrogen, F, Cl, Br, I, (C$_1$–C$_3$)-alkyl, (C$_1$–C$_3$)-perfluoroalkyl, OR(8), NR(8)R(9) or C(=O)N=C(NH$_2$)$_2$;

R(8) and R(9) independently of one another are hydrogen or (C$_1$–C$_3$)-alkyl, or R(8) and R(9) together are 4 or 5 methylene groups, of which one CH$_2$ group can be replaced by oxygen, S, NH, N—CH$_3$ or N-benzyl;

R(3), R(4), R(5), R(6) and R(7) independently of one another are hydrogen, F, Cl, Br, I, —C≡N, X$_k$—(CH$_2$)$_p$—(C$_q$F$_{2q+1}$), R(10a)—SO$_{bm}$, R(10b)R(10c)N—CO, R(11)—CO— or R(12)R(13)N—SO$_2$—, where the perfluoroalkyl group is straight-chain or branched;

X is oxygen, S or NR(14);
  R(14) is H or (C$_1$–C$_3$)-alkyl;

bm is zero, 1 or 2;
p is zero, 1 or 2;
k is zero or 1;
q 1, 2, 3, 4, 5 or 6;

R(10a), R(10b), R(11) and R(12) independently of one another are (C$_1$–C$_8$)-alkyl, (C$_3$–C$_6$)-alkenyl, —C$_n$H$_{2n}$—R(15) or (C$_1$–C$_8$)-perfluoroalkyl;
n is zero, 1, 2, 3 or 4;

R(15) is (C$_3$–C$_7$)-cycloalkyl or phenyl, which is not substituted or is substituted by 1–3 substituents selected from the group consisting of F, Cl, CF$_3$, methyl, methoxy and NR(16)R(17);
  R(16) and R(17) are H or C$_1$–C$_4$-alkyl; or R(10b), R(11) and R(12) are hydrogen;

R(10c) and R(13) independently are hydrogen or (C$_1$–C$_4$)-alkyl; or

R(10b) and R(10c) and R(12) and R(3) together are 4 or 5 methylene groups, of which one CH$_2$ group can be replaced by oxygen, sulfur, NH, N—CH$_3$ or N-benzyl; or R(3), R(4), R(5), R(6) and R(7) independently of one another are (C$_1$–C$_8$)-alkyl, —C$_{al}$H$_{2al}$R(18) or (C$_3$–C$_8$)-alkenyl;
al is zero, 1 or 2;

R(18) is (C$_3$–C$_8$)-cycloalkyl, phenyl, biphenylyl or naphthyl, where
  the aromatics are not substituted or are substituted by 1–3 A substituents selected from the group consisting of F, Cl, CF$_3$, methyl, methoxy and NR(19a)R(19b);
  R(19a) and R(19b) are hydrogen, (C$_1$–C$_4$)-alkyl or (C$_1$–C$_4$)-perfluoroalkyl; or R(3), R(4), R(5), R(6) and R(7) independently of one another are (C$_1$–C$_9$)-heteroaryl, which is linked via C or N and which is unsubstituted or substituted by 1–3 substituents from the group consisting of F, Cl, CF$_3$, CH$_3$, methoxy, hydroxyl, amino, methylamino or dimethylamino; or R(3), R(4), R(5), R(6) and R(7) independently of one another are

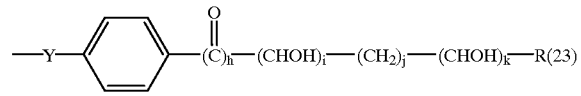

or

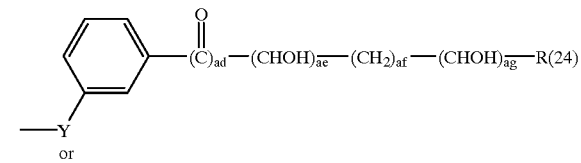

or

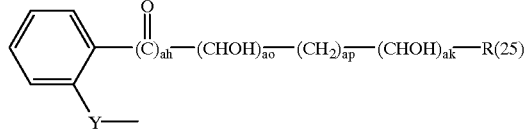

Y is oxygen, —S— or —NR(22)—;
h, ad, ah independently of one another are zero or 1;
i, j, k, ae, af, ag, ao, ap and ak independently of one another are zero, 1, 2, 3 or 4;
but where in each case
  h, i and k are not simultaneously zero,
  ad, ae and ag are not simultaneously zero, and
  ah, ao and ak are not simultaneously zero, R(23), R(24), R(25) and R(22) independently of one another are hydrogen or (C$_1$–C$_3$)-alkyl; or R(3), R(4), R(5), R(6) and R(7) a independently of one another are SR(29), —OR(30), —NR(31)R(32) or —CR(33)R(34)R(35);

R(29), R(30), R(31) and R(33) independently of one another are —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
a is zero, 1 or 2;

R(32), R(34) and R(35) independently of one another are defined as R(29) or are hydrogen, (C$_1$–C$_4$)-alkyl or (C$_1$–C$_4$)-perfluoroalkyl; or R(3), R(4), R(5), R(6) and R(7) independently of one another are

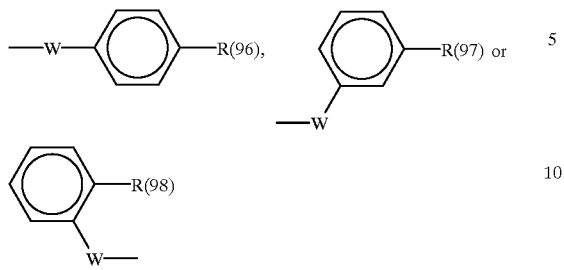

R(96), R(97) and R(98) independently of one another are $(C_1-C_9)$-heteroaryl, which is linked via C or N and which is unsubstitued or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl; or

R(3), R(4), R(5), R(6) and R(7) independently of one another are R(46)X(1)—;

X(1) is oxygen, S, NR(47), (D=O)A— or NR(48)C=MN$^{(*)}$R(49)—;

M is oxygen or sulfur;

A is oxygen or NR(50);

D is C or SO;

R(46) is $(C_1-C_8)$-alkyl, $(C_3-C_8)$-alkenyl, $(CH_2)_bC_dF_{2d+1}$ or $-C_xH_{2x}-$R(51);

b is zero or 1;

d is 1, 2, 3, 4, 5, 6 or 7;

x is zero, 1, 2, 3 or 4;

R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are hydrogen, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46); or

R(46) and R(47), or R(46) and R(48) together are 4 or 5 methylene groups, of which one $CH_2$ group can be replaced by oxygen, sulfur, NH, N—$CH_3$ or N-benzyl;

where A and N$^{(*)}$ are bonded to the phenyl nucleus of the heteroaroylguanidine parent structure; or R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$R(63);

R(64), R(65), R(66), R(67) and R(69) identically or differently are —$(CH_2)_y$—$(CHOH)_z$—$(CH_2)_{aa}$—$(CHOH)_t$—R(71) or —$(CH_2)_{ab}$—O—$(CH_2$—$CH_{20})_{ac}$—R(72);

R(71) and R(72) independently of one another are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen or $(C_1-C_6)$-alkyl; or R(69) and R(70), or R(54) and R(55) together with the carbon atom carrying them are a $(C_3-C_8)$-cycloalkyl;

R(63) is hydrogen, $(C_1-C_6)$-alkyl, $(C_3-C_8)$-cycloalkyl or —$C_eH_{2e}$—R(73);

e is zero, 1, 2, 3 or 4;

R(56), R(57) and R(73) independently are phenyl, which is unsubstituted or substituted by 1–3 substituents selected from the group consisting of F, Cl, $CF_3$, methyl, methoxy and NR(74)R(75);

R(74) and R(75) are hydrogen or $(C_1-C_4)$-alkyl; or

R(56), R(57) and R(73) independently are $(C_1-C_9)$-heteroaryl, which is unsubstituted or substituted as phenyl;

R(58), R(59), R(60), R(61) and R(62) are hydrogen or methyl; or

R(3), R(4), R(5), R(6) and R(7) independently of one another are R(76)—NH—$SO_2$—;

R(76) is R(77)R(78)N—(C=Y')—;

Y' is oxygen, S or N—R(79);

R(77) and R(78) identically or differently are hydrogen, $(C_1-C_9)$-alkyl, $(C_3-C_6)$-alkenyl or —$C_fH_{2f}$—R(80);

f is zero, 1, 2, 3 or 4;

R(80) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or R(77) and R(78) together are 4 or 5 methylene groups, of which one $CH_2$ group can be replaced by oxygen, sulfur, NH, N—$CH_3$ or N-benzyl;

R(79) is defined as R(77) or is amidine; or

R(3), R(4), R(5), R(6) and R(7) independently of one another are NR(84a)R(85), OR(84b), SR(84c) or —$C_nH_{2n}$—R(84d);

n is zero, 1, 2, 3 or 4;

R(84d) is $(C_3-C_7)$-cycloalkyl or phenyl, which is not substituted or is substituted by 1–3 substituents from the group consisting of F, Cl, $CF_3$, methyl, methoxy and NR(16)R(17);

R(16) and R(17) are hydrogen, or $C_1-C_4$-alkyl;

R(84a), R(84b), R(84c) and R(85) independently of one another are hydrogen, $(C_1-C_8)$-alkyl, $(C_1-C_8)$-perfluoroalkyl or $(CH_2)_{ax}$—R(84g);

ax is zero, 1, 2, 3 or 4;

R(84g) is $(C_3-C_7)$-cycloalkyl or phenyl, which is not substituted or is substituted by 1–3 substituents selected from the group consisting of F, Cl, $CF_3$, methyl, methoxy and NR(84u)R(84v);

R(84u) and R(84v) are hydrogen or $C_1-C_4$-alkyl; or

R(84a) and R(85) together are 4 or 5 methylene groups, of which one $CH_2$ group can be replaced by oxygen, sulfur, NH, N—$CH_3$ or N-benzyl, and their pharmaceutically tolerable salts;

(HOE 94/F 134-EP-A 686 627, NZ 272 103)

z) benzoylguanidines of the formula I

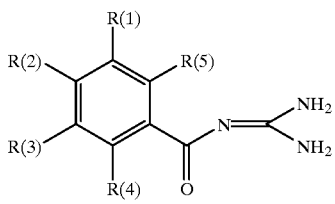

in which:
R(1) is R(6)—SO$_m$;
  m is zero, 1 or 2;
  R(6) is perfluoroalkyl having 1, 2, 3, 4, 5 or 6 carbon atoms, which is straight-chain or branched;
R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy; or
R(2) and R(3) independently of one another are pyrrol-1-yl, pyrrol-2-yl or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;
R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;
  R(7), R(8) and R(9) independently of one another are hydrogen or alkyl having 1, 2, 3 or 4 carbon atoms;
  n is zero or 1;
  o is zero, 1 or 2;
and their pharmacologically acceptable salts;
(HOE 94/F 168-EP-A 690 048, NZ 272 373)

ab) phenyl-substituted alkenylcarboxylic acid guanidides, carrying perfluoroalkyl groups, of the formula I

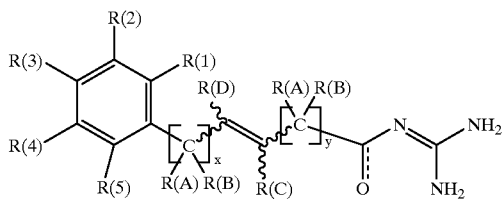

in which:
R(A) is hydrogen, F, Cl, Br, I, CN, OH, OR(6), (C$_1$–C$_8$)-alkyl, O$_r$(CH$_2$)$_a$C$_b$F$_{2b+1}$, (C$_3$–C$_8$)-cycloalkyl or NR(7)R(8);
  r is zero or 1;
  a is zero, 1, 2, 3 or 4;
  b is 1, 2, 3, 4, 5, 6, 7 or 8;
  R(6) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl;
    where the aromatics are not substituted or are substituted by 1–3 substituents from the group consisting of F, Cl, CF$_3$, methyl, methoxy and NR(9)R(10);
  R(9) and R(10) are H, (C$_1$–C$_4$)-alkyl or (C$_1$–C$_4$)-perfluoroalkyl;

R(7) and R(8) independently of one another are defined as R(6); or
R(7) and R(8) together are 4 or 5 methylene groups, of which one CH$_2$ group can be replaced by oxygen, sulfur, NH, N—CH$_3$ or N-benzyl;
R(B) independently is defined as R(A);
X is zero, 1 or 2;
Y is zero, 1 or 2;
R(C) is hydrogen, F, Cl, Br, I, CN, OR(12), (C$_1$–C$_8$)-alkyl, O$_p$(CH$_2$)$_f$C$_g$F$_{2g+1}$ or (C$_3$–C$_8$)-cycloalkyl;
  p is zero or 1;
  f is zero, 1, 2, 3 or 4;
  g is 1, 2, 3, 4, 5, 6, 7 or 8;
  R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl;
    where the aromatics phenyl or benzyl are not substituted or are substituted by 1–3 substituents from the group consisting of F, Cl, CF$_3$, methyl, methoxy and NR(13)R(14);
  R(13) and R(14) independently of one another are H, (C$_1$–C$_4$)-alkyl or (C$_1$–C$_4$)-perfluoroalkyl;
R(D) independently is defined as R(C),
R(1) is hydrogen, (C$_1$–C$_8$)-alkyl, —O$_t$(CH$_2$)$_d$C$_e$F$_{2e+1}$, (C$_3$–C$_8$)-cycloalkyl, F, Cl, Br, 1 or CN;
  t is zero or 1;
  d is zero, 1, 2, 3 or 4;
  e is 1, 2, 3, 4, 5, 6, 7 or 8;
R(2), R(3), R(4) and R(5) independently of one another are defined as R(1);
but with the condition that at least one of the substituents R(A), R(B), R(C), R(D), R(1), R(2), R(4) or R(5) is an O$_r$(CH$_2$)$_a$C$_b$F$_{2b+1}$, O$_p$(CH$_2$)$_f$C$_g$F$_{2g+1}$ or O$_t$(CH$_2$)$_d$C$_e$F$_{2e+1}$ group and R(3) is not an O$_t$(CH$_2$)$_d$C$_e$F$_{2e+1}$ group;
and their pharmaceutically tolerable salts;
(HOR 94/F 182-EP-A 690 048, NZ 272 449)

ac) ortho-amino-substituted benzoylguanidines of the formula I

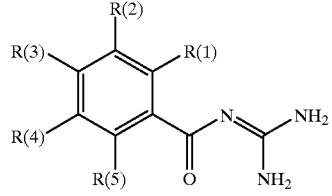

in which:
R(1) is NR(50)R(6),
  R(50) and R(6) independently of one another are hydrogen, (C$_1$–C$_8$)-alkyl or (C$_1$–C$_8$)-perfluoroalkyl;
R(2), R(3), R(4) and R(5) independently of one another are R(10)—SO$_a$—, R(11)R(12)N—CO—, R(13)—CO— or R(14)R(15)N—SO$_2$—;
  a is zero, 1 or 2,
  R(10), R(11), R(12), R(13), R(14) and R(15) independently of one another are (C$_1$–C$_8$)-alkyl, (C$_1$–C$_8$)-perfluoroalkyl, (C$_3$–C$_6$)-alkenyl or —C$_{ab}$H$_{2ab}$—R(16);
  ab is zero, 1, 2, 3 or 4;
  R(16) is (C$_3$–C$_7$)-cycloalkyl, phenyl, which is not substituted or is substituted by 1–3 substituents selected from the group consisting of F, Cl, CF$_3$, methyl, methoxy or NR(17)R(18);

R(17) and R(18) independently of one another are H, CF$_3$ or (C$_1$–C$_4$)-alkyl; or R(11), R(12), and also R(14) and R(15) together are 4 or 5 methylene groups, of which one CH$_2$ group can be replaced by oxygen, S, NH, N—CH$_3$ or N-benzyl; or R(11), R(12), R(14) and R(15) independently of one another are hydrogen; or R(2), R(3), R(4) and R(5) independently of one another are SR(21), —OR(22), —NR(23)R(24) or —CR(25)R(26)R(27);

R(21), R(22), R(23) and R(25) 4: independently of one another are —C$_b$H$_{2b}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

b is zero, 1 or 2;

R(24), R(26) and R(27) independently of one another are hydrogen, (C$_1$–C$_4$)-alkyl or (C$_1$–C$_4$)-perfluoroalkyl; or R(2), R(3), R(4) and R(5) independently of one another are hydrogen, F, Cl, Br, I, CN, —(Xa)$_{dg}$—C$_{da}$H$_{2da+1}$, —(X$_b$)$_{dh}$(CH$_2$)$_{db}$—CdeF$_{2de+1}$, (C$_3$–C$_8$)-alkenyl or —C$_{df}$H$_{2df}$R(30);

(Xa) is O, S or NR(33);

R(33) is H, (C$_1$–C$_4$)-alkyl or (C$_1$–C$_4$)-perfluoroalkyl;

dg is zero or 1;

(Xb) is O, S or NR(34);

R(34) is H, (C$_1$–C$_4$)-alkyl or (C$_1$–C$_4$)-perfluoroalkyl;

dh is zero or 1;

da is zero, 1, 2, 3, 4, 5, 6, 7, 8;

db is zero, 1, 2, 3, 4;

de is zero, 1, 2, 3, 4, 5, 6, 7;

df is zero, 1, 2, 3, 4;

R(30) is (C$_3$–C$_8$)-cycloalkyl, phenyl, biphenylyl or naphthyl, where
the aromatics phenyl, biphenylyl or naphthyl are not substituted or are substituted by 1–3 substituents selected from the group consisting of F, Cl, CF$_3$, methyl, methoxy and NR(31)R(32);

R(31) and R(32) are H, (C$_1$–C$_4$)-alkyl or (C$_1$–C$_4$)-perfluoroalkyl; or

R(2), R(3), R(4) and R(5) independently of one another are NR(40)R(41) or —(Xe)—(CH$_2$)$_{eb}$R(45);

R(40) and R(41) independently of one another are hydrogen, (C$_1$–C$_8$)-alkyl, (C$_1$–C$_8$)-perfluoroalkyl or (CH$_2$)$_e$—R(42);

e is zero, 1, 2, 3 or 4;

R(42) is (C$_3$–C$_7$)-cycloalkyl, phenyl, which is not substituted or is substituted by 1–3 substituents selected from the group consisting of F, Cl, CF$_3$, methyl, methoxy and NR(43)R(44);

R(43) and R(44) independently of one another are H, CF$_3$ or (C$_1$–C$_4$)-alkyl; or R(40) and R(41) together are 4 or 5 methylene groups, of which one CH$_2$ group can be replaced by oxygen, sulfur, NH, N—CH$_3$ or N-benzyl;

(Xe) is O, S or NR(47);

R(47) is H, (C$_1$–C$_4$)-alkyl or (C$_1$–C$_4$)-perfluoroalkyl;

eb is zero, 1, 2, 3 or 4;

R(45) is (C$_3$–C$_7$)-cycloalkyl, phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);

Xfa is CH$_2$, O, S or NR(48);

Xfb is O, S or NR(49);

ed is 1, 2, 3 or 4;

R(46) is H, (C$_1$–C$_4$)-alkyl or (C$_1$–C$_4$)-perfluoroalkyl;

R(48), R(49), R(50) and R(51) independently of one another are H or (C$_1$–C$_4$)-alkyl or (C$_1$–C$_4$)-perfluoroalkyl;

where R(3) and R(4), however, cannot be hydrogen, and their pharmaceutically tolerable salts;

HOE 94/F 265-NZ 272 946, EP-A 700 904)

ad) benzoylguanidines of the formula I in which:

one of the three substituents R(1), R(2) and R(3) is (C$_1$–C$_9$)-heteroaryl-N-oxide, which is linked via C or N and which is unsubstituted or substituted by 1–3 substituents selected from the group consisting of F, Cl, CF$_3$, CH$_3$, methoxy, hydroxyl, amino, methylamino and dimethylamino; or one of the three substituents R(1), R(2) and R(3) is —SR(10), —OR(10), —NR(10)R(11) or —CR(10)R(11)R(12);

R(10) is —C$_a$H$_{2a}$—(C$_1$–C$_9$)-heteroaryl-N-oxide, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(11) and R(12) independently of one another are defined as R(10), are hydrogen or (C$_1$–C$_4$)-alkyl;

and the other substituents R(1), R(2) and R(3) in each case independently of one another are (C$_1$–C$_8$)-alkyl, (C$_2$–C$_8$)-alkenyl or —C$_m$H$_{2m}$R(14);

m is zero, 1 or 2;

R(14) is (C$_3$–C$_8$)-cycloalkyl or phenyl, which is not substituted or is substituted by 1–3 substituents selected from the group consisting of F, Cl, CF$_3$, methyl, methoxy and NR(15)R(16), R(15) and R(16) are hydrogen or CH$_3$; or the other substituents R(1), R(2) and R(3) in each case independently of one another are hydrogen, F, Cl, Br, I, —C≡N, X—(CH$_2$)$_p$—(C$_q$F$_{2q+1}$), R(22)—SO$_u$, R(23)R(24)N—CO, R(25)—CO— or R(26)R(27)N—SO$_2$—, where the perfluoroalkyl group is straight—chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are (C$_1$–C$_8$)-alkyl, (C$_2$–C$_6$)-alkenyl, —C$_n$H$_{2n}$—R(29) or CF$_3$;

n is zero, 1, 2, 3 or 4;

R(28) is hydrogen or (C$_1$–C$_3$)-alkyl;

R(29) is (C$_3$–C$_7$)-cycloalkyl or phenyl; which is not substituted or is substituted by 1–3 substituents selected from the group consisting of F, Cl, $CF_3$, methyl, methoxy and NR(30)R(31);
R(30) and R(31) are hydrogen or $C_1$–$C_4$-alkyl, or
R(23), R(25) and R(26) are also hydrogen;
R(24) and R(27) independently of one another are hydrogen or ($C_1$–$C_4$)-alkyl; or
R(23) and R(24), and also R(26) and R(27) together are 4 or 5 methylene groups, of which one $CH_2$ group can be replaced by oxygen, S, NH, N—$CH_3$ or N-benzyl; or the other substituents R(1), R(2) and R(3) in each case independently of one another are OR(35) or NR(35)R(36);
R(35) and R(36) independently of one another are hydrogen or ($C_1$–$C_6$)-alkyl; or
R(35) and R(36) together are 4–7 methylene groups, of which one $CH_2$ group can be replaced by oxygen, S, NH, N—$CH_3$ or N-benzyl,
R(4) and R(5) independently of one another are hydrogen, ($C_1$–$C_4$)-alkyl, F, Cl, —OR(32), —NR(33)R(34) or $C_rF_{2r+1}$;
R(32), R(33) and R(34) independently of one another are hydrogen or ($C_1$–$C_3$)-alkyl;
r is 1, 2, 3 or 4;
and their pharmaceutically tolerable salts;
(HOE 94/F 266-EP-A 702 001, NZ 272 948)
ad) benzoylguanidines of the formula I

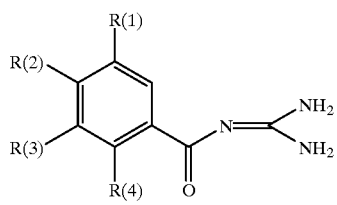

in which:
R(1) is hydrogen, F, Cl, Br, I, CN, $NO_2$, OH, ($C_1$–$C_8$)-alkyl, ($C_3$–$C_8$)-cycloalkyl, $O_a$—$(CH_2)_b$—$(CF_2)_c$—$CF_3$;
a is zero or 1;
b is zero, 1 or 2;
c is zero, 1, 2 or 3; or
R(1) is R(5)—$SO_m$ or R(6)R(7)N—$SO_2$—;
m is zero, 1 or 2;
R(5) and R(6) independently of one another are ($C_1$–$C_8$)-alkyl, ($C_3$–$C_6$)-alkenyl, $CF_3$ or—$C_nH_{2n}$—R(8);
n is zero, 1, 2, 3 or 4;
R(7) is hydrogen or ($C_1$–$C_4$)-alkyl;
R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);
R(9) and R(10) independently of one another are hydrogen or ($C_1$–$C_4$)-alkyl; or
R(6) is H;
or R(6) and R(7) together are 4 or 5 methylene groups, of which one $CH_2$ group can be replaced by oxygen, S, NH, N—$CH_3$ or N-benzyl, or
R(1) is —SR(11), —OR(11) or —CR(11)R(12)R(13);
R(11) is —$C_pH_{2p}$—($C_3$–$C_8$)-cycloalkyl, —($C_1$–$C_9$)-heteroaryl or phenyl,
where the aromatic systems are unsubstituted or substituted by 1–3 substituents selected from the group consisting of F, Cl, $CF_3$, $CH_3$, methoxy, hydroxyl, amino, methylamino and dimethylamino;
R(12), R(13) independently of one another are defined as R(11) or are hydrogen or ($C_1$–$C_4$)-alkyl;
p is zero, 1 or 2; or
R(1) is phenyl, naphthyl, biphenylyl or ($C_1$–$C_9$)-heteroaryl, the latter linked via C or N, which are unsubstituted or substituted by 1–3 substituents selected from the group consisting of F, Cl, $CF_3$, $CH_3$, methoxy, hydroxyl, amino, methylamino and dimethylamino;
R(2) is —$CF_2$R(14), —CF[R(15)][R(16)], —CF[($CF_2$)$_q$—$CF_3$][R(15)], —C[($CF_2$)$_r$—$CF_3$]=CR(15)R(16);
R(14) is ($C_1$–$C_4$)-alkyl or ($C_3$–$C_6$)-cycloalkyl;
R(15) and R(16) independently of one another are hydrogen or ($C_1$–$C_4$)-alkyl;
q is zero, 1 or 2;
r is zero, 1 or 2;
R(3) is defined as R(1);
R(4) is hydrogen, ($C_1$–$C_3$)-alkyl, F, Cl, Br, I, CN, —$(CH_2)_s$—$(CF_2)_t$—$CF_3$;
s is zero or 1;
t is zero, 1 or 2;
and their pharmaceutically tolerable salts;
(HOE 94/F 267-EP-A 700 899, NZ 272 947)
ae) benzoylguanidines of the formula I

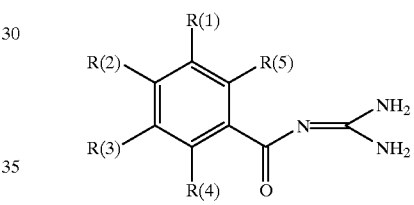

I in which:
one of the three substituents R(1), R(2) and R(3) is
—Y-4—[($CH_2$)$_k$—CHR(7)—(C=O)R(8)]-phenyl,
—Y-3—[($CH_2$)$_k$—CHR(7)—(C=O)R(8)]-phenyl or
—Y-2—[($CH_2$)$_k$—CHR(7)—(C=O)R(8)]-phenyl,
where the phenyl in each case is unsubstituted or substituted by 1–2 substituents from the group F, Cl, —$CF_3$, methyl, hydroxyl, methoxy, or —NR(37)R(38);
R(37) and R(38) independently of one another are hydrogen or —$CH_3$;
Y is a bond, oxygen, —S— or —NR(9);
R(9) is hydrogen or —($C_1$–$C_4$)-alkyl;
R(7) is —OR(10) or —NR(10)R(11);
R(10) and R(11) independently of one another are hydrogen, —($C_1$–$C_8$)-alkyl, —($C_1$–$C_8$)-alkanoyl, —($C_1$–$C_8$)-alkoxycarbonyl, benzyl, benzyloxycarbonyl; or
R(10) is trityl;
R(8) is —OR(12) or —NR(12)R(13);
R(12) and R(13) independently of one another are hydrogen, —($C_1$–$C_8$)-alkyl or benzyl;
k is zero, 1, 2, 3 or 4;
and the other radicals R(1), R(2) and R(3) in each case independently of one another are —($C_1$–$C_8$)-alkyl, —($C_2$–$C_8$)-alkenyl or —$(CH_2)_m$R(14);
m is zero, 1 or 2;
R(14) is —($C_3$–$C_8$)-cycloalkyl or phenyl, which is not substituted or is substituted by 1–3 substituents selected from the group consisting of F, Cl, —$CF_3$, methyl, methoxy and —NR(15)R(16);

R(15) and R(16) are hydrogen or —CH$_3$; or the other radicals R(1), R(2) and R(3) in each case independently of one another are R(18)R(19)N—(C=Y')—NH—SO$_2$—;
Y' is oxygen, —S— or —N—R(20);
R(18) and R(19) independently of one another are hydrogen, —(C$_1$–C$_8$)-alkyl, —(C$_3$–C$_6$)-alkenyl or —(CH$_2$)$_t$—R(21);
t is zero, 1, 2, 3 or 4;
R(21) is —(C$_5$–C$_7$)-cycloalkyl or phenyl, which is unsubstituted or substituted by 1–3 substituents selected from the group consisting of F, Cl, —CF$_3$, methoxy and —(C$_1$–C$_4$)-alkyl; or
R(18) and R(19) together are 4 or 5 methylene groups, of which one CH$_2$ group can be replaced by oxygen, —S—, —NH—, —N—CH$_3$ or —N-benzyl;
R(20) is defined as R(18) or is amidine; or the other radicals R(1), R(2) and R(3) in each case independently of one another are hydrogen, F, Cl, Br, I, —C≡N, X—(CH$_2$)$_p$—(C$_q$F$_{2q+1}$), R(22)—SO$_u$—, R(23)R(24)N—CO—, R(25)—CO— or R(26)R(27)N—SO$_2$—, where the perfluoroalkyl group is straight-chain or branched;
X is a bond, oxygen, —S— or —NR(28);
u is zero, 1 or 2;
p is zero, 1 or 2;
q is 1, 2, 3, 4, 5 or 6;
R(22), R(23), R(25) and R(26) independently of one another are —(C$_1$–C$_8$)-alkyl, —(C$_3$–C$_6$)-alkenyl, —(CH$_2$)$_n$—R(29) or —CF$_3$;
n is zero, 1, 2, 3 or 4;
R(28) is hydrogen or —(C$_1$–C$_3$)-alkyl;
R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);
R(30) and R(31) are hydrogen or —(C$_1$–C$_4$)-alkyl; or
R(23), R(25) and R(26) are hydrogen;
R(24) and R(27) independently of one another are hydrogen or —(C$_1$–C$_4$)-alkyl; or
R(23) and R(24), and also R(26) and R(27) together are 4 or 5 methylene groups, of which one CH$_2$ group can be replaced by oxygen, —S—, —NH—, —N—CH$_3$ or —N-benzyl; or the other radicals R(1), R(2) and R(3) in each case independently of one another are —OR(35) or —NR(35)R(36);
R(35) and R(36) independently of one another are hydrogen or —(C$_1$–C$_6$)-alkyl; or
R(35) and R(36) together are 4–7 methylene groups, of which one CH$_2$ group can be replaced by oxygen, —S—, —NH—, —N—CH$_3$ or —N-benzyl;
R(4) and R(5) independently of one another are hydrogen, —(C$_1$–C$_4$)-alkyl, F, Cl, —OR(32), —NR(33)R(34) or —C$_r$F$_{2r+1}$;
R(32), R(33) and R(34) independently of one another are hydrogen or —(C$_1$–C$_3$)-alkyl;
r is 1, 2, 3 or 4;
and their pharmaceutically tolerable salts;
(HOE 94/F 352-EP-A 713 684, NZ 280 517)

af) benzoylguanidines of the formula I in which:
R(1) is R(6)—CO or R(7)R(8)N—CO;
R(6) is (C$_1$–C$_8$)-alkyl, (C$_1$–C$_8$)-perfluoroalkyl, (C$_3$–C$_8$)-alkenyl or —C$_n$H$_{2n}$—R(9),
n is zero, 1, 2, 3 or 4;
R(9) is (C$_3$–C$_9$)-cycloalkyl, phenyl, biphenylyl or naphthyl,
where the aromatics are not substituted or are substituted by 1–3 substituents selected from the group consisting of F, Cl, CF$_3$, methyl, methoxy and NR(10)R(11),
R(10) and R(11) are H, (C$_1$–C$_4$)-alkyl or (C$_1$–C$_4$)-perfluoroalkyl;
R(7) is H, (C$_1$–C$_8$)-alkyl, (C$_1$–C$_8$)-perfluoroalkyl, (C$_3$–C$_8$)-alkenyl or —C$_n$H$_{2n}$—R(1 2);
n is zero, 1, 2, 3 or 4;
R(12) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl;
R(8) is H, (C$_1$–C$_4$)-alkyl or (C$_1$–C$_4$)-perfluoroalkyl; or
R(7) and R(8) together are 4 or 5 methylene groups, of which one CH$_2$ group can be replaced by oxygen, S, NH, N—CH$_3$ or N-benzyl;
R(2) is defined as R(1), or is H, OH, F, Cl, Br, I, CN, NO$_2$, (C$_1$–C$_8$)-alkyl, (C$_1$–C$_9$)-perfluoroalkyl, (C$_3$–C$_8$)-alkenyl or —C$_n$H$_{2n}$R(15);
n is zero, 1, 2, 3 or 4;
R(15) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(16)R(17);
R(16) and R(17) are H, (C$_1$–C$_4$)-alkyl or (C$_1$–C$_4$)-perfluoroalkyl; or
R(2) is (C$_1$–C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino; or
R(2) is SR(18), —OR(18), —NR(18)R(19) or —CR(18)R(19)R(20);
R(18) is —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino, dimethylamino;
a is zero, 1 or 2;
R(19) and R(20) independently of one another are defined as R(18) or are hydrogen, (C$_1$–C$_4$)-alkyl or (C$_1$–C$_4$)-perfluoroalkyl; or R(2) is R(21)—SO$_m$ or R(22)R(23)N—SO$_2$—;
  m is 1 or 2;
  R(21) is (C$_1$–C$_8$)-alkyl, (C$_1$–C$_8$)-perfluoroalkyl, (C$_3$–C$_8$)-alkenyl or —C$_n$H$_{2n}$—R(24);
  n is zero, 1, 2, 3 or 4;
    R(24) is (C$_3$–C$_8$)-cycloalkyl, phenyl, biphenylyl or naphthyl,
      where the aromatics are not substituted or are substituted by 1–3 substituents selected from the group consisting of F, Cl, CF$_3$, methyl, methoxy and NR(27)R(28);
        R(27) and R(28) are H, (C$_1$–C$_4$)-alkyl or (C$_1$–C$_4$)- perfluoroalkyl;
  R(22) is H, (C$_1$–C$_9$)-alkyl, (C$_1$–C$_8$)-perfluoroalkyl, (C$_3$–C$_8$)-alkenyl or —C$_n$H$_{2n}$—R(29);
  n is zero, 1, 2, 3 or 4;
    R(29) is (C$_3$–C$_8$)-cycloalkyl, phenyl, biphenylyl or naphthyl,
      where the aromatics are not substituted or are substituted by 1–3 substituents selected from the group consisting of F, Cl, CF$_3$, methyl, methoxy and NR(30)R(31);
        R(30) and R(31) are H, (C$_1$–C$_4$)-alkyl or (C$_1$–C$_4$)-perfluoroalkyl;
  R(23) is hydrogen, (C$_1$–C$_4$)-alkyl or (C$_1$–C$_4$)-perfluoroalkyl; or
  R(22) and R(23) together are 4 or 5 methylene groups, of which one CH$_2$ group can be replaced by oxygen, S, NH, N—CH$_3$ or N-benzyl; or
R(2) is R(33)X—;
  X is oxygen, S, NR(34), (D=O)A— or NR(34)C=MN$^{(*)}$R(35)—;
  M is oxygen or S;
  A is oxygen or NR(34);
  D is C or SO;
    R(33) is (C$_1$–C$_8$)-alkyl, (C$_3$–C$_8$)-alkenyl, (CH$_2$)$_b$C$_d$F$_{2d+1}$ or —C$_n$H$_{2n}$—R(36);
    b is zero or 1;
    d is 1, 2, 3, 4, 5, 6 or 7;
    n is zero, 1, 2, 3, or 4;
      R(36) is (C$_3$–C$_8$)-cycloalkyl, phenyl, biphenylyl or naphthyl,
        where the aromatics are not substituted or are substituted by 1–3 substituents selected from the group consisting of F, Cl, CF$_3$, methyl, methoxy and NR(37)R(38);
          R(37) and R(38) are H, (C$_1$–C$_4$)-alkyl or (C$_1$–C$_4$)-perfluoroalkyl;
    R(34) is hydrogen, (C$_1$–C$_4$)-alkyl or (C$_1$–C$_4$)-perfluoroalkyl;
    R(35) is defined as R(33); or
    R(33) and R(34) together are 4 or 5 methylene groups, of which one CH$_2$ group can be replaced by oxygen, S, NH, N—CH$_3$ or N-benzyl;
  where A and N$^{(*)}$ are bonded to the phenyl nucleus of the benzoylguanidine parent structure; or
R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);
  R(40) and R(41) independently of one another are —(CH$_2$)$_p$—(CHOH)$_q$—((H$_2$)$_r$—(CHOH)$_t$—R(51) or —(CH$_2$)$_p$—O—(CH$_2$—CH$_2$O)$_q$—R(51); R(51) is hydrogen or methyl;
  u is 1, 2, 3 or 4;
  v is zero, 1, 2, 3 or 4;
  p, q and r independently of one another are zero, 1, 2, 3 or 4;
  t is 1, 2, 3 or 4;
  R(42) and R(43) independently of one another are hydrogen or (C$_1$–C$_6$)-alkyl; or
  R(42) and R(43) together with the carbon atom carrying them are a (C$_3$–C$_8$)-cycloalkyl;
  R(44) is hydrogen, (C$_1$–C$_6$)-alkyl, (C$_3$–C$_8$)-cycloalkyl, —C$_e$H$_{2e}$—R(45);
  e is zero, 1, 2, 3 or 4;
  R(45) is phenyl, which is unsubstituted or substituted by 1–3 substituents selected from the group consisting of F, Cl, CF$_3$, methyl, methoxy and NR(52)R(53);
    R(52) and R(53) are H or (C$_1$–C$_4$)-alkyl; or
  R(45) is (C$_1$–C$_9$)-heteroaryl, which is unsubstituted or substituted as phenyl; or
  R(45) is (C$_1$–C$_6$)-alkyl, which is unsubstituted or substituted by 1–3 OH;
  R(46), R(47), R(48), R(49) and R(50) independently of one another are hydrogen or methyl; or
R(2) is R(55)—NH—SO$_2$—;
  R(55) is R(56)R(57)N—(C=Y)—;
  Y is oxygen, S or N—R(58);
    R(56) and R(57) independently of one another are hydrogen, (C$_1$–C$_8$)-alkyl, (C$_3$–C$_6$)-alkenyl or —C$_f$H$_{2f}$—R(59);
    f is zero, 1, 2, 3 or 4;
      R(59) is (C$_5$–C$_7$)-cycloalkyl, phenyl, which is unsubstituted or substituted by 1–3 substituents selected from the group consisting of F, Cl, CF$_3$, methoxy and (C$_1$–C$_4$)-alkyl; or
    R(56) and R(57) together are 4 or 5 methylene groups, of which one CH$_2$ group can be replaced by oxygen, S, NH, N—CH$_3$ or N-benzyl;
    (in R(58) is defined as R(56) or is amidine;
  R(3), R(4) and R(5) are independently of one another defined as R(1) or R(2), but where at least one of the substituents R(2), R(3), R(4) and R(5) must be OH;
and their pharmaceutically tolerable salts;
(HOE 95/F 007 K-EP-A 723 956, NZ 280 887)
ag) benzoylguanidines of the formula I

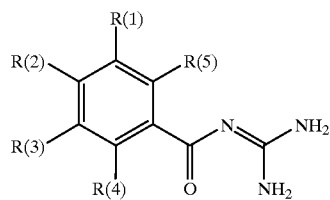

I in which:
one of the three substituents R(1), R(2) and R(3) is R(6)—A—B—D—;
R(6) is a basic protonatable radical, i.e. an amino group —NR(7)R(8), an amidino group R(7)R(8)N—C[=N—R(9)]— or a guanidino group

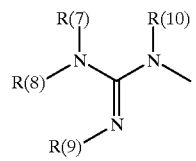

R(7), R(8), R(9) and R(10) independently of one another are hydrogen or alkyl having 1, 2, 3 or 4 carbon atoms; or R(7) and R(8) together are $C_aH_{2a}$;
a is 4, 5, 6 or 7;
where if a =5, 6 or 7 a methylene group of the group $C_aH_{2a}$ can be replaced by a heteroatom group O, $SO_m$ or NR(11), or
R(8) and R(9) or R(9) and R(10) or R(7) and R(10) are a group $C_aH_{2a}$;
a is 2, 3, 4 or 5;
where if a=3, 4 or 5 a methylene group of the group $C_aH_{2a}$ can be replaced by a heteroatom group O, $SO_m$ or NR(11);
m is zero, 1 or 2;
R(11) is hydrogen or methyl; or
R(6) is a basic heteroaromatic ring system having 1–9 carbon atoms;
A is $C_bH_{2b}$;
b is 1, 2, 3, 4, 5, 6, 7, 8, 9 or 10;
where in the group $C_bH_{2b}$, one or two methylene groups can be replaced by one of the groupings selected from the group consisting of —O—, —Co—, —CH[OR(20)]—, —$SO_m$—, —NR(20)—, —NR(20)—CO—, —NR(20)—CO—NH—, —NR(20)—CO—NH—$SO_2$—

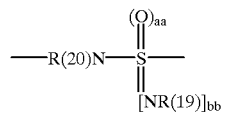

and —$SO_{aa}$[NR(19)]$_{bb}$—;
and where in the group $C_bH_{2b}$ a methylene group can be replaced by —CH—R(99), where R(99) together with R(7) forms a pyrrolidine or piperidine ring;
aa is 1 or 2;
bb is 0 or 1;
aa+bb=2;
R(19) is hydrogen or alkyl having 1, 2, 3 or 4 carbon a9a atoms;
R(20) is hydrogen or methyl;
B is a phenylene or naphthylene radical

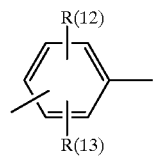 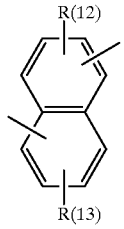

R(12) and R(13) independently of one another are hydrogen, methyl, F, Cl, Br, I, $CF_3$ or —$SO_w$—R(14);
R(14) is methyl or NR(15)R(16);
R(15) and R(16) independently of one another are hydrogen or alkyl having 1, 2, 3 or 4 carbon atoms;
w is zero, 1 or 2;
D is —$C_dH_{2d}$—$X_f$—;
d is zero, 1, 2, 3 or 4;
x is —O—, —CO—, —CH[OR(21)]—, —$SO_m$— or —NR(21)—;

f is zero or 1;
R(21) is hydrogen or methyl;
m is zero, 1 or 2;
and the other substituents R(1) and R(2) and R(3) in each case independently of one another are hydrogen, F, Cl, Br, I, —CN, —($C_1$-$C_8$)-alkyl, —($C_2$-$C_8$)-alkenyl, —NR(35)R(36) or R(17)—$C_gH_{2g}$—$Z_h$—;
g is zero, 1, 2, 3 or 4;
h is zero or 1;
R(35) and R(36) independently of one another are hydrogen or alkyl having 1, 2, 3, 4, 5 or 6 carbon atoms; or
R(35) and R(36) together are 4–7 methylene groups, of which one $CH_2$ group can be replaced by oxygen, —S—, —NH—, —$NCH_3$ or —N-benzyl;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
R(17) is hydrogen, cycloalkyl having 3, 5 or 6 carbon atoms or $C_kF_{2k+1}$—;
k is 1, 2 or 3, or
R(17) is pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —$CF_3$, methyl and methoxy; or
R(17) is —($C_3$-$C_8$)-cycloalkyl or phenyl, which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;
R(37) and R(38) are hydrogen or —$CH_3$;
R(4) and R(5) independently of one another are hydrogen, alkyl having 1, 2, 3 or 4 carbon atoms, F, Cl, —OR(32), —NR(33)R(34) or —$C_rF_{2r+1}$;
R(32), R(33) and R(34) independently of one another are hydrogen or alkyl having 1, 2, or 3 carbon atoms;
r is 1, 2, 3 or 4;
and their pharmacologically tolerable salts;
(HOE 95/F 072-EP-A 738 712, NZ 286 380)
ah) indenoylguanidines of the formula I

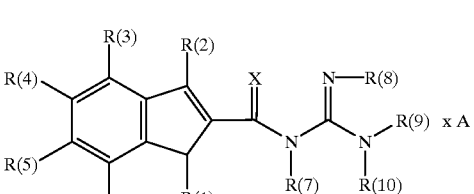

I in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)-alkyl having 1, 2, 3 or 4 carbon atoms or $C_mH_{2m}$—NR(12)R(13);
R(12) and R(13) independently of one another are hydrogen or alkyl having 1, 2, 3 or 4 carbon atoms;
m is zero, 1, 2, 3 or 4;
NH—C(=O)—$NH_2$, C(=O)—O-alkyl having 1, 2, 3 or 4 carbon atoms, C(=O)—$NH_2$, C(=O)—NH-alkyl having 1, 2, 3 or 4 carbon atoms, C(=O)—N (alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, $C_1$–$C_4$-alkyl-substituted aryl, $C_1$–$C_4$-alkylheteroaryl, $C_1$–$C_4$-alkenylheteroaryl, aminoalkylaryl having 1, 2, 3 or 4 carbon atoms in the alkyl group, substituted aryl, heteroaryl and substituted heteroaryl;

R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—$C_1$–$C_4$-alkylaryl, O—C(=O)—NH—$C_1$–$C_4$-alkyl, O—C(=O)—N($C_1$–$C_4$-alkyl)$_2$, NO$_2$, CN, CF$_3$, NH$_2$, NH—C(=O)—$C_1$–$C_4$-alkyl, NH—C(=O)—NH$_2$, COOH, C(=O)—O—$C_1$–$C_4$-alkyl, C(=O)—NH$_2$, C(=O)—NH—$C_1$–$C_4$-alkyl, C(=O)—N($C_1$–$C_4$-alkyl)$_2$, $C_1$–$C_4$—COOH, $C_1$–$C_4$-alkyl—C(=O)—O—$C_1$–$C_4$-alkyl, SO$_3$H, SO$_2$—alkyl, SO$_2$—alkylaryl, SO$_2$—N-(alkyl)$_2$, SO$_2$—N(alkyl)(alkylaryl), C(=O)—R(11), $C_1$–$C_{10}$-alkyl-C(=O)—R(11), $C_2$–$C_{10}$-alkenyl—C(=O)—R(11), $C_2$–$C_{10}$-alkynyl—C(=O)—R(11), NH—C(=O)—$C_1$–$C_{10}$-alkyl—C(=O)—R(11), O—$C_1$–$C_{11}$-alkyl—C(=O)—R(11);

R(11) is $C_1$–$C_4$-alkyl, $C_1$–$C_4$-alkynyl, aryl, substituted aryl, NH$_2$, NH—$C_1$–$C_4$-alkyl, N—($C_1$–$C_4$-alkyl)$_2$, SO$_3$H, SO$_2$—alkyl, SO$_2$—alkylaryl, SO$_2$—N-(alkyl)$_2$, SO$_2$—N(alkyl)(alkylaryl);

x is O, S or NH;

R(7), R(8), R(9) and R(10) independently of one another are hydrogen, alkyl, cycloalkyl, aryl, alkylaryl; or R(8) and R(9) together are part of a 5-, 6- or 7-membered heterocyclic ring;

A is absent or is a nontoxic organic or inorganic acid;

(HOE 95/F 109-EP 748 795, NZ 286 583)

ai) benzyloxycarbonylguanidines of the formula I

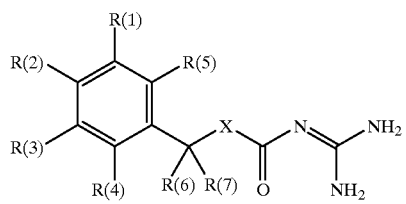

I in which:

R(1), R(2) and R(3) independently of one another are —Y—[4-R(8)-phenyl], —Y—[3—R(8)-phenyl] or —Y—[2-R(8)-phenyl], where the phenyl is in each case unsubstituted or substituted by 1–2 substituents from the group consisting of F, Cl, —CF$_3$, methyl, hydroxyl, methoxy and —NR(96)R(97);

R(96) and R(97) independently of one another are hydrogen or —CH$_3$;

Y is a bond, CH$_2$, oxygen, —S— or —NR(9);

R(9) is hydrogen or alkyl having 1, 2, 3 or 4 carbon atoms;

R(8) is SO$_a$[NR(98)]$_b$NR(99)R(10);

a is 1 or 2;

b is 0 or 1;

a+b=2;

R(98), R(99) and R(10) independently of one another are hydrogen, —($C_1$–$C_8$)-alkyl, benzyl, —($C_2$–$C_8$)-alkylene-NR(11)R(12), ($C_2$–$C_9$)-alkylene-NR(13)—($C_2$–$C_8$)-alkylene-NR(37)R(38) or (CO—$C_8$)-alkylene-CR(39)R(40)CR(41)R(42)(CO—$C_8$)-alkylene—NR(43)R(44);

R(11), R(12), R(13), R(37), R(38), R(43) and R(44) independently of one another are hydrogen, —($C_1$–$C_8$)-alkyl or benzyl;

R(39), R(40), R(41) and R(42) independently of one another are hydrogen, —($C_1$–$C_8$)-alkyl or —($C_0$–$C_3$)-alkylenephenyl, where the phenyl is not substituted or is substituted by 1–3 substituents selected from the group consisting of F, Cl, —CF$_3$, methyl and methoxy; or R(99) and R(10) together are 4–6 methylene groups, of which one CH$_2$ group can be replaced by oxygen, —S—, —NH—, —N—CH$_3$ or —N-benzyl; or R(8) is SO$_a$[NR(98))$_b$NR(95)—C[=N—R(94)]—NR(93)R(92);

R(92), R(93), R(94) and R(95) independently of one another are hydrogen or alkyl having 1, 2, 3 or 4 carbon atoms; or R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —CF$_3$, methyl, methoxy; or R(1), R(2) and R(3) independently of one another are hydrogen, —($C_1$–$C_9$)-alkyl, —($C_2$–$C_8$)-alkenyl or —(CH$_2$)$_m$R(14);

m is zero, 1 or 2;

R(14) is —($C_3$–$C_9$)-cycloalkyl or phenyl, which is not substituted or is substituted by 1–3 substituents selected from the group consisting of F and Cl, —CF$_3$, methyl, methoxy and —NR(15)R(16);

R(15) and R(16) are hydrogen or —CH$_3$; or

R(1), R(2) and R(3) independently of one another are —Q4—[(CH$_2$)$_k$—CHR(17)—(C=O)R(20)]-phenyl, —Q-3—(CH$_2$)$_k$—CHR(17)—(C=O)R(20)]-phenyl or —Q-2—[(CH$_2$)$_k$—CHR(17)—(C=O)R(20)1-phenyl, where the phenyl in each case is unsubstituted or substituted by 1–2 substituents from the group F, Cl, —CF$_3$, methyl, hydroxyl, methoxy and —NR(35)R(36);

R(35) and R(36) independently of one another are hydrogen or —CH$_3$;

Q is a bond, oxygen, —S— or —NR(18);

R(18) is hydrogen or —($C_1$–$C_4$)-alkyl;

R(17) is —OR(21) or —NR(21)R(22);

R(21) and R(22) independently of one another are hydrogen, —($C_1$–$C_8$)- alkyl, —($C_1$–$C_8$)-alkanoyl, —($C_1$–$C_8$)-alkoxycarbonyl, benzyl, benzyloxycarbonyl; or R(21) is trityl;

R(20) is —OR(23) or —NR(23)R(24);

R(23), R(24) independently of one another are hydrogen, —($C_1$–$C_8$)-alkyl or benzyl;

k is zero, 1, 2, 3 or 4; or

R(1), R(2) and R(3) independently of one another are ($C_1$–$C_9$)-heteroaryl, which is linked via C or N and which is unsubstituted or substituted by 1–3 substituents from the group F, Cl, $CF_3$, $CH_3$, methoxy, hydroxyl, amino, methylamino and dimethylamino; or R(1), R(2) and R(3) are —SR(25), —OR(25), —NR(25)R(26), —CR(25)R(26)R(27);
  R(25) is —$C_fH_{2f}$—($C_1$–$C_9$)-heteroaryl, which is unsubstituted or substituted by 1–3 substituents from the group F, Cl, $CF_3$, $CH_3$, methoxy, hydroxyl, amino, methylamino and dimethylamino;
  f is zero, 1 or 2;
  R(26) and R(27) independently of one another are defined as R(25) or are hydrogen or ($C_1$–$C_4$)-alkyl, or R(1), R(2) and R(3) independently of one another are ($C_1$–$C_9$)-heteroaryl—N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(1), R(2) and R(3) independently of one another are —SR(28), —OR(28), —NR(28)R(29) or —CR(28)R(29)R(30);
  R(28) is —$C_gH_{2g}$—($C_1$–$C_9$)-heteroaryl—N-oxide, which is unsubstituted or substituted by 1–3 substituents selected from the group consisting of F, Cl, $CF_3$, $CH_3$, methoxy, hydroxyl, amino, methylamino and dimethylamino;
  g is zero, 1 or 2;
  R(29), R(30) independently of one another are defined as R(28), hydrogen or ($C_1$–$C_4$)-alkyl; or R(1), R(2) and R(3) independently of one another are hydrogen, F, Cl, Br, I, —C≡N, T—$(CH_2)_h$—$(C_iF_{2i+l})$, R(31)$SO_l$—, R(32)R(33)N—CO—, R(34)—CO— or R(45)R(46)N—$SO_2$, where the perfluoroalkyl group is straight-chain or branched;
  T is a bond, oxygen, —S— or —NR(47);
  l is zero, 1 or 2;
  h is zero, 1 or 2;
  i is 1, 2, 3, 4, 5 or 6;
  R(31), R(32), R(34) and R(45) independently of one another are —($C_1$–$C_8$)-alkyl, —($C_3$–$C_6$)-alkenyl, $(CH_2)_nR(48)$ or —$CF_3$;
  n is zero, 1, 2, 3 or 4;
  R(47) is hydrogen or alkyl with 1, 2 or 3 carbon atoms;
  R(48) is —($C_3$–$C_7$)-cycloalkyl or phenyl, which is not substituted or is substituted by 1–3 substituents selected from the group consisting of F, Cl, —$CF_3$, methyl, methoxy and —NR(49)R(50);
  R(49) and R(50) are hydrogen or alkyl having 1, 2, 3 or 4 carbon atoms; or
  R(32), R(34) and R(45) are hydrogen;
  R(33) and R(46) independently of one another are hydrogen or alkyl having 1, 2, 3 or 4 carbon atoms; or
  R(32) and R(33), and R(45) and R(46) together are 5 or 6 methylene groups, of which one $CH_2$ group can be replaced by oxygen, —S—, —NH—, —$NCH_3$ or —N-benzyl; or R(1), R(2) and R(3) independently of one another are R(51)-A—G—D—;
  R(51) is a basic protonatable radical, i.e. an amino group —NR(52)R(53), an amidino group R(52)R(53)N—C(=N—R(54)]— or a guanidino group R(52)R(53)N—C[=N—R(54)]—NR(55)—;
  R(52), R(53), R(54) and R(55) independently of one another are hydrogen or alkyl having 1, 2, 3 or 4 carbon atoms; or R(52) and R(53) are. a group $C_\alpha H_{2\alpha}$;
  α is 4, 5, 6 or 7;
  where if α=5, 6 or 7 a carbon atom of the group $C_\alpha H_{2\alpha}$ can be replaced by a heteroatom group O, $SO_d$ or NR(56), or
  R(53) and R(54) or R(54) and R(55) or R(52) and R(55) are a group $C_\gamma H_{2\gamma}$;
  γ is 2, 3, 4 or 5;
  where if γ=3, 4 or 5 a carbon atom of the group $C_\gamma H_{2\gamma}$ can be replaced by a heteroatom group O, $SO_d$ or NR(56);
  d is zero, 1 or 2;
  R(56) is hydrogen or methyl; or
R(51) is a basic heteroaromatic ring system having 1–9 carbon atoms;
A is a group $C_eH_{2e}$;
  e is zero, 1, 2, 3, 4, 5, 6, 7, 8, 9 or 10;
  where in the group $C_eH_{2e}$ a carbon atom can be replaced by one of the groupings —O—, —CO—, —CH[OR(57)]—, —$SO_r$—, —NR(57)—, —NR(57)—CO—, —NR(57)—CO—NH—, —NR(57)—CO—NH—$SO_2$— or —NR(57)—$SO_2$—;
  r is zero, 1 or 2;
  R(57) is hydrogen or methyl;
G is a phenylene radical R(58) and R(59) independently of one another are hydrogen, methyl, methoxy, F, Cl, Br, I, $CF_3$ or —$SO_s$—R(60); R(60) is methyl or NR(61)R(62);
    R(61) and R(62) independently of one another are hydrogen or alkyl having 1, 2, 3 or 4 carbon atoms;
D is —$C_vH_{2v}$—$E_w$—;
  v is zero, 1, 2, 3 or 4;
  E is —O—, —CO—, —CH[OR(63)]-, —$SO_{aa}$— or —NR(63)—;
  w is zero or 1;
  aa is zero, 1 or 2 R(63) is hydrogen or methyl, or R(1), R(2) and R(3) independently of one another are —$CF_2$R(64), —CF[R(65)][R(66)], —CF[$(CF_2)_q$—$CF_3$][R(65)], —C[$(CF_2)_p$—$CF_3$]=CR(65)R(66);
  R(64) is alkyl having 1, 2, 3 or 4 carbon atoms or cycloalkyl having 3, 4, 5, 6 or 7 carbon atoms;
  R(65) and R(66) independently of one another are hydrogen or alkyl having 1, 2, 3 or 4 carbon atoms;
  q is zero, 1 or 2;
  p is zero, 1 or 2; or R(1), R(2) and R(3) independently of one another are —OR(67) or —NR(67)R(68);
  R(67) and R(68) independently of one another are hydrogen or alkyl having 1, 2, 3, 4, 5 or 6 carbon atoms; or
  R(67) and R(68) together are 4, 5, 6 or 7 methylene groups, of which one $CH_2$ group can be replaced by oxygen, —S—, $SO_2$, —NH—, —$NCH_3$ or —N-benzyl;

R(4) and R(5) independently of one another are hydrogen, alkyl having 1, 2, 3 or 4 carbon atoms, F, Cl, —OR(69), —NR(70)R(71) or —$C_zF_{2z+1}$;

R(69), R(70) and R(71) independently of one another are hydrogen or alkyl having 1, 2 or 3 carbon atoms;
z is 1, 2, 3 or 4;
R(6) and R(7) independently of one another are hydrogen or alkyl having 1, 2, 3 or 4 carbon atoms;
X is oxygen or NR(72);
R(72) is hydrogen or alkyl having 1, 2, 3 or 4 carbon atoms; and their pharmaceutically tolerable salts;
(HOE 95/F 115-EP 744 397, NZ 286 622)

ak) alkenylcarboxylic acid guanidides, carrying fluorophenyl groups, of the forumula I

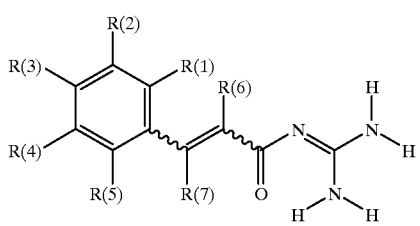

in which:
R(6) is hydrogen, $(C_1-C_8)$-alkyl, $(C_3-C_8)$-cycloalkyl or phenyl, where the phenyl group is not substituted or is substituted by 1–3 substituents selected from the group consisting of F, Cl, $CF_3$, methyl, methoxy and NR(9)R(10);
R(9) and R(10) are hydrogen, $(C_1-C_4)$-alkyl or $(C_1-C_4)$-perfluoroalkyl;
R(7) independently is defined as R(6);
R(1), R(2), R(3), R(4) and R(5) independently of one another are hydrogen or F;
where, however, at least one of the radicals R(1), R(2), R(3), R(4) and R(5) must be fluorine;
and their pharmaceutically tolerable salts;
(HOE 95/F 167-NZ 299 015)

al) benzoylguanidines of the formula I

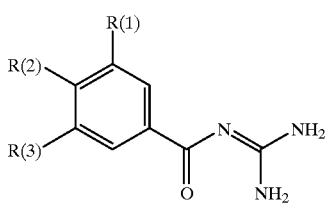

in which:
R(1) is R(4)—$SO_m$ or R(5)R(6)N—$SO_2$—;
m is 1 or 2;
R(4) and R(5) independently of one another are alkyl having 1, 2, 3, 4, 5, 6, 7 or 8 carbon atoms, alkenyl having 3, 4, 5 or 6 carbon atoms, $CF_3$ or —$C_nH_{2n}$—R(7);
n is zero, 1, 2, 3 or 4;
R(6) is H or alkyl having 1, 2, 3 or 4 carbon atoms;
R(7) is cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(8)R(9);
R(8) and R(9) are H or alkyl having 1, 2, 3 or 4 carbon atoms; or
R(5) is also hydrogen; or R(5) and R(6) together are 4 or 5 methylene groups, of which a $CH_2$ group can be replaced by oxygen, S, NH, N—CH 3 or N-benzyl; or
R(1) is —$O_p$—$(CH_2)_q$—$(CF_2)_r$—$CF_3$;
p is zero or 1;
q is zero, 1 or 2;
r is zero, 1, 2 or 3; or
R(1) is —SR(10), —OR(10) or —CR(10)R(11)R(12);
R(10), R(11) and R(12) independently of one another are hydrogen, alkyl having 1, 2, 3, 4, 5, 6, 7 or 8 carbon atoms, —$C_sH_{2s}$—$(C_3-C_8)$-cycloalkyl or an aromatic system selected from the group consisting of pyridyl, pyrrolyl, quinolyl, isoquinolyl, imidazolyl or phenyl; is zero, 1 or 2;
where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;
R(2) is —$(CH_2)_u$—$(CF_2)_t$—$CF_3$;
t is zero, 1, 2 or 3;
u is zero or 1;
R(3) is hydrogen or independently is defined as R(1);
and their pharmaceutically tolerable salts;
(HOE 95/F 173-NZ 299 052)

am) substituted cinnamic acid guanidides of the formula I

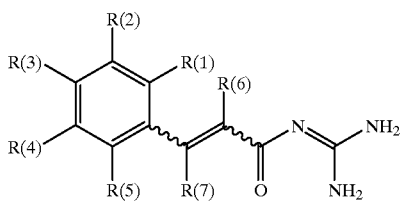

in which:
at least one of the substituents R(1), R(2), R(3), R(4) and R(5) is —$X_a$—$Y_b$—$L_n$—U;
X is CR(16)R(17), O, S or NR(18);
R(16), R(17) and R(18) independently of one another are H, alkyl having 1, 2, 3 or 4 carbon atoms or perfluoroalkyl having 1, 2, 3 or 4 carbon atoms;
a is zero or 1;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
T is NR(20), O, S or phenylene, where the phenylene is not substituted or is substituted by 1–3 substituents selected from the group consisting of F, Cl, $CF_3$, methyl, methoxy and NR(21)R(22);
R(20), R(21) and R(22) independently of one another are H, alkyl having 1, 2, 3 or 4 carbon atoms or perfluoroalkyl having 1, 2, 3 or 4 carbon atoms;
b is zero or 1;
L is O, S, NR(23) or $C_kH_{2k}$;
k is 1, 2, 3, 4, 5, 6, 7 or 8;
n is zero or 1;
U is NR(24)R(25) or an N-containing heterocycle having 1, 2, 3, 4, 5, 6, 7, 8 or 9 carbon atoms;
R(24) and R(25) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms; or

R(24) and R(25) together are 4 or 5 methylene groups, of which one $CH_2$ group can be replaced by oxygen, S, NH, N—$CH_3$ or N-benzyl;

where the N-containing heterocycles are N- or C-bridged and are not substituted or are substituted by 1–3 substituents selected from the group consisting of F, Cl, $CF_3$, methyl, methoxy and NR(27)R(28);

R(23), R(27) and R(28) independently of one another are H, alkyl having 1, 2, 3 or 4 carbon atoms or perfluoroalkyl having 1, 2, 3 or 4 carbon atoms;

and the other substituents R(1), R(2), R(3), R(4) and R(5) in each case independently of one another are H, F, Cl, Br, I, CN, —$O_n$—$C_mH_{2m+1}$, —$O_p$—$(CH_2)_s$—$C_qF_{2q+1}$ or —$C_rH_{2r}R(10)$;

n is zero or 1;
m is zero, 1, 2, 3, 4, 5, 6, 7 or 8;
p is zero or 1;
q is 1, 2, 3, 4, 5, 6, 7 or 8;
s is zero, 1, 2, 3 or 4;
r is zero, 1, 2, 3 or 4;

R(10) is cycloalkyl having 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(11)R(12);

R(11) and R(12) independently of one another are H, alkyl having 1, 2, 3 or 4 carbon atoms or perfluoroalkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;
(HOE 95/F 220-NZ 299 052)

an) benzoylguanidines of the formula I

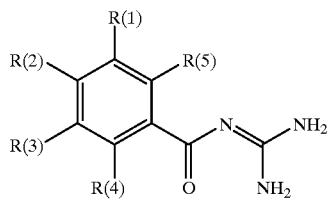

in which:
at least one of the substituents R(1), R(2) and R(3) is R(6)—C(OH)$_2$—;

R(6) is perfluoroalkyl having 1, 2 or 3 carbon atoms, which is straight-chain or branched;

and the other substituents R(1), R(2) and R(3) independently of one another are hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms, or phenoxy, which is unsubstituted or is substituted by 1–3 substituents selected from the group consisting of F, Cl, methyl and methoxy; or the other substituents R(1), R(2) and R(3) independently of one another are alkyl-$SO_x$, —CR(7)=CR(8)R(9) or —C≡CR(9);

x is zero, 1 or 2;
R(7) is hydrogen or methyl;

R(8) and R(9) independently of one another are hydrogen, alkyl having 1, 2, 3 or 4 carbon atoms, cycloalkyl having 3, 4, 5, 6, 7 or 8 carbon atoms, or phenyl, which is unsubstituted or is substituted by 1–3 substituents selected from the group consisting of F, Cl, $CF_3$, methyl and methoxy; or the other substituents R(1), R(2) and R(3) independently of one another are phenyl, $C_6H_5$—$(C_1$–$C_4)$-alkyl, naphthyl, biphenylyl, quinolinyl, isoquinolinyl or imidazolyl, where quinolinyl, isoquinolinyl or imidazolyl are bonded via C or N and where phenyl, $C_6H_5$—$(C_1$–$C_4)$-alkyl, naphthyl, biphenylyl, quinolinyl, isoquinolinyl and imidazolyl are unsubstituted or are substituted by 1–3 substituents selected from the group consisting of F, Cl, $CF_3$, $CH_3$, methoxy, hydroxyl, amino, methylamino and dimethylamino; or the other substituents R(1), R(2) and R(3) independently of one another are SR(10), —OR(10), —CR(10)R(11)R(12);

R(10) is —$C_fH_{2f}$—$(C_3$–$C_8)$-Cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, $CF_3$, $CH_3$, methoxy, hydroxyl, amino, methylamino and dimethylamino;

f is zero, 1 or 2;

R(11) and R(12) independently of one another are defined as R(10), hydrogen or alkyl having 1, 2, 3 or 4 carbon atoms;

R(4) and R(5) independently of one another are hydrogen, alkyl having 1, 2 or 3 carbon atoms, F, Cl, Br, I, CN, OR(13), NR(14)R(15), —$(CH_2)_n$—$(CF_2)_o$—$CF_3$;

R(13), R(14) and R(15) independently of one another are hydrogen or alkyl having 1, 2, 3 or 4 carbon atoms;

n is zero or 1;
o is zero, 1 or 2;

and their pharmacologically acceptable salts;
(HOE 95/F 253-NZ 299 682)

ao) sulfonimidamides of the formula I

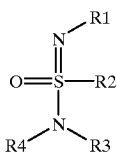

in which:
at least one of the three substituents R(1), R(2) and R(3) is a benzoylguanidine,

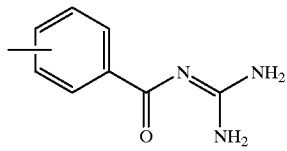

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22)SO$_2$—, R(23)R(24)N—CO—, R(25)—CO—, R(26)R(27)N—SO$_2$, —OR(35), —SR(35) or —NR(35)R(36); m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(1 5)R(1 6);

R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$; n is zero, 1, 2, 3 or 4;

R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);

R(30) and R(31) are hydrogen or alkyl having 1, 2, 3 or 4 carbon atoms; or

R(23), R(25) and R(26) are hydrogen;

R(24) and R(27) independently of one another are hydrogen or alkyl having 1, 2, 3 or 4 carbon atoms; or R(23) and R(24), and also R(26) and R(27) together are 5 or 6 methylene groups, of which one CH$_2$ group can be replaced by oxygen, —S—, —NH—, —NCH$_3$ or —N-benzyl;

R(35) and R(36) independently of one another are hydrogen or alkyl having 1, 2, 3, 4, 5 or 6 carbon atoms; or R(35) and R(36) together are 4–7 methylene groups, of which one CH$_2$ group can be replaced by oxygen, —S—, —NH—, —NCH$_3$ or —N-benzyl; or R(35) is phenyl, which is not substituted or is substituted by 1–3 substituents selected from the group consisting of F, Cl, —CF$_3$, methyl, methoxy, SO$_2$R (5), SO$_2$NR(6)R(7) and —NR(32)R(33);

R(5) is alkyl having 1, 2, 3, 4, 5 or 6 carbon atoms;

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms; or R(35) is C$_1$–C$_9$-heteroaryl, which is unsubstituted or substituted by 1–3 substituents selected from the group consisting of F, Cl, CF$_3$, CH$_3$, methoxy, hydroxyl, amino, methylamino and dimethylamino; and the other substituents R(1), R(2) and R(3) in each case independently of one another are alkyl having 1, 2, 3, 4, 5, 6, 7 or 8 carbon atoms, (CH$_2$)$_p$R(10);

p is zero, 1, 2, 3 or 4;

R(10) is phenyl, which is not substituted or is substituted by 1–3 substituents selected from the group consisting of F, Cl, —CF$_3$, methyl, methoxy, —SO$_2$NR(17)R(8) and —SO$_2$R(9);

R(17) and R(8) independently of one another are hydrogen or alkyl having 1, 2, 3 or 4 carbon atoms;

R(9) is alkyl having 1, 2, 3 or 4 carbon atoms; or the other radical R(1) or R(3) in each case is hydrogen, R(4) is hydrogen or alkyl having 1, 2, 3 or 4 carbon atoms;

and their pharmaceutically tolerable salts;

(HOE 95/F 265-NZ 299 739)

ap) benzoylguanidines of the formula I

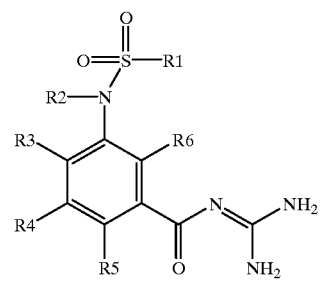

I in which:

R(1) is alkyl having 1, 2, 3, 4, 5, 6, 7 or 8 carbon atoms or NR(7)R(8);

R(7) and R(8) independently of one another are hydrogen or alkyl having 1, 2, 3, 4, 5, 6, 7 or 8 carbon atoms;

R(2) is hydrogen, alkyl having 1, 2, 3, 4, 5, 6, 7 or 8 carbon atoms or —SO$_2$R(9);

R(9) independently is defined as R(1);

R(3) is hydrogen, —SR(25), —OR(25), —NR(25)R(26) or —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino; or R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is hydrogen, F, Cl, Br, I, OH, —C≡N, CF$_3$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

R(5) and R(6) independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;
and their pharmaceutically tolerable salts;
(HOE 95/F 269 K-EP-A 774 458)

aq) benzenedirarboxylic acid diguanidides of the formula I

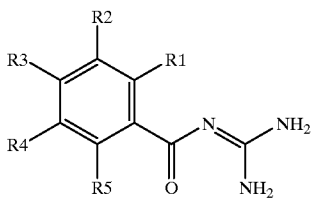

in which:
one of the radicals R(1), R(2), R(3) and R(4) is —CO—N═C(NH$_2$)$_2$;
and of the other radicals R(1), R(2), R(3) and R(4) in each case:
R(1) is hydrogen, alkyl having 1, 2, 3 or 4 carbon atoms, F, Cl, Br, I, —OR(32), —NR(33)R(34) or CF$_3$;
R(32), R(33) and R(34) independently of one another are hydrogen or alkyl having 1, 2, 3 or 4 carbon atoms;
R(2) and R(4) independently of one another are hydrogen, F, Cl, Br, I, OH, —CN, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) are hydrogen or —CH$_3$; or
R(2) and R(4) independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy; or
R(2) and R(4) independently of one another are R(22)—SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl; or
R(2) and R(4) independently of one another are —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27); R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino; or R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;
R(5) is alkyl having 1, 2, 3 or 4 carbon atoms, F, Cl, Br, I, X—(CH$_2$)$_y$—CF$_3$ or phenyl, which is not substituted or is substituted by 1–3 substituents selected from the group consisting of F and Cl, —CF$_3$, methyl, methoxy and —NR(6)R(7); R(6) and R(7) independently of one another are hydrogen or —CH$_3$;
X is a bond or oxygen;
y is zero, 1 or 2;
and their pharmaceutically tolerable salts;
(HOE 95/F 269 BK-EP-A 774 457)

ar) benzenedicarboxylic acid diguanidides of the formula I

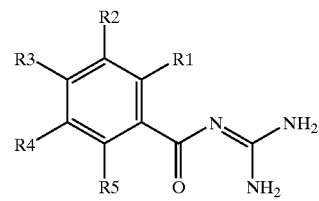

in which:
one of the radicals R(1), R(2), R(3) and R(5) is —CO—N═C(NH$_2$)$_2$;
and of the other radicals R(1), R(2), R(3) and R(5) in each case:
R(1) and R(5) independently of one another are hydrogen, alkyl having 1, 2, 3 or 4 carbon atoms, F, Cl, —OR(32), —NR(33)R(34) or CF$_3$;
R(32), R(33) and R(34) independently of one another are hydrogen or alkyl having 1, 2, 3 or 4 carbon atoms;
R(2) is hydrogen, F, Cl, Br, I, OH, —CN, CF$_3$, —CO—N═C(NH2)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$; or
R(2) is R(22)—SO$_2$—, R(23)R(24)N—CO—, R(28)—CO—or R(29)R(30)N—SO$_2$;
R(22) and R(28) independently of one another are methyl or —CF$_3$;
R(23), R(24), R(29) and R(30) independently of one another are hydrogen or methyl; or
R(2) is —OR(35) or —NR(35)R(36); R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27); R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, $CF_3$, $CH_3$, methoxy, hydroxyl, amino, methylamino and dimethylamino; or R(25) is —$(C_1$–$C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is $CF_3$, alkyl having 1, 2, 3, 4, 5, 6, 7 or 8 carbon atoms, alkenyl having 2, 3, 4, 5, 6, 7 or 8 carbon atoms, —$(C_3$–$C_8)$-cycloalkyl or —$(CH_2)_mR(14)$;

m is 1 or 2;

R(14) is —$(C_3$–$C_8)$-cycloalkyl or phenyl, which is not substituted or is substituted by 1–3 substituents selected from the group consisting of F and Cl, —$CF_3$, methyl, methoxy and —NR(15)R(16);

R(15) and R(16) independently of one another are hydrogen or —$CH_3$; or

R(4) is phenyl, which is substituted by 2, 3, 4 or five substituents selected from the group consisting of F, Cl, $CF_3$, methyl, methoxy and —NR(15)R(16);

R(15) and R(16) independently of one another are hydrogen or $CH_3$;

and their pharmaceutically tolerable salts;

(HOE 96/F 013-EP-A 787717)

as) diaryldicarboxylic acid diguanidides of the formula I

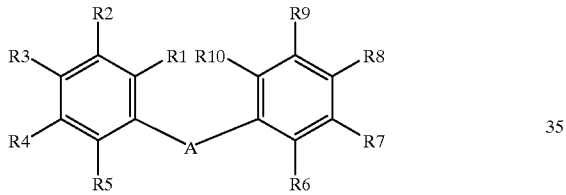

I in which:

one of the radicals R(1), R(2), R(3), R(4) and R(5) is —CO—N=C(NH$_2$)$_2$;

the other radicals R(1) and R(5) in each case independently of one another are hydrogen, alkyl having 1, 2, 3 or 4 carbon atoms, F, Cl, —OR(32), —NR(33)R(34) or $CF_3$;

R(32), R(33) and R(34) independently of one another are hydrogen or alkyl having 1, 2, 3 or 4 carbon atoms;

the other radicals R(2) and R(4) in each case independently of one another are hydrogen, F, Cl, Br, I, OH, —CN, $CF_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —$(CH_2)_mR(14)$;

m is zero, 1 or 2;

R(14) is —$(C_3$–$C_8)$-cycloalkyl or phenyl, which is not substituted or is substituted by 1–3 substituents selected from the group consisting of F and Cl, —$CF_3$, methyl, methoxy and —NR(15)R(16);

R(15) and R(16) are hydrogen or —$CH_3$; or the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, $(C_2$–$C_8)$-alkanoyl, $(C_2$–$C_8)$-alkoxycarbonyl, formyl, carboxyl, —$CF_3$, methyl, methoxy; or the other radicals R(2) and R(4) in each case are R(22)—SO$_2$—, R(23)R(24)N—CO—, R(28)—CO— or R(29)R(30)N—SO$_2$;

R(22) and R(28) independently of one another are methyl or —$CF_3$;

R(23), R(24), R(29) and R(30) independently of one another are hydrogen or methyl; or the other radicals R(2) and R(4) in each case independently of one another are —OR(35) or —NR(35)R(36);

R(35) and R(36) independently of one another are hydrogen or alkyl having 1, 2, 3, 4, 5 or 6 carbon atoms; or R(35) and R(36) together are 4–7 methylene groups, of which one $CH_2$ group can be replaced by oxygen, —S—, —NH—, —NCH$_3$ or —N-benzyl;

the other radical R(3) in each case is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, $CF_3$, $CH_3$, methoxy, hydroxyl, amino, methylamino and dimethylamino; or R(25) is —$(C_1$–$C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

one of the radicals R(6), R(7), R(8), R(9) and R(10) is —CO—N=C(NH$_2$)$_2$;

the other radicals R(6) and R(10) in each case independently of one another are hydrogen, alkyl having 1, 2, 3 or 4 carbon atoms, F, Cl, —OR(132), —NR(133)R(134) or $CF_3$;

R(132), R(133) and R(134) independently of one another are hydrogen or alkyl having 1, 2, 3 or 4 carbon atoms;

the other radicals R(7) and R(9) in each case independently of one another are hydrogen, F, Cl, Br, I, OH, —CN, $CF_3$, —CO—N=C(NH$_2$)2, alkyl having 1, 2, 3, 4, 5, 6, 7 or 8 carbon atoms, alkenyl having 2, 3, 4, 5, 6, 7 or 8 carbon atoms or —$(CH_2)_{mm}R(114)$;

mm is zero, 1 or 2;

R(114) is —$(C_3$–$C_8)$-cycloalkyl or phenyl, which is not substituted or is substituted by 1–3 substituents selected from the group consisting of F and Cl, —$CF_3$, methyl, methoxy and —NR(115)R(116);

R(115) and R(116) are hydrogen or —$CH_3$; or the other radicals R(7) and R(9) in each case independently of one another are pyrrol-1-yl, pyrrol-2-yl or pyrrol-3-yl, which is not substituted or is substituted by 1–4 substituents selected from the group consisting of F, Cl, Br, I, —CN, $(C_2$–$C_8)$-alkanoyl, $(C_2$–$C_8)$-alkoxycarbonyl, formyl, carboxyl, —$CF_3$, methyl and methoxy; or the other radicals R(7) and R(9) in each case are R(122)—SO$_2$—, R(123)R(124)N—CO—, R(128)—CO— or R(129)R(130)N—SO$_2$;

R(122) and R(128) independently of one another are methyl or —$CF_3$;

R(123), R(124), R(129) and R(130) independently of one another are hydrogen or methyl; or the other radicals R(7) and R(9) in each case independently of one another are —OR(135) or —NR(135)R(136);

R(135) and R(136) independently of one another are hydrogen or alkyl having 1, 2, 3, 4, 5 or 6 carbon atoms; or R(135) and R(136) together are 4–7 methylene groups, of which one $CH_2$ group can be replaced by oxygen, —S—, —NH—, —$NCH_3$ or —N-benzyl;

the other radical R(8) in each case is hydrogen, —SR(125), —OR(125), —NR(125)R(126) or —CR(125)R(126)R(127);

R(125) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino; or R(125) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

R(126) and R(127) independently of one another are defined as R(125) or are hydrogen or alkyl having 1, 2, 3, 4, 5, 6, 7 or 8 carbon atoms; is absent or is —NR(11)—CO—, —NR(12)—CO—NR(13)—, —NR(17)—CO—NR(18)—$SO_2$—, —NR(19)—$SO_2$—, —$SO_2$—NR(19)—$SO_2$—, —$SO_2$—NR(19)—CO—, —O—CO—NR(19)—$SO_2$ or —CR(20)=CR(21)—;

R(11), R(12), R(13), R(17), R(18), R(19), R(20) and R(21) independently of one another are hydrogen or alkyl having 1, 2, 3, 4, 5, 6, 7 or 8 carbon atoms and their pharmaceutically tolerable salts;

(HOE 96/F 026-EP-A 790 245)

at) substituted thiophenylalkenylcarboxylic acid guanidides of the formula I

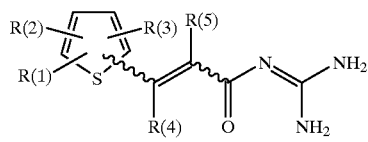

in which:

at least one of the substituents R(1), R(2) and R(3) is —$O_p$—$(CH_2)_s$—$C_qF_{2q+1}$, R(40)CO— or R(31)$SO_k$—;

p is zero or 1;

s is zero, 1, 2, 3 or 4;

q is 1, 2, 3, 4, 5, 6, 7 or 8;

k is zero, 1 or 2;

R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl and methoxy;

R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl or methoxy; or R(31) is NR(41)R(42);

R(41) and R(42) independently of one another are hydrogen, alkyl having 1, 2, 3 or 4 carbon atoms, perfluoroalkyl having 1, 2, 3 or 4 carbon atoms, or R(41) and R(42) together are 4 or 5 methylene groups, of which one $CH_2$ group can be replaced by oxygen, S, NH, N—$CH_3$ or N-benzyl;

and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}$R(10);

na is zero or 1;

ma is zero, 1, 2, 3, 4, 5, 6, 7 or 8;

ga is zero or 1;

ra is zero, 1, 2, 3 or 4;

R(10) is cycloalkyl having 3, 4, 5, 6, 7 or 8 carbon atoms or phenyl, where the phenyl is not substituted or is substituted by 1–3 substituents selected from the group consisting of F, Cl, $CF_3$, methyl and methoxy;

R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;

(HOE 96/F 032-EP-A 791 577)

au) ortho-substituted benzoylguanidines of the formula I

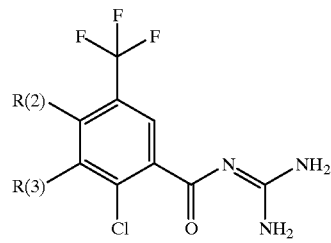

in which:

R(2) and R(3) independently of one another are hydrogen, Cl, Br, I, ($C_1$–$C_8$)-alkyl, ($C_3$–$C_8$)-cycloalkyl or —OR(5);

R(5) is ($C_1$–$C_8$)-alkyl or —$C_dH_{2d}$—($C_3$–$C_8$)-cycloalkyl;

d is zero, 1 or 2;

where one of the two substituents R(2) and R(3) is always hydrogen but both substituents R(2) and R(3) are not simultaneously hydrogen, and their pharmaceutically tolerable salts;

(HOE 96/F 042-EP-A 794 171)

av) benzoylguanidines of the formula I

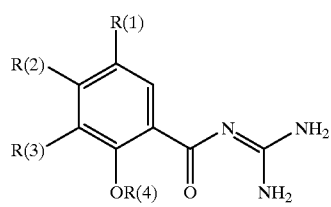

in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S, NR(5),
a is zero or 1;
b is zero, 1 or 2;
c is zero, 1, 2 or 3; R(5) is H, alkyl having 1, 2, 3 or 4 carbon atoms or —$C_dH_{2d}R(6)$;
d is zero, 1, 2, 3 or 4;
R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);
R(7) and R(8) independently are H or alkyl having 1, 2, 3 or 4 carbon atoms; or
R(1) is —SR(10), —OR(10) or —CR(10)R(11)R(12);
R(10) is —$C_fH_{2f}$-cycloalkyl having 3, 4, 5. 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;
f is zero, 1 or 2;
R(11) and R(12) independently of one another are defined as R(10) or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$R(24),
k is zero, 1, 2, 3 or 4;
l is zero, 1, 2, 3 or 4;
R(13) and R(14) identically or differently are —$(CH_2)_g$—$(CHOH)_h$—$(CH_2)_i$—$(CHOH)_j$—R(17) or —$(CH_2)_g$—O—$(CH_2$—$CH_2O)_h$—R(24);
R(17) is hydrogen or methyl,
g, h and i identically or differently are zero, 1, 2, 3 or 4;
j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18) is phenyl, which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms; or
R(18) is heteroaryl having 1, 2, 3, 4, 5, 6, 7, 8 or 9 carbon atoms, which is unsubstituted or substituted as phenyl; or
R(18) is alkyl having 1, 2, 3, 4, 5 or 6 carbon atoms, which is unsubstituted or substituted by 1–3 OH; or
R(18) is cycloalkyl having 3, 4, 5, 6, 7 or 8 carbon atoms;
R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —$C_mH_2m$—R(18);
m is 1, 2, 3 or 4;
R(2) and R(3) are defined as R(1);
R(4) is alkyl having 1, 2, 3 or 4 carbon atoms;
and their pharmaceutically tolerable salts;
(HOE 96/F 043-EP-A 794 172)
aw) orthosubstituted benzoylguanidines of the formula I in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S, NR(5),
a is zero or 1;
b is zero, 1 or 2;
c is zero, 1, 2 or 3;
R(5) is H, alkyl having 1, 2, 3 or 4 carbon atoms or —$C_dH_{2d}R(6)$; d is zero, 1, 2, 3 or 4;
R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);
R(7) and R(8) independently are H or alkyl having 1, 2, 3 or 4 carbon atoms; or
R(1) is —SR(10), —OR(10) or —CR(10)R(11)R(12);
R(10) is —$C_fH_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;
f is zero, 1 or 2;
R(11) and R(12) independently of one another are defined as R(10), or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
R(13) and R(14) identically or differently are —$(CH_2)_g$—$(CHOH)_h$—$(CH_2)_i$—$(CHOH)_j$—R(17) or —$(CH_2)_g$—O—$(CH_2$—$CH_2O)_h$—R(24);

R(17) is hydrogen or methyl,
g, h and i identically or differently are zero, 1, 2, 3 or 4;
j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18) is phenyl, which is unsubstituted or substituted by 1–3 substituents selected from the group consisting of F, Cl, $CF_3$, methyl, methoxy and NR(25)R(26);
R(25) and R(26) are H or alkyl having 1, 2, 3 or 4 carbon atoms; or
R(18) is heteroaryl having 1, 2, 3, 4, 5, 6, 7, 8 or 9 carbon atoms, which is unsubstituted or substituted as phenyl; or
R(18) is alkyl having 1, 2, 3, 4, 5 or 6 carbon atoms, which is unsubstituted or substituted by 1–3 OH; or
R(18) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —$C_mH_{2m}$—R(18); m is 1, 2, 3 or 4;
one of the two substituents R(2) and R(3) is hydroxyl; and
the other of the substituents R(2) and R(3) in each case is defined as R(1);
R(4) is alkyl having 1, 2, 3 or 4 carbon atoms; alkoxy having 1, 2, 3 or 4 carbon atoms, F, Cl, Br, I or —$(CH_2)_n$—$(CF_2)_o$—$CF_3$;
n is zero or 1;
o is zero or 1;
and their pharmaceutically tolerable salts;
(HOE 96/F 135-EP-A 810 207)
ax) bis-ortho-substituted benzoylguanidines of the formula I in which:
R(1), R(2) and R(3) independently of one another are R(10)—$SO_a$— or R(14)R(15)N—$SO_2$—; a is zero, 1 or 2,
R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —$C_{ab}H_{2ab}$—R(16);
ab is zero, 1, 2, 3 or 4;
R(16) is cycloalkyl having 3, 4, 5, 6 or 7 carbon atoms, or phenyl, which is not substituted or is substituted by 1–3 substituents selected from the group consisting of F, Cl, $CF_3$, methyl, methoxy and NR(17)R(18);
R(17) and R(18) independently of one another are hydrogen, $CF_3$ or alkyl having 1, 2, 3 or 4 carbon atoms; or R(14) and R(15) together are 4 or 5 methylene groups, of which one $CH_2$ group can be replaced by oxygen, sulfur, NH, N—$CH_3$ or N-benzyl; or
R(14) and R(15) are hydrogen; or
R(1), R(2) and R(3) independently of one another are SR(21), —OR(22), —NR(23)R(24) or —CR(25)R(26)R(27);
R(21), R(22), R(23) and R(25) independently of one another are —$C_bH_{2b}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
b is zero, 1 or 2;
R(24), R(26) and R(27) independently of one another are hydrogen, alkyl having 1, 2, 3 or 4 carbon atoms or perfluoroalkyl having 1, 2, 3 or 4 carbon atoms; or
R(1), R(2) and R(3) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, alkenyl having 3, 4, 5, 6, 7 or 8 carbon atoms or —$C_{df}H_{2df}$R(30);
(Xa) is oxygen, sulfur or NR(33);
R(33) is hydrogen, alkyl having 1, 2, 3 or carbon atoms or perfluoroalkyl having 1, 2, 3 or 4 carbon atoms;
dg is zero or 1;
(Xb) is oxygen, sulfur or NR(34); R(34) is hydrogen, alkyl having 1, 2, 3 or 4 carbon atoms or perfluoroalkyl having 1, 2, 3 or 4 carbon atoms;
dh is zero or 1;
da is zero, 1, 2, 3, 4, 5, 6, 7 or 8;
db is zero, 1, 2, 3 or 4;
de is zero, 1, 2, 3, 4, 5, 6 or 7;
df is zero, 1, 2, 3 or 4;
R(30) is cycloalkyl having 3, 4, 5, 6, 7 or 8 carbon atoms, phenyl, biphenylyl or naphthyl, where the aromatics phenyl, biphenylyl and naphthyl are not substituted or are substituted by 1–3 substituents selected from the group consisting of F, Cl, $CF_3$, methyl, methoxy and NR(31)R(32);
R(31) and R(32) are hydrogen, alkyl having 1, 2, 3 or 4 carbon atoms or perfluoroalkyl having 1, 2, 3 or 4 carbon atoms; or
R(1), R(2) and R(3) independently of one another are NR(40)R(41) or —(Xe)—$(CH_2)_{eb}$R(45);
R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or $(CH_2)_e$—R(42);
e is zero, 1, 2, 3 or 4;
R(42) is cycloalkyl having 3, 4, 5, 6 or 7 carbon atoms or phenyl, which is not substituted or is substituted by 1–3 substituents selected from the group consisting of F, Cl, $CF_3$, methyl, methoxy and NR(43)R(44);
R(43) and R(44) independently of one another are hydrogen, $CF_3$ or alkyl having 1, 2, 3 or 4 carbon atoms; or
R(40) and R(41) together are 4 or 5 methylene groups, of which one $CH_2$ group can be replaced by oxygen, sulfur, NH, N—$CH_3$ or N-benzyl;
(Xe) is oxygen, sulfur or NR(47); R(47) is hydrogen, alkyl having 1, 2, 3 or 4 carbon atoms or perfluoroalkyl having 1, 2, 3 or 4 carbon atoms;
eb is zero, 1, 2, 3 or 4;
R(45) is cycloalkyl having 3, 4, 5, 6 or 7 carbon atoms, or phenyl, which is not substituted or is substituted by 1–3 substituents selected from the group consisting of F, Cl, $CF_3$, methyl, methoxy, $NR(50)R(51)$ and —(Xfa)—$(CH_2)_{ed}$—(Xfb)R(46);
Xfa is $CH_2$, oxygen, sulfur or NR(48);
Xfb is oxygen, sulfur or NR(49);
R(48), R(49), R(50) and R(51) independently of one another are hydrogen, alkyl having 1, 2, 3 or 4 carbon atoms or perfluoroalkyl having 1, 2, 3 or 4 carbon atoms;
ed is 1, 2, 3 or 4;
R(46) is hydrogen, alkyl having 1, 2, 3 or 4 carbon atoms or perfluoroalkyl having 1, 2, 3 or 4 carbon atoms; or
R(1), R(2) and R(3) independently of one another are —CHR(52)R(53);
R(52) is —$(CH_2)_g$—$(CHOH)_h$—$(CH)_i$—$(CHOH)_k$—R(54) or —$(CH_2)_g$—O—$(CH_2$—$CH_2O)_h$—R(54);
R(54) is hydrogen or methyl;
g,h,i identically or differently are zero, 1, 2, 3 or 4;
k is 1, 2, 3 or 4;
R(53) is hydrogen or alkyl having 1, 2, 3 or 4 carbon atoms; or
R(1), R(2) and R(3) independently of one another are —C(OH)R(55)R(56);
R(55) and R(56) identically or differently are hydrogen or alkyl having 1, 2, 3 or 4 carbon atoms; or
R(55) and R(56) together are cycloalkyl having 3, 4, 5 or 6 carbon atoms; or
R(55) is —$CH_2OH$; and
R(4) and R(5) independently of one another are alkyl having 1, 2, 3 or 4 carbon atoms, alkoxy having 1, 2, 3 or 4 carbon atoms, OH, F, Cl, Br, I, CN, —$O_n$—$(CH_2)_o$—$(CF_2)_p$—$CF_3$;
n is zero or 1;
o is zero, 1 or 2;
p is zero, 1 or 2;
and their pharmaceutically tolerable salts;
(96/F 136-EP-A 810 205)
ay) substituted 1-naphthoylguanidines of the formula I

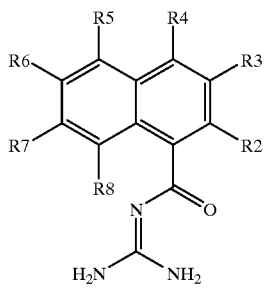

in which:
R2, $R_3$, R4, R5, R6, R7 and R8 independently of one another are H, F, Cl, Br, I, CN, $NO_2$, $CF_3$, $C_2F_5$ or $X_aY_bZ$;
X is O, S, NR(10), CR(11)R(12), C=O, C(=O)NR(10), C(=O)O, SO, $SO_2$, $SO_2NR(10)$, OC=O, NR(10)C=O or $NR(10)SO_2$, where the linkage with the naphthalene ring in each case takes place via the left atom;
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
a is zero or 1;

Y is alkylene having 1, 2, 3, 4, 5, 6, 7 or 8 $CH_2$ groups, where one of these $CH_2$ groups can be replaced by O, S, NR(1 3) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
b is zero or 1;
Z is H, alkyl having 1, 2, 3, 4, 5, 6 or 7 carbon atoms, cycloalkyl having 3, 4, 5, 6 or 7 carbon atoms, C(=O)R(15), $SO_2R(15)$, NR(16)R(17) orphenyl, which is not substituted or is substituted by 1–3 substituents selected from the group consisting of F, Cl, Br, $CF_3$, methyl, methoxy and NR(21)R(22);
R(21) and R(22) independently of one another are H or alkyl having 1, 2, 3 or 4 carbon atoms or perfluoroalkyl having 1, 2, 3 or 4 carbon atoms;
R(15) is N=$C(NH_2)_2$, NR(18)R(19), $N(CH_2)_cNR(18)R(19)$ or OR(20);
c is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups, of which one $CH_2$ group can be replaced by oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2. 3 or 4 carbon atoms; or
R(16) and R(17) together are 4 or 5 methylene groups, of which one $CH_2$ group can be replaced by oxygen, S, NH, N—$CH_3$, N-benzyl or N-(p-chlorophenyl); or
is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(21)R(22);
but where, in the case where R(4) is an alkoxy radical, at least one of the substituents R(2), R(3), R(5), R(6), R(7) and R(8) is not hydrogen; and their pharmaceutically tolerable salts;
(96/F 137-EP-A 810 206)
az) substituted 2-naphthoylguanidines of the formula I

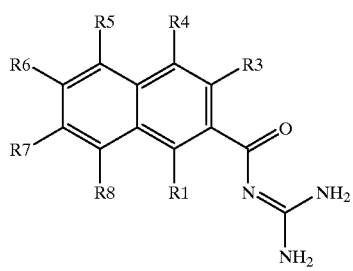

in which:
at least one of the substituents R1, $R_3$, R4, R5, R6, R7 and R8 is

XY$_a$WZ or X'Y$_a$WZ';
X is O, S, NR(10) or CR(11)R(12);
  R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 CH$_2$ groups, where one of these CH$_2$ groups can be replaced by O, S, NR(13) or o-, p- or m-phenylene;
  R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is CH$_2$, SO$_2$, S(=O)(=NH) or—if W does not immediately follow a heteroatom of the group XY$_a$- alternatively O or NR(14);
  R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is C(=O)R(15), SO$_2$R(15) or—if W is not O or NR(14)-alternatively NR(16)R(17);
  R(15) is N=C(NH$_2$)$_2$, NR(18)R(19), N(CH$_2$)$_b$NR(18)R(19) or OR(20);
    b is 2 or 3;
    R(18) and R(19) independently of one another are H, alkyl having 1, 2, 3, 4, 5, 6, 7 or 8 carbon atoms or perfluoroalkyl having 1, 2, 3 or 4 carbon atoms; or
    R(18) and R(19) together are 4 or 5 methylene groups, of which one CH$_2$ group can be replaced by oxygen, S, NH, N—CH$_3$, N-benzyl or N-(p-chlorophenyl);
    R(20) is H, alkyl having 1, 2, 3, 4, 5 or 6 carbon atoms, perluoroalkyl having 1, 2, 3 or 4 carbon atoms or cycloalkyl having 3, 4, 5, 6 or 7 carbon atoms;
  R(16) and R(17) independently of one another are H, alkyl having 1, 2, 3, 4, 5, 6, 7 or 8 carbon atoms or perfluoroalkyl having 1, 2, 3 or 4 carbon atoms; or,
  R(16) and R(17) together are 4 or 5 methylene groups, of which one CH$_2$ group can be replaced by oxygen, S, NH, N—CH$_3$, N-benzyl or N-(p-chlorophenyl);
X' is C=O, C(=O)NR(30), C(=O)O, SO, SO$_2$, SO$_2$NR(30), OC=O, NR(30)C=O or NR(30)SO$_2$, where the linkage with the naphthalene ring in each case takes place via the left atom;
  R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Z' is C(=O)R(15), SO$_2$R(15), an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(21)R(22);
  R(21) and R(22) independently of one another are H, alkyl having 1, 2, 3 or 4 carbon atoms or perfluoroalkyl having 1, 2, 3 or 4 carbon atoms;
R(15) is N=C(NH$_2$)$_2$, NR(18)R(19), N(CH$_2$)$_b$NR(18)R(19) or OR(20);
  R(18) and R(19) independently of one another are H, alkyl having 1, 2, 3, 4, 5, 6, 7 or 8 carbon atoms or perfluoroalkyl having 1, 2, 3 or 4 carbon atoms; or
  R(18) and R(19) together are 4 or 5 methylene groups, of which one CH$_2$ group can be replaced by oxygen, S, NH, N—CH$_3$, N-benzyl or N-(p-chlorophenyl);
  b is 2 or 3;
  R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms; or
Z'— if W is not O or NR(14)—is NR(16)R(17);
  R(16) and R(17) independently of one another are H, alkyl having 1, 2, 3, 4, 5, 6, 7 or 8 carbon atoms or perfluoroalkyl having 1, 2, 3 or 4 carbon atoms; or
  R(16) and R(17) together are 4 or 5 methylene groups, of which one CH$_2$ group can be replaced by oxygen, S, NH, N—CH$_3$, N-benzyl or N-(p-chloro-phenyl);
and the other substituents R1, R$_3$, R4, R5, R6, R7 and R8 in each case, which are still not allocated by the definitions given above, independently of one another are H, F, Cl, Br, I, CN, NO$_2$, CF$_3$, C$_2$F$_5$ or V$_p$Q$_q$U;
V is O, S, SO, SO$_2$, NR(60), OC=O, C=O, C(=O)NR(60), C(=O)O or CR(66)R(67);
  R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
p is zero or 1;
Q is alkylene having 1, 2, 3, 4, 5, 6, 7 or 8 CH$_2$ groups, where one of these CH$_2$ groups can be replaced by O, S, NR(68) or o-, p- or m-phenylene;
  R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
q is zero or 1;
U is H, alkyl having 1, 2, 3, 4, 5, 6 or 7 carbon atoms, cycloalkyl having 3, 4, 5, 6 or 7 carbon atoms, C(=O)R(65), SO$_2$R(65), NR(61)R(62) or phenyl, which is not substituted or is substituted by 1–3 substituents selected from the group consisting of F, Cl, Br, CF$_3$, methyl, methoxy and NR(63)R(64);
  R(63) and R(64) independently of one another are H, alkyl having 1, 2, 3 or 4 carbon atoms or perfluoroalkyl having 1, 2, 3 or 4 carbon atoms;
  R(65) is N=C(NH$_2$)$_2$, NR(61)R(62) or OR(60);
  R(61) and R(62) independently of one another are H, alkyl having 1, 2, 3, 4, 5, 6, 7 or 8 carbon atoms or perfluoroalkyl having 1, 2, 3 or 4 carbon atoms; or
  R(61) and R(62) together are 4 or 5 methylene groups, of which one CH$_2$ group can be replaced by oxygen, S, NH, N—CH$_3$, N-benzyl or N-(p-chlorophenyl); or
U is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(63)R(64);
but where at least one of the substituents R5, R6, R7 and R8 is not hydrogen; and their pharmaceutically tolerable salts;
(96/F 141-EP-A 811 610)

ba) ortho-substituted benzoylguanidines of the formula I

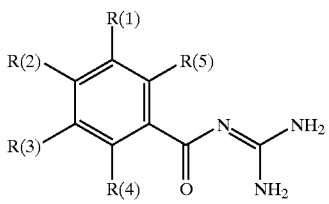

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, sulfur or NR(9);
a is zero or 1;
b is zero, 1 or 2;
c is zero, 1, 2 or 3;
   R(9) is H, alkyl having 1, 2, 3 or 4 carbon atoms or —C$_d$H$_{2d}$R(6); d is zero, 1, 2, 3 or 4;
      R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);
      R(7) and R(8) are independently, H or alkyl having 1, 2, 3 or 4 carbon atoms; or
R(1) is —SR(10), —OR(10) or —CR(10)R(11)R(12);
   R(10) is —C$_f$H$_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, CF$_3$, CH$_3$, methoxy, hydroxyl, amino, methylamino and dimethylamino;
   f is zero, 1 or 2;
   R(11) and (R12), independently of one another, are defined as R(10) or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, the latter linked via a carbon or nitrogen atom of the ring, each of which is unsubstituted or is substituted by 1–3 substituents selected from the group consisting of F, Cl, CF$_3$, CH$_3$, methoxy, hydroxyl, amino, methylamino and dimethylamino, or
(R1) is —SR(13), —OR(13), —NHR(13), —NR(13)R(14), —CHR(13)R(15), —C[R(15)R(16)]OH, —C≡—CR(18), —C[R(19)]=CHR(18), —C[R(20)R(21)]$_k$—(CO)—[CR(22)R(23)]$_l$—R(24),
   k is zero, 1, 2, 3 or 4;
   l is zero, 1, 2, 3 or 4;
   R(13) and R(14), identically or differently, are —(CH$_2$)$_g$—(CHOH)$_h$—(CH$_2$)$_i$—(CHOH)$_{kk}$—R(17) or —(CH$_2$)$_g$—O—(CH$_2$—CH$_2$O)$_h$—R(24);
      R(17) is hydrogen or methyl, g, h and i, identically or differently, are zero, 1, 2, 3 or 4;
      kk is 1, 2, 3 or 4;
   R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;

R(18) is phenyl, which is unsubstituted or is substituted by 1–3 substituents selected from the group consisting of F, Cl, CF$_3$, methyl, methoxy and NR(25)R(26);
   R(25) and R(26) are H or alkyl having 1, 2, 3 or 4 carbon atoms; or
R(18) is heteroaryl having 1, 2, 3, 4, 5, 6, 7, 8 or 9 carbon atoms, which is unsubstituted or is substituted as phenyl; or
R(18) is alkyl having 1, 2, 3, 4, 5 or 6 carbon atoms, which is unsubstituted or is substituted by 1–3 OH; or
R(18) is cycloalkyl having 3, 4, 5, 6, 7 or 8 carbon atoms;
R(19), R(20), R(21), R(22) and R(23), identically or differently, are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18); m is 1, 2, 3 or 4;
one of the two substituents R(2) and R(3) is —O—CO—R(27);
   R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolyl are unsubstituted or substituted by 1–3 substituents selected from the group consisting of F, Cl, CF$_3$, methyl, methoxy and NR(7)R(8);
      R(7) and R(8) independently of one another are hydrogen or alkyl having 1, 2, 3 or 4 carbon atoms;
where one of the substituents R(2) and R(3) is always defined as R(1);
R(4) and R(5) independently of one another are hydrogen, alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$,
n is zero or 1,
o is zero or 1,
and their pharmaceutically tolerable salts;
(96/F 154)
bb) benzoylguanidines of the formula I

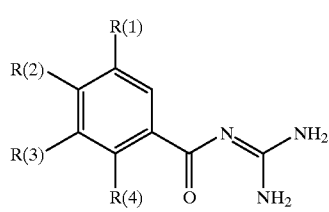

in which:
R(1) is R(13)—SO$_m$ or R(14)R(15)N—SO$_2$—;
m is 1 or 2;
R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(16),
n is zero, 1, 2, 3 or 4;
R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, CF$_3$, methyl, methoxy and NR(25)R(26);
R(25) and R(26) are, independently of each other, hydrogen, alkyl having 1, 2, 3 or 4 carbon atoms or perfluoroalkyl having 1, 2, 3 or 4 carbon atoms;

R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(27), n is zero, 1, 2, 3 or 4;

R(27) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(28)R(29);

$Cd^9$ R(28) and R(29), independently of each other, are hydrogen, alkyl having 1, 2, 3 or 4 carbon atoms or perfluoroalkyl having 1, 2, 3 or 4 carbon atoms;

R(15) is hydrogen, alkyl having 1, 2, 3 or 4 carbon atoms or perfluoroalkyl having 1, 2, 3 or 4 carbon atoms; or R(14) and R(15), together, are 4 or 5 methylene groups of which one $CH_2$ group can be replaced by oxygen, S, NH, N—$CH_3$ or N-benzyl;

one of the substituents R(2) and R(3) is hydrogen;

and the other of the substituents R(2) and R(3) in each case is —CHR(30)R(31);

R(30) is —$(CH_2)_g$—$(CHOH)_h$—$(CH_2)_i$—$(CHOH)_k$R(32) or —$(CH_2)_g$—O—$(CH_2$—$CH_2O)_h$—R(24);

R(24) and R(32), independently of each other, are hydrogen or methyl;

g, h and i, identically or differently, are zero, 1, 2, 3 or 4;

k is 1, 2, 3 or 4;

or the other of the substituents R(2) and R(3) in each case is —C(OH)R(33)R(34);

R(31), R(33) and R(34), identically or differently, are hydrogen or alkyl having 1, 2, 3 or 4 carbon atoms, or R(33) and R(34), together, are cycloalkyl having 3, 4, 5 or 6 carbon atoms; or R(33) is —$CH_2OH$;

R(4) is alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$;

n is zero or 1;

o is zero, 1 or 2;

and their pharmaceutically tolerable salts;

(HOE 96/F 202)

bc) indanylidineacetylguanidines of the formula I

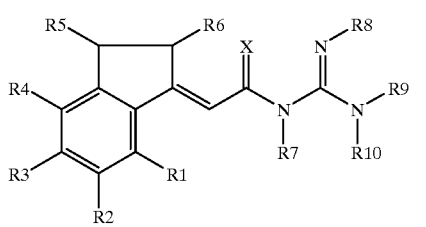

in which:

R1, R2, R3, R4, R5 and R6 independently of one another are H, $C_1$–$C_{10}$-alkyl; haloalkyl having 1–6 carbon atoms, O—$C_1$–$C_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O—C(=O)—$C_1$–$C_4$-alkylaryl, O—C(=O)—NH—$C_1$–$C_4$-alkyl, O—C(=O)—N($C_1$–$C_4$-alkyl)$_2$, $NO_2$, CN, $CF_3$, $NH_2$, NH—C(=O)—$C_1$–$C_4$-alkyl, NH—C(=O)—$NH_2$, COOH, C(=O)—O—$C_1$–$C_4$-alkyl, C(=O)—$NH_2$, C(=O)—NH-$C_1$–$C_4$-alkyl, C(=O)—N($C_1$–$C_4$-alkyl)$_2$, $C_1$–$C_4$—COOH, $C_1$–$C_4$-alkyl—C(=O)—O—$C_1$–$C_4$-alkyl, $SO_3H$, $SO_2$-alkyl; $SO_2$-alkylaryl, $SO_2$—N-(alkyl)$_2$, $SO_2$—N(alkyl)(alkylaryl), C(=O)—R11, $C_1$–$C_{10}$-alkyl—C(=O)—R11, $C_2$–$C_{10}$-alkenyl-C(=O)—R11, $C_2$–$C_{10}$-alkynyl-C(=O)—R11, NH—C(=O)—$C_1$–$C_{10}$-alkyl—C(=O)—R11 or O—$C_1$–$C_{11}$-alkyl—C(=O)—R11;

R11 is $C_1$–$C_4$-alkyl, $C_1$–$C_4$-alkynyl, aryl, substituted aryl, $NH_2$, NH—$C_1$–$C_4$-alkyl, N—($C_1$–$C_4$-alkyl)$_2$, $SO_3H$, $SO_2$-alkyl, $SO_2$-alkylaryl, $SO_2$—N-(alkyl)$_2$ or $SO_2$—N(alkyl)(alkylaryl);

X is O, S or NH;

R7, R8, R9 and R10 independently of one another are H, alkyl, cycloalkyl, aryl, alkylaryl, or R8 and R9 together are part of a 5-, 6- or 7-membered heterocyclic ring;

or their pharmaceutically acceptable salts;

(HOE 96/F 226)

bd) phenyl-substituted alkenylcarboxylic acid guanidides of the formula I

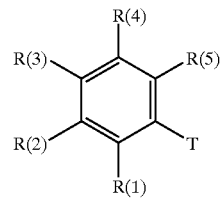

in which

T is:

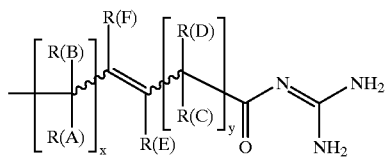

R(A) is hydrogen, F, Cl, Br, I, CN, OH, OR(6), ($C_1$–$C_4$)-alkyl, $O_r(CH_2)_aC_bF_{2b+1}$, ($C_3$–$C_8$)-cycloalkyl oder NR(7)R(8)

r is zero or 1;

a is zero, 1, 2, 3 or 4;

b is 1, 2, 3 or 4;

R(6) is ($C_1$–$C_4$)-alkyl, ($C_1$–$C_4$)-perfluoroalkyl, ($C_3$–$C_6$)-alkenyl, ($C_3$–$C_8$)-cycloalkyl, phenyl or benzyl, where the phenyl nucleus is not substituted or is substituted by 1–3 substituents selected from the group consisting of F, Cl, $CF_3$, methyl, methoxy and NR(9)R(10);

R(9) and R(10) are H, ($C_1$–$C_4$)-alkyl or ($C_1$–$C_4$)-perfluoroalkyl;

R(7) and R(8) independently of one another are defined as R(6); or

R(7) and R(8) together are 4 or 5 methylene groups, of which one $CH_2$ group can be replaced by oxygen, sulfur, NH, N—$CH_3$ or N-benzyl;

R(B), R(C) and R(D) independently are defined as R(A);

x is zero, 1 or 2;
y is zero, 1 or 2;
R(F) is hydrogen, F, Cl, Br, I, CN, OR(12), $(C_1–C_8)$-alkyl, $O_p(CH_2)_fC_gF_{2g+1}$, $(C_3–C_8)$-cycloalkyl or $(C_1–C_9)$-heteroaryl;
p is zero or 1;
f is zero, 1, 2, 3 or 4;
g is 1, 2, 3, 4, 5, 6, 7 or 8;
R(12) is $(C_1–C_8)$-alkyl, $(C_1–C_4)$-perfluoroalkyl, $(C_3–C_8)$-alkenyl, $(C_3–C_8)$-cycloalkyl, phenyl or benzyl, where the phenyl nucleus is not substituted or is substituted by 1–3 substituents selected from the group consisting of F, Cl, $CF_3$, methyl, methoxy and NR(13)R(14);
R(13) and R(14) are H, $(C_1–C_4)$-alkyl or $(C_1–C_4)$-perfluoroalkyl;
R(E) is defined independently as R(F);
R(1) is defined independently as T; or
R(1) is hydrogen, $—O_kC_mH_{2m+1}$, $—O_n(CH_2)_pC_qF_{2q+1}$, F, Cl, Br, I, CN, —(C═O)—N═C(NH_2)_2, $—SO_rR(17)$, $—SO_{r2}NR(31)R(32)$, $O_u(CH_2)_vC_6H_5$, $—O_{u2}—(C_1–C_9)$-heteroaryl or $—S_{u2}—(C_1–C_9)$-heteroaryl;
k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1–C_8)$-alkyl or $(C_1–C_8)$-perfluoroalkyl; or
R(31) and R(32) together are 4 or 5 methylene groups of which one $CH_2$ group can be replaced by oxygen, S, NH, N—$CH_3$ or N-benzyl;
R(17) is $(C_1–C_8)$-alkyl;
u is zero or 1;
u2 is zero or 1;
v is zero, 1, 2, 3 or 4;
where the phenyl nucleus is not substituted or is substituted by 1–3 substituents selected from the group consisting of F, Cl, $CF_3$, methyl, methoxy, $—(CH_2)_wNR(21)R(22)$, NR(18)R(19) and $(C_1–C_9)$-heteroaryl;
R(18), R(19), R(21) and R(22) independently of one another are $(C_1–C_4)$-alkyl or $(C_1–C_4)$-perfluoroalkyl;
w is 1, 2, 3 or 4;
where the heterocycle of the $(C_1–C_9)$-heteroaryl is unsubstituted or is substituted by 1–3 substituents selected from the group consisting of F, Cl, $CF_3$, methyl or methoxy;
R(2), R(3), R(4) and R(5) independently of one another are defined as R(1), or
R(1) and R(2) or R(2) and R(3) in each case together are —CH═CH—CH═CH—, which is not substituted or is substituted by 1–3 substituents selected from the group consisting of F, Cl, $CF_3$, methyl, methoxy, $—(CH_2)_{w2}NR(24)R(25)$ and NR(26)R(27);
R(24), R(25), R(26) and R(27) are H, $(C_1–C_4)$-alkyl or $(C_1–C_4)$-perfluoroalkyl;
w2 is 1, 2, 3 or 4;
where the radical T is present in the molecule at least twice, but only three times at most;
and their pharmaceutically tolerable salts;
(97/F 082)

be) benzoylguanidines of the formula I

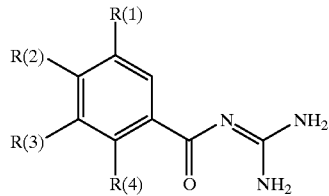

in which:
R(1) is $CF_3$; one of the substituents R(2) and R(3) is hydrogen;
and the other substituent R(2) or R(3) in each case is $—C(OH)(CH_3)—CH_2OH$, $—CH(CH_3)—CH_2OH$ or $—C(OH)(CH_3)_2$;
R(4) is methyl, methoxy, Cl or $CF_3$;
and their pharmaceutically tolerable salts.
(DE 195 02 895, DE 44 30 212, EP 667 341, DE 44 04 183, EP 708 088, EP 723 963, EP 0 694 537, DE 44 21 495, EP 699 660, EP 699 663, EP 699 666)

II. or compounds of the formula

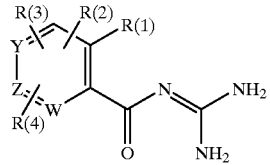

in which:
W, Y and Z are a nitrogen atom or a carbon atom substituted by R(2) or R(3) or R(4);
R(1) is hydrogen, A, Hal, $—CF_3$, $—CH_2F$, $—CHF_2$, $—CH_2CF_3$, $—C_2F_5$, —CN, $—NO_2$, -ethynyl, or an X—R';
A is alkyl having 1 to 6 carbon atoms;
Hal is F, Cl, Br or I;
X is oxygen, S or NR";
R" is hydrogen, A or a cyclic methylene chain having 3 to 7 carbon atoms;
R' is H, A, HO—A—, HOOC—A—, $(C_3–C_7)$-cycloalkyl, $(C_6–C_8)$-cycloalkylalkyl, $CF_3$, $CH_2F$, $CHF_2$, $CH_2—CF_3$, Ph, $—CH_2—Ph$ or Het;
Ph is phenyl, naphthyl or biphenylyl which is unsubstituted or mono-, di- or trisubstituted by A, OA, NR'R", Hal, $CF_3$;
Het is a mono- or binuclear saturated, unsaturated or aromatic heterocycle having 1 to 4 nitrogen, oxygen and/or sulfur atoms, which is unsubstituted or mono-, di- or trisubstituted by Hal, $CF_3$, A, OH, OA, —X—R', —CN, $—NO_2$, and/or carbonyl oxygen, where Het is bonded via N or an alkylene chain $C_mH_{2m}$ where m=zero to 6; or
R' and R" together are alkylene having 4–5 carbon atoms, in which one $CH_2$ group can also be replaced by oxygen, S, NH, N—A, N—Ph and N—$CH_2$—Ph;
R(2) and R(3) independently of one another are hydrogen, Hal, A, HO—A—, X—R', —C(═N—OH)—A, A—O—CO—$(C_1–C_4)$-alkyl-, CN, $NO_2$, COOH, halogen-substituted A, in particular $CF_3$, $CH_2F$, $CHF_2$, $C_2F_5$, $CH_2CF_3$, or $S(O)_nR'''$;

R''' is A, Ph or —Het;
n is zero, 1 or 2; or

R(2) and R(3) independently of one another are SO₂NR'R'', Ph or —O—Ph, —O—CH₂—Ph, —CO—A, —CHO, —COOA, —CSNR'R'', CONR'R'', —CH=CH—COOH, —CH=CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl; or R(2) and R(3) independently of one another are R(5)—O—; R(5) is hydrogen, A, (C₁–C₆)-alkenyl or (C₃–C₇)-cycloalkyl;

R(4) is Ph, Het, —O—Het; CF₃, S(O)ₙR''', —SO₂NR'R'', Alk;

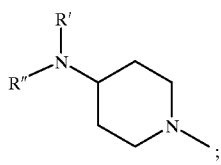

or two of the substituents R(1) to R(4) together are a group —O—CR(6)R(7)—CO—NR(8)—,

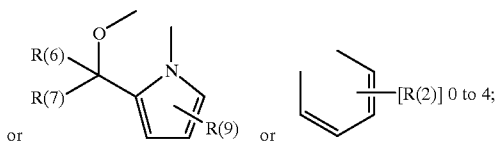

where R(2) has the meaning indicated;
R(6), R(7), R(8) and R(9) independently of one another are H or A; or
R(8) is (C₅–C₇)-cycloalkyl; or
R(9) is cyano;

Alk is straight-chain or branched (C₁–C₈)-alkyl or (C₃–C₈)-cycloalkyl, which is unsubstituted or mono-, di- or trisubstituted by A; or Alk is an ethenyl or ethynyl radical which is substituted by H, A, Ph or Het;
(DE 196 01 303-CAN 127:149157-AN 1997:556093) or compounds of the formula

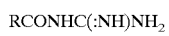

in which
R is substituted phenyl, such as, for example,

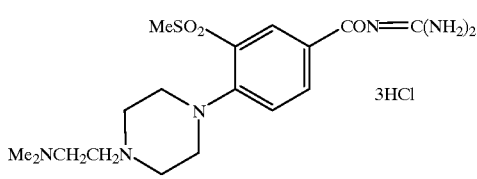

(WO99 33460-CAN 131:102102-AN 1999:468414) or compounds of the formula I

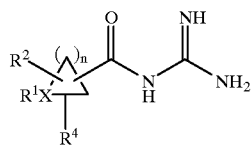

in which
n is 1–5;
X is N or CR5;
R5 is H, halogen, alkenyl, alkynyl, alkoxy, alkyl, aryl, heteroaryl;
R1–R4 are H, SH, OH, cyano, NO₂, alkyl, alkenyl, alkynyl, alkoxy, alkenyloxy, heteroaryloxy, alkyl, aryl, cycloalkyl, cycloalkenyl, amino, arylsulfonylamino, acyl;
(JP 09278767-CAN 127:358780-AN 1997:731402) or compounds of the formula

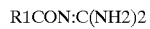

in which
R1 is an (un)substituted heterocyclic ring having 1 or 2 S atoms
(JP 10316647-CAN 130:38123-AN 1998:768072) or compounds of the formula

in which
R1 is phenyl, thienyl, pyridyl, furyl, unsubstituted or substituted by 1–3 lower alkyl, lower alkoxy, mono-, di- or trihalo-lower alkoxy, Cl, (un)protected hydroxyalkyl, acyl, cyano, acyl-lower alkenyl, di(lower alkyl)amino-lower alkoxy, amino, NO₂ or an (un) substituted heteropolycyclic group;
Y is CH₂, CR2R4R3R5, CR2:CR3;
(R2 and R3 are H, lower alkyl, lower alkanoylamino; or R2 and R3 together are alkylene;
R4, and R5 are H or lower alkyl);
(WO 98 55 475-CAN 130:52346-AN 1998:806652) or compounds of the formulae

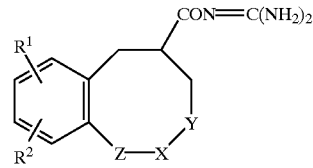

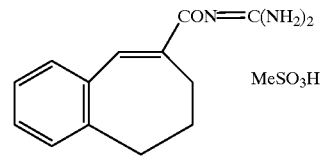

in which
X is CH₂, S, SO₂, O, NH;
Y is (CH₂)ₙ;
n is 0–3;
Z is (CH₂)ₘ;

is m is 0–2;

R1 and R2 are H, halogen, alkyl, alkoxy, NO$_2$, amino, aryl, heterocycle.

(WO 9426709-CAN 123:256771-AN 1995:835463) or compounds of the formulae

I

II in which

X, Y, Z are nitrogen or methine;

R2 is H or aryl;

R3 is H, alkoxy or hydroxyl;

(WO 9604241-CAN 125:33332-AN 1996:365475) or compounds of the formulae

I

II in which

R1 is H, hydroxyalkyl, protected hydroxyalkyl, acylalkoxy, acylalkenyl, acyl;

R2 is aralkenyl; disubstituted aryl, (un)substituted indenyl, indanyl, dihydrobenzocycloheptenyl, di- to decahydronaphthyl, cyclopentenyl, dihydrothienyl, dihydrofuryl or heterobicyclyl, alkylthienyl, mono- or dihalothienyl, haloalkylthienyl, acylthienyl, halofuryl, haloalkylfuryl;

(WO 9725310-CAN 127:149006-AN 1997:552669) or compounds of the formulae

I

II in which

R1 is di[(lower)alkylamino](lower)alkyl, morpholinyl (lower)alkyl, lower alkylpiperazinyl, [lower alkylpyrrolidinyl](lower)alkyl;

R2 is halogen, lower alkyl, lower alkoxy;

R3 is halogen, lower alkyl, lower alkoxy, mono- or di- or trihalo(lower)alkyl;

WO 9727183-CAN 127:190651-AN 1997:513628) or compounds of the formula

I in which

R1 is [mono-(or di-)(lower alkyl)amino](lower)alkyl, pyrrolidinyl, piperidyl;

R2 is dihalothienyl, dihalophenyl;

A is O, CH$_2$

U.S. Pat. No. 4,251,545-CAN 94:203837-AN 1981:203837) or compounds of the formula

RC(O)NHC(NH)NHR1 in which

R is C$_{7-30}$ alkoxyphenyl, alkenyloxyphenyl or alkoxynaphthyl, unsubstituted or substituted either in the aliphatic or the aromatic unit by halogen, OH or C$_{1-2}$-alkyl;

R1 is H, (C$_1$–C$_4$)-alkyl;

(EP 719 766-CAN 125:142752-AN 1996:497148) or compounds of the formula

I in which
R1 is H, (cyclo)alkyl;
R2 and R3 are H or alkyl one of R4 and R5 is CON:C(NH$_2$)$_2$ and the other is H;
(JP 08225513 CAN 125:328314-AN 1996:693764) or compounds of the formula

I in which
R is H, halogen or alkoxy
WO 9813357-CAN 128:244058-AN 1998:208536) or compounds of the formula

I in which
R1 is H or lower alkyl;
R2 and R3 are identical or different and are H or C$_{1-2}$-alkyl;
n is 0 or 2;
the guanidinocarbonyl substituent is in position 6 or 7;
(DE 195 02 895-CAN 125:167802-AN 1996:531770) or compounds of the formula

I in which
A is C$_{1-4}$-alkyl, halogen, (un)substituted phenyl;
R1 is A, CF$_3$, CH$_2$F, CHF$_2$, C$_2$F$_5$;
R2 is H, A cycloalkyl, (un)substituted phenyl, (un)substituted heterocyclyl;
(EP 758 644-DE 195 29 612-CAN 126:199350-AN 1997:211158) or compounds of the formula

I in which
R1 is alkyl, fluoroalkyl, CN, NO$_2$, halogen;
R2 is SO$_n$R$_4$, (un)substituted SO$_2$NH$_2$, NO$_2$, CF$_3$;
R3 is H, halogen, alkyl, OH, alkoxy, CN, NO$_2$, CF$_3$, fluoroalkyl;
R4 is alkyl, phenyl, heterocyclyl, cycloalkyl;
n is 1 or 2;
(EP 760 365-DE 195 31 138-CAN 126:250994-AN 1997:265436) or
compounds of the formulae

I

II in which
R1 and R2 are H, halogen, alkyl, cyano, NO$_2$, CF$_3$, CH$_2$F, CHF$_2$, C$_2$F$_5$, CH$_2$CF$_3$, SO$_n$R4;
R3 is CR5:CR6R7, CR5R6CR7:CR8R9, CR5R6CR7R8CR9:CR10OR11, cycloalkenyl, cycloalkenylalkyl;
R4 is alkyl, (un)substituted phenyl;
R5–R11 are H, alkyl;
n is 1 or 2;
(DE 195 48 708-CAN 127:121628-AN 1997:522550) or compounds of the formula

I in which
R1 and R2 are H, alkyl, CF$_3$, CH$_2$F, CHF$_2$, halogen, OH, alkoxy, amino, NO$_2$, cyano;
Q is (R8R9C)$_n$;
X is CR4R5, C:Z, O, S, imino;
Y is CR6R7, C:Z, O, imino;

Z is O, S, imino, NOH, CH$_2$;
R5–R8 are H, alkyl, halogen, OH, alkoxy, SH, alkylthio, amino; R5R6 or R7R8 are a bond; or
R4R5 is OCH$_2$CH$_2$O, O(CH$_2$)$_3$O;
R8 and R9 are H, alkyl;
n is 0 or 1;
(DE44 21 495-CAN 124:260851-AN 1996:211768) or compounds of the formula

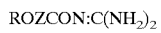

in which
R is heterocyclyl;
Z is (un)substituted phenylene;
(DE 44 30 212-CAN 124:316763-AN 1996:285034) or compounds of the formula

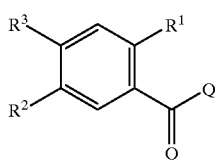

in which
Q N:C(NH$_2$)$_2$, Cl, Br, O$_2$CPh, OH, a nucleophilically substituted leaving group;
R1 is alkyl, CF$_3$, halogen;
R2 is CF$_3$, alkylsulfonyl, alkylsulfoxyl, phenylsulfonyl, phenyl-SO, (un)substituted SO$_2$NH$_2$;
R3 is CN, halogen, CHO, (un)substituted CONH$_2$, (un)substituted CSNH$_2$;
(EP 667 341-CAN 123:256532-AN 1995:846650) or compounds of the formula

in which
R is an aminopiperidino group Q;

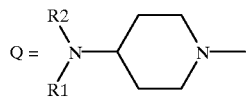

Z is (un)substituted phenylene;
R1 and R2 are H, (phenyl)alkyl, phenyl, alkanoyl;
NR1R2 is heterocyclyl;
(EP 699 663-CAN 124:342875-AN 1996:303737) or compounds of the formula

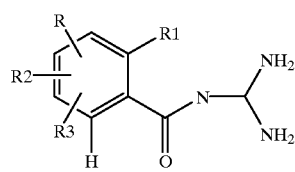

in which
R is alkyl, ethenyl, ethynyl;
R1 is fluoromethyl, halogen, alkyl, alkoxy;
R2 and R3 are H, halogen, alkyl, alkoxy;
(EP 699 666-CAN 124:343303-AN 1996:303752) or compounds of the formula

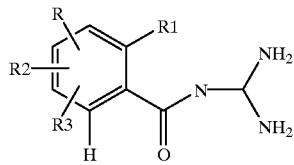

in which
R is heterocyclyl, heteroaryl;
R1 is fluoromethyl, halogen, alkyl, alkoxy;
R2 and R3 are H, halogen, alkyl, alkoxy
(EP 708 088-CAN 125:58122-AN 1996:377036) or compounds of the formula

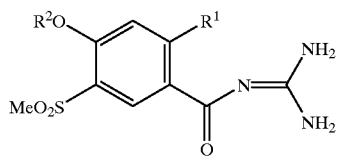

in which
R1 is methyl or ethyl;
R2 is H, alkyl, phenyl, CH$_2$Ph;
(EP 723 963-CAN 125:195210-AN 1996:548444) or compounds of the formula

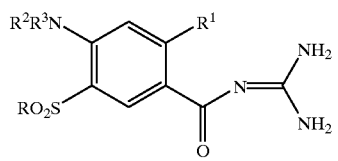

in which
R is alkyl;
R1 is alkyl, CF$_3$, CH$_2$F, CHF$_2$, C$_2$F$_5$;
R2 and R3 are H, (cyclo)alkyl, phenyl, heterocyclyl;
NR2R3 is heterocyclyl;
(EP 743 301-CAN 126:46984-AN 1997:213) or compounds of the formula

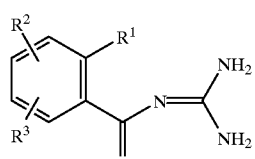

in which
R1 is H, F, Cl, Br, alkyl, CN, NO$_2$, C$_n$F$_m$H$_{(2n+1-m)}$O$_p$;
m is 1–7; but at most (2n+1);

n is 1–3;

p is 0 or 1;

R2 is $C_nF_mH_{(2n+1-m)}O_p$;

R3 is H, alkyl, F, Cl, Br, I, $C_nF_mH_{(2n+1-m)}O_p$;

(EP 726 254-CAN 125:221603-AN 1996:567309) or compounds of the formula

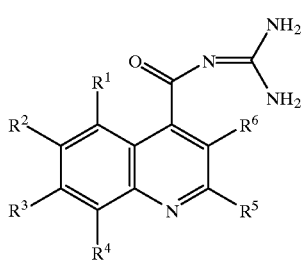

I in which

R1–R4 are H, halogen, alkyl, alkoxy;

R5 is (un)substituted phenyl;

R6 is H or alkyl;

(WO 8400875-CAN 101:191387-AN 1984:591387) or compounds of the formula

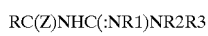

RC(Z)NHC(:NR1)NR2R3 in which

R is phenylalkyl, phenylalkenyl, heteroaryl;

Z is O or S;

R1 H oder Alkyl;

R2 and R3 are H, alkyl, haloalkyl, cycloalkyl, aralkyl, alkenyl, aryl, alkynyl, alkoxy, acyl, heteroaryl, or NR2R3 form a heterocycle;

(WO 95 04052-CAN 123:256498-AN 1995:849163) or compounds of the formula

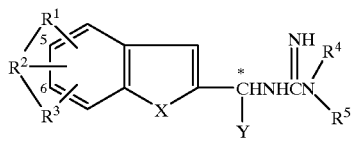

I in which

R1–R3 are H, halogen, alkyl, alkoxy, phenyl, phenyl-CH$_2$;

R4 and R5 are H, $C_{6-12}$-alkyl, benzohydryl, (un)substituted aralkyl;

X is O, S, (un)substituted NH;

Y is an (un)substituted heterocycle or 2,3-dihydroheterocycle;

R1–R3 are $C_{4-6}$ cyclic hydrocarbon;

(EP 622 356-CAN 123:169498-AN 1995:781759) or compounds of the formula

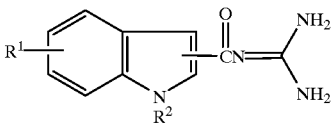

I in which

R1 is H, alkyl, alkenyl;

R2 is H, alkyl, cycloalkyl;

(EP 787 728-CAN 127:220587-AN 1997:553174) or compounds of the formulae

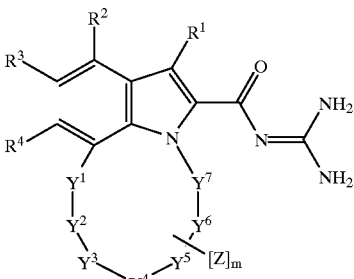

I

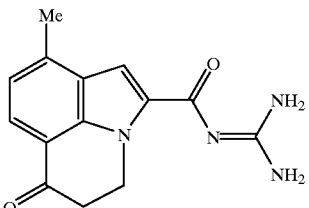

II in which

R1–R4 are H, alkyl, cycloalkyl;

Y1–Y7 are a single bond, CH$_2$, O;

Z is alkyl, alkenyl, alkynyl;

m is 2–5;

(EP 803501-CAN 128:13199-AN 1997:720110) or

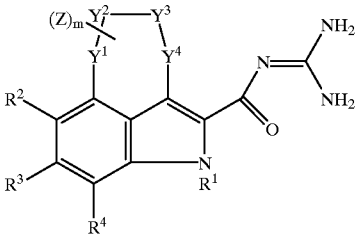

I

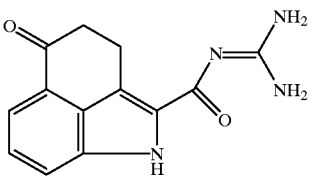

II compounds of the formulae in which
- R1 is H, alkyl, cycloalkyl;
- R2–R4 are H, alkyl, cycloalkyl;
- Y1–Y4 are a bond, $CH_2$, C(O), O;
- Z is alkyl, alkenyl, alkynyl;
- m is 0–2;

(JP 09268172-CAN 127:331294.-AN 1997:681908) or compounds of the formula

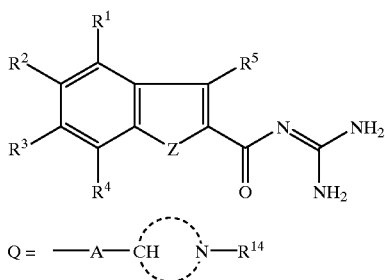

in which
- Z is CR6R7, CO, C:CR8R9;
- R1–R4 are H, (un)substituted alkyl, cycloalkyl, cycloalkenyl, saturated heterocyclyl, halogen, $NO_2$, $CO_2H$, alkoxycarbonyl, aryl, (un)substituted OH, $NH_2$, or $SO_2NH_2$, $S(O)_nR_{13}$ (n=0, 1 or 2), $(CR_aR_b)_s(CRcRd)_t(CReRf)_uR$ (R=CRg:CRhRi, C≡CRj, CORk), Q;
- R5–R9 are H, (un)substituted alkyl, cycloalkyl, cycloalkenyl, saturated heterocyclyl, halogen, $CO_2H$, alkoxycarbonyl, aryl, (un)substituted OH or $NH_2$, $(CR_aR_b)_s(CRcRd)_t(CReRf)_uR$ (R=CRg:CRhRi, C≡CRj, CORk), Q;
- R13 is (un)substituted alkyl, aryl;
- Ra–Rj are H, (un)substituted alkyl, cycloalkenyl, saturated heterocyclyl, aryl, $CO_2H$, alkoxycarbonyl;
- Rk is H, (un)substituted alkyl, cycloalkyl, cycloalkenyl, saturated heterocyclyl, aryl;
- s, t and u are 0 or 1;
- A is $S(O)_n$ (n=0, 1 or 2), (un)substituted NH;
- R14 is H, (un)substituted alkyl;

(JP 10237073-CAN 129:290150-AN 1998:594520) or compounds of the formulae

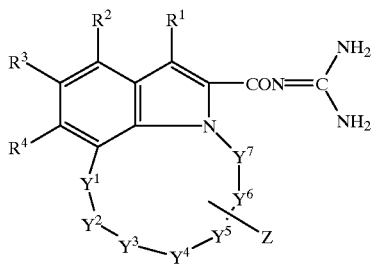

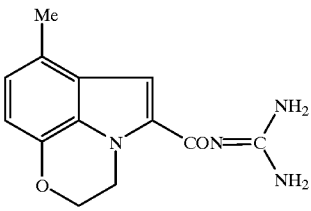

in which
- R1, R2, R3 and R4 are H, (un)substituted alkyl, cycloalkyl, cycloalkenyl, saturated heterocyclyl, halogen, $NO_2$, COOH, alkoxycarbonyl, aryl, acyl;
- Y1–Y7 are a bond, $CH_2O$, CO, (un)substituted $C(:CH_2)$, S, SO, $SO_2$, (un)substituted NH;
- Z is (un)substituted $NH_2$, $S(O)_nR8$;
- n is 0, 1 or 2;
- R8 is (un)substituted alkyl, aryl;

(EP 825187-CAN 128:204895-AN 1998:163375) or compounds of the formula

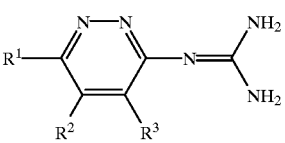

in which
- R1 is an (un)substituted aromatic ring;
- R2 and R3 are atoms which combine to form an (un)substituted fused-on (N-containing) aromatic ring;

(JP 10114744-CAN 128:308500-AN 1998:277363) or compounds of the formulae

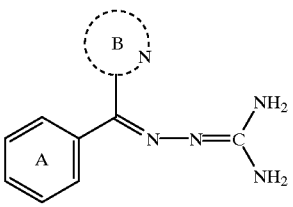

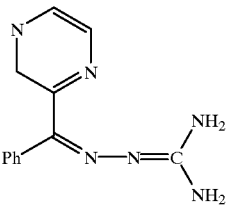

in which
- ring A is an (un)substituted benzene ring;
- ring B is an (un)substituted N-containing 6-membered aromatic ring, such as pyridine, pyrimidine, pyrazine or pyridazine;

(WO 9839300-CAN 129:230644-AN 1998:612074) or compounds of the formula

*Structure I: bicyclic pyridine with substituents B, D, E, R1, and A—C(=O)—N=C(NH2)(NH2) group* in which

R1 is H, halogen, lower alkyl, lower alkoxy, amino-lower alkyl, lower alkoxyalkyl, aryl, heterocyclyl, aralkyl, phenoxy-substituted lower alkyl or aralkyloxy-substituted lower alkyl;

R2 is H, halogen, lower alkoxy or nitro;

A is a bond or vinylene;

B is vinylene, —CH₂P1(R3)—;

R3 is H, halogen, OH, lower alkyl, lower alkylidene, lower alkoxy, hydroxy-lower alkyl, aralkyl, aralkylidene, phenoxy-lower alkyl, hydroxyimino, lower alkoxyimino, oxo, CH₂ONO₂, CH₂CH₂ONO₂;

P1 is methine or C;

D is a bond, methylene or ethylene;

E is vinylene, Q, —Q1(R5)—P2(R4)—;

R4 is H, halogen, (un)protected hydroxyl or oxo;

R5 H or lower alkyl;

P2 is methine or O;

(JP 09067332-CAN 126:277285-AN 1997:281002) or compounds of the formulae

*Structure I: naphthalene with R3, R4 substituents and CR¹=CR²CON=C(NH2)(NH2) group*

*Structure II: 1-methoxy-4-chloro-naphthalene with CH=C(Et)COR group* in which

R1 and R2 are H, halogen, lower (halo)alkyl;

R3 and R4 are H, lower(halo)alkyl, alkenyl, alkynyl, cycloalkyl, alkoxy, alkoxyalkoxy or alkoxycarbonyl, COOH, halogen, NO₂, NH₂, mono- or di(lower alkyl) amino, lower alkyl, alkanoyl, alkanoylamino or alkanoyloxy, OH, SH, lower alkylthio, alkylsulfonyl, SO₂NH₂, lower alkylsulfonylamino, (lower alkylsulfonyl)(lower alkyl)amino, CONH₂, di(lower alkyl))aminocarbonyl;

(JP 090 67 340-CAN 126:277384-AN 1997:265522) or compounds of the formulae

*Structure I: indole with R3, R4, R5 substituents and CR¹=CR²CON=C(NH2)(NH2) group*

*Structure II: N-methylindole with C(CH₂CH₃)=C(H)COX group* in which in R1 and R2 are H, halogen, substituted lower alkyl;

R3 and R4 are H, substituted lower alkyl, lower alkenyl or alkynyl;

R5 is H, substituted lower alkyl, aralkyl;

(JP 10175939-CAN 129:148825-AN 1998:423972) or compounds of the formula

*Structure I: R¹—A—[phenyl]ₙ—[X]ₘ—[phenyl]—C(R³)=C(R²)—CO—N=C(NH2)(NH2) with R4 substituent* in which

X is O or S;

n and m are 0 or 1;

A is lower alkylene;

R1 is protected OH, NH₂ or alkylamino;

R2 and R3 are H, halogen, (un)substituted alkyl;

R4 is H, halogen, lower alkoxy;

(JP 10237077-CAN 129:230648-AN 1998:586326) or compounds of the formula

*Structure: ring B—C(R1)(R2)—C(A)(R3)—C(=O)—N=C(N)(N)—ring A* in which ring A is (substituted) 5- or 6-membered heteroaryl;

ring B is (substituted) aryl;

R1–R3 are H, (F-substituted) lower alkyl (JP 09059245-CAN 126:277281-AN 1997:280921) or compounds of the formula

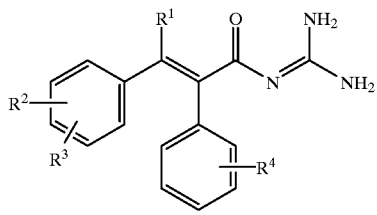

I in which
R1 is H, halogen, lower alkyl;
R2, R3 and R4 are H, lower (halo)alkyl, lower alkenyl, lower alkynyl, cycloalkyl, lower alkoxy, lower alkoy-lower alkyl, lower alkoxycarbonyl, COOH, halogen, $NO_2$, cyano, $NH_2$, mono- or di(lower alkyl)amino, lower alkanoyl, lower alkanoylamino, lower alkanoyloxy, OH, SH, lower alkylthio, lower alkylsulfonyl, mono- or di(lower alkyl)aminosulfonyl;
(WO 9711055-CAN 126:264101-AN 1997:284248) or compounds of the formula

in which
A is an (un)substituted fused benzene ring, a 5- or 6-membered heterocycle;
B is (un)substituted aryl;
R1 is H, halogen, non-halogenated or halogenated lower alkyl;
(WO 98 27 061-CAN 129:95491-AN 1998:424227) or compounds of the formulae

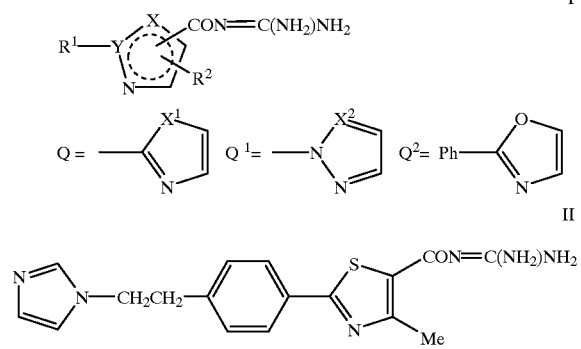

in which
the five-membered heteroaryl ring in formula I is Q or Q1;
X1 is oxygen, S or NR3;
X2 is N or CR4;
R1 is unsubstituted or substituted aryl or unsubstituted or substituted 5- or 6-membered monocyclic heteroaryl;
R2 is H, halogen, unsubstituted or halogen-substituted lower alkyl, lower alkoxy, lower alkylthio, or unprotected or protected amino;
R3 and R4 are H, or unsubstituted or halogen-substituted lower alkyl;
(EP 708091-CAN 125:58312-AN 1996:379686) or compounds of the formulae

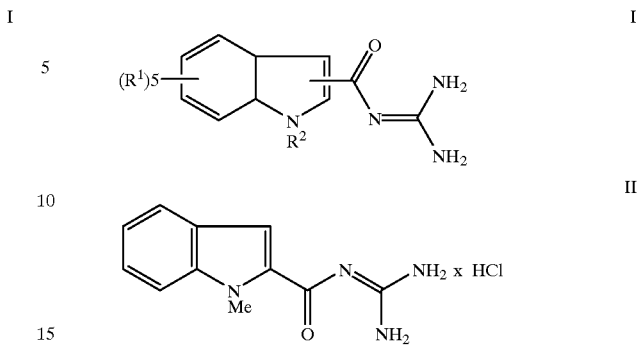

in which
R1 is H, (un)substituted alkyl, alkenyl, alkynyl, cycloalkyl, halogen, $NO_2$, acyl, COOH, alkoxycarbonyl, an aromatic group, (un)substituted OH, $NH_2$, $SO_2NH_2$;
R2 is H, (un)substituted alkyl, cycloalkyl, OH, alkoxy;
(DE 41 27 026, DE 43 37 609, JP 07025768, Edward J. Cragoe, Jr., DIURETICS—Chemistry, Pharmacology and Medicine), J. Wiley & Sons (1983), 303–341);
III. or compounds of the formula

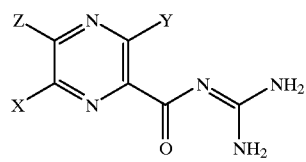

in which:
X is H, Hal, $(Hal)_3C-$, $(C_1-C_6)$-alkyl, $(C_3-C_6)$-cycloalkyl, substituted phenyl, $(C_1-C_5)$-alkyl-S— or $(C_1-C_5)$-alkyl—$SO_2$—;
Y is $NH_2$ or substituted amino; or
X and Z together form a —$(CH_2)_4$— or a 1,3-butadienylene chain; or
Z is H, Hal, OH, HS, $(C_1-C_5)$-alkyl, $(C_3-C_6)$-cycloalkyl, substituted phenyl; or
Z is an amino group —NR(1)R(2);
R(1) is H, straight-chain or branched, unsubstituted or substituted $(C_1-C_8)$-alkyl which may be interrupted by oxygen; or
R(1) is $(C_3-C_8)$-alkenyl, $(C_3-C_8)$-alkynyl, $(C_3-C_7)$-cycloalkyl or OH-substituted phenyl or OH-substituted phenyl-$(C_1-C_4)$-alkyl or OH-substituted $(C_3-C_7)$-cycloalkyl;
R(2) is 1-morpholino, hydrogen or a straight-chain or branched $(C_1-C_8)$-alkyl chain;
which may be interrupted by oxygen, an amino group, which straight-chain or branched $(C_1-C_8)$-alkyl chain is unsubstituted or substituted by a substituted or unsubstituted mono- or polycyclic heterocycle which contains nitrogen, oxygen or sulfur atoms; or
which alkyl chain is substituted by phenyl, unsubstituted or mono- or polysubstituted by $(C_1-C_4)$-alkoxy, unsubstituted or substituted by OH, alkylamino, alkyl or phenyl; or
by an aminocarbonyl group or
by hydroxyl, $(C_1-C_4)$-alkoxy groups, or R(2) is phenyl, unsubstituted or substituted by alkyl, alkoxy, an amino group which carries, as substituents:
H, a mono- or polycyclic heterocycle which contains nitrogen, oxygen or sulfur atoms, which is unsubstituted or substituted by H, Hal or ($C_1$–$C_4$)-alkyl;
a phenyl radical, unsubstituted or substituted by a substituent selected from the group consisting of ($C_1$–$C_4$)-alkyl, ($C_1$–$C_4$)-alkoxy, Hal and OH; or
R(2) is 1-piperidino, unsubstituted or substituted in the 4-position by an acyl radical of an aliphatic, alicyclic, aromatic or heteroaromatic carboxylic acid, ($C_1$–$C_8$)-alkyl, which for its part may be substituted by OH or ($C_1$–$C_4$)-alkoxy or a ($C_1$–$C_4$)-alkoxy-substituted phenyl radical; or
R(2) is amidino, which is unsubstituted or substituted by phenyl, which is unsubstituted or substituted by Hal or alkyl; or
R(2) is an acyl radical of an aliphatic, alicyclic, aromatic or heteroaromatic carboxylic acid, or
R(2) is a ($C_1$–$C_8$)-alkyl chain which may be substituted by a phenyl radical carrying OH, alkoxy or alkyl radicals, or
R(1) and R(2) together with the N atom to which they are attached form a piperazine ring, which is unsubstituted or carries, via a ($C_1$–$C_6$)-methylene chain, a mono- or polycyclic heterocycle, which contains nitrogen, oxygen or sulfur (DE 41 27 026 and DE 43 37 609);
Hal is F, Cl, Br or I;
(EP 708 091, EP 622 356, JP 5-125085)
IV. or indoloylguanidine derivatives of the formula

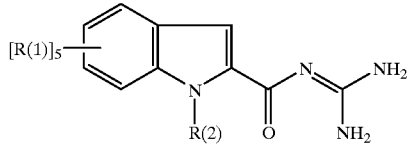

in which
R(2) is hydrogen, unsubstituted or substituted ($C_1$–$C_8$)-alkyl, ($C_3$–$C_7$)-cycloalkyl, OH, ($C_1$–$C_6$)-alkyl-O—, an aromatic radical or a group —$CH_2$—R(20);
R(20) is ($C_2$–$C_6$)-alkenyl or ($C_2$–$C_6$)-alkynyl;
R(1) is 1 to 5 identical or different substituents, which are: hydrogen, unsubstituted or substituted ($C_1$–$C_8$)-alkyl, ($C_2$–$C_6$)-alkenyl, ($C_2$–$C_6$)-alkynyl, ($C_3$–$C_7$)-cycloalkyl, halogen, —$NO_2$, ($C_2$–$C_8$)-alkanoyl, arylalkanoyl having up to 10 carbon atoms, aroyl having up to 11 carbon atoms, —COOH, ($C_2$–$C_6$)-alkoxycarbonyl, an aromatic group or one of the following groups: —OR(3), —NR(6)R(7) or —S(O)$_n$R40);
R(3) is hydrogen, ($C_1$–$C_8$)-alkyl, substituted ($C_1$–$C_8$)-alkyl, ($C_3$–$C_7$)-cycloalkyl, an aromatic radical or a group —$CH_2$—R(30); R(30) is alkenyl or alkynyl;
R(6) and R(7) independently of one another are hydrogen, unsubstituted or substituted ($C_1$–$C_8$)-alkyl, ($C_3$–$C_7$)-cycloalkyl, ($C_2$–$C_8$)-alkanoyl, an arylalkanoyl group having up to 10 carbon atoms, an aroyl group having up to 11 carbon atoms, an aromatic group or —$CH_2$—R(60);
R(60) is ($C_2$–$C_6$)-alkenyl or ($C_2$–$C_6$)-alkynyl; or
R(6) and R(7) together with the nitrogen atom are a 5–7-membered cyclic amine, which can additionally contain further heteroatoms in the ring;

n is zero, 1 or 2;
R(40) is unsubstituted or substituted ($C_1$–$C_8$)-alkyl, or an aromatic group, or a group

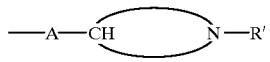

A is oxygen, —S(O)$_n$— or —N(R50)—; R(50) is hydrogen or ($C_1$–$C_8$)-alkyl;
R' is hydrogen, unsubstituted or substituted ($C_1$–$C_8$)-alkyl, in which the ring represents a saturated 3–8-membered heterocycle having a nitrogen atom,
said substituted alkyl carries one or more groups selected from the group consisting of halogen, —OH, ($C_1$–$C_6$)-alkoxy, —CN, —COOH, ($C_2$–$C_6$)-alkoxycarbonyl, ($C_2$–$C_8$)-alkanoyl, arylalkanoyl having up to 10 carbon atoms, aroyl having up to 11 carbon atoms, an aromatic group, —CONR(4)(R5),
R(4) and R(5) identically or differently are hydrogen or ($C_1$–$C_8$)-alkyl; or
R(4) and R(5) are connected to one another and together form a 5–7-membered cyclic amine which can additionally contain further heteroatoms in the ring,
or said substituted alkyl carries a group

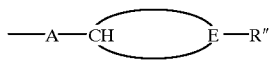

in which:
E is a nitrogen atom or a CH group;
R" is hydrogen, ($C_1$–$C_8$)-alkyl which is unsubstituted or substituted by OH or substituted ($C_1$–$C_8$)-alkyl, ($C_1$–$C_6$)-alkoxy, —CN, —COOH, ($C_2$–$C_6$)-alkoxycarbonyl, ($C_2$–$C_8$)-alkanoyl, aralkanoyl having up to 10 carbon atoms, aroyl having up to 11 carbon atoms, an aromatic group, —NR(6)R(7), —CONR(4)R(5);
R(4) and R(5) independently of one another are hydrogen or ($C_1$–$C_8$)-alkyl;
where the cyclic system of the formula

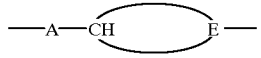

is a 3–8-membered saturated aliphatic or heterocyclic ring system having a nitrogen atom,
and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where the aryl radicals mentioned can be unsubstituted or substituted by unsubstituted ($C_1$–$C_8$)-alkyl or substituted ($C_1$–$C_8$)-alkyl, halogen, —$NO_2$, ($C_2$–$C_6$)-alkoxycarbonyl, COOH, —OR(3), NR(6)R(7), —CONR(4)R(5), —$SO_2$NR(6)R(7) or S(O)$_n$R40),
where R(1) and the guanidinocarbonyl radical can be in any desired position of the 5- or 6-membered ring of the indole system, and the appropriate pharmaceutically tolerable salts.

(WO 95 04052)
V. or heterocyclic guanidine derivatives of the formula

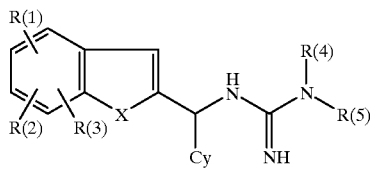

in which:
X is —O—, —S—, —NH—, —N[(C$_1$–C$_4$)-alkyl]- or —N(phenyl)-;
R(1), R(2) and R(3) are hydrogen, halogen, (C$_1$–C$_4$)-alkyl, (C$_1$–C$_4$)-alkyl-O—, phenyl, benzyl; or
two of the substituents R(1), R(2) and R(3) together with one side of the benzo system are a 4–6-membered carbocyclic ring;
R(4) and R(5) independently of one another are hydrogen, (C$_1$–C$_{12}$)-alkyl, benzhydryl, aralkyl, which is unsubstituted or substituted by one or more substituents from the groups halogen, (C$_1$–C$_4$)-alkyl, (C$_1$–C$_4$)-alkyl-O— or —CF$_3$, —(CH$_2$)$_m$—CH$_2$—T,
m is zero to 3;
T is —CO—O—T(1); T(1) is hydrogen or (C$_1$–C$_4$)-alkyl;
Cy is a benzo-fused unsaturated or dihydro-5-membered ring heterocycle,

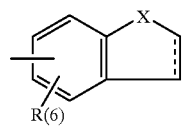

a pyrazole or imidazole ring of the formulae

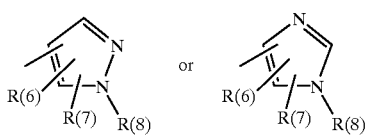

a naphthyl radical or a dihydro or tetrahydronaphthyl radical

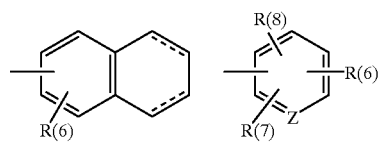

a 2-, 3- or 4-pyridyl radical
Z is N— or CH

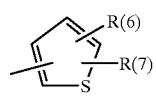

a thienyl radical
R(6) is hydrogen, halogen, hydroxyl, (C$_1$–C$_{10}$)-alkyl, (C$_1$–C$_{10}$)-alkyl-O—, phenoxy, (C$_1$–C$_{10}$)-alkyloxymethyloxy- or —(O)$_n$S—R(9);

R(9) is (C$_1$–C$_{10}$)-alkyl, thienyl, pyridyl, thiazolyl, thiadiazolyl, imidazolyl, pyrazolyl or phenyl, each of which is unsubstituted or mono- or disubstituted by halogen, (C$_1$–C$_4$)-alkyl or (C$_1$–C$_4$)-alkyl-O—;
R(7) and R(8) are hydrogen, halogen, hydroxyl, (C$_1$–C$_{10}$)-alkyl, (C$_1$–C$_{10}$)-alkyl- O—, phenyl, phenoxy or (C$_1$–C$_{10}$)-alkoxymethyloxy; or
Cy is phenyl, which is unsubstituted or is mono- or disubstituted by halogen, (C$_1$–C$_4$)-alkyl or (C$_1$–C$_4$)-alkyl-O—; or
Cy is —Gr—Am;
Gr is —R(13)—R(12)—(CH$_2$)$_q$—C[W][W(1)]—(CH$_2$)$_{q'}$—; R(13)R(14)— or —R(15)—;
R(12) is a single bond, —O—, —(O)$_n$S—, —CO— or —CONH—;
R(13) is a single bond, phenyl, thienyl, pyridyl, thiazolyl, thiadiazolyl, imidazolyl or pyrazolyl;
R(14) is a single bond or SO$_2$—;
R(15) is (C$_2$–C$_{10}$)-alkenyl or (C$_2$–C$_{10}$)-alkynyl;
W and W(1) independently of one another are hydrogen, (C$_1$–C$_4$)-alkyl; or
W and W(1) cyclically connected to one another are a (C$_3$–C$_8$)-hydrocarbon ring;
q and q' are zero to 9;
Am is —NR(10)R(11);
R(10) is hydrogen, (C$_1$–C$_4$)-alkyl or benzyl,
R(11) is (C$_1$–C$_4$)-alkyl, phenyl or benzyl; or
R(10) and R(11) together are a (C$_3$–C$_{10}$)-alkylene group, which is unsubstituted or substituted by —COOH, (C$_1$–C$_5$)-alkoxycarbonyl, (C$_2$–C$_4$)-hydroxyl-alkylene or benzyl; or
Am is pyrrolyl, pyridyl, pyrazolyl, morpholinyl, dihydropyridyl, tetrahydropyridyl, quinuclidinyl, imidazolyl, 3-azabicyclo[3.2.1]octyl, which is unsubstituted or substituted by (C$_1$–C$_4$)-alkyl, or
Am is azabicyclo[3.2.2]nonyl; or
Am is a piperazine group of the formula

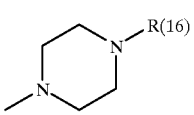

R(16) is hydrogen, (C$_1$–C$_4$)-alkyl, (C$_3$–C$_6$)-cycloalkyl, phenyl, tolyl, methoxyphenyl, halophenyl, diphenylmethylene, benzyl or pyridyl; or
Am is an azido group —(O)t—(CH$_2$)q—C[W][W(1)]—(CH$_2$)q'—N$_3$;
t is zero or 1;
where W and W(1) have the previously indicated meaning;

and the optical enantiomers and the pharmacologically tolerable salts.

VI. or guanidine compounds as described in

EP-743 301 (DE 195 17 848), EP 758 644 (DE 195 29 612), EP 760 365 (DE 195 31 138)

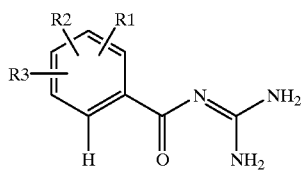

where R1=R2 is H, halogen, alkyl, CN, $NO_2$, perfluoroalkyl, $SO_nCF_3$; R3 is $CH=CH_2$, $CH_2-CH=CH_2$, $CH_2-CH_2-CH=CH_2$, cycloalkenyl, cycloalkenylalkyl; R4 is alkyl, (substituted) phenyl.

Preference is given to using the compounds described below:

(HOE 89/F 288 U.S. Pat. No. 5,292,755)

a) benzoylguanidines of the formula I

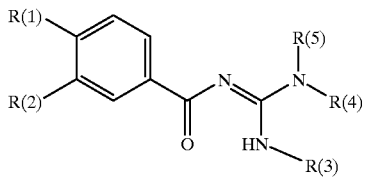

in which:
R(1) or R(2) is $R(6)-S(O)_n-$ or $R(7)R(8)N-O_2S-$;
and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chlorine, methyl and methoxy;
or the other substituent R(1) or R(2) in each case is $R(6)-S(O)_n$ or $R(7)R(8)N-$;
n is zero, 1 or 2;
R(6) is $(C_1-C_6)$-alkyl, $(C_5-C_7)$-cycloalkyl, cyclopentylmethyl, cyclohexylmethyl or phenyl, which is unsubstituted or substituted by 1–3 substituents selected from the group consisting of fluorine, chlorine, methyl and methoxy;
R(7) and R(8) identically or differently are H or $(C_1-C_6)$-alkyl; or
R(7) is phenyl-$(CH_2)_m$;
m is 1–4; or
R(7) is phenyl, which is unsubstituted or substituted by 1–2 substituents selected from the group consisting of fluorine, chlorine, methyl and methoxy; or
R(7) and R(8) together are a straight-chain or branched $(C_4-C_7)$-chain, where the chain can additionally be interrupted by O, S or NR(9);
R(9) is H or methyl; or
R(7) and R(8) together with the nitrogen atom to which they are bonded, are a dihydroindole, tetrahydroquinoline or tetrahydroisoquinoline system;
R(3), R(4) and R(5) independently of one another are H or $(C_1-C_2)$-alkyl, or
R(3) and R(4) together are a $(C_2-C_4)$-alkylene chain; or
R(4) and R(5) together are a $(C_4-C_7)$-alkylene chain;
and their pharmaceutically tolerable salts;

(HOE 92/F 34 U.S. Pat. No. 5,373,924)

b) benzoylguanidines of the formula I

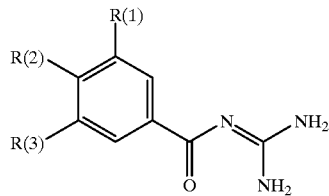

in which:
R(1) is $R(4)-SO_m$ or $R(5)R(6)N-SO_2-$;
m is zero, 1 or 2;
R(4) and R(5) are $C_1-C_8$-alkyl, $C_3-C_6$-alkenyl or $-C_nH_{2n}-R(7)$;
n is zero, 1, 2, 3 or 4;
R(7) is $C_5-C_7$-cycloalkyl or phenyl, which is unsubstituted or substituted by 1–3 substituents selected from the group consisting of F, Cl, $CF_3$, methyl, methoxy and NR(8)R(9);
R(8) and R(9) are H or $C_1-C_4$-alkyl; or
R(5) is H;
R(6) is H or $C_1-C_4$-alkyl, or
R(5) and R(6) together are 4 or 5 methylene groups, of which one $CH_2$ group can be replaced by an O, S, NH, $N-CH_3$ or N-benzyl;
R(2) is hydrogen, F, Cl, Br, $(C_1-C_4)$-alkyl-, $O-(CH_2)_mC_pF_{2p+1}$ or $-X-R(10)$;
m is zero or 1;
p is 1, 2 or 3;
X is O, S or NR(11);
R(10) is H, $C_1-C_6$-alkyl, $C_5-C_7$-cycloalkyl, cyclohexylmethyl, cyclopentylmethyl or $-C_nH_{2n}-R(12)$;
n is zero, 1, 2, 3 or 4;
R(12) is phenyl, which is unsubstituted or substituted by 1–3 substituents selected from the group consisting of F, Cl, $CF_3$, methyl, methoxy and NR(8)R(9);
R(8) and R(9) are H or $C_1-C_4$-alkyl;
R(11) is hydrogen or $C_1-C_3$-alkyl; or
R(10) and R(11) together are 4 or 5 methylene groups, of which one $CH_2$ group can be replaced by O, S, NH, $N-CH_3$ or N-benzyl;
R(3) is defined as R(1), or is $C_1-C_6$-alkyl, nitro, cyano, trifluoromethyl, F, Cl, Br, 1 or $-X-R(10)$;
X is O, S or NR(11);
R(10) is H, $C_1-C_6$-alkyl, $C_5-C_7$-cycloalkyl, cyclohexylmethyl, cyclopentylmethyl or $-C_nH_{2n}-R(12)$;
n is zero to 4;
R(12) is phenyl, which is unsubstituted or substituted by 1–3 substituents selected from the group consisting of F, Cl, $CF_3$, methyl, methoxy und NR(8)R(9);
R(8) and R(9) are H or $C_1-C_4$-alkyl;
R(11) is $C_1-C_3$-alkyl, or
R(10) and R(11) together are 4 or 5 methylene groups, of which one $CH_2$ group can be replaced by O, S, NH, $N-CH_3$ or N-benzyl;
and their pharmaceutically tolerable salts;

(HOE 92/F 035 EP-A 556 673)

c) ortho-substituted benzoylguanidines of the formula I

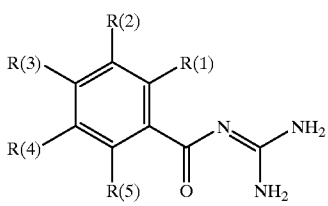

in which:
R(1) is F, Cl, Br, I, $C_1$–$C_6$-alkyl or —X—R(6);
X is O, S, NR(7) or Y—ZO;
Y is O or NR(7);
Z is C or SO;
R(6) is H, $C_1$–$C_6$-alkyl, $C_5$–$C_7$-cycloalkyl, cyclohexylmethyl, cyclopentylmethyl, —$(CH_2)_m C_p F_{2p+1}$ or —$C_n H_{2n}$—R(8);
m is zero or 1;
p is 1–3;
n is zero to 4;
R(8) is phenyl, which is unsubstituted or substituted by 1–3 substituents selected from the group consisting of the groups F, Cl, $CF_3$, methyl, methoxy and NR(9)R(10);
R(9) and R(10) are H or $C_1$–$C_4$-alkyl;
R(7) is H or $C_1$–$C_3$–alkyl; or
R(6) and R(7) together are 4 or 5 methylene groups, of which one $CH_2$ group can be replaced by O, S, NH, N—$CH_3$ or N-benzyl;
R(3) is H or —X—R(6);
X is O, S, NR(7) or Y—ZO;
R(7) is H or $C_1$–$C_3$-alkyl;
Y is O or NR(7); where Y is bonded to the phenyl radical of the formula I,
Z is C or SO;
R(6) is H, $C_1$–$C_6$-alkyl, $C_5$–$C_7$-cycloalkyl, cyclohexylmethyl, cyclopentylmethyl, —$(CH_2)_m C_p F_{2p+1}$ or —$C_n H_{2n}$—R(8);
m is zero or 1;
p is 1–3;
n is zero to 4;
R(8) is phenyl, which is unsubstituted or substituted by 1–3 substituents selected from the group consisting of F, Cl, $CF_3$, methyl, methoxy and NR(9)R(10);
R(9) and R(10) are H or $C_1$–$C_4$-alkyl; or
R(6) and R(7) together are 4 or 5 methylene groups, of which one $CH_2$ group can be replaced by O, S, NH, N—$CH_3$ or N-benzyl;
R(2) and R(4) identically or differently are R(11)—$SO_q$— or R(12)R(13)N—$SO_2$—;
q is zero–2;
R(11) is $C_1$–$C_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
R(12) and R(13) are defined as R(6) and R(7);
or one of the two radicals R(2) or R(4) is hydrogen or is defined as R(1);
R(5) is H, methyl, F, Cl or methoxy,
and their pharmaceutically tolerable salts;
(HOE 92/F 036 U.S. Pat. No. 5,364,868)

d) benzoylguanidine of the formula I

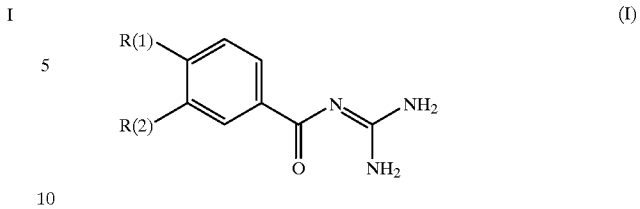

in which:
R(1) or R(2) is an amino group —NR(3)R(4);
R(3) and R(4) identically or differently are H, $C_1$–$C_6$-alkyl or $C_3$–$C_7$-cycloalkyl; or
R(3) is phenyl—$(CH_2)_p$—; p is 0, 1, 2, 3 or 4; or
R(3) is phenyl, where the phenyl in each case is unsubstituted or carries one to two substituents selected from the group consisting of fluorine, chlorine, methyl and methoxy; or
R(3) and R(4) together can be a straight-chain or branched $C_4$–$C_7$-methylene chain, where one —$CH_2$—member of the methylene chain can be replaced by oxygen, S or NR(5); R(5) is H or lower alkyl;
the other substituent R(1) or R(2) in each case is H, F, Cl, $C_1$–$C_4$-alkyl, $C_1$–$C_4$-alkoxy, $CF_3$, $C_m F_{2m+1}$—$CH_2$—, benzyl or phenoxy, where the respective phenyl radical is unsubstituted or carries one to two substituents selected from the group consisting of methyl, methoxy, fluorine and chlorine;
m is 1, 2 or 3;
and their pharmaceutically tolerable salts;
(92/F 197K-NZ 248 013)

e) benzoylguanidines of the formula I

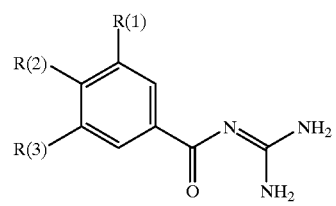

in which:
R(1) is R(4)—$SO_m$ or R(5)R(6)N—$SO_2$—;
m is zero, s or 2;
R(4) and R(5) are $C_1$–$C_8$-alkyl, $C_3$–$C_6$-alkenyl or —$C_n H_{2n}$—R(7);
n is zero,1, 2, 3 or 4;
R(7) is $C_5$–$C_7$-cycloalkyl or phenyl, which is unsubstituted or substituted by 1–3 substituents selected from the group consisting of F, Cl, $CF_3$, methyl, methoxy and NR(8)R(9);
R(8) and R(9) are H or $C_1$–$C_4$-alkyl; or
R(5) is H;
R(6) is H or $C_1$–$C_4$-alkyl; or
R(5) and R(6) together are 4 or 5 methylene groups, of which one $CH_2$ group can be replaced by an O, S. NH, N—$CH_3$ or N-benzyl;
R(2) is hydrogen, straight-chain or branched $(C_5$–$C_8)$-alkyl, —CR(13)=CHR(12) or —C≡CR(12);
R(12) is phenyl, which is unsubstituted or substituted by 1–3 substituents selected from the group consisting of F, Cl, $CF_3$, methyl, methoxy and NR(14)R(15);

R(14) and R(15) are H or (C$_1$-C$_4$)-alkyl; or
R(12) is (C$_1$-C$_9$)-heteroaryl, which is unsubstituted or substituted as phenyl, or
R(12) is (C$_1$-C$_6$)-alkyl, which is unsubstituted or substituted by 1–3 OH, or
R(12) is (C$_3$-C$_8$)-cycloalkyl;
R(13) is hydrogen or methyl, or
R(12) is (C$_3$-C$_8$)-cycloalkyl, (C$_3$-C$_8$)-cycloalkyl-(C$_1$-C$_4$)-alkyl, phenyl, C$_6$H$_5$—(C$_1$-C$_4$)-alkyl, naphthyl, biphenylyl, 1,1-diphenyl-(C$_1$-C$_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2);
and where the aromatic substituents R(2) and R(3) are unsubstituted or substituted by 1–3 substituents from the groups F, Cl, CF$_3$, (C$_1$-C$_4$)-alkyl or -alkoxy, or NR(10)R(11) with R(10) and R(11) being H or (C$_1$-C$_4$)-alkyl;
and their pharmaceutically tolerable salts;
(HOE 92/F 303K -EP-A 589 336, NZ 248 703)
f) benzoylguanidines of the formula I

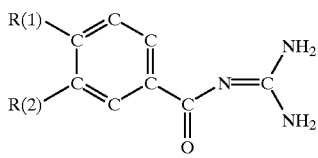

in which:
R(1) or R(2) is R(3)—S(O)$_n$— or R(4)R(5)N—SO$_2$—
the other substituent R(1) or R(2) in each case is H, OH, F, Cl, Br, I, C$_1$-C$_4$-alkyl, C$_1$-C$_4$-alkoxy, benzyloxy or phenoxy, which is unsubstituted or carries one to three substituents selected from the group consisting of fluorine, chlorine, methyl, methoxy, hydroxyl or benzyloxy,
R(3)—S(O)$_n$, —NR(4)R(5) or 3,4-dehydropiperidine
R(3) is C$_1$-C$_6$-alkyl, C$_5$-C$_7$-cycloalkyl, cyclopentylmethyl, cyclohexylmethyl or phenyl, which is unsubstituted or carries one to three substituents selected from the group consisting of fluorine, chlorine, methyl and methoxy;
R(4) and R(5) identically or differently, are H or C$_1$-C$_6$-alkyl; or
R(4) is phenyl-(CH$_2$)$_m$—;
m is 1, 2, 3 or 4; or
R(4) is phenyl, which is unsubstituted or carries one to two substituents selected from the group consisting of fluorine, chlorine, methyl and methoxy; or
R(4) and R(5) together are a straight-chain or branched C$_4$-C$_7$-chain, where the chain can additionally be interrupted by O, S or NR(6),
R(6) is H or methyl; or
R(4) and R(5) together with the nitrogen atom to which they are bonded, are a dihydroindole, tetrahydroquinoline or tetrahydroisoquinoline system;
n is zero, 1 or 2;
and their pharmaceutically tolerable salts;
(92/F 304 U.S. Pat. No. 5,416,094)

g) isoquinolines of the formula I

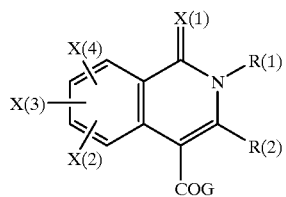

in which
R(1) is hydrogen, alkyl, cycloalkyl, arylalkyl, alkenyl, substituted aminoalkyl or an aryl or heteroaryl ring;
where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl,
R(2) is hydrogen, halogen, alkyl or aryl;
which is unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl,
G is —N=C{[NR(3)R(4)][N(R5)R(6)]} X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;
X(1) is hydrogen, oxygen, sulfur or NR(7);
R(7) is hydrogen, alkyl, cycloalkyl, arylalkyl, alkenyl, substituted aminoalkyl or an aryl or a heteroaryl ring;
which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;
in which substituents each alkyl chain or alkenyl chain can be interrupted by oxygen, sulfur or NR(8);
R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;
and their pharmaceutically acceptable salts;
(92/F 404-EP 602 522, NZ 250 438)
h) compounds of the formula I

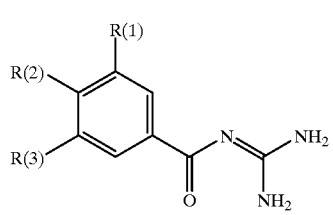

in which:
R(1) is hydrogen, F, Cl, Br, I, —NO$_2$, —C≡N, —CF$_3$, R(4)—SO$_m$ or R(5)R(6)N—SO$_2$—;
m is zero, 1 or 2;

R(4) and R(5) are $(C_1-C_8)$-alkyl, $(C_3-C_6)$-alkenyl, $-C_nH_{2n}-R(7)$ or $CF_3$;
n is zero, 1, 2, 3 or 4;
R(7) is $(C_3-C_7)$-cycloalkyl or phenyl, which is not substituted or is substituted by 1–3 substituents selected from the group consisting of F, Cl, $CF_3$, methyl, methoxy and NR(8)R(9);
R(8) and R(9) are H or $C_1-C_4$-alkyl; or
R(5) is H;
R(6) is H or $(C_1-C_4)$-alkyl; or
R(5) and R(6) together are 4 or 5 methylene groups, of which one $CH_2$ group can be replaced by oxygen, S, NH, N—$CH_3$ or N-benzyl;
R(2) is —SR(10), —OR(10), —NHR(10), —NR(10)R(11), —CH R(10)R(12), —[CR(12)R(13)OR(13')], —{C—[CH$_2$—OR(13')]R(12)(R(13)} or —[CR(18)R(17)]$_p$—(CO)—[CR(19)R(20)]$_q$—R(14);
R(10) and R(11) identically or differently are —[CHR(16)]$_s$—(CH$_2$)$_p$—(CHOH)$_q$—(CH$_2$)$_r$—(CHOH)$_t$R(21) or —(CH$_2$)$_p$—O—(CH$_2$—CH$_2$O)$_q$—R(21),
R(21) is hydrogen, methyl,
p, q, r identically or differently are zero, 1, 2, 3 or 4;
s is zero or 1;
t is 1, 2, 3 or 4;
R(12) and R(13) identically or differently are hydrogen, $(C_1-C_6)$-alkyl or, together with the carbon atom carrying them, are a $(C_3-C_8)$-cycloalkyl,
R(13') is hydrogen or $(C_1-C_4)$-alkyl;
R(14) is H, $(C_1-C_6)$-alkyl, $(C_3-C_8)$-cycloalkyl or $-C_aH_{2a}-R(15)$;
a is zero, 1, 2, 3 or 4;
R(15) is phenyl, which is unsubstituted or substituted by 1–3 substituents selected from the group consisting of F, Cl, $CF_3$, methyl, methoxy and NR(8)R(9);
R(8) and R(9) are H or $(C_1-C_4)$-alkyl; or
R(15) is $(C_1-C_9)$-heteroaryl, which is unsubstituted or substituted as phenyl, or
R(15) is $(C_1-C_6)$-alkyl, which is unsubstituted or substituted by 1–3 OH;
R(16), R(17), R(18), R(19) and R(20) are hydrogen or $(C_1-C_3)$-alkyl;
R(3) is defined as R(1), or
R(3) is $(C_1-C_6)$-alkyl or —X—R(22);
X is oxygen, S or NR(16);
R(16) is H or $(C_1-C_3)$-alkyl; or
R(22) and R(16) together are 4 or 5 methylene groups, of which one $CH_2$ group can be replaced by oxygen, S, NH, N—$CH_3$ or N-benzyl;
R(22) is defined as R(14);
and their pharmaceutically tolerable salts;
(HOE 92/F 405-EP 602 523, NZ 250 437)
i) benzoylguanidines of the formula I

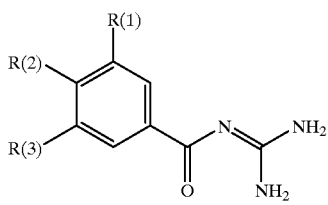
(I)

in which:
R(1) is hydrogen, F, Cl, Br, I, —NO$_2$, —C≡N, R(16)—C$_p$H$_{2p}$—O$_q$, R(4)—SO$_m$ or R(5)R(6)N—SO$_2$—;
m is zero, 1 or 2;
p is zero or 1;
q is zero, 1, 2 or 3;
R(16) is $C_rF_{2r+1}$;
r is 1, 2 or 3;
R(4) and R(5) are $(C_1-C_8)$-alkyl, $(C_3-C_6)$-alkenyl, $-C_nH_{2n}-R(7)$ or $CF_3$;
n is zero, 1, 2, 3 or 4;
R(7) is $(C_3-C_7)$-cycloalkyl or phenyl, which is not substituted or is substituted by 1–3 substituents selected from the group consisting of F, Cl, $CF_3$, methyl, methoxy and NR(8)R(9);
R(8) and R(9) are H or $C_1-C_4$-alkyl; or
R(5) is H;
R(6) is H or $(C_1-C_4)$-alkyl; or
R(5) and R(6) together are 4 or 5 methylene groups, of which one $CH_2$ group can be replaced by oxygen, S, NH, N—$CH_3$ or N-benzyl,
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is —SR(10), —OR(10), —NR(10)R(11), —CR(10)R(11)R(12);
R(10) is $-C_aH_{2a}-(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10) or are hydrogen or $(C_1-C_4)$-alkyl;
R(3) is defined as R(1), or is $(C_1-C_6)$-alkyl or —X—R(13);
X is oxygen, S, or NR(14);
R(14) is H or $(C_1-C_3)$-alkyl;
R(13) is H, $(C_1-C_6)$-alkyl, $(C_3-C_8)$-cycloalkyl or $-C_bH_{2b}-R(15)$;
b is zero, 1, 2, 3 or 4; or
R(13) and R(14) together are 4 or 5 methylene groups, of which one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(8)R(9);
R(8) and R(9) are H or $(C_1-C_4)$-alkyl;
and their pharmaceutically tolerable salts;
(HOE 92/F 411-NZ 250 450, EP 603 650)
k) benzoylguanidines of the formula I

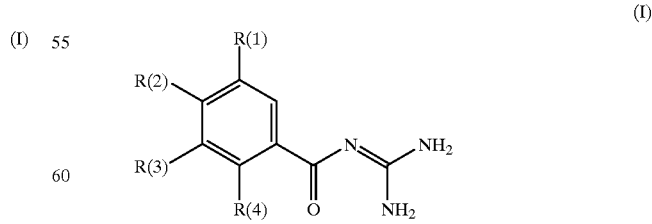
(I)

in which:
one of the substituents R(1), R(2), R(3) or R(4):
is an amino group —NR(5)[C$_n$H$_{2n}$—R(6)];
R(5) is hydrogen or $C_{(1-6)}$-alkyl;

n is zero, 1, 2, 3 or 4;
R(6) is H or $C_{(1-4)}$-alkyl;
in which one $CH_2$ group can be replaced by 1 sulfur atom or a group NR(7);
R(7) is hydrogen, methyl or ethyl; or
R(6) is $C_{(3-8)}$-cycloalkyl or phenyl, which is unsubstituted or carries 1, 2 or 3 substituents selected from the group consisting of F, Cl, Br, methyl, methoxy, —NR(8)R(9);
R(8) and R(9) are H, methyl or ethyl; or
R(5) and R(6) together with the nitrogen atom are a 5-, 6- or 7-membered ring, in which 1 carbon atom can be replaced by oxygen, S or NR(10);
R(10) is H, $C_{(1-3)}$-alkyl or benzyl;
and the other substituents R(1), R(2), R(3), R(4) in each case are:
hydrogen, F, Cl, Br, I, CN, $CF_3$, $NO_2$, $CF_3$—O—, $C_mF_{2m+1}$—$CH_2$—O— or
R(11)—$C_qH_{2q}$—$X_p$—;
m is 1, 2 or 3;
q is zero, 1, 2, 3 or 4;
p is zero or 1;
X is oxygen or NR(12); R(12) is H or $C_{(1-3)}$-alkyl;
R(11) is hydrogen, $C_{(1-6)}$-alkyl, $C_{(3-8)}$-cycloalkyl or phenyl, which is unsubstituted or substituted by 1, 2 or 3 substituents selected from the group consisting of F, Cl, $CH_3$, $CH_3$—O— and NR(13)R(14);
R(13), R(14) are H, methyl or ethyl;
and their pharmaceutically tolerable salts;
(HOE 92/F 422-EP 604 852)

l) benzoylguanidines of the formula I

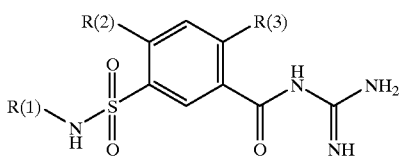

in which
R(1) is R(4)R(5)N—C(X)—;
X is oxygen, S or N—R(6);
R(4) and R(5) identically or differently, are H, $(C_1-C_8)$-alkyl, $(C_3-C_6)$-alkenyl or —$C_nH_{2n}$—R(7);
n is zero, 1, 2, 3 or 4;
R(7) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or
R(4) and R(5) together are 4 or 5 methylene groups, of which one $CH_2$ group can be replaced by oxygen, S, NH, N—$CH_3$ or N-benzyl; R(6) is defined as R(4) or is amidine;
R(2) is H, F, Cl, Br, I, $(C_1-C_8)$-alkyl, 1-alkenyl or 1-alkynyl, $(C_3-C_8)$-cycloalkyl, $(C_3-C_8)$-cycloalkyl-$(C_1-C_4)$-alkyl, phenyl, $C_6H_5$—$(C_1-C_4)$-alkyl, naphthyl, biphenylyl, 1,1-diphenyl-$(C_1-C_4)$-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);
W is oxygen, S or NR(9);
R(8) is H, $(C_1-C_6)$-alkyl, $(C_5-C_7)$-cycloalkyl, cyclohexylmethyl, cyclopentylmethyl, —$(CH_2)_mC_pF_{2p+1}$ or —$C_qH_{2q}$—R(10);
m is zero or 1;
p is 1, 2 or 3;
q is zero, 1, 2, 3 or 4;
R(10) is phenyl, which is unsubstituted or substituted by 1–3 substituents selected from the group consisting of F, Cl, $CF_3$, methyl, methoxy and NR(11)R(12);
R(11) and R(12) are H or $(C_1-C_4)$-alkyl;
R(9) is H or $(C_1-C_3)$-alkyl; or
R(8) and R(9) together are 4 or 5 methylene groups, of which one $CH_2$ group can be replaced by oxygen, S, NH, N—$CH_3$ or N-benzyl;
R(3) is H, F, Cl, Br, I, $(C_1-C_6)$-alkyl or —W—R(8) as defined for R(2),
and their pharmaceutically acceptable salts;
(93/F 054-NZ 250 919, EP-A 612 723)

m) benzoylguanidines of the formula I

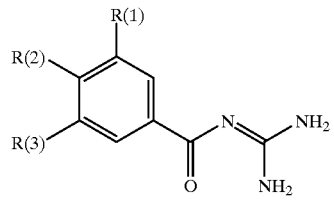

in which:
R(1), R(2), R(3) are hydrogen, F, Cl, Br, 1 or $(C_1-C_{12})$-alkyl;
one of the substituents R(1), R(2) or R(3) is $N_3$, CN, OH or $(C_1C_{10})$-alkyloxy, if at least one of the remaining substituents R(1), R(2) or R(3) is a sufficiently lipophilic alkyl radical having 3 to 12 carbon atoms; or
one of the substituents R(1), R(2) or R(3) is R(4)—$C_nH_{2n}$—$O_m$—;
m is zero or 1;
n is zero, 1, 2 or 3;
R(4) is $C_pF_{2p+1}$;
p is 1, 2 or 3, if n is zero or 1; or
R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or $(C_1-C_4)$-alkyl;
or one of the substituents R(1), R(2) or R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl,
which is unsubstituted or substituted as phenyl, or
R(5) is $(C_1-C_6)$-alkyl, which is unsubstituted or substituted by 1–3 OH; or
R(5) is $(C_3-C_9)$-cycloalkyl,
R(6) is hydrogen or methyl;
and their pharmacologically acceptable salts
(93/F 153-EP-A 627 413, NZ 260 660)

o) benzoylguanidines of the formula I

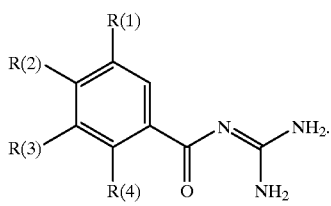

(I)

in which:
R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where
  X is oxygen, S or NR(14);
  m is zero, 1 or 2;
  o is zero or 1;
  p is zero, 1 or 2;
  q is zero, 1, 2, 3, 4, 5 or 6;
  R(5) and R(6) are ($C_1$–$C_8$)-alkyl, ($C_3$–$C_6$)-alkenyl, —$C_nH_{2n}$—R(8) or $CF_3$;
    n is zero, 1, 2, 3 or 4;
    R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);
      R(9) and R(10) are H or $C_1$–$C_4$-alkyl; or
  R(6) is H;
  R(7) is H or ($C_1$–$C_4$)-alkyl; or
  R(6) and R(7) together are 4 or 5 methylene groups, of which one $CH_2$ group can be replaced by oxygen, S, NH, N—$CH_3$ or N-benzyl;

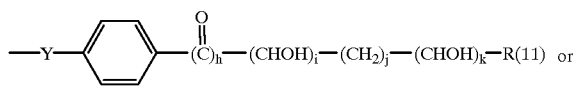

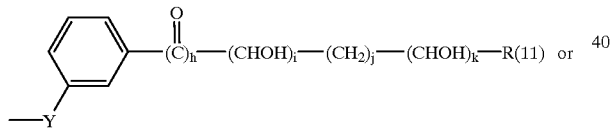

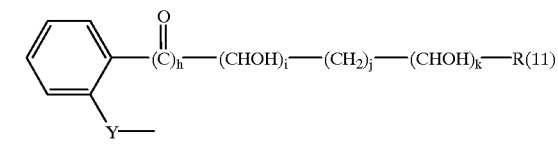

Y is oxygen, —S— or —NR(12)—;
R(11) and R(12) are hydrogen or ($C_1$–$C_3$)-alkyl;
h is zero or 1;
i, j and k independently are zero, 1, 2, 3 or 4;
but where h, i and k are not simultaneously zero,
R(3) is defined as R(1), or is ($C_1$–$C_6$)-alkyl or —X—R(13);
  X is oxygen, S or NR(14);
    R(14) is H or ($C_1$–$C_3$)-alkyl;
  R(13) is H, ($C_1$–$C_6$)-alkyl, ($C_3$–$C_8$)-cycloalkyl or —$C_bH_{2b}$—R(15);
    b is zero, 1, 2, 3 or 4; or
  R(13) and R(14) together are 4 or 5 methylene groups, where one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(9)R(10); R(9) and R(10) are H or ($C_1$–$C_4$)-alkyl;
R(4) is hydrogen, —OR(16) or —NR(16)R(17);
  R(16) and R(17) independently are hydrogen or ($C_1$–$C_3$)-alkyl;
and their pharmaceutically tolerable salts;
(HOE 93/F 154-EP-A 628 543, NZ 260 681)

p) benzoylguanidines of the formula I

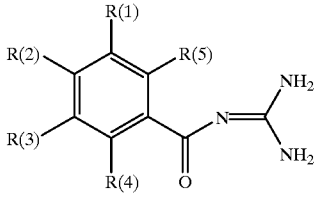

I in which:
R(1) is R(6)—CO or R(7)R(8)N—CO;
  R(6) is ($C_1$–$C_8$)-alkyl, ($C_1$–$C_8$)-perfluoroalkyl, ($C_3$–$C_8$)-alkenyl or —$C_nH_{2n}$—R(9);
    n is zero, 1, 2, 3 or 4;
    R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
      R(10) and R(11) are H, ($C_1$–$C_4$)-alkyl or ($C_1$–$C_4$)-perfluoroalkyl;
  R(7) is H, ($C_1$–$C_8$)-alkyl, ($C_1$–$C_8$)-perfluoroalkyl, ($C_3$–$C_8$)-alkenyl or —$C_nH_{2n}$—R(12);
    n is zero, 1, 2, 3 or 4;
    R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
      R(13) and R(14) are H, ($C_1$–$C_4$)-alkyl or ($C_1$–$C_4$)-perfluoroalkyl;
  R(8) is H, ($C_1$–$C_4$)-alkyl or ($C_1$–$C_4$)-perfluoroalkyl; or
  R(7) and R(8) together are 4 or 5 methylene groups, of which one $CH_2$ group can be replaced by oxygen, S, NH, N—$CH_3$ or N-benzyl;
R(2) is defined as R(1), or is H, F, Cl, Br, I, CN, $NO_2$, ($C_1$–$C_8$)-alkyl, ($C_1$–$C_8$)-perfluoroalkyl, ($C_3$–$C_8$)-alkenyl or —$C_nH_{2n}$R(15);
  n is zero, 1, 2, 3 or 4;
  R(15) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
    R(16) and R(17) are H, ($C_1$–$C_4$)-alkyl or ($C_1$–$C_4$)-perfluoroalkyl; or
R(2) is ($C_1$–$C_9$)-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is SR(18), —OR(18), —NR(18)R(19), ~CR(18)R(19)R(20);
  R(18) is —$C_aH_{2a-(Chd\ 1}$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;
R(19) and R(20) independently of one another are defined as R(18) or are hydrogen, $(C_1-C_4)$-alkyl or $(C_1-C_4)$-perfluoroalkyl; or
R(2) is R(21)—$SO_m$ or R(22)R(23)N—$SO_2$—;
m is 1 or 2;
R(21) is $(C_1-C_8)$-alkyl, $(C_1-C_8)$-perfluoroalkyl, $(C_3-C_8)$-alkenyl, —$C_nH_{2n}$—R(24),
n is zero, 1, 2, 3 or 4;
R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
R(27) and R(28) are H, $(C_1-C_4)$-alkyl or $(C_1-C_4)$-perfluoroalkyl;
R(22) is H, $(C_1-C_8)$-alkyl, $(C_1-C_8)$-perfluoroalkyl, $(C_3-C_8)$-alkenyl, —$C_nH_{2n}$—R(29);
n is zero, 1, 2, 3 or 4;
R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
R(30) and R(31) are H, $(C_1-C_4)$-alkyl or $(C_1-C_4)$-perfluoroalkyl;
R(23) is H, $(C_1-C_4)$-alkyl or $(C_1-C_4)$-perfluoroalkyl; or
R(22) and R(23) together are 4 or 5 methylene groups, of which one $CH_2$ group can be replaced by oxygen, S, NH, N—$CH_3$ or N-benzyl; or
R(2) is R(33)X—;
X is oxygen, S, NR(34), (D=O)A—, NR(34)C=MN$^{(*)}$R(35)—;
M is oxygen or S;
A is oxygen or NR(34);
D is C or SO;
R(33) is $(C_1-C_8)$-alkyl, $(C_3-C_8)$-alkenyl, $(CH_2)_bC_dF_{2d+1}$, —$C_nH_{2n}$—R(36),
b is zero or 1;
d is 1, 2, 3, 4, 5, 6 or 7;
n is zero, 1, 2, 3 or 4;
R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
R(37) and R(38) are H, $(C_1-C_4)$-alkyl or $(C_1-C_4)$-perfluoroalkyl;
R(34) is H, $(C_1-C_4)$-alkyl or $(C_1-C_4)$-perfluoroalkyl;
R(35) is defined as R(33); or
R(33) and R(34) together are 4 or 5 methylene groups, of which one $CH_2$ group can be replaced by oxygen, S, NH, N—$CH_3$ or N-benzyl;
where A and N$^{(*)}$ are bonded to the phenyl nucleus of the benzoylguanidine parent structure; or
R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR(49)R(50)]$_v$—R(44);
R(40), R(41) identically or differently are —$(CH_2)p$—$(CHOH)_q$—$(CH_2)_r$—$(CHOH)_t$—R(51) or —$(CH_2)_p$—O—$(CH_2$—$CH_2O)_q$—R(51);
R(51) is hydrogen or methyl;
u is 1, 2, 3 or 4;
v is zero, 1, 2, 3 or 4;
p, q, r identically or differently are zero, 1, 2, 3 or 4;
t is 1, 2, 3 or 4;

R(42) and R(43) identically or differently are hydrogen or $(C_1-C_6)$-alkyl; or
R(42) and R(43) together with the carbon atom carrying them form a $(C_3-C_8)$-cycloalkyl;
R(44) is H, $(C_1-C_6)$-alkyl, $(C_3-C_8)$-cycloalkyl or —$C_eH_{2e}$—R(45);
e is zero, 1, 2, 3 or 4;
R(45) is phenyl, which is unsubstituted or substituted by 1–3 substituents from the group consisting of F, Cl, $CF_3$, methyl, methoxy and NR(52)R(53);
R(52) and R(53) are H or $(C_1-C_4)$-alkyl, or
R(45) is $(C_1-C_9)$-heteroaryl, which is unsubstituted or substituted as phenyl; or
R(45) is $(C_1-C_6)$-alkyl, which is unsubstituted or substituted by 1–3 OH;
R(46), R(47), R(48), R(49) and R(50) are hydrogen or methyl; or
R(2) is R(55)—NH—$SO_2$—;
R(55) is R(56)R(57)N—(C=Y)—;
Y is oxygen, S or N—R(58);
R(56) and R(57) identically or differently are H, $(C_1-C_8)$-alkyl, $(C_3-C_6)$-alkenyl or —$C_fH_{2f}$—R(59);
f is zero, 1, 2, 3 or 4;
R(59) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or
R(56) and R(57) together are 4 or 5 methylene groups, of which one $CH_2$ group can be replaced by oxygen, S, NH, N—$CH_3$ or N-benzyl;
R(58) is defined as R(56) or is amidine;
R(3), R(4) and R(5) independently of one another are defined as R(1) or R(2);
and their pharmaceutically tolerable salts;
(HOE 93/F 220-EP-A 640 593, NZ 264 117)
q) benzoylguanidines of the formula I (I)

in which:
R(1) is hydrogen, F, Cl, Br, I, —$NO_2$, —CN, —$X_o$—$(CH_2)_p$—$(CF_2)_q$—$CF_3$, R(5)—$SO_m$—, R(6)—CO—, R(6)R(7)N—CO— or R(6)R(7)N—$SO_2$—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are $(C_1-C_8)$-alkyl, $(C_3-C_6)$-alkenyl, —$C_nH_{2n}$—R(8) or $CF_3$;
n is zero, 1, 2, 3 or 4;
R(8) is $(C_3-C_7)$-cycloalkyl, phenyl, which is not substituted or is substituted by 1 to 3 substituents selected from the group consisting of F, Cl, $CF_3$, methyl, methoxy and NR(9)R(10);
R(9) and R(10) are H or $(C_1-C_4)$-alkyl; or
R(6) is hydrogen;
R(7) is hydrogen or $(C_1-C_4)$-alkyl; or R(6) and R(7) together are 4 or 5 methylene groups, of which one CH$_2$ group can be replaced by oxygen, S, NH, N—CH$_3$ or N-benzyl;

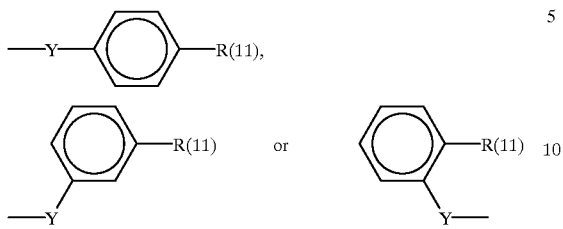

R(2)
R(11) is (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino and benzyl;
Y is oxygen, —S— or NR(12);
R(12) is H or (C$_1$–C$_4$)-alkyl:
R(3) is defined as R(1); or
R(3) is (C$_1$–C$_6$)-alkyl or —X—R(13);
X is oxygen, —S— or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);
b is zero, 1, 2, 3 or 4; or
R(13) and R(14) together are 4 or 5 methylene groups, of which one CH$_2$ group can be replaced by oxygen, S, NH, N—CH$_3$ or N-benzyl;
R(15) is phenyl, which is unsubstituted or substituted by 1–3 substituents selected from the group consisting of F, Cl, CF$_3$, methyl, methoxy and NR(9)R(10);
R)9) and R(10) are H or (C$_1$–C$_4$)-alkyl;
R(4) is hydrogen, —OR(16), —NR(16)R(17) or C$_r$F$_{2r+1}$;
R(16) and R(17) independently are hydrogen or (C$_1$–C$_3$)-alkyl;
r is 1, 2, 3 or 4;
and their pharmaceutically tolerable salts;
(HOE 93/F 223 K-EP 639 573, NZ 264 130)
r) benzo-fused 5-membered ring heterocycles of the formula I

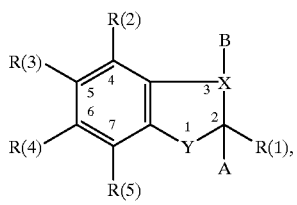

(I)

in which:
X is N or CR(6);
Y is oxygen, S or NR(7);
A, B together are a bond or
A, B are both hydrogen, if X is CR(6) and Y is NR(7) simultaneously;
one of the substituents R(1) to R(6) is a —CO—N═C(NH$_2$)$_2$ group;
the other substituents R(1) to R(6) in each case are hydrogen, F, Cl, Br, I or (C$_1$–C$_6$)-alkyl;
up to two of the other substituents R(1) to R(6) are CN, NO$_2$, N$_3$, (C$_1$–C$_4$)-alkyloxy or CF$_3$;
up to one of the other substituents is R(8)—C$_n$H$_{2n}$—Z—;
n is zero to 10; where the alkylene chain —C$_n$H$_{2n}$— is straight-chain or branched and where one carbon atom can be replaced by an oxygen or sulfur atom or by a nitrogen atom;
R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH═CH—, and in which one methylene group can be replaced by an oxygen or sulfur atom or by a nitrogen atom; or
R(8) is phenyl, which is unsubstituted or substituted by 1 to 3 substituents selected from the group consisting of F, Cl, Br, I, CF$_3$, CH$_3$—S(O)$_s$— or R(9)-W$_y$—;
s is zero, 1 or 2;
R(9) is H, methyl, ethyl,
W is oxygen or NR(10);
R(10) is H or methyl;
y is zero or 1; or
R(8) is C$_m$F$_{2m+1}$;
m is 1 to 3; or
R(8) is 1- or 2-naphthyl, pyridyl, quinolyl or iso-quinolyl;
Z is —CO—, —CH$_2$— or —[CR(11)(OH)]q—;
q is 1, 2 or 3;
R(11) is H or methyl; or
Z is oxygen or —NR(12)—;
R(12) is H or methyl; or
Z is —S(O)$_s$—;
s is zero, 1 or 2; or
Z is —SO$_2$—NR(13)—;
R(13) is H or (C$_1$–C$_4$)-alkyl;
R(7) is hydrogen, (C$_1$–C$_{10}$)-alkyl, (C$_2$–C$_{10}$)-alkenyl or R(8)—C$_n$H$_{2n}$—;
and their pharmaceutically tolerable salts;
(HOE 93/F 236-EP-A 638 548, NZ 264 216)
s) benzoylguanidines of the formula I

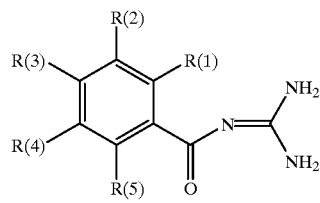

(I)

in which:
R(1), R(3) or R(4) is —NR(6) C═X NR(7)R(8);
X is oxygen or S;
R(6) is hydrogen, (C$_1$–C$_8$)-alkyl, (C$_1$–C$_8$)-perfluoroalkyl, (C$_3$–C$_8$)-alkenyl or —C$_n$H$_{2n}$—R(9);
n is zero, 1, 2, 3 or 4;
R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);
R(10) and R(11) are H, (C$_1$–C$_4$)-alkyl or (C$_1$–C$_4$)-perfluoroalkyl;
R(7) is hydrogen, (C$_1$–C$_8$)-alkyl, (C$_1$–C$_8$)-perfluoroalkyl, (C$_3$–C$_8$)-alkenyl or —C$_o$H$_{2o}$—R(12);
o is zero, 1, 2, 3 or 4;

R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);

R(13) and R(14) are H, $(C_1-C_4)$-alkyl or $(C_1-C_4)$-perfluoroalkyl;

R(8) is defined as R(7); or

R(7) and R(8) together are 4 or 5 methylene groups, of which one $CH_2$ group can be replaced by oxygen, S, NH, N—$CH_3$ or N-benzyl;

the remaining substituents R(2), R(3), R(4), R(5) or R(1), R(2), R(4), R(5) or R(1), R(2), R(3), R(5) in each case independently of one another are hydrogen, F, Cl, Br, I, —$O_{ta}(C_1-C_8)$-alkyl, —$O_{tb}(C_3-C_8)$-alkenyl, —$O_{tc}(CH_2)_bC_dF_{2d+1}$, —$O_{td}C_pH_{2p}R(18)$, or up to 2 groups CN, $NO_2$, NR(16)R(17), b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;

R(18) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(19)R(20);

R(19) and R(20) are hydrogen or $(C_1-C_4)$-alkyl or $(C_1-C_4)$-perfluoroalkyl;

R(16) is hydrogen, $(C_1-C_8)$-alkyl, $(C_1-C_8)$-perfluoroalkyl, $(C_3-C_8)$-alkenyl, —$C_qH_{2q}$—R(21), q is zero, 1, 2, 3 or 4;

R(21) is $(C_3-C_8)$-cycloalkyl, phenyl, biphenylyl or naphthyl, where the aromatics are not substituted or are substituted by 1–3 substituents from the group F, Cl, $CF_3$, methyl, methoxy or NR(22)R(23), R(22) and R(23) are hydrogen, $(C_1-C_4)$-alkyl or $(C_1-C_4)$-perfluoroalkyl;

R(17) is hydrogen, $(C_1-C_8)$-alkyl, $(C_1-C_8)$-perfluoroalkyl, $(C_3-C_8)$-alkenyl, —$C_rH_{2r}$—R(24);

r is zero, 1, 2, 3 or 4;

R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(25)R(26);

R(25) and R(26) are hydrogen, $(C_1-C_4)$-alkyl or $(C_1-C_4)$-perluoroalkyl; or R(16) and R(17) together are 4 or 5 methylene groups, of which one $CH_2$ group can be replaced by oxygen, S, NH, N—$CH_3$ or N-benzyl;

and their pharmaceutically tolerable salts;

(HOE 93/F 249-EP-A 640 587, NZ 264 282)

t) diacyl-substituted guanidines of the formula I $$X(1)\diagdown\underset{O}{C}\diagup NH\diagdown\underset{NH}{C}\diagup NH\diagdown\underset{O}{C}\diagup X(2)$$

I in which:

X(1) and X(2) are

[structure with R(101), R(102), R(103), R(104), R(105), {C[R(A)R(B)]}$_{T1}$—]

T1 is zero, 1, 2, 3 or 4;

R(A) and R(B) independently are hydrogen, F, Cl, Br, I, CN, OR(106), $(C_1-C_8)$-alkyl, $(C_3-C_8)$-cycloalkyl, $O_{zk}(CH_2)_{zl}C_{zm}F_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110); R(109) and R(110) are hydrogen, $(C_1-C_4)$-alkyl or $(C_1-C_4)$-perfluoroalkyl;

zl is zero, 1, 2, 3 or 4;
zk is zero or 1;
zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(111)R(112);

R(111) and R(112) are hydrogen, $(C_1-C_4)$-alkyl or $(C_1-C_4)$-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl; or X(1) and X(2) are

[structure with R(101), R(102), R(103), R(104), R(105), {C[R(A)R(B)]}$_{T2a}$, R(B), R(A), {C[R(A)R(B)]}$_{T2b}$—]

T2a and T2b independently of one another are zero, 1 or 2;

where the double bond can have the (E)— or (Z)-configuration; or

X(1) and X(2) are

[structure with R(101), R(102), R(103), R(104), R(Y1), R(Y2), R(Z1), R(Z2), R(D), R(U1), R(U2), YY, Z, U, {C[R(A)R(B)]}$_{T3}$—]

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;

zla is zero, 1, 2, 3 or 4;

zma is 1, 2, 3, 4, 5, 6, 7 or 8;

R(1 14) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as R(114); or

R(115) and R(116) together are 4 or 5 methylene groups, of which one $CH_2$ group can be replaced by oxygen, S, NH, N—$CH_3$ or N-benzyl; but where the constitution of U being nitrogen (N), YY being nitrogen (N) and Z being carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO—or R(112a)R(113a)N—$SO_2$—; where the perfluoroalkyl group is straight-chain or branched, X is oxygen, S or NR(114a);

R(114a) is H or $(C_1-C_3)$-alkyl;

zoa is zero or 1;

zbm is zero, 1 or 2;

zpa is zero, 1, 2, 3 or 4;

zqa is 1, 2, 3, 4, 5, 6, 7 or 8;

R(110a), R(110b), R(111a) and R(112a) independently are $(C_1-C_8)$-alkyl, $(C_3-C_8)$-alkenyl, —$C_{zn}H_{2zn}$—R(115a) or $(C_1-C_8)$-perfluoroalkyl;

zn is zero, 1, 2, 3 or 4;

R(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);

R(116a) and R(117a) are hydrogen, $(C_1-C_4)$-perfluoroalkyl or $(C_1-C_4)$-alkyl; or R(110b), R(111a) and R(112a) are hydrogen;

R(110c) and R(113a) independently are hydrogen, $(C_1-C_4)$-perfluoroalkyl or $(C_1-C_4)$-alkyl; or R(110b) and R(110c) and R(112a) and R(113a) together are 4 or 5 methylene groups, of which one $CH_2$ group can be replaced by oxygen, sulfur, NH, N—$CH_3$ or N-benzyl; or R(101), R(102), R(103), R(104), R(105) independently of one another are $(C_1-C_8)$-alkyl, —$C_{zal}H_{2zal}$R(118a) or $(C_3-C_8)$-alkenyl, zal is zero, 1, 2, 3 or 4;

R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(1 19b);

R(119a) and R(119b) are hydrogen, $(C_1-C_4)$-alkyl or $(C_1-C_4)$-perfluoroalkyl; or R(101), R(102), R(103), R(104), R(105) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino; or R(101), R(102), R(103), R(104), R(105) independently of one another are —C≡C—R(193);

R(193) is phenyl which is not substituted or is substituted by 1–3 substituents from the group consisting of F, Cl, $CF_3$, methyl, methoxy or NR(194)R(195);

R(194) and R(195) are hydrogen or $CH_3$; or

R(101), R(102), R(103), R(104), R(105) independently of one another are

—Y-para-$C_6H_4$—$(CO)_{zh}$—$(CHOH)_{zi}$—$(CH_{2zj}$—$(CHOH)_{zk}$—R(123), —Y-meta-$C_6H_4$—$(CO)_{zad}$—$(CHOH)_{zae}$—$(CH_2)_{zaf}$—$(CHOH)_{zag}$—R(124) or —Y-ortho-$C_6H_4$—$(CO)_{zah}$—$(CHOH)_{zao}$—$(CH_2)_{zap}$—$(CHOH)_{zak}$—R(125);

Y is oxygen, —S— or —NR(122d)—;

zh, zad, zah independently are zero or 1;

zi, zj, zk, zae, zaf, zag, zao, zap and zak independently are zero, 1, 2, 3 or 4;

but where in each case zh, zi and zk are not simultaneously zero, zad, zae and zag are not simultaneously zero, and zah, zao and zak are not simultaneously zero, R(123), R(124), R(125) and R(122d) independently are hydrogen or $(C_1-C_3)$-alkyl; or R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1-C_9)$-heteroaryl, which is unsubstituted or substituted by 1–3 substituents from the group consisting of F, Cl, $CF_3$, $CH_3$, methoxy, hydroxyl, amino, methylamino and dimethylamino;

zab is zero, 1 or 2;

R(132), R(134) and R(135) independently of one another are defined as R(129) or are hydrogen, $(C_1-C_4)$-alkyl or $(C_1-C_4)$-perfluoroalkyl; or R(101), R(102), R(103), R(104) and R(105) independently of one another are —W-para-$(C_6H_4)$-R(196), —W-meta-$(C_6H_4)$-R(197) or —W-ortho-$(C_6H_4)$-R(198);

R(196), R(197) and R(198) independently are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;

W is oxygen, S or NR(136)—;

R(136) is hydrogen or $(C_1-C_4)$-alkyl; or

R(101), R(102), R(103), R(104) and R(105) independently of one another are R(146)X(1a)—;

121

X(1a) is oxygen, S, NR(147), (D=O)A—, NR(148)C=MN$^{(*)}$R(149)—;

M is oxygen or sulfur;

A is oxygen or NR(150);

D is C or SO;

R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);

zbz is zero or 1;

zdz is 1, 2, 3, 4, 5, 6, or 7;

zxa is zero, 1, 2, 3 or 4;

R(151) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);

R(152) and R(153) are hydrogen, $(C_1-C_4)$-alkyl or $(C_1-C_4)$-perfluoroalkyl;

R(147), R(148) and R(150) independently are hydrogen, $(C_1-C_4)$-alkyl, $(C_1-C_4)$-perfluoroalkyl;

R(149) is defined as R(146), or

R(146) and R(147), or R(146) and R(148) together are 4 or 5 methylene groups, of which one $CH_2$ group can be replaced by oxygen, sulfur, NH, N—$CH_3$ or N-benzyl;

where A and N$^{(*)}$ are bonded to the phenyl nucleus of the alkanoyl parent structure; or R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —[CR(159)R(160)]$_{zu}$—(C=O)—[CR(161)R(162)]$_{zv}$—R(163);

R(164), R(165), R(166), R(167), R(169) identically or differently are —$(CH_2)_{zy}$—(CHOH)$_{zz}$—$(CH_2)_{zaa}$—(CHOH)$_{zt}$—R(171) or —$(CH_2)_{zab}$—O—$(CH_2-CH_2O)_{zac}$—R(172);

R(171) and R(172) are hydrogen or methyl;

zu is 1, 2, 3 or 4;

zv is zero, 1, 2, 3 or 4;

zy, zz, zaa, zab, zac identically or differently are zero, 1, 2, 3 or 4;

zt is 1, 2, 3 or 4;

R(168), R(170), R(154), R(155) identically or differently are hydrogen or $(C_1-C_6)$-alkyl, or R(169) and R(170), or R(154) and R(155) together with the carbon atom carrying them are a $(C_3-C_8)$-cycloalkyl;

R(163) is hydrogen, $(C_1-C_6)$-alkyl, $(C_3-C_8)$-cycloalkyl or —$C_{zeb}H_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, $CF_3$, methyl, methoxy and NR(174)R(175);

R(174) and R(175) are hydrogen or $(C_1-C_4)$-alkyl; or

R(156), R(157) and R(173) independently are $(C_1-C_9)$-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—$SO_2$—;

R(176) is R(177)R(178)N—(C=Y')—;

Y' is oxygen, S or N—R(179);

R(177) and R(178) identically or differently are hydrogen, $(C_1-C_8)$-alkyl, $(C_3-C_6)$-alkenyl or —$C_{zfa}H_{2zfa}$—R(180);

122 zfa is zero, 1, 2, 3 or 4;

R(180) is $(C_5-C_7)$-cycloalkyl or phenyl, which is unsubstituted or substituted by 1–3 substituents selected from the group consisting of F, Cl, $CF_3$, methoxy or $(C_1-C_4)$-alkyl; or R(177) and R(178) together are 4 or 5 methylene groups, of which one $CH_2$ group can be replaced by oxygen, sulfur, NH, N—$CH_3$ or N-benzyl;

R(1 79) is defined as R(177) or is amidine, or

R(101), R(102), R(103), R(104), R(105) independently of one another are NR(184a)R(185), OR(184b), SR(184c) or —$C_{znx}H_{2znx}$—R(184d);

znx is zero, 1, 2, 3 or 4;

R(184d) is $(C_3-C_7)$-cycloalkyl or phenyl, which is not substituted or is substituted by 1–3 substituents from the group consisting of F, Cl, $CF_3$, methyl, methoxy and NR(116k)R(117k);

R(116k) and R(117k) are hydrogen or $C_1-C_4$-alkyl;

R(184a), R(184b), R(184c), R(185) independently of one another are hydrogen, $(C_1-C_8)$-alkyl, $(C_1-C_8)$-perfluoroalkyl or $(CH_2)_{zao}$-R(184g);

zao is zero, 1, 2, 3 or 4;

184g is $(C_3-C_7)$-cycloalkyl or phenyl, which is not substituted or is substituted by 1–3 substituents from the group consisting of F, Cl, $CF_3$, methyl, methoxy and NR(184u)R(184v);

R(184u) and R(184v) are hydrogen or $C_1-C_4$-alkyl; or

R(184a) and R(185) together are 4 or 5 methylene groups, of which one $CH_2$ group can be replaced by oxygen, sulfur, NH, N—$CH_3$ or N-benzyl;

and their pharmaceutically tolerable salts;

(HOE 93/F 254-EP-A 640 588, NZ 264 307)

u) benzoylguanidines of the formula I in which:

R(1) is H, F, Cl, Br, I, CN, $NO_2$, $(C_1-C_8)$-alkyl, $(C_3-C_8)$-cycloalkyl or $X_a$—$(CH_2)_b$—$(CF_2)_c$—$CF_3$;

X is oxygen, S or NR(5);

a is zero or 1;

b is zero, 1 or 2;

c is zero, 1, 2 or 3;

R(5) is H, $(C_1-C_4)$-alkyl or —$C_dH_{2d}R(6)$;

d is zero, 1, 2, 3 or 4;

R(6) is $(C_3-C_8)$-cycloalkyl, phenyl, biphenylyl or naphthyl, where the aromatics are not substituted or are substituted by 1 to 3 substituents selected from the group consisting of F, Cl, $CF_3$, methyl, methoxy and NR(7)R(8);

R(7) and R(8) independently are H or $(C_1-C_4)$-alkyl; or

R(1) is —SR(10), —OR(10) or —CR(10)R(11)R(12);

R(10) is —$C_fH_{2f}$—$(C_3-C_8)$-cycloalkyl, —$(C_1-C_9)$-heteroaryl or phenyl, where the aromatic systems are unsubstituted or substituted by 1 to 3 substituents selected from the group consisting of F, Cl, $CF_3$, $CH_3$, methoxy, hydroxyl, amino, methylamino and dimethylamino;

f is zero, 1 or 2;

R(11) and R(12) independently of one another are defined as R(10) or are hydrogen or $(C_1-C_4)$-alkyl; or R(1) is phenyl, naphthyl, biphenylyl or $(C_1-C_9)$-heteroaryl, the latter linked via C or N, and which are unsubstituted or substituted by 1 to 3 substituents selected from the group consisting of F, Cl, $CF_3$, $CH_3$, methoxy, hydroxyl, amino, methylamino and dimethylamino; or R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)-[CR(22)R(23)R(24)]$_l$ R(13) and R(14) identically or differently are —(CH$_2$)$_g$—(CHOH)$_h$—(CH$_2$)$_i$—(CHOH)$_j$—R(17), R(17) is hydrogen or methyl;

—(CH$_2$)$_g$—O—(CH$_2$—CH$_2$O)$_h$—R(24), g,h,i identically or differently are zero, 1, 2, 3 or 4; j is 1, 2, 3 or 4;

R(15) and R(16) identically or differently are hydrogen, $(C_1-C_6)$-alkyl or together with the carbon atom carrying them are a $(C_3-C_8)$-cycloalkyl;

R(18) is phenyl, which is unsubstituted or substituted by 1 to 3 substituents selected from the group consisting of F, Cl, $CF_3$, methyl, methoxy and NR(25)R(26);

R(25) and R(26) are H or $(C_1-C_4)$-alkyl; or

R(18) is $(C_1-C_9)$-heteroaryl, which is unsubstituted or substituted as phenyl; or R(18) is $(C_1-C_6)$-alkyl, which is unsubstituted or substituted by 1 to 3 OH; or R(18) is $(C_3-C_8)$-cycloalkyl;

R(19), R(20), R(21), R(22) and R(23) are hydrogen or methyl;

k is zero, 1, 2, 3 or 4;

l is zero, 1, 2, 3 or 4;

R(24) is H, $(C_1-C_6)$-alkyl, $(C_3-C_8)$-cycloalkyl or —C$_{m2m}$—R(18);

m is 1, 2, 3 or 4;

R(2) and R(3) independently of one another are defined as R(1);

R(4) is $(C_1-C_3)$-alkyl, F, Cl, Br, l, CN or—(CH$_2$)$_n$—(CF$_2$)$_o$—CF$_3$;

is zero or 1;

o is zero, 1 or 2;

and their pharmaceutically tolerable salts;

(HOE 93/F 436-EP-A 659 748), NZ 270 264)

v) acylguanidines of the formula I

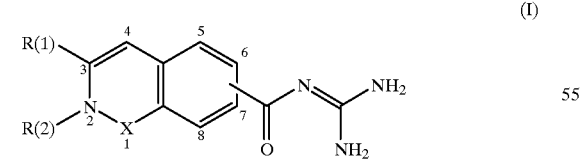

in which:

X is carbonyl, sulfonyl,

R(1) is H, $(C_1-C_8)$-alkyl, unsubstituted or substituted by hydroxyl, $(C_3-C_8)$-cycloalkyl, phenyl, which is unsubstituted or substituted by 1–3 substituents from the group F, Cl, $CF_3$, $CH_3$, methbxy, hydroxyl, amino, methylamino or dimethylamino, R(2) is H, $(C_1-C_4)$-alkyl, and their pharmaceutically tolerable salts;

(HOE 94/F 014K-EP-A 666 252, NZ 270 370)

w) phenyl-substituted alkylcarboxylic acid guanidides, carrying perfluoroalkyl groups, of the formula I

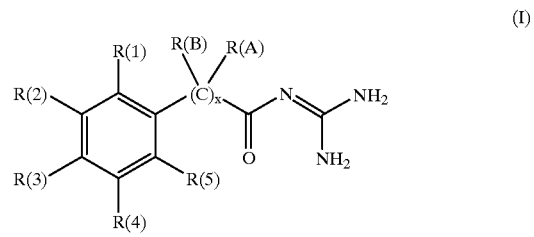

in which:

R(A) is hydrogen, F, Cl, Br, I, CN, OR(6), $(C_1-C_8)$-alkyl, $(C_3-C_8)$-cycloalkyl, O$_r$(CH$_2$)$_a$C$_b$F$_{2b+1}$ or NR(7)R(8);

r is zero or 1;

a is zero, 1, 2, 3 or 4;

b is 1, 2, 3, 4, 5, 6, 7 or 8;

R(6) is hydrogen, $(C_1-C_8)$-alkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(9)R(10);

R(9) and R(10) are H, $(C_1-C_4)$-alkyl or $(C_1-C_4)$-perfluoroalkyl;

R(7) and R(8) independently of one another are defined as R(6);

R(B) independently is defined as R(A);

x is 1, 2 or 3;

R(1) is hydrogen, $(C_1-C_8)$-alkyl, $(C_3-C_8)$-cycloalkyl, —O$_t$(CH$_2$)$_d$C$_e$F$_{2e+1}$, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1);

but with the condition that at least one of the substituents R(1), R(2), R(3), R(4), R(5), R(A) and R(B) is an —O$_t$(CH$_2$)$_d$C$_e$F$_{2e+1}$ or an O$_r$(CH$_2$)$_a$C$_b$F$_{2b+1}$ group.

and their pharmaceutically tolerable salts;

(HOE 94/F 094-EP-A 676 395, NZ 270 894)

x) heteroaroylguanidines of the formula I

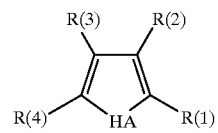

in which:

HA is SO$_m$, O or NR(5);

m is zero, 1 or 2;

R(5) is hydrogen, $(C_1-C_8)$-alkyl or —C$_{am}$H$_{2am}$R(81);

am is zero, 1 or 2;

R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);

R(82) and R(83) are H or $CH_3$; or

R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

one of the two substituents R(1) and R(2) is —CO—N=C(NH$_2$)$_2$;

and the other in each case is hydrogen, F, Cl, Br, I, $(C_1-C_3)$-alkyl, —OR(6), $C_rF_{2r+1}$, —CO—N=C(NH$_2$)$_2$ or —NR(6)R(7);

R(6) and R(7) independently are hydrogen or $(C_1-C_3)$-alkyl;

r is 1, 2, 3 or 4;

R(3) and R(4) independently of one another are hydrogen, F, Cl, Br, I, —C≡N, X—(CH$_2$)$_p$—(C$_q$—F$_{2q+1}$), R(8)—SO$_{bm}$, R(9R(10)N—CO, R(11)—CO— or R(12)R(13)N—SO$_2$—, where the perfluoroalkyl group is straight-chain or branched, X is oxygen, S or NR(14);

R(14) is H or $(C_1-C_3)$-alkyl;

bm is zero, 1 or 2;

p is zero, 1 or 2;

q is zero, 1, 2, 3, 4, 5 or 6;

R(8), R(9), R(11) and R(12) independently are $(C_1-C_8)$-alkyl, $(C_3-C_6)$-alkenyl, —C$_n$H$_{2n}$—R(15), CF$_3$;

n is zero, 1, 2, 3 or 4;

R(15) is $(C_3-C_7)$-cycloalkyl or phenyl, which is not substituted or is substituted by 1–3 substituents selected from the group consisting of F, Cl, CF$_3$, methyl, methoxy or NR(16)R(17);

R(16) and R(17) are H or $C_1-C_4$-alkyl; or

R(9), R(11) and R(12) are H;

R(10) and R(13) independently are H or $(C_1-C_4)$-alkyl; or

R(9) and R(10), and R(12) and R(13) together are 4 or 5 methylene groups, of which one CH$_2$ group can be replaced by oxygen, S, NH, N—CH$_3$ or N-benzyl, or R(3) and R(4) independently of one another are $(C_1-C_8)$-alkyl or —C$_{al}$H$_{2al}$R(18) al is zero, 1 or 2;

R(18) is $(C_3-C_8)$-cycloalkyl or phenyl; which is not substituted or is substituted by 1–3 substituents selected from the group consisting of F, Cl, CF$_3$, methyl, methoxy and NR(19)R(20);

R(19) and R(20) are H or CH$_3$; or

R(3) and R(4) independently of one another are $(C_1-C_9)$-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino; or R(3) and R(4) independently of one another are

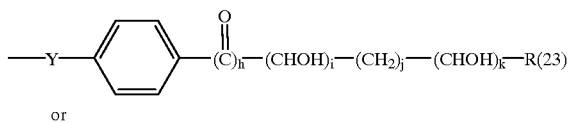

or

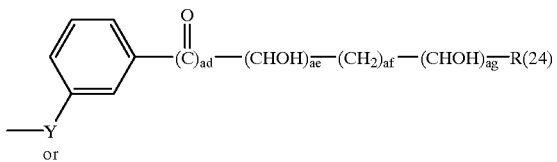

or

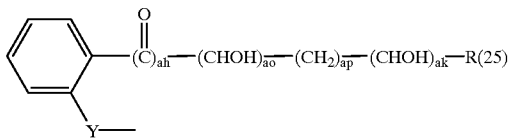

Y is oxygen, —S— or —NR(22)—;

h, ad, ah independently are zero or 1;

i, j, k, ae, af, ag, ao, ap and ak independently are zero, 1, 2, 3, 4, but where in each case h, i and k are not simultaneously zero, ad, ae and ag are not simultaneously zero, and ah, ao and ak are not simultaneously zero, R(23), R(24), R(25) and R(22) independently are hydrogen or $(C_1-C_3)$-alkyl; or R(3) and R(4) independently of one another are hydrogen, F, Cl, Br, I, CN, $(C_1-C_8)$-alkyl, $(C_1-C_8)$-perfluoroalkyl, $(C_3-C_8)$-alkenyl or —C$_g$H$_{2g}$R(26); g is zero, 1, 2, 3 or 4;

R(26) is $(C_3-C_8)$-cycloalkyl, phenyl, biphenylyl or naphthyl, where the aromatics are not substituted or are substituted by 1–3 substituents selected from the group consisting of F, Cl, CF$_3$, methyl, methoxy and NR(27)R(28);

R(27) and R(28) are H, $(C_1-C_4)$-alkyl or $(C_1-C_4)$-perfluoroalkyl; or

R(3) and R(4) independently of one another are SR(29), —OR(30), —NR(31)R(32) or —CR(33)R(34)R(35);

R(29), R(30), R(31) and R(33) independently are —C$_a$h$_{2a}$—$(C_1-C_9)$-heteroaryl, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl; or R(3) and R(4) independently of one another are

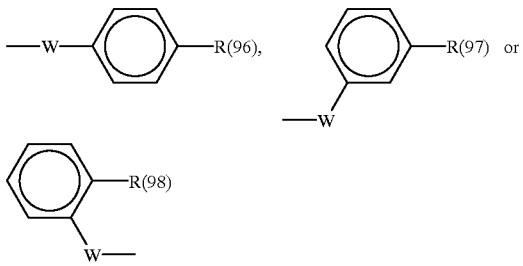

R(96), R(97) and R(98) independently are $(C_1-C_9)$-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino or benzyl;

W is oxygen, S or NR(36)—;

R(36) is H or $(C_1-C_4)$-alkyl; or

R(3) and R(4) independently of one another are R(37)—SO$_{cm}$ or R(38)R(39) N—SO$_2$—;

cm is 1 or 2;

R(37) is $(C_1-C_8)$-alkyl, $(C_1-C_8)$-perfluoroalkyl, $(C_3-C_8)$-alkenyl or —C$_s$H$_{2s}$R(40);

is zero, 1, 2, 3 or 4;
R(40) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(41)R(42);
R(41) and R(42) are H, (C$_1$–C$_4$)-alkyl or (C$_1$–C$_4$)-perfluoroalkyl;
R(38) is H, (C$_1$–C$_9$)-alkyl, (C$_1$–C$_8$)-perfluoroalkyl, (C$_3$–C$_8$)-alkenyl or —C$_w$H$_{2w}$—R(43);
w is zero, 1, 2, 3 or 4;
R(43) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(44)R(45);
R(44) and R(45) are H, (C$_1$–C$_4$)-alkyl or (C$_1$–C$_4$)-perfluoroalkyl;
R(39) is H, (C$_1$–C$_4$)-alkyl or (C$_1$–C$_4$)-perfluoroalkyl; or
R(38) and R(39) together are 4 or 5 methylene groups, of which one CH$_2$ group can be replaced by oxygen, S, NH, N—CH$_3$ or N-benzyl; or
R(3) and R(4) independently of one another are R(46)X(1)—;
X(1) is oxygen, S, NR(47), (D═O)A—, NR(48)C═MN$^{(*)}$R(49)—,
M is oxygen or S;
A is oxygen or NR(50);
D is C or SO;
R(46) is (C$_1$–C$_8$)-alkyl, (C$_3$–C$_8$)-alkenyl, (CH$_2$)$_b$C$_d$F$_{2d+1}$ or —C$_x$H$_{2x}$—R(51);
b is zero or 1;
d is 1, 2, 3, 4, 5, 6 or 7;
x is zero, 1, 2, 3 or 4;
a R(51) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, a methoxy and NR(52)R(53);
R(52) and R(53) are H, (C$_1$–C$_4$)-alkyl or (C$_1$–C$_4$)-perfluoroalkyl;
R(47), R(48) and R(50) independently are hydrogen, (C$_1$–C$_4$)-alkyl or (C$_1$–C$_4$)-perfluoroalkyl;
R(49) is defined as R(46); or
R(46) and R(47), or R(46) and R(48) together are 4 or 5 methylene groups, of which one CH$_2$ group can be replaced by oxygen, S, NH, N—CH$_3$ or N-benzyl,
where A and N$^{(*)}$ are bonded to the phenyl nucleus of the benzoylguanidine parent structure; or
R(3) and R(4) independently of one another are —SR(64), —OR(65), —NHR(66), —NR(67)R(68), —CHR(69)R(70), —C(OH)R(54)R(55), —C≡CR(56), —CR(58)═CHR(57), —[CR(59)R(60)]$_u$—(CO)—[CR(61)R(62)]$_v$—R(63);
R(64), R(65), R(66), R(67) and R(69) identically or differently are —(CH$_2$)$_y$—(CHOH)$_z$—(CH$_2$)$_{aa}$—(CH$_{2O}$H)$_t$—R(71) or —(CH$_2$)$_{ab}$—O—(CH$_2$—CH$_2$O)$_{ac}$—R(72), R(71) and R(72) are hydrogen or methyl;
u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen, (C$_1$–C$_6$)-alkyl; or R(69) and R(70), or R(54) and R(55) together with the carbon atom carrying them are a (C$_3$–C$_8$)-cycloalkyl;
R(63) is H, (C$_1$–C$_6$)-alkyl, (C$_3$–C$_8$)-cycloalkyl or —C$_e$H$_{2e}$—R(73);
e is zero, 1, 2, 3 or 4;
R(56), R(57) and R(73) independently are phenyl, which is unsubstituted or substituted by 1–3 substituents selected from the group consisting of F, Cl, CF$_3$, methyl, methoxy and NR(74)R(75);
R(74) and R(75) are H or (C$_1$–C$_4$)-alkyl; or
R(56), R(57) and R(73) independently are (C$_1$–C$_9$)-heteroaryl, which is unsubstituted or substitued as phenyl;
R(58), R(59), R(60), R(61) and R(62) are hydrogen or methyl, or
R(3) and R(4) independently of one another are R(76)-NH—SO$_2$—;
R(76) is R(77)R(78)N—(C═Y')—;
Y' is oxygen, S or N—R(79);
R(77) and R(78) identically or differently are H, (C$_1$–C$_8$)-alkyl, (C$_3$–C$_6$)-alkenyl, —C$_f$H$_{2f}$—R(80);
f is zero, 1, 2, 3 or 4;
R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(77) and R(78) together are 4 or 5 methylene groups, of which one CH$_2$ group can be replaced by oxygen, S, NH, N—CH$_3$ or N-benzyl,
R(79) is defined as R(77) or is amidine; or
R(3) and R(4) independently of one another are NR(84)R(85);
R(84) and R(85) independently of one another are H, (C$_1$–C$_4$)-alkyl, or together are 4 or 5 methylene groups, of which one CH$_2$ group can be replaced by oxygen, S, NH, N—CH$_3$ or N-benzyl; or of which one or two CH$_2$ groups can be replaced by CH—C$_{cm}$H$_{2dm+1}$,
and their pharmaceutically tolerable salts;
(HOE 94/F 123-EP-A 682 017, NZ 272 058)
y) bicyclic heteroaroylguanidines of the formula I

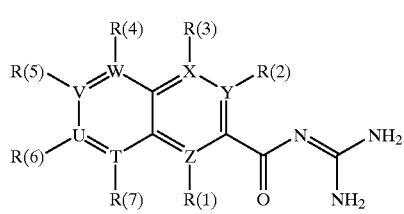

in which:
T, U, V, W, X, Y and Z independently of one another are nitrogen or carbon; but with the restriction that X and Z are not simultaneously nitrogen, and that T, U, V, W, X, Y and Z carry no substituents if they are nitrogen, and that no more than four of them are simultaneously nitrogen,
R(1) and R(2) independently of one another are hydrogen, F, Cl, Br, I, (C$_1$–C$_3$)-alkyl, (C$_1$–C$_3$)-perfluoroalkyl, OR(8), NR(8)R(9) or C(═O)N═C(NH$_2$)$_2$; R(8) and R(9) independently of one another are hydrogen or (C$_1$–C$_3$)-alkyl, or
R(8) and R(9) together are 4 or 5 methylene groups, of which one CH$_2$ group can be replaced by oxygen, S, NH, N—CH$_3$ or N-benzyl;

R(3), R(4), R(5), R(6) and R(7) independently of one another are hydrogen, F, Cl, Br, I, —C≡N, $X_k$—$(CH_2)_p$—$(C_qF_{2q+1})$, R(10a)—$SO_{bm}$, R(10b)R(10c)N—CO, R(11)—CO— or R(12)R(13)N—$SO_2$—, where the perfluoroalkyl group is straight-chain or branched;

X is oxygen, S or NR(14);
  R(14) is H or $(C_1-C_3)$-alkyl;
bm is zero, 1 or 2;
p is zero, 1 or 2;
k is zero or 1;
q 1, 2, 3, 4, 5 or 6;
R(10a), R(10b), R(11) and R(12) independently of one another are $(C_1-C_8)$-alkyl, $(C_{3-C6})$-alkenyl, —$C_nH_{2n}$—R(15) or $(C_1-C_8)$-perfluoroalkyl;
  n is zero, 1, 2, 3 or 4;
  R(15) is $(C_3-C_7)$-cycloalkyl or phenyl, which is not substituted or is substituted by 1–3 substituents selected from the group consisting of F, Cl, $CF_3$, methyl, methoxy and NR(16)R(17);
    R(16) and R(17) are H or $C_{1-C4}$-alkyl; or
R(10b), R(11) and R(12) are hydrogen;
R(10c) and R(13) independently are hydrogen or $(C_1-C_4)$-alkyl; or
R(10b) and R(10c) and R(12) and R(13) together are 4 or 5 methylene groups, of which one $CH_2$ group can be replaced by oxygen, sulfur, NH, N—$CH_3$ or N-benzyl; or R(3), R(4), R(5), R(6) and R(7) independently of one another are $(C_1-C_8)$-alkyl, —$C_{al}H_{2al}$R(18) or $(C_3-C_8)$-alkenyl;
al is zero, 1 or 2;
5: R(18) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(19a)R(19b);
  R(19a) and R(19b) are hydrogen, $(C_1-C_4)$-alkyl or $(C_1-C_4)$-perfluoroalkyl; or R(3), R(4), R(5), R(6) and R(7) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino or dimethylamino; or R(3), R(4), R(5), R(6) and R(7) independently of one another are

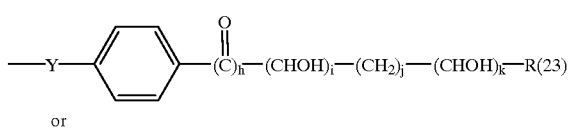

or

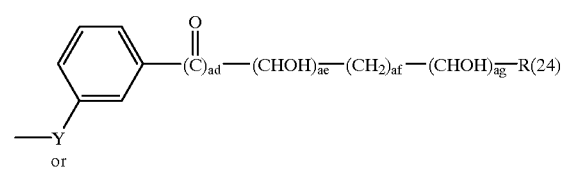

or

-continued

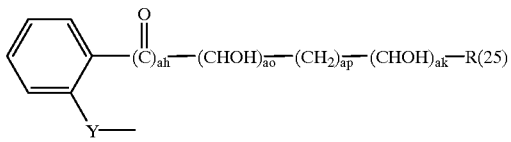

Y is oxygen, —S— or —NR(22)—;
h, ad, ah independently of one another are zero or 1;
i, j, k, ae, af, ag, ao, ap and ak independently of one another are zero, 1, 2, 3 or 4;
  but where in each case h, i and k are not simultaneously zero, ad, ae and ag are not simultaneously zero, and ah, ao and ak are not simultaneously zero,
R(23), R(24), R(25) and R(22) independently of one another are hydrogen or $(C_1-C_3)$-alkyl; or
R(3), R(4), R(5), R(6) and R(7) independently of one another are SR(29), —OR(30), —NR(31)R(32) or —CR(33)R(34)R(35);
R(29), R(30), R(31) and R(33) independently of one another are —$C_aH_{2a}$—$(C_{1-C9})$-heteroaryl, which is unsubstituted or substituted by 1–3 substituents selected from the group consisting of F, Cl, $CF_3$, $CH_3$, methoxy, hydroxyl, amino, methylamino and dimethylamino; a is zero, 1 or 2;
R(32), R(34) and R(35) independently of one another are defined as R(29) or are hydrogen, $(C_1-C_4)$-alkyl or $(C_1-C_4)$-perfluoroalkyl; or
R(3), R(4), R(5), R(6) and R(7) independently of one another are

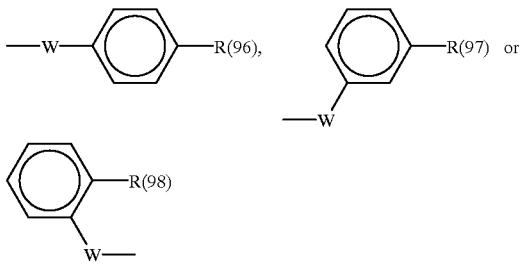

R(96), R(97) and R(98) independently of one another are $(C_1-C_9)$-heteroaryl, which is linked via C or N and which is unsubstitued or substituted by 1 to 3 substituents from the group consisting of F, Cl, $CF_3$, $CH_3$, methoxy, hydroxyl, amino, methylamino, dimethylamino or benzyl;
W is oxygen, S or NR(36)—; R(36) is H or $(C_1-C_4)$-alkyl; or
R(3), R(4), R(5), R(6) and R(7) independently of one another are R(46)×(1)—;
X(1) is oxygen, S, NR(47), (D=O)A— or NR(48)C=MN$^{(*)}$R(49)—;
M is oxygen or sulfur;
A is oxygen or NR(50);
D is C or SO;
R(46) is $(C_1-C_8)$-alkyl, $(C_3-C_8)$-alkenyl, $(CH_2)_bC_dF_{2d+1}$ or —$C_xH_{2x}$—R(51);
b is zero or 1;
d is 1, 2, 3, 4, 5, 6 or 7;
x is zero, 1, 2, 3 or 4;
R(51) is $(C_3-C_8)$-cycloalkyl, phenyl, biphenylyl or naphthyl, where the aromatics are not substituted or are substituted by 1–3 substituents selected from the group consisting of F, Cl, CF$_3$, methyl, methoxy and NR(52)R(53);

R(52) and R(53) are hydrogen, (C$_1$–C$_4$)-alkyl or (C$_1$–C$_4$)-perfluoroalkyl;

R(47), R(48) and R(50) independently are hydrogen, (C$_1$–C$_4$)-alkyl or (C$_1$–C$_4$)-perfluoroalkyl; R(49) is defined as R(46); or R(46) and R(47), or R(46) and R(48) together are 4 or 5 methylene groups, of which one CH$_2$ group can be replaced by oxygen, sulfur, NH, N—CH$_3$ or N-benzyl;

where A and N$^{(*)}$ are bonded to the phenyl nucleus of the heteroaroylguanidine parent structure; or R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$—R(63);

R(64), R(65), R(66), R(67) and R(69) identically or differently are —(CH$_2$)$_y$—(CHOH)$_z$—(CH$_2$)$_{aa}$—(CHOH)$_t$—R(71) or —(CH$_2$)$_{ab}$—O—(CH$_{2-H2}$O)$_{ac}$—R(72);

R(71) and R(72) independently of one another are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen or (C$_1$–C$_6$)-alkyl; or R(69) and R(70), or R(54) and R(55) together with the carbon atom carrying them are a (C$_3$–C$_8$)-cycloalkyl;

R(63) is hydrogen, (C$_1$–C$_6$)-alkyl, (C$_3$–C$_8$)-cycloalkyl or —C$_e$h$_{2e}$—R(73);

e is zero, 1, 2, 3 or 4;

R(56), R(57) and R(73) independently are phenyl, which is unsubstituted or substituted by 1–3 substituents selected from the group consisting of F, Cl, CF$_3$, methyl, methoxy and NR(74)R(75);

R(74) and R(75) are hydrogen or (C$_1$–C$_4$)-alkyl; or

R(56), R(57) and R(73) independently are (C$_1$–C$_9$)-heteroaryl, which is unsubstituted or substituted as phenyl;

R(58), R(59), R(60), R(61) and R(62) are hydrogen or methyl; or

R(3), R(4), R(5), R(6) and R(7) independently of one another are R(76)-NH—SO$_2$—;

R(76) is R(77)R(78)N—(C=Y')—;

Y' is oxygen, S or N—R(79);

R(77) and R(78) identically or differently are hydrogen, (C$_1$–C$_8$)-alkyl, (C$_{3–C6}$)-alkenyl or —C$_f$H$_{2f}$—R(80);

f is zero, 1, 2, 3 or 4;

R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or R(77) and R(78) together are 4 or 5 methylene groups, of which one CH$_2$ group can be replaced by oxygen, sulfur, NH, N—CH$_3$ or N-benzyl;

R(79) is defined as R(77) or is amidine; or

R(3), R(4), R(5), R(6) and R(7) independently of one another are NR(84a)R(85), OR(84b), SR(84c) or —C$_n$H$_{2n}$—R(84d);

n is zero, 1, 2, 3 or 4;

R(84d) is (C$_3$–C$_7$)-cycloalkyl or phenyl, which is not substituted or is substituted by 1–3 substituents from the group consisting of F, Cl, CF$_3$, methyl, methoxy and NR(16)R(17);

R(16) and R(17) are hydrogen, or C$_1$–C$_4$-alkyl;

R(84a), R(84b), R(84c) and R(85) independently of one another are hydrogen, (C$_{1–C8}$)-alkyl, (C$_1$–C$_8$)-perfluoroalkyl or (CH$_{2ax}$—R(84g); ax is zero, 1, 2, 3 or 4;

R(84g) is (C$_3$–C$_7$)-cycloalkyl or phenyl, which is not substituted or is substituted by 1–3 substituents selected from the group consisting of F, Cl, CF$_3$, methyl, methoxy and NR(84u)R(84v);

R(84u) and R(84v) are hydrogen or C$_1$–C$_4$-alkyl; or

R(84a) and R(85) together are 4 or 5 methylene groups, of which one CH$_2$ group can be replaced by oxygen, sulfur, NH, N—CH$_3$ or N-benzyl, and their pharmaceutically tolerable salts;

(HOE 94/F 134-EP-A 686 627, NZ 272 103)

z) benzoylguanidines of the formula I in which:

R(1) is R(6)—SO$_m$;

m is zero, 1 or 2;

R(6) is perfluoroalkyl having 1, 2, 3, 4, 5 or 6 carbon atoms, which is straight-chain or branched;

R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy; or R(2) and R(3) independently of one another are pyrrol-1-yl, pyrrol-2-yl or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;

R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;

R(7), R(8) and R(9) independently of one another are hydrogen or alkyl having 1, 2, 3 or 4 carbon atoms;

n is zero or 1;

o is zero, 1 or 2;

and their pharmacologically acceptable salts;

(HOE 94/F 168-EP-A 690 048, NZ 272 373)

ab) phenyl-substituted alkenylcarboxylic acid guanidides, carrying perfluoroalkyl groups, of the formula I

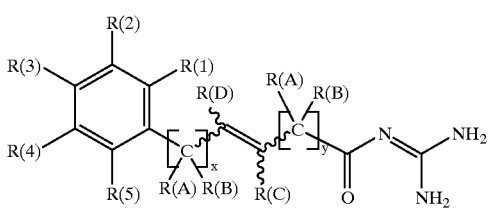
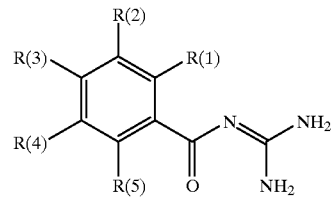

in which:

R(A) is hydrogen, F, Cl, Br, I, CN, OH, OR(6), $(C_1-C_8)$-alkyl, $O_r(CH_2)_aC_bF_{2b-1}$, $(C_3-C_8)$-cycloalkyl or NR(7)R(8);
r is zero or 1;
a is zero, 1, 2, 3 or 4;
b is 1, 2, 3, 4, 5, 6, 7 or 8;
R(6) is $(C_1-C_8)$-alkyl, $(C_1-C_4)$-perfluoroalkyl, $(C_3-C_8)$-alkenyl, $(C_3-C_8)$-cycloalkyl, phenyl or benzyl;
where the aromatics are not substituted or are substituted by 1–3 substituents from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6); or
R(7) and R(8) together are 4 or 5 methylene groups, of which one $CH_2$ group can be replaced by oxygen, sulfur, NH, N—$CH_3$ or N-benzyl;
R(B) independently is defined as R(A);
X is zero, 1 or 2;
Y is zero, 1 or 2;
R(C) is hydrogen, F, Cl, Br, I, CN, OR(12), $(C_1-C_8)$-alkyl, $O_p(CH_2)_fC_gF_{2g+1}$ or $(C_3-C_8)$-cycloalkyl;
p is zero or 1;
f is zero, 1, 2, 3 or 4;
g is 1, 2, 3, 4, 5, 6, 7 or 8;
R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl;
where the aromatics phenyl or benzyl are not substituted or are substituted by 1–3 substituents from the group consisting of F, Cl, $CF_3$, methyl, methoxy and NR(13)R(14);
R(13) and R(14) independently of one another are H, $(C_1-C_4)$-alkyl or $(C_1-C_4)$-perfluoroalkyl;
R(D) independently is defined as R(C),
R(1) is hydrogen, $(C_1-C_8)$-alkyl, $—O_t(CH_2)_dC_eF_{2e+1}$, $(C_3-C_8)$-cycloalkyl, F, Cl, Br, I or CN;
t is zero or 1;
d is zero, 1, 2, 3 or 4;
e is 1, 2, 3, 4, 5, 6, 7 or 8;
R(2), R(3), R(4) and R(5) independently of one another are defined as R(1);
but with the condition that at least one of the substituents R(A), R(B), R(C), R(D), R(1), R(2), R(4) or R(5) is an $O_r(CH_2)_aC_bF_{2b}$, $O_p(CH_2)_fC_gF_{2g+1}$ or $O_t(CH_2)_dC_eF_{2e+1}$ group and R(3) is not an $O_t(CH_2)_dC_eF_{2e+1}$ group;
and their pharmaceutically tolerable salts;
(HOE 94/F 182-EP-A 690 048, NZ 272 449)

ac) or tho-amino-substituted benzoylguanidines of the formula I in which:

R(1) is NR(50)R(6), R(50) and R(6) independently of one another are hydrogen, $(C_1-C_8)$-alkyl or $(C_1-C_8)$-perfluoroalkyl;
R(2), R(3), R(4) and R(5) independently of one another are R(10)—$SO_a$—, R(11)R(12)N—CO—, R(13)—CO— or R(14)R(15)N—$SO_2$—;
a is zero, 1 or 2,
R(10), R(11), R(12), R(13), R(14) and R(15) independently of one another are $(C_1-C_8)$-alkyl, $(C_1-C_8)$-perfluoroalkyl, $(C_3-C_6)$-alkenyl or —$C_{ab}H_{2ab}$—R(16);
ab is zero, 1, 2, 3 or 4;
R(16) is $(C_3-C_7)$-cycloalkyl, phenyl, which is not substituted or is substituted by 1–3 substituents selected from the group consisting of F, Cl, $CF_3$, methyl, methoxy or NR(17)R(18);
R(17) and R(18) independently of one another are H, $CF_3$ or $(C_1-C_4)$-alkyl; or
R(11), R(12), and also R(14) and R(15) together are 4 or 5 methylene groups, of which one $CH_2$ group can be replaced by oxygen, S, NH, N—$CH_3$ or N-benzyl; or
R(11), R(12), R(14) and R(15) independently of one another are hydrogen; or
R(2), R(3), R(4) and R(5) independently of one another are SR(21), —OR(22), —NR(23)R(24) or —CR(25)R(26)R(27);
R(21), R(22), R(23) and R(25) independently of one another are —$C_bH_{2b}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
b is zero, 1 or 2;
R(24), R(26) and R(27) independently of one another are hydrogen, $(C_1-C_4)$-alkyl or $(C_1-C_4)$-perfluoroalkyl; or
R(2), R(3), R(4) and R(5) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, $(C_3-C_8)$-alkenyl or —$C_{df}h_{2df}R(30)$;
(Xa) is O, S or NR(33);
R(33) is H, $(C_1-C_4)$-alkyl or $(C_1-C_4)$-perfluoroalkyl;
dg is zero or 1;
(Xb) is O, S or NR(34);
R(34) is H, $(C_1-C_4)$-alkyl or $(C_1-C_4)$-perfluoroalkyl;
dh is zero or 1;
da is zero, 1, 2, 3, 4, 5, 6, 7, 8;
db is zero, 1, 2, 3, 4;
de is zero, 1, 2, 3, 4, 5, 6, 7;
df is zero, 1, 2, 3, 4;
R(30) is $(C_3-C_8)$-cycloalkyl, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(31)R(32);

R(31) and R(32) are H, $(C_1–C_4)$-alkyl or $(C_1–C_4)$-perfluoroalkyl; or

R(2), R(3), R(4) and R(5) independently of one another are NR(40)R(41) or —(Xe)—$(CH_2)_{eb}$R(45);

R(40) and R(41) independently of one another are hydrogen, $(C_1–C_8)$-alkyl, $(C_1–C_8)$-perfluoroalkyl or $(CH_2)_e$—R(42); e is zero, 1, 2, 3 or 4;

R(42) is $(C_3–C_7)$-cycloalkyl, phenyl, which is not substituted or is substituted by 1–3 substituents selected from the group consisting of F, Cl, $CF_3$, methyl, methoxy and NR(43)R(44);

R(43) and R(44) independently of one another are H, $CF_3$ or $(C_1–C_4)$-alkyl; or R(40) and R(41) together are 4 or 5 methylene groups, of which one $CH_2$ group can be replaced by oxygen, sulfur, NH, N—$CH_3$ or N-benzyl;

(Xe) is O, S or NR(47); R(47) is H, $(C_1–C_4)$-alkyl or $(C_1–C_4)$-perfluoroalkyl;

eb is zero, 1, 2, 3 or 4;

R(45) is $(C_3–C_7)$-cycloalkyl, phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);

Xfa is $CH_2O$, S or NR(48);

Xfb is O, S or NR(49);

ed is 1, 2, 3 or 4;

R(46) is H, $(C_1–C_4)$-alkyl or $(C_1–C_4)$-perfluoroalkyl;

R(48), R(49), R(50) and R(51) independently of one another are H or $(C_1–C_4)$-alkyl or $(C_{1-C4})$-perfluoroalkyl;

where R(3) and R(4), however, cannot be hydrogen, and their pharmaceutically tolerable salts;

HOE 94/F 265-NZ 272 946, EP-A 700 904)

ad) benzoylguanidines of the formula I

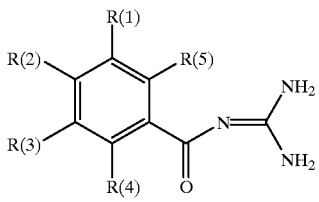

I in which:

one of the three substituents R(1), R(2) and R(3) is $(C_1–C_9)$-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or one of the three substituents R(1), R(2) and R(3) is —SR(10), —OR(10), —NR(10)R(11) or —CR(10)R(11)R(12);

R(10) is —$C_aH_{2a}$—$(C_{1-C9})$-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino; a is zero, 1 or 2;

R(11) and R(12) independently of one another are defined as R(10), are hydrogen or $(C_1–C_4)$-alkyl;

and the other substituents R(I), R(2) and R(3) in each case independently of one another are $(C_1–C_8)$-alkyl, $(C_2–C_8)$-alkenyl or —$C_mH_{2m}$R(14);

m is zero, 1 or 2;

R(14) is $(C_{3–C8})$-cycloalkyl or phenyl, which is not substituted or is substituted by 1–3 substituents selected from the group consisting of F, Cl, $CF_3$, methyl, methoxy and NR(15)R(16), R(15) and R(16) are hydrogen or $CH_3$; or the other substituents R(1), R(2) and R(3) in each case independently of one another are hydrogen, F, Cl, Br, I, —C≡N, X—$(CH_2)_p$—$(C_qF_{2q+})$, R(22)—$SO_u$, R(23)R(24)N—CO, R(25)—CO— or R(26)R(27)N—$SO_2$—, where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are $(C_1–C_9)$-alkyl, $(C_{2-C6})$-alkenyl, —$C_nH_{2n}$—R(29) or $CF_3$;

n is zero, 1, 2, 3 or 4;

R(28) is hydrogen or $(C_1–C_3)$-alkyl;

R(29) is $(C_{3-C7})$-cycloalkyl or phenyl; which is not substituted or is substituted by 1–3 substituents selected from the group consisting of F, Cl, $CF_3$, methyl, methoxy and NR(30)R(31);

R(30) and R(31) are hydrogen or $C_1–C_4$-alkyl, or

R(23), R(25) and R(26) are also hydrogen;

R(24) and R(27) independently of one another are hydrogen or $(C_1–C_4)$-alkyl; or R(23) and R(24), and also R(26) and R(27) together are 4 or 5 methylene groups, of which one $CH_2$ group can be replaced by oxygen, S, NH, N—$CH_3$ or N-benzyl; or the other substituents R(1), R(2) and R(3) in each case independently of one another are OR(35) or NR(35)R(36);

R(35) and R(36) independently of one another are hydrogen or $(C_1–C_6)$-alkyl; or R(35) and R(36) together are 4–7 methylene groups, of which one $CH_2$ group can be replaced by oxygen, S, NH, N—$CH_3$ or N-benzyl, R(4) and R(5) independently of one another are hydrogen, $(C_1–C_4)$-alkyl, F, Cl, —OR(32), —NR(33)R(34) or $C_rF_{2r+1}$;

R(32), R(33) and R(34) independently of one another are hydrogen or $(C_1–C_3)$-alkyl;

r is 1, 2, 3 or 4;

and their pharmaceutically tolerable salts;

(HOE 94/F 266-EP-A 702 001, NZ 272 948)

ad) benzoylguanidines of the formula I

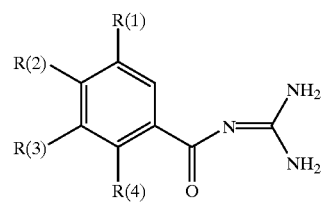

in which:

R(1) is hydrogen, F, Cl, Br, I, CN, $NO_2$, OH, $(C_1–C_8)$-alkyl, $(C_3–C_8)$-cycloalkyl, $O_a$—$(CH_2)_b$—$(CF_2)_c$—$CF_3$;

a is zero or 1;

b is zero, 1 or 2;

c is zero, 1, 2 or 3; or

R(1) is R(5)—SO$_m$— or R(6)R(7)N—SO$_2$—;
  m is zero, 1 or 2;
  R(5) and R(6) independently of one another are (C$_1$–C$_8$)-alkyl, (C$_3$–C$_6$)-alkenyl, CF$_3$ or —C$_n$H$_{2n}$—R(8);
    n is zero, 1, 2, 3 or 4;
  R(7) is hydrogen or (C$_1$–C$_4$)-alkyl;
  R(8) is (C$_3$–C$_7$)-cycloalkyl or phenyl, which is not substituted or is substituted by 1–3 substituents selected from the group consisting of F, Cl, CF$_3$, methyl, methoxy and NR(9)R(10);
    R(9) and R(10) independently of one another are hydrogen or (C$_1$–C$_4$)-alkyl; or
  R(6) is H;
  or R(6) and R(7) together are 4 or 5 methylene groups, of which one CH$_2$ group can be replaced by oxygen, S, NH, N—CH$_3$ or N-benzyl, or
R(1) is —SR(11), —OR(11) or —CR(11)R(12)R(13);
  R(11) is —C$_p$H$_{2p}$—(C$_3$–C$_8$)-cycloalkyl, —(C$_1$–C$_9$)-heteroaryl or phenyl, where the aromatic systems are unsubstituted or substituted by 1–3 substituents selected from the group consisting of F, Cl, CF$_3$, CH$_3$, methoxy, hydroxyl, amino, methylamino and dimethylamino;
    R(12), R(13) independently of one another are defined as R(11) or are hydrogen or (C$_1$–C$_4$)-alkyl;
    p is zero, 1 or 2; or
R(1) is phenyl, naphthyl, biphenylyl or (C$_1$–C$_9$)-heteroaryl, the latter linked via C or N, which are unsubstituted or substituted by 1–3 substituents selected from the group consisting of F, Cl, CF$_3$, CH$_3$, methoxy, hydroxyl, amino, methylamino and dimethylamino;
R(2) is —CF$_2$R(14), —CF[R(15)][R(16)], —CF[(CF$_2$)$_q$—CF$_3$][R(15)], —C[(CF$_2$)$_r$—CF$_3$]=CR(15)R(16);
  R(14) is (C$_1$–C$_4$)-alkyl or (C$_3$–C$_6$)-cycloalkyl;
  R(15) and R(16) independently of one another are hydrogen or (C$_1$–C$_4$)-alkyl;
  q is zero, 1 or 2;
  r is zero, 1 or 2;
R(3) is defined as R(1);
R(4) is hydrogen, (C$_1$–C$_3$)-alkyl, F, Cl, Br, I, CN, —(CH$_2$)$_s$—(CF$_2$)$_t$—CF$_3$;
  s is zero or 1;
  t is zero, 1 or 2;
and their pharmaceutically tolerable salts;
(HOE 94/F 267-EP-A 700 899, NZ 272 947)
ae) benzoylguanidines of the formula I

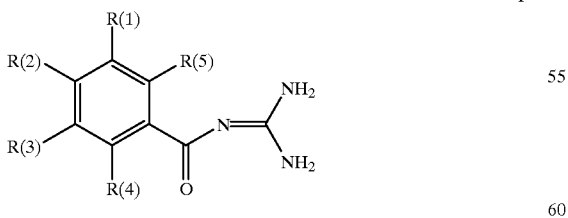

I in which:
one of the three substituents R(1), R(2) and R(3) is
  —Y4-[(CH$_2$)$_k$—CHR(7)—(C=O)R(8)]-phenyl,
  —Y-3—[(CH$_2$)$_k$—CHR(7)—(C=O)R(8)]-phenyl or
  —Y-2-[(CH$_2$)$_k$—CHR(7)—(C=O)R(8)]-phenyl,
  where the phenyl in each case is unsubstituted or substituted by 1–2 substituents from the group F, Cl, —CF$_3$, methyl, hydroxyl, methoxy, or —NR(37)R(38);
    R(37) and R(38) independently of one another are hydrogen or —CH$_3$;
  Y is a bond, oxygen, —S— or —NR(9);
    R(9) is hydrogen or —(C$_{1-C4}$)-alkyl;
  R(7) is —OR(10) or —NR(10)R(11);
    R(10) and R(11) independently of one another are hydrogen, —(C$_1$–C$_8$)-alkyl, —(C$_1$–C$_8$)-alkanoyl, —(C$_1$–C$_8$)-alkoxycarbonyl, benzyl, benzyloxycarbonyl; or
    R(10) is trityl;
  R(8) is —OR(12) or —NR(12)R(13);
    R(12) and R(13) independently of one another are hydrogen, —(C$_1$–C$_8$)-alkyl or benzyl;
  k is zero, 1, 2, 3 or 4;
and the other radicals R(1), R(2) and R(3) in each case independently of one another are —(C$_1$–C$_8$)-alkyl, —(C$_2$–C$_8$)-alkenyl or —(CH$_2$)$_m$R(14);
  m is zero, 1 or 2;
  R(14) is —(C$_3$–C$_8$)-cycloalkyl or phenyl, which is not substituted or is substituted by 1–3 substituents selected from the group consisting of F, Cl, —CF$_3$, methyl, methoxy and —NR(15)R(16);
    R(15) and R(16) are hydrogen or —CH$_3$; or
the other radicals R(1), R(2) and R(3) in each case independently of one another are R(18)R(19)N—(C=Y')—NH—SO$_2$—;
  Y' is oxygen, —S— or —N—R(20);
  R(18) and R(19) independently of one another are hydrogen, —(C$_1$–C$_8$)-alkyl, —(C$_3$–C$_6$)-alkenyl or —(CH$_2$)$_t$—R(21);
    t is zero, 1, 2, 3 or 4;
    R(21) is —(C$_5$–C$_7$)-cycloalkyl or phenyl, which is unsubstituted or substituted by 1–3 substituents selected from the group consisting of F, Cl, —CF$_3$, methoxy and —(C$_1$–C$_4$)-alkyl; or
  R(18) and R(19) together are 4 or 5 methylene groups, of which one CH$_2$ group can be replaced by oxygen, —S—, —NH—, —N—CH$_3$ or —N-benzyl;
  R(20) is defined as R(18) or is amidine; or
the other radicals R(1), R(2) and R(3) in each case independently of one another are hydrogen, F, Cl, Br, I, —C≡N, X—(CH$_2$)$_p$—(C$_q$F$_{2q+1}$), R(22)—SO$_u$—, R(23)R(24)N—CO—, R(25)—CO— or R(26)R(27)N—SO$_2$—, where the perfluoroalkyl group is straight-chain or branched;
  X is a bond, oxygen, —S—or —NR(28);
  u is zero, 1 or 2;
  p is zero, 1 or 2;
  q is 1, 2, 3, 4, 5 or 6;
  R(22), R(23), R(25) and R(26) independently of one another are —(C$_1$–C$_8$)-alkyl, —(C$_3$–C$_6$)-alkenyl, —(CH$_2$)$_n$—R(29) or —CF$_3$;
    n is zero, 1, 2, 3 or 4;
    R(28) is hydrogen or —(C$_1$–C$_3$)-alkyl;
    R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);
      R(30) and R(31) are hydrogen or —(C$_1$–C$_4$)-alkyl; or
  R(23), R(25) and R(26) are hydrogen;
  R(24) and R(27) independently of one another are hydrogen or —(C$_1$–C$_4$)-alkyl; or
  R(23) and R(24), and also R(26) and R(27) together are 4 or 5 methylene groups, of which one CH$_2$ group can be replaced by oxygen, —S—, —NH—, —N—CH$_3$ or —N-benzyl; or the other radicals R(1), R(2) and R(3) in each case independently of one another are —OR(35) or —NR(35)R(36);

R(35) and R(36) independently of one another are hydrogen or —(C$_1$–C$_6$)-alkyl; or R(35) and R(36) together are 4–7 methylene groups, of which one CH$_2$ group can be replaced by oxygen, —S—, —NH—, —N—CH$_3$ or —N-benzyl;

R(4) R(5) independently of one another are hydrogen, —(C$_1$–C$_4$)-alkyl, F, Cl, —OR(32), —NR(33)R(34) or —C$_r$F$_{2r+1}$;

R(32), R(33) and R(34) independently of one another are hydrogen or —(C$_1$–C$_3$)-alkyl;

r is 1, 2, 3 or 4;

and their pharmaceutically tolerable salts;
(HOE 94/F 352-EP-A 713 684, NZ 280 517)

af) benzoylguanidines of the formula I

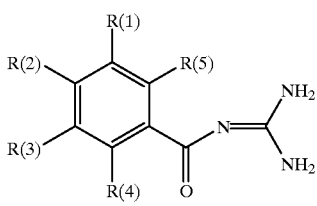

I in which:

R(1) is R(6)—CO or R(7)R(8)N—CO;

R(6) is (C$_1$–C$_8$)-alkyl, (C$_1$–C$_8$)-perluoroalkyl, (C$_3$–C$_8$)-alkenyl or —C$_n$H$_{2n}$—R(9), n is zero, 1, 2, 3 or 4;

R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11), R(10) and R(11) are H, (C$_1$–C$_4$)-alkyl or (C$_1$–C$_4$)-perfluoroalkyl;

R(7) is H, (C$_1$–C$_8$)-alkyl, (C$_1$–C$_8$)-perfluoroalkyl, (C$_3$–C$_8$)-alkenyl or —C$_n$H$_{2n}$—R(12);

n is zero, 1, 2, 3 or 4;

R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);

R(13) and R(14) are H, (C$_1$–C$_4$)-alkyl or (C$_1$–C$_4$)-perfluoroalkyl;

R(8) is H, (C$_1$–C$_4$)-alkyl or (C$_1$–C$_4$)-perfluoroalkyl; or

R(7) and R(8) together are 4 or 5 methylene groups, of which one CH$_2$ group can be replaced by oxygen, S, NH, N—CH$_3$ or N-benzyl;

R(2) is defined as R(1), or is H, OH, F, Cl, Br, I, CN, NO$_2$,(C$_1$–C$_8$)-alkyl, (C$_1$–C$_8$)-perfluoroalkyl, (C$_3$–C$_8$)-alkenyl or —C$_n$H$_{2n}$R(15);

n is zero, 1, 2, 3 or 4;

R(15) is (C$_{3-8}$)-cycloalkyl, phenyl, biphenylyl or naphthyl, where the aromatics are not substituted or are substituted by 1–3 substituents selected from the group consisting of F, Cl, CF$_3$, methyl, methoxy and NR(16)R(17);

R(16) and R(17) are H, (C$_1$–C$_4$)-alkyl or (C$_1$–C$_4$)-perfluoroalkyl; or

R(2) is (C$_1$–C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino; or R(2) is SR(18), —OR(18), —NR(18)R(19) or —CR(18)R(19)R(20);

R(18) is —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino, dimethylamino;

a is zero, 1 or 2;

R(19) and R(20) independently of one another are defined as R(18) or are hydrogen, (C$_1$–C$_4$)-alkyl or (C$_1$–C$_4$)-perfluoroalkyl; or R(2) is R(21)—SO$_m$ or R(22)R(23)N—SO$_2$—;

m is 1 or 2;

R(21) is (C$_1$–C$_8$)-alkyl, (C$_1$–C$_8$)-perfluoroalkyl, (C$_3$–C$_8$)-alkenyl or —C$_n$H$_{2n}$—R(24);

n is zero, 1, 2, 3 or 4;

R(24) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(27)R(28);

R(27) and R(28) are H, (C$_1$–C$_4$)-alkyl or (C$_1$–C$_4$)-perfluoroalkyl;

R(22) is H, (C$_1$–C$_8$)-alkyl, (C$_1$–C$_8$)-perfluoroalkyl, (C$_{3-C8}$)-alkenyl or —C$_n$H$_{2n}$—R(29);

n is zero, 1, 2, 3 or 4;

R(29) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(30)R(31);

R(30) and R(31) are H, (C$_1$–C$_4$)-alkyl or (C$_1$–C$_4$)-perfluoroalkyl;

R(23) is hydrogen, (C$_1$–C$_4$)-alkyl or (C$_1$–C$_4$)-perfluoroalkyl; or

R(22) and R(23) together are 4 or 5 methylene groups, of which one CH$_2$ group can be replaced by oxygen, S, NH, N—CH$_3$ or N-benzyl; or R(2) is R(33)X—;

X is oxygen, S, NR(34), (D=O)A— or NR(34)C=MN$^{(*)}$R(35)—;

M is oxygen or S;

A is oxygen or NR(34);

D is C or SO;

R(33) is (C$_1$–C$_8$)-alkyl, (C$_3$–C$_8$)-alkenyl, (CH$_2$)$_b$C$_d$F$_{2d+1}$ or —C$_n$H$_{2n}$—R(36);

b is zero or 1;

d is 1, 2, 3, 4, 5, 6 or 7;

n is zero, 1, 2, 3, or 4;

R(36) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(37)R(38);

R(37) and R(38) are H, (C$_1$–C$_4$)-alkyl or (C$_1$–C$_4$)-perfluoroalkyl;

R(34) is hydrogen, (C$_1$–C$_4$)-alkyl or (C$_1$–C$_4$)-perfluoroalkyl;

R(35) is defined as R(33); or

R(33) and R(34) together are 4 or 5 methylene groups, of which one CH$_2$ group can be replaced by oxygen, S, NH, N—CH$_3$ or N-benzyl; where A and N(*) are bonded to the phenyl nucleus of the benzoylguanidine parent structure; or R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);

R(40) and R(41) independently of one another are —(CH$_2$)$_p$—(CHOH)$_q$—(CH$_2$)$_r$—(CHOH)$_t$—R(51) or —(CH$_2$)$_p$—O—(CH$_2$–H$_2$O)$_q$—R(51);

R(51) is hydrogen or methyl;

u is 1, 2, 3 or 4;

v is zero, 1, 2, 3 or 4;

p,q and r independently of one another are zero, 1, 2, 3 or 4;

t is 1, 2, 3 or 4;

R(42) and R(43) independently of one another are hydrogen or (C$_1$–C$_6$)-alkyl; or R(42) and R(43) together with the carbon atom carrying them are a (C$_3$–C$_8$)-cycloalkyl;

R(44) is hydrogen, (C$_1$–C$_6$)-alkyl, (C$_3$–C$_8$)-cycloalkyl, —C$_e$H$_{2e}$—R(45);

e is zero, 1, 2, 3 or 4;

R(45) is phenyl, which is unsubstituted or substituted by 1–3 substituents selected from the group consisting of F, Cl, CF$_3$, methyl, methoxy and NR(52)R(53);

R(52) and R(53) are H or (C$_1$–C$_4$)-alkyl; or

R(45) is (C$_1$–C$_9$)-heteroaryl, which is unsubstituted or substituted as phenyl; or R(45) is (C$_1$–C$_6$)-alkyl, which is unsubstituted or substituted by 1–3 OH;

R(46), R(47), R(48), R(49) and R(50) independently of one another are hydrogen or methyl; or R(2) is R(55)—NH—SO$_2$—;

R(55) is R(56)R(57)N—(C=Y)—;

Y is oxygen, S or N—R(58);

R(56) and R(57) independently of one another are hydrogen, (C$_1$–C$_8$)-alkyl, (C$_3$–C$_6$)-alkenyl or —C$_f$H$_{2f}$—R(59)

f is zero, 1, 2, 3 or 4;

R(59) is (C$_5$–C$_7$)-cycloalkyl, phenyl, which is unsubstituted or substituted by 1–3 substituents selected from the group consisting of F, Cl, CF$_3$, methoxy and (C$_1$–C$_4$)-alkyl; or R(56) and R(57) together are 4 or 5 methylene groups, of which one CH$_2$ group can be replaced by oxygen, S, NH, N—CH$_3$ or N-benzyl;

R(58) is defined as R(56) or is amidine;

R(3), R(4) and R(5) are independently of one another defined as R(1) or R(2), but where at least one of the substituents R(2), R(3), R(4) and R(5) must be OH;

and their pharmaceutically tolerable salts;

(HOE 95/F 007K-EP-A 723 956, NZ 280 887)

ag) benzoylguanidines of the formula I

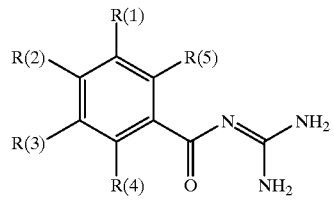

I in which:

one of the three substituents R(1), R(2) and R(3) is R(6)—A—B—D—;

R(6) is a basic protonatable radical, i.e. an amino group —NR(7)R(8), an amidino group R(7)R(8)N—C[=N—R(9)]— or a guanidino group

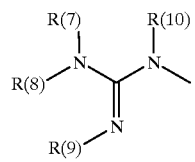

R(7), R(8), R(9) and R(10) independently of one another are hydrogen or alkyl having 1, 2, 3 or 4 carbon atoms; or R(7) and R(8) together are C$_a$H$_{2a}$;

a is 4, 5, 6 or 7;

where if a=5, 6 or 7 a methylene group of the group C$_a$H$_{2a}$ a can be replaced by a heteroatom group O, SO$_m$ or NR(11), or R(8) and R(9) or R(9) and R(10) or R(7) and R(10) are a group C$_a$H$_{2a}$;

a is 2, 3, 4 or 5; where if a=3, 4 or 5 a methylene group of the group C$_a$H$_{2a}$ can be replaced by a heteroatom group O, SO$_m$ or NR(11);

m is zero, 1 or 2;

R(11) is hydrogen or methyl; or

R(6) is a basic heteroaromatic ring system having 1–9 carbon atoms;

A is C$_b$H$_{2b}$;

b is 1, 2, 3, 4, 5, 6, 7, 8, 9 or 10; where in the group C$_b$H$_{2b}$ one or two methylene groups can be replaced by one of the groupings selected from the group consisting of —O—, —CO—, —CH[OR(20)]—, —SO$_m$—, —NR(20)—, —NR(20)—CO—, —NR(20)—CO—NH—, —NR(20)—CO—NH—SO$_2$—

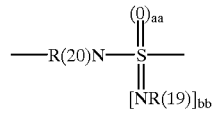

and —SO$_{aa}$[NR(19)]$_{bb}$—; and where in the group C$_b$H$_{2b}$ a methylene group can be replaced by —CH—R(99), where R(99) together with R(7) for ms a pyrrolidine or piperidine ring;

aa is 1 or 2;

bb is 0 or 1;

aa+bb=2;

R(19) is hydrogen or alkyl having 1, 2, 3 or 4 carbon atoms;
R(20) is hydrogen or methyl;
B is a phenylene or naphthylene radical

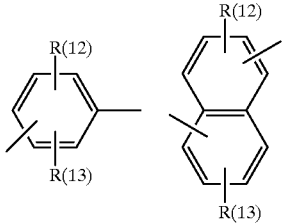

R(12) and R(13) independently of one another are hydrogen, methyl, F, Cl, Br, I, $CF_3$ or $-SO_w-$R(14);
R(14) is methyl or NR(15)R(16);
R(15) and R(16) independently of one another are hydrogen or alkyl having 1, 2, 3 or 4 carbon atoms;
w is zero, 1 or 2;
D is $-C_dH_{2d}-X_f-$;
d is zero, 1, 2, 3 or 4;
X is $-O-$, $-CO-$, $-CH[OR(21)]-$, $-SO_m-$ or $-NR(21)-$;
f is zero or 1;
R(21) is hydrogen or methyl;
m is zero, 1 or 2;
and the other substituents R(1) and R(2) and R(3) in each case independently of one another are hydrogen, F, Cl, Br, I, $-CN$, $-(C_1-C_8)$-alkyl, $-(C_2-C_8)$-alkenyl, $-NR(35)R(36)$ or $R(17)-C_gH_{2g}-Z_h-$;
is zero, 1, 2, 3 or 4;
h is zero or 1;
R(35) and R(36) independently of one another are hydrogen or alkyl having 1, 2, 3, 4, 5 or 6 carbon atoms; or
R(35) and R(36) together are 4–7 methylene groups, of which one $CH_2$ group can be replaced by oxygen, $-S-$, $-NH-$, $-NCH_3$ or $-N$-benzyl;
Z is $-O-$, $-CO-$, $-SO_v-$, $-NR(18)-$, $-NR(18)-CO-$, $-NR(18)-CO-NH-$ or $-NR(18)-SO_2-$;
R(18) is hydrogen or methyl;
v is zero, 1 or 2;
R(17) is hydrogen, cycloalkyl having 3, 5 or 6 carbon atoms or $C_kF_{2k+1}-$;
k is 1, 2 or 3, or
R(17) is pyrrol-1-yl, pyrrol-2-yl or pyrrol-3-yl, which is not substituted or is substituted by 1–4 substituents selected from the group consisting of F, Cl, Br, I, $-CN$, $(C_2-C_8)$-alkanoyl, $(C_2-C_8)$-alkoxycarbonyl, formyl, carboxyl, $-CF_3$, methyl and methoxy; or
R(17) is $-(C_3-C_8)$-cycloalkyl or phenyl, which is not substituted or is substituted by 1–3 substituents selected from the group consisting of F and Cl, $-CF_3$, methyl, hydroxyl, methoxy, $-NR(37)R(38)$, $CH_3SO_2-$ and $H_2NO_2S-$;
R(37) and R(38) are hydrogen or $-CH_3$;
R(4) and R(5) independently of one another are hydrogen, alkyl having 1, 2, 3 or 4 carbon atoms, F, Cl, $-OR(32)$, $-NR(33)R(34)$ or $-C_rF_{2r+1}$;
R(32), R(33) and R(34) independently of one another are hydrogen or alkyl having 1, 2 or 3 carbon atoms;
r is 1, 2, 3 or 4;

and their pharmacologically tolerable salts;
(HOE 95/F 072-EP-A 738 712, NZ 286 380)

ah) indenoylguanidines of the formula I

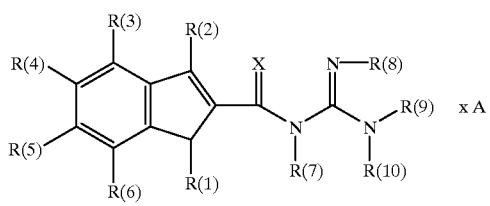

in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, $O-C(=O)$-alkyl having 1, 2, 3 or 4 carbon atoms or $C_mH_{2m}-NR(12)R(13)$;
R(12) and R(13) independently of one another are hydrogen or alkyl having 1, 2, 3 or 4 carbon atoms;
m is zero, 2, 3 or 4;
$NH-C(=O)-NH_2$, $C(=O)-O$-alkyl having 1, 2, 3 or 4 carbon atoms, $C(=O)-NH_2$, $C(=O)-NH$-alkyl having 1, 2, 3 or 4 carbon atoms, $C(=O)-N(alkyl)_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, $C_1-C_4$-alkyl-substituted aryl, $C_1-C_4$-alkylheteroaryl, $C_1-C_4$-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, $O-C(=O)-C_1-C_4$-alkylaryl, $O-C(=O)-NH-C_1-C_4$-alkyl, $O-C(=O)-N(C_1-C_4$-alkyl)$_2$, $NO_2$, $CN$, $CF_3$, $NH_2$, $NH-C(=O)-C_1-C_4$-alkyl, $NH-C(=O)-NH_2$, $COOH$, $C(=O)-O-C_1-C_4$-alkyl, $C(=O)-NH_2$, $C(=O)-NH-C_1-C_4$-alkyl, $C(=O)-N(C_1-C_4$-alkyl)$_2$, $C_1-C_4-COOH$, $C_1-C_4$-alkyl-$C(=O)-O-C_1-C_4$-alkyl, $SO_3H$, $SO_2$-alkyl, $SO_2$-alkylaryl, $SO_2-N$-(alkyl)$_2$, $SO_2-N(alkyl)(alkylaryl)$, $C(=O)-R(11)$, $C_1-C_{10}$-alkyl $-C(=O)-R(11)$, $C_2-C_{10}$-alkenyl-$C(=O)-R(11)$, $C_2-C_{10}$-alkynyl-$C(=O)-R(11)$, $NH-C(=O)-C_1-C_{10}$-alkyl-$C(=O)-R(11)$, $O-C_1-C_{11}$-alkyl-$C(=O)-R(11)$;
R(11) is $C_1-C_4$-alkyl, $C_1-C_4$-alkynyl, aryl, substituted aryl, $NH_2$, $NH-C_1-C_4$-alkyl, $N-(C_1-C_4$-alkyl)$_2$, $SO_3H$, $SO_2$-alkyl, $SO_2$-alkylaryl, $SO_2-N-$(alkyl)$_2$, $SO_2-N(alkyl)(alkylaryl)$;
X is O, S or NH;
R(7), R(8), R(9) and R(10) independently of one another are hydrogen, alkyl, cycloalkyl, aryl, alkylaryl; or R(8) and R(9) together are part of a 5-, 6- or 7-membered heterocyclic ring;

A is absent or is a nontoxic organic or inorganic acid.
(HOE 95/F 109-EP 748 795, NZ 286 583)

ai) benzyloxycarbonylguanidines of the formula I

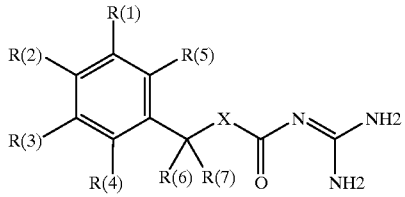

I in which:
R(1), R(2) and R(3) independently of one another are —Y-[4-R(8)-phenyl], —Y-[3-R(8)-phenyl] or —Y-[2-R(8)-phenyl], where the phenyl is in each case unsubstituted or substituted by 1–2 substituents from the group consisting of F, Cl, —CF$_3$, methyl, hydroxyl, methoxy and —NR(96)R(97);

R(96) and R(97) independently of one another are hydrogen or —CH$_3$;

Y is a bond, CH$_2$, oxygen, —S— or —NR(9); R(9) is hydrogen or alkyl having 1, 2, 3 or 4 carbon atoms;

R(8) is SO$_a$[NR(98)]$_b$NR(99)R(10);
a is 1 or 2;
b is 0 or 1;
a+b=2;

R(98), R(99) and R(10) independently of one another are hydrogen, —(C$_1$–C$_8$)-alkyl, benzyl, —(C$_2$–C$_8$)-alkylene—NR(11)R(12), (C$_2$–C$_8$)-alkylene-NR(13)—(C$_2$–C$_8$)-alkylene-NR(37)R(38) or (C$_0$–C$_8$)-alkylene-CR(39)R(40)CR(41)R(42)(C$_0$–C$_8$)-alkylene-NR(43)R(44);

R(11), R(12), R(13), R(37), R(38), R(43) and R(44) independently of one another are hydrogen, —(C$_1$–C$_8$)-alkyl or benzyl;

R(39), R(40), R(41) and R(42) independently of one another are hydrogen, —(C$_1$–C$_8$)-alkyl or —(C$_0$–C$_3$)-alkylenephenyl, where the phenyl is not substituted or is substituted by 1–3 substituents selected from the group consisting of F, Cl, —CF$_3$, methyl and methoxy; or R(99) and R(10) together are 4–6 methylene groups, of which one CH$_2$ group can be replaced by oxygen, —S—, —NH—, —N—CH$_3$ or —N-benzyl; or R(8) is SO$_a$[NR(98)]$_b$NR(95)—C[═N—R(94)]—NR(93)R(92);

R(92), R(93), R(94) and R(95) independently of one another are hydrogen or alkyl having 1, 2, 3 or 4 carbon atoms;

R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, C$_2$–C$_8$)-alkanoyl, (C$_2$–C$_8$)-alkoxycarbonyl, formyl, carboxyl, —CF$_3$, methyl, methoxy; or R(1), R(2) and R(3) independently of one another are hydrogen, —(C$_1$–C$_8$)-alkyl, —(C$_2$–C$_8$)-alkenyl or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) are hydrogen or —CH$_3$; or

R(1), R(2) and R(3) independently of one another are —Q-4-[(CH$_2$)$_k$—CHR(17)—(C═O)R(20)]-phenyl, —Q-3-[(CH$_2$)$_k$—CHR(17)—(C═O)R(20)]-phenyl or —Q-2-[(CH$_2$)$_k$—CHR(17)—(C═O)R(20)]-phenyl, where the phenyl in each case is unsubstituted or substituted by 1–2 substituents from the group F, Cl, —CF$_3$, methyl, hydroxyl, methoxy and —NR(35)R(36); R(35) and R(36) independently of one another are hydrogen or —CH$_3$;

Q is a bond, oxygen, —S— or —NR(18); R(18) is hydrogen or —(C$_1$–C$_4$)-alkyl;

R(17) is —OR(21) or —NR(21)R(22);

R(21) and R(22) independently of one another are hydrogen, —(C$_1$–C$_8$)-alkyl, —(C$_1$–C$_8$)-alkanoyl, —(C$_1$–C$_8$)-alkoxycarbonyl, benzyl, benzyloxycarbonyl; or R(21) is trityl;

R(20) is —OR(23) or —NR(23)R(24); R(23), R(24) independently of one another are hydrogen, —(C$_1$–C$_8$)-alkyl or benzyl;

k is zero, 1, 2, 3 or 4; or

R(1), R(2) and R(3) independently of one another are (C$_1$–C$_9$)-heteroaryl, which is linked via C or N and which is unsubstituted or substituted by 1–3 substituents from the group F, Cl, CF$_3$, CH$_3$, methoxy, hydroxyl, amino, methylamino and dimethylamino; or R(1), R(2) and R(3) are —SR(25), —OR(25), —NR(25)R(26), —CR(25)R(26)R(27); R(25) is —C$_f$H$_{2f}$—(C$_1$–C$_9$)-heteroaryl, which is unsubstituted or substituted by 1–3 substituents from the group F, Cl, CF$_3$, CH$_3$, methoxy, hydroxyl, amino, methylamino and dimethylamino;

f is zero, 1 or 2;

R(26) and R(27) independently of one another are defined as R(25) or are hydrogen or (C$_1$–C$_4$)-alkyl, or R(1), R(2) and R(3) independently of one another are (C$_1$–C$_9$)-heteroaryl-N-oxide, which is linked via C or N and which is unsubstituted or substituted by 1–3 substituents selected from the group consisting of F, Cl, CF$_3$, CH$_3$, methoxy, hydroxyl, amino, methylamino and dimethylamino; or R(1), R(2) and R(3) independently of one another are —SR(28), —OR(28), —NR(28)R(29) or —CR(28)R(29)R(30);

R(28) is —C$_g$H$_{2g}$—(C$_1$–C$_9$)-heteroaryl-N-oxide, which is unsubstituted or substituted by 1–3 substituents selected from the group consisting of F, Cl, CF$_3$, CH$_3$, methoxy, hydroxyl, amino, methylamino and dimethylamino;

g is zero, 1 or 2;

R(29), R(30) independently of one another are defined as R(28), hydrogen or (C$_1$–C$_4$)-alkyl; or R(1), R(2) and R(3) independently of one another are hydrogen, F, Cl, Br, I, —C≈N, T—(CH$_2$)$_h$—(C$_i$F$_{2i+1}$), R(31)SO$_l$—, R(32)R(33)N—CO—, R(34)—CO— or R(45)R(46)N—SO$_2$, where the perfluoroalkyl group is straight-chain or branched;

T is a bond, oxygen, —S— or —NR(47);

l is zero, 1 or 2;

h is zero, 1 or 2;

i is 1, 2, 3, 4, 5 or 6;

R(31), R(32), R(34) and R(45) independently of one another are —(C$_1$–C$_8$)-alkyl, —(C$_3$–C$_6$)-alkenyl, (CH$_2$)$_n$R(48) or —CF$_3$;

n is zero, 1, 2, 3 or 4;
R(47) is hydrogen or alkyl with 1, 2 or 3 carbon atoms;
R(48) is —($C_3$–$C_7$)-cycloalkyl or phenyl, which is not substituted or is substituted by 1–3 substituents selected from the group consisting of F, Cl, —$CF_3$, methyl, methoxy and —NR(49)R(50);
R(49) and R(50) are hydrogen or alkyl having 1, 2, 3 or 4 carbon atoms; or
R(32), R(34) and R(45) are hydrogen;
R(33) and R(46) independently of one another are hydrogen or alkyl having 1, 2, 3 or 4 carbon atoms; or
R(32) and R(33), and R(45) and R(46) together are 5 or 6 methylene groups, of which one $CH_2$ group can be replaced by oxygen, —S—, —NH—, —$NCH_3$ or —N-benzyl; or
R(1), R(2) and R(3) independently of one another are R(51)—A—G—D—;
R(51) is a basic protonatable radical, i.e. an amino group —NR(52)R(53), an amidino group R(52)R(53)N—C[═N—R(54)]— or a guanidino group R(52)R(53)N—C[═N—R(54)]—NR(55)—;
R(52), R(53), R(54) and R(55) independently of one another are hydrogen or alkyl having 1, 2, 3 or 4 carbon atoms; or
R(52) and R(53) are a group $C_\alpha H_{2\alpha}$;
α is 4, 5, 6 or 7;
where if a α=5, 6 or 7 a carbon atom of the group $C_\alpha H_{2\alpha}$ can be replaced by a heteroatom group O, $SO_d$ or NR(56), or
R(53) and R(54) or R(54) and R(55) or R(52) and R(55) are a group $C_\gamma H_{2\gamma}$;
γ is 2, 3, 4 or 5;
where if γ=3, 4 or 5 a carbon atom of the group $C_\gamma H_{2\gamma}$ can be replaced by a heteroatom group O, $SO_d$ or NR(56);
d is zero, 1 or 2;
R(56) is hydrogen or methyl; or
R(51) is a basic heteroaromatic ring system having 1–9 carbon atoms;
A is a group $C_e H_{2e}$;
e is zero, 1, 2, 3, 4, 5, 6, ,7, 8, 9 or 10;
where in the group $C_e H_{2e}$ a carbon atom can be replaced by one of the groupings —O—, —CO—, —CH[OR(57)]—, 13 $SO_r$—, —NR(57)—, —NR(57)—O—, —NR(57)—CO—NH—, —NR(57)—CO—NH—$SO_2$— or —NR(57)—$SO_2$—;
r is zero, 1 or 2;
R(57) is hydrogen or methyl;
G is a phenylene radical

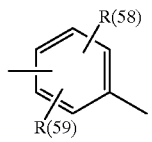

R(58) and R(59) independently of one another are hydrogen, methyl, methoxy, F, Cl, Br, I, $CF_3$ or —$SO_s$—R(60);
R(60) is methyl or NR(61)R(62);
R(61) and R(62) independently of one another are hydrogen or alkyl having 1, 2, 3 or 4 carbon atoms;
D is —$C_v H_{2v}$—$E_w$—;

v is zero, 1, 2, 3 or 4;
E is —O—, —CO—, —CH[OR(63)]—, —$SO_{aa}$— or —NR(63)—;
w is zero or 1;
aa is zero, 1 or 2
R(63) is hydrogen or methyl, or
R(1), R(2) and R(3) independently of one another are —$CF_2$R(64), —CF[R(65)][R(66)], —CF[($CF_2$)$_q$—$CF_3$][R(65)], —C[($CF_2$)$_p$—$CF_3$]═CR(65)R(66);
R(64) is alkyl having 1, 2, 3 or 4 carbon atoms or cycloalkyl having 3, 4, 5, 6 or 7 carbon atoms;
R(65) and R(66) independently of one another are hydrogen or alkyl having 1, 2, 3 or 4 carbon atoms;
q is zero, 1 or 2;
p is zero, 1 or 2; or
R(1), R(2) and R(3) independently of one another are —OR(67) or —NR(67)R(68);
R(67) and R(68) independently of one another are hydrogen or alkyl having 1, 2, 3, 4, 5 or 6 carbon atoms; or
R(67) and R(68) together are 4, 5, 6 or 7 methylene groups, of which one $CH_2$ group can be replaced by oxygen, —S—, —$SO_2$, —NH—, —$NCH_3$ or —N-benzyl;
R(4) and R(5) independently of one another are hydrogen, alkyl having 1, 2, 3 or 4 carbon atoms, F, Cl, —OR(69), —NR(70)R(71) or —$C_z F_{2z+1}$;
R(69), R(70) and R(71) independently of one another are hydrogen or alkyl having 1, 2 or 3 carbon atoms;
z is 1, 2, 3 or 4;
R(6) and R(7) independently of one another are hydrogen or alkyl having 1, 2, 3 or 4 carbon atoms;
X is oxygen or NR(72);
R(72) is hydrogen or alkyl having 1, 2, 3 or 4 carbon atoms; and their pharmaceutically tolerable salts;
(HOE 95/F 115-EP 744 397, NZ 286 622)
ak) alkenylcarboxylic acid guanidides, carrying flu or ophenyl groups, of the formula I

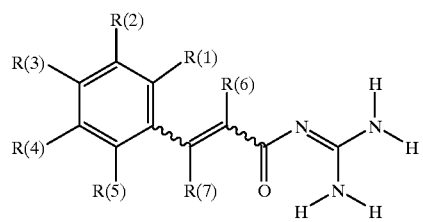

in which:
R(6) is hydrogen, ($C_1$–$C_8$)-alkyl, ($C_3$–$C_8$)-cycloalkyl or phenyl, where the phenyl group is not substituted or is substituted by 1–3 substituents selected from the group consisting of F, Cl, $CF_3$, methyl, methoxy and NR(9)R(10);
R(9) and R(10) are hydrogen, ($C_1$–$C_4$)-alkyl or ($C_1$–$C_4$)-perfluoroalkyl;
R(7) independently is defined as R(6);
R(1), R(2), R(3), R(4) and R(5) independently of one another are hydrogen or F;
where, however, at least one of the radicals R(1), R(2), R(3), R(4) and R(5) must be fluorine;
and their pharmaceutically tolerable salts;
(HOE 95/F 167-NZ 299 015)

al) benzoylguanidines of the formula I

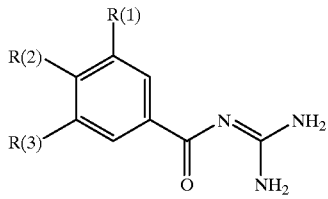

in which:
R(1) is R(4)—SO$_m$ or R(5)R(6)N—SO$_2$—;
  m is 1 or 2;
  R(4) and R(5) independently of one another are alkyl having 1, 2, 3, 4, 5, 6, 7 or 8 carbon atoms, alkenyl having 3, 4, 5 or 6 carbon atoms, CF$_3$ or —C$_n$H$_{2n}$—R(7);
    n is zero, 1, 2, 3 or 4;
  R(6) is H or alkyl having 1, 2, 3 or 4 carbon atoms;
  R(7) is cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(8)R(9);
    R(8) and R(9) are H or alkyl having 1, 2, 3 or 4 carbon atoms; or
  R(5) is also hydrogen; or
  R(5) and R(6) together are 4 or 5 methylene groups, of which a CH$_2$ group ru can be replaced by oxygen, S, NH, N—CH$_3$ or N-benzyl; or
R(1) is —O$_p$—(CH$_2$)$_q$—(CF$_2$)$_r$—CF$_3$;
  p is zero or 1;
  q is zero, 1 or 2;
  r is zero, 1, 2 or 3; or
R(1) is —SR(10), —OR(10) or —CR(10)R(11)R(12);
  R(10), R(11) and R(12) independently of one another are hydrogen, alkyl having 1, 2, 3, 4, 5, 6, 7 or 8 carbon atoms, —C$_s$H$_{2s}$—(C$_3$–C$_8$)-cycloalkyl or an aromatic system selected from the group consisting of pyridyl, pyrrolyl, quinolyl, isoquinolyl, imidazolyl or phenyl;
    s is zero, 1 or 2;
    where the aromatic systems pyridyl, pyrrolyl, quinolyl, isoquinolyl, imidazolyl and phenyl are unsubstituted or substituted by 1–3 substituents selected from the group consisting of F, Cl, CF$_3$, CH$_3$, methoxy, hydroxyl, amino, methylamino and dimethylamino;
  R(2) is —(CH$_2$)$_u$—(CF$_2$)$_t$—CF$_3$;
    t is zero, 1, 2 or 3;
    u is zero or 1;
  R(3) is hydrogen or independently is defined as R(1);

and their pharmaceutically tolerable salts;

(HOE 95/F 173-NZ 299 052)

am) substituted cinnamic acid guanidides of the formula I

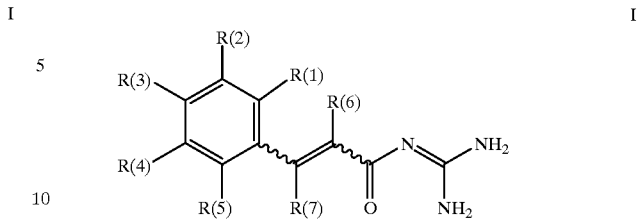

in which:
at least one of the substituents R(1), R(2), R(3), R(4) and R(5) is —X$_a$—Y$_b$—L$_n$U;
  X is CR(16)R(17), O, S or NR(18);
    R(16), R(17) and R(18) independently of one another are H, alkyl having 1, 2, 3 or 4 carbon atoms or perluoroalkyl having 1, 2, 3 or 4 carbon atoms;
  a is zero or 1;
  Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
    T is NR(20), O, S or phenylene, where the phenylene is not substituted or is substituted by 1–3 substituents selected from the group consisting of F, Cl, CF$_3$, methyl, methoxy and NR(21)R(22);
      R(20), R(21) and R(22) independently of one another are H, alkyl having 1, 2, 3 or 4 carbon atoms or perfluoroalkyl having 1, 2, 3 or 4 carbon atoms;
  b is zero or 1;
  L is O, S, NR(23) or C$_k$H$_{2k}$;
  k is 1, 2, 3, 4, 5, 6, ,7 or 8;
  n is zero or 1;
  U is NR(24)R(25) or an N-containing heterocycle having 1, 2, 3, 4, 5, 6, 7, 8 or 9 carbon atoms;
    R(24) and R(25) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms; or
    R(24) and R(25) together are 4 or 5 methylene groups, of which one CH$_2$ group can be replaced by oxygen, S, NH, N—CH$_3$ where or N-benzyl;
    where the N-containing heterocycles are N- or C-bridged and are not substituted or are substituted by 1–3 substituents selected from the group consisting of F, Cl, CF$_3$, methyl, methoxy and NR(27)R(28);
      R(23), R(27) and R(28) independently of one another are H, alkyl having 1, 2, 3 or 4 carbon atoms or perfluoroalkyl having 1, 2, 3 or 4 carbon atoms;
and the other substituents R(1), R(2), R(3), R(4) and R(5) in each case independently of one another are H, F, Cl, Br, I, CN, —O$_n$—C$_m$H$_{2m+1}$, —O$_p$—(CH$_2$)$_s$—C$_q$F$_{2q+1}$ or —C$_r$H$_{2r}$R(10);
  n is zero or 1;
  m is zero, 1, 2, 3, 4, 5, 6, ,7 or 8;
  p is zero or 1;
  q is 1, 2, 3, 4, 5, 6, 7 or 8;
  s is zero, 1, 2, 3 or 4;
  r is zero, 1, 2, 3 or 4;
  R(10) is cycloalkyl having 3, 4, 5, 6, 7 or 8 carbon atoms, or phenyl, where the phenyl is not substituted or is substituted by 1–3 substituents selected from the group consisting of F, Cl, CF$_3$, methyl, methoxy and NR(11)R(12);

R(11) and R(12) independently of one another are H, alkyl having 1, 2, 3 or 4 carbon atoms or perfluoroalkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, CF$_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;
(HOE 95/F 220-NZ 299 052)
an) benzoylguanidines of the formula I

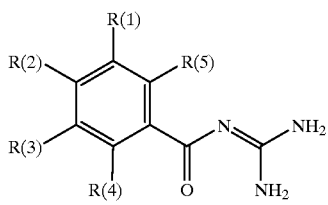

in which:
at least one of the substituents R(1), R(2) and R(3) is R(6)—C(OH)$_2$—;
R(6) is perfluoroalkyl having 1, 2 or 3 carbon atoms, which is straight-chain or branched;
and the other substituents R(1), R(2) and R(3) independently of one another are hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms, or phenoxy, which is unsubstituted or is substituted by 1–3 substituents selected from the group consisting of F, Cl, methyl and methoxy; or
the other substituents R(1), R(2) and R(3) independently of one another are alkyl-SO$_x$, —CR(7)=CR(8)R(9) or —C≡CR(9);
x is zero, 1 or 2;
R(7) is hydrogen or methyl;
R(8) and R(9) independently of one another are hydrogen, alkyl having 1, 2, 3 or 4 carbon atoms, cycloalkyl having 3, 4, 5, 6, 7 or 8 carbon atoms, or phenyl, which is unsubstituted or is substituted by 1–3 substituents selected from the group consisting of F, Cl, CF$_3$, methyl and methoxy; or
the other substituents R(1), R(2) and R(3) independently of one another are phenyl, C$_6$H$_5$—(C$_1$–C$_4$)-alkyl, naphthyl, biphenylyl, quinolinyl, isoquinolinyl or imidazolyl, isoquinolinyl or imidazolyl are bonded via C or N and where phenyl, C$_6$H$_5$—(C$_1$–C$_4$)-alkyl, naphthyl, biphenylyl, quinolinyl, isoquinolinyl and imidazolyl are unsubstituted or are substituted by 1–3 substituents selected from the group consisting of F, Cl, CF$_3$, CH$_3$, methoxy, hydroxyl, amino, methylamino and dimethylamino; or
the other substituents R(1), R(2) and R(3) independently of one another are SR(10), —OR(10), —CR(10)R(11)R(12);

R(10) is —C$_f$H$_{2f}$—(C$_3$–C$_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, CF$_3$, CH$_3$, methoxy, hydroxyl, amino, methylamino and dimethylamino;
f is zero, 1 or 2;
R(11) and R(12) independently of one another are defined as R(10), hydrogen or alkyl having 1, 2, 3 or 4 carbon atoms;
R(4) and R(5) independently of one another are hydrogen, alkyl having 1, 2 or 3 carbon atoms, F, Cl, Br, I, CN, OR(13), NR(14)R(15), —(CH$_2$)$_n$—(CF$_2$)$_o$—CF$_3$;
R(13), R(14) and R(15) independently of one another are hydrogen or alkyl having 1, 2, 3 or 4 carbon atoms;
n is zero or 1;
is zero, 1 or 2;
and their pharmacologically acceptable salts;
(HOE 95/F 253-NZ 299 682)
ao) sulfonimidamides of the formula I

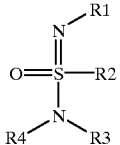

in which:
at least one of the three substituents R(1), R(2) and R(3) is a benzoylguanidine,

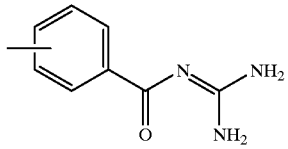

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22)SO$_2$—, R(23)R(24)N—CO—, R(25)—CO—, R(26)R(27)N—SO$_2$, —OR(35), —SR(35) or —NR(35)R(36);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$;
R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;
n is zero, 1, 2, 3 or 4;
R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);

R(30) and R(31) are hydrogen or alkyl having 1, 2, 3 or 4 carbon atoms; or

R(23), R(25) and R(26) are hydrogen;

R(24) and R(27) independently of one another are hydrogen or alkyl having 1, 2, 3 or 4 carbon atoms; or R(23) and R(24), and also R(26) and R(27) together are 5 or 6 methylene groups, of which one $CH_2$ group can be replaced by oxygen, —S—, —NH—, —$NCH_3$ or —N-benzyl;

R(35) and R(36) independently of one another are hydrogen or alkyl having 1, 2, 3, 4, 5 or 6 carbon atoms; or R(35) and R(36) together are 4–7 methylene groups, of which one $CH_2$ group can be replaced by oxygen, —S—, —NH—, —$NCH_3$ or —N-benzyl; or R(35) is phenyl, which is not substituted or is substituted by 1–3 substituents selected from the group consisting of F, Cl, —$CF_3$, methyl, methoxy, $SO_2R(5)$, $SO_2NR(6)R(7)$ and —NR(32)R(33);

R(5) is alkyl having 1, 2, 3, 4, 5 or 6 carbon atoms;

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms; or R(35) is $C_1$–$C_9$-heteroaryl, which is unsubstituted or substituted by 1–3 substituents selected from the group consisting of F, Cl, $CF_3$, $CH_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, $(CH_2)_pR(10)$;

p is zero, 1, 2, 3 or 4;

R(10) is phenyl, which is not substituted or is substituted by 1–3 substituents selected from the group consisting of F, Cl, —$CF_3$, methyl, methoxy, —$SO_2NR(17)R(8)$ and —$SO_2R(9)$;

R(17) and R(8) independently of one another are hydrogen or alkyl having 1, 2, 3 or 4 carbon atoms;

R(9) is alkyl having 1, 2, 3 or 4 carbon atoms; or the other radical R(1) or R(3) in each case is hydrogen, R(4) is hydrogen or alkyl having 1, 2, 3 or 4 carbon atoms;

and their pharmaceutically tolerable salts;

(HOE 95/F 265-NZ 299 739)

ap) benzoylguanidines of the formula I

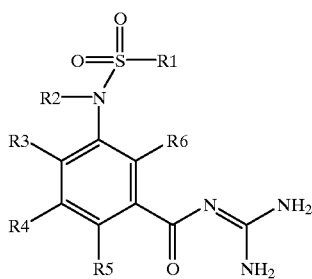

I in which:

R(1) is alkyl having 1, 2, 3, 4, 5, 6, 7 or 8 carbon atoms or NR(7)R(8);

R(7) and R(8) independently of one another are hydrogen or alkyl having 1, 2, 3, 4, 5, 6, 7 or 8 carbon atoms;

R(2) is hydrogen, alkyl having 1, 2, 3, 4, 5, 6, 7 or 8 carbon atoms or —$SO_2R(9)$;

R(9) independently is defined as R(1);

R(3) is hydrogen, —SR(25), —OR(25), —NR(25)R(26) or —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, $CF_3$, $CH_3$, methoxy, hydroxyl, amino, methylamino and dimethylamino; or R(25) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is hydrogen, F, Cl, Br, I, OH, —C≡N, $CF_3$, alkyl having 1, 2, 3, 4, 5, 6, 7 or 8 carbon atoms, alkenyl having 2, 3, 4, 5, 6, 7 or 8 carbon atoms or —$(CH_2)_mR(14)$;

m is zero, 1 or 2;

R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) independently of one another are hydrogen or —$CH_3$;

R(5) and R(6) independently of one another are hydrogen, alkyl having 1, 2, 3 or 4 carbon atoms, F, Cl, —OR(32), —NR(33)R(34) or $CF_3$;

R(32), R(33) and R(34) independently of one another are hydrogen or alkyl having 1, 2, 3 or 4 carbon atoms;

and their pharmaceutically tolerable salts;

(HOE 95/F 269 K-EP-A 774 458)

aq) benzenedicarboxylic acid diguanidides of the formula I

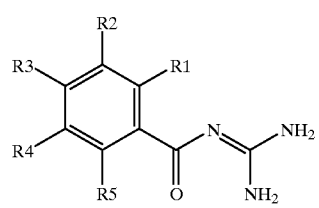

I in which:

one of the radicals R(1), R(2), R(3) and R(4) is —CO—N=C(NH₂)₂;

and of the other radicals R(1), R(2), R(3) and R(4) in each case:

R(1) is hydrogen, alkyl having 1, 2, 3 or 4 carbon atoms, F, Cl, Br, I, —OR(32), —NR(33)R(34) or $CF_3$;

R(32), R(33) and R(34) independently of one another are hydrogen or alkyl having 1, 2, 3 or 4 carbon atoms;

R(2) and R(4) independently of one another are hydrogen, F, Cl, Br, I, OH, —CN, $CF_3$, —CO—N=C(NH₂)₂, alkyl having 1, 2, 3, 4, 5, 6, 7 or 8 carbon atoms, alkenyl having 2, 3, 4, 5, 6, 7 or 8 carbon atoms or —$(CH_2)_mR(14)$;

m is zero, 1 or 2;

R(14) is —($C_3$–$C_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) are hydrogen or —CH$_3$; or R(2) and R(4) independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy; or R(2) and R(4) independently of one another are R(22)—SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl; or R(2) and R(4) independently of one another are —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or -N-benzyl;

R(3) is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino; or
R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;

R(5) is alkyl having 1, 2, 3 or 4 carbon atoms, F, Cl, Br, I, X—(CH$_2$)$_y$—CF$_3$ or phenyl, which is not substituted or is substituted by 1–3 substituents selected from the group consisting of F and Cl, —CF$_3$, methyl, methoxy and —NR(6)R(7);
R(6) and R(7) independently of one another are hydrogen or —CH$_3$;
X is a bond or oxygen;
y is zero, 1 or 2;

and their pharmaceutically tolerable salts;
(HOE 95/F 269 BK-EP-A 774 457)

ar) benzenedicarboxylic acid diguanidides of the formula I

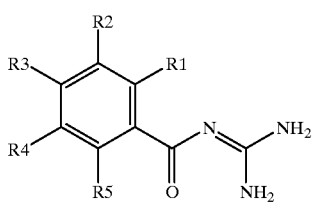

I in which:
one of the radicals R(1), R(2), R(3) and R(5) is —CO—N═C(NH$_2$)$_2$;
and of the other radicals R(1), R(2), R(3) and R(5) in each case:

R(1) and R(5) independently of one another are hydrogen, alkyl having 1, 2, 3 or 4 carbon atoms, F, Cl, —OR(32), —NR(33)R(34) or CF$_3$;
R(32), R(33) and R(34) independently of one another are hydrogen or alkyl having 1, 2, 3 or 4 carbon atoms;

R(2) is hydrogen, F, Cl, Br, I, OH, —CN, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is—(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$; or R(2) is R(22)—SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl; or R(2) is —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino; or
R(25) is —(C$_1$–C$_8$)-heteroaryl, which is unsubstituted or substituted by 1–3 substituents selected from the group consisting of F, Cl, CF$_3$, CH$_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);
m is 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$; or R(4) is phenyl, which is substituted by 2, 3, 4 or five substituents selected from the group consisting of F, Cl, CF$_3$, methyl, methoxy and —NR(1 5)R(1 6);
R(15) and R(16) independently of one another are hydrogen or CH$_3$;

and their pharmaceutically tolerable salts;
(HOE 96/F 013-EP-A 787717)

as) diaryidicarboxylic acid diguanidides of the formula I

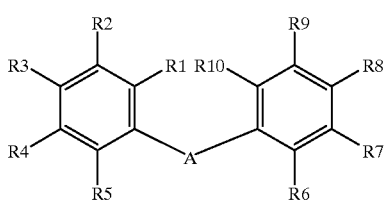

in which:
one of the radicals R(1), R(2), R(3), R(4) and R(5) is
—CO—N═C(NH$_2$)$_2$;
the other radicals R(1) and R(5) in each case independently of one another are hydrogen, alkyl having 1, 2, 3 or 4 carbon atoms, F, Cl, —OR(32), —NR(33)R(34) or CF$_3$;
R(32), R(33) and R(34) independently of one another are hydrogen or alkyl having 1, 2, 3 or 4 carbon atoms;
the other radicals R(2) and R(4) in each case independently of one another are hydrogen, F, Cl, Br, I, OH, —CN, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$-C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) are hydrogen or —CH$_3$; or
the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$-C$_8$)-alkanoyl, (C$_2$-C$_8$)-alkoxycarbonyl, formyl, carboxyl, —CF$_3$, methyl, methoxy; or
the other radicals R(2) and R(4) in each case are R(22)—SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl; or
the other radicals R(2) and R(4) in each case independently of one another are —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or -N-benzyl;
the other radical R(3) in each case is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino; or
R(25) is —(C$_1$-C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;
one of the radicals R(6), R(7), R(8), R(9) and R(10) is
—CO—N═C(NH$_2$)$_2$;
the other radicals R(6) and R(10) in each case independently of one another are hydrogen, alkyl having 1, 2, 3 or 4 carbon atoms, F, Cl, —OR(132), —NR(133)R(134) or CF$_3$;
R(132), R(133) and R(134) independently of one another are hydrogen or alkyl having 1, 2, 3 or 4 carbon atoms;
the other radicals R(7) and R(9) in each case independently of one another are hydrogen, F, Cl, Br, I, OH, —CN, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_{mm}$R(114);
mm is zero, 1 or 2;
R(114) is —(C$_3$-C$_8$)-cycloalkyl or phenyl, which is not substituted or is substituted by 1–3 substituents selected from the group consisting of F and Cl, —CF$_3$, methyl, methoxy and —NR(115)R(116);
R(115) and R(116) are hydrogen or —CH$_3$; or
the other radicals R(7) and R(9) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$-C$_8$)-alkanoyl, (C$_2$-C$_8$)-alkoxycarbonyl, formyl, carboxyl, —CF$_3$, methyl and methoxy; or
the other radicals R(7) and R(9) in each case are R(122)—SO$_2$—, R(123)R(124)N—CO—, R(128)—CO— or R(129)R(130)N—SO$_2$;
R(122) and R(128) independently of one another are methyl or —CF$_3$;
R(123), R(124), R(129) and R(130) independently of one another are hydrogen or methyl; or
the other radicals R(7) and R(9) in each case independently of one another are —OR(135) or —NR(135)R(136);
R(135) and R(136) independently of one another are hydrogen or alkyl having 1, 2, 3, 4, 5 or 6 carbon atoms; or
R(135) and R(136) together are 4–7 methylene groups, of which one CH$_2$ group can be replaced by oxygen, —S—, —NH—, —NCH$_3$ or -N-benzyl;
the other radical R(8) in each case is hydrogen, —SR(125), —OR(125), —NR(125)R(126) or —CR(125)R(126)R(127);
R(125) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino; or
R(125) is —(C$_1$-C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
R(126) and R(127) independently of one another are defined as R(125) or are hydrogen or alkyl having 1, 2, 3, 4, 5, 6, 7 or 8 carbon atoms;
A is absent or is —NR(11)—CO—, —NR(12)—CO—NR(13)—, —NR(17)—CO—NR(18)—SO$_2$—, —NR(19)—SO$_2$—, —SO$_2$—NR(19)—SO$_2$—, —SO$_2$—NR(19)—CO—, —O—CO—NR(19)—SO$_2$— or —CR(20)═CR(21)—;

R(11), R(12), R(13), R(17), R(18), R(19), R(20) and R(21) independently of one another are hydrogen or alkyl having 1, 2, 3, 4, 5, 6, 7 or 8 carbon atoms and their pharmaceutically tolerable salts;

(HOE 96/F 026-EP-A 790 245)

at) substituted thiophenylalkenylcarboxylic acid guanidides of the formula I

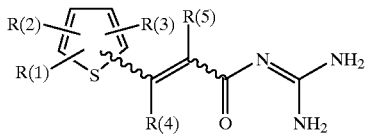

in which:

at least one of the substituents R(1), R(2) and R(3) is —$O_p$—$(CH_2)_s$—$C_qF_{2q+1}$, R(40)CO— or R(31)$SO_k$—;
p is zero or 1;
s is zero, 1, 2, 3 or 4;
q is 1, 2, 3, 4, 5, 6, ,7 or 8;
k is zero, 1 or 2;
R(40) is alkyl having 1, 2, 3, 4, 5, 6, 7 or 8 carbon atoms, perluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl and methoxy;
R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl or methoxy; or
R(31) is NR(41)R(42);
R(41) and R(42) independently of one another are hydrogen, alkyl having 1, 2, 3 or 4 carbon atoms, perfluoroalkyl having 1, 2, 3 or 4 carbon atoms, or
R(41) and R(42) together are 4 or 5 methylene groups, of which one $CH_2$ group can be replaced by oxygen, S, NH, N—$CH_3$ Cl or N-benzyl;

and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}$R(10);
na is zero or 1;
ma is zero, 1, 2, 3, 4, 5, 6, 7 or 8;
ga is zero or 1;
ra is zero, 1, 2, 3 or 4;
R(10) is cycloalkyl having 3, 4, 5, 6, 7 or 8 carbon atoms or phenyl, where the phenyl is not substituted or is substituted by 1–3 substituents selected from the group consisting of F, Cl, $CF_3$, methyl and methoxy;
R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;

(HOE 96/F 032-EP-A 791 577)

au) ortho-substituted benzoylguanidines of the formula I

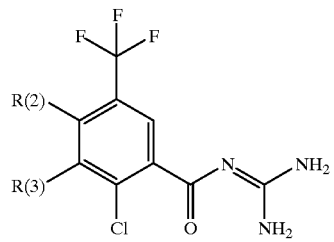

in which:

R(2) and R(3) independently of one another are hydrogen, Cl, Br, I, ($C_1$–$C_8$)-alkyl, ($C_3$–$C_8$)-cycloalkyl or —OR(5);
R(5) is ($C_1$–$C_8$)-alkyl or —$C_dh_{2d}$—($C_3$–$C_8$)-cycloalkyl;
d is zero, 1 or 2;

where one of the two substituents R(2) and R(3) is always hydrogen but both substituents R(2) and R(3) are not simultaneously hydrogen, and their pharmaceutically tolerable salts;

(HOE 96/F 042-EP-A 794 171)

av) benzoylguanidines of the formula I

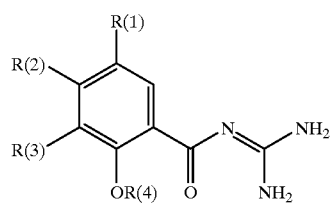

in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S, NR(5),
a is zero or 1;
b is zero, 1 or 2;
c is zero, 1, 2 or 3;
R(5) is H, alkyl having 1, 2, 3 or 4 carbon atoms or —$C_dH_{2d}$R(6);
d is zero, 1, 2, 3 or 4;
R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);
R(7) and R(8) independently are H or alkyl having 1, 2, 3 or 4 carbon atoms; or
R(1) is —SR(10), —OR(10) or —CR(10)R(11)R(12);
R(10) is —$C_fH_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10) or are hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[R(19)]═CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—Ch$_2$O)$_h$—R(24);

R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(18) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms, which is unsubstituted or substituted as phenyl; or R(18) is alkyl having 1, 2, 3, 4, 5 or 6 carbon atoms, which is unsubstituted or substituted by 1–3 OH; or R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

R(2) and R(3) are defined as R(1);

R(4) is alkyl having 1, 2, 3 or 4 carbon atoms;

and their pharmaceutically tolerable salts;

(HOE 96/F 043-EP-A 794 172)

aw) ortho-substituted benzoylguanidines of the formula I

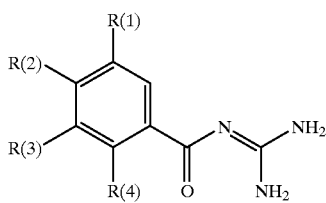

in which:

R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;

X is oxygen, S, NR(5), a is zero or 1;

b is zero, 1 or 2;

c is zero, 1, 2 or 3;

R(5) is H, alkyl having 1, 2, 3 or 4 carbon atoms or —C$_d$h$_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);

R(7) and R(8) independently are H or alkyl having 1, 2, 3 or 4 carbon atoms; or

R(1) is —SR(10), —OR(10) or —CR(10)R(11)R(12);

R(10) is —C$_f$H$_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10), or are hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[(R(19)]═CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are (CH$_2$)$_g$—(CHOH)$_h$—(CH$_2$)$_i$—(CHOH)$_j$—R(17) or —(CH$_2$)$_g$—O—(CH$_2$-H$_2$O)$_h$—R(24);

R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(1 8) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms, which is unsubstituted or substituted as phenyl; or R(18) is alkyl having 1, 2, 3, 4, 5 or 6 carbon atoms, which is unsubstituted or substituted by 1–3 OH; or R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —$C_mH_{2m}$—R(18);
m is 1, 2, 3 or 4;
one of the two substituents R(2) and R(3) is hydroxyl; and the other of the substituents R(2) and R(3) in each case is defined as R(1);
R(4) is alkyl having 1, 2, 3 or 4 carbon atoms; alkoxy having 1, 2, 3 or 4 carbon atoms, F, Cl, Br, 1 or —$(CH_2)_n$—$(CF_2)_o$—$CF_3$;
n is zero or 1;
o is zero or 1;
and their pharmaceutically tolerable salts;
(HOE 96/F 135-EP-A 810 207)
ax) bis-ortho-substituted benzoylguanidines of the formula I

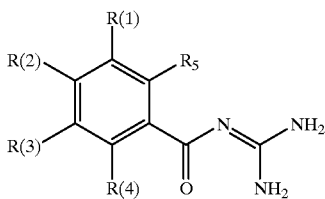

which:
R(1), R(2) and R(3) independently of one another are R(10)—$SO_a$— or R(14)R(15)N—$SO_2$—;
a is zero, 1 or 2,
R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —$C_{ab}H_{2ab}$—R(16);
ab is zero, 1, 2, 3 or 4;
R(16) is cycloalkyl having 3, 4, 5, 6 or 7 carbon atoms, or phenyl, which is not substituted or is substituted by 1–3 substituents selected from the group consisting of F, Cl, $CF_3$, methyl, methoxy and NR(17)R(18);
R(17) and R(18) independently of one another are hydrogen, $CF_3$ or alkyl having 1, 2, 3 or 4 carbon atoms; or
R(14) and R(15) together are 4 or 5 methylene groups, of which one $CH_2$ group can be replaced by oxygen, sulfur, NH, C—$CH_3$ or N-benzyl; or
R(14) and R(15) are hydrogen; or
R(1), R(2) and R(3) independently of one another are SR(21), —OR(22), —NR(23)R(24) or —CR(25)R(26)R(27);
R(21), R(22), R(23) and R(25) independently of one another are —$C_bH_{2b}$—($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;
b is zero, 1 or 2;
R(24), R(26) and R(27) independently of one another are hydrogen, alkyl having 1, 2, 3 or 4 carbon atoms or perfluoroalkyl having 1, 2, 3 or 4 carbon atoms; or
R(1), R(2) and R(3) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, alkenyl having 3, 4, 5, 6, 7 or 8 carbon atoms or —$C_{df}H_{2df}$R(30);
(Xa) is oxygen, sulfur or NR(33);
R(33) is hydrogen, alkyl having 1, 2, 3 or 4 carbon atoms or perfluoroalkyl having 1, 2, 3 or 4 carbon atoms;
dg is zero or 1;
(Xb) is oxygen, sulfur or NR(34);
R(34) is hydrogen, alkyl having 1, 2, 3 or 4 carbon atoms or perfluoroalkyl having 1, 2, 3 or 4 carbon atoms;
dh is zero or 1;
da is zero, 1, 2, 3, 4, 5, 6, 7 or 8;
db is zero, 1, 2, 3 or 4;
de is zero, 1, 2, 3, 4, 5, 6 or 7;
df is zero, 1, 2, 3 or 4;
R(30) is cycloalkyl having 3, 4, 5, 6, 7 or 8 carbon atoms, phenyl, biphenylyl or naphthyl,
where the aromatics phenyl, biphenylyl and naphthyl are not substituted or are substituted by 1–3 substituents selected from the group consisting of F, Cl, $CF_3$, methyl, methoxy and NR(31)R(32);
R(31) and R(32) are hydrogen, alkyl having 1, 2, 3 or 4 carbon atoms or perfluoroalkyl having 1, 2, 3 or 4 carbon atoms; or
R(1), R(2) and R(3) independently of one another are NR(40)R(41) or —(Xe)—$(CH_2)_{eb}$R(45);
R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or $(CH_2)_e$—R(42);
e is zero, 1, 2, 3 or 4;
R(42) is cycloalkyl having 3, 4, 5, 6 or 7 carbon atoms or phenyl, which is not substituted or is substituted by 1–3 substituents selected from the group consisting of F, Cl, $CF_3$, methyl, methoxy and NR(43)R(44);
R(43) and R(44) independently of one another are hydrogen, $CF_3$ or alkyl having 1, 2, 3 or 4 carbon atoms; or
R(40) and R(41) together are 4 or 5 methylene groups, of which one $CH_2$ group can be replaced by oxygen, sulfur, NH, C—$CH_3$ or N-benzyl;
(Xe) is oxygen, sulfur or NR(47); R(47) is hydrogen, alkyl having 1, 2, 3 or 4 carbon atoms or perfluoroalkyl having 1, 2, 3 or 4 carbon atoms;
eb is zero, 1, 2, 3 or 4;
R(45) is cycloalkyl having 3, 4, 5, 6 or 7 carbon atoms, or phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);
Xfa is $CH_2$, oxygen, sulfur or NR(48);
Xfb is oxygen, sulfur or NR(49);
R(48), R(49), R(50) and R(51) independently of one another are hydrogen, alkyl having 1, 2, 3 or 4 carbon atoms or perfluoroalkyl having 1, 2, 3 or 4 carbon atoms;
ed is 1, 2, 3 or 4;
R(46) is hydrogen, alkyl having 1, 2, 3 or 4 carbon atoms or perfluoroalkyl having 1, 2, 3 or 4 carbon atoms; or
R(1), R(2) and R(3) independently of one another are —CHR(52)R(53);
R(52) is —$(CH_2)_g$—$(CHOH)_h$—$(CH)_i$—$(CHOH)_k$—R(54) or —$(CH_2)_g$—O—$(CH_2$—$CH_{20})_h$—R(54);
R(54) is hydrogen or methyl;
g, h, i identically or differently are zero, 1, 2, 3 or 4;
k is 1, 2, 3 or 4;
R(53) is hydrogen or alkyl having 1, 2, 3 or 4 carbon atoms; or
R(1), R(2) and R(3) independently of one another are —C(OH)R(55)R(56);

R(55) and R(56) identically or differently are hydrogen or alkyl having 1, 2, 3 or 4 carbon atoms; or R(55) and R(56) together are cycloalkyl having 3, 4, 5 or 6 carbon atoms; or R(55) is —CH$_2$OH; and R(4) and R(5) independently of one another are alkyl having 1, 2, 3 or 4 carbon atoms, alkoxy having 1, 2, 3 or 4 carbon atoms, OH, F, Cl, Br, I, CN, —O$_n$—(CH$_2$)$_o$13 (CF$_2$)$_p$—CF$_3$;

n is zero or 1;
o is zero, 1 or 2;
p is zero, 1 or 2;

and their pharmaceutically tolerable salts;
(96/F 136-EP-A 810 205)

ay) substituted 1-naphthoylguanidines of the formula I

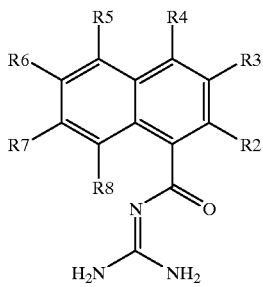

in which:

R2, R3, R4, R5, R6, R7 and R8 independently of one another are H, F, Cl, Br, I, CN, NO$_2$, CF$_3$, C$_2$F$_5$ or X$_a$Y$_b$Z;

X is O, S, NR(10), CR(11)R(12), C=O, C(=O)NR(10), C(=O)O, SO, SO$_2$, SO$_2$NR(10), OC=O, NR(10)C=O or NR(10)SO$_2$, where the linkage with the naphthalene ring in each case takes place via the left atom;

R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is zero or 1;

Y is alkylene having 1, 2, 3, 4, 5, 6, 7 or 8 CH$_2$ groups, where one of these CH$_2$ groups can be replaced by O, S, NR(13) or o-, p- or m-phenylene;

R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is H, alkyl having 1, 2, 3, 4, 5, 6 or 7 carbon atoms, cycloalkyl having 3, 4, 5, 6 or 7 carbon atoms, C(=O)R(15), SO$_2$R(15), NR(16)R(17) or phenyl, which is not substituted or is substituted by 1–3 substituents selected from the group consisting of F, Cl, Br, CF$_3$, methyl, methoxy and NR(21)R(22);

R(21) and R(22) independently of one another are H or alkyl having 1, 2, 3 or 4 carbon atoms or perfluoroalkyl having 1, 2, 3 or 4 carbon atoms;

R(15) is N=C(NH$_2$)$_2$, NR(18)R(19), N(CH$_2$)$_c$NR(18)R(19) or OR(20);

c is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms; or R(18) and R(19) together are 4 or 5 methylene groups, of which one CH$_2$ group can be replaced by oxygen, S, NH, C—CH$_3$, N-benzyl or N-(p-chlorophenyl);

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one CH$_2$ group can be replaced by oxygen, S, NH, C—CH$_3$, N-benzyl or N-(p-chlorophenyl); or Z is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(21)R(22);

but where, in the case where R(4) is an alkoxy radical, at least one of the substituents R(2), R(3), R(5), R(6), R(7) and R(8) is not hydrogen;

and their pharmaceutically tolerable salts.
(96/F 137-EP-A 810 206)

az) substituted 2-naphthoyiguanidines of the formula I

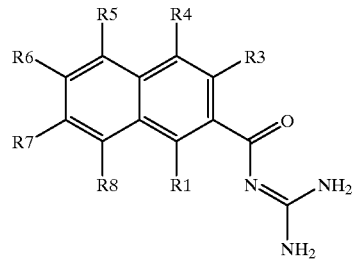

in which:

at least one of the substituents R1, R3, R4, R5, R6, R7 and R8 is XY$_a$WZ or X'Y$_a$WZ';

X is O, S, NR(10) or CR(11)R(12);

R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

Y is alkylene having 1, 2, 3, 4, 5, 6, 7 or 8 CH$_2$ groups, where one of these CH$_2$ groups can be replaced by O, S, NR(1 3) or o-, p- or m-phenylene;

R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

a is zero or 1;

W is CH$_2$, SO$_2$, S(=O)(=NH) or—if W does not immediately follow a heteroatom of the group XY$_a$—alternatively O or NR(14);

R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

Z is C(=O)R(15), SO$_2$R(15) or—if W is not O or NR(14)—alternatively NR(16)R(17);

R(15) is N=C(NH$_2$)$_2$, NR(18)R(19), N(CH$_2$)$_b$NR(18)R(19) or OR(20);

b is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms; or R(18) and R(19) together are 4 or 5 methylene groups, of which one $CH_2$ group can be replaced by oxygen, S, NH, C—$CH_3$, N-benzyl or N-(p-chlorophenyl);

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one $CH_2$ group can be replaced by oxygen, S, NH, C—$CH_3$, N-benzyl or N-(p-chlorophenyl);

X' is C=O, C(=O)NR(30), C(=O)O, SO, $SO_2$, $SO_2$NR(30), OC=O, NR(30)C=O or NR(30)$SO_2$, where the linkage with the naphthalene ring in each case takes place via the left atom;

R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

Z' is C(=O)R(15), $SO_2$R(15), an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(21)R(22);

R(21) and R(22) independently of one another are H, alkyl having 1, 2, 3 or 4 carbon atoms or perfluoroalkyl having 1, 2, 3 or 4 carbon atoms;

R(15) is N=C($NH_2$)$_2$, NR(18)R(19), N($CH_2$)$_b$NR(18)R(19) or OR(20);

R(18) and R(19) independently of one another are H, alkyl having 1, 2, 3, 4, 5, 6, 7 or 8 carbon atoms or perfluoroalkyl having 1, 2, 3 or 4 carbon atoms; or R(18) and R(19) together are 4 or 5 methylene groups, of which one $CH_2$ group can be replaced by oxygen, S, NH, C—$CH_3$, N-benzyl or N-(p-chlorophenyl);

b is 2 or 3;

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms; or Z'—if W is not O or NR(14)—is NR(16)R(17);

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one $CH_2$ group can be replaced by oxygen, S, NH, C—$CH_3$, N-benzyl or N-(p-chlorophenyl);

and the other substituents R1, R3, R4, R5, R6, R7 and R8 in each case, which are still not allocated by the definitions given above, independently of one another are H, F, Cl, Br, I, CN, $NO_2$, $CF_3$, $C_2F_5$ or $V_pQ_qU$;

V is O, S, SO, $SO_2$, NR(60), OC=O, C=O, C(=O)NR(60), C(=O)O or CR(66)R(67);

R(60), R(66) and R(67) independently of one another are H, alkyl having 1, 2, 41 3, 4, 5 or 6 carbon atoms, perfluoroalkyl having 1, 2, 3 or 4 carbon atoms or cycloalkyl having 3, 4, 5, 6 or 7 carbon atoms;

p is zero or 1;

Q is alkylene having 1, 2, 3, 4, 5, 6, 7 or 8 $CH_2$ groups, where one of these $CH_2$ groups can be replaced by O, S, NR(68) or o-, p- or m-phenylene;

R(68) is H, alkyl having 1, 2, 3, 4, 5 or 6 carbon atoms, perguoroalkyl having 1, 2, 3 or 4 carbon atoms or cycloalkyl having 3, 4, 5 or 6 carbon atoms;

q is zero or 1;

U is H, alkyl having 1, 2, 3, 4, 5, 6 or 7 carbon atoms, cycloalkyl having 3, 4, 5, 6 or 7 carbon atoms, C(=O)R(65), $SO_2$R(65), NR(61)R(62) or phenyl, which is not substituted or is substituted by 1–3 substituents selected from the group consisting of F, Cl, Br, $CF_3$, methyl, methoxy and NR(63)R(64);

R(63) and R(64) independently of one another are H, alkyl having 1, 2, 3 or 4 carbon atoms or perfluoroalkyl having 1, 2, 3 or 4 carbon atoms;

R(65) is N=C($NH_2$)$_2$, NR(61)R(62) or OR(60);

R(61) and R(62) independently of one another are H, alkyl having 1, 2, 3, 4, 5, 6, 7 or 8 carbon atoms or perfluoroalkyl having 1, 2, 3 or 4 carbon atoms; or R(61) and R(62) together are 4 or 5 methylene groups, of which one $CH_2$ group can be replaced by oxygen, S, NH, C—$CH_3$, N-benzyl or N-(p-chlorophenyl); or U is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(63)R(64);

but where at least one of the substituents R5, R6, R7 and R8 is not hydrogen; and their pharmaceutically tolerable salts.

(96/F 141-EP-A 811 610)

ba) ortho-substituted benzoylguanidines of the formula I in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—($CH_2$)$_b$—($CF_2$)$_c$—$CF_3$;

X is oxygen, sulfur or NR(9);

a is zero or 1;

b is zero, 1 or 2;

c is zero, 1, 2 or 3;

R(9) is H, alkyl having 1, 2, 3 or 4 carbon atoms or —$C_dH_{2d}$R(6);

d is zero, 1, 2, 3 or 4;
R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);
R(7) and R(8) are independently, H or alkyl having 1, 2, 3 or 4 carbon atoms; or R(1) is —SR(10), —OR(10) or —CR(10)R(11)R(12);
R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, $CF_3$, $CH_3$, methoxy, hydroxyl, amino, methylamino and dimethylamino;
f is zero, 1 or 2;
R(11) and (R12), independently of one another, are defined as R(10) or are hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, the latter linked via a carbon or nitrogen atom of the ring, each of which is unsubstituted or is substituted by 1–3 substituents selected from the group consisting of F, Cl, $CF_3$, $CH_3$, methoxy, hydroxyl, amino, methylamino and dimethylamino, or (R1) is —SR(13), —OR(13), —NHR(13), —NR(13)R(14), —CHR(13)R(15), —C[R(15)R(16)]OH, —C≡CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
R(13) and R(14), identically or differently, are —$(CH_2)_g$—$(CHOH)_h$—$(CH_2)_i$—$(CHOH)_{kk}$—R(17) or —$(CH_2)_g$—O—$(CH_2$—$CH_2O)_h$—R(24);
R(17) is hydrogen or methyl,
g, h and i, identically or differently, are zero, 1, 2, 3 or 4;
kk is 1, 2, 3 or 4;
R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;
R(18) is phenyl, which is unsubstituted or is substituted by 1–3 substituents selected from the group consisting of F, Cl, $CF_3$, methyl, methoxy and NR(25)R(26);
R(25) and R(26) are H or alkyl having 1, 2, 3 or 4 carbon atoms; or
R(18) is heteroaryl having 1, 2, 3, 4, 5, 6, 7, 8 or 9 carbon atoms, which is unsubstituted or is substituted as phenyl; or
R(18) is alkyl having 1, 2, 3, 4, 5 or 6 carbon atoms, which is unsubstituted or is substituted by 1–3 OH; or
R(18) is cycloalkyl having 3, 4, 5, 6, 7 or 8 carbon atoms;
R(19), R(20), R(21), R(22) and R(23), identically or differently, are hydrogen or methyl;
R(24) is H, alkyl having 1, 2, 3, 4, 5 or 6 carbon atoms, cycloalkyl having 3, 4, 5, 6, 7 or 8 carbon atoms or —$C_mH_{2m}$—R(18);
m is 1, 2, 3 or 4; one of the two substituents R(2) and R(3) is —O—CO—R(27);

R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolinyl are unsubstituted or substituted by 1–3 substituents selected from the group consisting of F, Cl, $CF_3$, methyl, methoxy and NR(7)R(8);
R(7) and R(8) independently of one another are hydrogen or alkyl having 1, 2, 3 or 4 carbon atoms;
where one of the substituents R(2) and R(3) is always defined as R(1);
R(4) and R(5) independently of one another are hydrogen, alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$,
n is zero or 1,
o is zero or 1,
and their pharmaceutically tolerable salts.
(96/F 154-EP-A 814 077)
bb) benzoylguanidines of the formula I

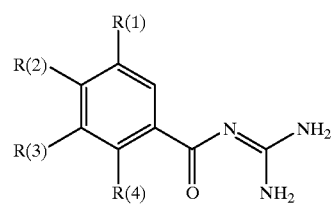

in which:
R(1) is R(13)—$SO_m$ or R(14)R(15)N—$SO_2$—;
m is 1 or 2;
R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(16),
n is zero, 1, 2, 3 or 4;
R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(25)R(26);
R(25) and R(26), independently of one another, are hydrogen, alkyl having 1, 2, 3 or 4 carbon atoms or perfluoroalkyl having 1, 2, 3 or 4 carbon atoms;
R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(27),
n is zero, 1, 2, 3 or 4;
R(27) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(28)R(29);
R(28) and R(29), independently of one another, are hydrogen, alkyl having 1, 2, 3 or 4 carbon atoms or perfluoroalkyl having 1, 2, 3 or 4 carbon atoms;
R(15) is hydrogen, alkyl having 1, 2, 3 or 4 carbon atoms or perfluoroalkyl having 1, 2, 3 or 4 carbon atoms; or
R(14) and R(15), together, are 4 or 5 methylene groups of which one $CH_2$ group can be replaced by oxygen, S, NH, C—$CH_3$ or N-benzyl;

one of the substituents R(2) and R(3) is hydrogen;
and the other of the substituents R(2) and R(3) in each case is —CHR(30)R(31);
R(30) is —(CH$_2$)$_g$—(CHOH)$_h$—(CH$_2$)$_i$—(CHOH)$_k$—R(32) or —(CH$_2$)$_g$—O—(CH$_2$—CH$_2$O)$_h$—R(24);
R(24) and R(32), independently of one another, are hydrogen or methyl;
g, h and i, identically or differently, are zero, 1, 2, 3 or 4;
k is 1, 2, 3 or 4; or the other of the substituents R(2) and R(3) in each case is —C(OH)R(33)R(34);
R(31), R(33) and R(34), identically or differently, are hydrogen or alkyl having 1, 2, 3 or 4 carbon atoms, or
R(33) and R(34), together, are cycloalkyl having 3, 4, 5 or 6 carbon atoms; or
R(33) is —CH$_2$OH;
R(4) is alkyl having 1, 2, 3 or 4 carbon atoms, alkoxy having 1, 2, 3 or 4 carbon atoms, F, Cl, Br, I, CN or —(CH$_2$)$_n$—(CF2)$_o$—CF$_3$;
n is zero or 1;
o is zero, 1 or 2;
and their pharmaceutically tolerable salts.
(HOE 96/F 202-EP-A 837 055)
bc) indanylidineacetylguanidines of the formula I

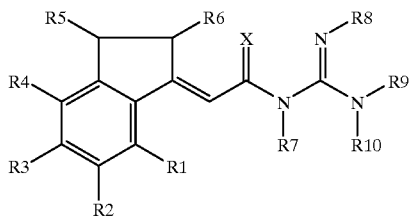

in which:
R1, R2, R3, R4, R5 and R6 independently of one another are H, C$_1$–C$_{10}$-alkyl; haloalkyl having 1–6 carbon atoms, O—C$_1$–C$_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O—C(=O)—C$_1$–C$_4$-alkylaryl, O—C(=O)—NH—C$_1$–C$_4$-alkyl, O—C(=O)—N(C$_1$–C$_4$-alkyl)$_2$, NO$_2$, CN, CF$_3$, NH$_2$, NH—C(=O)—C$_1$–C$_4$-alkyl, NH—C(=O)—NH$_2$, COOH, C(=O)—O—C$_1$–C$_4$-alkyl, C(=O)—NH$_2$, C(=O)—NH—C$_1$–C$_4$-alkyl, C(=O)—N(C$_1$–C$_4$-alkyl)$_2$, C$_1$–C$_4$—COOH, C$_1$–C$_4$-alkyl-C(=O)—O—C$_1$–C$_4$-alkyl, SO$_3$H, SO$_2$-alkyl; SO$_2$-alkylaryl, SO$_2$—N—(alkyl)2, SO$_2$—N(alkyl)(alkylaryl), C(=O)—R11, C$_1$–C$_{10}$-alkyl-C(=O)—R11, C$_2$–C$_{10}$-alkenyl-C(=O)—R11, C$_2$–C$_{10}$-alkynyl-C(=O)—R11, NH—C(=O)—C$_1$–C$_{10}$-alkyl-C(=O)—R11 or O—C$_1$–C$_1$-alkyl-C(=O)—R11;
R11 is C$_1$–C$_4$-alkyl, C$_1$–C$_4$-alkynyl, aryl, substituted aryl, NH$_2$, NH—C$_1$–C$_4$-alkyl, N—(C$_1$–C$_4$-alkyl)$_2$, S03H, SO$_2$-alkyl, SO$_2$-alkylaryl, SO$_2$—N-(alkyl)$_2$ or SO$_2$—N(alkyl)(alkylaryl);
X is O, S or NH;
R7, R8, R9 and R10 independently of one another are H, alkyl, cycloalkyl, aryl, alkylaryl, or
R8 and R9 together are part of a 5-, 6- or 7-membered heterocyclic ring;
or their pharmaceutically acceptable salts.
(HOE 96/F 226-EP-A 825 178)

bd) phenyl-substituted alkenylcarboxylic acid guanidides of the formula I

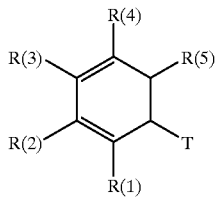

in which is
T:

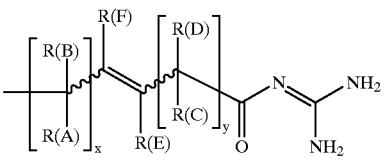

R(A) is hydrogen, F, Cl, Br, I, CN, OH, OR(6), (C$_1$–C$_4$)-alkyl, O$_r$(CH$_2$)$_a$C$_b$F$_{2b+1}$, (C$_3$–C$_8$)-cycloalkyl or NR(7)R(8)
r is zero or 1;
a is zero, 1, 2, 3 or 4;
b is 1, 2, 3 or 4;
R(6) is (C$_1$–C$_4$)-alkyl, (C$_1$–C$_4$)-perfluoroalkyl, (C$_3$–C$_6$)-alkenyl, (C$_3$–C$_8$)-cycloalkyl, phenyl or benzyl, where the phenyl nucleus is unsubstituted or is substituted by 1–3 substituents selected from the group consisting of F, Cl, CF$_3$, methyl, methoxy and NR(9)R(10);
R(9) and R(10) are H, (C$_1$–C$_4$)-alkyl or (C$_1$–C$_4$)-perfluoroalkyl;
R(7) and R(8) independently of one another are defined as R(6); or
R(7) and R(8) together are 4 or 5 methylene groups, of which one CH$_2$ group can be replaced by oxygen, sulfur, NH, C—CH$_3$ or N-benzyl;
R(B), R(C) and R(D) independently are defined as R(A);
x is zero, 1 or 2;
y is zero, 1 or 2;
R(F) is hydrogen, F, Cl, Br, I, CN, OR(12), (C$_1$–C$_8$)-alkyl, O$_p$(CH$_2$)$_f$C$_g$F$_{2g+1}$, (C$_3$–C$_8$)-cycloalkyl or (C$_1$–C$_9$)-heteroaryl;
p is zero or 1;
f is zero, 1, 2, 3 or 4;
g is 1, 2, 3, 4, 5, 6, 7 or 8;
R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl, where the phenyl nucleus is unsubstituted or is substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl;
R(E) is defined independently as R(F);
R(1) is defined independently as T; or
R(1) is hydrogen, —O$_k$C$_m$H$_{2m+1}$, —O$_n$(CH$_2$)$_p$C$_q$F$_{2q+1}$, F, Cl, Br, I, CN, —(C=O)—N=C(NH$_2$)$_2$, —SO$_r$R(17), —SO$_{r2}$NR(31)R(32), —O$_u$(CH$_2$)$_v$C$_6$H$_5$, —O$_{u2}$—(C$_1$–C$_9$)-heteroaryl or —S$_{u2}$—(C$_1$–C$_9$)-heteroaryl;

k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl; or
R(31) and R(32) together are 4 or 5 methylene groups of which one $CH_2$ group can be replaced by oxygen, S, NH, N—$CH_3$ or N-benzyl;
R(17) is $(C_1-C_8)$-alkyl;
u is zero or 1;
u2 is zero or 1;
v is zero, 1, 2, 3 or 4;
  where the phenyl nucleus is unsubstituted or is substituted by 1–3 substituents selected from the group consisting of F, Cl, $CF_3$, methyl, methoxy, —$(CH_2)_w$NR(21)R(22), NR(18)R(19) and $(C_1-C_9)$-heteroaryl;
R(18), R(19), R(21) and R(22) independently of one another are $(C_1-C_4)$-alkyl or $(C_1-C_4)$-perfluoroalkyl;
w is 1, 2, 3 or 4; where the heterocycle of the $(C_1-C_9)$-heteroaryl is unsubstituted or is substituted by 1–3 substituents selected from the group consisting of F, Cl, $CF_3$, methyl or methoxy;
R(2), R(3), R(4) and R(5) independently of one another are defined as R(1), or
R(1) and R(2) or R(2) and R(3) in each case together are —CH—CH=CH—CH—, which is not substituted or is substituted by 1–3 substituents selected from the group consisting of F, Cl, $CF_3$, methyl, methoxy, —$(CH_2)_{w2}$NR(24)R(25) and NR(26)R(27);
R(24), R(25), R(26) and R(27) are H, $(C_1-C_4)$-alkyl or $(C_1-C_4)$-perfluoroalkyl;
w2 is 1, 2, 3 or 4;
where the radical T is present in the molecule at least twice, but only three times at most;
and their pharmaceutically tolerable salts.
(97/ F 082-EP-A 869 116)
be) benzoylguanidines of the formula I

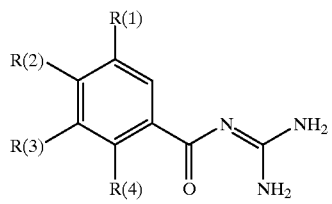

I in which:
R(1) is $CF_3$;
one of the substituents R(2) and R(3) is hydrogen;
and the other substituent R(2) or R(3) in each case is —C(OH)($CH_3$)—$CH_2$OH, —CH($CH_3$)—$CH_2$OH or —C(OH)($CH_3$)$_2$;
R(4) is methyl, methoxy, Cl or $CF_3$;
and their pharmaceutically tolerable salts.
Very particular preference is given to the use of the compound cariporide

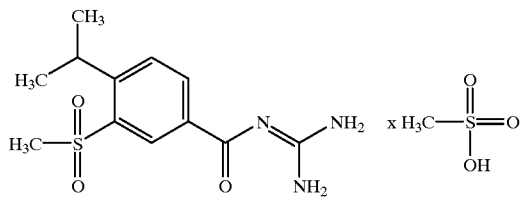

What is claimed is:

1. A method for the treatment or prophylaxis of an age-related disorder, comprising administering to a patient in need thereof a pharmaceutically effective amount of a $Na^+/H^+$ exchange inhibitor.

2. The method as claimed in claim 1, wherein the age-related disorder is an age-related organ dysfunction.

3. A method as claimed in claim 1, wherein the age-related disorder is insufficient responsiveness and reactivity of blood vessels to contraction and relaxation reactions.

4. A method as claimed in claim 1, wherein the age-related disorder is the blockage or delay of age-related progressive endothelial dysfunction.

5. A method as claimed in claim 1, wherein the age-related disorder is the decreased pumping performance of the heart.

6. A method as claimed in claim 1, wherein the $Na^+/H^+$ exchange inhibitor is administered simultaneously or sequentially with an active compound.

7. A method as claimed in claim 1, wherein the the $Na^+/H^+$ exchange inhibitor is selected from
a) a benzoylguanidine of the formula

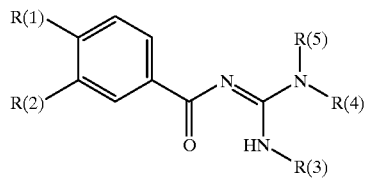

in which:
R(1) or R(2) is R(6)—S(O)n— or R(7)R(8)N—$O_2$S—;
and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chlorine, methyl and methoxy;
or the other substituent R(1) or R(2) in each case is R(6)—S(O)$_n$ or R(7)R(8)N—;
n is zero, 1 or 2;
R(6) is $(C_1-C_6)$-alkyl, $(C_5-C_7)$-cycloalkyl, cyclopentylmethyl, cyclohexylmethyl or phenyl, which is unsubstituted or substituted by 1–3 substituents selected from the group consisting of fluorine, chlorine, methyl and methoxy;
R(7) and R(8) identically or differently are H or $(C_1-C_6)$-alkyl; or
R(7) is phenyl-$(CH_2)_m$;
m is 1–4; or
R(7) is phenyl, which is unsubstituted or substituted by 1–2 substituents selected from the group consisting of fluorine, chlorine, methyl and methoxy; or
R(7) and R(8) together are a straight-chain or branched $(C_4-C_7)$-chain, where the chain can additionally be interrupted by O, S or NR(9);
R(9) is H or methyl; or R(7) and R(8) together with the nitrogen atom to which they are bonded, are a dihydroindole, tetrahydroquinoline or tetrahydroisoquinoline. system;

R(3), R(4) and R(5) independently of one another are H or (C$_1$–C$_2$)-alkyl, or R(3) and R(4) together are a (C$_2$–C$_4$)-alkylene chain; or R(4) and R(5) together are a (C$_4$–C$_7$)-alkylene chain;

or a pharmaceutically tolerable salt thereof;

b) a benzoylguanidine of the formula

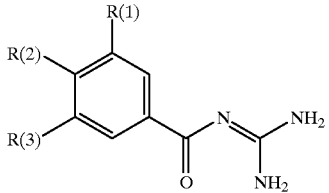

in which:

R(1) is R(4)—SO$_m$ or R(5)R(6)N—SO$_2$—;
  m is zero, 1 or 2;
  R(4) and R(5) are C$_1$–C$_8$-alkyl, C$_3$–C$_6$-alkenyl or —C$_n$H$_{2n}$—R(7);
    n is zero, 1, 2, 3 or 4;
    R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);
      R(8) and R(9) are H or C$_1$–C$_4$-alkyl; or
  R(5) is H;
  R(6) is H or C$_1$–C$_4$-alkyl, or
  R(5) and R(6) together are 4 or 5 methylene groups, of which one CH$_2$ group can be replaced by an O, S, NH, C—CH$_3$ or N-benzyl; R(2) isHhydrogen, F, Cl, Br, (C$_1$–C$_4$)-alkyl-, O—(CH$_2$)$_m$C$_p$F$_{2p+1}$ or —X—R(10);
    m is zero or 1;
    p is 1, 2 or 3;
    X is O, S or NR(11);
    R(10) is H, C$_1$–C$_6$-alkyl, C$_5$–C$_7$-cycloalkyl, cyclohexylmethyl, cyclopentylmethyl or —C$_n$H$_{2n}$—R(12);
      n is zero, 1, 2, 3 or 4;
      R(12) is phenyl, which is unsubstituted or substituted by 1–3 substituents selected from the group consisting of F, Cl, CF$_3$, methyl, methoxy and NR(8)R(9);
        R(8) and R(9) are H or C$_1$–C$_4$-alkyl;
    R(11) is hydrogen or C$_1$–C$_3$-alkyl; or
    R(10) and R(11) together are 4 or 5 methylene groups, of which one CH$_2$ group can be replaced by O, S, NH, N—CH$_3$ or N-benzyl;
R(3) is defined as R(1), or is C$_1$–C$_6$-alkyl, nitro, cyano, trifluoromethyl, F, Cl, Br, I or —X—R(10);
  X is O, S or NR(11); R(10) is H, C$_1$–C$_6$-alkyl, C$_5$–C$_7$-cycloalkyl, cyclohexylmethyl, cyclopentylmethyl or —C$_n$H$_{2n}$—R(12);
    n is zero to 4;
    R(12) is phenyl, which is unsubstituted or substituted by 1–3 substituents selected from the group consisting of F, Cl, CF$_3$, methyl, methoxy und NR(8)R(9);
      R(8) and R(9) are H or C$_1$–C$_4$-alkyl;
    R(11) is C$_1$–C$_3$-alkyl, or
  R(10) and R(11) together are 4 or 5 methylene groups, of which one CH$_2$ group can be replaced by O, S, NH, N—CH$_3$ or N-benzyl;

or a pharmaceutically tolerable salt thereof;

c) an ortho-substituted benzoylguanidine of the formula

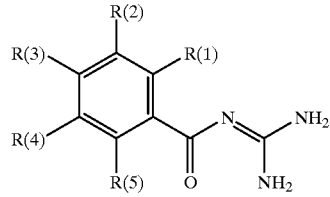

in which:

R(1) is F, Cl, Br, I, C$_1$–C$_6$-alkyl or —X—R(6);
  X is O, S, NR(7) or Y—ZO;
    Y is O or NR(7);
    Z is C or SO;
  R(6) is H, C$_1$–C$_6$-alkyl, C$_5$–C$_7$-cycloalkyl, cyclohexylmethyl, cyclopentylmethyl, —(CH$_2$)$_m$C$_p$F$_{2p+1}$ or —C$_n$H$_{2n}$—R(8);
    m is zero or 1;
    p is 1–3;
    n is zero to 4;
    R(8) is phenyl, which is unsubstituted or substituted by 1–3 substituents selected from the group consisting of the groups F, Cl, CF$_3$, methyl, methoxy and NR(9)R(10);
      R(9) and R(10) are H or C$_1$–C$_4$-alkyl;
    R(7) is H or C$_1$–C$_3$-alkyl; or
  R(6) and R(7) together are 4 or 5 methylene groups, of which one CH$_2$ group can be replaced by O, S, NH, N—CH$_3$ or N-benzyl;
R(3) is H or —X—R(6);
  X is O, S, NR(7) or Y—ZO;
    R(7) is H or C$_1$–C$_3$-alkyl;
    Y is O or NR(7);
      where Y is bonded to the phenyl radical of the formula 1,
    Z is C or SO;
  R(6) is H, C$_1$–C$_6$-alkyl, C$_5$–C$_7$-cycloalkyl, cyclohexylmethyl, cyclopentylmethyl, —(CH$_2$)$_m$C$_p$F$_{2p+1}$ or —C$_n$H$_{2n}$—R(8);
    m is zero or 1;
    p is 1–3;
    n is zero to 4;
    R(8) is phenyl, which is unsubstituted or substituted by 1–3 substituents selected from the group consisting of F, Cl, CF$_3$, methyl, methoxy and NR(9)R(10);
      R(9) and R(10) are H or C$_1$–C$_4$-alkyl; or
  R(6) and R(7) together are 4 or 5 methylene groups, of which one CH$_2$ group can be replaced by O, S, NH, N—CH$_3$ or N-benzyl;
R(2) and R(4) identically or differently are R(11)—SO$_q$— or R(12)R(13)N—SO$_2$—;
  q is zero–2;
  R(11) is C$_1$–C$_4$-alkyl, which is unsubstituted or carries phenyl as a substituent, where phenyl is unsubstituted or substituted by 1–3 substituents selected from the group consisting of F, Cl, CF$_3$, methyl, methoxy and NR(9)R(10);
    R(9) and R(10) are H or C$_1$–C$_4$-alkyl;
  R(12) and R(13) are defined as R(6) and R(7); or one of the two radicals R(2) or R(4) is hydrogen or is defined as R(1);
R(5) is H, methyl, F, Cl or methoxy,
or a pharmaceutically tolerable salt thereof;
d) a benzoylguanidine of the formula

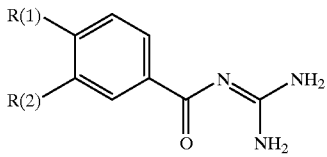

in which:
R(1) or R(2) is an amino group —NR(3)R(4);
R(3) and R(4) identically or differently are H, $C_1$–$C_6$-alkyl or $C_3$–$C_7$-cycloalkyl; or
R(3) is phenyl-$(CH_2)_p$—;
p is 0, 1, 2, 3 or 4; or
R(3) is phenyl, where the phenyl in each case is unsubstituted or carries one to two substituents selected from the group consisting of fluorine, chlorine, methyl and methoxy; or
R(3) and R(4) together can be a straight-chain or branched $C_4$–$C_7$-methylene chain, where one —$CH_2$— member of the methylene chain can be replaced by oxygen, S or NR(5); R(5) is H or lower alkyl;
the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy, where the respective phenyl radical is unsubstituted or carries one to two substituents selected from the group consisting of methyl, methoxy, fluorine and chlorine;
m is 1, 2 or 3;
or a pharmaceutically tolerable salt thereof;
e) a benzoylguanidine of the formula

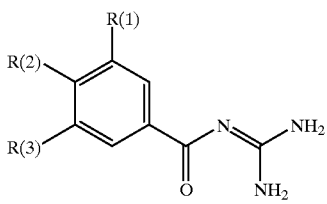

in which:
R(1) is R(4)—$SO_m$ or R(5)R(6)N—$SO_2$—;
m is zero, 1 or 2;
R(4) and R(5) are $C_1$–$C_8$-alkyl, $C_3$–$C_6$-alkenyl or —$C_nH_{2n}$—R(7);
n is zero, 1, 2, 3 or 4;
R(7) is $C_5$–$C_7$-cycloalkyl or phenyl, which is unsubstituted or substituted by 1–3 substituents selected from the group consisting of F, Cl, $CF_3$, methyl, methoxy and NR(8)R(9);
R(8) and R(9) are H or $C_1$–$C_4$-alkyl; or
R(5) is H;
R(6) is H or $C_1$–$C_4$-alkyl; or
R(5) and R(6) together are 4 or 5 methylene groups, of which one $CH_2$ group can be replaced by an O, S, NH, N—$CH_3$ or N-benzyl;
R(2) is hydrogen, straight-chain or branched $(C_5$–$C_8)$-alkyl, —CR(13)=CHR(12) or —C≡CR(12);
R(12) is phenyl, which is unsubstituted or substituted by 1–3 substituents selected from the group consisting of F, Cl, $CF_3$, methyl, methoxy and NR(14)R(15);

R(14) and R(15) are H or $(C_1$–$C_4)$-alkyl; or
R(12) is $(C_1$–$C_9)$-heteroaryl, which is unsubstituted or substituted as phenyl, or
R(12) is $(C_1$–$C_6)$-alkyl, which is unsubstituted or substituted by 1–3 OH, or
R(12) is $(C_3$–$C_9)$-cycloalkyl;
R(13) is hydrogen or methyl, or
R(12) is $(C_3$–$C_8)$-cycloalkyl, $(C_3$–$C_8)$-cycloalkyl-$(C_1$–$C_4)$-alkyl, phenyl, $C_6H_5$-$(C_1$–$C_4)$-alkyl, naphthyl, biphenylyl, 1,1-diphenyl-$(C_1$–$C_4)$-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2);
and where the aromatic substituents R(2) and R(3) are unsubstituted or substituted by 1–3 substituents from the groups F, Cl, $CF_3$, $(C_1$–$C_4)$-alkyl or -alkoxy, or NR(10)R(11) with R(10) and R(11) being H or $(C_1$–$C_4)$-alkyl;
or a pharmaceutically tolerable salt thereof;
f) a benzoylguanidine of the formula

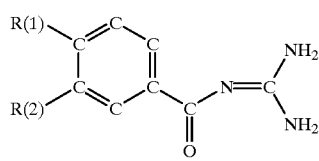

in which:
R(1) or R(2) is R(3)—S(O)$_n$— or R(4)R(5)N—$SO_2$—
the other substituent R(1) or R(2) in each case is H, OH, F, Cl, Br, I, $C_1$–$C_4$-alkyl, $C_1$–$C_4$-alkoxy, benzyloxy or phenoxy, which is unsubstituted or carries one to three substituents selected from the group consisting of fluorine, chlorine, methyl, methoxy, hydroxyl or benzyloxy,
R(3)—S(O)$_n$, —NR(4)R(5) or 3,4-dehydropiperidine
R(3) is $C_1$–$C_6$-alkyl, $C_5$–$C_7$-cycloalkyl, cyclopentylmethyl, cyclohexylmethyl or phenyl, which is unsubstituted or carries one to three substituents selected from the group consisting of fluorine, chlorine, methyl and methoxy;
R(4) and R(5) identically or differently, are H or $C_1$–$C_6$-alkyl; or
R(4) is phenyl-$(CH_2)_m$—;
m is 1, 2, 3 or 4; or
R(4) is phenyl, which is unsubstituted or carries one to two substituents selected from the group consisting of fluorine, chlorine, methyl and methoxy; or
R(4) and R(5) together are a straight-chain or branched $C_4$–$C_7$-chain, where the chain can additionally be interrupted by O, S or NR(6),
R(6) is H or methyl; or
R(4) and R(5) together with the nitrogen atom to which they are bonded, are a dihydroindole, tetrahydroquinoline or tetrahydroisoquinoline system;
n is zero, 1 or 2;
or a pharmaceutically tolerable salt thereof;

g) an isoquinoline of the formula

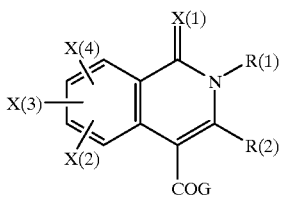

in which:
R(1) is hydrogen, alkyl, cycloalkyl, arylalkyl, alkenyl, substituted aminoalkyl or an aryl or heteroaryl ring; where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl, R(2) is hydrogen, halogen, alkyl or aryl; which is unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, G is —N=C{[NR(3)R(4)][N(R5)R(6)]}

X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;

X(1) is hydrogen, oxygen, sulfur or NR(7);
  R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;
    in which substituents each alkyl chain or alkenyl chain can be interrupted by oxygen, sulfur or NR(8);
  R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;

or a pharmaceutically tolerable salt thereof;

h) a compound of the formula

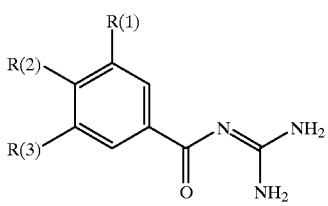

in which:
R(1) is hydrogen, F, Cl, Br, I, —NO$_2$, —C≡N, —CF$_3$, R(4)—SO$_m$ or R(5)R(6)N—SO$_2$—;
m is zero, 1 or 2;
  R(4) and R(5) are (C$_1$–C$_8$)-alkyl, (C$_3$–C$_6$)-alkenyl, —C$_n$H$_{2n}$—R(7) or CF$_3$;

n is zero, 1, 2, 3 or 4;
  R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);
    R(8) and R(9) are H or C$_1$–C$_4$-alkyl; or
R(5) is H;
R(6) is H or (C$_1$–C$_4$)-alkyl; or
R(5) and R(6) together are 4 or 5 methylene groups, of which one CH$_2$ group can be replaced by oxygen, S, NH, N—CH$_3$ or N-benzyl;

R(2) is —SR(10), —OR(10), —NHR(10), —NR(10)R(11), —CHR(10)R(12), —[CR(12)R(13)OR(13')], —{C—[CH$_2$—OR(13')]R(12)(R(13)} or —[CR(18)R(17)]$_p$—(CO)—[CR(19)R(20)]$_q$—R(14);
  R(10) and R(11) identically or differently are —[CHR(16)]$_s$—(CH$_2$)$_p$—(CHOH)$_q$—(CH$_2$)$_r$—(CHOH)$_t$—R(21) or —(CH$_2$)$_p$—O—(CH$_2$—CH$_2$O)$_q$—R(21),
  R(21) is hydrogen, methyl, p, q, r identically or differently are zero, 1, 2, 3 or 4;
  s is zero or 1;
  t is 1, 2, 3 or 4;
  R(12) and R(13) identically or differently are hydrogen, (C$_1$–C$_6$)-alkyl or, together with the carbon atom carrying them, are a (C$_3$–C$_8$)-cycloalkyl,
  R(13') is hydrogen or (C$_1$–C$_4$)-alkyl;
    R(14) is H, (C$_1$–C$_6$)-alkyl, (C$_3$–C$_8$)-cycloalkyl or —C$_a$H$_{2a}$—R(15); a is zero, 1, 2, 3 or 4;
    R(15) is phenyl, which is unsubstituted or substituted by 1–3 substituents selected from the group consisting of F, Cl, CF$_3$, methyl, methoxy and NR(8)R(9);
      R(8) and R(9) are H or (C$_1$–C$_4$)-alkyl; or
    R(15) is (C$_1$–C$_9$)-heteroaryl, which is unsubstituted or substituted as phenyl, or
    R(15) is (C$_1$–C$_6$)-alkyl, which is unsubstituted or substituted by 1–3 OH;
    R(16), R(17), R(18), R(19) and R(20) are hydrogen or (C$_1$–C$_3$)-alkyl;
R(3) is defined as R(1), or
R(3) is (C$_1$–C$_6$)-alkyl or —X—R(22);
  X is oxygen, S or NR(16);
  R(16) is H or (C$_1$–C$_3$)-alkyl; or
  R(22) and R(16) together are 4 or 5 methylene groups, of which one CH$_2$ group can be replaced by oxygen, S, NH, N—CH$_3$ or N-benzyl;
  R(22) is defined as R(14);

or a pharmaceutically tolerable salt thereof;

i) a benzoylguanidine of the formula

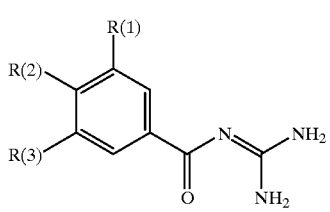

in which:
R(1) is hydrogen, F, Cl, Br, I, —NO$_2$, —C≡N, R(16)—C$_p$H$_{2p}$—O$_q$, R(4)—SO$_{m\ or\ R(}$5)R(6)N—SO$_2$—;
m is zero, 1 or 2;
p is zero or 1;
q is zero, 1, 2 or 3;

R(16) is $C_rF_{2r+1}$;
r is 1, 2 or 3;
R(4) and R(5) are $(C_1-C_8)$-alkyl, $(C_3-C_6)$-alkenyl, —$C_nH_{2n}$—R(7) or $CF_3$;
n is zero, 1, 2, 3 or 4;
R(7) is $(C_3-C_7)$-cycloalkyl or phenyl, which is not substituted or is substituted by 1–3 substituents selected from the group consisting of F, Cl, $CF_3$, methyl, methoxy and NR(8)R(9);
R(8) and R(9) are H or $C_1-C_4$-alkyl; or
R(5) is H;
R(6) is H or $(C_1-C_4)$-alkyl; or
R(5) and R(6) together are 4 or 5 methylene groups, of which one $CH_2$ group can be replaced by oxygen, S, NH, N—$CH_3$ or N-benzyl,
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is —SR(10), —OR(10), —NR(10)R(11), —CR(10)R(11)R(12); R(10) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10) or are hydrogen or $(C_1-C_4)$-alkyl;
R(3) is defined as R(1), or is $(C_1-C_6)$-alkyl or —X—R(13);
X is oxygen, S, or NR(14);
R(14) is H or $(C_1-C_3)$-alkyl;
R(13) is H, $(C_1-C_6)$-alkyl, $(C_3-C_8)$-cycloalkyl or —$C_bH_{2b}$—R(15);
b is zero, 1, 2, 3 or 4; or
R(13) and R(14) together are 4 or 5 methylene groups, of which one $CH_2$ group can be replaced by oxygen, S, NH, N—$CH_3$ or N-benzyl; R(15) is phenyl, which is unsubstituted or substituted by 1–3 substituents selected from the group consisting of F, Cl, $CF_3$, methyl, methoxy and NR(8)R(9); R(8) and R(9) are H or $(C_1-C_4)$-alkyl;
or a pharmaceutically tolerable salt thereof;
k) a benzoylguanidine of the formula

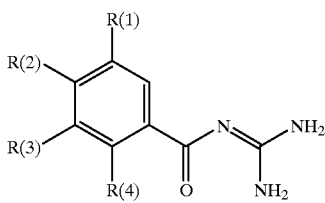

in which:
one of the substituents R(1), R(2), R(3) or R(4):
is an amino group —NR(5)[$C_nH_{2n}$—R(6)];
R(5) is hydrogen or $C_{(1-6)}$-alkyl;
is zero, 1, 2, 3 or 4;
R(6) is H or $C_{(1-4)}$-alkyl;
in which one $CH_2$ group can be replaced by 1 sulfur atom or a group NR(7);
R(7) is hydrogen, methyl or ethyl; or
R(6) is $C_{(3-8)}$-cycloalkyl or phenyl, which is unsubstituted or carries 1, 2 or 3 substituents selected from the group consisting of F, Cl, Br, methyl, methoxy, —NR(8)R(9);
R(8) and R(9) are H, methyl or ethyl; or
R(5) and R(6) together with the nitrogen atom are a 5-, 6- or 7-membered ring, in which 1 carbon atom can be replaced by oxygen, S or NR(10);
R(10) is H, $C_{(1-3)}$-alkyl or benzyl; and the other substituents R(1), R(2), R(3), R(4) in each case are: hydrogen, F. Cl, Br, I, CN, $CF_3$, $NO_2$, $CF_3$—O—, $C_mF_{2m+1}$—$CH_2$—O— or R(11)—$C_qH_{2q}$—$X_p$—;
m is 1, 2 or 3;
q is zero, 1, 2, 3 or 4;
p is zero or 1;
X is oxygen or NR(12); R(12) is H or $C_{(1-3)}$-alkyl;
R(11) is hydrogen, $C_{(1-6)}$-alkyl, $C_{(3-8)}$-cycloalkyl or phenyl, which is unsubstituted or substituted by 1, 2 or 3 substituents selected from the group consisting of F, Cl, $CH_3$, $CH_3$—O— and NR(13)R(14);
R(13), R(14) are H, methyl or ethyl;
or a pharmaceutically tolerable salt thereof;
l) a benzoylguanidine of the formula in which
R(1) is R(4)R(5)N—C(X)—;
X is oxygen, S or N—R(6);
R(4) and R(5) identically or differently, are H, $(C_1-C_8)$-alkyl, $(C_3-C_6)$-alkenyl or —$C_nH_{2n}$—R(7);
n is zero, 1, 2, 3 or 4;
R(7) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or
R(4) and R(5) together are 4 or 5 methylene groups, of which one $CH_2$ group can be replaced by oxygen, S, NH, N—$CH_3$ or N-benzyl; R(6) is defined as R(4) or is amidine;
R(2) is H, F, Cl, Br, I, $(C_1-C_8)$-alkyl, 1-alkenyl or 1-alkynyl, $(C_3-C_8)$-cycloalkyl, $(C_3-C_8)$-cycloalkyl-$(C_1-C_4)$-alkyl, phenyl, $C_6H_5$-$(C_1-C_4)$-alkyl, naphthyl, biphenylyl, 1,1-diphenyl-$(C_1-C_4)$-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);
W is oxygen, S or NR(9);
R(8) is H, $(C_1-C_6)$-alkyl, $(C_5-C_7)$-cycloalkyl, cyclohexylmethyl, cyclopentylmethyl, —$(CH_2)_mC_pF_{2p+1}$ or —$C_qH_{2q}$—R(10);
m is zero or 1;
p is 1, 2 or 3;
q is zero, 1, 2, 3 or 4;
R(10) is phenyl, which is unsubstituted or substituted by 1–3 substituents selected from the group consisting of F, Cl, $CF_3$, methyl, methoxy and NR(11)R(12);
R(11) and R(12) are H or $(C_1-C_4)$-alkyl;
R(9) is H or $(C_1-C_3)$-alkyl; or
R(8) and R(9) together are 4 or 5 methylene groups, of which one $CH_2$ group can be replaced by oxygen, S, NH, N—$CH_3$ or N-benzyl;

R(3) is H, F, Cl, Br, I, ($C_1$–$C_6$)-alkyl or —W—R(8) as defined for R(2),
or a pharmaceutically tolerable salt thereof;
m) a benzoylguanidine of the formula

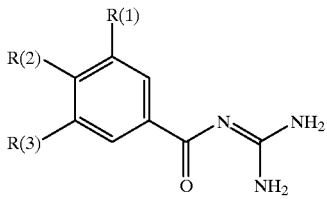

in which:
R(1), R(2), R(3) are hydrogen, F, Cl, Br, I or ($C_1$–$C_{12}$)-alkyl;
one of the substituents R(1), R(2) or R(3) is $N_3$, CN, OH or ($C_1$–$C_{10}$)-alkyloxy, if at least one of the remaining substituents R(1), R(2) or R(3) is a sufficiently lipophilic alkyl radical having 3 to 12 carbon atoms; or
one of the substituents R(1), R(2) or R(3) is R(4)—$C_nH_{2n}$—$O_m$—;
m is zero or 1;
n is zero, 1, 2 or 3;
R(4) is $C_pF_{2p+1}$;
p is 1, 2 or 3, if n is zero or 1; or
R(4) is ($C_3$–$C_{12}$)-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or ($C_1$–$C_4$)-alkyl;
or one of the substituents R(1), R(2) or R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino, ($C_1$–$C_9$)-heteroaryl, which is unsubstituted or substituted as phenyl, or
R(5) is ($C_1$–$C_6$)-alkyl, which is unsubstituted or substituted by 1–3 OH; or
R(5) is ($C_3$–$C_8$)-cycloalkyl,
R(6) is hydrogen or methyl;
or a pharmaceutically tolerable salt thereof;
o) a benzoylguanidine of the formula

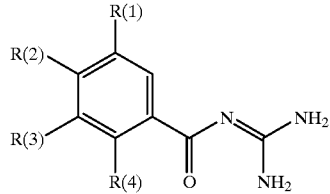

in which:
R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where
X is oxygen, S or NR(14);
m is zero, 1 or 2;
o is zero or 1;
p is zero, 1 or 2;
q is zero, 1, 2, 3, 4, 5 or 6;

R(5) and R(6) are ($C_1$–$C_8$)-alkyl, ($C_3$–$C_6$)-alkenyl, —$C_nH_{2n}$—R(8) or $CF_3$;
n is zero, 1, 2, 3 or 4;
R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);
R(9) and R(10) are H or $C_1$–$C_4$-alkyl; or
R(6) is H;
R(7) is H or ($C_1$–$C_4$)-alkyl; or
R(6) and R(7) together are 4 or 5 methylene groups, of which one $CH_2$ group can be replaced by oxygen, S, NH, N—$CH_3$ or N-benzyl;

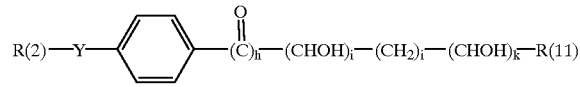

or

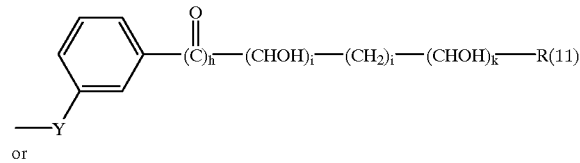

or

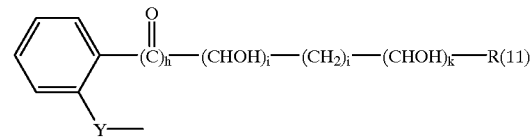

Y is oxygen, —S— or —NR(12)—;
R(11) and R(12) are hydrogen or ($C_1$–$C_3$)-alkyl;
h is zero or 1;
i, j and k independently are zero, 1, 2, 3 or 4;
but where h, i and k are not simultaneously zero,
R(3) is defined as R(1), or is ($C_1$–$C_6$)-alkyl or —X—R(13);
X is oxygen, S or NR(14);
R(14) is H or ($C_1$–$C_3$)-alkyl;
R(13) is H, ($C_1$–$C_6$)-alkyl, ($C_3$–$C_8$)-cycloalkyl or —$C_bH_{2b}$—R(15);
b is zero, 1, 2, 3 or 4; or
R(13) and R(14) together are 4 or 5 methylene groups, where one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(9)R(10);
R(9) and R(10) are H or ($C_1$–$C_4$)-alkyl;
R(4) is hydrogen, —OR(16) or —NR(16)R(17);
R(16) and R(17) independently are hydrogen or ($C_1$–$C_3$)-alkyl;

or a pharmaceutically tolerable salt thereof;

p) a benzoylguanidine of the formula

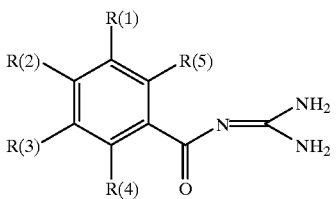

in which:
R(1) is R(6)—CO or R(7)R(8)N—CO;
  R(6) is $(C_1-C_8)$-alkyl, $(C_1-C_8)$-perfluoroalkyl, $(C_3-C_8)$-alkenyl or —$C_nH_{2n}$—R(9);
  n is zero, 1, 2, 3 or 4;
  R(9) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
    R(10) and R(11) are H, $(C_1-C_4)$-alkyl or $(C_1-C_4)$-perfluoroalkyl;
  R(7) is H, $(C_1-C_8)$-alkyl, $(C_1-C_8)$-perfluoroalkyl, $(C_3-C_8)$-alkenyl or —$C_nH_{2n}$—R(12);
  n is zero, 1, 2, 3 or 4;
  R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
    R(13) and R(14), are H, $(C_1-C_4)$-alkyl or $(C_1-C_4)$-perfluoroalkyl;
  R(8) is H, $(C_1-C_4)$-alkyl or $(C_1-C_4)$-perfluoroalkyl; or
  R(7) and R(8) together are 4 or 5 methylene groups, of which one $CH_2$ group can be replaced by oxygen, S, NH, N—$CH_3$ or N-benzyl;
R(2) is defined as R(1), or is H, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}$R(15);
  n is zero, 1, 2, 3 or 4;
  R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
    R(16) and R(17) are H, $(C_1-C_4)$-alkyl or $(C_1-C_4)$-perfluoroalkyl; or
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is SR(18), —OR(18), —NR(18)R(19), —CR(18)R(19)R(20);
  R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
  a is zero, 1 or 2;
  R(19) and R(20) independently of one another are defined as R(18) or are hydrogen, $(C_1-C_4)$-alkyl or $(C_1-C_4)$-perfluoroalkyl; or
R(2) is R(21)—$SO_m$ or R(22)R(23)N—$SO_2$—;
  m is 1 or 2;
  R(21) is $(C_1-C_8)$-alkyl, $(C_1-C_8)$-perfluoroalkyl, $(C_3-C_8)$-alkenyl, —$C_nH_{2n}$—R(24),
  n is zero, 1, 2, 3 or 4;
  R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
    R(27) and R(28) are H, $(C_1-C_4)$-alkyl or $(C_1-C_4)$-perfluoroalkyl;
  R(22) is H, $(C_1-C_8)$-alkyl, $(C_1-C_8)$-perfluoroalkyl, $(C_3-C_8)$-alkenyl, —$C_nH_{2n}$—R(29);
  n is zero, 1, 2, 3 or 4;
  R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
    R(30) and R(31) are H, $(C_1-C_4)$-alkyl or $(C_1-C_4)$-perfluoroalkyl;
  R(23) is H, $(C_1-C_4)$-alkyl or $(C_1-C_4)$-perfluoroalkyl; or
  R(22) and R(23) together are 4 or 5 methylene groups, of which one $CH_2$ group can be replaced by oxygen, S, NH, N—$CH_3$ or N-benzyl; or
R(2) is R(33)X—;
  X is oxygen, S, NR(34), (D=O)A—, NR(34)C=MN$^{(*)}$R(35)—;
  M is oxygen or S;
  A is oxygen or NR(34);
  D is C or SO;
  R(33) is $(C_1-C_8)$-alkyl, $(C_3-C_8)$-alkenyl, $(CH_2)_bC_dF_{2d+1}$, —$C_nH_{2n}$—R(36),
  b is zero or 1;
  d is 1, 2, 3, 4, 5, 6 or 7;
  n is zero, 1, 2, 3 or 4;
  R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
    R(37) and R(38) are H, $(C_1-C_4)$-alkyl or $(C_1-C_4)$-perfluoroalkyl;
  R(34) is H, $(C_1-C_4)$-alkyl or $(C_1-C_4)$-perfluoroalkyl;
  R(35) is defined as R(33); or
  R(33) and R(34) together are 4 or 5 methylene groups, of which one $CH_2$ group can be replaced by oxygen, S, NH, N—$CH_3$ or N-benzyl;
  where A and N$^{(*)}$ are bonded to the phenyl nucleus of the benzoylguanidine parent structure; or
R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR(49)R(50)]$_v$—R(44);
  R(40), R(41) identically or differently are —$(CH_2)_p$—(CHOH)$_q$—$CH_2)_r$—(CHOH)$_t$—R(51) or —$(CH_2)_p$—O—($CH_2$—$CH_2O)_q$—R(51);
  R(51) is hydrogen or methyl;
  u is 1, 2, 3 or 4;
  v is zero, 1, 2, 3 or 4;
  p, q, r identically or differently are zero, 1, 2, 3 or 4;
  t is 1, 2, 3 or 4;
  R(42) and R(43) identically or differently are hydrogen or $(C_1-C_6)$-alkyl; or
  R(42) and R(43) together with the carbon atom carrying them form a $(C_3-C_8)$-cycloalkyl;
  R(44) is H, $(C_1-C_6)$-alkyl, $(C_3-C_8)$-cycloalkyl or —$C_eH_{2e}$—R(45);

e is zero, 1, 2, 3 or 4;
R(45) is phenyl, which is unsubstituted or substituted by 1–3 substituents from the group consisting of F, Cl, CF$_3$, methyl, methoxy and NR(52)R(53);
R(52) and R(53) are H or (C$_1$–C$_4$)-alkyl, or
R(45) is (C$_1$–C$_9$)-heteroaryl, which is unsubstituted or substituted as phenyl; or
R(45) is (C$_1$–C$_6$)-alkyl, which is unsubstituted or substituted by 1–3 OH;
R(46), R(47), R(48), R(49) and R(50) are hydrogen or methyl; or R(2) is R(55)—NH—SO$_2$—;
R(55) is R(56)R(57)N—(C=Y)—;
Y is oxygen, S or N—R(58);
R(56) and R(57) identically or differently are H, (C$_1$–C$_8$)-alkyl, (C$_3$–C$_6$)-alkenyl or —C$_f$H$_{2f}$—R(59);
f is zero, 1, 2, 3 or 4;
R(59) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(56) and R(57) together are 4 or 5 methylene groups, of which one CH$_2$ group can be replaced by oxygen, S, NH, N—CH$_3$ or N-benzyl;
R(58) is defined as R(56) or is amidine;

R(3), R(4) and R(5) independently of one another are defined as R(1) or R(2);
or a pharmaceutically tolerable salt thereof;
q) a benzoylguanidine of the formula

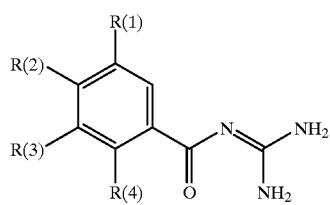

in which:
R(1) is hydrogen, F, Cl, Br, I, —NO$_2$, —C N, —X$_o$—(CH$_2$)$_p$—(CF$_2$)$_q$—CF$_3$, R(5)—SO$_m$—, R(6)—CO—, R(6)R(7)N—CO— or R(6)R(7)N—SO$_2$—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are (C$_1$–C$_8$)-alkyl, (C$_3$–C$_6$)-alkenyl, —C$_n$H$_{2n}$—R(8) or CF$_3$;
n is zero, 1, 2, 3 or 4;
R(8) is (C$_3$–C$_7$)-cycloalkyl, phenyl, which is not substituted or is substituted by 1 to 3 substituents selected from the group consisting of F, Cl, CF$_3$, methyl, methoxy and NR(9)R(10);
R(9) and R(10) are H or (C$_1$–C$_4$)-alkyl; or
R(6) is hydrogen;
R(7) is hydrogen or (C$_1$–C$_4$)-alkyl; or
R(6) and R(7) together are 4 or 5 methylene groups, of which one CH$_2$ group can be replaced by oxygen, S, NH, N—CH$_3$ or N-benzyl;

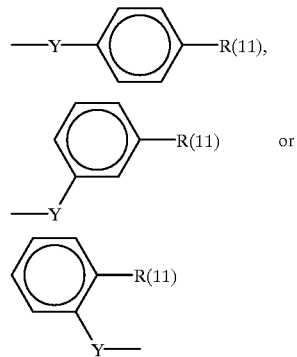

R(2)
R(11) is (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino and benzyl;
Y is oxygen, —S— or NR(12);
R(12) is H or (C$_1$–C$_4$)-alkyl;
R(3) is defined as R(1); or
R(3) is (C$_1$–C$_6$)-alkyl or —X—R(13);
x is oxygen, —S— or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);
b is zero, 1, 2, 3 or 4; or
R(13) and R(14) together are 4 or 5 methylene groups, of which one CH$_2$ group can be replaced by oxygen, S, NH, N—CH$_3$ or N-benzyl;
R(15) is phenyl, which is unsubstituted or substituted by 1–3 substituents selected from the group consisting of F, Cl, CF$_3$, methyl, methoxy and NR(9)R(10);
R)9) and R(10) are H or (C$_1$–C$_4$)-alkyl;
R(4) is hydrogen, —OR(16), —NR(16)R(17) or C$_r$F$_{2r+1}$;
R(16) and R(17) independently are hydrogen or (C$_1$–C$_3$)-alkyl;
r is 1, 2, 3 or 4;
or a pharmaceutically tolerable salt thereof;
r) a benzofused 5-membered ring heterocycle of the formula

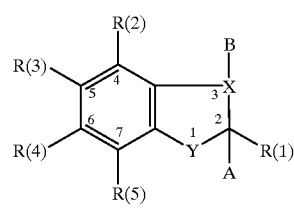

in which:
X is N or CR(6);
Y is oxygen, S or NR(7);
A, B together are a bond or
A, B are both hydrogen, if X is CR(6) and Y is NR(7) simultaneously; one of the substituents R(1) to R(6) is a —CO—N=C(NH$_2$)$_2$ group;
the other substituents R(1) to R(6) in each case are hydrogen, F, Cl, Br, I or (C$_1$–C$_6$)-alkyl;
up to two of the other substituents R(1) to R(6) are CN, NO$_2$, N$_3$, (C$_1$–C$_4$)-alkyloxy or CF$_3$;

up to one of the other substituents is R(8)—$C_nH_{2n}$—Z—;
n is zero to 10;
where the alkylene chain —$C_nH_{2n}$— is straight-chain or branched and where one carbon atom can be replaced by an oxygen or sulfur atom or by a nitrogen atom;
R(8) is hydrogen, ($C_2$–$C_6$)-alkenyl or ($C_3$–$C_{10}$)-cycloalkyl, which is unsubstituted or substituted by 1 to 4 methyl groups or an OH group, or can contain an ethylene group —CH=CH—, and in which one methylene group can be replaced by an oxygen or sulfur atom or by a nitrogen atom; or
R(8) is phenyl, which is unsubstituted or substituted by 1 to 3 substituents selected from the group consisting of F, Cl, Br, I, $CF_3$, $CH_3$—S(O)$_s$— or R(9)—W$_y$—;
s is zero, 1 or 2;
R(9) is H, methyl, ethyl,
W is oxygen or NR(10);
R(10) is H or methyl;
y is zero or 1; or
R(8) is $C_mF_{2m+1}$;
m is 1 to 3; or
R(8) is 1- or 2-naphthyl, pyridyl, quinolyl or isoquinolyl;
Z is —CO—, —$CH_2$— or —[CR(11)(OH)]$_q$—;
q is 1, 2 or 3;
R(11) is H or methyl; or
Z is oxygen or —NR(12)—;
R(12) is H or methyl; or
Z is —S(O)$_s$—;
s is zero, 1 or 2; or
Z is —$SO_2$—NR(13)—;
R(13) is H or ($C_1$–$C_4$)-alkyl;
R(7) is hydrogen, ($C_1$–$C_{10}$)-alkyl, ($C_2$–$C_{10}$)-alkenyl or R(8)—$C_nH_{2n}$—;
or a pharmaceutically tolerable salt thereof;
s) a benzoylguanidine of the formula I

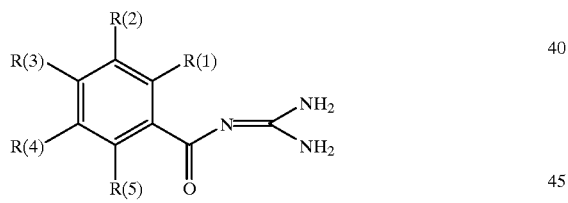

in which:
R(1), R(3) or R(4) is —NR(6) C=X NR(7)R(8);
X is oxygen or S;
R(6) is hydrogen, ($C_1$–$C_8$)-alkyl, ($C_1$–$C_8$)-perfluoroalkyl, ($C_3$–$C_8$)-alkenyl or —$C_nH_{2n}$—R(9);
n is zero, 1, 2, 3 or 4;
R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
R(10) and R(11) are H, ($C_1$–$C_4$)-alkyl or ($C_1$–$C_4$)-perfluoroalkyl;
R(7) is hydrogen, ($C_1$–$C_8$)-alkyl, ($C_1$–$C_8$)-perfluoroalkyl, ($C_3$–$C_8$)-alkenyl or —$C_oH_{2o}$—R(12);
o is zero, 1, 2, 3 or 4;
R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
R(13) and R(14) are H, ($C_1$–$C_4$)-alkyl or ($C_1$–$C_4$)-perfluoroalkyl;
R(8) is defined as R(7); or
R(7) and R(8) together are 4 or 5 methylene groups, of which one $CH_2$ group can be replaced by oxygen, S, NH, N—$CH_3$ or N-benzyl;
the remaining substituents R(2), R(3), R(4), R(5) or R(1), R(2), R(4), R(5) or R(1), R(2), R(3), R(5) in each case independently of one another are hydrogen, F, Cl, Br, I, —$O_{ta}$($C_1$–$C_8$)-alkyl, —$O_{tb}$($C_3$–$C_8$)-alkenyl, —$O_{tc}$($CH_2$)$_b$$C_dF_{2d+1}$, —$O_{td}C_pH_{2p}$R(18), or up to 2 groups CN, $NO_2$, NR(16)R(17),
b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;
R(18) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(19)R(20);
R(19) and R(20) are hydrogen or ($C_1$–$C_4$)-alkyl or ($C_1$–$C_4$)-perfuoroalkyl;
R(16) is hydrogen, ($C_1$–$C_8$)-alkyl, ($C_1$–$C_8$)-perfluoroalkyl, ($C_3$–$C_8$)-alkenyl, —$C_qH_{2q}$—R(21),
q is zero, 1, 2, 3 or 4;
R(21) is ($C_3$–$C_8$)-cycloalkyl, phenyl, biphenylyl or naphthyl, where the aromatics are not substituted or are substituted by 1–3 substituents from the group F, Cl, $CF_3$, methyl, methoxy or NR(22)R(23), R(22) and R(23) are hydrogen, ($C_1$–$C_4$)-alkyl or ($C_1$–$C_4$)-perfluoroalkyl;
R(17) is hydrogen, ($C_1$–$C_8$)-alkyl, ($C_1$–$C_8$)-perfluoroalkyl, ($C_3$–$C_8$)-alkenyl, —$C_rH_{2r}$—R(24);
r is zero, 1, 2, 3 or 4;
R(24) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(25)R(26);
R(25) and R(26) are hydrogen, ($C_1$–$C_4$)-alkyl or ($C_1$–$C_4$)-perfluoroalkyl; or
R(16) and R(17) together are 4 or 5 methylene groups, of which one $CH_2$ group can be replaced by oxygen, S, NH, N—$CH_3$ or N-benzyl;

or a pharmaceutically tolerable salt thereof;
t) a diacyl-substituted guanidine of the formula

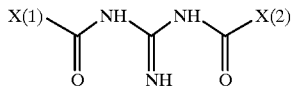

in which:

X(1) and X(2) are

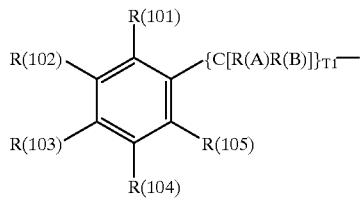

T1 is zero, 1, 2, 3 or 4;

R(A) and R(B)
independently are hydrogen, F, Cl, Br, I, CN, OR(106), $(C_1-C_8)$-alkyl, $(C_3-C_8)$-cycloalkyl, $O_{zk}(CH_2)_{zl}C_{zm}F_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110);

R(109) and R(110) are hydrogen, $(C_1-C_4)$-alkyl or $(C_1-C_4)$-perfluoroalkyl;

zl is zero, 1, 2, 3 or 4;
zk is zero or 1;
zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(111)R(112);

R(111) and R(112) are hydrogen, $(C_1-C_4)$-alkyl or $(C_1-C_4)$-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl; or X(1) and X(2) are

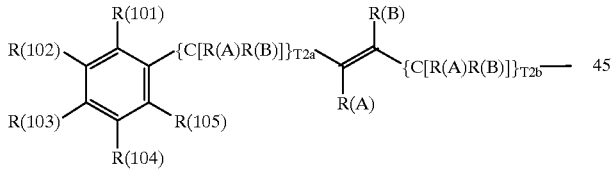

T2a and T2b independently of one another are zero, 1 or 2; where the double bond can have the (E)- or (Z)-configuration; or X(1) and X(2) are

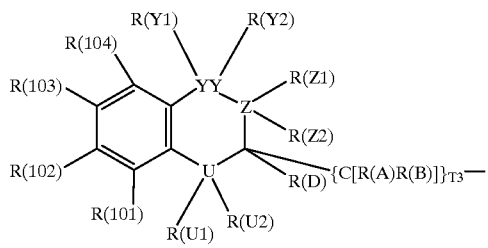

T3 is zero, 1 or 2;

U, YY and Z independently of one another are C or N, where U, YY, Z can carry the following number of in substituents:

| U, YY or Z | Bonded in the ring to a double bond | Number of permitted substituents |
| --- | --- | --- |
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl,

R(U1), R(U2), R(Y1), R(Y2), R(Z1), R(Z2)
independently of one another are hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;
zla is zero, 1, 2, 3 or 4;
zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as

R(114); or

R(115) and R(116) together are 4 or 5 methylene groups, of which one $CH_2$ group can be replaced by oxygen, S, NH, N—$CH_3$ or N-benzyl;

but where the constitution of U being nitrogen (N), YY being nitrogen (N) and Z being carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—, where the perfluoroalkyl group is straight-chain or branched, X is oxygen, S or NR(114a);
R(114a) is is H or $(C_1-C_3)$-alkyl;
zoa is zero or 1;
zbm is zero, 1 or 2;
zpa is zero, 1, 2, 3 or 4;
zqa is 1, 2, 3, 4, 5, 6, 7 or 8;

R(110a), R(110b), R(111a) and R(112a) independently are $(C_1-C_8)$-alkyl, $(C_3-C_8)$-alkenyl, —$C_{zn}H_{2zn}$—R(115a) or $(C_1-C_8)$-perfluoroalkyl;

zn is zero, 1, 2, 3 or 4;

R(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);

R(116a) and R(117a) are hydrogen, $(C_1-C_4)$-perfluoroalkyl or $(C_1-C_4)$-alkyl; or R(110b), R(111a) and R(112a) are hydrogen;

R(110c) and R(113a) independently are hydrogen, $(C_1-C_4)$-perfluoroalkyl or $(C_1-C_4)$-alkyl; or R(110b) and R(110c) and R(112a) and R(113a) together are 4 or 5 methylene groups, of which one $CH_2$ group can be replaced by oxygen, sulfur, NH, N—$CH_3$ or N-benzyl; or R(101), R(102), R(103), R(104), R(105) independently of one another are $(C_1-C_8)$-alkyl, —$C_{zal}H_{2zal}R(118a)$ or $(C_3-C_8)$-alkenyl, zal is zero, 1, 2, 3 or 4;

R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(119b);

R(119a) and R(119 b) are hydrogen, $(C_1-C_4)$-alkyl or $(C_1-C_4)$-perfluoroalkyl; or R(101), R(102), R(103), R(104), R(105) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino; or R(101), R(102), R(103), R(104), R(105) independently of one another are —C≡C—R(193);

R(193) is phenyl which is not substituted or is substituted by 1–3 substituents from the group consisting of F, Cl, $CF_3$, methyl, methoxy or NR(194)R(195); R(194) and R(195) are hydrogen or $CH_3$; or R(101), R(102), R(103), R(104), R(105) independently of one another are —Y-para-$C_6H_4$—$(CO)_{zh}$—$(CHOH)_{zi}$—$(CH_2)_{zj}$—$(CHOH)_{zk}$—R(123), —Y-meta-$C_6H_4$—$(CO)_{zad}$—$(CHOH)_{zae}$—$(CH_2)_{zaf}$—$(CHOH)_{zag}$—R(124) or —Y-ortho-$C_6H_4$—$(CO)_{zah}$—$(CHOH)_{zao}$—$(CH_2)_{zap}$—$(CHOH)_{zak}$—R(125);

Y is oxygen, —S— or —NR(122d)—;.

zh, zad, zah independently are zero or 1;

zi, zj, zk, zae, zaf, zag, zao, zap and zak independently are zero, 1, 2, 3 or 4;

but where in each case zh, zi and zk are not simultaneously zero, zad, zae and zag are not simultaneously zero, and zah, zao and zak are not simultaneously zero, R(123), R(124), R(125) and R(122d) independently are hydrogen or $(C_1-C_3)$-alkyl; or R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1-C_9)$-heteroaryl, which is unsubstituted or substituted by 1–3 substituents from the group consisting of F, Cl, $CF_3$, $CH_3$, methoxy, hydroxyl, amino, methylamino and dimethylamino; zab is zero, 1 or 2;

R(132), R(134) and R(135) independently of one another are defined as R(129) or are hydrogen, $(C_1-C_4)$-alkyl or $(C_1-C_4)$-perfluoroalkyl; or R(101), R(102), R(103), R(104) and R(105) independently of one another are —W-para-$(C_6H_4)$—R(196), —W-meta- $(C_6H_4)$—R(197) or —W-ortho-$(C_6H_4)$—R(198);

R(196), R(197) and R(198) independently are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;

W is oxygen, S or NR(136)—;

R(136) is hydrogen or $(C_1-C_4)$-alkyl; or

R(101), R(102). R(103), R(104) and R(105) independently of one another are R(146)X(1a)—;

X(1a) is oxygen, S, NR(147), (D=O)A—, NR(148) C=MN$^{(*)}$R(149)—;

M is oxygen or sulfur;

A is oxygen or NR(150);

D is C or SO;

R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);

zbz is zero or 1;

zdz is 1, 2, 3, 4, 5, 6 or 7;

zxa is zero, 1, 2, 3 or 4;

R(151) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);

R(152) and R(153) are hydrogen, $(C_1-C_4)$-alkyl or $(C_1-C_4)$-perfluoroalkyl;

R(147), R(148) and R(150) independently are hydrogen, $(C_1-C_4)$-alkyl, $(C_1-C_4)$-perfluoroalkyl;

R(149) is defined as R(146), or

R(146) and R(147), or R(146) and R(148) together are 4 or 5 methylene groups, of which one $CH_2$ group can be replaced by oxygen, sulfur, NH, N—$CH_3$ or N-benzyl;

where A and N$^{(*)}$ are bonded to the phenyl nucleus of the alkanoyl parent structure; or R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —[CR(159)R(160)]$_{zu}$—(C=O)—[CR(161)R(162)]$_{zv}$—R(163);

R(164), R(165), R(166), R(167), R(169) identically or differently are —$(CH_2)_{zy}(CHOH)_{zz}$—$(CH_2)_{zaa}$—$(CHOH)_{zt}$—R(171) or —$(CH_2)_{zab}$—O—$(CH_2$—$CH_2O)_{zac}$—R(172);

R(171) and R(172) are hydrogen or methyl;

zu is 1, 2, 3 or 4;

zv is zero, 1, 2, 3 or 4;

zy, zz, zaa, zab, zac identically or differently are zero, 1, 2, 3 or 4;

zt is 1, 2, 3 or 4;

R(168), R(170), R(154), R(155) identically or differently are hydrogen or $(C_1-C_6)$-alkyl, or R(169) and R(170), or R(154) and R(155) together with the carbon atom carrying them are a $(C_3-C_8)$-cycloalkyl;

R(163) is hydrogen, $(C_1-C_6)$-alkyl, $(C_3-C_8)$-cycloalkyl or —$C_{zeb}H_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, $CF_3$, methyl, methoxy and NR(174)R(175);

R(174) and R(175) are hydrogen or $(C_1-C_4)$-alkyl; or

R(156), R(157) and R(173) independently are $(C_1-C_9)$-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—SO$_2$—;
R(176) is R(177)R(178)N—(C=Y')—;
Y' is oxygen, S or N—R(179);
R(177) and R(178) identically or differently are hydrogen, (C$_1$–C$_8$)-alkyl, (C$_3$–C$_6$)-alkenyl or —C$_{zfa}$H$_{2zfa}$—R(180);
zfa is zero, 1, 2, 3 or 4;
R(180) is (C$_5$–C$_7$)-cycloalkyl or phenyl, which is unsubstituted or substituted by 1–3 substituents selected from the group consisting of F, Cl, CF$_3$, methoxy or (C$_1$–C$_4$)-alkyl; or
R(177) and R(178) together are 4 or 5 methylene groups, of which one CH$_2$ group can be replaced by oxygen, sulfur, NH, N—CH$_3$ or N-benzyl;
R(179) is defined as R(177) or is amidine, or R(101), R(102), R(103), R(104), R(105) independently of one another are NR(184a)R(185), OR(184b), SR(184c) or —C$_{znx}$H$_{2znx}$—R(184d);
znx is zero, 1, 2, 3 or 4;
R(184d) is (C$_3$–C$_7$)-cycloalkyl or phenyl, which is not substituted or is substituted by 1–3 substituents from the group consisting of F, Cl, CF$_3$, methyl, methoxy and NR(116k)R(117k);
R(116k) and R(117k) are hydrogen or C$_1$–C$_4$-alkyl;
R(184a), R(184b), R(184c), R(185) independently of one another are hydrogen, (C$_1$–C$_8$)-alkyl, (C$_1$–C$_8$)-perfluoroalkyl or (CH$_2$)$_{zao}$—R(184g);
zao is zero, 1, 2, 3 or 4;
184g is (C$_3$–C$_7$)-cycloalkyl or phenyl, which is not substituted or is substituted by 1–3 substituents from the group consisting of F, Cl, CF$_3$, methyl, methoxy and NR(184u)R(184v);
R(184u) and R(184v) are hydrogen or C$_1$–C$_4$-alkyl; or
R(184a) and R(185) together are 4 or 5 methylene groups, of which one CH$_2$ group can be replaced by oxygen, sulfur, NH, N—CH$_3$ or N-benzyl;

or a pharmaceutically tolerable salt thereof;

u) a benzoylguanidine of the formula

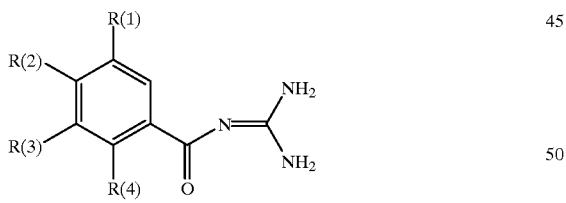

in which:
R(1) is H, F, Cl, Br, I, CN, NO$_2$, (C$_1$–C$_8$)-alkyl, (C$_3$–C$_8$)-cycloalkyl or Xa—(CH$_2$)$_b$—(CF$_2$)$_c$—CF$_3$;
X is oxygen, S or NR(5);
a is zero or 1;
b is zero, 1 or 2;
c is zero, 1, 2 or 3;
R(5) is H, (C$_1$–C$_4$)-alkyl or —C$_d$H$_{2d}$R(6);
d is zero, 1, 2, 3 or 4;
R(6) is (C$_3$–C$_8$)-cycloalkyl, phenyl, biphenylyl or naphthyl, where the aromatics are not substituted or are substituted by 1 to 3 substituents selected from the group consisting of F, Cl, CF$_3$, methyl, methoxy and NR(7)R(8);

R(7) and R(8) independently are H or (C$_1$–C$_4$)-alkyl; or

R(1) is —SR(10), —OR(10) or —CR(10)R(11)R(12);
R(10) is —C$_f$H$_{2f}$—(C$_3$–C$_8$)-cycloalkyl, —(C$_1$–C$_9$)-heteroaryl or phenyl, where the aromatic systems are unsubstituted or substituted by 1 to 3 substituents selected from the group consisting of F, Cl, CF$_3$, CH$_3$, methoxy, hydroxyl, amino, methylamino and dimethylamino;
f is zero, 1 or 2;
R(11) and R(12) independently of one another are defined as R(10) or are hydrogen or (C$_1$–C$_4$)-alkyl; or R(1) is phenyl, naphthyl, biphenylyl or (C$_1$–C$_9$)-heteroaryl, the latter linked via C or N, and which are unsubstituted or substituted by 1 to 3 substituents selected from the group consisting of F, Cl, CF$_3$, CH$_3$, methoxy, hydroxyl, amino, methylamino and dimethylamino; or R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$
R(13) and R(14) identically or differently are —(CH$_2$)$_g$—(CHOH)$_h$—(CH$_2$)$_i$—(CHOH)$_j$—R(17),
R(17) is hydrogen or methyl;
—(CH$_2$)$_g$—O—(CH$_2$—CH$_2$O)$_h$—R(24),
g,h,i identically or differently are zero, 1, 2, 3 or 4;
j is 1, 2, 3 or 4;
R(15) and R(16) identically or differently are hydrogen, (C$_1$–C$_6$)-alkyl or together with the carbon atom carrying them are a (C$_3$–C$_8$)-cycloalkyl;
R(18) is phenyl, which is unsubstituted or substituted by 1 to 3 substituents selected from the group consisting of F, Cl, CF$_3$, methyl, methoxy and NR(25)R(26);
R(25) and R(26) are H or (C$_1$–C$_4$)-alkyl; or
R(18) is (C$_1$–C$_9$)-heteroaryl, which is unsubstituted or substituted as phenyl; or
R(18) is (C$_1$–C$_6$)-alkyl, which is unsubstituted or substituted by 1 to 3 OH; or
R(18) is (C$_3$–C$_8$)-cycloalkyl;
R(19), R(20), R(21), R(22) and R(23) are hydrogen or methyl;
k is zero, 1, 2, 3 or 4;
l is zero, 1, 2, 3 or 4;
R(24) is H, (C$_1$–C$_6$)-alkyl, (C$_3$–C$_8$)-cycloalkyl or —C$_m$H$_{2m}$—R(18);
m is 1, 2, 3 or 4;

R(2) and R(3) independently of one another are defined as R(1);
R(4) is (C$_1$–C$_3$)-alkyl, F, Cl, Br, I, CN or —(CH$_2$)$_n$—(CF$_2$)$_o$—CF$_3$;
n is zero or 1;
o is zero, 1 or 2;

or a phanmaceutically tolerable salt thereof;

v) an acylguanidine of the formula

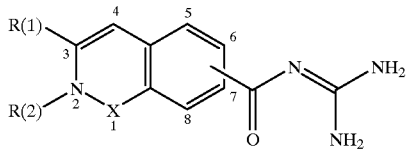

in which:

X is carbonyl, sulfonyl,

R(1) is H, $(C_1-C_8)$-alkyl, unsubstituted or substituted by hydroxyl,
$(C_3-C_8)$-cycloalkyl, phenyl, which is unsubstituted or substituted by 1–3 substituents from the group F, Cl, $CF_3$, $CH_3$, methoxy, hydroxyl, amino, methylamino or dimethylamino, R(2) is H, $(C_1-C_4)$-alkyl, or a pharmaceutically tolerable salt thereof;

w) a phenyl-substituted alkylcarboxylic acid guanidide, carrying at least one perfluoroalkyl groups, of the formula

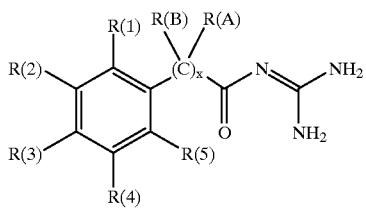

in which:

R(A) is hydrogen, F, Cl, Br, I, CN, OR(6), $(C_1-C_8)$-alkyl, $(C_3-C_8)$-cycloalkyl, $O_r(CH_2)_aC_bF_{2b+1}$ or NR(7)R(8);
r is zero or 1;
a is zero, 1, 2, 3 or 4;
b is 1, 2, 3, 4, 5, 6, 7 or 8;
R(6) is hydrogen, $(C_1-C_8)$-alkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6);

R(B) independently is defined as R(A);

X is 1, 2 or 3;

R(1) is hydrogen, $(C_1-C_8)$-alkyl, $(C_3-C_8)$-cycloalkyl, $-O_t(CH_2)_dC_eF_{2e+1}$, F, Cl, Br, I or CN;
t is zero or 1;
d is zero, 1, 2, 3 or 4;
e is 1, 2, 3, 4, 5, 6, 7 or 8;

R(2), R(3), R(4) and R(5) independently of one another are defined as R(1);

but with the condition that at least one of the substituents R(1), R(2), R(3), R(4), R(5), R(A) and R(B) is an $-O_t(CH_2)_dC_eF_{2e+1}$ or an $O_r(CH_2)_aC_bF_{2b+1}$ group, or a pharmaceutically tolerable salt thereof;

x) a heteroaroylguanidine of the formula

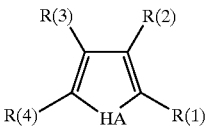

in which:

HA is $SO_m$, O or NR(5);
m is zero, 1 or 2;
R(5) is hydrogen, $(C_1-C_8)$-alkyl or $-C_{am}H_{2am}R(81)$;
am is zero, 1 or 2;
R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);
R(82) and R(83) are H or $CH_3$; or
R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

one of the two substituents R(1) and R(2) is $-CO-N=C(NH_2)2$;

and the other in each case is hydrogen, F, Cl, Br, I, $(C_1-C_3)$-alkyl, $-OR(6)$, $C_rF_{2r+1}$, $-CO-N=C(NH_2)_2$ or $-NR(6)R(7)$;
R(6) and R(7) independently are hydrogen or $(C_1-C_3)$-alkyl;
r is 1, 2, 3 or 4;

R(3) and R(4) independently of one another are hydrogen, F, Cl, Br, I, $-C\equiv N$, $X-(CH_2)_p-(C_q-F_{2q+1})$, $R(8)-SO_{bm}$, $R(9)R(10)N-CO$, $R(11)-CO-$ or $R(12)R(13)N-SO_2-$, where the perfluoroalkyl group is straight-chain or branched,
X is oxygen, S or NR(14);
R(14) is H or $(C_1-C_3)$-alkyl;
bm is zero, 1 or 2;
p is zero, 1 or 2;
q is zero, 1, 2, 3, 4, 5 or 6;
R(8), R(9), R(11) and R(12) independently are $(C_1-C_8)$-alkyl, $(C_3-C_6)$-alkenyl, $-C_nH_{2n}-R(15)$, $CF_3$;
n is zero, 1, 2, 3 or 4;
R(15) is $(C_3-C_7)$-cycloalkyl or phenyl, which is not substituted or is substituted by 1–3 substituents selected from the group consisting of F, Cl, $CF_3$, methyl, methoxy or NR(16)R(17);
R(16) and R(17) are H or $C_1-C_4$-alkyl; or
R(9), R(11) and R(12) are H;
R(10) and R(13) independently are H or $(C_1-C_4)$-alkyl; or
R(9) and R(10), and R(12) and R(13) together are 4 or 5 methylene groups, of which one $CH_2$ group can be replaced by oxygen, S, NH, $N-CH_3$ or N-benzyl, or R(3) and R(4) independently of one another are $(C_1-C_8)$-alkyl or $-C_{al}H_{2al}R(18)$;
al is zero, 1 or 2;
R(18) is $(C_3-C_8)$-cycloalkyl or phenyl; which is not substituted or is substituted by 1–3 substituents selected from the group consisting of F, Cl, $CF_3$, methyl, methoxy and NR(19)R(20);
R(19) and R(20) are H or $CH_3$; or R(3) and R(4) independently of one another are $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(3) and R(4) independently of one another are

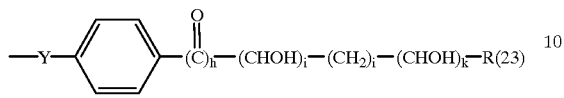

or

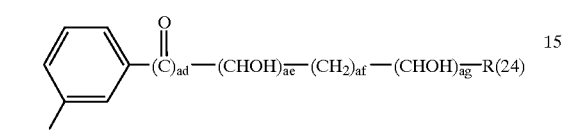

or

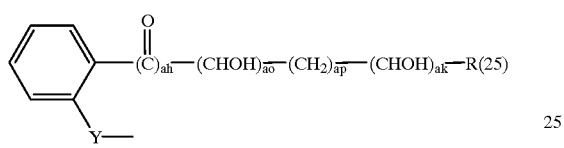

Y is oxygen, —S— or —NR(22)—;
h, ad, ah independently are zero or 1;
i, j, k, ae, af, ag, ao, ap and ak independently are zero, 1, 2, 3, 4,
but where in each case h, i and k are not simultaneously zero, ad, ae and ag are not simultaneously zero, and ah, ao and ak are not simultaneously zero,
R(23), R(24), R(25) and R(22) independently are hydrogen or $(C_1-C_3)$-alkyl; or R(3) and R(4) independently of one another are hydrogen, F, Cl, Br, I, CN, $(C_1-C_8)$-alkyl, $(C_1-C_8)$-perfluoroalkyl, $(C_3-C_8)$-alkenyl or $—C_gH_{2g}R(26)$;
g is zero, 1, 2, 3 or 4;
R(26) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
R(27) and R(28) are H, $(C_1-C_4)$-alkyl or $(C_1-C_4)$-perfluoroalkyl; or R(3) and R(4) independently of one another are SR(29), —OR(30), —NR(31)R(32) or —CR(33)R(34)R(35);
R(29), R(30), R(31) and R(33) independently are $—C_aH_{2a}—(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino; is zero, 1 or 2;
R(32), R(34) and R(35) independently of one another are defined as R(29) or are hydrogen, $(C_1-C_4)$-alkyl or $(C_1-C_4)$-perfluoroalkyl; or R(3) and R(4) independently of one another are

-continued

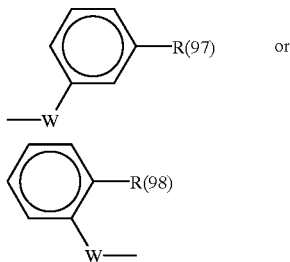

R(96), R(97) and R(98) independently are $(C_1-C_g)$-heteroaryl, which is linked via C or N and which is unsubstituted or substituted by 1 to 3 substituents selected from the group consisting of F, Cl, $CF_3$, $CH_3$, methoxy, hydroxyl, amino, methylamino, dimethylamino or benzyl;
W is oxygen, S or NR(36)—;
R(36) is H or $(C_1-C_4)$-alkyl; or R(3) and R(4) independently of one another are R(37)—$SO_{cm}$ or R(38)R(39)N—$SO_2$—;
cm is 1 or 2;
R(37) is $(C_1-C_8)$-alkyl, $(C_1-C_8)$-perfluoroalkyl, $(C_3-C_8)$-alkenyl or $—C_sH_{2s}R(40)$;
s is zero, 1, 2, 3 or 4;
R(40) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(41)R(42);
R(41) and R(42) are H, $(C_1-C_4)$-alkyl or $(C_1-C_4)$-perfluoroalkyl;
R(38) is H, $(C_1-C_8)$-alkyl, $(C_1-C_8)$-perfluoroalkyl, $(C_3-C_8)$-alkenyl or $—C_wH_{2w}—R(43)$;
w is zero, 1, 2, 3 or 4;
R(43) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(44)R(45);
R(44) and R(45) are H, $(C_1-C_4)$-alkyl or $(C_1-C_4)$-perfluoroalkyl;
R(39) is H, $(C_1-C_4)$-alkyl or $(C_1-C_4)$-perfluoroalkyl; or
R(38) and R(39) together are 4 or 5 methylene groups, of which one $CH_2$ group can be replaced by oxygen, S, NH, N—$CH_3$ or N-benzyl; or R(3) and R(4) independently of one another are R(46)X(1)—;
X(1) is oxygen, S, NR(47), (D=O)A—, NR(48)C=MN$^{(+)}$R(49)—,
M is oxygen or S;
A is oxygen or NR(50);
D is C or SO;
R(46) is $(C_1-C_8)$-alkyl, $(C_3-C_8)$-alkenyl, $(CH_2)_bC_dF_{2d+1}$ or $—C_xH_{2x}—R(51)$;
b is zero or 1;
d is 1, 2, 3, 4, 5, 6 or 7;
x is zero, 1, 2, 3 or 4;
R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);
R(52) and R(53) are H, $(C_1-C_4)$-alkyl or $(C_1-C_4)$-perfluoroalkyl;

R(47), R(48) and R(50) independently are hydrogen, (C$_1$–C$_4$)-alkyl or (C$_1$–C$_4$)-perfuoroalkyl;
R(49) is defined as R(46); or
R(46) and R(47), or R(46) and R(48) together are 4 or 5 methylene groups, of which one CH$_2$ group can be replaced by oxygen, S, NH, N—CH$_3$ or N-benzyl, where A and N$^{(*)}$ are bonded to the phenyl nucleus of the benzoylguanidine parent structure; or
R(3) and R(4) independently of one another are —SR(64), —OR(65), —NHR(66), —NR(67)R(68), —CHR(69)R(70), —C(OH)R(54)R(55), +C≡CR(56), —CR(58)=CHR(57), —[CR(59)R(60)]$_u$—(CO)—[CR(61)R(62)]$_v$—R(63);
R(64), R(65), R(66), R(67) and R(69) identically or differently are —(CH$_2$)$_y$(CHOH)$_z$—(CH$_2$)$_{aa}$—(CH$_2$OH)$_t$—R(71) or —(CH$_2$)$_{ab}$—O—(CH$_2$—CH$_2$O)$_{ac}$—R(72),
R(71) and R(72) are hydrogen or methyl;
u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen, (C$_1$–C$_6$)-alkyl; or
R(69) and R(70), or R(54) and R(55) together with the carbon atom carrying them are a (C$_3$–C$_8$)-cycloalkyl;
R(63) is H, (C$_1$–C$_6$)-alkyl, (C$_3$–C$_8$)-cycloalkyl or —C$_e$H$_{2e}$—R(73);
e is zero, 1, 2, 3 or 4;
R(56), R(57) and R(73) independently are phenyl, which is unsubstituted or substituted by 1–3 substituents selected from the group consisting of F, Cl, CF$_3$, methyl, methoxy and NR(74)R(75);
R(74) and R(75) are H or (C$_1$–C$_4$)-alkyl; or
R(56), R(57) and R(73) independently are (C$_1$–C$_9$)-heteroaryl, which is unsubstituted or substitued as phenyl;
R(58), R(59), R(60), R(61) and R(62) are hydrogen or methyl, or
R(3) and R(4) independently of one another are R(76)—NH—SO$_2$—;
R(76) is R(77)R(78)N—(C=Y')—;
Y' is oxygen, S or N—R(79);
R(77) and R(78) identically or differently are H, (C$_1$–C$_8$)-alkyl, (C$_3$–C$_6$)-alkenyl, —C$_f$H$_{2f}$R(80);
f is zero, 1, 2, 3 or 4;
R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(77) and R(78) together are 4 or 5 methylene groups, of which one CH$_2$ group can be replaced by oxygen, S, NH, N—CH$_3$ or N-benzyl,
R(79) is defined as R(77) or is amidine; or
R(3) and R(4) independently of one another are NR(84)R(85);
R(84) and R(85) independently of one another are H, (C$_1$–C$_4$)-alkyl, or together are 4 or 5 methylene groups, of which one CH$_2$ group can be replaced by oxygen, S, NH, N—CH$_3$ or N-benzyl; or of which one or two CH$_2$ groups can be replaced by CH—C$_{dm}$H$_{2dm+1}$,
or a pharmaceutically tolerable salt thereof;

y) a bicyclic heteroaroylguanidine of the formula I in which:
T, U, V, W, X, Y and Z independently of one another are nitrogen or carbon;
but with the restriction that X and Z are not simultaneously nitrogen, and that T, U, V, W. X, Y and Z carry no substituents if they are nitrogen, and that no more than four of them are simultaneously nitrogen,
R(1) and R(2) independently of one another are hydrogen, F, Cl, Br, I, (C$_1$–C$_3$)-alkyl, (C$_1$–C$_3$)-perfluoroalkyl, OR(8), NR(8)R(9) or C(=O)N=C(NH$_2$)$_2$;
R(8) and R(9) independently of one another are hydrogen or (C$_1$–C$_3$)-alkyl, or
R(8) and R(9) together are 4 or 5 methylene groups, of which one CH$_2$ group can be replaced by oxygen, S, NH, N—CH$_3$ or N-benzyl;
R(3), R(4), R(5), R(6) and R(7) independently of one another are hydrogen, F, Cl, Br, I, —C≡N, X$_k$—(CH$_2$)$_p$—(C$_q$F$_{2q+1}$), R(10a)—SO$_{bm}$, R(10b)R(10c)N—CO, R(11)—CO— or R(12)R(13)N—SO$_2$—, where the perfluoroalkyl group is straight-chain or branched;
X is oxygen, S or NR(14);
R(14) is H or (C$_1$–C$_3$)-alkyl;
bm is zero, 1 or 2;
p is zero, 1 or 2;
k is zero or 1;
q 1, 2, 3, 4, 5 or 6;
R(10a), R(10b), R(11) and R(12) independently of one another are (C$_1$–C$_8$)-alkyl, (C$_3$–C$_6$)-alkenyl, —C$_n$H$_{2n}$—R(15) or (C$_1$–C$_8$)-perfluoroalkyl;
n is zero, 1, 2, 3 or 4;
R(15) is (C$_3$–C$_7$)-cycloalkyl or phenyl, which is not substituted or is substituted by 1–3 substituents selected from the group consisting of F, Cl, CF$_3$, methyl, methoxy and NR(16)R(17);
R(16) and R(17) are H or C$_1$–C$_4$-alkyl; or
R(10b), R(11) and R(12) are hydrogen;
R(10c) and R(13) independently are hydrogen or (C$_1$–C$_4$)-alkyl; or
R(10b) and R(10c) and R(12) and R(13) together are 4 or 5 methylene groups, of which one CH$_2$ group can be replaced by oxygen, sulfur, NH, N—CH$_3$ or N-benzyl; or
R(3), R(4), R(5), R(6) and R(7) independently of one another are (C$_1$–C$_8$)-alkyl, —C$_{al}$H$_{2al}$R(18) or (C$_3$–C$_8$)-alkenyl;
al is zero, 1 or 2;
R(18) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(19a)R(19b);
R(19a) and R(19b) are hydrogen, (C$_1$–C$_4$)-alkyl or (C$_1$–C$_4$)-perfluoroalkyl; or
R(3), R(4), R(5), R(6) and R(7) independently of one another are (C$_1$–C$_9$)-heteroaryl, which is linked via C or N and which is unsubstituted or substituted by 1–3 substituents from the group consisting of F, Cl, $CF_3$, $CH_3$, methoxy, hydroxyl, amino, methylamino or dimethylamino; or R(3), R(4), R(5), R(6) and R(7) independently of one another are

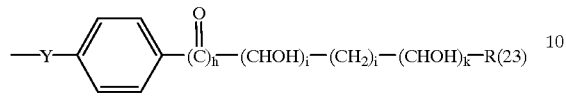

or

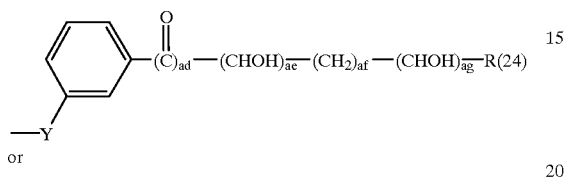

or

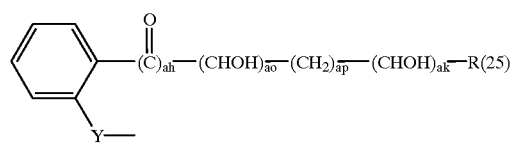

Y is oxygen, —S— or —NR(22)—;

h, ad, ah independently of one another are zero or 1;

i, j, k, ae, af, ag, ao, ap and ak independently of one another are zero, 1, 2, 3 or 4;

but where in each case
  h, i and k are not simultaneously zero,
  ad, ae and ag are not simultaneously zero, and
  ah, ao and ak are not simultaneously zero, R(23), R(24), R(25) and R(22) independently of one another are hydrogen or $(C_1-C_3)$-alkyl; or R(3), R(4), R(5), R(6) and R(7) independently of one another are SR(29), —OR(30), —NR(31)R(32) or —CR(33)R(34)R(35);

R(29), R(30), R(31) and R(33) independently of one another are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl; or R(3), R(4), R(5), R(6) and R(7) independently of one another are

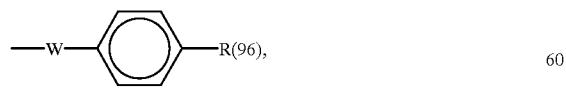

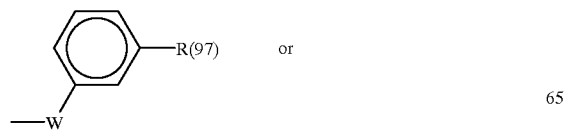

or

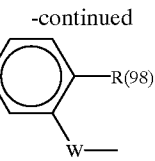

R(96), R(97) and R(98) independently of one another are $(C_1-C_9)$-heteroaryl, which is linked via C or N and which is unsubstitued or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl; or

R(3), R(4), R(5), R(6) and R(7) independently of one another are R(46)X(1)—;

X(1) is oxygen, S, NR(47), (D=O)A— or NR(48) C=MN$^{(+)}$R(49)—;

M is oxygen or sulfur;

A is oxygen or NR(50);

D is C or SO;

R(46) is $(C_1-C_8)$-alkyl, $(C_3-C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are hydrogen, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46); or

R(46) and R(47), or R(46) and R(48) together are 4 or 5 methylene groups, of which one $CH_2$ group can be replaced by oxygen, sulfur, NH, N—$CH_3$ or N-benzyl;

where A and N$^{(+)}$ are bonded to the phenyl nucleus of the heteroaroylguanidine parent structure; or R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$—R(63);

R(64), R(65), R(66), R(67) and R(69) identically or differently are —$(CH_2)_y$—$(CHOH)_z$—$(CH_2)_{aa}$—$(CHOH)_t$—R(71) or —$(CH_2)_{ab}$—O—$(CH_2-CH_2O)_{ac}$—R(72);

R(71) and R(72) independently of one another are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen or $(C_1-C_6)$-alkyl; or R(69) and R(70), or R(54) and R(55) together with the carbon atom carrying them are a $(C_3-C_8)$-cycloalkyl;

R(63) is hydrogen, $(C_1-C_6)$-alkyl, $(C_3-C_8)$-cycloalkyl or —$C_eH_{2e}$—R(73);

e is zero, 1, 2, 3 or 4;

R(56), R(57) and R(73) independently are phenyl, which is unsubstituted or substituted by 1–3 substituents selected from the group consisting of F, Cl, CF$_3$, methyl, methoxy and NR(74)R(75);

R(74) and R(75) are hydrogen or (C$_1$–C$_4$)-alkyl; or

R(56), R(57) and R(73) independently are (C$_1$–C$_9$)-heteroaryl, which is unsubstituted or substituted as phenyl;

R(58), R(59), R(60), R(61) and R(62) are hydrogen or methyl; or

R(3), R(4), R(5), R(6) and R(7) independently of one another are R(76)—NH—SO$_2$—;

R(76) is R(77)R(78)N—(C=Y')—;

Y' is oxygen, S or N—R(79);

R(77) and R(78) identically or differently are hydrogen, (C$_1$–C$_8$)-alkyl, (C$_3$–C$_6$)-alkenyl or —C$_f$H$_{2f}$—R(80);

f is zero, 1, 2, 3 or 4;

R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or R(77) and R(78) together are 4 or 5 methylene groups, of which one CH$_2$ group can be replaced by oxygen, sulfur, NH, N—C—CH$_3$ or N-benzyl;

R(79) is defined as R(77) or is amidine; or

R(3), R(4), R(5), R(6) and R(7) independently of one another are NR(84a)R(85), OR(84b), SR(84c) or —C$_n$H$_{2n}$—R(84d);

n is zero, 1, 2, 3 or 4;

R(84d) is (C$_3$–C$_7$)-cycloalkyl or phenyl, which is not substituted or is substituted by 1–3 substituents from the group consisting of F, Cl, CF$_3$, methyl, methoxy and NR(16)R(17);

R(16) and R(17) are hydrogen, or C$_1$–C$_4$-alkyl;

R(84a), R(84b), R(84c) and R(85) independently of one another are hydrogen, (C$_1$–C$_8$)-alkyl, (C$_1$–C$_8$)-perfluoroalkyl or (CH$_2$)$_{ax}$—R(84g);

ax is zero, 1, 2, 3 or 4;

R(84g) is (C$_3$–C$_7$)-cycloalkyl or phenyl, which is not substituted or is substituted by 1–3 substituents selected from the group consisting of F, Cl, CF$_3$, methyl, methoxy and NR(84u)R(84v);

R(84u) and R(84v) are hydrogen or C$_1$–C$_4$-alkyl; or

R(84a) and R(85) together are 4 or 5 methylene groups, of which one CH$_2$ group can be replaced by oxygen, sulfur, NH, N—CH$_3$ or N-benzyl, or a pharmaceutically tolerable salt thereof;

z) a benzoylguanidine of the formula in which:

R(1) is R(6)—SO$_m$;

m is zero, 1 or 2;

R(6) is perfluoroalkyl having 1, 2, 3, 4, 5 or 6 carbon atoms, which is straight-chain or branched;

R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy; or R(2) and R(3) independently of one another are pyrrol-1-yl, pyrrol-2-yl or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;

R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;

R(7), R(8) and R(9) independently of one another are hydrogen or alkyl having 1, 2, 3 or 4 carbon atoms;

n is zero or 1;

o is zero, 1 or 2;

or a pharmaceutically tolerable salt thereof;

ab) a phenyl-substituted alkenylcarboxylic acid guanidide, carrying at least one perfluoroalkyl groups, of the formula in which:

R(A) is hydrogen, F, Cl, Br, I, CN, OH, OR(6), (C$_1$–C$_8$)-alkyl, O$_r$(CH$_2$)$_a$C$_b$F$_{2b+1}$, (C$_3$–C$_8$)-cycloalkyl or NR(7)R(8);

r is zero or 1;

a is zero, 1, 2, 3 or 4;

b is 1, 2, 3, 4, 5, 6, 7 or 8;

R(6) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics are not substituted or are substituted by 1–3 substituents from the group consisting of F, Cl, CF$_3$, methyl, methoxy and NR(9)R(10);

R(9) and R(10) are H, (C$_1$–C$_4$)-alkyl or (C$_1$–C$_4$)-perfluoroalkyl;

R(7) and R(8) independently of one another are defined as R(6); or

R(7) and R(8) together are 4 or 5 methylene groups, of which one CH$_2$ group can be replaced by oxygen, sulfur, NH, N—CH$_3$ or N-benzyl;

R(B) independently is defined as R(A);

X is zero, 1 or 2;

Y is zero, 1 or 2;

R(C) is hydrogen, F, Cl, Br, I, CN, OR(12), (C$_1$–C$_8$)-alkyl, O$_p$(CH$_2$)$_f$C$_g$F$_{2g+1}$ or (C$_3$–C$_8$)-cycloalkyl;

p is zero or 1;

f is zero,1, 2, 3 or 4;

g is 1, 2, 3, 4, 5, 6, 7 or 8;

R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl;

where the aromatics phenyl or benzyl are not substituted or are substituted by 1–3 substituents from the group consisting of F, Cl, CF$_3$, methyl, methoxy and NR(13)R(14);

R(13) and R(14) independently of one another are H, $(C_1-C_4)$-alkyl or $(C_1-C_4)$-perfluoroalkyl;

R(D) independently is defined as R(C),

R(1) is hydrogen, $(C_1-C_8)$-alkyl, $-O_t(CH_2)_dC_eF_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1);

but with the condition that at least one of the substituents R(A), R(B), R(C), R(D), R(1), R(2), R(4) or R(5) is an $O_r(CH_2)_aC_bF_{2b+1}$, $O_p(CH_2)_fC_gF_{2g+1}$ or $O_t(CH_2)_dC_eF_{2e+1}$ group and R(3) is not an $O_t(CH_2)_dC_eF_{2e+1}$ group;

or a pharmaceutically tolerable salt thereof;

ac) an ortho-amino-substituted benzoylguanidine of the formula

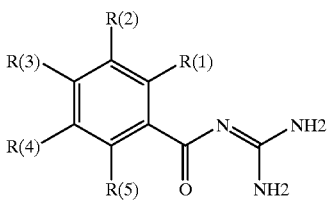

in which:

R(1) is NR(50)R(6),

R(50) and R(6) independently of one another are hydrogen, $(C_1-C_8)$-alkyl or $(C_1-C_8)$-perfluoroalkyl;

R(2), R(3), R(4) and R(5) independently of one another are R(10)—SO$_a$—, R(11)R(12)N—CO—, R(13)—CO— or R(14)R(15)N—SO$_2$—;

a is zero, 1 or 2,

R(10), R(11), R(12), R(13), R(14) and R(15) independently of one another are $(C_1-C_8)$-alkyl, $(C_1-C_8)$-perfluoroalkyl, $(C_3-C_6)$-alkenyl or —$C_{ab}H_{2ab}$—R(16);

ab is zero, 1, 2, 3 or 4;

R(16) is $(C_3-C_7)$-cycloalkyl, phenyl, which is not substituted or is substituted by 1–3 substituents selected from the group consisting of F, Cl, CF$_3$, methyl, methoxy or NR(17)R(18);

R(17) and R(18) independently of one another are H, CF$_3$ or $(C_1-C_4)$-alkyl; or R(11), R(12), and also R(14) and R(15) together are 4 or 5 methylene groups, of which one CH$_2$ group can be replaced by oxygen, S, NH, N—CH$_3$ or N-benzyl; or R(11), R(12), R(14) and R(15) independently of one another are hydrogen; or R(2), R(3), R(4) and R(5) independently of one another are SR(21), —OR(22), —NR(23)R(24) or —CR(25)R(26)R(27);

R(21), R(22), R(23) and R(25) independently of one another are —$C_bH_{2b}$—$(C_1-C_9)$-heteroaryl, which is unsubstituted or substituted by 1–3 substituents selected from the group consisting of F, Cl, CF$_3$, CH$_3$, methoxy, hydroxyl, amino, methylamino and dimethylamino;

b is zero, 1 or 2;

R(24), R(26) and R(27) independently of one another are hydrogen, $(C_1-C_4)$-alkyl or $(C_1-C_4)$-perfluoroalkyl; or R(2), R(3), R(4) and R(5) independently of one another are hydrogen, F, Cl, Br, I, CN, —(Xa)$_{dg}$—$C_{da}H_{2da+1}$, —(Xb)$_{dh}$—(CH$_2$)$_{db}$—$C_{de}F_{2de+1}$, $(C_3-C_8)$-alkenyl or —$C_{df}H_{2df}$R(30);

(Xa) is O, S or NR(33);

R(33) is H, $(C_1-C_4)$-alkyl or $(C_1-C_4)$-perfluoroalkyl;

dg is zero or 1;

(Xb) is O, S or NR(34);

R(34) is H, $(C_1-C_4)$-alkyl or $(C_1-C_4)$-perfluoroalkyl;

dh is zero or 1;

da is zero, 1, 2, 3, 4, 5, 6, 7, 8;

db is zero, 1, 2, 3, 4;

de is zero, 1, 2, 3, 4, 5, 6, 7;

df is zero, 1, 2, 3, 4;

R(30) is $(C_3-C_8)$-cycloalkyl, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(31)R(32);

R(31) and R(32) are H, $(C_1-C_4)$-alkyl or $(C_1-C_4)$-perfluoroalkyl; or

R(2), R(3), R(4) and R(5) independently of one another are NR(40)R(41) or —(Xe)—(CH$_2$)$_{eb}$R(45);

R(40) and R(41) independently of one another are hydrogen, $(C_1-C_8)$-alkyl, $(C_1-C_8)$-perfluoroalkyl or (CH$_2$)$_e$—R(42);

e is zero, 1, 2, 3 or 4;

R(42) is $(C_3-C_7)$-cycloalkyl, phenyl, which is not substituted or is substituted by 1–3 substituents selected from the group consisting of F, Cl, CF$_3$, methyl, methoxy and NR(43)R(44);

R(43) and R(44) independently of one another are H, CF$_3$ or $(C_1-C_4)$-alkyl; or R(40) and R(41) together are 4 or 5 methylene groups, of which one CH$_2$ group can be replaced by oxygen, sulfur, NH, N—CH$_3$ or N-benzyl;

(Xe) is O, S or NR(47);

R(47) is H, $(C_1-C_4)$-alkyl or $(C_1-C_4)$-perfluoroalkyl;

eb is zero, 1, 2, 3 or 4;

R(45) is $(C_3-C_7)$-cycloalkyl, phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);

Xfa is CH$_2$, O, S or NR(48);

Xfb is O, S or NR(49);

ed is 1, 2, 3 or 4;

R(46) is H, $(C_1-C_4)$-alkyl or $(C_1-C_4)$-perfluoroalkyl;

R(48), R(49), R(50) and R(51) independently of one another are H or $(C_1-C_4)$-alkyl or $(C_1-C_4)$-perfluoroalkyl;

where R(3) and R(4), however, cannot be hydrogen, or a pharmaceutically tolerable salt thereof;

ad) a benzoylguanidine of the formula

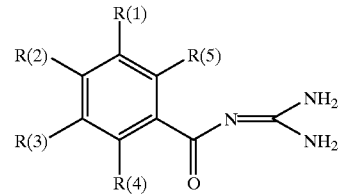

in which:

one of the three substituents R(1), R(2) and R(3) is $(C_1-C_9)$-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or one of the three substituents R(1), R(2) and R(3) is —SR(10), —OR(10), —NR(10)R(11) or —CR(10)R(11)R(12);

R(10) is —$C_aH_{2a}$—$(C_1–C_9)$-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(11) and R(12) independently of one another are defined as R(10), are hydrogen or $(C_1–C_4)$-alkyl;

and the other substituents R(1), R(2) and R(3) in each case independently of one another are $(C_1–C_8)$-alkyl, $(C_2–C_8)$-alkenyl or —$C_mH_{2m}R(14)$;

m is zero, 1 or 2;

R(14) is $(C_3–C_8)$-cycloalkyl or phenyl, which is not substituted or is substituted by 1–3 substituents selected from the group consisting of F, Cl, $CF_3$, methyl, methoxy and NR(15)R(16), R(15) and R(16) are hydrogen or $CH_3$; or the other substituents R(1), R(2) and R(3) in each case independently of one another are hydrogen, F, Cl, Br, I, —C≡N, X—$(CH_2)_p$—$(C_qF_{2q+1})$, R(22)—$SO_u$, R(23)R(24)N—CO, R(25)—CO— or R(26)R(27)N—$SO_2$—, where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are $(C_1–C_8)$-alkyl, $(C_2–C_6)$-alkenyl, —$C_nH_{2n}$—R(29) or $CF_3$;

n is zero, 1, 2, 3 or 4;

R(28) is hydrogen or $(C_1–C_3)$-alkyl;

R(29) is $(C_3–C_7)$-cycloalkyl or phenyl; which is not substituted or is substituted by 1–3 substituents selected from the group consisting of F, Cl, $CF_3$, methyl, methoxy and NR(30)R(31);

R(30) and R(31) are hydrogen or $C_1–C_4$-alkyl, or R(23), R(25) and R(26) are also hydrogen;

R(24) and R(27) independently of one another are hydrogen or $(C_1–C_4)$-alkyl; or R(23) and R(24), and also R(26) and R(27) together are 4 or 5 methylene groups, of which one $CH_2$ group can be replaced by oxygen, S, NH, N—$CH_3$ or N-benzyl; or the other substituents R(1), R(2) and R(3) in each case independently of one another are OR(35) or NR(35)R(36);

R(35) and R(36) independently of one another are hydrogen or $(C_1–C_6)$-alkyl; or R(35) and R(36) together are 4–7 methylene groups, of which one $CH_2$ group can be replaced by oxygen, S, NH, N—$CH_3$ or N-benzyl, R(4) and R(5) independently of one another are hydrogen, $(C_1–C_4)$-alkyl, F, Cl, —OR(32), —NR(33)R(34) or $C_rF_{2r+1}$;

R(32), R(33) and R(34) independently of one another are hydrogen or $(C_1–C_3)$-alkyl;

r is 1, 2, 3 or 4;

or a pharmaceutically tolerable salt thereof;

ad) benzoylguanidines of the formula I

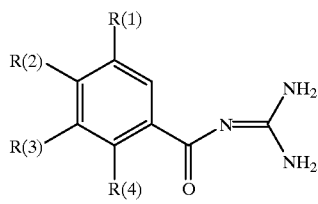

in which:

R(1) is hydrogen, F, Cl, Br, I, CN, $NO_2$, OH, $(C_1–C_8)$-alkyl, $(C_3–C_8)$-cycloalkyl, $O_a$—$(CH_2)_b$—$(CF_2)_c$—$CF_3$;

a is zero or 1;

b is zero, 1 or 2;

c is zero, 1, 2 or 3; or

R(1) is $R(^5)$—$SO_m$ or R(6)R(7)N—$SO_2$—;

m is zero, 1 or 2;

R(5) and R(6) independently of one another are $(C_1–C_8)$-alkyl, $(C_3–C_6)$-alkenyl, $CF_3$ or —$C_nH_{2n}$—R(8);

n is zero, 1, 2, 3 or 4;

R(7) is hydrogen or $(C_1–C_4)$-alkyl;

R(8) is $(C_3–C_7)$-cycloalkyl or phenyl, which is not substituted or is substituted by 1–3 substituents selected from the group consisting of F, Cl, $CF_3$, methyl, methoxy and NR(9)R(10);

R(9) and R(10) independently of one another are hydrogen or $(C_1–C_4)$-alkyl; or R(6) is H;

or R(6) and R(7) together are 4 or 5 methylene groups, of which one $CH_2$ group can be replaced by oxygen, S, NH, N—$CH_3$ or N-benzyl, or R(1) is —SR(11), —OR(11) or —CR(11)R(12)R(13);

R(11) is —$C_pH_{2p}$—$(C_3–C_8)$-cycloalkyl, —$(C_1–C_9)$-heteroaryl or phenyl, where the aromatic systems are unsubstituted or substituted by 1–3 substituents selected from the group consisting of F, Cl, $CF_3$, $CH_3$, methoxy, hydroxyl, amino, methylamino and dimethylamino;

R(12), R(13) independently of one another are defined as R(11) or are hydrogen or $(C_1–C_4)$-alkyl;

p is zero, 1 or 2; or

R(1) is phenyl, naphthyl, biphenylyl or $(C_1–C_9)$-heteroaryl, the lafter linked via C or N, which are unsubstituted or substituted by 1–3 substituents selected from the group consisting of F, Cl, $CF_3$, $CH_3$, methoxy, hydroxyl, amino, methylamino and dimethylamino;

R(2) is —$CF_2R(14)$, —CF[R(15)][R(16)], —CF[$(CF_2)_q$—$CF_3$][R(15)], —C[$(CF_2)_r$—$CF_3$]=CR(15)R(16);

R(14) is $(C_1–C_4)$-alkyl or $(C_3–C_6)$-cycloalkyl;

R(15) and R(16) independently of one another are hydrogen or $(C_1–C_4)$-alkyl;

q is zero, 1 or 2;

r is zero, 1 or 2;

R(3) is defined as R(1);

R(4) is hydrogen, $(C_1–C_3)$-alkyl, F, Cl, Br, I, CN, —$(CH_2)_s$—$(CF_2)_t$—$CF_3$;

s is zero or 1;

t is zero, 1 or 2;

or a pharmaceutically tolerable salt thereof;

ae) a benzoylguanidine of the formula

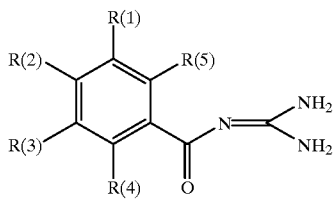

in which:
one of the theree substituents R(1), R(2) and R(3) is
—Y-4—[(CH$_2$)$_k$—CHR(7)—(C═O)R(8)]-phenyl,
—Y-3—(CH$_2$)$_k$—CHR(7)—(C═O)R(8)]-phenyl or
—Y-2—[(CH$_2$)$_k$—CHR(7)—(C═O)R(8)]-phenyl,
where the phenyl in each case is unsubstituted or substituted by 1–2 substituents from the group F, Cl, —CF$_3$, methyl, hydroxyl, methoxy, or —NR(37)R(38);
R(37) and R(38) independently of one another are hydrogen or —CH$_3$;
Y is a bond, oxygen, —S— or —NR(9);
R(9) is hydrogen or —(C$_1$–C$_4$)-alkyl;
R(7) is —OR(10) or —NR(10)R(11);
R(10) and R(11) independently of one another are hydrogen, —(C$_1$–C$_8$)- alkyl, —(C$_1$–C$_8$)-alkanoyl, -(C$_1$–C$_8$)-alkoxycarbonyl, benzyl, benzyloxycarbonyl; or
R(10) is trityl;
R(8) is —OR(12) or —NR(12)R(13);
R(12) and R(13) independently of one another are hydrogen, —(C$_1$–C$_8$)-alkyl or benzyl;
k is zero, 1, 2, 3 or 4;
and the other radicals R(1), R(2) and R(3) in each case independently of one another are —(C$_1$–C$_8$)-alkyl, —(C$_2$–C$_8$)-alkenyl or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F, Cl, —CF$_3$, methyl, methoxy and —NR(15)R(16);
R(15) and R(16) are hydrogen or —CH$_3$; or
the other radicals R(1), R(2) and R(3) in each case independently of one another are R(18)R(19)N—(C═Y')—NH—SO$_2$—;
Y' is oxygen, —S— or —N—R(20);
R(18) and R(19) independently of one another are hydrogen, —(C$_1$–C$_8$)-alkyl, —(C$_3$–C$_6$)-alkenyl or —(CH$_2$)$_t$—R(21);
t is zero, 1, 2, 3 or 4;
R(21) is —(C$_5$–C$_7$)-cycloalkyl or phenyl, which is unsubstituted or substituted by 1–3 substituents selected from the group consisting of F, Cl, —CF$_3$, methoxy and —(C$_1$–C$_4$)-alkyl; or
R(18) and R(19) together are 4 or 5 methylene groups, of which one CH$_2$ group can be replaced by oxygen, —S—, —NH—, —N—CH$_3$ or —N-benzyl;
R(20) is defined as R(1 8) or is amidine; or
the other radicals R(1), R(2) and R(3) in each case independently of one another are hydrogen, F, Cl, Br, I, —C≡N, X—(CH$_2$)$_p$—(C$_q$F$_{2q+1}$), R(22)—SO$_u$—, R(23)R(24)N—CO—, R(25)—CO— or R(26)R(27)N—SO$_2$—, where the perfluoroalkyl group is straight-chain or branched,
X is a bond, oxygen, —S— or —NR(28);

u is zero, 1 or 2;
p is zero, 1 or 2;
q is 1, 2, 3, 4, 5 or 6;
R(22), R(23), R(25) and R(26) independently of one another are —(C$_1$–C$_8$)-alkyl, —(C$_3$–C$_6$)-alkenyl, —(CH$_2$)$_n$—R(29) or —CF$_3$;
n is zero, 1, 2, 3 or 4;
R(28) is hydrogen or —(C$_1$–C$_3$)-alkyl;
R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);
R(30) and R(31) or are hydrogen or —(C$_1$–C$_4$)-alkyl; or
R(23), R(25) and R(26) are hydrogen;
R(24) and R(27) independently of one another are hydrogen or —(C$_1$–C$_4$)-alkyl; or
R(23) and R(24), and also R(26) and R(27) together are 4 or 5 methylene groups, of which one CH$_2$ group can be replaced by oxygen, —S—, —NH—, —N—C—CH$_3$ or —N-benzyl; or
the other radicals R(1), R(2) and R(3) in each case independently of one another are —OR(35) or —NR(35)R(36);
R(35) and R(36) independently of one another are hydrogen or —(C$_1$–C$_6$)-alkyl; or
R(35) and R(36) together are 4–7 methylene groups, of which one CH$_2$ group can be replaced by oxygen, —S—, —NH—, —C—CH$_3$ or —N-benzyl;
R(4) and R(5) independently of one another are hydrogen, —(C$_1$–C$_4$)-alkyl, F, Cl, —OR(32), —NR(33)R(34) or —C$_r$F$_{2r+1}$;
R(32), R(33) and R(34) independently of one another are hydrogen or —(C$_1$–C$_3$)-alkyl;
r is 1, 2, 3 or 4;
or a pharmaceutically tolerable salt thereof;
af) a benzoyiguanidine of the formula

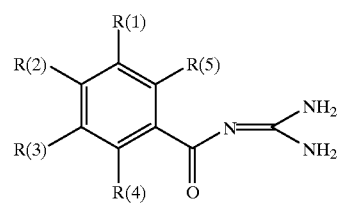

in which:
R(1) is R(6)—CO or R(7)R(8)N—CO;
R(6) is (C$_1$–C$_8$)-alkyl, (C$_1$–C$_8$)-perfluoroalkyl, (C$_3$–C$_8$)-alkenyl or —C$_n$H$_{2n}$—R(9),
n is zero, 1, 2, 3 or 4;
R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11),
R(10) and R(11) are H, (C$_1$–C$_4$)-alkyl or (C$_1$–C$_4$)-perfluoroalkyl;
R(7) is H, (C$_1$–C$_8$)-alkyl, (C$_1$–C$_8$)-perfluoroalkyl, (C$_3$–C$_8$)-alkenyl or —C$_n$H$_{2n}$—R(12);
n is zero, 1, 2, 3 or 4;
R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);

R(13) and R(14) are H, $(C_1-C_4)$-alkyl or $(C_1-C_4)$-perfluoroalkyl;
R(8) is H, $(C_1-C_4)$-alkyl or $(C_1-C_4)$-perfluoroalkyl; or
R(7) and R(8) together are 4 or 5 methylene groups, of which one $CH_2$ group can be replaced by oxygen, S, NH, N—$CH_3$ or N-benzyl;
R(2) is defined as R(1), or is H, OH, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}$R(15);
n is zero, 1, 2, 3 or 4;
R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
R(16) and R(17) are H, $(C_1-C_4)$-alkyl or $(C_1-C_4)$-perfluoroalkyl; or
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is SR(18), —OR(18), —NR(18)R(19) or —CR(18)R(19)R(20);
R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino, dimethylamino;
a is zero, 1 or 2;
R(19) and R(20) independently of one another are defined as R(18) or are hydrogen, $(C_1-C_4)$-alkyl or $(C_1-C_4)$-perfluoroalkyl; or
R(2) is R(21)—$SO_m$ or R(22)R(23)N—$SO_2$—;
m is 1 or 2;
R(21) is $(C_1-C_8)$-alkyl, $(C_1-C_8)$-perfluoroalkyl, $(C_3-C_8)$-alkenyl or —$C_nH_{2n}$—R(24);
n is zero, 1, 2, 3 or 4;
R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
R(27) and R(28) are H, $(C_1-C_4)$-alkyl or $(C_1-C_4)$-perfluoroalkyl;
R(22) is H, $(C_1-C_8)$-alkyl, $(C_1-C_8)$-perfluoroalkyl, $(C_3-C_8)$-alkenyl or —$C_nH_{2n}$—R(29);
n is zero, 1, 2, 3 or 4;
R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
R(30) and R(31) are H, $(C_1-C_4)$-alkyl or $(C_1-C_4)$-perfluoroalkyl;
R(23) is hydrogen, $(C_1-C_4)$-alkyl or $(C_1-C_4)$-perfluoroalkyl; or
R(22) and R(23) together are 4 or 5 methylene groups, of which one $CH_2$ group can be replaced by oxygen, S, NH, N—$CH_3$ or N-benzyl; or
R(2) is R(33)X—;
X is oxygen, S, NR(34), (D=O)A— or NR(34)C=$MN^{(*)}$R(35)—;
M is oxygen or S;
A is oxygen or NR(34);
D is C or SO;
R(33) is $(C_1-C_8)$-alkyl, $(C_3-C_8)$-alkenyl, $(CH_2)_bC_dF_{2d+1}$ or —$C_nH_{2n}$—R(36);
b is zero or 1;
d is 1, 2, 3, 4, 5, 6 or 7;
n is zero, 1, 2, 3, or 4;
R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
R(37) and R(38) are H, $(C_1-C_4)$-alkyl or $(C_1-C_4)$-perfluoroalkyl;
R(34) is hydrogen, $(C_1-C_4)$-alkyl or $(C_1-C_4)$-perfluoroalkyl;
R(35) is defined as R(33); or
R(33) and R(34) together are 4 or 5 methylene groups, of which one $CH_2$ group can be replaced by oxygen, S, NH, N—$CH_3$ or N-benzyl;
where A and $N^{(*)}$ are bonded to the phenyl nucleus of the benzoylguanidine parent structure; or R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$R(44);
R(40) and R(41) independently of one another are —$(CH_2)_p$—$(CHOH)_q$—$(CH_2)_r$—$(CHOH)_t$—R(51) or —$(CH_2)_p$—O—$(CH_2$—$CH_2O)_q$—R(51);
R(51) is hydrogen or methyl;
u is 1, 2, 3 or 4;
v is zero, 1, 2, 3 or 4;
p, q and r independently of one another are zero, 1, 2, 3 or 4;
t is 1, 2, 3 or 4;
R(42) and R(43) independently of one another are hydrogen or $(C_1-C_6)$-alkyl; or
R(42) and R(43) together with the carbon atom carrying them are a $(C_3-C_8)$-cycloalkyl;
R(44) is hydrogen, $(C_1-C_6)$-alkyl, $(C_3-C_8)$-cycloalkyl, —$C_eH_{2e}$—R(45);
e is zero, 1, 2, 3 or 4;
R(45) is phenyl, which is unsubstituted or substituted by 1–3 substituents selected from the group consisting of F, Cl, $CF_3$, methyl, methoxy and NR(52)R(53);
R(52) and R(53) are H or $(C_1-C_4)$-alkyl; or
R(45) is $(C_1-C_9)$-heteroaryl, which is unsubstituted or substituted as phenyl; or
R(45) is $(C_1-C_6)$-alkyl, which is unsubstituted or substituted by 1–3 OH;
R(46), R(47), R(48), R(49) and R(50) independently of one another are hydrogen or methyl; or
R(2) is R(55)—NH—$SO_2$—;
R(55) is R(56)R(57)N—(C=Y)—;
Y is oxygen, S or N—R(58);
R(56) and R(57) independently of one another are hydrogen, $(C_1-C_8)$-alkyl, $(C_3-C_6)$-alkenyl or —$C_fH_{2f}$—R(59);
f is zero, 1, 2, 3 or 4;
R(59) is $(C_5-C_7)$-cycloalkyl, phenyl, which is unsubstituted or substituted by 1–3 substituents selected from the group consisting of F, Cl, $CF_3$, methoxy and $(C_1-C_4)$-alkyl; or
R(56) and R(57) together are 4 or 5 methylene groups, of which one $CH_2$ group can be replaced by oxygen, S, NH, N—$CH_3$ or N-benzyl;
R(58) is defined as R(56) or is amidine;

R(3), R(4) and R(5) are independently of one another defined as R(1) or R(2), but where at least one of the substituents R(2), R(3), R(4) and R(5) must be OH;
or a pharmaceutically tolerable salt thereof;
ag) a benzoylguanidine of the formula

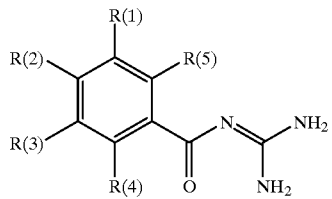

in which:
one of the three substituents R(1), R(2) and R(3) is R(6)—A—B—D—;
R(6) is a basic protonatable radical, i.e. an amino group —NR(7)R(8), an amidino group R(7)R(8)N—C[=N—R(9)]— or a guanidino group

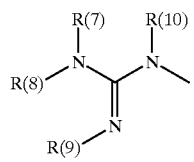

R(7), R(8), R(9) and R(10) independently of one another are hydrogen or alkyl having 1, 2, 3 or 4 carbon atoms; or
R(7) and R(8) together are $C_aH_{2a}$;
a is 4, 5, 6 or 7;
where if a=5, 6 or 7 a methylene group of the group $C_aH_{2a}$ can be replaced by a heteroatom group O, $SO_m$ or NR(11), or
R(8) and R(9) or R(9) and R(10) or R(7) and R(10) are a group $C_aH_{2a}$;
a is 2, 3, 4 or 5; where if a=3, 4 or 5 a methylene group of the group $C_aH_{2a}$ can be replaced by a heteroatom group O, $SO_m$ or NR(11);
m is zero, 1 or 2;
R(11) is hydrogen or methyl; or
R(6) is a basic heteroaromatic ring system having 1–9 carbon atoms;
A is $C_bH_{2b}$;
b is 1, 2, 3, 4, 5, 6, 7, 8, 9 or 10; where in the group $C_bH_{2b}$ one or two methylene groups can be replaced by one of the groupings selected from the group consisting of —O—, —CO—, —CH[OR(20)]—, —$SO_m$—, —NR(20)—, —NR(20)—CO—, —NR(20)—CO—NH—, —NR(20)—CO—NH—$SO_2$—

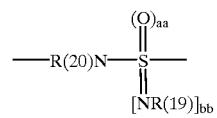

and —$SO_{aa}$[NR(19)]$_{bb}$—;
and where in the group $C_bH_{2b}$ a methylene group can be replaced by —CH—R(99), where R(99) together with R(7) forms a pyrrolidine or piperidine ring;

aa is 1 or 2;
bb is 0 or 1;
aa+bb=2;
R(19) is hydrogen or alkyl having 1, 2, 3 or 4 carbon atoms;
R(20) is hydrogen or methyl;
B is a phenylene or naphthylene radical

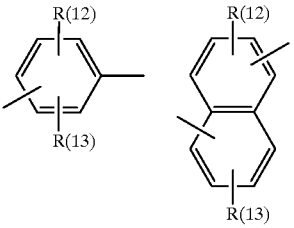

R(12) and R(13) independently of one another are hydrogen, methyl, F, Cl, Br, I, $CF_3$ or —$SO_wR(14)$;
R(14) is methyl or NR(15)R(16);
R(15) and R(16) independently of one another are hydrogen or alkyl having 1, 2, 3 or 4 carbon atoms;
w is zero, 1 or 2;
D is —$C_dH_{2d}$—$X_f$—;
d is zero, 1, 2, 3 or 4;
x is —O—, —CO—, —CH[OR(21)]—, —$SO_m$— or —NR(21)—;
f is zero or 1;
R(21) is hydrogen or methyl;
m is zero, 1 or 2;
and the other substituents R(1) and R(2) and R(3) in each case independently of one another are hydrogen, F, Cl, Br, I, —CN, —($C_1$-$C_8$)-alkyl, —($C_2$-$C_8$)-alkenyl, —NR(35)R(36) or R(17)—$C_gH_{2g}$—$Z_h$—;
g is zero, 1, 2, 3 or 4;
h is zero or 1;
R(35) and R(36) independently of one another are hydrogen or alkyl having 1, 2, 3, 4, 5 or 6 carbon atoms; or
R(35) and R(36) together are 4–7 methylene groups, of which one $CH_2$ group can be replaced by oxygen, —S—, —NH—, —$NCH_3$ or —N-benzyl;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
R(17) is hydrogen, cycloalkyl having 3, 5 or 6 carbon atoms or $C_kF_{2k+1}$—;
k is 1, 2 or 3, or
R(17) is pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —$CF_3$, methyl and methoxy; or
R(17) is —($C_3$-$C_8$)-cycloalkyl or phenyl, which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;
R(37) and R(38) are hydrogen or —$CH_3$;
R(4) and R(5) independently of one another are hydrogen, alkyl having 1, 2, 3 or 4 carbon atoms, F, Cl, —OR(32), —NR(33)R(34) or —$C_rF_{2r+1}$;

R(32), R(33) and R(34) independently of one another are hydrogen or alkyl having 1, 2 or 3 carbon atoms;
r is 1, 2, 3 or 4;
or a pharmacologically tolerable salt thereof;
ah) an indenoylguanidine of the formula

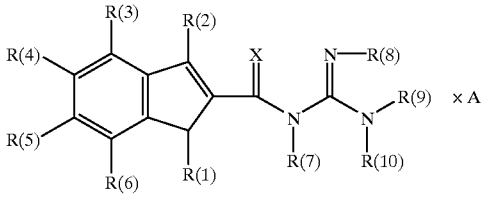

in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)-alkyl having 1, 2, 3 or 4 carbon atoms or $C_mH_{2m}$—NR(12)R(13);
R(12) and R(13) independently of one another are hydrogen or alkyl having 1, 2, 3 or 4 carbon atoms;
m is zero, 1, 2, 3 or 4;
NH—C(=O)—NH$_2$, C(=O)—O-alkyl having 1, 2, 3 or 4 carbon atoms, C(=O)—NH$_2$, C(=O)—NH-alkyl having 1, 2, 3 or 4 carbon atoms, C(=O)—N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, $C_1$–$C_4$-alkyl-substituted aryl, $C_1$–$C_4$-alkylheteroaryl, $C_1$–$C_4$-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—$C_1$–$C_4$-alkylaryl, O—C(=O)—NH—$C_1$–$C_4$-alkyl, O—C(=O)—N($C_1$–$C_4$-alkyl)$_2$, NO$_2$, CN, CF$_3$, NH$_2$, NH—C(=O)—$C_1$–$C_4$-alkyl, NH—C(=O)—NH$_2$, COOH, C(=O)—O—$C_1$–$C_4$-alkyl, C(=O)—NH$_2$, C(=O)—NH—$C_1$–$C_4$-alkyl, C(=O)—N($C_1$–$C_4$-alkyl)$_2$, $C_1$–$C_4$—COOH, $C_1$–$C_4$-alkyl-C(=O)—O—$C_1$–$C_4$-alkyl, SO$_3$H, SO$_2$-alkyl, SO$_2$-alkylaryl, SO$_2$—N-(alkyl)$_2$, SO$_2$—N(alkyl)(alkylaryl), C(=O)—R(11), $C_1$–$C_{10}$-alkyl-C(=O)—R(11), $C_2$–$C_{10}$-alkenyl-C(=O)—R(11), $C_2$–$C_{10}$-alkynyl-C(=O)—R(11), NH—C(=O)—$C_1$–$C_{10}$-alkyl-C(=O)—R(11), O—$C_1$–$C_{11}$-alkyl-C(=O)—R(11);
R(11) is $C_1$–$C_4$-alkyl, $C_1$–$C_4$-alkynyl, aryl, substituted aryl, NH$_2$, NH—$C_1$–$C_4$-alkyl, N—($C_1$–$C_4$-alkyl)$_2$, SO$_3$H, SO$_2$-alkyl, SO$_2$-alkylaryl, SO$_2$—N-(alkyl)$_2$, SO$_2$-N(alkyl)(alkylaryl);
X is O, S or NH;
R(7), R(8), R(9) and R(10) independently of one another are hydrogen, alkyl, cycloalkyl, aryl, alkylaryl; or
R(8) and R(9) together are part of a 5-, 6- or 7-membered heterocyclic ring;

A is absent or is a nontoxic organic or inorganic acid;
ai) a benzyloxycarbonylguanidine of the formula

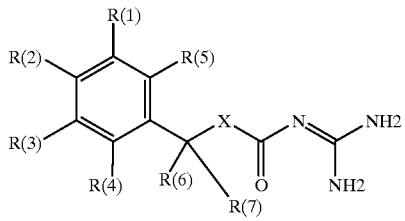

in which:
R(1), R(2) and R(3) independently of one another are —Y-[4—R(8)-phenyl], —Y-[3-R(8)-phenyl] or —Y-[2—R(8)-phenyl], where the phenyl is in each case unsubstituted or substituted by 1–2 substituents from the group consisting of F, Cl, —CF$_3$, methyl, hydroxyl, methoxy and —NR(96)R(97);
R(96) and R(97) independently of one another are hydrogen or —CH$_3$;
Y is a bond, CH$_2$, oxygen, —S— or —NR(9);
R(9) is hydrogen or alkyl having 1, 2, 3 or 4 carbon atoms;
R(8) is SO$_a$[NR(98)]$_b$NR(99)R(10);
a is 1 or 2;
b is 0 or 1;
a+b=2;
R(98), R(99) and R(10) independently of one another are hydrogen, —(C$_1$–C$_8$)-alkyl, benzyl, —(C$_2$–C$_8$)-alkylene-NR(11)R(12), (C$_2$–C$_8$)-alkylene-NR(13)—(C$_2$–C$_8$)-alkylene-NR(37)R(38) or (C$_0$–C$_8$)-alkylene-CR(39)R(40)CR(41)R(42)(C$_0$–C$_8$)-alkylene-NR(43)R(44);
R(11), R(12), R(13), R(37), R(38), R(43) and R(44) independently of one another are hydrogen, —(C$_1$–C$_8$)-alkyl or benzyl;
R(39), R(40), R(41) and R(42) independently of one another are hydrogen, —(C$_1$–C$_8$)-alkyl or —(C$_0$–C$_3$)-alkylenephenyl, where the phenyl is not substituted or is substituted by 1–3 substituents selected from the group consisting of F, Cl, —CF$_3$, methyl and methoxy; or
R(99) and R(10) together are 4–6 methylene groups, of which one CH$_2$ group can be replaced by oxygen, —S—, —NH—, —N—CH$_3$ or —N-benzyl; or
R(8) is SO$_a$[NR(98)]$_b$NR(95)—C[=N—R(94)]—NR(93)R(92);
R(92), R(93), R(94) and R(95) independently of one another are hydrogen or alkyl having 1, 2, 3 or 4 carbon atoms; or
R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy; or
R(1), R(2) and R(3) independently of one another are hydrogen, —(C$_1$–C$_8$)-alkyl, —(C$_2$–C$_8$)-alkenyl or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) are hydrogen or —CH$_3$; or
R(1), R(2) and R(3) independently of one another are
—Q4-[(CH$_2$)$_k$—CHR(17)—(C=O)R(20)]-phenyl,
—Q-3-(CH$_2$)$_k$—CHR(17)-(C=O)R(20)]-phenyl or
—Q-2-[(CH$_2$)$_k$—CHR(17)—(C=O)R(20)]-phenyl,
where the phenyl in each case is unsubstituted or substituted by 1–2 substituents from the group F, Cl, —CF$_3$, methyl, hydroxyl, methoxy and —NR(35)R(36);
R(35) and R(36) independently of one another are hydrogen or —CH$_3$;
Q is a bond, oxygen, —S— or —NR(18);
R(18) is hydrogen or —(C$_1$–C$_4$)-alkyl;
R(17) is —OR(21) or —NR(21)R(22);
R(21) and R(22) independently of one another are hydrogen, —(C$_1$–C$_8$)-alkyl, —(C$_1$–C$_8$)-alkanoyl, —(C$_1$–C$_8$)-alkoxycarbonyl, benzyl, benzyloxycarbonyl;
or
R(21) is trityl;
R(20) is —OR(23) or —NR(23)R(24);
R(23), R(24) independently of one another are hydrogen, —(C$_1$–C$_8$)-alkyl or benzyl;
k is zero, 1, 2, 3 or 4; or
R(1), R(2) and R(3) independently of one another are (C$_1$–C$_8$)-heteroaryl, which is linked via C or N and which is unsubstituted or substituted by 1–3 substituents from the group F, Cl, CF$_3$, CH$_3$, methoxy, hydroxyl, amino, methylamino and dimethylamino; or
R(1), R(2) and R(3) are —SR(25), —OR(25), —NR(25)R(26), —CR(25)R(26)R(27);
R(25) is —C$_f$H$_{2f}$(C$_1$–C$_8$)-heteroaryl, which is unsubstituted or substituted by 1–3 substituents from the group F, Cl, CF$_3$, CH$_3$, methoxy, hydroxyl, amino, methylamino and dimethylamino;
f is zero, 1 or 2;
R(26) and R(27) independently of one another are defined as R(25) or are hydrogen or (C$_1$–C$_4$)-alkyl, or
R(1), R(2) and R(3) independently of one another are (C$_1$–C$_8$)-heteroaryl-N-oxide, which is linked via C or N and which is unsubstituted or substituted by 1–3 substituents selected from the group consisting of F, Cl, CF$_3$, CH$_3$, methoxy, hydroxyl, amino, methylamino and dimethylamino; or
R(1), R(2) and R(3) independently of one another are —SR(28), —OR(28), —NR(28)R(29) or —CR(28)R(29)R(30);
R(28) is —C$_g$H$_{2g}$—(C$_1$–C$_9$)-heteroaryl-N-oxide, which is unsubstituted or substituted by 1–3 substituents selected from the group consisting of F, Cl, CF$_3$, CH$_3$, methoxy, hydroxyl, amino, methylamino and dimethylamino;
g is zero, 1 or 2;
R(29), R(30) independently of one another are defined as R(28), hydrogen or (C$_1$–C$_4$)-alkyl; or
R(1), R(2) and R(3) independently of one another are hydrogen, F, Cl, Br, I, —C≡N, T—(CH$_2$)$_l$—(C$_i$F$_{2i+1}$), R(31)SO$_h$—, R(32)R(33)N—CO—, R(34)—CO— or R(45)R(46)N—SO$_2$, where the perfluoroalkyl group is straight-chain or branched;
T is a bond, oxygen, —S— or —NR(47);
l is zero, 1 or 2;
h is zero, 1 or 2;
i is 1, 2, 3, 4, 5 or 6;
R(31), R(32), R(34) and R(45) independently of one another are —(C$_1$–C$_8$)-alkyl, —(C$_3$–C$_6$)-alkenyl, (CH$_2$)$_n$R(48) or —CF$_3$;
n is zero, 1, 2, 3 or 4;
R(47) is hydrogen or alkyl with 1, 2 or 3 carbon atoms;
R(48) is —(C$_3$–C$_7$)-cycloalkyl or phenyl, which is not substituted or is substituted by 1–3 substituents selected from the group consisting of F, Cl, —CF$_3$, methyl, methoxy and —NR(49)R(50);
R(49) and R(50) are hydrogen or alkyl having 1, 2, 3 or 4 carbon atoms; or
R(32), R(34) and R(45) are hydrogen;
R(33) and R(46) independently of one another are hydrogen or alkyl having 1, 2, 3 or 4 carbon atoms; or
R(32) and R(33), and R(45) and R(46) together are 5 or 6 methylene groups, of which one CH$_2$ group can be replaced by oxygen, —S—, —NH—, —NCH$_3$ or —N-benzyl; or
R(1), R(2) and R(3) independently of one another are R(51)—A—G—D—;
R(51) is a basic protonatable radical, i.e. an amino group —NR(52)R(53), an amidino group R(52)R(53)N—C[=N—R(54)]— or a guanidino group R(52)R(53)N-C[=N—R(54)]-NR(55)—;
R(52), R(53), R(54) and R(55) independently of one another are hydrogen or alkyl having 1, 2, 3 or 4 carbon atoms; or
R(52) and R(53) are a group C$_\alpha$H$_{2\alpha}$;
α is 4, 5, 6 or 7;
where if α=5, 6 or 7 a carbon atom of the group C$_\alpha$H$_{2\alpha}$ can be replaced by a heteroatom group O, SO$_d$ or NR(56), or
R(53) and R(54) or R(54) and R(55) or R(52) and R(55) are a group C$_\gamma$H$_{2\gamma}$;
γ is 2, 3, 4 or 5;
where if γ=3, 4 or 5 a carbon atom of the group C$_\gamma$H$_{2\gamma}$ can be replaced by a heteroatom group O, SO$_d$ or NR(56);
d is zero, 1 or 2;
R(56) is hydrogen or methyl; or
R(51) is a basic heteroaromatic ring system having 1–9 carbon atoms;
A is a group C$_e$H$_{2e}$;
e is zero, 1, 2, 3, 4, 5, 6, 7, 8, 9 or 10;
where in the group C$_e$H$_{2e}$ a carbon atom can be replaced by one of the groupings —O—, —CO—, —CH[OR(57)]—, —SO$_r$—, —NR(57)—, —NR(57)—CO—, —NR(57)—CO—NH—, —NR(57)—CO—NH—SO$_2$— or —NR(57)—SO$_2$—;
r is zero, 1 or 2;
R(57) is hydrogen or methyl;
G is a phenylene radical

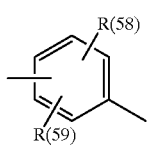

R(58) and R(59) independently of one another are hydrogen, methyl, methoxy, F, Cl, Br, I, CF$_3$ or —SO$_s$—R(60);
R(60) is methyl or NR(61)R(62);
R(61) and R(62) independently of one another are hydrogen or alkyl having 1, 2, 3 or 4 carbon atoms;
D is —C$_v$H$_{2v}$—E$_w$;
v is zero, 1, 2, 3 or 4;

E is —O—, —CO—, —CH[OR(63)]—, —SO$_{aa}$— or —NR(63)—;
w is zero or 1;
aa is zero, 1 or 2
R(63) is hydrogen or methyl, or
R(1), R(2) and R(3) independently of one another are —CF$_2$R(64), —CF[R(65)][R(66)], —CF[(CF$_2$)$_q$—CF$_3$][R(65)], —C[(CF$_2$)$_p$—CF$_3$]=CR(65)R(66);
R(64) is alkyl having 1, 2, 3 or 4 carbon atoms or cycloalkyl having 3, 4, 5, 6 or 7 carbon atoms;
R(65) and R(66) independently of one another are hydrogen or alkyl having 1, 2, 3 or 4 carbon atoms;
q is zero, 1 or 2;
p is zero, 1 or 2; or
R(1), R(2) and R(3) independently of one another are —OR(67) or —NR(67)R(68);
R(67) and R(68) independently of one another are hydrogen or alkyl having 1, 2, 3, 4, 5 or 6 carbon atoms; or
R(67) and R(68) together are 4, 5, 6 or 7 methylene groups, of which one CH$_2$ group can be replaced by oxygen, —S—, SO$_2$, —NH—, —NCH$_3$ or —N-benzyl;
R(4) and R(5) independently of one another are hydrogen, alkyl having 1, 2, 3 or 4 carbon atoms, F, Cl, —OR(69), —NR(70)R(71) or —C$_z$F$_{2z+1}$;
R(69), R(70) and R(71) independently of one another are hydrogen or alkyl having 1, 2 or 3 carbon atoms;
z is 1, 2, 3 or 4;
R(6) and R(7) independently of one another are hydrogen or alkyl having 1, 2, 3 or 4 carbon atoms;
X is oxygen or NR(72);
R(72) is hydrogen or alkyl having 1, 2, 3 or 4 carbon atoms;
or a pharmaceutically tolerable salt thereof;
ak) an alkenylcarboxylic acid guanidide, carrying at least one fluorophenyl group, of the formula

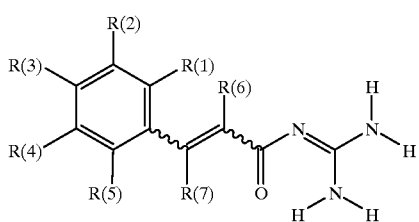

n which:
R(6) is hydrogen, (C$_1$–C$_8$)-alkyl, (C$_3$–C$_8$)-cycloalkyl or phenyl, where the phenyl group is not substituted or is substituted by 1–3 substituents selected from the group consisting of F, Cl, CF$_3$, methyl, methoxy and NR(9)R(10);
R(9) and R(10) are hydrogen, (C$_1$–C$_4$)-alkyl or (C$_1$–C$_4$)-perfluoroalkyl;
R(7) independently is defined as R(6);
R(1), R(2), R(3), R(4) and R(5) independently of one another are hydrogen or F;
where, however, at least one of the radicals R(1), R(2), R(3), R(4) and R(5) must be fluorine;
or a pharmaceutically tolerable salt thereof;

al) a benzoylguanidine of the formula

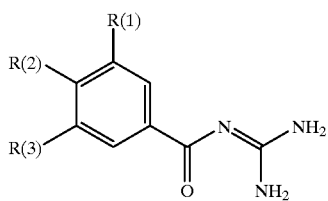

in which:
R(1) is R(4)—SO$_m$ or R(5)R(6)N—SO$_2$—;
m is 1 or 2;
R(4) and R(5) independently of one another are alkyl having 1, 2, 3, 4, 5, 6, 7 or 8 carbon atoms, alkenyl having 3, 4, 5 or 6 carbon atoms, CF$_3$ or —C$_n$H$_{2n}$—R(7);
n is zero, 1, 2, 3 or 4;
R(6) is H or alkyl having 1, 2, 3 or 4 carbon atoms;
R(7) is cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(8)R(9);
R(8) and R(9) are H or alkyl having 1, 2, 3 or 4 carbon atoms; or
R(5) is also hydrogen; or
R(5) and R(6) together are 4 or 5 methylene groups, of which a CH$_2$ group can be replaced by oxygen, S, NH, N—CH$_3$ or N-benzyl; or
R(1) is —O$_p$—(CH$_2$)$_q$—(CF$_2$)$_r$—CF$_3$;
p is zero or 1;
q is zero, 1 or 2;
r is zero, 1, 2 or 3; or
R(1) is —SR(10), —OR(10) or —CR(10)R(11)R(12);
R(10), R(11) and R(12) independently of one another are hydrogen, alkyl having 1, 2, 3, 4, 5, 6, 7 or 8 carbon atoms, —C$_s$H$_{2s}$—(C$_3$-C$_8$)-cycloalkyl or an aromatic system selected from the group consisting of pyridyl, pyrrolyl, quinolyl, isoquinolyl, imidazolyl or phenyl;
s is zero, 1 or 2; where the aromatic systems pyridyl, pyrrolyl, quinolyl, isoquinolyl, imidazolyl and phenyl are unsubstituted or substituted by 1–3 substituents selected from the group consisting of F, Cl, CF$_3$, CH$_3$, methoxy, hydroxyl, amino, methylamino and dimethylamino;
R(2) is —(CH$_2$)$_u$—(CF$_2$)$_t$CF$_3$;
t is zero, 1, 2 or 3;
u is zero or 1;
R(3) is hydrogen or independently is defined as R(1);
or a pharmaceutically tolerable salt thereof;
am) a substituted cinnamic acid guanidide of the formula

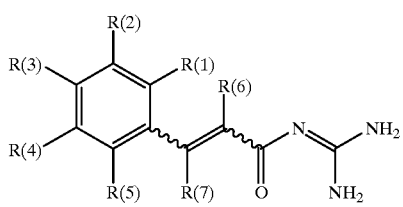

in which:
at least one of the substituents R(1), R(2), R(3), R(4) and R(5) is —X$_a$—Y$_b$—L$_n$—U;

X is CR(16)R(17), O, S or NR(18);
  R(16), R(17) and R(18) independently of one another are H, alkyl having 1, 2, 3 or 4 carbon atoms or perfluoroalkyl having 1, 2, 3 or 4 carbon atoms;
a is zero or 1;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
  T is NR(20), O, S or phenylene, where the phenylene is not substituted or is substituted by 1–3 substituents selected from the group consisting of F, Cl, $CF_3$, methyl, methoxy and NR(21)R(22);
    R(20), R(21) and R(22) independently of one another are H, alkyl having 1, 2, 3 or 4 carbon atoms or perfluoroalkyl having 1, 2, 3 or 4 carbon atoms;
b is zero or 1;
L is O, S, NR(23) or $C_kH_{2k}$;
  k is 1, 2, 3, 4, 5, 6, 7 or 8;
n is zero or 1;
U is NR(24)R(25) or an N-containing heterocycle having 1, 2, 3, 4, 5, 6, 7, 8 or 9 carbon atoms;
  R(24) and R(25) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms; or
  R(24) and R(25) together are 4 or 5 methylene groups, of which one $CH_2$ group can be replaced by oxygen, S, NH, N—$CH_3$ or N-benzyl;
  where the N-containing heterocycles are N- or C-bridged and are not substituted or are substituted by 1–3 substituents selected from the group consisting of F, Cl, $CF_3$, methyl, methoxy and NR(27)R(28);
  R(23), R(27) and R(28) independently of one another are H, alkyl having 1, 2, 3 or 4 carbon atoms or perfluoroalkyl having 1, 2, 3 or 4 carbon atoms;
and the other substituents R(1), R(2), R(3), R(4) and R(5) in each case independently of one another are H, F, Cl, Br, I, CN, —$O_n$—$C_mH_{2m+1}$, —$O_p$—$(CH_2)_s$—$C_qF_{2q+1}$ or —$C_rH_{2r}$R(10);
  n is zero or 1;
  m is zero, 1, 2, 3, 4, 5, 6, 7 or 8;
  p is zero or 1;
  q is 1, 2, 3, 4, 5, 6, 7 or 8;
  s is zero, 1, 2, 3 or 4;
  r is zero, 1, 2, 3 or 4;
  R(10) is cycloalkyl having 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(1)R(12);
  R(11) and R(12) independently of one another are H, alkyl having 1, 2, 3 or 4 carbon atoms or perfluoroalkyl having 1, 2, 3 or 4 carbon atoms;
R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;
or a pharmaceutically tolerable salt thereof;
an) a benzoylguanidine of the formula

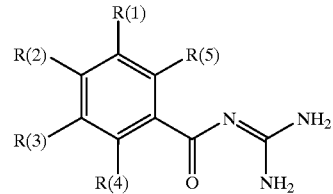

in which:
at least one of the substituents R(1), R(2) and R(3) is R(6)—C(OH)$_2$—;
  R(6) is perluoroalkyl having 1, 2 or 3 carbon atoms, which is straight-chain or branched;
and the other substituents R(1), R(2) and R(3) independently of one another are hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms, or phenoxy, which is unsubstituted or is substituted by 1–3 substituents selected from the group consisting of F, Cl, methyl and methoxy; or
the other substituents R(1), R(2) and R(3) independently of one another are alkyl-$SO_x$, —CR(7)=CR(8)R(9) or —C≡CR(9);
  x is zero, 1 or 2;
  R(7) is hydrogen or methyl;
  R(8) and R(9) independently of one another are hydrogen, alkyl having 1, 2, 3 or 4 carbon atoms, cycloalkyl having 3, 4, 5, 6, 7 or 8 carbon atoms, or phenyl, which is unsubstituted or is substituted by 1–3 substituents selected from the group consisting of F, Cl, $CF_3$, methyl and methoxy; or
the other substituents R(1), R(2) and R(3) independently of one another are phenyl, $C_6H_5$—$(C_1$-$C_4)$-alkyl, naphthyl, biphenylyl, quinolinyl, isoquinolinyl or imidazolyl, where quinolinyl, isoquinolinyl or imidazolyl are bonded via C or N and where phenyl, $C_6H_5$—$(C_1$-$C_4)$-alkyl, naphthyl, biphenylyl, quinolinyl, isoquinolinyl and imidazolyl are unsubstituted or are substituted by 1–3 substituents selected from the group consisting of F, Cl, $CF_3$, $CH_3$, methoxy, hydroxyl, amino, methylamino and dimethylamino; or
the other substituents R(1), R(2) and R(3) independently of one another are SR(10), —OR(10), —CR(10)R(11) R(12);
  R(10) is —$C_fH_{2f}(C_3$-$C_8)$-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, $CF_3$, $CH_3$, methoxy, hydroxyl, amino, methylamino and dimethylamino;
  f is zero, 1 or 2;
  R(11) and R(12) independently of one another are defined as R(10), hydrogen or alkyl having 1, 2, 3 or 4 carbon atoms;
R(4) and R(5) independently of one another are hydrogen, alkyl having 1, 2 or 3 carbon atoms, F, Cl, Br, I, CN, OR(13), NR(14)R(15), —$(CH_2)_n$—$(CF_2)_o$—$CF_3$;
  R(13), R(14) and R(15) independently of one another are hydrogen or alkyl having 1, 2, 3 or 4 carbon atoms;

n is zero or 1;
o is zero, 1 or 2;
or a pharmaceutically tolerable salt thereof;
ao) a sulfonimidamide of the formula

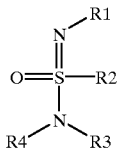

in which:
at least one of the three substituents R(1), R(2) and R(3) is a benzoylguanidine,

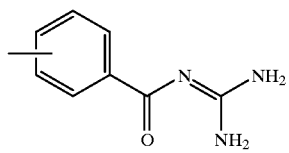

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22) SO$_2$—, R(23)R(24)N—CO—, R(25)—CO—, R(26)R (27)N—SO$_2$, —OR(35), —SR(35) or —NR(35)R(36);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
  R(15) and R(16) independently of one another are hydrogen or —CH$_3$;
R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;
n is zero, 1, 2, 3 or 4;
  R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);
    R(30) and R(31) are hydrogen or alkyl having 1, 2, 3 or 4 carbon atoms; or
R(23), R(25) and R(26) are hydrogen;
R(24) and R(27) independently of one another are hydrogen or alkyl having 1, 2, 3 or 4 carbon atoms; or
R(23) and R(24), and also R(26) and R(27) together are 5 or 6 methylene groups, of which one CH$_2$ group can be replaced by oxygen, —S—, —NH—, —NCH$_3$ or —N-benzyl;
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl; or
R(35) is phenyl, which is not substituted or is substituted by 1–3 substituents selected from the group consisting of F, Cl, —CF$_3$, methyl, methoxy, SO$_2$R (5), SO$_2$NR(6)R(7) and —NR(32)R(33);
  R(5) is alkyl having 1, 2, 3, 4, 5 or 6 carbon atoms;
  R(6) and R(7) independently of one another are hydrogen or alkyl having 1, 2, 3 or 4 carbon atoms;
  R(32) and R(33) independently of one another are hydrogen or alkyl having 1, 2, 3 or 4 carbon atoms; or
R(35) is C$_1$–C$_9$-heteroaryl, which is unsubstituted or substituted by 1–3 substituents selected from the group consisting of F, Cl, CF$_3$, CH$_3$, methoxy, hydroxyl, amino, methylamino and dimethylamino;
and the other substituents R(1), R(2) and R(3) in each case independently of one another are alkyl having 1, 2, 3, 4, 5, 6, 7 or 8 carbon atoms, (CH$_2$)$_p$R(10);
p is zero, 1, 2, 3 or 4;
R(10) is phenyl, which is not substituted or is substituted by 1–3 substituents selected from the group consisting of F, Cl, —CF$_3$, methyl, methoxy, —SO$_2$NR(17)R(8) and —SO$_2$R(9);
  R(17) and R(8) independently of one another are hydrogen or alkyl having 1, 2, 3 or 4 carbon atoms;
  R(9) is alkyl having 1, 2, 3 or 4 carbon atoms; or
the other radical R(1) or R(3) in each case is hydrogen,
R(4) is hydrogen or alkyl having 1, 2, 3 or 4 carbon atoms;
or a pharmaceutically tolerable salt thereof;
ap) a benzoylguanidine of the formula

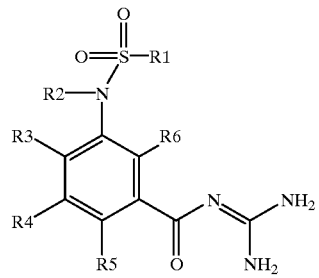

in which:
R(1) is alkyl having 1, 2, 3, 4, 5, 6, 7 or 8 carbon atoms or NR(7)R(8);
  R(7) and R(8) independently of one another are hydrogen or alkyl having 1, 2, 3, 4, 5, 6, 7 or 8 carbon atoms;
R(2) is hydrogen, alkyl having 1, 2, 3, 4, 5, 6, 7 or 8 carbon atoms or —SO$_2$R(9);
  R(9) independently is defined as R(1);
R(3) is hydrogen, —SR(25), —OR(25), —NR(25)R(26) or —CR(25)R(26)R(27);
  R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino; or
  R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
  R(26) and R(27) independently of one another are defined as R(25) or are hydrogen or alkyl having 1, 2, 3, 4, 5, 6, 7 or 8 carbon atoms;
R(4) is hydrogen, F, Cl, Br, I, OH, —C≡N, CF$_3$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;
R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);
R(15) and R(16) independently of one another are hydrogen or —$CH_3$;
R(5) and R(6) independently of one another are hydrogen, alkyl having 1, 2, 3 or 4 carbon atoms, F, Cl, —OR(32), —NR(33)R(34) or $CF_3$;
R(32), R(33) and R(34) independently of one another are hydrogen or alkyl having 1, 2, 3 or 4 carbon atoms;
or a pharmaceutically tolerable salt thereof;
aq) a benzenedicarboxylic acid diguanidide of the formula

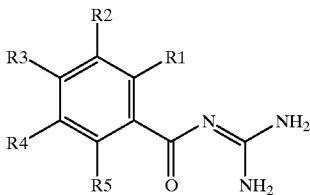

in which:
one of the radicals R(1), R(2), R(3) and R(4) is —CO—N=C($NH_2$)$_2$;
and of the other radicals R1), R(2), R(3) and R(4) in each case:
R(1) is hydrogen, alkyl having 1, 2, 3 or 4 carbon atoms, F, Cl, Br, I, —OR(32), —NR(33)R(34) or $CF_3$;
R(32), R(33) and R(34) independently of one another are hydrogen or alkyl having 1, 2, 3 or 4 carbon atoms;
R(2) and R(4) independently of one another are hydrogen, F, Cl, Br, I, OH, —CN, $CF_3$, —CO—N=C($NH_2$)$_2$, alkyl having 1, 2, 3, 4, 5, 6, 7 or 8 carbon atoms, alkenyl having 2, 3, 4, 5, 6, 7 or 8 carbon atoms or —($CH_2$)$_m$R(14);
m is zero, 1 or 2;
R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);
R(15) and R(16) are hydrogen or —$CH_3$; or
R(2) and R(4) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl, methoxy; or
R(2) and R(4) independently of one another are R(22)—$SO_2$—, R(23)R(24)N—CO—, R(28)—CO— or R(29)R(30)N—$SO_2$;
R(22) and R(28) independently of one another are methyl or —$CF_3$;
R(23), R(24), R(29) and R(30) independently of one another are hydrogen or methyl; or
R(2) and R(4) independently of one another are —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one $CH_2$ group can be replaced by oxygen, —S—, —NH—, —$NCH_3$ or —N-benzyl;

R(3) is hydrogen, —SR(25), —OR(25), —NR(25)R(26), —CR(25)R(26)R(27); R(25) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino; or
R(25) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;
R(5) is alkyl having 1, 2, 3 or 4 carbon atoms, F, Cl, Br, I, X—($CH_2$)$_y$—$CF_3$ or phenyl, which is not substituted or is substituted by 1–3 substituents selected from the group consisting of F and Cl, —$CF_3$, methyl, methoxy and —NR(6)R(7);
R(6) and R(7) independently of one another are hydrogen or —$CH_3$;
X is a bond or oxygen;
y is zero, 1 or 2;
or a pharmaceutically tolerable salt thereof;
ar) a benzenedicarboxylic acid diguanidide of the formula

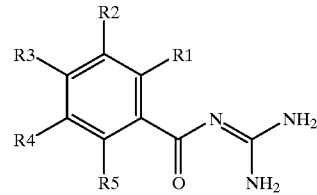

in which:
one of the radicals R(1), R(2), R(3) and R(5) is —CO—N=C($NH_2$)$_2$;
and of the other radicals R(1), R(2), R(3) and R(5) in each case:
R(1) and R(5) independently of one another are hydrogen, alkyl having 1, 2, 3 or 4 carbon atoms, F, Cl, —OR(32), —NR(33)R(34) or $CF_3$;
R(32), R(33) and R(34) independently of one another are hydrogen or alkyl having 1, 2, 3 or 4 carbon atoms;
R(2) is hydrogen, F, Cl, Br, I, OH, —CN, $CF_3$, —CO—N=C($NH_2$)$_2$, alkyl having 1, 2, 3, 4, 5, 6, 7 or 8 carbon atoms, alkenyl having 2, 3, 4, 5, 6, 7 or 8 carbon atoms or —($CH_2$)$_m$R(14);
m is zero, 1 or 2;
R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);
R(15) and R(16) independently of one another are hydrogen or —$CH_3$; or
R(2) is R(22)—$SO_2$—, R(23)R(24)N—CO—, R(28)—CO— or R(29)R(30)N—$SO_2$;
R(22) and R(28) independently of one another are methyl or —$CF_3$;
R(23), R(24), R(29) and R(30) independently of one another are hydrogen or methyl; or
R(2) is —OR(35) or —NR(35)R(36);
R(35) and R(36) independently of one another are hydrogen or alkyl having 1, 2, 3, 4, 5 or 6 carbon atoms; or

229

R(35) and R(36) together are 4–7 methylene groups, of which one $CH_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino; or R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);

m is 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$; or

R(4) is phenyl, which is substituted by 2, 3, 4 or five substituents selected from the group consisting of F, Cl, CF$_3$, methyl, methoxy and —NR(15)R(16);

R(15) and R(16) independently of one another are hydrogen or CH$_3$;

or a pharmaceutically tolerable salt thereof;

as) a diaryldicarboxylic acid diguanidide of the formula

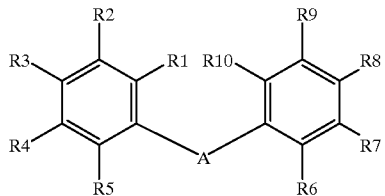

in which:

one of the radicals R(1), R(2), R(3), R(4) and R(5) is —CO—N=C(NH$_2$)$_2$;

the other radicals R(1) and R(5) in each case independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

the other radicals R(2) and R(4) in each case independently of one another are hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) are hydrogen or —CH$_3$; or

230 the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy; or the other radicals R(2) and R(4) in each case are R(22)—SO$_2$—, R(23)R(24)N—CO—, R(28)—CO— or R(29)R(30)N—SO$_2$;

R(22) and R(28) independently of one another are methyl or —CF$_3$;

R(23), R(24), R(29) and R(30) independently of one another are hydrogen or methyl; or the other radicals R(2) and R(4) in each case independently of one another are —OR(35) or —NR(35)R(36);

R(35) and R(36) independently of one another are hydrogen or alkyl having 1, 2, 3, 4, 5 or 6 carbon atoms; or R(35) and R(36) together are 4–7 methylene groups, of which one $CH_2$ group can be replaced by oxygen, —S—, —NH—, —NCH$_3$ or —N-benzyl;

the other radical R(3) in each case is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$,CH$_3$, methoxy, hydroxyl, amino, methylamino and dimethylamino; or R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

one of the radicals R(6), R(7), R(8), R(9) and R(10) is —CO—N=C(NH$_2$)$_2$;

the other radicals R(6) and R(10) in each case independently of one another are hydrogen, alkyl having 1, 2, 3 or 4 carbon atoms, F, Cl, —OR(132), —NR(133)R(134) or CF$_3$;

R(132), R(133) and R(134) independently of one another are hydrogen or alkyl having 1, 2, 3 or 4 carbon atoms;

the other radicals R(7) and R(9) in each case independently of one another are hydrogen, F, Cl, Br, I, OH, —CN, CF$_3$,—CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_{mm}$R(114);

mm is zero, 1 or 2;

R(114) is —(C$_3$–C$_8$)-cycloalkyl or phenyl, which is not substituted or is substituted by 1–3 substituents selected from the group consisting of F and Cl, —CF$_3$, methyl, methoxy and —NR(115)R(116);

R(115) and R(116) are hydrogen or —CH$_3$; or the other radicals R(7) and R(9) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl and methoxy; or the other radicals R(7) and R(9) in each case are R(122)—SO$_2$—, R(123)R(124)N—CO—, R(128)—CO— or R(129)R(130)N—SO$_2$;

R(122) and R(128) independently of one another are methyl or —$CF_3$;

R(123), R(124), R(129) and R(130) independently of one another are hydrogen or methyl; or the other radicals R(7) and R(9) in each case independently of one another are —OR(135) or —NR(135)R(136);

R(135) and R(136) independently of one another are hydrogen or alkyl having 1, 2, 3, 4, 5 or 6 carbon atoms; or R(135) and R(136) together are 4–7 methylene groups, of which one $CH_2$ group can be replaced by oxygen, —S—, —NH—, —$NCH_3$ or —N-benzyl;

the other radical R(8) in each case is hydrogen, —SR(125), —OR(125), —NR(125)R(126) or —CR(125)R(126)R(127);

R(125) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino; or R(125) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

R(126) and R(127) independently of one another are defined as R(125) or are hydrogen or alkyl having 1, 2, 3, 4, 5, 6, 7 or 8 carbon atoms;

A is absent or is —NR(11)—CO—, —NR(12)—CO—NR(13)—, —NR(17)—CO—NR(18)—$SO_2$—, —NR(19)—$SO_2$—, —$SO_2$—NR(19)—$SO_2$—, —$SO_2$—NR(19)—CO—, —O—CO—NR(19)—$SO_2$— or —CR(20)=CR(21)—;

R(11), R(12), R(13), R(17), R(18), R(19), R(20) and R(21) independently of one another are hydrogen or alkyl having 1, 2, 3, 4, 5, 6, 7 or 8 carbon atoms or a pharmaceutically tolerable salt thereof;

at) a substituted thiophenylalkenylcarboxylic acid guanidide of the formula

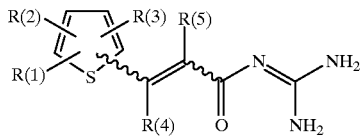

in which:

at least one of the substituents R(1), R(2) and R(3) is —$O_p$—$(CH_2)_s$—$C_qF_{2q+1}$, R(40)CO— or R(31)$SO_k$—;

p is zero or 1;
s is zero, 1, 2, 3 or 4;
q is 1, 2, 3, 4, 5, 6, 7 or 8;
k is zero, 1 or 2;

R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl and methoxy;

R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl or methoxy; or R(31) is NR(41)R(42);

R(41) and R(42) independently of one another are hydrogen, alkyl having 1, 2, 3 or 4 carbon atoms, perfluoroalkyl having 1, 2, 3 or 4 carbon atoms, or R(41) and R(42) together are 4 or 5 methylene groups, of which one $CH_2$ group can be replaced by oxygen, S, NH, N—$CH_3$ or N-benzyl;

and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}$R(10);

na is zero or 1;
ma is zero, 1, 2, 3, 4, 5, 6, 7, or 8;
ga is zero or 1;
ra is zero, 1, 2, 3 or 4;

R(10) is cycloalkyl having 3, 4, 5, 6, 7 or 8 carbon atoms or phenyl, where the phenyl is not substituted or is substituted by 1–3 substituents selected from the group consisting of F, Cl, $CF_3$, methyl and methoxy;

R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

or a pharmaceutically tolerable salt thereof;

au) an ortho-substituted benzoylguanidine of the formula

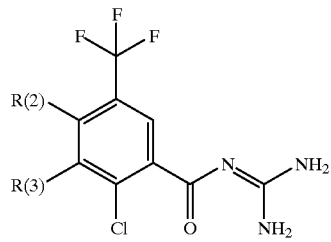

in which:

R(2) and R(3) independently of one another are hydrogen, Cl, Br, I, ($C_1$–$C_8$)-alkyl, ($C_3$–$C_8$)-cycloalkyl or —OR(5);

R(5) is ($C_1$–$C_8$)-alkyl or —$C_dH_{2d}$—($C_3$–$C_8$)-cycloalkyl;

d is zero, 1 or 2;

where one of the two substituents R(2) and R(3) is always hydrogen but both substituents R(2) and R(3) are not simultaneously hydrogen, or a pharmaceutically tolerable salt thereof;

av) a benzoylguanidine of the formula

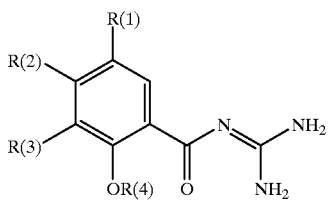

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S, NR(5),
a is zero or 1;
b is zero, 1 or 2;
c is zero, 1, 2 or 3;
  R(5) is H, alkyl having 1, 2, 3 or 4 carbon atoms or —C$_d$H$_{2d}$R(6);
    d is zero, 1, 2, 3 or 4;
    R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);
    R(7) and R(8) independently are H or alkyl having 1, 2, 3 or 4 carbon atoms; or
R(1) is —SR(10), —OR(10) or —CR(10)R(11)R(12);
  R(10) is —C$_f$H$_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;
  f is zero, 1 or 2;
  R(11) and R(12) independently of one another are defined as R(10) or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
  R(13) and R(14) identically or differently are —(CH$_2$)$_g$—(CHOH)$_h$— (CH$_2$)$_i$—(CHOH)$_j$—R(17) or —(CH$_2$)$_g$—O—(CH$_2$—CH$_2$O)$_h$—R(24);
  R(17) is hydrogen or methyl,
  g, h and i identically or differently are zero, 1, 2, 3 or 4;
  j is 1, 2, 3 or 4;
  R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
  R(18) is phenyl, which is unsubstituted or substituted by 1–3 substituents selected from the group consisting of F, Cl, CF$_3$, methyl, methoxy and NR(25)R(26);
    R(25) and R(26) are H or alkyl having 1, 2, 3 or 4 carbon atoms; or
  R(18) is heteroaryl having 1, 2, 3, 4, 5, 6, 7, 8 or 9 carbon atoms, which is unsubstituted or substituted as phenyl; or
  R(18) is alkyl having 1, 2, 3, 4, 5 or 6 carbon atoms, which is unsubstituted or substituted by 1–3 OH; or
  R(18) is cycloalkyl having 3, 4, 5, 6, 7 or 8 carbon atoms;
  R(19), R(20), R(21), R(22) and R(23) identically or differently are hydrogen or methyl;
  R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
  m is 1, 2, 3 or 4;
R(2) and R(3) are defined as R(1);
R(4) is alkyl having 1, 2, 3 or 4 carbon atoms;
or a pharmaceutically tolerable salt thereof;
aw) an orthosubstituted benzoylguanidine of the formula

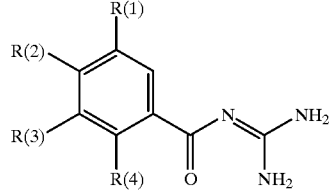

n which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S, NR(5),
a is zero or 1;
b is zero, 1 or 2;
c is zero, 1, 2 or 3;
  R(5) is H, alkyl having 1, 2, 3 or 4 carbon atoms or —C$_d$H$_{2d}$R(6);
    d is zero, 1, 2, 3 or 4;
    R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);
    R(7) and R(8) independently are H or alkyl having 1, 2, 3 or 4 carbon atoms; or
R(1) is —SR(10), —OR(10) or —CR(10)R(11)R(12);
  R(10) is —C$_f$H$_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;
  f is zero, 1 or 2;
  R(11) and R(12) independently of one another are defined as R(10), or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino, R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);

R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(18) is phenyl, which is unsubstituted or substituted by 1–3 substituents selected from the group consisting of F, Cl, $CF_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms, which is unsubstituted or substituted as phenyl; or R(18) is alkyl having 1, 2, 3, 4, 5 or 6 carbon atoms, which is unsubstituted or substituted by 1–3 OH; or R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

one of the two substituents R(2) and R(3) is hydroxyl; and the other of the substituents R(2) and R(3) in each case is defined as R(1);

R(4) is alkyl having 1, 2, 3 or 4 carbon atoms; alkoxy having 1, 2, 3 or 4 carbon atoms, F, Cl, Br, I or —(CH$_2$)$_n$—(CF$_2$)$_o$—CF$_3$;

n is zero or 1;

o is zero or 1;

or a pharmaceutically tolerable salt thereof;

ax) a bis-ortho-substituted benzoylguanidine of the formula

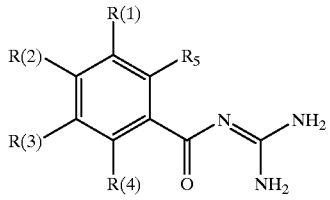

in which:

R(1), R(2) and R(3) independently of one another are R(10)—SO$_a$— or R(14)R(15)N—SO$_2$—;

a is zero, 1 or 2;

R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —C$_{ab}$H$_{2ab}$—R(16);

ab is zero, 1, 2, 3 or 4;

R(16) is cycloalkyl having 3, 4, 5, 6 or 7 carbon atoms, or phenyl, which is not substituted or is substituted by 1–3 substituents selected from the group consisting of F, Cl, $CF_3$, methyl, methoxy and NR(17)R(18);

R(17) and R(18) independently of one another are hydrogen, $CF_3$ or alkyl having 1, 2, 3 or 4 carbon atoms; or R(14) and R(15) together are 4 or 5 methylene groups, of which one CH$_2$ group can be replaced by oxygen, sulfur, NH, N—CH$_3$ or N-benzyl; or R(14) and R(15) are hydrogen; or R(1), R(2) and R(3) independently of one another are SR(21), —OR(22), —NR(23)R(24) or —CR(25)R(26)R(27);

R(21), R(22), R(23) and R(25) independently of one another are —C$_b$H$_{2b}$—(C$_1$-C$_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

b is zero, 1 or 2;

R(24), R(26) and R(27) independently of one another are hydrogen, alkyl having 1, 2, 3 or 4 carbon atoms or perfluoroalkyl having 1, 2, 3 or 4 carbon atoms; or R(1), R(2) and R(3) independently of one another are hydrogen, F, Cl, Br, I, CN, —(Xa)$_{dg}$—C$_{da}$H$_{2da+1}$, —(Xb)$_{dh}$—(CH$_2$)$_{db}$—C$_{de}$F$_{2de+1}$, alkenyl having 3, 4, 5, 6, 7 or 8 carbon atoms or —C$_{df}$H$_{2df}$R(30);

(Xa) is oxygen, sulfur or NR(33);

R(33) is hydrogen, alkyl having 1, 2, 3 or 4 carbon atoms or perfluoroalkyl having 1, 2, 3 or 4 carbon atoms;

dg is zero or 1;

(Xb) is oxygen, sulfur or NR(34);

R(34) is hydrogen, alkyl having 1, 2, 3 or 4 carbon atoms or perfluoroalkyl having 1, 2, 3 or 4 carbon atoms;

dh is zero or 1;

da is zero, 1, 2, 3, 4, 5, 6, 7 or 8;

db is zero, 1, 2, 3 or 4;

de is zero, 1, 2, 3, 4, 5, 6 or 7;

df is zero, 1, 2, 3 or 4;

R(30) is cycloalkyl having 3, 4, 5, 6, 7 or 8 carbon atoms, phenyl, biphenylyl or naphthyl, where the aromatics phenyl, biphenylyl and naphthyl are not substituted or are substituted by 1–3 substituents selected from the group consisting of F, Cl, $CF_3$, methyl, methoxy and NR(31)R(32);

R(31) and R(32) are hydrogen, alkyl having 1, 2, 3 or 4 carbon atoms or perluoroalkyl having 1, 2, 3 or 4 carbon atoms; or R(1), R(2) and R(3) independently of one another are NR(40)R(41) or —(Xe)—(CH$_2$)$_{eb}$R(45);

R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or (CH$_2$)$_e$—R(42);

e is zero, 1, 2, 3 or 4;

R(42) is cycloalkyl having 3, 4, 5, 6 or 7 carbon atoms or phenyl, which is not substituted or is substituted by 1–3 substituents selected from the group consisting of F, Cl, $CF_3$, methyl, methoxy and NR(43)R(44);

R(43) and R(44) independently of one another are hydrogen, $CF_3$ or alkyl having 1, 2, 3 or 4 carbon atoms; or R(40) and R(41) together are 4 or 5 methylene groups, of which one $CH_2$ group can be replaced by oxygen, sulfur, NH, N—$CH_3$ or N-benzyl;

(Xe) is oxygen, sulfur or NR(47);

R(47) is hydrogen, alkyl having 1, 2, 3 or 4 carbon atoms or perfluoroalkyl having 1, 2, 3 or 4 carbon atoms;

eb is zero, 1, 2, 3 or 4;

R(45) is cycloalkyl having 3, 4, 5, 6 or 7 carbon atoms, or phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);

Xfa is $CH_2$, oxygen, sulfur or NR(48);

Xfb is oxygen, sulfur or NR(49);

R(48), R(49), R(50) and R(51) independently of one another are hydrogen, alkyl having 1, 2, 3 or 4 carbon atoms or perfluoroalkyl having 1, 2, 3 or 4 carbon atoms;

ed is 1, 2, 3 or 4;

R(46) is hydrogen, alkyl having 1, 2, 3 or 4 carbon atoms or perfluoroalkyl having 1, 2, 3 or 4 carbon atoms; or R(1), R(2) and R(3) independently of one another are —CHR(52)R(53);

R(52) is —$(CH_2)_g$—$(CHOH)_h$—$(CH)_i$—$(CHOH)_k$—R(54) or —$(CH_2)_g$—O—$(CH_2$—$CH_2O)_h$—R(54);

R(54) is hydrogen or methyl;

g, h, i identically or differently are zero, 1, 2, 3 or 4;

k is 1, 2, 3 or 4;

R(53) is hydrogen or alkyl having 1, 2, 3 or 4 carbon atoms; or

R(1), R(2) and R(3) independently of one another are —C(OH)R(55)R(56);

R(55) and R(56) identically or differently are hydrogen or alkyl having 1, 2, 3 or 4 carbon atoms; or R(55) and R(56) together are cycloalkyl having 3, 4, 5 or 6 carbon atoms;

R(55) is —$CH_2OH$; and

R(4) and R(5) independently of one another are alkyl having 1, 2, 3 or 4 carbon atoms, alkoxy having 1, 2, 3 or 4 carbon atoms, OH, F, Cl, Br, I, CN, —$O_n$—$(CH_2)_o$—$(CF_2)_p$—$CF_3$;

n is zero or 1;

o is zero, 1 or 2;

p is zero, 1 or 2;

or a pharmaceutically tolerable salt thereof;

ay) a substituted 1-naphthoylguanidine of the formula

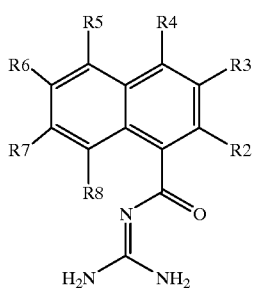

in which:

R2, R3, R4, R5, R6, R7 and R8 independently of one another are H, F, Cl, Br, I, CN, $NO_2$, $CF_3$, $C_2F_5$ or $X_aY_bZ$;

X is O, S, NR(10), CR(11)R(12), C=O, C(=O)NR(10), C(=O)O, SO, $SO_2$, $SO_2$NR(10), OC=O, NR(10)C=O or NR(10)$SO_2$, where the linkage with the naphthalene ring in each case takes place via the left atom;

R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is zero or 1;

Y is alkylene having 1, 2, 3, 4, 5, 6, 7 or 8 $CH_2$ groups, where one of these $CH_2$ groups can be replaced by O, S, NR(13) or o-, p- or m-phenylene;

R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is H, alkyl having 1, 2, 3, 4, 5, 6 or 7 carbon atoms, cycloalkyl having 3, 4, 5, 6 or 7 carbon atoms, C(=O)R(15), $SO_2$R(15), NR(16)R(17) or phenyl, which is not substituted or is substituted by 1–3 substituents selected from the group consisting of F, Cl, Br, $CF_3$, methyl, methoxy and NR(21)R(22);

R(21) and R(22) independently of one another are H or alkyl having 1, 2, 3 or 4 carbon atoms or perfluoroalkyl having 1, 2, 3 or 4 carbon atoms;

R(15) is N=C(NH$_2$)$_2$, NR(18)R(19), N(CH$_2$)$_c$NR(18)R(19) or OR(20);

c is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms; or R(18) and R(19) together are 4 or 5 methylene groups, of which one $CH_2$ group can be replaced by oxygen, S, NH, N—$CH_3$, N-benzyl or N-(p-chlorophenyl);

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one $CH_2$ group can be replaced by oxygen, S, NH, N—$CH_3$, N-benzyl or N-(p-chlorophenyl); or Z is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(21)R(22);

but where, in the case where R(4) is an alkoxy radical, at least one of the substituents R(2), R(3), R(5), R(6), R(7) and R(8) is not hydrogen;

or a pharmaceutically tolerable salt thereof;

az) a substituted 2-naphthoylguanidine of the formula

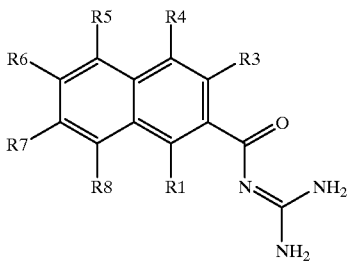

in which:
at least one of the substituents R1, R3, R4, R5, R6, R7 and R8 is $XY_aWZ$ or $X'Y_aWZ'$;
X is O, S, NR(10) or CR(11)R(12);
R(10), R(11) and R(12) independently of one another are H, alkyl having 1, 2, 3, 4, 5 or 6 carbon atoms, perluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 $CH_2$ groups, where one of these $CH_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is $CH_2$, $SO_2$, S(=O)(=NH) or—if W does not immediately follow a heteroatom of the group $XY_a$—alternatively O or NR(14);
R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is C(=O)R(15), $SO_2R(15)$ or—if W is not O or NR(14)—alternatively NR(16)R(17);
R(15) is $N=C(NH_2)_2$, NR(18)R(19), $N(CH_2)_bNR(18)R(19)$ or OR(20);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups, of which one $CH_2$ group can be replaced oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms; or,
R(16) and R(17) together are 4 or 5 methylene groups, of which one $CH_2$ group can be replaced by oxygen, S, NH, N—$CH_3$, N-benzyl or N-(p-chlorophenyl);
X' is C=O, C(=O)NR(30), C(=O)O, SO, $SO_2$, $SO_2NR(30)$, OC=O, NR(30)C=O or $NR(30)SO_2$, where the linkage with the naphthalene ring in each case takes place via the left atom;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

Z' is C(=O)R(15), $SO_2R(15)$, an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is $N=C(NH_2)_2$, NR(18)R(19), $N(CH_2)_bNR(18)R(19)$ or OR(20);
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups, of which one $CH_2$ group can be replaced by oxygen, S, NH, N—$CH_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms; or
Z'—if W is not O or NR(14)—is NR(16)R(17);
R(16) and R(17) independently of one another are H, alkyl having 1, 2, 3, 4, 5, 6, 7 or 8 carbon atoms or perfluoroalkyl having 1, 2, 3 or 4 carbon atoms; or
R(16) and R(17) together are 4 or 5 methylene groups, of which one $CH_2$ group can be replaced by oxygen, S, NH, N—$CH_3$, N-benzyl or N-(p-chlorophenyl); and the other substituents R1, R3, R4, R5, R6, R7 and R8 in each case, which are still not allocated by the definitions given above, independently of one another are H, F, Cl, Br, I, CN, $NO_2$, $CF_3$, $C_2F5$ or $V_pQ_qU$;
V is O, S, SO, $SO_2$, NR(60), OC=O, C=O, C(=O)NR(60), C(=O)O or CR(66)R(67);
R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
p is zero or 1;
Q is alkylene having 1, 2, 3, 4, 5, 6, 7 or 8 $CH_2$ groups, where one of these $CH_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
q is zero or 1;
U is H, alkyl having 1, 2, 3, 4, 5, 6 or 7 carbon atoms, cycloalkyl having 3, 4, 5, 6 or 7 carbon atoms, C(=O)R(65), $SO_2R(65)$, NR(61)R(62) or phenyl, which is not substituted or is substituted by 1–3 substituents selected from the group consisting of F, Cl, Br, $CF_3$, methyl, methoxy and NR(63)R(64);
R(63) and R(64) independently of one another are H, alkyl having 1, 2, 3 or 4 carbon atoms or perfluoroalkyl having 1, 2, 3 or 4 carbon atoms;
R(65) is $N=C(NH_2)_2$, NR(61)R(62) or OR(60);
R(61) and R(62) independently of one another are H, alkyl having 1, 2, 3, 4, 5, 6, 7 or 8 carbon atoms or perfluoroalkyl having 1, 2, 3 or 4 carbon atoms; or R(61) and R(62) together are 4 or 5 methylene groups, of which one $CH_2$ group can be replaced by oxygen, S, NH, N—$CH_3$, N-benzyl or N-(p-chlorophenyl); or U is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(63)R(64);

but where at least one of the substituents R5, R6, R7 and R8 is not hydrogen; or a pharmaceutically tolerable salt thereof;

ba) an ortho-substituted benzoylguanidine of the formula

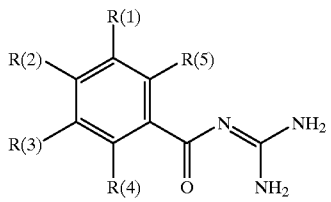

in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;

x is oxygen, sulfur or NR(9);

a is zero or 1;

b is zero, 1 or 2;

c is zero, 1, 2 or 3;

R(9) is H, alkyl having 1, 2, 3 or 4 carbon atoms or —$C_dH_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);

R(7) and R(8) are independently, H or alkyl having 1, 2, 3 or 4 carbon atoms; or R(1) is —SR(10), —OR(10) or —CR(10)R(11)R(12);

R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, $CF_3$, $CH_3$, methoxy, hydroxyl, amino, methylamino and dimethylamino;

f is zero, 1 or 2;

R(11) and (R12), independently of one another, are defined as R(10) or are hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, the latter linked via a carbon or nitrogen atom of the ring, each of which is unsubstituted or is substituted by 1–3 substituents selected from the group consisting of F, Cl, $CF_3$, $CH_3$, methoxy, hydroxyl, amino, methylamino and dimethylamino, or (R1) is —SR(13), —OR(13), —NHR(13), —NR(13)R(14), —CHR(13)R(15), —C[R(15)R(16)]OH, —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14), identically or differently, are —$(CH_2)_g$—$(CHOH)_h$—$(CH_2)_i$—$(CHOH)_{kk}$—R(17) or —$(CH_2)_g$—O—$(CH_2$—$CH_2$O)$_h$—R(24);

R(17) is hydrogen or methyl, g, h and i, identically or differently, are zero, 1, 2, 3 or 4;

kk is 1, 2, 3 or 4;

R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;

R(18) is phenyl, which is unsubstituted or is substituted by 1–3 substituents selected from the group consisting of F, Cl, $CF_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms, which is unsubstituted or is substituted as phenyl;

R(18) is alkyl having 1, 2, 3, 4, 5 or 6 carbon atoms, which is unsubstituted or is substituted by 1–3 OH;

R(18) is cycloalkyl having 3, 4, 5, 6, 7 or 8 carbon atoms;

R(19), R(20), R(21), R(22) and R(23), identically or differently, are hydrogen or methyl;

R(24) is H, alkyl having 1, 2, 3, 4, 5 or 6 carbon atoms, cycloalkyl having 3, 4, 5, 6, 7 or 8 carbon atoms or —$C_mH_{2m}$—R(18);

m is 1, 2, 3 or 4;

one of the two substituents R(2) and R(3) is —O—CO—R(27);

R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolyl are unsubstituted or substituted by 1–3 substituents selected from the group consisting of F, Cl, $CF_3$, methyl, methoxy and NR(7)R(8);

R(7) and R(8) independently of one another are hydrogen or alkyl having 1, 2, 3 or 4 carbon atoms;

where one of the substituents R(2) and R(3) is always defined as R(1);

R(4) and R(5) independently of one another are hydrogen, alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$, n is zero or 1, o is zero or 1, or a pharmaceutically tolerable salt thereof;

bb) a benzoylguanidine of the formula

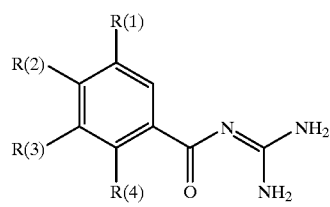

in which:

R(1) is R(13)—SO$_m$ or R(14)R(15)N—SO$_2$—;
  m is 1 or 2;
  R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(16),
    n is zero, 1, 2, 3 or 4;
    R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, CF$_3$, methyl, methoxy and NR(25)R(26);
      R(25) and R(26) are, independently of each other, hydrogen, alkyl having 1, 2, 3 or 4 carbon atoms or perfluoroalkyl having 1, 2, 3 or 4 carbon atoms;
  R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(27),
    n is zero, 1, 2, 3 or 4;
    R(27) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, CF$_3$, methyl, methoxy and NR(28)R(29);
      R(28) and R(29), independently of each other, are hydrogen, alkyl having 1, 2, 3 or 4 carbon atoms or perfluoroalkyl having 1, 2, 3 or 4 carbon atoms;
  R(15) is hydrogen, alkyl having 1, 2, 3 or 4 carbon atoms or perfluoroalkyl having 1, 2, 3 or 4 carbon atoms; or
  R(14) and R(15), together, are 4 or 5 methylene groups of which one CH$_2$ group can be replaced by oxygen, S, NH, N—CH$_3$ or N-benzyl;
one of the substituents R(2) and R(3) is hydrogen;
and the other of the substituents R(2) and R(3) in each case is —CHR(30)R(31);
  R(30) is —(CH$_2$)$_g$—(CHOH)$_h$—(CH$_2$)$_i$—(CHOH)$_k$—R(32) or —(CH$_2$)$_g$—O—(CH$_2$—CH$_2$O)$_n$—R(24);
  R(24) and R(32), independently of each other, are hydrogen or methyl;
  g, h and i, identically or differently, are zero, 1, 2, 3 or 4;
  k is 1, 2, 3 or 4;
or the other of the substituents R(2) and R(3) in each case is —C(OH)R(33)R(34);
  R(31), R(33) and R(34), identically or differently, are hydrogen or alkyl having 1, 2, 3 or 4 carbon atoms, or
  R(33) and R(34), together, are cycloalkyl having 3, 4, 5 or 6 carbon atoms; or
  R(33) is —CH$_2$OH;
R(4) is alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;
  n is zero or 1;
  o is zero, 1 or 2;
or a pharmaceutically tolerable salt thereof;

bc) an indanylidineacetylguanidine of the formula

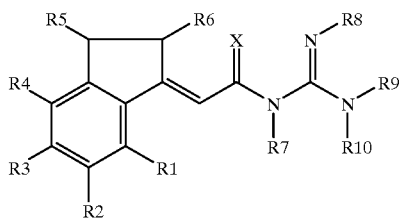

in which:
R1, R2, R3, R4, R5 and R6 independently of one another are H, C$_1$–C$_{10}$-alkyl; haloalkyl having 1–6 carbon atoms, O—C$_1$–C$_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O—C(=O)—C$_1$-C$_4$-alkylaryl, O—C(=O)—NH—C$_1$-C$_4$-alkyl, O—C(=O)—N(C$_1$-C$_4$-alkyl)$_2$, NO$_2$, CN, CF$_3$, NH$_2$, NH—C(=O)—C$_1$-C$_4$-alkyl, NH—C(=O)—NH$_2$, COOH, C(=O)—O—C$_1$-C$_4$-alkyl, C(=O)—NH$_2$, C(=O)—NH—C$_1$-C$_4$-alkyl, C(=O)—N(C$_1$-C$_4$-alkyl)$_2$, C$_1$-C$_4$—COOH, C$_1$-C$_4$-alkyl-C(=O)—O—C$_1$-C$_4$-alkyl, SO$_3$H, SO$_2$-alkyl; SO$_2$-alkylaryl, SO$_2$—N-(alkyl)$_2$, SO$_2$—N(alkyl)(alkylaryl), C(=O)—R11, C$_1$-C$_{10}$-alkyl-C(=O)—R11, C$_2$-C$_{10}$-alkenyl-C(=O)—R11, C$_2$-C$_{10}$-alkynyl-C(=O)—R11, NH—C(=O)—C$_1$-C$_{10}$-alkyl-C(=O)—R11 or O—C$_1$-C$_{11}$-alkyl-C(=O)—R11;
R11 is C$_1$-C$_4$-alkyl, C$_1$-C$_4$-alkynyl, aryl, substituted aryl, NH$_2$, NH—C$_1$-C$_4$-alkyl, N—(C$_1$-C$_4$-alkyl)$_2$, SO$_3$H, SO$_2$-alkyl, SO$_2$-alkylaryl, SO$_2$—N-(alkyl)$_2$ or SO$_2$—N(alkyl)(alkylaryl);
X is O, S or NH;
R7, R8, R9 and R10 independently of one another are H, alkyl, cycloalkyl, aryl, alkylaryl, or
R8 and R9 together are part of a 5-, 6- or 7-membered heterocyclic ring;
or a pharmaceutically tolerable salt thereof;
bd) a phenyl-substituted alkenylcarboxylic acid guanidide of the formula

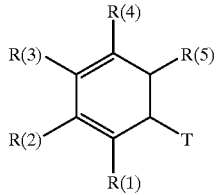

in which
T is:

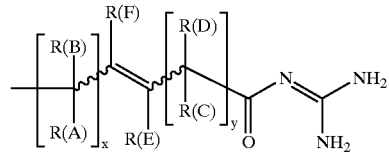

R(A) is hydrogen, F, Cl, Br, I, CN, OH, OR(6), (C$_1$–C$_4$)-alkyl, O$_r$(CH$_2$)$_a$C$_b$F$_2$+1, (C$_3$–C$_8$)-cycloalkyl oder NR(7)R(8)

r is zero or 1;
a is zero, 1, 2, 3 or 4;
b is 1, 2, 3 or 4;
R(6) is $(C_1-C_4)$-alkyl, $(C_1-C_4)$-perfluoroalkyl, $(C_3-C_6)$-alkenyl, $(C_3-C_8)$-cycloalkyl, phenyl or benzyl, where the phenyl nucleus is not substituted or is substituted by 1–3 substituents selected from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6); or
R(7) and R(8) together are 4 or 5 methylene groups, of which one $CH_2$ group can be replaced by oxygen, sulfur, NH, N—$CH_3$ or N-benzyl;
R(B), R(C) and R(D) independently are defined as R(A);
x is zero, 1 or 2;
y is zero, 1 or 2;
R(F) is hydrogen, F, Cl, Br, I, CN, OR(12), $(C_1-C_8)$-alkyl, $O_p(CH_2)_f C_g F_{2g+1}$, $(C_3-C_8)$-cycloalkyl or $(C_1-C_9)$-heteroaryl;
p is zero or 1;
f is zero, 1, 2, 3 or 4;
g is 1, 2, 3, 4, 5, 6, 7, or 8;
R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl, where the phenyl nucleus is not substituted or is substituted by 1–3 substituents selected from the group consisting of F, Cl, $CF_3$, methyl, methoxy and NR(13)R(14);
R(13) and R(14) are H, $(C_1-C_4)$-alkyl or $(C_1-C_4)$-perfluoroalkyl;
R(E) is defined independently as R(F);
R(1) is defined independently as T; or
R(1) is hydrogen, —$O_k C_m H_{2m+1}$, —$O_n(CH_2)_p C_q F_{2q+1}$, F, Cl, Br, I, CN, —(C=O)—N=C(NH$_2$)$_2$, —$SO_r R(17)$, —$SO_{r2}NR(31)R(32)$, —$O_u(CH_2)_v C_6H_5$, —$O_{u2}$—$(C_1-C_9)$-heteroaryl or —$S_{u2}$—$(C_1-C_9)$-heteroaryl;
k is zero or 1;
m is zero, 1, 2, 3, 4, 5, 6, 7, or 8;
n is zero or 1;
p is zero, 1, 2, 3 or 4;
q is 1, 2, 3, 4, 5, 6, 7, or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl; or
R(31) and R(32) together are 4 or 5 methylene groups of which one $CH_2$ group can be replaced by oxygen, S, NH, N—$CH_3$ or N-benzyl;
R(17) is $(C_1-C_8)$-alkyl;
u is zero or 1;
u2 is zero or 1;
v is zero, 1, 2, 3 or 4;
where the phenyl nucleus is not substituted or is substituted by 1–3 substituents selected from the group consisting of F, Cl, $CF_3$, methyl, methoxy, —$(CH_2)_w NR(21)R(22)$, NR(18)R(19) and $(C_1-C_9)$-heteroaryl;
R(18), R(19), R(21) and R(22) independently of one another are $(C_1-C_4)$-alkyl or $(C_1-C_4)$-perfluoroalkyl;
w is 1, 2, 3 or 4;
where the heterocycle of the $(C_1-C_9)$-heteroaryl is unsubstituted or is substituted by 1–3 substituents selected from the group consisting of F, Cl, $CF_3$, methyl or methoxy;
R(2), R(3), R(4) and R(5) independently of one another are defined as R(1), or
R(1) and R(2) or R(2) and R(3) in each case together are —CH=CH—CH=CH—, which is not substituted or is substituted by 1–3 substituents selected from the group consisting of F, Cl, $CF_3$, methyl, methoxy, —$(CH_2)_{w2}NR(24)R(25)$ and NR(26)R(27);
R(24), R(25), R(26) and R(27) are H, $(C_1-C_4)$-alkyl or $(C_1-C_4)$-perfluoroalkyl;
w2 is 1, 2, 3 or 4;
where the radical T is present in the molecule at least twice, but only three times at most;
or a pharmaceutically tolerable salt thereof;
be) a benzoylguanidine of the formula in which:
R(1) is $CF_3$;
one of the substituents R(2) and R(3) is hydrogen;
and the other substituent R(2) or R(3) in each case is —C(OH)(CH$_3$)—CH$_2$OH, —CH(CH$_3$)—CH$_2$OH or —C(OH)(CH$_3$)$_2$;
R(4) is methyl, methoxy, Cl or $CF_3$;
or a pharmaceutically tolerable salt thereof;
bf) a compound of the formula in which:
W, Y and Z are a nitrogen atom or a carbon atom substituted by R(2) or R(3) or R(4);
R(1) is hydrogen, A, Hal, —$CF_3$, —$CH_2F$, —$CHF_2$, —$CH_2CF_3$, —$C_2F_5$, —CN, —$NO_2$, -ethynyl, or an X—R';
A is alkyl having 1 to 6 carbon atoms;
Hal is F, Cl, Br or I;
X is oxygen, S or NR";
R" is hydrogen, A or a cyclic methylene chain having 3 to 7 carbon atoms;
R' is H, A, HO—A—, HOOC—A—, $(C_3-C_7)$-cycloalkyl, $(C_6-C_8)$-cycloalkylalkyl, $CF_3$, $CH_2F$, $CHF_2$, $CH_2$—$CF_3$, Ph, —$CH_2$—Ph or Het;
Ph is phenyl, naphthyl or biphenylyl which is unsubstituted or mono-, di- or trisubstituted by A, OA, NR'R", Hal, $CF_3$;
Het is a mono- or binuclear saturated, unsaturated or aromatic heterocycle having 1 to 4 nitrogen, oxygen and/or sulfur atoms, which is unsubstituted or mono-, di- or trisubstituted by Hal, $CF_3$, A, OH, OA, —X—R', —CN, —$NO_2$, and/or carbonyl oxygen, where Het is bonded via N or an alkylene chain $C_mH_{2m}$ where m=zero to 6; or R' and R" together are alkylene having 4–5 carbon atoms, in which one $CH_2$ group can also be replaced by oxygen, S, NH, N—A, N—Ph and N—$CH_2$—Ph;

R(2) and R(3) independently of one another are hydrogen, Hal, A, HO—A—, X—R', —C(=N—OH)—A, A—O—CO—$(C_1-C_4)$-alkyl-, CN, $NO_2$, COOH, halogen-substituted A, in particular $CF_3$, $CH_2F$, $CHF_2$, $C_2F_5$, $CH_2CF_3$, or $S(O)_nR'''$;

R''' is A, Ph or —Het;

n is zero, 1 or 2; or

R(2) and R(3) independently of one another are $SO_2NR'R''$, Ph or —O—Ph, —O—$CH_2$—Ph, —CO—A, —CHO, —COOA, —CSNR'R", CONR'R", —CH=CH—COOH, —CH=CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl; or R(2) and R(3) independently of one another are R(5)—O—; R(5) is hydrogen, A, $(C_1-C_6)$-alkenyl or $(C_3-C_7)$-cycloalkyl;

R(4) is Ph, Het, —O—Het; $CF_3$, $S(O)_nR'''$, —$SO_2NR'R''$, Alk;

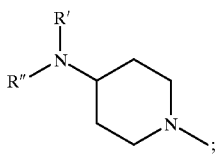

or two of the substituents R(1) to R(4) together are a group —O—CR(6)R(7)—CO—NR(8)—,

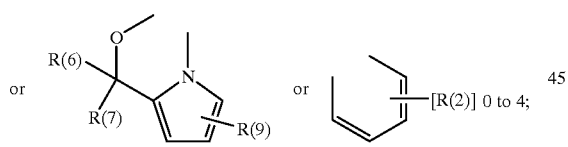

where R(2) has the meaning indicated;

R(6), R(7), R(8) and R(9) independently of one another are H or A; or

R(8) is $(C_5-C_7)$-cycloalkyl; or

R(9) is cyano;

Alk is straight-chain or branched $(C_1-C_8)$-alkyl or $(C_3-C_8)$-cycloalkyl, which is unsubstituted or mono-, di- or trisubstituted by A; or Alk is an ethenyl or ethynyl radical which is substituted by H, A, Ph or Het;

bg) a compound of the formula

RCONHC(:NH)NH2 in which

R is substituted phenyl;

bh) a compound of the formula

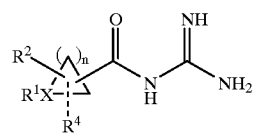

in which n is 1–5;

X is N or CR5;

R5 is H, halogen, alkenyl, alkynyl, alkoxy, alkyl, aryl, heteroaryl;

R1–R4 are H, SH, OH, cyano, $NO_2$, alkyl, alkenyl, alkynyl, alkoxy, alkenyloxy, heteroaryloxy, alkyl, aryl, cycloalkyl, cycloalkenyl, amino, arylsulfonylamino, acyl;

bi) a compound of the formula

R1CON:C(NH2)2 in which

R1 is an (un)substituted heterocyclic ring having 1 or 2 S atoms;

bj) a compounds of the formula

R1YCON:C(NH2)2 in which

R1 is phenyl, thienyl, pyridyl, furyl, unsubstituted or substituted by 1–3 lower alkyl, lower alkoxy, mono-, di- or trihalo-lower alkoxy, Cl, (un)protected hydroxyalkyl, acyl, cyano, acyl-lower alkenyl, di(lower alkyl)amino-lower alkoxy, amino, $NO_2$ or an (un)substituted heteropolycyclic group;

Y is $CH_2$, CR2R4R3R5, CR2:CR3; (R2 and R3 are H, lower alkyl, lower alkanoylamino; or R2 and R3 together are alkylene;

R4, and R5 are H or lower alkyl);

bk) compound of the formulae

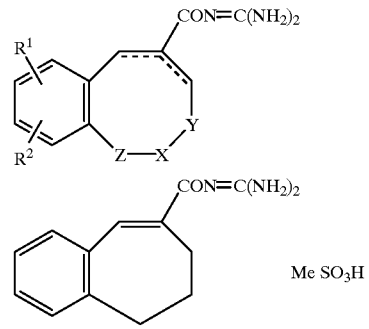

in which

X is $CH_2$, S, $SO_2$, O, NH;

Y is $(CH_2)_n$;

is 0–3;

Z is (CH$_2$)$_m$;

m is 0–2;

R1 and R2 are H, halogen, alkyl, alkoxy, NO$_2$, amino, aryl, heterocycle, bl) compounds of the formulae

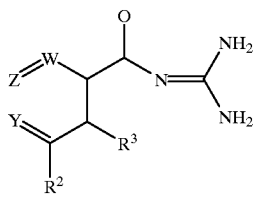

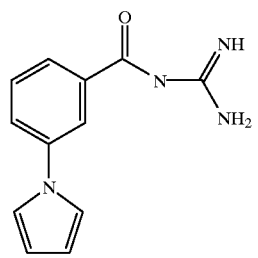

in which

X, Y, Z are nitrogen or methine;

R2 is H or aryl;

R3 is H, alkoxy or hydroxyl;

bm) a compounds of the formulae

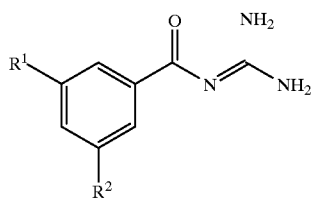

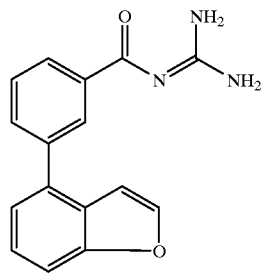

in which

R1 is H, hydroxyalkyl, protected hydroxyalkyl, acylalkoxy, acylalkenyl, acyl;

R2 is aralkenyl; disubstituted aryl, (un)substituted indenyl, indanyl, dihydrobenzocycloheptenyl, di- to decahydronaphthyl, cyclopentenyl, dihydrothienyl, dihydrofuryl or heterobicyclyl, alkylthienyl, mono- or dihalothienyl, haloalkylthienyl, acylthienyl, halofuryl, haloalkylfuryl;

bn) compounds of the formulae

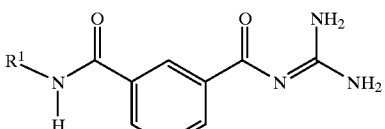

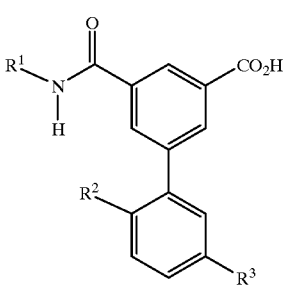

in which

R1 is di[(lower)alkylamino](lower)alkyl, morpholinyl (lower)alkyl, lower alkylpiperazinyl, [lower alkylpyrrolidinyl](lower)alkyl;

R2 is halogen, lower alkyl, lower alkoxy;

R3 is halogen, lower alkyl, lower alkoxy, mono- or di- or trihalo(lower)alkyl;

bo) a compound of the formula

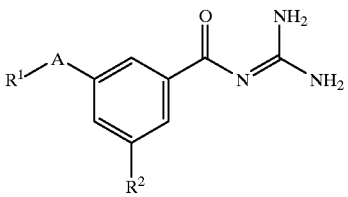

in which

R1 is [mono-(or di-)(lower alkyl)amino](lower)alkyl, pyrrolidinyl, piperidyl;

R2 is dihalothienyl, dihalophenyl;

A is O, CH$_2$ bp) a compound of the formula

RC(O)NHC(NH)NHR1 in which

R is C$_{7-30}$ alkoxyphenyl, alkenyloxyphenyl or alkoxynaphthyl, unsubstituted or substituted either in the aliphatic or the aromatic unit by halogen, OH or C$_{1-2}$-alkyl;

R1 is H, (C$_1$–C$_4$)-alkyl;

bu) a compound of the formula

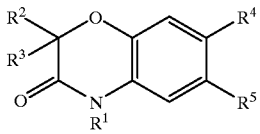

in which

R1 is H, (cyclo)alkyl;

R2 and R3 are H or alkyl one of R4 and R5 is CON:C(NH$_2$)$_2$ and the other is H;

br) a compound of the formula

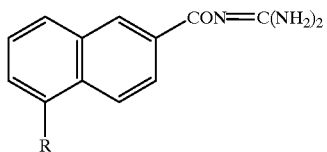

in which

R is H, halogen or alkoxy;

bs) a compound of the formula

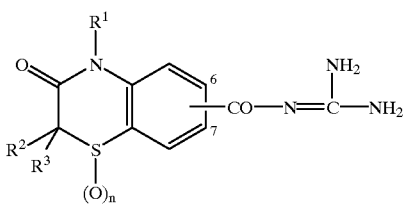

in which

R is H or lower alkyl;

R2 and R3 are identical or different and are H or C$_{1-2}$-alkyl;

n is 0 or 2;

the guanidinocarbonyl substituent is in position 6 or 7;

bt) a compound of the formula

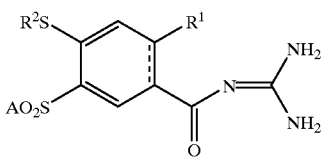

in which

A is C$_{1-4}$-alkyl, halogen, (un)substituted phenyl;

R1 is A, CF$_3$, CH$_2$F, CHF$_2$, C$_2$F$_5$;

R2 is H, A cycloalkyl, (un)substituted phenyl, (un)substituted heterocyclyl;

bu) a compound of the formula

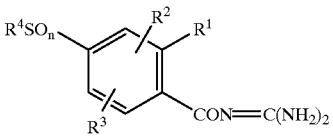

in which

R1 is alkyl, fluoroalkyl, CN, NO$_2$, halogen;

R2 is SO$_n$R$_4$, (un)substituted SO$_2$NH$_2$, NO$_2$, CF$_3$;

R3 is H, halogen, alkyl, OH, alkoxy, CN, NO$_2$, CF$_3$, fluoroalkyl;

R4 is alkyl, phenyl, heterocyclyl, cycloalkyl;

n is 1 or 2;

bv) compounds of the formulae

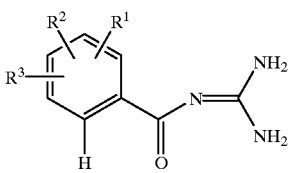

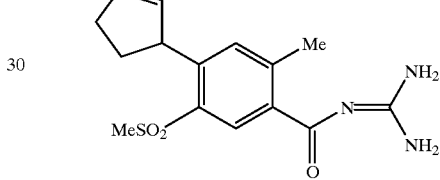

in which

R1 and R2 are H, halogen, alkyl, cyano, NO$_2$, CF$_3$, CH$_2$F, CHF$_2$, C$_2$F$_5$, CH$_2$CF$_3$, SO$_n$R4;

R3 is CR5:CR6R7, CR5R6CR7:CR8R9, CR5R6CR7R8CR9:CR10R11, cycloalkenyl, cycloalkenylalkyl;

R4 is alkyl, (un)substituted phenyl;

R5–R11 are H, alkyl;

n is 1 or 2;

bw) a compound of the formula

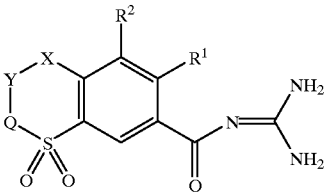

in which

R1 and R2 are H, alkyl, CF$_3$, CH$_2$F, CHF$_2$, halogen, OH, alkoxy, amino, NO$_2$, cyano;

Q is (R8R9C)$_n$;

X is CR4R5, C:Z, O, S, imino;

Y is CR6R7, C:Z, O, imino;

Z is O, S, imino, NOH, CH$_2$;

R5–R8 are H, alkyl, halogen, OH, alkoxy, SH, alkylthio, amino;

R5R6 or R7R8 are a bond; or
R4R5 is OCH$_2$CH$_2$O, O(CH$_2$)$_3$O;
R8 and R9 are H, alkyl;
n is 0 or 1;
bx) a compound of the formula

in which
R is heterocyclyl;
Z is (un)substituted phenylene;
by) a compound of the formula

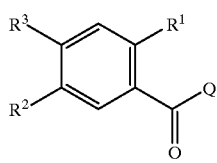

in which
Q N:C(NH$_2$)$_2$, Cl, Br, O$_2$CPh, OH, a nucleophilically substituted leaving group;
R1 is alkyl, CF$_3$, halogen;
R2 is CF$_3$, alkylsulfonyl, alkylsulfoxyl, phenylsulfonyl, phenyl-SO, (un)substituted SO$_2$NH$_2$;
R3 is CN, halogen, CHO, (un)substituted CONH$_2$, (un)substituted CSNH$_2$;
bz) a compound of the formula

in which
R is an aminopiperidino group Q;

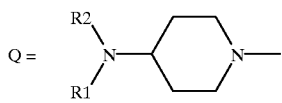

Z is (un)substituted phenylene;
R1 and R2 are H, (phenyl)alkyl, phenyl, alkanoyl;
NR1R2 is heterocyclyl;
ca) a compound of the formula

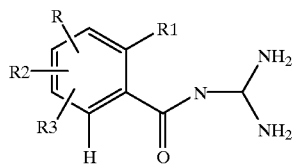

in which
R is alkyl, ethenyl, ethynyl;
R1 is fluoromethyl, halogen, alkyl, alkoxy;
R2 and R3 are H, halogen, alkyl, alkoxy;

cb) a compound of the formula

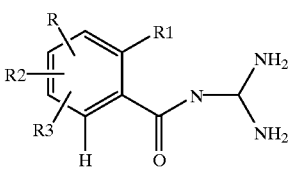

in which
R is heterocyclyl, heteroaryl;
R1 is fluoromethyl, halogen, alkyl, alkoxy;
R2 and R3 are H, halogen, alkyl, alkoxy
cc) a compound of the formula

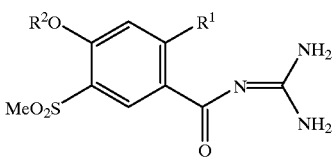

in which
R1 is methyl or ethyl;
R2 is H, alkyl, phenyl, CH$_2$Ph;
cd) a compound of the formula

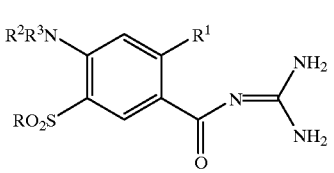

in which
R is alkyl;
R1 is alkyl, CF$_3$, CH$_2$F, CHF$_2$, C$_2$F$_5$;
R2 and R3 are H, (cyclo)alkyl, phenyl, heterocyclyl;
NR2R3 is heterocyclyl;
ce) a compound of the formula

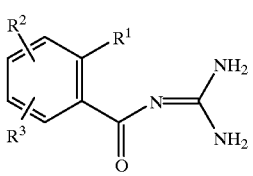

in which
R1 is H, F, Cl, Br, alkyl, CN, NO$_2$, C$_n$F$_m$H$_{(2n+1-m)}$O$_p$;
m is 1–7; but at most (2n+1);
n is 1–3;
p is 0 or 1;
R2 is C$_n$F$_m$H$_{(2n+1-m)}$O$_p$;
R3 is H, alkyl, F, Cl, Br, I, C$_n$F$_m$H$_{(2n+1-m)}$O$_p$;

cf) a compound of the formula

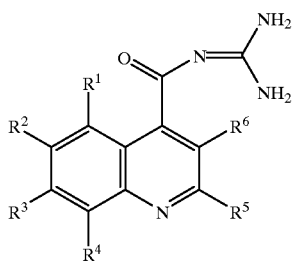

in which

R1–R4 are H, halogen, alkyl, alkoxy;

R5 is (un)substituted phenyl;

R6 is H or alkyl;

cg) a compound of the formula

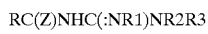

in which

R is phenylalkyl, phenylalkenyl, heteroaryl;

Z is O or S;

R1 H or Alkyl;

R2 and R3 are H, alkyl, haloalkyl, cycloalkyl, aralkyl, alkenyl, aryl, alkynyl, alkoxy, acyl, heteroaryl, or NR2R3 form a heterocycle;

ch) a compound of the formula

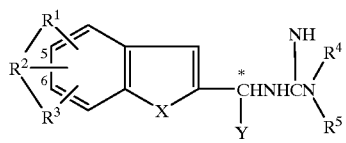

in which

R1–R3 are H, halogen, alkyl, alkoxy, phenyl, phenyl-CH$_2$;

R4 and R5 are H, C$_{6-12}$-alkyl, benzohydryl, (un)substituted aralkyl;

X is O, S, (un)substituted NH;

Y is an (un)substituted heterocycle or 2,3-dihydroheterocycle;

R1–R3 are C$_{4-6}$ cyclic hydrocarbon;

ci) a compound of the formula

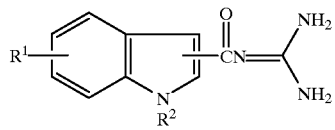

in which

R1 is H, alkyl, alkenyl;

R2 is H, alkyl, cycloalkyl;

cj) compounds of the formulae

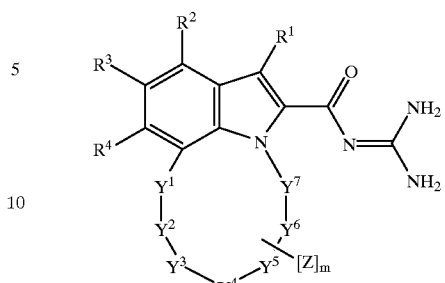

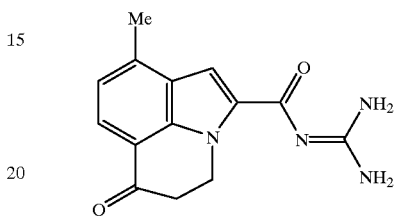

in which

R1–R4 are H, alkyl, cycloalkyl;

Y1–Y7 are a single bond, CH$_2$, O;

Z is alkyl, alkenyl, alkynyl;

m is 2–5;

ck) compounds of the formulae

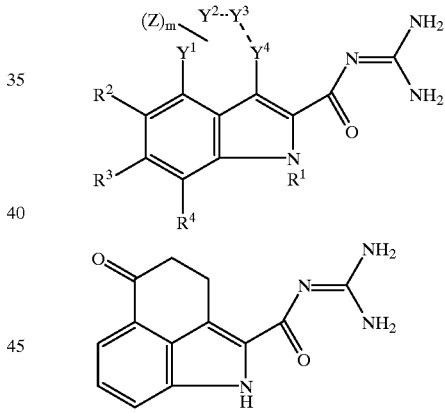

in which

R1 is H, alkyl, cycloalkyl;

R2–R4 are H, alkyl, cycloalkyl;

Y1–Y4 are a bond, CH$_2$, C(O), O;

Z is alkyl, alkenyl, alkynyl;

m is 0–2;

cl) a compound of the formula

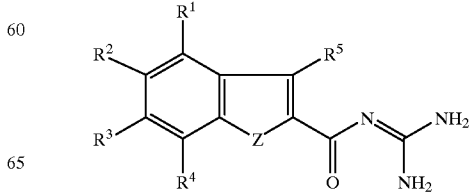

-continued

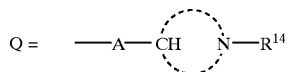

in which

Z is CR6R7, CO, C:CR8R9;

R1–R4 are H, (un)substituted alkyl, cycloalkyl, cycloalkenyl, saturated heterocyclyl, halogen, $NO_2$, $CO_2H$, alkoxycarbonyl, aryl, (un)substituted OH, $NH_2$, or $SO_2NH_2$, $S(O)_nR13$ (n=0, 1 or 2), $(CR_aR_b)_s$ $(CRcRd)_t(CReRf)_uR(R=CRg:CRhRi, C≡CRj, CORk)$, Q;

R5–R9 are H, (un)substituted alkyl, cycloalkyl, cycloalkenyl, saturated heterocyclyl, halogen, $CO_2H$, alkoxycarbonyl, aryl, (un)substituted OH or $NH_2$, $(CRaRb)_s(CRcRd)_t(CReRf)_uR(R=CRg:CRhRi, C≡CRj, CORk)$, Q;

R13 is (un)substituted alkyl, aryl;

Ra–Rj are H, (un)substituted alkyl, cycloalkenyl, saturated heterocyclyl, aryl, $CO_2H$, alkoxycarbonyl;

Rk is H, (un)substituted alkyl, cycloalkyl, cycloalkenyl, saturated heterocyclyl, aryl;

s, t and u are 0 or 1;

A is $S(O)_n$ (n=0, 1 or 2), (un)substituted NH;

R14 is H, (un)substituted alkyl;

cm) a compound of the formula

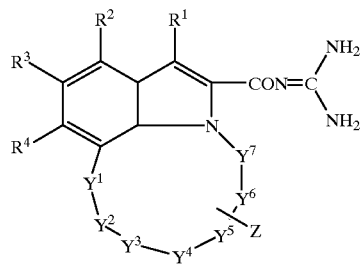

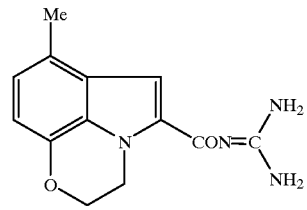

in which

R1, R2, R3 and R4 are H, (un)substituted alkyl, cycloalkyl, cycloalkenyl, saturated heterocyclyl, halogen, $NO_2$, COOH, alkoxycarbonyl, aryl, acyl;

Y1–Y7 are a bond, $CH_2$, O, CO, (un)substituted C(:$CH_2$), S, SO, $SO_2$, (un)substituted NH;

Z is (un)substituted $NH_2$, $S(O)_nR8$;

n is 0, 1 or 2;

R8 is (un)substituted alkyl, aryl;

cn) a compound of the formula

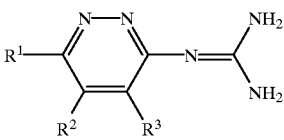

in which

R1 is an (un)substituted aromatic ring;

R2 and R3 are atoms which combine to form an (un)substituted fused-on (N-containing) aromatic ring;

co) a compound of the formula

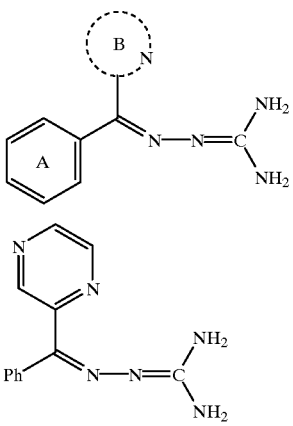

in which ring A is an (un)substituted benzene ring;

ring B is an (un)substituted N-containing 6-membered aromatic ring, such as pyridine, pyrimidine, pyrazine or pyridazine;

cp) a compound of the formula

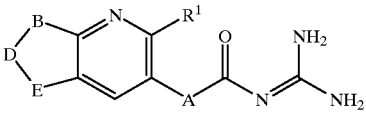

in which

R1 is H, halogen, lower alkyl, lower alkoxy, amino-lower alkyl, lower alkoxyalkyl, aryl, heterocyclyl, aralkyl, phenoxy-substituted lower alkyl or aralkyloxy-substituted lower alkyl;

R2 is H, halogen, lower alkoxy or nitro;

A is a bond or vinylene;

B is vinylene, —$CH_2P1(R3)$—;

R3 is H, halogen, OH, lower alkyl, lower alkylidene, lower alkoxy, hydroxy-lower alkyl, aralkyl, aralkylidene, phenoxy-lower alkyl, hydroxyimino, lower alkoxyimino, oxo, $CH_2ONO_2$, $CH_2CH_2ONO_2$;

P1 is methine or C;

D is a bond, methylene or ethylene;

E is vinylene, Q,

Q1(R5)-P2(R4)—;

R4 is H, halogen, (un)protected hydroxyl or oxo;

R5 H or lower alkyl;

P2 is methine or 0;

cq) a compound of the formula

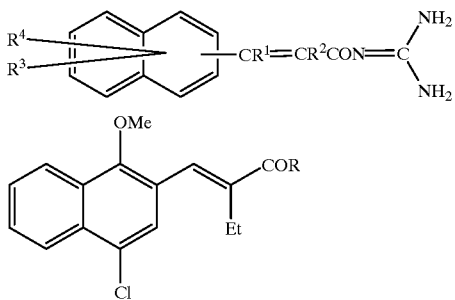

in which
R1 and R2 are H, halogen, lower (halo)alkyl;
R3 and R4 are H, lower(halo)alkyl, alkenyl, alkynyl, cycloalkyl, alkoxy, alkoxyalkoxy or alkoxycarbonyl, COOH, halogen, $NO_2$, $NH_2$, mono- or di(lower alkyl) amino, lower alkyl, alkanoyl, alkanoylamino or alkanoyloxy, OH, SH, lower alkylthio, alkylsulfonyl, $SO_2NH_2$, lower alkylsulfonylamino, (lower alkylsulfonyl)(lower alkyl)amino, $CONH_2$z di(lower alkyl))aminocarbonyl;

cr) a compound of the formula

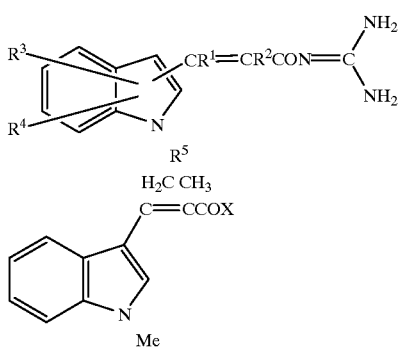

in which
R1 and R2 are H, halogen, substituted lower alkyl;
R3 and R4 are H, substituted lower alkyl, lower alkenyl or alkynyl;
R5 is H, substituted lower alkyl, aralkyl;

cs) a compound of the formula

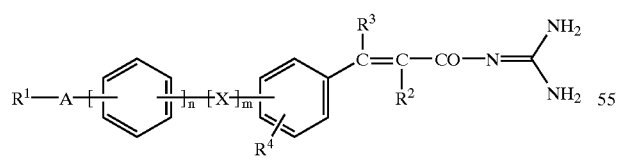

in which
X is O or S;
n and m are 0 or 1;
A is lower alkylene;
R1 is protected OH, $NH_2$ or alkylamino;
R2 and R3 are H, halogen, (un)substituted alkyl;
R4 is H, halogen, lower alkoxy;

ct) a compound of the formula

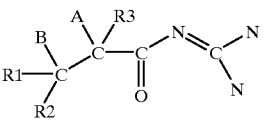

in which
ring A is (substituted) 5- or 6-membered heteroaryl;
ring B is (substituted) aryl;
R1–R3 are H, (F-substituted) lower alkyl;

cu) a compound of the formula

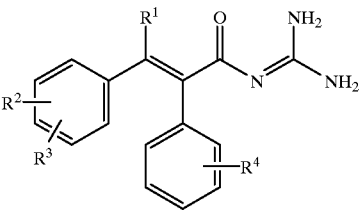

in which
R1 is H, halogen, lower alkyl;
R2, R3 and R4 are H, lower (halo)alkyl, lower alkenyl, lower alkynyl, cycloalkyl, lower alkoxy, lower alkoxy-lower alkyl, lower alkoxycarbonyl, COOH, halogen, $NO_2$, cyano, $NH_2$, mono- or di(lower alkyl)amino, lower alkanoyl, lower alkanoylamino, lower alkanoyloxy, OH, SH, lower alkylthio, lower alkylsulfonyl, mono- or di(lower alkyl)aminosulfonyl;

cv) a compound of the formula

BCR1:CACON:C(NH$_2$)$_2$ in which
A is an (un)substituted fused benzene ring, a 5- or 6-membered heterocycle;
B is (un)substituted aryl;
R1 is H, halogen, non-halogenated or halogenated lower alkyl;

cw) compounds of the formulae

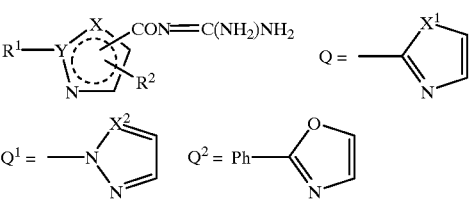

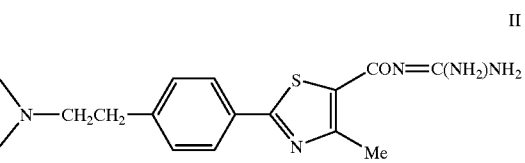

in which
the five-membered heteroaryl ring in formula I is Q or Q1;
X1 is oxygen, S or NR3;
X2 is N or CR4;

R1 is unsubstituted or substituted aryl or unsubstituted or substituted 5- or 6-membered monocyclic heteroaryl;

R2 is H, halogen, unsubstituted or halogen-substituted lower alkyl, lower alkoxy, lower alkylthio, or unprotected or protected amino;

R3 and R4 are H, or unsubstituted or halogen-substituted lower alkyl;

cx) compounds of the formulae in which

R1 is H, (un)substituted alkyl, alkenyl, alkynyl, cycloalkyl, halogen, $NO_2$, acyl, COOH, alkoxycarbonyl, an aromatic group, (un)substituted OH, $NH_2$, $SO_2NH_2$;

R2 is H, (un)substituted alkyl, cycloalkyl, OH, alkoxy;

cy) a compound of the formula in which:

X is H, Hal, $(Hal)_3C$—, $(C_1-C_6)$-alkyl, $(C_3-C_6)$-cycloalkyl, substituted phenyl, $(C_1-C_5)$-alkyl-S— or $(C_1-C_5)$-alkyl-$SO_2$—;

Y is $NH_2$ or substituted amino; or

X and Z together form a —$(CH_2)_4$- or a 1,3-butadienylene chain; or

Z is H, Hal, OH, HS, $(C_1-C_5)$-alkyl, $(C_3-C_6)$-cycloalkyl, substituted phenyl; or Z is an amino group —NR(1)R(2);

R(1) is H, straight-chain or branched, unsubstituted or substituted $(C_1-C_8)$-alkyl which may be interrupted by oxygen; or R(1) is $(C_3-C_8)$-alkenyl, $(C_3-C_8)$-alkynyl, $(C_3-C_7)$-cycloalkyl or OH-substituted phenyl or OH-substituted phenyl-$(C_1-C_4)$-alkyl or OH-substituted $(C_3-C_7)$-cycloalkyl;

R(2) is 1-morpholino, hydrogen or a straight-chain or branched $(C_1-C_8)$-alkyl chain;

which may be interrupted by oxygen, an amino group, which straight-chain or branched $(C_1-C_8)$-alkyl chain is unsubstituted or substituted by a substituted or unsubstituted mono- or polycyclic heterocycle which contains nitrogen, oxygen or sulfur atoms; or which alkyl chain is substituted by phenyl, unsubstituted or mono- or polysubstituted by $(C_1-C_4)$-alkoxy, unsubstituted or substituted by OH, alkylamino, alkyl or phenyl; or by an aminocarbonyl group or by hydroxyl, $(C_1-C_4)$-alkoxy groups, or R(2) is phenyl, unsubstituted or substituted by alkyl, alkoxy, an amino group which carries, as substituents:

H, a mono- or polycyclic heterocycle which contains nitrogen, oxygen or sulfur atoms, which is unsubstituted or substituted by H, Hal or $(C_1-C_4)$-alkyl;

a phenyl radical, unsubstituted or substituted by a substituent selected from the group consisting of $(C_1-C_4)$-alkyl, $(C_1-C_4)$-alkoxy, Hal and OH; or R(2) is 1-piperidino, unsubstituted or substituted in the 4-position by an acyl radical of an aliphatic, alicyclic, aromatic or heteroaromatic carboxylic acid, $(C_1-C_8)$-alkyl, which for its part may be substituted by OH or $(C_1-C_4)$-alkoxy or a $(C_1-C_4)$-alkoxy-substituted phenyl radical; or R(2) is amidino, which is unsubstituted or substituted by phenyl, which is unsubstituted or substituted by Hal or alkyl; or R(2) is an acyl radical of an aliphatic, alicyclic, aromatic or heteroaromatic carboxylic acid, or R(2) is a $(C_1-C_8)$-alkyl chain which may be substituted by a phenyl radical carrying OH, alkoxy or alkyl radicals, or R(1) and R(2) together with the N atom to which they are attached form a piperazine ring, which is unsubstituted or carries, via a $(C_1-C_6)$-methylene chain, a mono- or polycyclic heterocycle, which contains nitrogen, oxygen or sulfur;

Hal is F, Cl, Br or I;

cz) an indoloylguanidine derivative of the formula in which

R(2) is hydrogen, unsubstituted or substituted $(C_1-C_8)$-alkyl, $(C_3-C_7)$-cycloalkyl, OH, $(C_1-C_6)$-alkyl-O—, an aromatic radical or a group —$CH_2$—R(20);

R(20) is $(C_2-C_6)$-alkenyl or $(C_2-C_6)$-alkynyl;

R(1) is 1 to 5 identical or different substituents, which are:

hydrogen, unsubstituted or substituted $(C_1-C_8)$-alkyl, $(C_2-C_6)$-alkenyl, $(C_2-C_6)$-alkynyl, $(C_3-C_7)$-cycloalkyl, halogen, —$NO_2$, $(C_2-C_8)$-alkanoyl, arylalkanoyl having up to 10 carbon atoms, aroyl having up to 11 carbon atoms, —COOH, $(C_2-C_6)$-alkoxycarbonyl, an aromatic group or one of the following groups: —OR(3), —NR(6)R(7) or —S(O)$_n$R(40);

R(3) is hydrogen, $(C_1-C_8)$-alkyl, substituted $(C_1-C_8)$-alkyl, $(C_3-C_7)$-cycloalkyl, an aromatic radical or a group —$CH_2$—R(30); R(30) is alkenyl or alkynyl;

R(6) and R(7) independently of one another are hydrogen, unsubstituted or substituted $(C_1-C_8)$-alkyl, $(C_3-C_7)$-cycloalkyl, $(C_2-C_8)$-alkanoyl, an arylalkanoyl group having up to 10 carbon atoms, an aroyl group having up to 11 carbon atoms, an aromatic group or —$CH_2$—R(60); R(60) is $(C_2-C_6)$-alkenyl or $(C_2-C_6)$-alkynyl; or R(6) and R(7) together with the nitrogen atom are a 5–7-membered cyclic amine, which can additionally contain further heteroatoms in the ring;

n is zero, 1 or 2;

R(40) is unsubstituted or substituted ($C_1$–$C_8$)-alkyl, or an aromatic group, or a group

A is oxygen, —S(O)$_n$— or —N(R50)—; R(50) is hydrogen or ($C_1$–$C_8$)-alkyl;

R' is hydrogen, unsubstituted or substituted ($C_1$–$C_8$)-alkyl, in which the ring represents a saturated 3–8-membered heterocycle having a nitrogen atom, said substituted alkyl carries one or more groups selected from the group consisting of halogen, —OH, ($C_1$–$C_6$)-alkoxy, —CN, —COOH, ($C_2$–$C_6$)-alkoxycarbonyl, ($C_2$–$C_8$)-alkanoyl, arylalkanoyl having up to 10 carbon atoms, aroyl having up to 11 carbon atoms, an aromatic group, —CONR(4)(R5), R(4) and R(5) identically or differently are hydrogen or ($C_1$–$C_8$)-alkyl; or R(4) and R(5) are connected to one another and together form a 5–7-membered cyclic amine which can additionally contain further heteroatoms in the ring, or said substituted alkyl carries a group

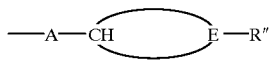

in which:

E is a nitrogen atom or a CH group;

R" is hydrogen, ($C_1$–$C_8$)-alkyl which is unsubstituted or substituted by OH or substituted ($C_1$–$C_8$)-alkyl, ($C_1$–$C_6$)-alkoxy, —CN, —COOH, ($C_2$–$C_6$)-alkoxycarbonyl, ($C_2$–$C_8$)-alkanoyl, aralkanoyl having up to 10 carbon atoms, aroyl having up to 11 carbon atoms, an aromatic group, —NR(6)R(7), —CONR(4)R(5);

R(4) and R(5) independently of one another are hydrogen or ($C_1$–$C_8$)-alkyl;

where the cyclic system of the formula

is a 3–8-membered saturated aliphatic or heterocyclic ring system having a nitrogen atom, and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where the aryl radicals mentioned can be unsubstituted or substituted by unsubstituted ($C_1$–$C_8$)-alkyl or substituted ($C_1$–$C_8$)-alkyl, halogen, —NO$_2$, ($C_2$–$C_6$)-alkoxycarbonyl, COOH, —OR(3), NR(6)R(7), —CONR(4)R(5), —SO$_2$ NR(6)R(7) or S(O)$_n$R(40), where R(1) and the guanidinocarbonyl radical can be in any desired position of the 5- or 6-membered ring of the indole system, or a pharmaceutically tolerable salt thereof;

da) a heterocyclic guanidine derivative of the formula

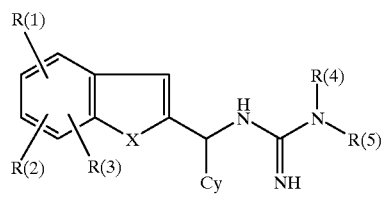

in which:

X is —O—, —S—, —NH—, —N[($C_1$–$C_4$)-alkyl]- or —N(phenyl)-;

R(1), R(2) and R(3) are hydrogen, halogen, ($C_1$–$C_4$)-alkyl, ($C_1$–$C_4$)-alkyl-O—, phenyl, benzyl; or two of the substituents R(1), R(2) and R(3) together with one side of the benzo system are a 4–6-membered carbocyclic ring;

R(4) and R(5) independently of one another are hydrogen, ($C_1$–$C_{12}$)-alkyl, benzhydryl, aralkyl, which is unsubstituted or substituted by one or more substituents from the groups halogen, ($C_1$–$C_4$)-alkyl, ($C_1$–$C_4$)-alkyl-O— or —CF$_3$, —(CH$_2$)$_m$—CH$_2$—T, m is zero to 3;

T is —CO—O—T(1);

T(1) is hydrogen or ($C_1$–$C_4$)-alkyl;

Cy is a benzo-fused unsaturated or dihydro-5-membered ring heterocycle,

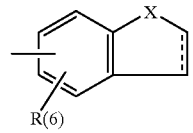

a pyrazole or imidazole ring of the formulae

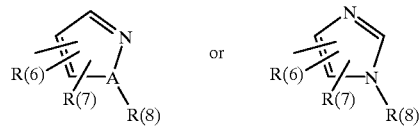

a naphthyl radical or a dihydro or tetrahydronaphthyl radical

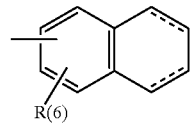

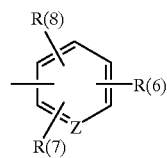

a 2-, 3- or 4-pyridyl radical R(7)
Z is N— or CH;

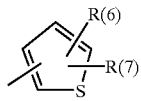

a thienyl radical

R(6) is hydrogen, halogen, hydroxyl, $(C_1-C_{10})$-alkyl, $(C_1-C_{10})$-alkyl-O—, phenoxy, $(C_1-C_{10})$-alkyloxymethyloxy- or —(O)$_n$S—R(9);

R(9) is $(C_1-C_{10})$-alkyl, thienyl, pyridyl, thiazolyl, thiadiazolyl, imidazolyl, pyrazolyl or phenyl, each of which is unsubstituted or mono- or disubstituted by halogen, $(C_1-C_4)$-alkyl or $(C_1-C_4)$-alkyl-O—;

R(7) and R(8) are hydrogen, halogen, hydroxyl, $(C_1-C_{10})$-alkyl, $(C_1-C_{10})$-alkyl-O—, phenyl, phenoxy or $(C_1-C_{10})$-alkoxymethyloxy; or Cy is phenyl, which is unsubstituted or is mono- or disubstituted by halogen, $(C_1-C_4)$-alkyl or $(C_1-C_4)$-alkyl-O—; or Cy is —Gr—Am;

Gr is —R(13)—R(12)—(CH$_2$)$_q$—C[W][W(1)]—(CH$_2$)$_{q'}$—; R(13)R(14)— or —R(15)—;

R(12) is a single bond, —O—, —(O)$_n$S—, —CO— or —CONH—;

R(13) is a single bond, phenyl, thienyl, pyridyl, thiazolyl, thiadiazolyl, imidazolyl or pyrazolyl;

R(14) is a single bond or SO$_2$—;

R(15) is $(C_2-C_{10})$-alkenyl or $(C_2-C_{10})$-alkynyl;

W and W(1) independently of one another are hydrogen, $(C_1-C_4)$-alkyl; or

W and W(1) cyclically connected to one another are a $(C_3-C_8)$-hydrocarbon ring;

q and q' are zero to 9;

Am is —NR(10)R(11);

R(10) is hydrogen, $(C_1-C_4)$-alkyl or benzyl,

R(11) is $(C_1-C_4)$-alkyl, phenyl or benzyl; or

R(10) and R(11) together are a $(C_3-C_{10})$-alkylene group, which is unsubstituted or substituted by —COOH, $(C_1-C_5)$-alkoxycarbonyl, $(C_2-C_4)$-hydroxylalkylene or benzyl; or Am is pyrrolyl, pyridyl, pyrazolyl, morpholinyl, dihydropyridyl, tetrahydropyridyl, quinuclidinyl, imidazolyl, 3-azabicyclo[3.2.1]octyl, which is unsubstituted or substituted by $(C_1-C_4)$-alkyl, or Am is azabicyclo[3.2.2]nonyl; or Am is a piperazine group of the formula

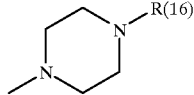

R(16) is hydrogen, $(C_1-C_4)$-alkyl, $(C_3-C_6)$-cycloalkyl, phenyl, tolyl, methoxyphenyl, halophenyl, diphenylmethylene, benzyl or pyridyl; or Am is an azido group —(O)t—(CH$_2$)q—C[W][W(1)]—(CH$_2$)q'—N$_3$;

t is zero or 1;

where W and W(1) have the previously indicated meaning;

or a optical enantiomer or pharmacologically tolerable salt thereof; and db) a guanidine compound of the formula

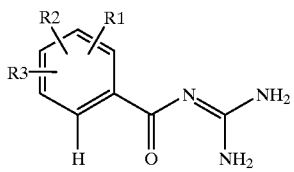

where R1=R2 is H, halogen, alkyl, CN, NO$_2$, perfluoroalkyl, SO$_n$CF$_3$; R3 is CH=CH$_2$, CH$_2$—CH=CH$_2$, CH$_2$—CH$_2$—CH=CH$_2$, cycloalkenyl, cycloalkenylalkyl; R4 is alkyl, (substituted) phenyl, or a pharmacologically tolerable salt thereof.

8. A method as claimed in claim 7, wherein the compound bg) of the formula RCONHC(:NH)NH$_2$ is

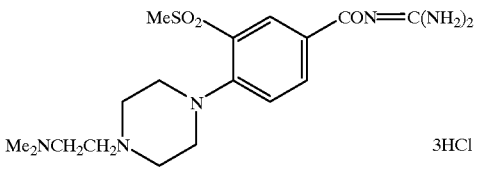

3HCl

9. A method as claimed in claim 1, wherein the Na$^+$/H$^+$ exchange inhibitor is selected from a) a benzoylguanidine of the formula

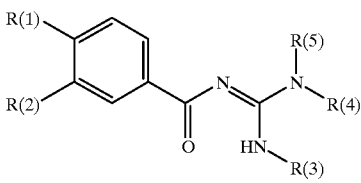

in which:

R(1) or R(2) is R(6)—S(O)$_n$— or R(7)R(8)N—O$_2$S—;

and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chlorine, methyl and methoxy;

or the other substituent R(1) or R(2) in each case is R(6)—S(O)$_n$ or R(7)R(8)N—;

n is zero, 1 or 2;

R(6) is $(C_1-C_6)$-alkyl, $(C_5-C_7)$-cycloalkyl, cyclopentylmethyl, cyclohexylmethyl or phenyl, which is unsubstituted or substituted by 1–3 substituents selected from the group consisting of fluorine, chlorine, methyl and methoxy;

R(7) and R(8) identically or differently are H or $(C_1-C_6)$-alkyl; or

R(7) is phenyl-(CH$_2$)$_m$;

m is 1–4; or

R(7) is phenyl, which is unsubstituted or substituted by 1–2 substituents selected from the group consisting of fluorine, chlorine, methyl and methoxy; or R(7) and R(8) together are a straight-chain or branched $(C_4-C_7)$-chain, where the chain can additionally be interrupted by O, S or NR(9);

R(9) is H or methyl; or

R(7) and R(8) together with the nitrogen atom to which they are bonded, are a dihydroindole, tetrahydroquinoline or tetrahydroisoquinoline system;

R(3), R(4) and R(5) independently of one another are H or ($C_1$–$C_2$)-alkyl, or R(3) and R(4) together are a ($C_2$–$C_4$)-alkylene chain; or R(4) and R(5) together are a ($C_4$–$C_7$)-alkylene chain;

or a pharmaceutically tolerable salt thereof;

b) a benzoylguanidine of the formula

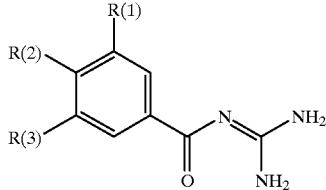

in which:

R(1) is R(4)—$SO_m$ or R(5)R(6)N—$SO_2$—;

m is zero, 1 or 2;

R(4) and R(5) are $C_1$–$C_8$-alkyl, $C_3$–$C_6$-alkenyl or —$C_nH_{2n}$—R(7);

n is zero, 1, 2, 3 or 4;

R(7) is $C_5$–$C_7$-cycloalkyl or phenyl, which is unsubstituted or substituted by 1–3 substituents selected from the group consisting of F, Cl, $CF_3$, methyl, methoxy and NR(8)R(9);

R(8) and R(9) are H or $C_1$–$C_4$-alkyl; or

R(5) is H;

R(6) is H or $C_1$–$C_4$-alkyl, or

R(5) and R(6) together are 4 or 5 methylene groups, of which one $CH_2$ group can be replaced by an O, S, NH, N—$CH_3$ or N-benzyl;

R(2) is hydrogen, F, Cl, Br, ($C_1$–$C_4$)-alkyl-, O—$(CH_2)_mC_pF_{2p+1}$ or —X—R(10);

m is zero or 1;

p is 1, 2 or 3;

X is O, S or NR(11);

R(10) is H, $C_1$–$C_6$-alkyl, $C_5$–$C_7$-cycloalkyl, cyclohexylmethyl, cyclopentylmethyl or —$C_nH_{2n}$—R(12);

n is zero, 1, 2, 3 or 4;

R(12) is phenyl, which is unsubstituted or substituted by 1–3 substituents selected from the group consisting of F, Cl, $CF_3$, methyl, methoxy and NR(8)R(9);

R(8) and R(9) are H or $C_1$–$C_4$-alkyl;

R(11) is hydrogen or $C_1$–$C_3$-alkyl; or

R(10) and R(11) together are 4 or 5 methylene groups, of which one $CH_2$ group can be replaced by O, S, NH, N—$CH_3$ or N-benzyl;

R(3) is defined as R(1), or is $C_1$–$C_6$-alkyl, nitro, cyano, trifluoromethyl, F, Cl, Br, I or —X—R(10);

X is O, S or NR(11);

R(10) is H, $C_1$–$C_6$-alkyl, $C_5$–$C_7$-cycloalkyl, cyclohexylmethyl, cyclopentylmethyl or —$C_nH_{2n}$—R(12);

n is zero to 4;

R(12) is phenyl, which is unsubstituted or substituted by 1–3 substituents selected from the group consisting of F, Cl, $CF_3$, methyl, methoxy und NR(8)R(9);

R(8) and R(9) are H or $C_1$–$C_4$-alkyl;

R(11) is $C_1$–$C_3$-alkyl, or

R(10) and R(11) together are 4 or 5 methylene groups, of which one $CH_2$ group can be replaced by O, S, NH, N—$CH_3$ or N-benzyl;

or a pharmaceutically tolerable salt thereof;

c) an ortho-substituted benzoylguanidine of the formula

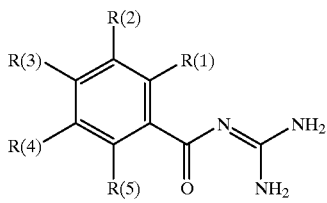

in which:

R(1) is F, Cl, Br, I, $C_1$–$C_6$-alkyl or —X—R(6);

X is O, S, NR(7) or Y—ZO;

Y is O or NR(7);

Z is C or SO;

R(6) is H, $C_1$–$C_6$-alkyl, $C_5$–$C_7$-cycloalkyl, cyclohexylmethyl, cyclopentylmethyl, —$(CH_2)_mC_pF_{2p+1}$ or —$C_nH_{2n}$—R(8);

m is zero or 1;

p is 1–3;

n is zero to 4;

R(8) is phenyl, which is unsubstituted or substituted by 1–3 substituents selected from the group consisting of the groups F, Cl, $CF_3$, methyl, methoxy and NR(9)R(10);

R(9) and R(10) are H or $C_1$–$C_4$-alkyl;

R(7) is H or $C_1$–$C_3$-alkyl; or

R(6) and R(7) together are 4 or 5 methylene groups, of which one $CH_2$ group can be replaced by O, S, NH, N—$CH_3$ or N-benzyl;

R(3) is H or —X—R(6);

X is O, S, NR(7) or Y—ZO;

R(7) is H or $C_1$–$C_3$-alkyl;

Y is O or NR(7); where Y is bonded to the phenyl radical of the formula I, z is C or SO;

R(6) is H, $C_1$–$C_6$-alkyl, $C_5$–$C_7$-cycloalkyl, cyclohexylmethyl, cyclopentylmethyl, —$(CH_2)_mC_pF_{2p+1}$ or —$C_nH_{2n}$—R(8);

m is zero or 1;

p is 1–3;

n is zero to 4;

R(8) is phenyl, which is unsubstituted or substituted by 1–3 substituents selected from the group consisting of F, Cl, $CF_3$, methyl, methoxy and NR(9)R(10);

R(9) and R(10) are H or $C_1$–$C_4$-alkyl; or

R(6) and R(7) together are 4 or 5 methylene groups, of which one $CH_2$ group can be replaced by O, S, NH, N—$CH_3$ or N-benzyl;

R(2) and R(4) identically or differently are R(11)—$SO_q$— or R(12)R(13)N—$SO_2$—;

q is zero–2;

R(11) is $C_1$–$C_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);

R(9) and R(10) are H or $C_1$–$C_4$-alkyl;

R(12) and R(13) are defined as R(6) and R(7);

or one of the two radicals R(2) or R(4) is hydrogen or is defined as R(1);

R(5) is H, methyl, F, Cl or methoxy, or a pharmaceutically tolerable salt thereof;

d) a benzoylguanidine of the formula

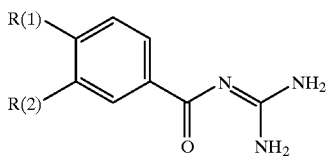

in which:
R(1) or R(2) is an amino group —NR(3)R(4);
R(3) and R(4) identically or differently are H, $C_1$–$C_6$-alkyl or $C_3$–$C_7$-cycloalkyl; or
R(3) is phenyl-$(CH_2)_p$—;
p is 0, 1, 2, 3 or 4; or
R(3) is phenyl, where the phenyl in each case is unsubstituted or carries one to two substituents selected from the group consisting of fluorine, chlorine, methyl and methoxy; or
R(3) and R(4) together can be a straight-chain or branched $C_4$–$C_7$-methylene chain, where one —$CH_2$— member of the methylene chain can be replaced by oxygen, S or NR(5); R(5) is H or lower alkyl;
the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy, where the respective phenyl radical is unsubstituted or carries one to two substituents selected from the group consisting of methyl, methoxy, fluorine and chlorine;
m is 1, 2 or 3;
or a pharmaceutically tolerable salt thereof;
e) a benzoylguanidine of the formula

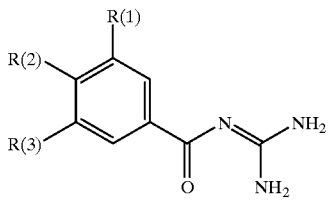

in which:
R(1) is R(4)—$SO_m$ or R(5)R(6)N—$SO_2$—;
m is zero, 1 or 2;
R(4) and R(5) are $C_1$–$C_8$-alkyl, $C_3$–$C_6$-alkenyl or —$C_nH_{2n}$—R(7);
n is zero, 1, 2, 3 or 4;
R(7) is $C_5$–$C_7$-cycloalkyl or phenyl, which is unsubstituted or substituted by 1–3 substituents selected from the group consisting of F, Cl, $CF_3$, methyl, methoxy and NR(8)R(9);
R(8) and R(9) or are H or $C_1$–$C_4$-alkyl; or
R(5) is H;
R(6) is H or $C_1$–$C_4$-alkyl; or
R(5) and R(6) together are 4 or 5 methylene groups, of which one $CH_2$ group can be replaced by an O, S, NH, N—$CH_3$ or N-benzyl;
R(2) is hydrogen, straight-chain or branched $(C_5$–$C_8)$-alkyl, —CR(13)=CHR(12) or —C≡CR(12);
R(12) is phenyl, which is unsubstituted or substituted by 1–3 substituents selected from the group consisting of F, Cl, $CF_3$, methyl, methoxy and NR(14)R(15);
R(14) and R(15) are H or $(C_1$–$C_4)$-alkyl; or R(12) is $(C_1$–$C_9)$-heteroaryl, which is unsubstituted or substituted as phenyl, or
R(12) is $(C_1$–$C_6)$-alkyl, which is unsubstituted or substituted by 1–3 OH, or
R(12) is $(C_3$–$C_8)$-cycloalkyl;
R(13) is hydrogen or methyl, or
R(12) is $(C_3$–$C_8)$-cycloalkyl, $(C_3$–$C_8)$-cycloalkyl-$(C_1$–$C_4)$-alkyl, phenyl, $C_6H_5$—$(C_1$–$C_4)$-alkyl, naphthyl, biphenylyl, 1,1-diphenyl-$(C_1$–$C_4)$-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2);
and where the aromatic substituents R(2) and R(3) are unsubstituted or substituted by 1–3 substituents from the groups F, Cl, $CF_3$, $(C_1$–$C_4)$-alkyl or -alkoxy, or NR(10)R(11) with R(10) and R(11) being H or $(C_1$–$C_4)$-alkyl;
or a pharmaceutically tolerable salt thereof;
f) a benzoylguanidine of the formula

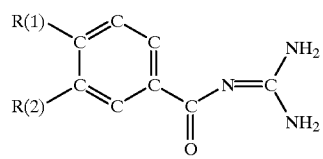

in which:
R(1) or R(2) is R(3)—$S(O)_n$— or R(4)R(5)N—$SO_2$—
the other substituent R(1) or R(2) in each case is H, OH, F, Cl, Br, I, $C_1$–$C_4$-alkyl, $C_1$–$C_4$-alkoxy, benzyloxy or phenoxy, which is unsubstituted or carries one to three substituents selected from the group consisting of fluorine, chlorine, methyl, methoxy, hydroxyl or benzyloxy,
R(3)—$S(O)_n$, —NR(4)R(5) or 3,4-dehydropiperidine
R(3) is $C_1$–$C_6$-alkyl, $C_5$–$C_7$-cycloalkyl, cyclopentylmethyl, cyclohexylmethyl or phenyl, which is unsubstituted or carries one to three substituents selected from the group consisting of fluorine, chlorine, methyl and methoxy;
R(4) and R(5) identically or differently, are H or $C_1$–$C_6$-alkyl;
R(4) is phenyl-$(CH_2)_m$—;
m is 1, 2, 3 or 4; or
R(4) is phenyl, which is unsubstituted or carries one to two substituents selected from the group consisting of fluorine, chlorine, methyl and methoxy; or
R(4) and R(5) together are a straight-chain or branched $C_4$–$C_7$-chain, where the chain can additionally be interrupted by O, S or NR(6),
R(6) is H or methyl; or
R(4) and R(5) together with the nitrogen atom to which they are bonded, are a dihydroindole, tetrahydroquinoline or tetrahydroisoquinoline system;
n is zero, 1 or 2;
or a pharmaceutically tolerable salt thereof;

g) an isoquinoline of the formula

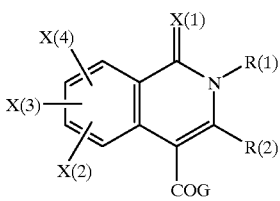

in which:
R(1) is hydrogen, alkyl, cycloalkyl, arylalkyl, alkenyl, substituted aminoalkyl or an aryl or heteroaryl ring; where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl, R(2) is hydrogen, halogen, alkyl or aryl; which is unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, G is —N=C{[NR(3)R(4)][N(R5)R(6)]}

X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;

X(1) is hydrogen, oxygen, sulfur or NR(7);
  R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;
    in which substituents each alkyl chain or alkenyl chain can be interrupted by oxygen, sulfur or NR(8);
  R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;

or a pharmaceutically tolerable salt thereof;

h) a compound of the formula

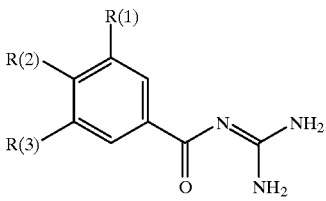

in which:
R(1) is hydrogen, F, Cl, Br, I, —NO$_2$, —C≡N, —CF$_3$, R(4)—SO$_m$ or R(5)R(6)N—SO$_2$—;
  m is zero, 1 or 2;
  R(4) and R(5) are (C$_1$–C$_8$)-alkyl, (C$_3$–C$_6$)-alkenyl, —C$_n$H$_{2n}$—R(7) or CF3;
    n is zero, 1, 2, 3 or 4;
    R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);
      R(8) and R(9) are H or C$_1$–C$_4$-alkyl; or
  R(5) is H;
  R(6) is H or (C$_1$–C$_4$)-alkyl; or
  R(5) and R(6) together are 4 or 5 methylene groups, of which one CH$_2$ group can be replaced by oxygen, S, NH, N—CH$_3$ or N-benzyl;

R(2) is —SR(10), —OR(10), —NHR(10), —NR(10)R(11), —CHR(10)R(12), —[CR(12)R(13)OR(13')], —{C—[CH$_2$—OR(13')]R(12)(R(13)} or —[CR(18)R(17)]$_p$—(CO)—[CR(19)R(20)]$_q$—R(14);
  R(10) and R(11) identically or differently are —[CHR(16)]$_s$—(CH$_2$)$_p$—(CHOH)$_q$—(CH$_2$)$_r$—(CHOH)$_t$—R(21) or —(CH$_2$)$_p$—O—(CH$_2$—CH$_2$O)$_q$—R(21),
  R(21) is hydrogen, methyl, p, q, r identically or differently
    are zero, 1, 2, 3 or 4;
  s is zero or 1;
  t is 1, 2, 3 or 4;
  R(12) and R(13) identically or differently are hydrogen, (C$_1$–C$_6$)-alkyl or, together with the carbon atom carrying them, are a (C$_3$–C$_8$)-cycloalkyl,
  R(13') is hydrogen or (C$_1$–C$_4$)-alkyl;
  R(14) is H, (C$_1$–C$_6$)-alkyl, (C$_3$–C$_8$)-cycloalkyl or —C$_a$H$_{2a}$—R(15);
    a is zero, 1, 2, 3 or 4;
    R(15) is phenyl, which is unsubstituted or substituted by 1–3 substituents selected from the group consisting of F, Cl, CF$_3$, methyl, methoxy and NR(8)R(9);
      R(8) and R(9) are H or (C$_1$–C$_4$)-alkyl; or
    R(15) is (C$_1$–C$_9$)-heteroaryl, which is unsubstituted or substituted as phenyl, or
    R(15) is (C$_1$–C$_6$)-alkyl, which is unsubstituted or substituted by 1–3 OH;
  R(16), R(17), R(18), R(19) and R(20) are hydrogen or (C$_1$–C$_3$)-alkyl;

R(3) is defined as R(1), or
R(3) is (C$_1$–C$_6$)-alkyl or —X—R(22);
  X is oxygen, S or NR(16);
    R(16) is H or (C$_1$–C$_3$)-alkyl; or
    R(22) and R(16) together are 4 or 5 methylene groups, of which one CH$_2$ group can be replaced by oxygen, S, NH, N—CH$_3$ or N-benzyl;
  R(22) is defined as R(14);

or a pharmaceutically tolerable salt thereof;
i) a benzoylguanidine of the formula

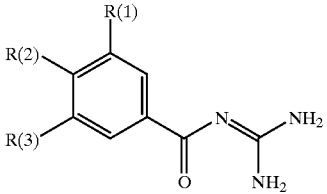

in which:
R(1) is hydrogen, F, Cl, Br, I, —NO$_2$, —C≡N, R(16)—C$_p$H$_{2p}$—O$_q$, R(4)—SO$_m$ or R(5)R(6)N—SO$_2$—;
  m is zero, 1 or 2;
  p is zero or 1;
  q is zero, 1, 2 or 3;

R(16) is $C_rF_{2r+1}$;
r isn 1, 2 or 3;
R(4) and R(5) are $(C_1–C_8)$-alkyl, $(C_3–C_6)$-alkenyl, $—C_nH_{2n}—R(7)$ or $CF_3$;
n is zero, 1, 2, 3 or 4;
R(7) is $(C_3–C_7)$-cycloalkyl or phenyl, which is not substituted or is substituted by 1–3 substituents selected from the group consisting of F, Cl, $CF_3$, methyl, methoxy and NR(8)R(9);
R(8) and R(9) are H or $C_1–C_4$-alkyl; or
R(5) is H;
R(6) is H or $(C_1–C_4)$-alkyl; or
R(5) and R(6) together are 4 or 5 methylene groups, of which one $CH_2$ group can be replaced by oxygen, S, NH, N—$CH_3$ or N-benzyl,
R(2) is $(C_1–C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is —SR(10), —OR(10), —NR(10)R(11), —CR(10)R(11)R(12);
R(10) is $—C_aH_{2a}—(C_1–C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10) or are hydrogen or $(C_1–C_4)$-alkyl;
R(3) is defined as R(1), or is $(C_1–C_6)$-alkyl or —X—R(13);
X is oxygen, S, or NR(14);
R(14) is H or $(C_1–C_3)$-alkyl;
R(13) is H, $(C_1–C_6)$-alkyl, $(C_3–C_8)$-cycloalkyl or $—C_bH_{2b}—R(15)$;
b is zero, 1, 2, 3 or 4; or
R(13) and R(14) together are 4 or 5 methylene groups, of which one $CH_2$ group can be replaced by oxygen, S, NH, N—$CH_3$ or N-benzyl; R(15) is phenyl, which is unsubstituted or substituted by 1–3 substituents selected from the group consisting of F, Cl, $CF_3$, methyl, methoxy and NR(8)R(9);
R(8) and R(9) are H or $(C_1–C_4)$-alkyl;
or a pharmaceutically tolerable salt thereof;
k) a benzoylguanidine of the formula

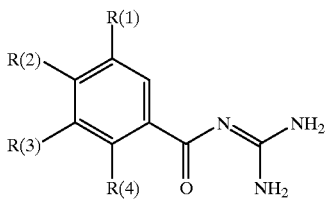

in which:
one of the substituents R(1), R(2), R(3) or R(4):
is an amino group —NR(5)[$C_nH_{2n}$—R(6)];
R(5) is hydrogen or $C_{(1-6)}$-alkyl;
n is zero, 1, 2, 3 or 4;
R(6) is H or $C_{(1-4)}$-alkyl;
in which one $CH_2$ group can be replaced by 1 sulfur atom or a group NR(7);
R(7) is hydrogen, methyl or ethyl; or
R(6) is $C_{(3-8)}$-cycloalkyl or phenyl, which is unsubstituted or carries 1, 2 or 3 substituents selected from the group consisting of F, Cl, Br, methyl, methoxy, —NR(8)R(9);
R(8) and R(9) are H, methyl or ethyl; or
R(5) and R(6) together with the nitrogen atom are a 5-, 6- or 7-membered ring, in which 1 carbon atom can be replaced by oxygen, S or NR(10);
R(10) is H, $C_{(1-3)}$-alkyl or benzyl;
and the other substituents R(1), R(2), R(3), R(4) in each case are:
hydrogen, F, Cl, Br, I, CN, $CF_3$, $NO_2$, $CF_3$—O—, $C_mF_{2m+1}$—$CH_2$—O— or
R(11)—$C_qH_{2q}$—$X_p$—;
m is 1, 2 or 3;
q is zero, 1, 2, 3 or 4;
p is zero or 1;
X is oxygen or NR(12);
R(12) is H or $C_{(1-3)}$-alkyl;
R(11) is hydrogen, $C_{(1-6)}$-alkyl, $C_{(3-8)}$-cycloalkyl or phenyl, which is unsubstituted or substituted by 1, 2 or 3 substituents selected from the group consisting of F, Cl, $CH_3$, $CH_3$—O— and NR(13)R(14);
R(13), R(14) are H, methyl or ethyl;
or a pharmaceutically tolerable salt thereof;
l) a benzoylguanidine of the formula

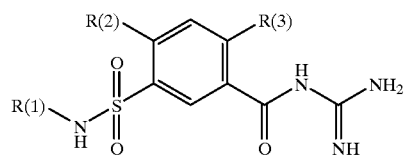

in which
R(1) is R(4)R(5)N—C(X)—;
X is oxygen, S or N—R(6);
R(4) and R(5) identically or differently, are H, $(C_1–C_8)$-alkyl, $(C_3–C_6)$-alkenyl or $—C_nH_{2n}$—R(7);
n is zero, 1, 2, 3 or 4;
R(7) is $(C_5–C_7)$-cycloalkyl or phenyl, which is unsubstituted or substituted by 1–3 substituents selected from the group consisting of F, Cl, $CF_3$, methoxy and $(C_1–C_4)$-alkyl; or
R(4) and R(5) together are 4 or 5 methylene groups, of which one $CH_2$ group can be replaced by oxygen, S, NH, N—$CH_3$ or N-benzyl; R(6) is defined as R(4) or is amidine;
R(2) is H, F, Cl, Br, I, $(C_1–C_8)$-alkyl, 1-alkenyl or 1-alkynyl, $(C_3–C_8)$-cycloalkyl, $(C_3–C_8)$-cycloalkyl-$(C_1–C_4)$-alkyl, phenyl, $C_6H_5$—$(C_1–C_4)$-alkyl, naphthyl, biphenylyl, 1,1-diphenyl-$(C_1–C_4)$-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);
W is oxygen, S or NR(9);
R(8) is H, $(C_1–C_6)$-alkyl, $(C_5–C_7)$-cycloalkyl, cyclohexylmethyl, cyclopentylmethyl, —$(CH_2)_mC_pF_{2p+1}$ or —$C_qH_{2q}$—R(10);
m is zero or 1;
p is 1, 2 or 3;
q is zero, 1, 2, 3 or 4;
R(10) is phenyl, which is unsubstituted or substituted by 1–3 substituents selected from the group consisting of F, Cl, $CF_3$, methyl, methoxy and NR(11)R(12);
R(11) and R(12) are H or $(C_1–C_4)$-alkyl;

R(9) is H or ($C_1$–$C_3$)-alkyl; or

R(8) and R(9) together are 4 or 5 methylene groups, of which one $CH_2$ group can be replaced by oxygen, S, NH, N—$CH_3$ or N-benzyl;

R(3) is H, F, Cl, Br, I, ($C_1$–$C_6$)-alkyl or —W—R(8) as defined for R(2), and their pharmaceutically acceptable salts;

m) a benzoylguanidine of the formula

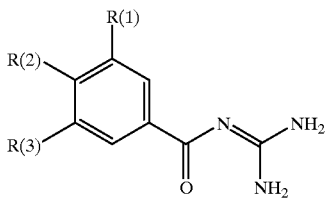

in which:

R(1), R(2), R(3) are hydrogen, F, Cl, Br, I or ($C_1$–$C_{12}$)-alkyl;

one of the substituents R(1), R(2) or R(3) is $N_3$, CN, OH or ($C_1$–$C_{10}$)-alkyloxy, if at least one of the remaining substituents R(1), R(2) or R(3) is a sufficiently lipophilic alkyl radical having 3 to 12 carbon atoms; or one of the substituents R(1), R(2) or R(3) is R(4)—$C_nH_{2n}$—$O_m$—;

m is zero or 1;

n is zero, 1, 2 or 3;

R(4) is $C_pF_{2p+1}$;

p is 1, 2 or 3, if n is zero or 1; or

R(4) is ($C_3$–$C_{12}$)-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);

R(5) and R(6) are hydrogen or ($C_1$–$C_4$)-alkyl;

or one of the substituents R(1), R(2) or R(3) is —C≡CR(5) or —C[R(6)]=CR(5);

R(5) is phenyl, which is unsubstituted or substituted by 1–3 substituents selected from the group consisting of F, Cl, $CF_3$, methyl, methoxy, hydroxyl, amino, methylamino and dimethylamino, ($C_1$–$C_9$)-heteroaryl, which is unsubstituted or substituted as phenyl, or R(5) is ($C_1$–$C_6$)-alkyl, which is unsubstituted or substituted by 1–3 OH; or R(5) is ($C_3$–$C_8$)-cycloalkyl, R(6) is hydrogen or methyl;

or a pharmaceutically tolerable salt thereof;

o) a benzoylguanidine of the formula

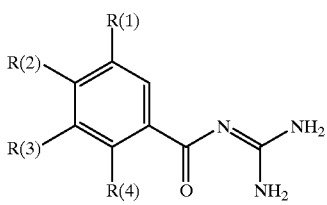

in which:

R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where X is oxygen, S or NR(14);

m is zero, 1 or 2;

o is zero or 1;

p is zero, 1 or 2;

q is zero, 1, 2, 3, 4, 5 or 6;

R(5) and R(6) are ($C_1$–$C_8$)-alkyl, ($C_3$–$C_6$)-alkenyl, —$C_nH_{2n}$—R(8) or $CF_3$;

n is zero, 1, 2, 3 or 4;

R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);

R(9) and R(10) are H or $C_1$–$C_4$-alkyl; or

R(6) is H;

R(7) is H or ($C_1$–$C_4$)-alkyl; or

R(6) and R(7) together are 4 or 5 methylene groups, of which one $CH_2$ group can be replaced by oxygen, S, NH, N—$CH_3$ or N-benzyl;

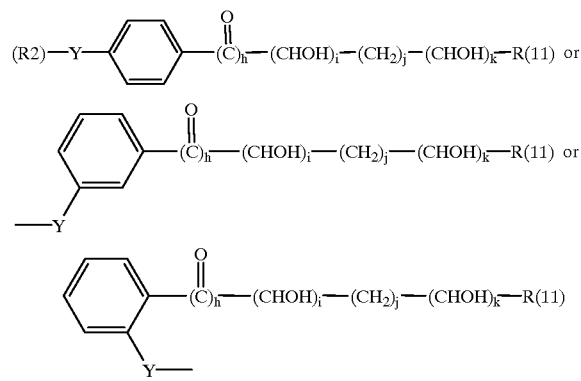

Y is oxygen, —S— or —NR(12)—;

R(11) and R(12) are hydrogen or ($C_1$–$C_3$)-alkyl;

h is zero or 1;

i, j and k independently are zero, 1, 2, 3 or 4;

but where h, i and k are not simultaneously zero,

R(3) is defined as R(1), or is ($C_1$–$C_6$)-alkyl or —X—R(13);

X is oxygen, S or NR(14);

R(14) is H or ($C_1$–$C_3$)-alkyl;

R(13) is H, ($C_1$–$C_6$)-alkyl, ($C_3$–$C_8$)-cycloalkyl or —$C_bH_{2b}$—R(15);

b is zero, 1, 2, 3 or 4; or

R(13) and R(14) together are 4 or 5 methylene groups, where one $CH_2$ group can be replaced by oxygen, S, NH, N—$CH_3$ or N-benzyl;

R(15) is phenyl, which is unsubstituted or substituted by 1–3 substituents selected from the group consisting of F, Cl, $CF_3$, methyl, methoxy and NR(9)R(10);

R(9) and R(10) are H or ($C_1$–$C_4$)-alkyl;

R(4) is hydrogen, —OR(16) or —NR(16)R(17); R(16) and R(17) independently are hydrogen or ($C_1$–$C_3$)-alkyl;

or a pharmaceutically tolerable salt thereof;

p) a benzoylguanidine of the formula

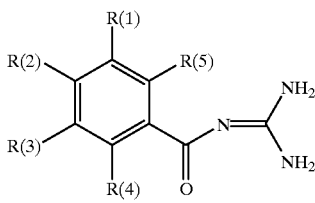

in which:
R(1) is R(6)—CO or R(7)R(8)N—CO;
R(6) is $(C_1-C_8)$-alkyl, $(C_1-C_8)$-perfluoroalkyl, $(C_3-C_8)$-alkenyl or —$C_nH_{2n}$—R(9);
n is zero, 1, 2, 3 or 4;
R(9) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
R(10) and R(11) are H, $(C_1-C_4)$-alkyl or $(C_1-C_4)$-perfluoroalkyl;
R(7) is H, $(C_1-C_8)$-alkyl, $(C_1-C_8)$-perfluoroalkyl, $(C_3-C_8)$-alkenyl or —$C_nH_{2n}$—R(12);
n is zero, 1, 2, 3 or 4;
R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
R(13) and R(14) are H, $(C_1-C_4)$-alkyl or $(C_1-C_4)$-perfluoroalkyl;
R(8) is H, $(C_1-C_4)$-alkyl or $(C_1-C_4)$-perfluoroalkyl; or
R(7) and R(8) together are 4 or 5 methylene groups, of which one $CH_2$ group can be replaced by oxygen, S, NH, N—$CH_3$ or N-benzyl;
R(2) is defined as R(1), or is H, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}$R(15);
n is zero, 1, 2, 3 or 4;
R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
R(16) and R(17) are H, $(C_1-C_4)$-alkyl or $(C_1-C_4)$-perfluoroalkyl; or
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is SR(18), —OR(18), —NR(18)R(19), —CR(18)R(19)R(20); R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(19) and R(20) independently of one another are defined as R(18) or are hydrogen, $(C_1-C_4)$-alkyl or $(C_1-C_4)$-perfluoroalkyl; or
R(2) is R(21)—$SO_m$ or R(22)R(23)N—$SO_2$—;
m is 1 or 2;
R(21) is $(C_1-C_8)$-alkyl, $(C_1-C_8)$-perfluoroalkyl, $(C_3-C_8)$-alkenyl, —$C_nH_{2n}$—R(24),
n is zero, 1, 2, 3 or 4;
R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
R(27) and R(28) are H, $(C_1-C_4)$-alkyl or $(C_1-C_4)$-perfluoroalkyl;
R(22) is H, $(C_1-C_8)$-alkyl, $(C_1-C_8)$-perfluoroalkyl, $(C_3-C_8)$-alkenyl, —$C_nH_{2n}$—R(29);
n is zero, 1, 2, 3 or 4;
R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
R(30) and R(31) are H, $(C_1-C_4)$-alkyl or $(C_1-C_4)$-perfluoroalkyl;
R(23) is H, $(C_1-C_4)$-alkyl or $(C_1-C_4)$-perfluoroalkyl; or
R(22) and R(23) together are 4 or 5 methylene groups, of which one $CH_2$ group can be replaced by oxygen, S, NH, N—$CH_3$ or N-benzyl; or
R(2) is R(33)X—;
X is oxygen, S, NR(34), (D=O)A—, NR(34)C=MN$^{(*)}$R(35)—;
M is oxygen or S;
A is oxygen or NR(34);
D is C or SO;
R(33) is $(C_1-C_8)$-alkyl, $(C_3-C_8)$-alkenyl, $(CH_2)_bC_dF_{2d+1}$, —$C_nH_{2n}$—R(36),
b is zero or 1;
d is 1, 2, 3, 4, 5, 6 or 7;
n is zero, 1, 2, 3 or 4;
R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
R(37) and R(38) are H, $(C_1-C_4)$-alkyl or $(C_1-C_4)$-perfluoroalkyl;
R(34) is H, $(C_1-C_4)$-alkyl or $(C_1-C_4)$-perfluoroalkyl;
R(35) is defined as R(33); or
R(33) and R(34) together are 4 or 5 methylene groups, of which one $CH_2$ group can be replaced by oxygen, S, NH, N—$CH_3$ or N-benzyl;
where A and $N^{(*)}$ are bonded to the phenyl nucleus of the benzoylguanidine parent structure; or
R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR(49)R(50)]$_v$—R(44);
R(40), R(41) identically or differently are —$(CH_2)_p$—$(CHOH)_q$—$(CH_2)_r$—$(CHOH)_t$—R(51) or —$(CH_2)_p$—O—$(CH_2—CH_2O)_q$—R(51);
R(51) is hydrogen or methyl;
u is 1, 2, 3 or 4;
v is zero, 1, 2, 3 or 4;
p, q, r identically or differently are zero, 1, 2, 3 or 4;
t is 1, 2, 3 or 4;
R(42) and R(43) identically or differently are hydrogen or $(C_1-C_6)$-alkyl; or
R(42) and R(43) together with the carbon atom carrying them form a $(C_3-C_8)$-cycloalkyl;
R(44) is H, $(C_1-C_6)$-alkyl, $(C_3-C_8)$-cycloalkyl or —$C_eH_{2e}$—R(45);
e is zero, 1, 2, 3 or 4;
R(45) is phenyl, which is unsubstituted or substituted by 1–3 substituents from the group consisting of F, Cl, CF$_3$, methyl, methoxy and NR(52)R(53);
R(52) and R(53) are H or (C$_1$–C$_4$)-alkyl, or
R(45) is (C$_1$–C$_9$)-heteroaryl, which is unsubstituted or substituted as phenyl; or
R(45) is (C$_1$–C$_6$)-alkyl, which is unsubstituted or substituted by 1–3 OH;
R(46), R(47), R(48), R(49) and R(50) are hydrogen or methyl; or R(2) is R(55)—NH—SO$_2$—;
R(55) is R(56)R(57)N—(C=Y)—;
Y is oxygen, S or N—R(58);
R(56) and R(57) identically or differently are H, (C$_1$–C$_8$)-alkyl, (C$_3$–C$_6$)-alkenyl or —C$_f$H$_{2f}$—R(59);
f is zero, 1, 2, 3 or 4;
R(59) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(56) and R(57) together are 4 or 5 methylene groups, of which one CH$_2$ group can be replaced by oxygen, S, NH, N—CH$_3$ or N-benzyl;
R(58) is defined as R(56) or is amidine;

R(3), R(4) and R(5) independently of one another are defined as R(1) or R(2);

or a pharmaceutically tolerable salt thereof;

q) a benzoylguanidine of the formula

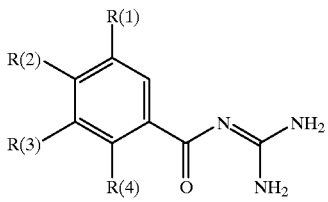

in which:
R(1) is hydrogen, F, Cl, Br, I, —NO$_2$, —CN, —X$_o$—(CH$_2$)$_p$—(CF$_2$)$_q$—CF$_3$, R(5)—SO$_m$—, R(6)—CO—, R(6)R(7)N—CO— or R(6)R(7)N—SO$_2$—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are (C$_1$–C$_8$)-alkyl, (C$_3$–C$_6$)-alkenyl, —C$_n$H$_{2n}$—R(8) or CF$_3$;
n is zero, 1, 2, 3 or 4;
R(8) is (C$_3$–C$_7$)-cycloalkyl, phenyl, which is not substituted or is substituted by 1 to 3 substituents selected from the group consisting of F, Cl, CF$_3$, methyl, methoxy and NR(9)R(10);
R(9) and R(10) are H or (C$_1$–C$_4$)-alkyl; or
R(6) is hydrogen;
R(7) is hydrogen or (C$_1$–C$_4$)-alkyl; or
R(6) and R(7) together are 4 or 5 methylene groups, of which one CH$_2$ group can be replaced by oxygen, S, NH, N—CH$_3$ or N-benzyl;

 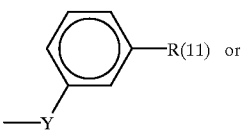

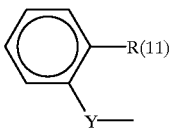

R(2)
R(11) is (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino and benzyl;
Y is oxygen, —S— or NR(12);
R(12) is H or (C$_1$–C$_4$)-alkyl;
R(3) is defined as R(1); or
R(3) is (C$_1$–C$_6$)-alkyl or —X—R(13);
X is oxygen, —S— or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);
b is zero, 1, 2, 3 or 4; or
R(13) and R(14) together are 4 or 5 methylene groups, of which one CH$_2$ group can be replaced by oxygen, S, NH, N—CH$_3$ or N-benzyl;
R(15) is phenyl, which is unsubstituted or substituted by 1–3 substituents selected from the group consisting of F, Cl, CF$_3$, methyl, methoxy and NR(9)R(10);
R(9) and R(10) are H or (C$_1$–C$_4$)-alkyl;
R(4) is hydrogen, —OR(16), —NR(16)R(17) or C$_r$F$_{2r+1}$;
R(16) and R(17) independently are hydrogen or (C$_1$–C$_3$)-alkyl;
r is 1, 2, 3 or 4;

or a pharmaceutically tolerable salt thereof;

r) a benzo-fused 5-membered ring heterocycle of the formula

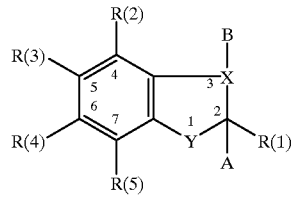

in which:
X is N or CR(6);
Y is oxygen, S or NR(7);
A, B together are a bond or
A, B are both hydrogen, if X is CR(6) and Y is NR(7) simultaneously; one of the substituents R(1) to R(6) is a —CO—N=C(NH$_2$)$_2$ group;
the other substituents R(1) to R(6) in each case are hydrogen, F, Cl, Br, I or (C$_1$–C$_6$)-alkyl;
up to two of the other substituents R(1) to R(6) are CN, NO$_2$, N$_3$, (C$_1$–C$_4$)-alkyloxy or CF$_3$;
up to one of the other substituents is R(8)—C$_n$H$_{2n}$—Z—;
n is zero to 10; where the alkylene chain —C$_n$H$_{2n}$— is straight-chain or branched and where one carbon atom can be replaced by an oxygen or sulfur atom or by a nitrogen atom;
R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH=CH—, and in which one methylene group can be replaced by an oxygen or sulfur atom or by a nitrogen atom; or R(8) is phenyl, which is unsubstituted or substituted by 1 to 3 substituents selected from the group consisting of F, Cl, Br, I, $CF_3$, $CH_3$—S(O)$_s$— or R(9)—W$_y$—;

s is zero, 1 or 2;
R(9) is H, methyl, ethyl,
W is oxygen or NR(10);
R(10) is H or methyl;
y is zero or 1; or R(8) is $C_mF_{2m+1}$;
m is 1 to 3; or R(8) is 1- or 2-naphthyl, pyridyl, quinolyl or isoquinolyl;

Z is —CO—, —$CH_2$— or —[CR(11)(OH)]$_q$—;
q is 1, 2 or 3;
R(11) is H or methyl; or z is oxygen or —NR(12)—;
R(12) is H or methyl; or z is —S(O)$_s$—;
s is zero, 1 or 2; or z is —$SO_2$—NR(13)—;
R(13) is H or ($C_1$–$C_4$)-alkyl;

R(7) is hydrogen, ($C_1$–$C_{10}$)-alkyl, ($C_2$–$C_{10}$)-alkenyl or R(8)—$C_nH_{2n}$—;

or a pharmaceutically tolerable salt thereof;

s) a benzoylguanidine of the formula

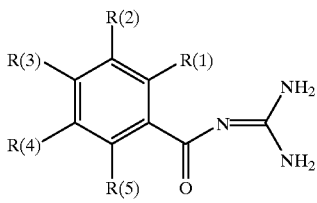

in which:

R(1), R(3) or R(4) is —NR(6) C=X NR(7)R(8);
X is oxygen or S;
R(6) is hydrogen, ($C_1$–$C_8$)-alkyl, ($C_1$–$C_8$)-perfluoroalkyl, ($C_3$–$C_8$)-alkenyl or —$C_nH_{2n}$—R(9);
n is zero, 1, 2, 3 or 4;
R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
R(10) and R(11) are H, ($C_1$–$C_4$)-alkyl or ($C_1$–$C_4$)-perfluoroalkyl;

R(7) is hydrogen, ($C_1$–$C_8$)-alkyl, ($C_1$–$C_8$)-perfluoroalkyl, ($C_3$–$C_8$)-alkenyl or —$C_oH_{2o}$—R(12);
o is zero, 1, 2, 3 or 4;
R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
R(13) and R(14) are H, ($C_1$–$C_4$)-alkyl or ($C_1$–$C_4$)-perfluoroalkyl;
R(8) is defined as R(7); or R(7) and R(8) together are 4 or 5 methylene groups, of which one $CH_2$ group can be replaced by oxygen, S, NH, N—$CH_3$ or N-benzyl;

the remaining substituents R(2), R(3), R(4), R(5) or R(1), R(2), R(4), R(5) or R(1), R(2), R(3), R(5) in each case independently of one another are hydrogen, F, Cl, Br, I, —$O_{ta}$($C_1$–$C_8$)-alkyl, —$O_{tb}$($C_3$–$C_8$)-alkenyl, —$O_{tc}$($CH_2$)$_b$$C_dF_{2d+1}$, —$O_{td}C_pH_{2p}$R(18), or up to 2 groups CN, $NO_2$, NR(16)R(17),
b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;
R(18) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(19)R(20);
R(19) and R(20) are hydrogen or ($C_1$–$C_4$)-alkyl or ($C_1$–$C_4$)-perfluoroalkyl;
R(16) is hydrogen, ($C_1$–$C_8$)-alkyl, ($C_1$–$C_8$)-perfluoroalkyl, ($C_3$–$C_8$)-alkenyl, —$C_qH_{2q}$—R(21),
q is zero, 1, 2, 3 or 4;
R(21) is ($C_3$–$C_8$)-cycloalkyl, phenyl, biphenylyl or naphthyl, where the aromatics are not substituted or are substituted by 1–3 substituents from the group F, Cl, $CF_3$, methyl, methoxy or NR(22)R(23), R(22) and R(23) are hydrogen, ($C_1$–$C_4$)-alkyl or ($C_1$–$C_4$)-perfluoroalkyl;
R(17) is hydrogen, ($C_1$–$C_8$)-alkyl, ($C_1$–$C_8$)-perfluoroalkyl, ($C_3$–$C_8$)-alkenyl, —$C_rH_{2r}$—R(24);
r is zero, 1, 2, 3 or 4;
R(24) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(25)R(26);
R(25) and R(26) are hydrogen, ($C_1$–$C_4$)-alkyl or ($C_1$–$C_4$)-perfluoroalkyl; or
R(16) and R(17) together are 4 or 5 methylene groups, of which one $CH_2$ group can be replaced by oxygen, S, NH, N—$CH_3$ or N-benzyl;

or a pharmaceutically tolerable salt thereof;

t) a diacyl-substituted guanidine of the formula I

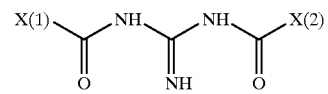

in which:
X(1) and X(2) are

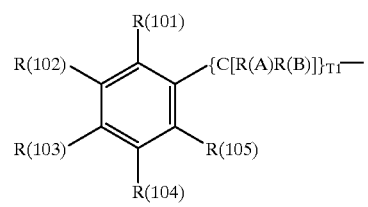

T1 is zero, 1, 2, 3 or 4;
R(A) and R(B) independently are hydrogen, F, Cl, Br, I, CN, OR(106), ($C_1$–$C_8$)-alkyl, ($C_3$–$C_8$)-cycloalkyl, $O_{zk}$($CH_2$)$_{zl}C_{zm}F_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110);

R(109) and R(110) are hydrogen, $(C_1-C_4)$-alkyl or $(C_1-C_4)$-perfluoroalkyl;

zl is zero, 1, 2, 3 or 4;

zk is zero or 1;

zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(111)R(112);

R(111) and R(112) are hydrogen, $(C_1-C_4)$-alkyl or $(C_1-C_4)$-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl; or X(1) and X(2) are

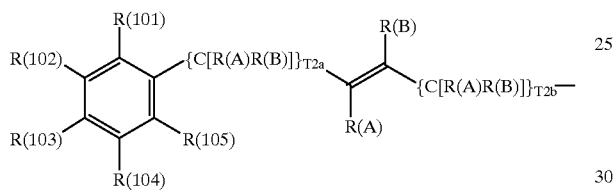

T2a and T2b independently of one another are zero, 1 or 2;
where the double bond can have the (E)- or (Z)-configuration; or X(1) and X(2) are

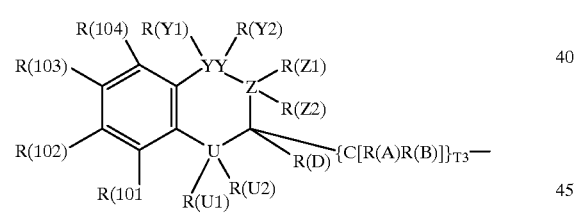

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl,

R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka}$ $(CH_2)_{zla}C_{zma}F_{2zma+1}$, NR(115)R(116), phenyl orbenzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;

zla is zero, 1, 2, 3 or 4;

zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as R(114); or

R(115) and R(116) together are 4 or 5 methylene groups, of which one $CH_2$ group can be replaced by oxygen, S, NH, N—$CH_3$ or N-benzyl; but where the constitution of U being nitrogen (N), YY being nitrogen (N) and Z being carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—, where the perfluoroalkyl group is straight-chain or branched, X is oxygen, S or NR(114a);
R(114a) is H or $(C_1-C_3)$-alkyl;
zoa is zero or 1;
zbm is zero, 1 or 2;
zpa is zero, 1, 2, 3 or 4;
zqa is 1, 2, 3, 4, 5, 6, 7 or 8;
R(110a), R(110b), R(111a) and R(112a) independently are $(C_1-C_8)$-alkyl, $(C_3-C_8)$-alkenyl, —$C_{zn}H_{2zn}$—R(115a) or $(C_1-C_8)$-perfluoroalkyl;
zn is zero, 1, 2, 3 or 4;
(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);
R(116a) and R(117a) are hydrogen, $(C_1-C_4)$-perfluoroalkyl or $(C_1-C_4)$-alkyl; or
R(110b), R(111a) and R(112a) are hydrogen;
R(110c) and R(113a) independently are hydrogen, $(C_1-C_4)$-perfluoroalkyl or $(C_1-C_4)$-alkyl; or
R(110b) and R(110c) and R(112a) and R(113a) together are 4 or 5 methylene groups, of which one $CH_2$ group can be replaced by oxygen, sulfur, NH, N—$CH_3$ or N-benzyl; or R(101), R(102), R(103), R(104), R(105) independently of one another are $(C_1-C_8)$-alkyl, —$C_{zal}H_{2zal}$R(118a) or $(C_3-C_8)$-alkenyl, zal is zero, 1, 2, 3 or 4;
R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(119b);
R(119a) and R(119b) are hydrogen, $(C_1-C_4)$-alkyl or $(C_1-C_4)$-perfluoroalkyl; or R(101), R(102), R(103), R(104), R(105) independently of one another are $(C_1-C_9)$-heteroaryl, which is linked via C or N and which is unsubstituted or substituted by 1–3 substituents from the group consisting of F, Cl, CF$_3$, CH$_3$, methoxy, hydroxyl, amino, methylamino and dimethylamino; or R(101), R(102), R(103), R(104), R(105) independently of one another are —C≡C—R(193);
R(193) is phenyl which is not substituted or is substituted by 1–3 substituents from the group consisting of F, Cl, CF$_3$, methyl, methoxy or NR(194)R(195);
R(194) and R(195) are hydrogen or CH$_3$; or R(101), R(102), R(103), R(104), R(105) independently of one another are —Y-para-C$_6$H$_4$—(CO)$_{zh}$—(CHOH)$_{zi}$—(CH$_2$)$_{zj}$—(CHOH)$_{zk}$—R(123),
—Y-meta-C$_6$H$_4$—(CO)$_{zad}$—(CHOH)$_{zae}$—(CH$_2$)$_{zaf}$—(CHOH)$_{zag}$—R(124) or
—Y-ortho-C$_6$H$_4$—(CO)$_{zah}$—(CHOH)$_{zao}$—(CH$_2$)$_{zap}$—(CHOH)$_{zak}$—R(125);
Y is oxygen, —S— or —NR(122d)—;
zh, zad, zah independently are zero or 1;
zi, zj, zk, zae, zaf, zag, zao, zap and zak independently are zero, 1, 2, 3 or 4;
but where in each case zh, zi and zk are not simultaneously zero, zad, zae and zag are not simultaneously zero, and zah, zao and zak are not simultaneously zero,
R(123), R(124), R(125) and R(122d) independently are hydrogen or (C$_1$–C$_3$)-alkyl; or R(101), R(102), R(103), R(104) and R(105) independently of one another are SR(129), —OR(130), —NR(131)R(132) or —CR(133)R(134)R(135);
R(129), R(130), R(131) and R(133) independently are —C$_{zab}$H$_{2zab}$—(C$_1$–C$_9$)-heteroaryl, which is unsubstituted or substituted by 1–3 substituents from the group consisting of F, Cl, CF$_3$, CH$_3$, methoxy, hydroxyl, amino, methylamino and dimethylamino;
zab is zero, 1 or 2;
R(132), R(134) and R(135) independently of one another are defined as R(129) or are hydrogen, (C$_1$–C$_4$)-alkyl or (C$_1$–C$_4$)-perfluoroalkyl; or R(101), R(102), R(103), R(104) and R(105) independently of one another are —W-para-(C$_6$H$_4$)—R(196), —W-meta-(C$_6$H$_4$)—R(197) or —W-ortho-(C$_6$H$_4$)—R(198);
R(196), R(197) and R(198) independently are (C$_1$–C$_9$)-heteroaryl, which is linked via C or N and which is unsubstituted or substituted by 1 to 3 substituents from the group consisting of F, Cl, CF$_3$, CH$_3$, methoxy, hydroxyl, amino, methylamino, dimethylamino and benzyl;
W is oxygen, S or NR(136)—;
R(136) is hydrogen or (C$_1$–C$_4$)-alkyl; or R(101), R(102), R(103), R(104) and R(105) independently of one another are R(146)X(1a)—;
X(1a) is oxygen, S, NR(147), (D=O)A—, NR(148)C=MN$^{(*)}$R(149)—;
M is oxygen or sulfur;
A is oxygen or NR(150);
D is C or SO;
R(146) is (C$_1$–C$_8$)-alkyl, (C$_3$–C$_8$)-alkenyl, (CH$_2$)$_{zbz}$C$_{zdz}$F$_{2zdz+1}$ or —C$_{zxa}$H$_{2zxa}$—R(151);
zbz is zero or 1;
zdz is 1, 2, 3, 4, 5, 6 or 7;
zxa is zero, 1, 2, 3 or 4;
R(151) is (C$_3$–C$_8$)-cycloalkyl, phenyl, biphenylyl or naphthyl, where the aromatics are not substituted or are substituted by 1–3 substituents from the group consisting of F, Cl, CF$_3$, methyl, methoxy and NR(152)R(153);
R(152) and R(153) are hydrogen, (C$_1$–C$_4$)-alkyl or (C$_1$–C$_4$)-perfluoroalkyl;
R(147), R(148) and R(150) independently are hydrogen, (C$_1$–C$_4$)-alkyl, (C$_1$–C$_4$)-perfluoroalkyl;
R(149) is defined as R(146), or
R(146) and R(147), or R(146) and R(148) together are 4 or 5 methylene groups, of which one CH$_2$ group can be replaced by oxygen, sulfur, NH, N—CH$_3$ or N-benzyl;
where A and N$^{(*)}$ are bonded to the phenyl nucleus of the alkanoyl parent structure; or R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —[CR(159)R(160)]$_{zu}$—(C=O)—[CR(161)R(162)]$_{zv}$—R(163);
R(164), R(165), R(166), R(167), R(169) identically or differently are —(CH$_2$)$_{zy}$—(CHOH)$_{zz}$—(CH$_2$)$_{zaa}$—(CHOH)$_{zt}$—R(171) or —(CH$_2$)$_{zab}$—O—(CH$_2$—CH$_2$O)$_{zac}$—R(172);
R(171) and R(172) are hydrogen or methyl;
zu is 1, 2, 3 or 4;
zv is zero, 1, 2, 3 or 4;
zy, zz, zaa, zab, zac identically or differently are zero, 1, 2, 3 or 4;
zt is 1, 2, 3 or 4;
R(168), R(170), R(154), R(155) identically or differently are hydrogen or (C$_1$–C$_6$)-alkyl, or
R(169) and R(170), or R(154) and R(155) together with the carbon atom carrying them are a (C$_3$–C$_8$)-cycloalkyl;
R(163) is hydrogen, (C$_1$–C$_6$)-alkyl, (C$_3$–C$_8$)-cycloalkyl or —C$_{zeb}$H$_{2zeb}$—R(173);
zeb is zero, 1, 2, 3 or 4;
R(156), R(157) and R(173) independently are phenyl which is unsubstituted or is substituted by 1–3 substituents from the group consisting of F, Cl, CF$_3$, methyl, methoxy and NR(174)R(175);
R(174) and R(175) are hydrogen or (C$_1$–C$_4$)-alkyl; or
R(156), R(157) and R(173) independently are (C$_1$–C$_9$)-heteroaryl, which is unsubstituted or substituted as phenyl;
R(158), R(159), R(160), R(161) and R(162) are hydrogen or methyl, or R(101), R(102), R(103), R(104), R(105) independently of one another are R(176)—NH—SO$_2$—;
R(176) is R(177)R(178)N—(C=Y')—;
Y' is oxygen, S or N—R(179);
R(177) and R(178) identically or differently are hydrogen, (C$_1$–C$_8$)-alkyl, (C$_3$–C$_6$)-alkenyl or —C$_{zfa}$H$_{2zfa}$—R(180);
zfa is zero, 1, 2, 3 or 4;
R(180) is (C$_5$–C$_7$)-cycloalkyl or phenyl, which is unsubstituted or substituted by 1–3 substituents selected from the group consisting of F, Cl, CF$_3$, methoxy or (C$_1$–C$_4$)-alkyl; or
R(177) and R(178) together are 4 or 5 methylene groups, of which one CH$_2$ group can be replaced by oxygen, sulfur, NH, N—CH$_3$ or N-benzyl;
R(179) is defined as R(177) or is amidine, or R(101), R(102), R(103), R(104), R(105) independently of one another are NR(184a)R(185), OR(184b), SR(184c) or —C$_{znx}$H$_{2znx}$—R(184d);

znx is zero, 1, 2, 3 or 4;
R(184d) is ($C_3$–$C_7$)-cycloalkyl or phenyl, which is not substituted or is substituted by 1–3 substituents from the group consisting of F, Cl, $CF_3$, methyl, methoxy and NR(116k)R(117k);
R(116k) and R(117k) are hydrogen or $C_1$–$C_4$-alkyl;
R(184a), R(184b), R(184c), R(185) independently of one another are hydrogen, ($C_1$–$C_8$)-alkyl, ($C_1$–$C_8$)-perfluoroalkyl or $(CH_2)_{zao}$—R(184g);
zao is zero, 1, 2, 3 or 4;
184g is ($C_3$–$C_7$)-cycloalkyl or phenyl, which is not substituted or is substituted by 1–3 substituents from the group consisting of F, Cl, $CF_3$, methyl, methoxy and NR(184u)R(184v); R(184u) and R(184v) are hydrogen or $C_1$–$C_4$-alkyl; or
R(184a) and R(185) together are 4 or 5 methylene groups, of which one $CH_2$ group can be replaced by oxygen, sulfur, NH, N—$CH_3$ or N-benzyl;
or a pharmaceutically tolerable salt thereof;
u) a benzoylguanidine of the formula

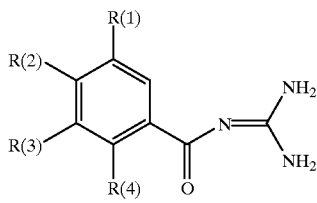

in which:
R(1) is H, F, Cl, Br, I, CN, $NO_2$, ($C_1$–$C_8$)-cycloalkyl or $X_a$—$(CH_2)_b$—$(CF_2)_c$—$CF_3$;
X is oxygen, S or NR(5);
a is zero or 1;
b is zero, 1 or 2;
c is zero, 1, 2 or 3;
R(5) is H, ($C_1$–$C_4$)-alkyl or —$C_dH_{2d}$R(6);
d is zero, 1, 2, 3 or 4;
R(6) is ($C_3$–$C_8$)-cycloalkyl, phenyl, biphenylyl or naphthyl, where the aromatics are not substituted or are substituted by 1 to 3 substituents selected from the group consisting of F, Cl, $CF_3$, methyl, methoxy and NR(7)R(8);
R(7) and R(8) independently are H or ($C_1$–$C_4$)-alkyl; or
R(1) is —SR(10), —OR(10) or —CR(10)R(11)R(12);
R(10) is —$C_fH_{2f}$—($C_3$–$C_8$)-cycloalkyl, —($C_1$–$C_9$)-heteroaryl or phenyl, where the aromatic systems are unsubstituted or substituted by 1 to 3 substituents selected from the group consisting of F, Cl, $CF_3$, $CH_3$, methoxy, hydroxyl, amino, methylamino and dimethylamino;
f is zero, 1 or 2;
R(11) and R(12) independently of one another are defined as R(10) or are hydrogen or ($C_1$–$C_4$)-alkyl; or
R(1) is phenyl, naphthyl, biphenylyl or ($C_1$–$C_9$)-heteroaryl, the latter linked via C or N, and which are unsubstituted or substituted by 1 to 3 substituents selected from the group consisting of F, Cl, $CF_3$, $CH_3$, methoxy, hydroxyl, amino, methylamino and dimethylamino; or
R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$ R(13) and R(14) identically or differently are —$(CH_2)_g$—$(CHOH)_h$—$(CH_2)_i$—$(CHOH)_j$—R(17),
R(17) is hydrogen or methyl;
—$(CH_2)_g$—O—$(CH_2$—$CH_2O)_h$—R(24),
g,h,i identically or differently are zero, 1, 2, 3 or 4;
j is 1, 2, 3 or 4;
R(15) and R(16) identically or differently are hydrogen, ($C_1$–$C_6$)-alkyl or together with the carbon atom carrying them are a ($C_3$–$C_8$)-cycloalkyl;
R(18) is phenyl, which is unsubstituted or substituted by 1 to 3 substituents selected from the group consisting of F, Cl, $CF_3$, methyl, methoxy and NR(25)R(26);
R(25) and R(26) are H or ($C_1$–$C_4$)-alkyl; or
R(18) is ($C_1$–$C_9$)-heteroaryl, which is unsubstituted or substituted as phenyl; or
R(18) is ($C_1$–$C_6$)-alkyl, which is unsubstituted or substituted by 1 to 3 OH; or
R(18) is ($C_3$–$C_8$)-cycloalkyl;
R(19), R(20), R(21), R(22) and R(23) are hydrogen or methyl;
k is zero, 1, 2, 3 or 4;
l is zero, 1, 2, 3 or 4;
R(24) is H, ($C_1$–$C_6$)-alkyl, ($C_3$–$C_8$)-cycloalkyl or —$C_mH_{2m}$—R(18);
m is 1, 2, 3 or 4;
R(2) and R(3) independently of one another are defined as R(1);
R(4) is ($C_1$–$C_3$)-alkyl, F, Cl, Br, I, CN or —$(CH_2)_n$—$(CF_2)_o$—$CF_3$;
n is zero or 1;
o is zero, 1 or 2;
or a pharmaceutically tolerable salt thereof;
v) an acylguanidine of the formula

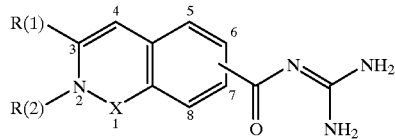

in which:
X is carbonyl, sulfonyl,
R(1) is H, ($C_1$–$C_8$)-alkyl, unsubstituted or substituted by hydroxyl,
($C_3$–$C_8$)-cycloalkyl, phenyl, which is unsubstituted or substituted by 1–3 substituents from the group F, Cl, $CF_3$, $CH_3$, methoxy, hydroxyl, amino, methylamino or dimethylamino,
R(2) is H, ($C_1$–$C_4$)-alkyl,
or a pharmaceutically tolerable salt thereof;
w) a phenyl-substituted alkylcarboxylic acid guanidide, carrying at least one perfluoroalkyl group, of the formula

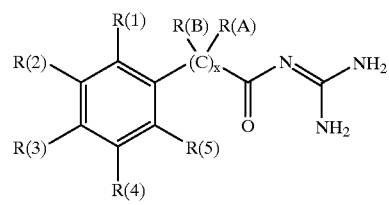

in which:
R(A) is hydrogen, F, Cl, Br, I, CN, OR(6), ($C_1$–$C_8$)-alkyl, ($C_3$–$C_8$)-cycloalkyl, $O_r(CH_2)_aC_bF_{2b+1}$ or NR(7)R(8);

r is zero or 1;
a is zero, 1, 2, 3 or 4;
b is 1, 2, 3, 4, 5, 6, 7 or 8;
R(6) is hydrogen, $(C_1-C_8)$-alkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6);

R(8) independently is defined as R(A);
X is 1, 2 or 3;
R(1) is hydrogen, $(C_1-C_8)$-alkyl, $(C_3-C_8)$-cycloalkyl, $-O_t(CH_2)_dC_eF_{2e+1}$, F, Cl, Br, I or CN;
t is zero or 1;
d is zero, 1, 2, 3 or 4;
e is 1, 2, 3, 4, 5, 6, 7 or 8;
R(2), R(3), R(4) and R(5) independently of one another are defined as R(1);
but with the condition that at least one of the substituents R(1), R(2), R(3), R(4), R(5), R(A) and R(B) is an $-O_t(CH_2)_dC_eF_{2e+1}$ or an $O_rCH_2)_aC_bF_{2b+1}$ group,
or a pharmaceutically tolerable salt thereof;
x) a heteroaroylguanidine of the formula

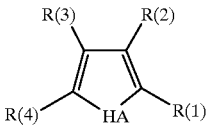

in which:
HA is $SO_m$, O or NR(5);
m is zero, 1 or 2;
R(5) is hydrogen, $(C_1-C_8)$-alkyl or $-C_{am}H_{2am}R(81)$;
am is zero, 1 or 2;
R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);
R(82) and R(83) are H or $CH_3$; or
R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
one of the two substituents R(1) and R(2) is $-CO-N=C(NH_2)_2$;
and the other in each case is hydrogen, F, Cl, Br, I, $(C_1-C_3)$-alkyl, $-OR(6)$, $C_rF_{2r+1}$, $-CO-N=C(NH_2)_2$ or $-NR(6)R(7)$;
R(6) and R(7) independently are hydrogen or $(C_1-C_3)$-alkyl;
r is 1, 2, 3 or 4;
R(3) and R(4) independently of one another are hydrogen, F, Cl, Br, I, $-C\equiv N$, $X-(CH_2)_p-(C_q-F_{2q+1})$, $R(8)-SO_{bm}$, R(9)R(10)N-CO, R(11)-CO- or R(12)R(13)N-$SO_2$-, where the perfluoroalkyl group is straight-chain or branched,
X is oxygen, S or NR(14);
R(14) is H or $(C_1-C_3)$-alkyl;
bm is zero, 1 or 2;
p is zero, 1 or 2;
q is zero, 1, 2, 3, 4, 5 or 6;
R(8), R(9), R(11) and R(12) independently are $(C_1-C_8)$-alkyl, $(C_3-C_6)$-alkenyl, $-C_nH_{2n}-R(15)$, $CF_3$;
n is zero, 1, 2, 3 or 4;
R(15) is $(C_3-C_7)$-cycloalkyl or phenyl, which is not substituted or is substituted by 1–3 substituents selected from the group consisting of F, Cl, $CF_3$, methyl, methoxy or NR(16)R(17);
R(16) and R(17) are H or $C_1-C_4$-alkyl; or
R(9), R(11) and R(12) are H;
R(10) and R(13) independently are H or $(C_1-C_4)$-alkyl; or
R(9) and R(10), and R(12) and R(13) together are 4 or 5 methylene groups, of which one $CH_2$ group can be replaced by oxygen, S, NH, N-$CH_3$ or N-benzyl, or
R(3) and R(4) independently of one another are $(C_1-C_8)$-alkyl or $-C_{al}H_{2al}R(18)$;
al is zero, 1 or 2;
R(18) is $(C_3-C_8)$-cycloalkyl or phenyl; which is not substituted or is substituted by 1–3 substituents selected from the group consisting of F, Cl, $CF_3$, methyl, methoxy and NR(19)R(20);
R(19) and R(20) are H or $CH_3$; or
R(3) and R(4) independently of one another are $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(3) and R(4) independently of one another are

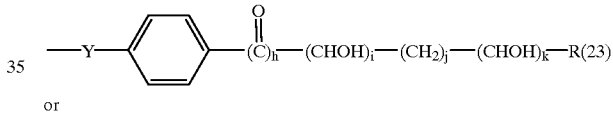

or

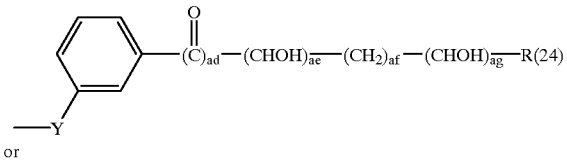

or

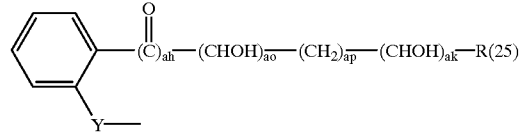

Y is oxygen, $-S-$ or $-NR(22)-$;
h, ad, ah independently are zero or 1;
i, j, k, ae, af, ag, ao, ap and ak independently are zero, 1, 2, 3, 4,
but where in each case h, i and k are not simultaneously zero, ad, ae and ag are not simultaneously zero, and ah, ao and ak are not simultaneously zero,
R(23), R(24), R(25) and R(22) independently are hydrogen or $(C_1-C_3)$-alkyl; or
R(3) and R(4) independently of one another are hydrogen, F, Cl, Br, I, CN, $(C_1-C_8)$-alkyl, $(C_1-C_8)$-perfluoroalkyl, $(C_3-C_8)$-alkenyl or $-C_gH_{2g}R(26)$;
g is zero, 1, 2, 3 or 4;
R(26) is $(C_3-C_8)$-cycloalkyl, phenyl, biphenylyl or naphthyl, where the aromatics are not substituted or are substituted by 1–3 substituents selected from the group consisting of F, Cl, CF$_3$, methyl, methoxy and NR(27)R(28);
R(27) and R(28) are H, (C$_1$–C$_4$)-alkyl or (C$_1$–C$_4$)-perfluoroalkyl; or
R(3) and R(4) independently of one another are SR(29), —OR(30), —NR(31)R(32) or —CR(33)R(34)R(35);
R(29), R(30), R(31) and R(33) independently are —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
a is zero, 1 or 2;
R(32), R(34) and R(35) independently of one another are defined as R(29) or are hydrogen, (C$_1$–C$_4$)-alkyl or (C$_1$–C$_4$)-perfluoroalkyl; or
R(3) and R(4) independently of one another are

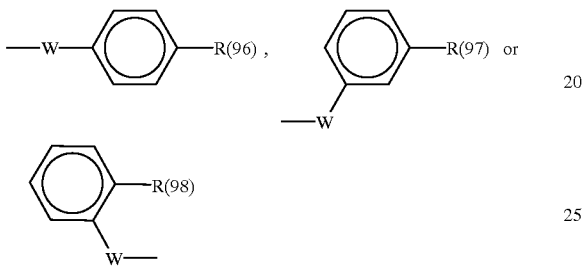

R(96), R(97) and R(98) independently are (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino or benzyl;
W is oxygen, S or NR(36)—;
R(36) is H or (C$_1$–C$_4$)-alkyl; or
R(3) and R(4) independently of one another are R(37)—SO$_{cm}$ or R(38)R(39) N—SO$_2$—;
cm is 1 or 2;
R(37) is (C$_1$–C$_8$)-alkyl, (C$_1$–C$_8$)-perfluoroalkyl, (C$_3$–C$_8$)-alkenyl or —C$_s$H$_{2s}$R(40);
s is zero, 1, 2, 3 or 4;
R(40) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(41)R(42);
R(41) and R(42) are H, (C$_1$–C$_4$)-alkyl or (C$_1$–C$_4$)-perfluoroalkyl;
R(38) is H, (C$_1$–C$_8$)-alkyl, (C$_1$–C$_8$)-perfluoroalkyl, (C$_3$–C$_8$)-alkenyl or —C$_w$H$_{2w}$—R(43);
w is zero, 1, 2, 3 or 4;
R(43) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(44)R(45);
R(44) and R(45) are H, (C$_1$–C$_4$)-alkyl or (C$_1$–C$_4$)-perfluoroalkyl;
R(39) is H, (C$_1$–C$_4$)-alkyl or (C$_1$–C$_4$)-perfluoroalkyl; or
R(38) and R(39) together are 4 or 5 methylene groups, of which one CH$_2$ group can be replaced by oxygen, S, NH, N—CH$_3$ or N-benzyl; or
R(3) and R(4) independently of one another are R(46)X(1)—;
X(1) is oxygen, S, NR(47), (D=O)A—, NR(48) C=MN$^{(*)}$R(49)—, M is oxygen or S;
A is oxygen or NR(50);
D is C or SO;
R(46) is (C$_1$–C$_8$)-alkyl, (C$_3$–C$_8$)-alkenyl, (CH$_2$)$_b$C$_d$F$_{2d+1}$ or —C$_x$H$_{2x}$—R(51);
b is zero or 1;
d is 1, 2, 3, 4, 5, 6 or 7;
x is zero, 1, 2, 3 or 4;
R(51) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(52)R(53);
R(52) and R(53) are H, (C$_1$–C$_4$)-alkyl or (C$_1$–C$_4$)-perfluoroalkyl;
R(47), R(48) and R(50) independently are hydrogen, (C$_1$–C$_4$)-alkyl or (C$_1$–C$_4$)-perfluoroalkyl;
R(49) is defined as R(46); or
R(46) and R(47), or R(46) and R(48) together are 4 or 5 methylene groups, of which one CH$_2$ group can be replaced by oxygen, S, NH, N—CH$_3$ or N-benzyl,
where A and N$^{(*)}$ are bonded to the phenyl nucleus of the benzoylguanidine parent structure; or
R(3) and R(4) independently of one another are —SR(64), —OR(65), —NHR(66), —NR(67)R(68), —CHR(69)R(70), —C(OH)R(54)R(55), —C≡CR(56), —CR(58)=CHR(57), —[CR(59)R(60)]$_u$—(CO)—[CR(61)R(62)]$_v$—R(63);
R(64), R(65), R(66), R(67) and R(69) identically or differently are —(CH$_2$)$_y$—(CHOH)$_z$—(CH$_2$)$_{aa}$—(CH$_2$OH)$_t$—R(71) or —(CH$_2$)$_{ab}$—O—(CH$_2$—CH$_2$O)$_{ac}$—R(72),
R(71) and R(72) are hydrogen or methyl;
u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen, (C$_1$–C$_6$)-alkyl; or
R(69) and R(70), or R(54) and R(55) together with the carbon atom carrying them are a (C$_3$–C$_8$)-cycloalkyl;
R(63) is H, (C$_1$–C$_6$)-alkyl, (C$_3$–C$_8$)-cycloalkyl or —C$_e$H$_{2e}$—R(73);
e is zero, 1, 2, 3 or 4;
R(56), R(57) and R(73) independently are phenyl, which is unsubstituted or substituted by 1–3 substituents selected from the group consisting of F, Cl, CF$_3$, methyl, methoxy and NR(74)R(75);
R(74) and R(75) are H or (C$_1$–C$_4$)-alkyl; or
R(56), R(57) and R(73) independently are (C$_1$–C$_9$)-heteroaryl, which is unsubstituted or substitued as phenyl;
R(58), R(59), R(60), R(61) and R(62) are hydrogen or methyl, or
R(3) and R(4) independently of one another are R(76)—NH—SO$_2$—;
R(76) is R(77)R(78)N—(C=Y')—;
Y' is oxygen, S or N—R(79);
R(77) and R(78) identically or differently are H, (C$_1$–C$_8$)-alkyl, (C$_3$–C$_6$)-alkenyl, —C$_f$H$_{2f}$—R(80);
f is zero, 1, 2, 3 or 4;
R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or R(77) and R(78) together are 4 or 5 methylene groups, of which one $CH_2$ group can be replaced by oxygen, S, NH, N—$CH_3$ or N-benzyl, R(79) is defined as R(77) or is amidine; or R(3) and R(4) independently of one another are NR(84)R(85);

R(84) and R(85) independently of one another are H, $(C_1-C_4)$-alkyl, or together are 4 or 5 methylene groups, of which one $CH_2$ group can be replaced by oxygen, S, NH, N—$CH_3$ or N-benzyl; or of which one or two $CH_2$ groups can be replaced by CH—$C_{dm}H_{2dm+1}$, or a pharmaceutically tolerable salt thereof;

y) a bicyclic heteroaroylguanidine of the formula

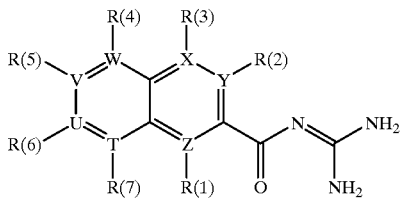

in which:

T, U, V, W, X, Y and Z independently of one another are nitrogen or carbon;

but with the restriction that X and Z are not simultaneously nitrogen, and that T, U, V, W, X, Y and Z carry no substituents if they are nitrogen, and that no more than four of them are simultaneously nitrogen, R(1) and R(2) independently of one another are hydrogen, F, Cl, Br, I, $(C_1-C_3)$-alkyl, $(C_1-C_3)$-perfluoroalkyl, OR(8), NR(8)R(9) or C(=O)N=C(NH_2)_2;

R(8) and R(9) independently of one another are hydrogen or $(C_1-C_3)$-alkyl, or R(8) and R(9) together are 4 or 5 methylene groups, of which one $CH_2$ group can be replaced by oxygen, S, NH, N—$CH_3$ or N-benzyl;

R(3), R(4), R(5), R(6) and R(7) independently of one another are hydrogen, F, Cl, Br, I, —C≡N, $X_k$—$(CH_2)_p$—$(C_qF_{2q+1})$, R(10a)—$SO_{bm}$, R(10b)R(10c)N—CO, R(11)—CO— or R(12)R(13)N—$SO_2$—, where the perfluoroalkyl group is straight-chain or branched;

X is oxygen, S or NR(14);

R(14) is H or $(C_1-C_3)$-alkyl;

bm is zero, 1 or 2;

p is zero, 1 or 2;

k is zero or 1;

q 1, 2, 3, 4, 5 or 6;

R(10a), R(10b), R(11) and R(12) independently of one another are $(C_1-C_8)$-alkyl, $(C_3-C_6)$-alkenyl, —$C_nH_{2n}$—R(15) or $(C_1-C_8)$-perfluoroalkyl;

n is zero, 1, 2, 3 or 4;

R(15) is $(C_3-C_7)$-cycloalkyl or phenyl, which is not substituted or is substituted by 1–3 substituents selected from the group consisting of F, Cl, $CF_3$, methyl, methoxy and NR(16)R(17);

R(16) and R(17) are H or $C_1-C_4$-alkyl; or

R(10b), R(11) and R(12) are hydrogen;

R(10c) and R(13) independently are hydrogen or $(C_1-C_4)$-alkyl; or

R(10b) and R(10c) and R(12) and R(13) together are 4 or 5 methylene groups, of which one $CH_2$ group can be replaced by oxygen, sulfur, NH, N—$CH_3$ or N-benzyl; or R(3), R(4), R(5), R(6) and R(7) independently of one another are $(C_1-C_8)$-alkyl, —$C_{al}H_{2al}R(18)$ or $(C_3-C_8)$-alkenyl;

al is zero, 1 or 2;

R(18) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(19a)R(19b);

R(19a) and R(19b) are hydrogen, $(C_1-C_4)$-alkyl or $(C_1-C_4)$-perfluoroalkyl; or R(3), R(4), R(5), R(6) and R(7) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino or dimethylamino; or R(3), R(4), R(5), R(6) and R(7) independently of one another are

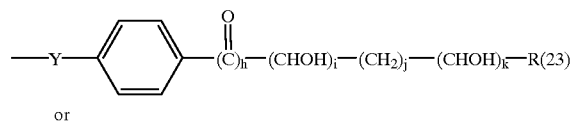

or

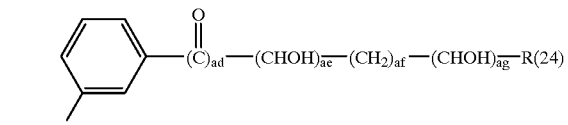

or

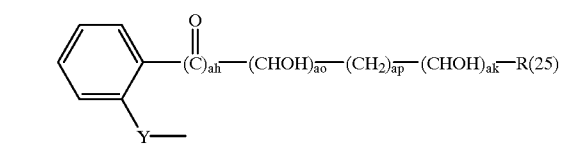

Y is oxygen, —S— or —NR(22)—;

h, ad, ah independently of one another are zero or 1;

i, j, k, ae, af, ag, ao, ap and ak independently of one another are zero, 1, 2, 3 or 4;

but where in each case h, i and k are not simultaneously zero, ad, ae and ag are not simultaneously zero, and ah, ao and ak are not simultaneously zero, R(23), R(24), R(25) and R(22) independently of one another are hydrogen or $(C_1-C_3)$-alkyl; or R(3), R(4), R(5), R(6) and R(7) independently of one another are SR(29), —OR(30), —NR(31)R(32) or —CR(33)R(34)R(35);

R(29), R(30), R(31) and R(33) independently of one another are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl; or R(3), R(4), R(5), R(6) and R(7) independently of one another are

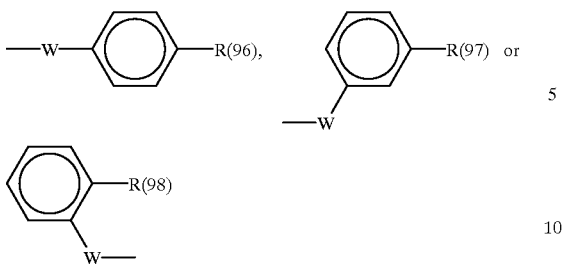

R(96), R(97) and R(98) independently of one another are $(C_1-C_9)$-heteroaryl, which is linked via C or N and which is unsubstitued or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;
R(36) is H or $(C_1-C_4)$-alkyl; or

R(3), R(4), R(5), R(6) and R(7) independently of one another are R(46)X(1)—;
X(1) is oxygen, S, NR(47), (D=O)A— or NR(48)C=MN$^{(*)}$R(49)—;
M is oxygen or sulfur;
A is oxygen or NR(50);
D is C or SO;
R(46) is $(C_1-C_8)$-alkyl, $(C_3-C_8)$-alkenyl, $(CH_2)_bC_dF_{2d+1}$ or —$C_xH_{2x}$—R(51);
b is zero or 1;
d is 1, 2, 3, 4, 5, 6 or 7;
x is zero, 1, 2, 3 or 4;
R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);
R(52) and R(53) are hydrogen, $(C_1-C_4)$-alkyl or $(C_1-C_4)$-perfluoroalkyl;
R(47), R(48) and R(50) independently are hydrogen, $(C_1-C_4)$-alkyl or $(C_1-C_4)$-perfluoroalkyl;
R(49) is defined as R(46); or
R(46) and R(47), or R(46) and R(48) together are 4 or 5 methylene groups, of which one $CH_2$ group can be replaced by oxygen, sulfur, NH, N—$CH_3$ or N-benzyl;
where A and N$^{(*)}$ are bonded to the phenyl nucleus of the heteroaroylguanidine parent structure; or R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$—R(63);
R(64), R(65), R(66), R(67) and R(69) identically or differently are —$(CH_2)_y$—$(CHOH)_z$—$(CH_2)_{aa}$—$(CHOH)_t$—R(71) or —$(CH_2)_{ab}$—O—$(CH_2$—$CH_2O)_{ac}$—R(72);
R(71) and R(72) independently of one another are hydrogen or methyl;
u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen or $(C_1-C_6)$-alkyl; or R(69) and R(70), or R(54) and R(55) together with the carbon atom carrying them are a $(C_3-C_8)$-cycloalkyl;
R(63) is hydrogen, $(C_1-C_6)$-alkyl, $(C_3-C_8)$-cycloalkyl or —$C_eH_{2e}$—R(73);
e is zero, 1, 2, 3 or 4;
R(56), R(57) and R(73) independently are phenyl, which is unsubstituted or substituted by 1–3 substituents selected from the group consisting of F, Cl, $CF_3$, methyl, methoxy and NR(74)R(75);
R(74) and R(75) are hydrogen or $(C_1-C_4)$-alkyl; or
R(56), R(57) and R(73) independently are $(C_1-C_9)$-heteroaryl, which is unsubstituted or substituted as phenyl;
R(58), R(59), R(60), R(61) and R(62) are hydrogen or methyl; or R(3), R(4), R(5), R(6) and R(7) independently of one another are R(76)—NH—$SO_2$—;
R(76) is R(77)R(78)N—(C=Y')—;
Y' is oxygen, S or N—R(79);
R(77) and R(78) identically or differently are hydrogen, $(C_1-C_8)$-alkyl, $(C_3-C_6)$-alkenyl or —$C_fH_{2f}$—R(80);
f is zero, 1, 2, 3 or 4;
R(80) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or
R(77) and R(78) together are 4 or 5 methylene groups, of which one $CH_2$ group can be replaced by oxygen, sulfur, NH, N—$CH_3$ or N-benzyl;
R(79) is defined as R(77) or is amidine; or R(3), R(4), R(5), R(6) and R(7) independently of one another are NR(84a)R(85), OR(84b), SR(84c) or —$C_nH_{2n}$—R(84d);
n is zero, 1, 2, 3 or 4;
R(84d) is $(C_3-C_7)$-cycloalkyl or phenyl, which is not substituted or is substituted by 1–3 substituents from the group consisting of F, Cl, $CF_3$, methyl, methoxy and NR(16)R(17);
R(16) and R(17) are hydrogen, or $C_1-C_4$-alkyl;
R(84a), R(84b), R(84c) and R(85) independently of one another are hydrogen, $(C_1-C_8)$-alkyl, $(C_1-C_8)$-perfluoroalkyl or $(CH_2)_{ax}$—R(84g);
ax is zero, 1, 2, 3 or 4;
R(84g) is $(C_3-C_7)$-cycloalkyl or phenyl, which is not substituted or is substituted by 1–3 substituents selected from the group consisting of F, Cl, $CF_3$, methyl, methoxy and NR(84u)R(84v);
R(84u) and R(84v) are hydrogen or $C_1-C_4$-alkyl; or
R(84a) and R(85) together are 4 or 5 methylene groups, of which one $CH_2$ group can be replaced by oxygen, sulfur, NH, N—$CH_3$ or N-benzyl, or a pharmaceutically tolerable salt thereof;

z) a benzoylguanidine of the formula

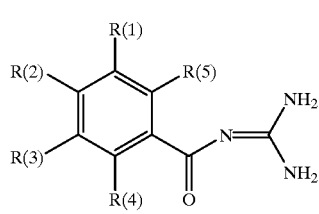

in which:
R(1) is R(6)—SO$_m$;
m is zero, 1 or 2;
R(6) is perfluoroalkyl having 1, 2, 3, 4, 5 or 6 carbon atoms, which is straight-chain or branched;
R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy; or
R(2) and R(3) independently of one another are pyrrol-1-yl, pyrrol-2-yl or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;
R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;
R(7), R(8) and R(9) independently of one another are hydrogen or alkyl having 1, 2, 3 or 4 carbon atoms;
n is zero or 1;
o is zero, 1 or 2;
or a pharaceutically tolerable salt thereof;
ab) a phenyl-substituted alkenylcarboxylic acid guanidide, carrying at least one perfluoroalkyl group, of the formula I

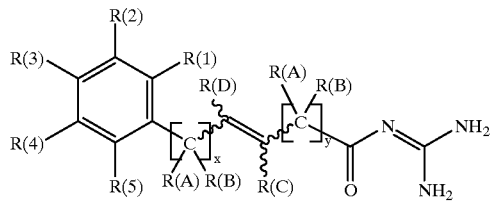

in which:
R(A) is hydrogen, F, Cl, Br, I, CN, OH, OR(6), (C$_1$–C$_8$)-alkyl, O$_r$(CH$_2$)$_a$C$_b$F$_{2b+1}$, (C$_3$–C$_8$)-cycloalkyl or NR(7)R(8);
r is zero or 1;
a is zero, 1, 2, 3 or 4;
b is 1, 2, 3, 4, 5, 6, 7 or 8;
R(6) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics are not substituted or are substituted by 1–3 substituents from the group consisting of F, Cl, CF$_3$, methyl, methoxy and NR(9)R(10);
R(9) and R(10) are H, (C$_1$–C$_4$)-alkyl or (C$_1$–C$_4$)-perfluoroalkyl;
R(7) and R(8) independently of one another are defined as R(6); or
R(7) and R(8) together are 4 or 5 methylene groups, of which one CH$_2$ group can be replaced by oxygen, sulfur, NH, N—CH$_3$ or N-benzyl;
R(8) independently is defined as R(A);
X is zero, 1 or 2;
Y is zero, 1 or 2;
R(C) is hydrogen, F, Cl, Br, I, CN, OR(12), (C$_1$–C$_8$)-alkyl, O$_p$(CH$_2$)$_f$C$_g$F$_{2g+1}$ or (C$_3$–C$_8$)-cycloalkyl;
p is zero or 1;
f is zero, 1, 2, 3 or 4;
g is 1, 2, 3, 4, 5, 6, 7 or 8;
R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics phenyl or benzyl are not substituted or are substituted by 1–3 substituents from the group consisting of F, Cl, CF$_3$, methyl, methoxy and NR(13)R(14);
R(13) and R(14) independently of one another are H, (C$_1$–C$_4$)-alkyl or (C$_1$–C$_4$)-perfluoroalkyl;
R(D) independently is defined as R(C),
R(1) is hydrogen, (C$_1$–C$_8$)-alkyl, —O$_t$(CH$_2$)$_d$C$_e$F$_{2e+1}$, (C$_3$–C$_8$)-cycloalkyl, F, Cl, Br, 1 or CN;
t is zero or 1;
d is zero, 1, 2, 3 or 4;
e is 1, 2, 3, 4, 5, 6, 7 or 8;
R(2), R(3), R(4) and R(5) independently of one another are defined as R(1);
but with the condition that at least one of the substituents R(A), R(B), R(C), R(D), R(1), R(2), R(4) or R(5) is an O$_r$(CH$_2$)$_a$C$_b$F$_{2b+1}$, O$_p$(CH$_2$)$_f$C$_g$F$_{2g+1}$ or O$_t$(CH$_2$)$_d$C$_e$F$_{2e+1}$ group and R(3) is not an O$_t$(CH$_2$)$_d$C$_e$F$_{2e+1}$ group;
or a pharmaceutically tolerable salt thereof;
ac) an ortho-amino-substituted benzoylguanidine of the formula

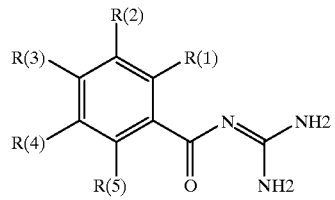

in which:
R(1) is NR(50)R(6),
R(50) and R(6) independently of one another are hydrogen, (C$_1$–C$_8$)-alkyl or (C$_1$–C$_8$)-perfluoroalkyl;
R(2), R(3), R(4) and R(5) independently of one another are R(10)—SO$_a$—, R(11)R(12)N—CO—, R(13)—CO— or R(14)R(15)N—SO$_2$—;
a is zero, 1 or 2,
R(10), R(11), R(12), R(13), R(14) and R(15) independently of one another are (C$_1$–C$_8$)-alkyl, (C$_1$–C$_8$)-perfluoroalkyl, (C$_3$–C$_6$)-alkenyl or —C$_{ab}$H$_{2ab}$—R(16);
ab is zero, 1, 2, 3 or 4;
R(16) is (C$_3$–C$_7$)-cycloalkyl, phenyl, which is not substituted or is substituted by 1–3 substituents selected from the group consisting of F, Cl, CF$_3$, methyl, methoxy or NR(17)R(18);
R(17) and R(18) independently of one another are H, CF$_3$ or (C$_1$–C$_4$)-alkyl; or
R(11), R(12), and also R(14) and R(15) together are 4 or 5 methylene groups, of which one CH$_2$ group can be replaced by oxygen, S, NH, N—CH$_3$ or N-benzyl; or
R(11), R(12), R(14) and R(15) independently of one another are hydrogen; or
R(2), R(3), R(4) and R(5) independently of one another are SR(21), —OR(22), —NR(23)R(24) or —CR(25)R(26)R(27);
R(21), R(22), R(23) and R(25) independently of one another are —C$_b$H$_{2b}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

b is zero, 1 or 2;

R(24), R(26) and R(27) independently of one another are hydrogen, $(C_1-C_4)$-alkyl or $(C_1-C_4)$-perfluoroalkyl; or R(2), R(3), R(4) and R(5) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, $(C_3-C_8)$-alkenyl or —$C_{df}H_{2df}R(30)$;

(Xa) is O, S or NR(33);

R(33) is H, $(C_1-C_4)$-alkyl or $(C_1-C_4)$-perfluoroalkyl;

dg is zero or 1;

(Xb) is O, S or NR(34);

R(34) is H, $(C_1-C_4)$-alkyl or $(C_1-C_4)$-perfluoroalkyl;

dh is zero or 1;

da is zero, 1, 2, 3, 4, 5, 6, 7, 8;

db is zero, 1, 2, 3, 4;

de is zero, 1, 2, 3, 4, 5, 6, 7;

df is zero, 1, 2, 3, 4;

R(30) is $(C_3-C_8)$-cycloalkyl, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(31)R(32);

R(31) and R(32) are H, $(C_1-C_4)$-alkyl or $(C_1-C_4)$-perfluoroalkyl; or

R(2), R(3), R(4) and R(5) independently of one another are NR(40)R(41) or —(Xe)—$(CH_2)_{eb}$R(45);

R(40) and R(41) independently of one another are hydrogen, $(C_1-C_8)$-alkyl, $(C_1-C_8)$-perfluoroalkyl or $(CH_2)_e$—R(42);

e is zero, 1, 2, 3 or 4;

R(42) is $(C_3-C_7)$-cycloalkyl, phenyl, which is not substituted or is substituted by 1–3 substituents selected from the group consisting of F, Cl, $CF_3$, methyl, methoxy and NR(43)R(44);

R(43) and R(44) independently of one another are H, $CF_3$ or $(C_1-C_4)$-alkyl; or R(40) and R(41) together are 4 or 5 methylene groups, of which one $CH_2$ group can be replaced by oxygen, sulfur, NH, N—$CH_3$ or N-benzyl;

(Xe) is O, S or NR(47);

R(47) is H, $(C_1-C_4)$-alkyl or $(C_1-C_4)$-perfluoroalkyl;

eb is zero, 1, 2, 3 or 4;

R(45) is $(C_3-C_7)$-cycloalkyl, phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);

Xfa is $CH_2$, O, S or NR(48);

Xfb is O, S or NR(49);

ed is 1, 2, 3 or 4;

R(46) is H, $(C_1-C_4)$-alkyl or $(C_1-C_4)$-perfluoroalkyl;

R(48), R(49), R(50) and R(51) independently of one another are H or $(C_1-C_4)$-alkyl or $(C_1-C_4)$-perfluoroalkyl;

where R(3) and R(4), however, cannot be hydrogen, or a pharmaceutically tolerable salt thereof;

ad) a benzoylguanidine of the formula in which:

one of the three substituents R(1), R(2) and R(3) is $(C_1-C_9)$-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or one of the three substituents R(1), R(2) and R(3) is —SR(10), —OR(10), —NR(10)R(11) or —CR(10)R(11)R(12);

R(10) is —$C_aH_{2a}$—$(C_1-C_9)$-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(11) and R(12) independently of one another are defined as R(10), are hydrogen or $(C_1-C_4)$-alkyl;

and the other substituents R(1), R(2) and R(3) in each case independently of one another are $(C_1-C_8)$-alkyl, $(C_2-C_8)$-alkenyl or —$C_mH_{2m}R(14)$;

m is zero, 1 or 2;

R(14) is $(C_3-C_8)$-cycloalkyl or phenyl, which is not substituted or is substituted by 1–3 substituents selected from the group consisting of F, Cl, $CF_3$, methyl, methoxy and NR(15)R(16), R(15) and R(16) are hydrogen or $CH_3$; or the other substituents R(1), R(2) and R(3) in each case independently of one another are hydrogen, F, Cl, Br, I, —C≡N, X—$(CH_2)_p$—$(C_qF_{2q+1})$, R(22)—$SO_u$, R(23)R(24)N—CO, R(25)—CO— or R(26)R(27)N—$SO_2$—, where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are $(C_1-C_8)$-alkyl, $(C_2-C_6)$-alkenyl, —$C_nH_{2n}$—R(29) or $CF_3$;

n is zero, 1, 2, 3 or 4;

R(28) is hydrogen or $(C_1-C_3)$-alkyl;

R(29) is $(C_3-C_7)$-cycloalkyl or phenyl; which is not substituted or is substituted by 1–3 substituents selected from the group consisting of F, Cl, $CF_3$, methyl, methoxy and NR(30)R(31);

R(30) and R(31) are hydrogen or $C_1-C_4$-alkyl, or

R(23), R(25) and R(26) are also hydrogen;

R(24) and R(27) independently of one another are hydrogen or $(C_1-C_4)$-alkyl; or R(23) and R(24), and also R(26) and R(27) together are 4 or 5 methylene groups, of which one $CH_2$ group can be replaced by oxygen, S, NH, N—$CH_3$ or N-benzyl; or the other substituents R(1), R(2) and R(3) in each case independently of one another are OR(35) or NR(35)R(36);

R(35) and R(36) independently of one another are hydrogen or $(C_1-C_6)$-alkyl; or R(35) and R(36) together are 4–7 methylene groups, of which one $CH_2$ group can be replaced by oxygen, S, NH, N—$CH_3$ or N-benzyl, R(4) and R(5) independently of one another are hydrogen, $(C_1-C_4)$-alkyl, F, Cl, —OR(32), —NR(33)R(34) or $C_rF_{2r+1}$;

R(32), R(33) and R(34) independently of one another are hydrogen or $(C_1-C_3)$-alkyl;

r is 1, 2, 3 or 4;

or a pharmaceutically tolerable salt thereof;

ad) a benzoylguanidines of the formula

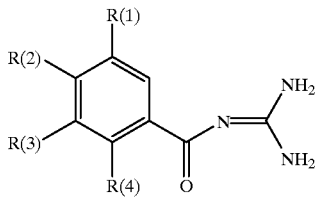

in which:

R(1) is hydrogen, F, Cl, Br, I, CN, $NO_2$, OH, $(C_1-C_8)$-alkyl, $(C_3-C_8)$-cycloalkyl, $O_a$—$(CH_2)_b$—$(CF_2)_c$—$CF_3$;

a is zero or 1;
b is zero, 1 or 2;
c is zero, 1, 2 or 3; or

R(1) is R(5)—$SO_m$ or R(6)R(7)N—$SO_2$—;
m is zero, 1 or 2;

R(5) and R(6) independently of one another are $(C_1-C_8)$-alkyl, $(C_3-C_6)$-alkenyl, $CF_3$ or —$C_nH_{2n}$—R(8);
n is zero, 1, 2, 3 or 4;
R(7) is hydrogen or $(C_1-C_4)$-alkyl;
R(8) is $(C_3-C_7)$-cycloalkyl or phenyl, which is not substituted or is substituted by 1–3 substituents selected from the group consisting of F, Cl, $CF_3$, methyl, methoxy and NR(9)R(10);
R(9) and R(10) independently of one another are hydrogen or $(C_1-C_4)$-alkyl; or
R(6) is H;

or R(6) and R(7) together are 4 or 5 methylene groups, of which one $CH_2$ group can be replaced by oxygen, S, NH, N—$CH_3$ or N-benzyl, or R(1) is —SR(11), —OR(11) or —CR(11)R(12)R(13);
R(11) is —$C_pH_{2p}$—$(C_3-C_8)$-cycloalkyl, —$(C_1-C_9)$-heteroaryl or phenyl, where the aromatic systems are unsubstituted or substituted by 1–3 substituents selected from the group consisting of F, Cl, $CF_3$, $CH_3$, methoxy, hydroxyl, amino, methylamino and dimethylamino;
R(12), R(13) independently of one another are defined as R(11) or are hydrogen or $(C_1-C_4)$-alkyl;
p is zero, 1 or 2; or R(1) is phenyl, naphthyl, biphenylyl or $(C_1-C_9)$-heteroaryl, the latter linked via C or N, which are unsubstituted or substituted by 1–3 substituents selected from the group consisting of F, Cl, $CF_3$, $CH_3$, methoxy, hydroxyl, amino, methylamino and dimethylamino;

R(2) is —$CF_2$R(14), —CF[R(15)][R(16)], —CF[$(CF_2)_qCF_3$][R(15)], —C[$(CF_2)_rCF_3$]=CR(15)R(16);

R(14) is $(C_1-C_4)$-alkyl or $(C_3-C_6)$-cycloalkyl;
R(15) and R(16) independently of one another are hydrogen or $(C_1-C_4)$-alkyl;
q is zero, 1 or 2;
r is zero, 1 or 2;
R(3) is defined as R(1);
R(4) is hydrogen, $(C_1-C_3)$-alkyl, F, Cl, Br, I, CN, —$(CH_2)_s$—$(CF_2)_t$—$CF_3$;
s is zero or 1;
t is zero, 1 or 2;

or a pharmaceutically tolerable salt thereof;

ae) a benzoylguanidine of the formula

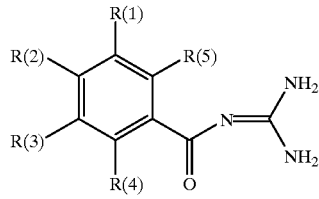

in which:

one of the three substituents R(1), R(2) and R(3) is
—Y-4-[$(CH_2)_k$—CHR(7)—(C=O)R(8)]-phenyl,
—Y-3-$(CH_2)_k$—CHR(7)—(C=O)R(8)]-phenyl or
—Y-2-[$(CH_2)_k$—CHR(7)—(C=O)R(8)]-phenyl,
where the phenyl in each case is unsubstituted or substituted by 1–2 substituents from the group F, Cl, —$CF_3$, methyl, hydroxyl, methoxy, or —NR(37)R(38);
R(37) and R(38) independently of one another are hydrogen or —$CH_3$;
Y is a bond, oxygen, —S— or —NR(9);
R(9) is hydrogen or —$(C_1-C_4)$-alkyl;
R(7) is —OR(10) or —NR(10)R(11);
R(10) and R(11) independently of one another are hydrogen, —$(C_1-C_8)$-alkyl, —$(C_1-C_8)$-alkanoyl, —$(C_1-C_8)$-alkoxycarbonyl, benzyl, benzyloxycarbonyl; or
R(10) is trityl;
R(8) is —OR(12) or —NR(12)R(13);
R(12) and R(13) independently of one another are hydrogen, —$(C_1-C_8)$-alkyl or benzyl;
k is zero, 1, 2, 3 or 4;

and the other radicals R(1), R(2) and R(3) in each case independently of one another are —$(C_1-C_8)$-alkyl, —$(C_2-C_8)$-alkenyl or —$(CH_2)_mR(14)$;
m is zero, 1 or 2;
R(14) is —$(C_3-C_8)$-cycloalkyl or phenyl, which is not substituted or is substituted by 1–3 substituents selected from the group consisting of F, Cl, —$CF_3$, methyl, methoxy and —NR(15)R(16);
R(15) and R(16) are hydrogen or —$CH_3$; or the other radicals R(1), R(2) and R(3) in each case independently of one another are R(18)R(19)N—(C=Y')—NH—$SO_2$—;
Y' is oxygen, —S— or —N—R(20);
R(18) and R(19) independently of one another are hydrogen, —$(C_1-C_8)$-alkyl, —$(C_3-C_6)$-alkenyl or —$(CH_2)_tR(21)$;
t is zero, 1, 2, 3 or 4;
R(21) is —$(C_5-C_7)$-cycloalkyl or phenyl, which is unsubstituted or substituted by 1–3 substituents selected from the group consisting of F, Cl, —$CF_3$, methoxy and —$(C_1-C_4)$-alkyl; or R(18) and R(19) together are 4 or 5 methylene groups, of which one $CH_2$ group can be replaced by oxygen, —S—, —NH—, —N—$CH_3$ or —N-benzyl;

R(20) is defined as R(18) or is amidine; or the other radicals R(1), R(2) and R(3) in each case independently of one another are hydrogen, F, Cl, Br, I, —C≡N, X—$(CH_2)_p$—$(C_qF_{2q+1})$, R(22)—$SO_u$—, R(23)R(24)N—CO—, R(25)—CO— or R(26)R(27)N—$SO_2$—, where the perfluoroalkyl group is straight-chain or branched;

X is a bond, oxygen, —S— or —NR(28);

u is zero, 1 or 2;

p is zero, 1 or 2;

q is 1, 2, 3, 4, 5 or 6;

R(22), R(23), R(25) and R(26) independently of one another are —$(C_1-C_8)$-alkyl, —$(C_3-C_6)$-alkenyl, —$(CH_2)_n$—R(29) or —$CF_3$;

n is zero, 1, 2, 3 or 4;

R(28) is hydrogen or —$(C_1-C_3)$-alkyl;

R(29) is —$(C_3-C_7)$-cycloalkyl or phenyl, which is not substituted or is substituted by 1–3 substituents selected from the group consisting of F, Cl, —$CF_3$, methyl, methoxy and —NR(30)R(31);

R(30) and R(31) are hydrogen or —$(C_1-C_4)$-alkyl; or

R(23), R(25) and R(26) are hydrogen;

R(24) and R(27) independently of one another are hydrogen or —$(C_1-C_4)$-alkyl; or R(23) and R(24), and also R(26) and R(27) together are 4 or 5 methylene groups, of which one $CH_2$ group can be replaced by oxygen, —S—, —NH—, —N—$CH_3$ or —N-benzyl; or the other radicals R(1), R(2) and R(3) in each case independently of one another are —OR(35) or —NR(35)R(36);

R(35) and R(36) independently of one another are hydrogen or —$(C_1-C_6)$-alkyl; or R(35) and R(36) together are 4–7 methylene groups, of which one $CH_2$ group can be replaced by oxygen, —S—, —NH—, —N—$CH_3$ or —N-benzyl;

R(4) and R(5) independently of one another are hydrogen, —$(C_1-C_4)$-alkyl, F, Cl, —OR(32), —NR(33)R(34) or —$C_rF_{2r+1}$;

R(32), R(33) and R(34) independently of one another are hydrogen or —$(C_1-C_3)$-alkyl;

r is 1, 2, 3 or 4;

or a pharmaceutically tolerable salt thereof;

af) a benzoylguanidine of the formula

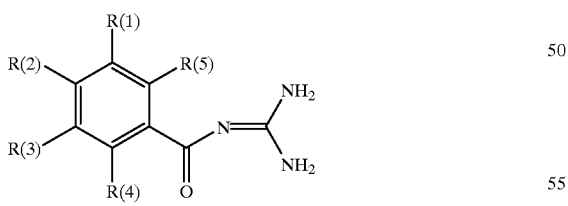

in which:

R(1) is R(6)—CO or R(7)R(8)N—CO;

R(6) is $(C_1-C_8)$-alkyl, $(C_1-C_8)$-perfluoroalkyl, $(C_3-C_8)$-alkenyl or —$C_nH_{2n}$—R(9), n is zero, 1, 2, 3 or 4;

R(9) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11), R(10) and R(11) are H, $(C_1-C_4)$-alkyl or $(C_1-C_4)$-perfluoroalkyl;

R(7) is H, $(C_1-C_8)$-alkyl, $(C_1-C_8)$-perfluoroalkyl, $(C_3-C_8)$-alkenyl or —$C_nH_{2n}$—R(12);

n is zero, 1, 2, 3 or 4;

R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);

R(13) and R(14) are H, $(C_1-C_4)$-alkyl or $(C_1-C_4)$-perfluoroalkyl;

R(8) is H, $(C_1-C_4)$-alkyl or $(C_1-C_4)$-perfluoroalkyl; or

R(7) and R(8) together are 4 or 5 methylene groups, of which one $CH_2$ group can be replaced by oxygen, S, NH, N—$CH_3$ or N-benzyl;

R(2) is defined as R(1), or is H, OH, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}$R(15);

n is zero, 1, 2, 3 or 4;

R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);

N) R(16) and R(17) are H, $(C_1-C_4)$-alkyl or $(C_1-C_4)$-perfluoroalkyl; or

R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(2) is SR(18), —OR(18), —NR(18)R(19) or —CR(18)R(19)R(20);

R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino, dimethylamino;

a is zero, 1 or 2;

R(19) and R(20) independently of one another are defined as R(18) or are hydrogen, $(C_1-C_4)$-alkyl or $(C_1-C_4)$-perfluoroalkyl; or R(2) is R(21)—$SO_m$ or R(22)R(23)N—$SO_2$—;

m is 1 or 2;

R(21) is $(C_1-C_8)$-alkyl, $(C_1-C_8)$-perfluoroalkyl, $(C_3-C_8)$-alkenyl or —$C_nH_{2n}$—R(24);

n is zero, 1, 2, 3 or 4;

R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, $(C_1-C_4)$-alkyl or $(C_1-C_4)$-perfluoroalkyl;

R(22) is H, $(C_1-C_8)$-alkyl, $(C_1-C_8)$-perfluoroalkyl, $(C_3-C_8)$-alkenyl or —$C_nH_{2n}$—R(29);

n is zero, 1, 2, 3 or 4;

R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);

R(30) and R(31) are H, $(C_1-C_4)$-alkyl or $(C_1-C_4)$-perfluoroalkyl;

R(23) is hydrogen, $(C_1-C_4)$-alkyl or $(C_1-C_4)$-perfluoroalkyl; or

R(22) and R(23) together are 4 or 5 methylene groups, of which one $CH_2$ group can be replaced by oxygen, S, NH, N—$CH_3$ or N-benzyl; or R(2) is R(33)X—;
  X is oxygen, S, NR(34), (D=O)A— or NR(34)C=MN$^{(*)}$R(35)—;
  M is oxygen or S;
  A is oxygen or NR(34);
  D is C or SO;
  R(33) is $(C_1–C_8)$-alkyl, $(C_3–C_8)$-alkenyl, $(CH_2)_b C_d F_{2d+1}$ or —$C_n H_{2n}$—R(36);
    b is zero or 1;
    d is 1, 2, 3, 4, 5, 6 or 7;
    n is zero, 1, 2, 3 or 4;
    R(36) is $(C_3–C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
    R(37) and R(38) are H, $(C_1–C_4)$-alkyl or $(C_1–C_4)$-perfuoroalkyl;
  R(34) is hydrogen, $(C_1–C_4)$-alkyl or $(C_1–C_4)$-perfluoroalkyl;
  R(35) is defined as R(33); or
  R(33) and R(34) together are 4 or 5 methylene groups, of which one $CH_2$ group can be replaced by oxygen, S, NH, N—$CH_3$ or N-benzyl;
  where A and $N^{(*)}$ are bonded to the phenyl nucleus of the benzoylguanidine parent structure; or R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);
  R(40) and R(41) independently of one another are —$(CH_2)_p$—$(CHOH)_q$—$(CH_2)_r$—$(CHOH)_t$R(51) or —$(CH_2)_p$—O—$(CH_2$—$CH_2O)_q$—R(51);
  R(51) is hydrogen or methyl;
  u is 1, 2, 3 or 4;
  v is zero, 1, 2, 3 or 4;
    p, q and r independently of one another are zero, 1, 2, 3 or 4;
    t is 1, 2, 3 or 4;
  R(42) and R(43) independently of one another are hydrogen or $(C_1–C_6)$-alkyl; or
  R(42) and R(43) together with the carbon atom carrying them are a $(C_3–C_8)$-cycloalkyl;
  R(44) is hydrogen, $(C_1–C_6)$-alkyl, $(C_3–C_8)$-cycloalkyl, —$C_e H_{2e}$—R(45);
    e is zero, 1, 2, 3 or 4;
  R(45) is phenyl, which is unsubstituted or substituted by 1–3 substituents selected from the group consisting of F, Cl, $CF_3$, methyl, methoxy and NR(52)R(53);
  R(52) and R(53) are H or $(C_1–C_4)$-alkyl; or
  R(45) is $(C_1–C_9)$-heteroaryl, which is unsubstituted or substituted as phenyl; or
  R(45) is $(C_1–C_6)$-alkyl, which is unsubstituted or substituted by 1–3 OH;
  R(46), R(47), R(48), R(49) and R(50) independently of one another are hydrogen or methyl; or R(2) is R(55)—NH—$SO_2$—;
  R(55) is R(56)R(57)N—(C=Y)—;
  Y is oxygen, S or N—R(58);
  R(56) and R(57) independently of one another are hydrogen, $(C_1–C_8)$-alkyl, $(C_3–C_6)$-alkenyl or —$C_f H_{2f}$—R(59);
    f is zero, 1, 2, 3 or 4;
    R(59) is $(C_5–C_7)$-cycloalkyl, phenyl, which is unsubstituted or substituted by 1–3 substituents selected from the group consisting of F, Cl, $CF_3$, methoxy and $(C_1–C_4)$-alkyl; or
  R(56) and R(57) together are 4 or 5 methylene groups, of which one $CH_2$ group can be replaced by oxygen, S, NH, N—$CH_3$ or N-benzyl;
  R(58) is defined as R(56) or is amidine;

R(3), R(4) and R(5) are independently of one another defined as R(1) or R(2), but where at least one of the substituents R(2), R(3), R(4) and R(5) must be OH;

or a pharmaceutically tolerable salt thereof;

ag) a benzoylguanidine of the formula in which:

one of the three substituents R(1), R(2) and R(3) is R(6)—A—B—D—;
  R(6) is a basic protonatable radical, i.e. an amino group —NR(7)R(8), an amidino group R(7)R(8)N—C[=N—R(9)]— or a guanidino group R(7), R(8), R(9) and R(10) independently of one another are hydrogen or alkyl having 1, 2, 3 or 4 carbon atoms; or
  R(7) and R(8) together are $C_a H_{2a}$;
    a is 4, 5, 6 or 7;
    where if a=5, 6 or 7 a methylene group of the group $C_a H_{2a}$ can be replaced by a heteroatom group O, $SO_m$ or NR(11), or
  R(8) and R(9) or R(9) and R(10) or R(7) and R(10) are a group $C_a H_{2a}$;
    a is 2, 3, 4 or 5; where if a=3, 4 or 5 a methylene group of the group $C_a H_{2a}$ can be replaced by a heteroatom group O, $SO_m$ or NR(11);
    m is zero, 1 or 2;
    R(11) is hydrogen or methyl; or
  R(6) is a basic heteroaromatic ring system having 1–9 carbon atoms;
A is $C_b H_{2b}$;
  b is 1, 2, 3, 4, 5, 6, 7, 8, 9 or 10;
    where in the group $C_b H_{2b}$ one or two methylene groups can be replaced by one of the groupings selected from the group consisting of —O—, —CO—, —CH[OR(20)]—, —$SO_m$—, —NR(20)—, —NR(20)—CO—, —NR(20)—CO—NH—, —NR(20)—CO—NH—$SO_2$—

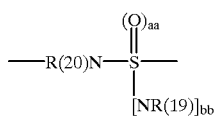

and —SO$_{aa}$[NR(19)]$_{bb}$—;
and where in the group C$_b$H$_{2b}$ a methylene group can be replaced by —CH—R(99), where R(99) together with R(7) forms a pyrrolidine or piperidine ring;
aa is 1 or 2;
bb is 0 or 1;
aa+bb=2;
R(19) is hydrogen or alkyl having 1, 2, 3 or 4 carbon atoms;
R(20) is hydrogen or methyl;
B is a phenylene or naphthylene radical

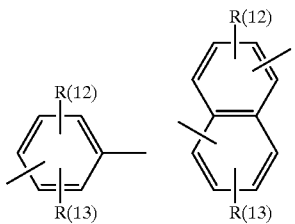

R(12) and R(13) independently of one another are hydrogen, methyl, F, Cl, Br, I, CF$_3$ or —SO$_w$—R(14);
R(14) is methyl or NR(15)R(16);
R(15) and R(16) independently of one another are hydrogen or alkyl having 1, 2, 3 or 4 carbon atoms;
w is zero, 1 or 2;
D is —C$_d$H$_{2d}$—X$_f$—;
d is zero, 1, 2, 3 or 4;
X is —O—, —CO—, —CH[OR(21)]—, —SO$_m$— or —NR(21)—;
f is zero or 1;
R(21) is hydrogen or methyl;
m is zero, 1 or 2;
and the other substituents R(1) and R(2) and R(3) in each case independently of one another are hydrogen, F, Cl, Br, I, —CN, —(C$_1$–C$_8$)-alkyl, —(C$_2$–C$_8$)-alkenyl, —NR(35)R(36) or R(17)—C$_g$H$_{2g}$—Z$_h$—;
g is zero, 1, 2, 3 or 4;
h is zero or 1;
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl;
z is —O—, —CO—, —SO$_v$—, —NR(18)—, —NR(18)—CO—, —NR(18)—CO—NH— or —NR(18)—SO$_2$—;
R(18) is hydrogen or methyl;
v is zero, 1 or 2;
R(17) is hydrogen, cycloalkyl having 3, 5 or 6 carbon atoms or
C$_k$F$_{2k+1}$—;
k is 1, 2 or 3, or
R(17) is pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl and methoxy; or
R(17) is —(C$_3$–C$_8$)-cycloalkyl or phenyl, which is not substituted or is substituted by 1–3 substituents selected from the group consisting of F and Cl, —CF$_3$, methyl, hydroxyl, methoxy, —NR(37)R(38), CH$_3$SO$_2$— and H$_2$NO$_2$S—;
R(37) and R(38) are hydrogen or —CH$_3$;
R(4) and R(5) independently of one another are hydrogen, alkyl having 1, 2, 3 or 4 carbon atoms, F, Cl, —OR(32), —NR(33)R(34) or —C$_r$F$_{2r+1}$;
R(32), R(33) and R(34) independently of one another are hydrogen or alkyl having 1, 2 or 3 carbon atoms;
r is 1, 2, 3 or 4;
or a pharmaceutically tolerable salt thereof;
ah) an indenoylguanidine of the formula

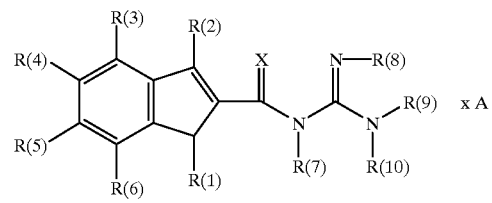

in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)-alkyl having 1, 2, 3 or 4 carbon atoms or C$_m$H$_{2m}$—NR(12)R(13);
R(12) and R(13) independently of one another are hydrogen or alkyl having 1, 2, 3 or 4 carbon atoms;
m is zero, 2, 3 or 4; NH—C(=O)—NH$_2$, C(=O)—O-alkyl having 1, 2, 3 or 4 carbon atoms, C(=O)—NH$_2$, C(=O)—NH-alkyl having 1, 2, 3 or 4 carbon atoms, C(=O)—N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, C$_1$–C$_4$-alkyl-substituted aryl, C$_1$–C$_4$-alkylheteroaryl, C$_1$–C$_4$-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—C$_1$–C$_4$-alkylaryl, O—C(=O)—NH—C$_1$–C$_4$-alkyl, O—C(=O)—N(C$_1$–C$_4$-alkyl)$_2$, NO$_2$, CN, CF$_3$, NH$_2$, NH—C(=O)—C$_1$–C$_4$-alkyl, NH—C(=O)—NH$_2$, COOH, C(=O)—O—C$_1$–C$_4$-alkyl, C(=O)—NH$_2$, C(=O)—NH—C$_1$–C$_4$-alkyl, C(=O)—N(C$_1$–C$_4$-alkyl)$_2$, C$_1$–C$_4$-COOH, C$_1$–C$_4$-alkyl-C(=O)—O—C$_1$–C$_4$-alkyl, SO$_3$H, SO$_2$-alkyl, SO$_2$-alkylaryl, SO$_2$—N-(alkyl)$_2$, SO$_2$—N(alkyl)(alkylaryl), C(=O)—R(11), C$_1$–C$_{10}$-alkyl-C(=O)—R(11), C$_2$–C$_{10}$-alkenyl-C (=O)—R(11), $C_2$-$C_{10}$-alkynyl-C(=O)—R(11), NH—C(=O)—$C_1$-$C_{10}$-alkyl-C(=O)—R(11), O—$C_1$-$C_{11}$-alkyl-C(=O)—R(11);

R(11) is $C_1$-$C_4$-alkyl, $C_1$-$C_4$-alkynyl, aryl, substituted aryl, $NH_2$, NH—$C_1$-$C_4$-alkyl, N—($C_1$-$C_4$-alkyl)$_2$, $SO_3H$, $SO_2$-alkyl, $SO_2$-alkylaryl, $SO_2$—N-(alkyl)$_2$, $SO_2$—N(alkyl)(alkylaryl);

X is O, S or NH;

R(7), R(8), R(9) and R(10) independently of one another are hydrogen, alkyl, cycloalkyl, aryl, alkylaryl; or R(8) and R(9) together are part of a 5-, 6- or 7-membered heterocyclic ring;

A is absent or is a nontoxic organic or inorganic acid.

ai) a benzyloxycarbonylguanidine of the formula

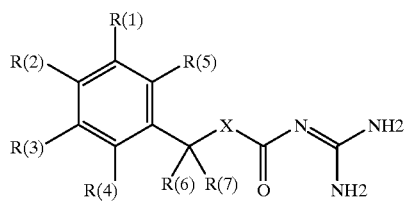

in which:

R(1), R(2) and R(3) independently of one another are —Y-[4-R(8)-phenyl], —Y-[3-R(8)-phenyl] or -Y-[2-R(8)-phenyl], where the phenyl is in each case unsubstituted or substituted by 1–2 substituents from the group consisting of F, Cl, —$CF_3$, methyl, hydroxyl, methoxy and —NR(96)R(97);

R(96) and R(97) independently of one another are hydrogen or —$CH_3$;

Y is a bond, $CH_2$, oxygen, —S— or —NR(9); R(9) is hydrogen or alkyl having 1, 2, 3 or 4 carbon atoms;

R(8) is $SO_a$[NR(98)]$_b$NR(99)R(10);

a is 1 or 2;
b is 0 or 1;
a+b=2;

R(98), R(99) and R(10) independently of one another are hydrogen, —($C_1$-$C_8$)-alkyl, benzyl, —($C_2$-$C_8$)-alkylene-NR(11)R(12), ($C_2$-$C_8$)-alkylene-NR(13)—($C_2$-$C_8$)-alkylene-NR(37)R(38) or ($C_0$-$C_8$)-alkylene-CR(39)R(40)CR(41)R(42)($C_0$-$C_8$)—$C_3$ alkylene-NR(43)R(44);

R(11), R(12), R(13), R(37), R(38), R(43) and R(44) independently of one another are hydrogen, —($C_1$-$C_8$)-alkyl or benzyl;

R(39), R(40), R(41) and R(42) independently of one another are hydrogen, —($C_1$-$C_8$)-alkyl or —($C_0$-$C_3$)-alkylenephenyl, where the phenyl is not substituted or is substituted by 1–3 substituents selected from the group consisting of F, Cl, —$CF_3$, methyl and methoxy; or R(99) and R(10) together are 4–6 methylene groups, of which one $CH_2$ group can be replaced by oxygen, —S—, —NH—, —N—$CH_3$ or —N-benzyl; or R(8) is $SO_a$[NR(98)]$_b$NR(95)—C[=N—R(94)]—NR(93)R(92);

R(92), R(93), R(94) and R(95) independently of one another are hydrogen or alkyl having 1, 2, 3 or 4 carbon atoms; or R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —$CF_3$, methyl, methoxy; or R(1), R(2) and R(3) independently of one another are hydrogen, —($C_1$-$C_8$)-alkyl, —($C_2$-$C_8$)-alkenyl or —($CH_2$)$_m$R(14);

m is zero, 1 or 2;

R(14) is —($C_3$-$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) are hydrogen or —$CH_3$; or

R(1), R(2) and R(3) independently of one another are —Q-4-[($CH_2$)$_k$—CHR(17)—(C=O)R(20)]-phenyl, —Q-3-[($CH_2$)$_k$—CHR(17)—(C=O)R(20)]-phenyl or —Q-2-[($CH_2$)$_k$—CHR(17)—(C=O)R(20)]-phenyl, where the phenyl in each case is unsubstituted or substituted by 1–2 substituents from the group F, Cl, —$CF_3$, methyl, hydroxyl, methoxy and —NR(35)R(36);

R(35) and R(36) independently of one another are hydrogen or —$CH_3$;

Q is a bond, oxygen, —S— or —NR(18);

R(18) is hydrogen or —($C_1$-$C_4$)-alkyl;

R(17) is —OR(21) or —NR(21)R(22);

R(21) and R(22) independently of one another are hydrogen, —($C_1$-$C_8$)-alkyl, —($C_1$-$C_8$)-alkanoyl, —($C_1$-$C_8$)-alkoxycarbonyl, benzyl, benzyloxycarbonyl; or R(21) is trityl;

R(20) is —OR(23) or —NR(23)R(24);

R(23), R(24) independently of one another are hydrogen, —($C_1$-$C_8$)-alkyl or benzyl;

k is zero, 1, 2, 3 or 4; or

R(1), R(2) and R(3) independently of one another are ($C_1$-$C_9$)-heteroaryl, which is linked via C or N and which is unsubstituted or substituted by 1–3 substituents from the group F, Cl, $CF_3$, $CH_3$, methoxy, hydroxyl, amino, methylamino and dimethylamino; or R(1), R(2) and R(3) are —SR(25), —OR(25), —NR(25)R(26), —CR(25)R(26)R(27);

R(25) is —$C_fH_{2f}$—($C_1$-$C_9$)-heteroaryl, which is unsubstituted or substituted by 1–3 substituents from the group F, Cl, $CF_3$, $CH_3$, methoxy, hydroxyl, amino, methylamino and dimethylamino;

f is zero, 1 or 2;

R(26) and R(27) independently of one another are defined as R(25) or are hydrogen or ($C_1$-$C_4$)-alkyl, or R(1), R(2) and R(3) independently of one another are ($C_1$-$C_9$)-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(1), R(2) and R(3) independently of one another are —SR(28), —OR(28), —NR(28)R(29) or —CR(28)R(29)R(30);

R(28) is —$C_gH_{2g}$—($C_1$-$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

g is zero, 1 or 2;

R(29), R(30) independently of one another are defined as R(28), hydrogen or ($C_1$-$C_4$)-alkyl; or R(1), R(2) and R(3) independently of one another are hydrogen, F, Cl, Br, I, —C≡N, T—(CH$_2$)$_h$—(C$_i$F$_{2i+1}$), R(31)SO$_l$—, R(32)R(33)N—CO—, R(34)—CO— or R(45)R(46)N—SO$_2$, where the perfluoroalkyl group is straight-chain or branched;

T is a bond, oxygen, —S— or —NR(47);

l is zero, 1 or 2;

h is zero, 1 or 2;

i is 1, 2, 3, 4, 5 or 6;

R(31), R(32), R(34) and R(45) independently of one another are —(C$_1$–C$_8$)-alkyl, —(C$_3$–C$_6$)-alkenyl, (CH$_2$)$_n$R(48) or —CF$_3$;

n is zero, 1, 2, 3 or 4;

R(47) is hydrogen or alkyl with 1, 2 or 3 carbon atoms;

R(48) is —(C$_3$–C$_7$)-cycloalkyl or phenyl, which is not substituted or is substituted by 1–3 substituents selected from the group consisting of F, Cl, —CF$_3$, methyl, methoxy and —NR(49)R(50);

R(49) and R(50) are hydrogen or alkyl having 1, 2, 3 or 4 carbon atoms; or

R(32), R(34) and R(45) are hydrogen;

R(33) and R(46) independently of one another are hydrogen or alkyl having 1, 2, 3 or 4 carbon atoms; or R(32) and R(33), and R(45) and R(46) together are 5 or 6 methylene groups, of which one CH$_2$ group can be replaced by oxygen, —S—, —NH—, —NCH$_3$ or —N-benzyl; or R(1), R(2) and R(3) independently of one another are R(51)—A—G—D—;

R(51) is a basic protonatable radical, i.e. an amino group —NR(52)R(53), an amidino group R(52)R(53)N—C[=N—R(54)]— or a guanidino group R(52)R(53)N—C[=N—R(54)]—NR(55)—;

R(52), R(53), R(54) and R(55) independently of one another are hydrogen or alkyl having 1, 2, 3 or 4 carbon atoms; or R(52) and R(53) are a group C$_\alpha$H$_{2\alpha}$;

α is 4, 5, 6 or 7;

where if α=5, 6 or 7 a carbon atom of the group C$_\alpha$H$_{2\alpha}$ can be replaced by a heteroatom group O, SO$_d$ or NR(56), or R(53) and R(54) or R(54) and R(55) or R(52) and R(55) are a group C$_\gamma$H$_{2\gamma}$;

γ is 2, 3, 4 or 5;

where if γ=3, 4 or 5 a carbon atom of the group C$_\gamma$H$_{2\gamma}$ can be replaced by a heteroatom group O, SO$_d$ or NR(56);

d is zero, 1 or 2;

R(56) is hydrogen or methyl; or

R(51) is a basic heteroaromatic ring system having 1–9 carbon atoms;

A is a group C$_e$H$_{2e}$;

e is zero, 1, 2, 3, 4, 5, 6, 7, 8, 9 or 10;

where in the group C$_e$H$_{2e}$ a carbon atom can be replaced by one of the groupings —O—, —CO—, —CH[OR(57)]—, —SO$_r$—, —NR(57)—, —NR(57)—CO—, —NR(57)—CO—NH—, —NR(57)—CO—NH—SO$_2$— or —NR(57)—SO$_2$—;

r is zero, 1 or 2;

R(57) is hydrogen or methyl;

G is a phenylene radical

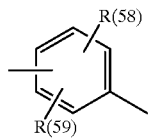

R(58) and R(59) independently of one another are hydrogen, methyl, methoxy, F, Cl, Br, I, CF$_3$ or —SO$_s$—R(60); R(60) is methyl or NR(61)R(62); R(61) and R(62) independently of one another are hydrogen or alkyl having 1, 2, 3 or 4 carbon atoms;

D is —C$_v$H$_{2v}$—E$_w$;

v is zero, 1, 2, 3 or 4;

E is —O—, —CO—, —CH[OR(63)]—, —SO$_{aa}$— or —NR(63)—;

w is zero or 1;

aa is zero, 1 or 2

R(63) is hydrogen or methyl, or

R(1), R(2) and R(3) independently of one another are —CF$_2$R(64), —CF[R(65)][R(66)], —CF[(CF$_2$)$_q$—CF$_3$][R(65)], —C[(CF$_2$)$_p$—CF$_3$]=CR(65)R(66);

R(64) is alkyl having 1, 2, 3 or 4 carbon atoms or cycloalkyl having 3, 4, 5, 6 or 7 carbon atoms;

R(65) and R(66) independently of one another are hydrogen or alkyl having 1, 2, 3 or 4 carbon atoms;

q is zero, 1 or 2;

p is zero, 1 or 2; or

R(1), R(2) and R(3) independently of one another are —OR(67) or —NR(67)R(68);

R(67) and R(68) independently of one another are hydrogen or alkyl having 1, 2, 3, 4, 5 or 6 carbon atoms; or R(67) and R(68) together are 4, 5, 6 or 7 methylene groups, of which one CH$_2$ group can be replaced by oxygen, —S—, SO$_2$, —NH—, —NCH$_3$ or —N-benzyl;

R(4) and R(5) independently of one another are hydrogen, alkyl having 1, 2, 3 or 4 carbon atoms, F, Cl, —OR(69), —NR(70)R(71) or —C$_z$F$_{2z+1}$;

R(69), R(70) and R(71) independently of one another are hydrogen or alkyl having 1, 2 or 3 carbon atoms;

z is 1, 2, 3 or 4;

R(6) and R(7) independently of one another are hydrogen or alkyl having 1, 2, 3 or 4 carbon atoms;

X is oxygen or NR(72); R(72) is hydrogen or alkyl having 1, 2, 3 or 4 carbon atoms;

or a pharmaceutically tolerable salt thereof;

ak) an alkenylcarboxylic acid guanidide, carrying at least one fluorophenyl group, of the formula

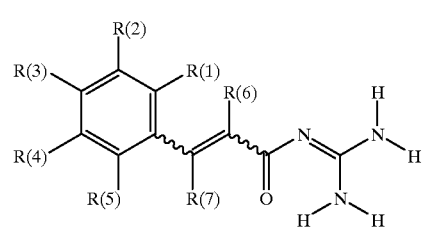

in which:

R(6) is hydrogen, (C$_1$–C$_8$)-alkyl, (C$_3$–C$_8$)-cycloalkyl or phenyl, where the phenyl group is not substituted or is substituted by 1–3 substituents selected from the group consisting of F, Cl, CF$_3$, methyl, methoxy and NR(9)R(10);
R(9) and R(10) are hydrogen, (C$_1$–C$_4$)-alkyl or (C$_1$–C$_4$)-perfluoroalkyl;
R(7) independently is defined as R(6);
R(1), R(2), R(3), R(4) and R(5) independently of one another are hydrogen or F;
where, however, at least one of the radicals R(1), R(2), R(3), R(4) and R(5) must be fluorine;
or a pharmaceutically tolerable salt thereof;
al) a benzoylguanidine of the formula

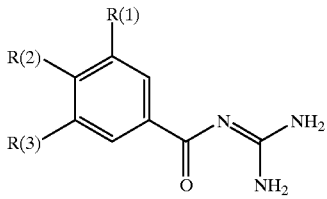

in which:
R(1) is R(4)—SO$_m$ or R(5)R(6)N—SO$_2$—;
m is 1 or 2;
R(4) and R(5) independently of one another are alkyl having 1, 2, 3, 4, 5, 6, 7 or 8 carbon atoms, alkenyl having 3, 4, 5 or 6 carbon atoms, CF$_3$ or —C$_n$H$_{2n}$—R(7);
n is zero, 1, 2, 3 or 4;
R(6) is H or alkyl having 1, 2, 3 or 4 carbon atoms;
R(7) is cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(8)R(9);
R(8) and R(9) are H or alkyl having 1, 2, 3 or 4 carbon atoms; or
R(5) is also hydrogen; or
R(5) and R(6) together are 4 or 5 methylene groups, of which a CH$_2$ group can be replaced by oxygen, S, NH, N—CH$_3$ or N-benzyl; or
R(1) is —O$_p$—(CH$_2$)$_q$—(CF$_2$)$_r$—CF$_3$;
p is zero or 1;
q is zero, 1 or 2;
r is zero, 1, 2 or 3; or
R(1) is —SR(10), —OR(10) or —CR(10)R(11)R(12);
R(10), R(11) and R(12) independently of one another are hydrogen, alkyl having 1, 2, 3, 4, 5, 6, 7 or 8 carbon atoms, —C$_s$H$_{2s}$—(C$_3$–C$_8$)-cycloalkyl or an aromatic system selected from the group consisting of pyridyl, pyrrolyl, quinolyl, isoquinolyl, imidazolyl or phenyl;
s is zero, 1 or 2;
where the aromatic systems pyridyl, pyrrolyl, quinolyl, isoquinolyl, imidazolyl and phenyl are unsubstituted or substituted by 1–3 substituents selected from the group consisting of F, Cl, CF$_3$, CH$_3$, methoxy, hydroxyl, amino, methylamino and dimethylamino;
R(2) is —(CH$_2$)$_u$—(CF$_2$)$_t$CF$_3$;
t is zero, 1, 2 or 3;
u is zero or 1;
R(3) is hydrogen or independently is defined as R(1);
or a pharmaceutically tolerable salt thereof;

am) a substituted cinnamic acid guanidide of the formula in which:
at least one of the substituents R(1), R(2), R(3), R(4) and R(5) is —X$_a$—Y$_b$—L$_n$—U;
X is CR(16)R(17), O, S or NR(18);
R(16), R(17) and R(18) independently of one another are H, alkyl having 1, 2, 3 or 4 carbon atoms or perfluoroalkyl having 1, 2, 3 or 4 carbon atoms;
a is zero or 1;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
T is NR(20), O, S or phenylene, where the phenylene is not substituted or is substituted by 1–3 substituents selected from the group consisting of F, Cl, CF$_3$, methyl, methoxy and NR(21)R(22);
R(20), R(21) and R(22) independently of one another are H, alkyl having 1, 2, 3 or 4 carbon atoms or perfluoroalkyl having 1, 2, 3 or 4 carbon atoms;
b is zero or 1;
L is O, S, NR(23) or C$_k$H$_{2k}$;
k is 1, 2, 3, 4, 5, 6, 7 or 8;
n is zero or 1;
U is NR(24)R(25) or an N-containing heterocycle having 1, 2, 3, 4, 5, 6, 7, 8 or 9 carbon atoms;
R(24) and R(25) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms; or
R(24) and R(25) together are 4 or 5 methylene groups, of which one CH$_2$ group can be replaced by oxygen, S, NH, N—CH$_3$ or N-benzyl;
where the N-containing heterocycles are N— or C-bridged and are not substituted or are substituted by 1–3 substituents selected from the group consisting of F, Cl, CF$_3$, methyl, methoxy and NR(27)R(28);
R(23), R(27) and R(28) independently of one another are H, alkyl having 1, 2, 3 or 4 carbon atoms or perfluoroalkyl having 1, 2, 3 or 4 carbon atoms;
and the other substituents R(1), R(2), R(3), R(4) and R(5) in each case independently of one another are H, F, Cl, Br, I, CN, —O$_n$—C$_m$H$_{2m+1}$, —O$_p$—(CH$_2$)$_s$—C$_q$F$_{2q+1}$ or —C$_r$H$_{2r}$R(10);
n is zero or 1;
m is zero, 1, 2, 3, 4, 5, 6, 7 or 8;
p is zero or 1;
q is 1, 2, 3, 4, 5, 6, 7 or 8;
s is zero, 1, 2, 3 or 4;
r is zero, 1, 2, 3 or 4;
R(10) is cycloalkyl having 3, 4, 5, 6, 7 or 8 carbon atoms, or phenyl, where the phenyl is not substituted or is substituted by 1–3 substituents selected from the group consisting of F, Cl, CF$_3$, methyl, methoxy and NR(11)R(12);

R(11) and R(12) independently of one another are H, alkyl having 1, 2, 3 or 4 carbon atoms or perfluoroalkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

or a pharmaceutically tolerable salt thereof;

an) a benzoylguanidine of the formula

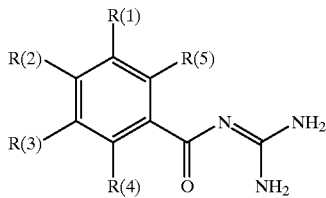

in which:

at least one of the substituents R(1), R(2) and R(3) is R(6)—C(OH)$_2$—;

R(6) is perfluoroalkyl having 1, 2 or 3 carbon atoms, which is straight-chain or branched;

and the other substituents R(1), R(2) and R(3) independently of one another are hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms, or phenoxy, which is unsubstituted or is substituted by 1–3 substituents selected from the group consisting of F, Cl, methyl and methoxy; or the other substituents R(1), R(2) and R(3) independently of one another are alkyl-SO$_x$, —CR(7)=CR(8)R(9) or —C≡CR(9);

x is zero, 1 or 2;

R(7) is hydrogen or methyl;

R(8) and R(9) independently of one another are hydrogen, alkyl having 1, 2, 3 or 4 carbon atoms, cycloalkyl having 3, 4, 5, 6, 7 or 8 carbon atoms, or phenyl, which is unsubstituted or is substituted by 1–3 substituents selected from the group consisting of F, Cl, $CF_3$, methyl and methoxy; or the other substituents R(1), R(2) and R(3) independently of one another are phenyl, $C_6H_5$—($C_1$–$C_4$)-alkyl, naphthyl, biphenylyl, quinolinyl, isoquinolinyl or imidazolyl, where quinolinyl, isoquinolinyl or imidazolyl are bonded via C or N and where phenyl, $C_6H_5$—($C_1$–$C_4$)-alkyl, naphthyl, biphenylyl, quinolinyl, isoquinolinyl and imidazolyl are unsubstituted or are substituted by 1–3 substituents selected from the group consisting of F, Cl, $CF_3$, $CH_3$, methoxy, hydroxyl, amino, methylamino and dimethylamino; or the other substituents R(1), R(2) and R(3) independently of one another are SR(10), —OR(10), —CR(10)R(11)R(12);

R(10) is —$C_fH_{2f}$—($C_3$–$C_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, $CF_3$, $CH_3$, methoxy, hydroxyl, amino, methylamino and dimethylamino;

f is zero, 1 or 2;

R(11) and R(12) independently of one another are defined as R(10), hydrogen or alkyl having 1, 2, 3 or 4 carbon atoms;

R(4) and R(5) independently of one another are hydrogen, alkyl having 1, 2 or 3 carbon atoms, F, Cl, Br, I, CN, OR(13), NR(14)R(15), —(CH$_2$)$_n$—(CF$_2$)$_o$—CF$_3$;

R(13), R(14) and R(15) independently of one another are hydrogen or alkyl having 1, 2, 3 or 4 carbon atoms;

n is zero or 1;

o is zero, 1 or 2;

or a pharmaceutically tolerable salt thereof;

ao) a sulfonimidamide of the formula

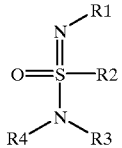

in which:

at least one of the three substituents R(1), R(2) and R(3) is a benzoylguanidine,

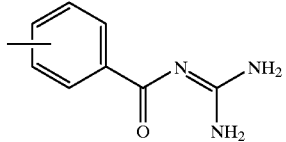

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, $CF_3$, R(22)SO$_2$—, R(23)R(24)N—CO—, R(25)—CO—, R(26)R(27)N—SO$_2$, —OR(35), —SR(35) or —NR(35)R(36);

m is zero, 1 or 2;

R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) independently of one another are hydrogen or —$CH_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —$CF_3$;

n is zero, 1, 2, 3 or 4;

R(29) is —($C_3$–$C_7$)-cycloalkyl or phenyl, which is not substituted or is substituted by 1–3 substituents selected from the group consisting of F, Cl, —$CF_3$, methyl, methoxy and —NR(30)R(31);

R(30) and R(31) are hydrogen or alkyl having 1, 2, 3 or 4 carbon atoms; or

R(23), R(25) and R(26) are hydrogen;

R(24) and R(27) independently of one another are hydrogen or alkyl having 1, 2, 3 or 4 carbon atoms; or R(23) and R(24), and also R(26) and R(27) together are 5 or 6 methylene groups, of which one CH$_2$ group can be replaced by oxygen, —S—, —NH—, —NCH₃ or —N-benzyl;

R(35) and R(36) independently of one another are hydrogen or alkyl having 1, 2, 3, 4, 5 or 6 carbon atoms; or R(35) and R(36) together are 4–7 methylene groups, of which one CH₂ group can be replaced by oxygen, —S—, —NH—, —NCH₃ or —N-benzyl;

R(35) is phenyl, which is not substituted or is substituted by 1–3 substituents selected from the group consisting of F, Cl, —CF₃, methyl, methoxy, SO₂R(5), SO₂NR(6)R(7) and —NR(32)R(33);

R(5) is alkyl having 1, 2, 3, 4, 5 or 6 carbon atoms;

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms; or R(35) is C₁–C₉-heteroaryl, which is unsubstituted or substituted by 1–3 substituents selected from the group consisting of F, Cl, CF₃, CH₃, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH₂)ₚR(10);

p is zero, 1, 2, 3 or 4;

R(10) is phenyl, which is not substituted or is substituted by 1–3 substituents selected from the group consisting of F, Cl, —CF₃, methyl, methoxy, —SO₂NR(17)R(8) and —SO₂R(9);

R(17) and R(8) independently of one another are hydrogen or alkyl having 1, 2, 3 or 4 carbon atoms;

R(9) is alkyl having 1, 2, 3 or 4 carbon atoms; or the other radical R(1) or R(3) in each case is hydrogen, R(4) is hydrogen or alkyl having 1, 2, 3 or 4 carbon atoms;

or a pharmaceutically tolerable salt thereof;

ap) a benzoylguanidine of the formula

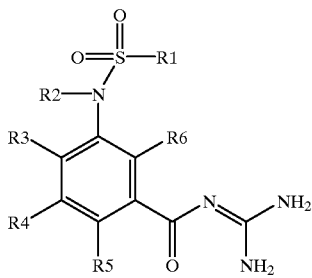

in which:

R(1) is alkyl having. 1, 2, 3, 4, 5, 6, 7 or 8 carbon atoms or NR(7)R(8);

R(7) and R(8) independently of one another are hydrogen or alkyl having 1, 2, 3, 4, 5, 6, 7 or 8 carbon atoms;

R(2) is hydrogen, alkyl having 1, 2, 3, 4, 5, 6, 7 or 8 carbon atoms or —SO₂R(9);

R(9) independently is defined as R(1); R(3) is hydrogen, —SR(25), —OR(25), —NR(25)R(26) or —CR(25)R(26)R(27); R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF₃, CH₃, methoxy, hydroxyl, amino, methylamino and dimethylamino; or R(25) is —(C₁–C₉)-heteroaryl, which is unsubstituted or substituted by 1–3 substituents selected from the group consisting of F, Cl, CF₃, CH₃, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is hydrogen, F, Cl, Br, I, OH, —C≡N, CF₃, alkyl having 1, 2, 3, 4, 5, 6, 7 or 8 carbon atoms, alkenyl having 2, 3, 4, 5, 6, 7 or 8 carbon atoms or —(CH₂)ₘR(14);

m is zero, 1 or 2;

R(14) is —(C₃–C₈)-cycloalkyl or phenyl, which is not substituted or is substituted by 1–3 substituents selected from the group consisting of F and Cl, —CF₃, methyl, methoxy and —NR(15)R(16);

R(15) and R(16) independently of one another are hydrogen or —CH₃;

R(5) and R(6) independently of one another are hydrogen, alkyl having 1, 2, 3 or 4 carbon atoms, F, Cl, —OR(32), —NR(33)R(34) or CF₃;

R(32), R(33) and R(34) independently of one another are hydrogen or alkyl having 1, 2, 3 or 4 carbon atoms;

or a pharmaceutically tolerable salt thereof;

aq) a benzenedicarboxylic acid diguanidide of the formula

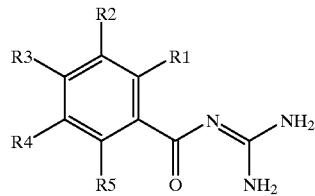

in which:

one of the radicals R(1), R(2), R(3) and R(4) is —CO—N=C(NH₂)₂;

and of the other radicals R(1), R(2), R(3) and R(4) in each case:

R(1) is hydrogen, alkyl having 1, 2, 3 or 4 carbon atoms, F, Cl, Br, I, —OR(32), —NR(33)R(34) or CF₃;

R(32), R(33) and R(34) independently of one another are hydrogen or alkyl having 1, 2, 3 or 4 carbon atoms;

R(2) and R(4) independently of one another are hydrogen, F, Cl, Br, I, OH, —CN, CF₃, —CO—N=C(NH₂)₂, alkyl having 1, 2, 3, 4, 5, 6, 7 or 8 carbon atoms, alkenyl having 2, 3, 4, 5, 6, 7 or 8 carbon atoms or —(CH₂)ₘR(14);

m is zero, 1 or 2;

R(14) is —(C₃–C₈)-cycloalkyl or phenyl, which is not substituted or is substituted by 1–3 substituents selected from the group consisting of F and Cl, —CF₃, methyl, methoxy and —NR(15)R(16);

R(15) and R(16) are hydrogen or —CH₃; or

R(2) and R(4) independently of one another are pyrrol-1-yl, pyrrol-2-yl or pyrrol-3-yl, which is not substituted or is substituted by 1–4 substituents selected from the group consisting of F, Cl, Br, I, —CN, (C₂–C₈)-alkanoyl, (C₂–C₈)-alkoxycarbonyl, formyl, carboxyl, —CF₃, methyl, methoxy; or R(2) and R(4) independently of one another are R(22)—SO₂—, R(23)R(24)N—CO—, R(28)—CO— or R(29)R(30)N—SO₂;

R(22) and R(28) independently of one another are methyl or —CF$_3$;

R(23), R(24), R(29) and R(30) independently of one another are hydrogen or methyl; or R(2) and R(4) independently of one another are —OR(35) or —NR(35)R(36);

R(35) and R(36) independently of one another are hydrogen or alkyl having 1, 2, 3, 4, 5 or 6 carbon atoms; or R(35) and R(36) together are 4–7 methylene groups, of which one CH$_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27); R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino; or R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(5) is alkyl having 1, 2, 3 or 4 carbon atoms, F, Cl, Br, I, X—(CH$_2$)$_y$—CF$_3$ or phenyl, which is not substituted or is substituted by 1–3 substituents selected from the group consisting of F and Cl, —CF$_3$, methyl, methoxy and —NR(6)R(7);

R(6) and R(7) independently of one another are hydrogen or —CH$_3$;

X is a bond or oxygen;

y is zero, 1 or 2;

or a pharmaceutically tolerable salt thereof;

ar) a benzenedicarboxylic acid diguanidide of the formula

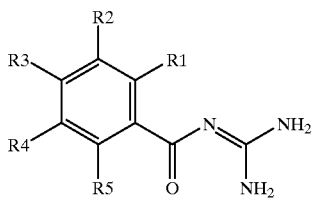

in which:

one of the radicals R(1), R(2), R(3) and R(5) is —CO—N═C(NH$_2$)$_2$;

and of the other radicals R(1), R(2), R(3) and R(5) in each case:

R(1) and R(5) independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

R(2) is hydrogen, F, Cl, Br, I, OH, —CN, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$; or

R(2) is R(22)—SO$_2$—, R(23)R(24)N—CO—, R(28)—CO— or R(29)R(30)N—SO$_2$;

R(22) and R(28) independently of one another are methyl or —CF$_3$;

R(23), R(24), R(29) and R(30) independently of one another are hydrogen or methyl; or R(2) is —OR(35) or —NR(35)R(36);

R(35) and R(36) independently of one another are hydrogen or alkyl having 1, 2, 3, 4, 5 or 6 carbon atoms; or R(35) and R(36) together are 4–7 methylene groups, of which one CH$_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino; or R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);

m is 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$; or

R(4) is phenyl, which is substituted by 2, 3, 4 or five substituents selected from the group consisting of F, Cl, CF$_3$, methyl, methoxy and —NR(15)R(16);

R(15) and R(16) independently of one another are hydrogen or CH$_3$;

or a pharmaceutically tolerable salt thereof;

as) a diaryldicarboxylic acid diguanidide of the formula

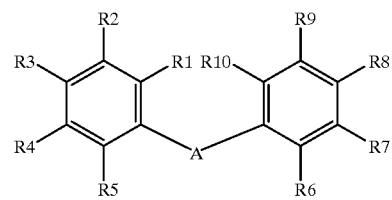

in which:

one of the radicals R(1), R(2), R(3), R(4) and R(5) is —CO—N═C(NH$_2$)$_2$;

the other radicals R(1) and R(5) in each case independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

the other radicals R(2) and R(4) in each case independently of one another are hydrogen, F, Cl, Br, I, OH, —CN, $CF_3$, —CO—N═$C(NH_2)_2$, alkyl having 1, 2, 3, 4, 5, 6, 7 or 8 carbon atoms, alkenyl having 2, 3, 4, 5, 6, 7 or 8 carbon atoms or —$(CH_2)_m$R(14);

m is zero, 1 or 2;

R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) are hydrogen or —$CH_3$; or the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl, methoxy; or the other radicals R(2) and R(4) in each case are R(22)—$SO_2$—, R(23)R(24)N—CO—, R(28)—CO— or R(29)R(30)N—$SO_2$;

R(22) and R(28) independently of one another are methyl or —$CF_3$;

R(23), R(24), R(29) and R(30) independently of one another are hydrogen or methyl; or the other radicals R(2) and R(4) in each case independently of one another are —OR(35) or —NR(35)R(36);

R(35) and R(36) independently of one another are hydrogen or alkyl having 1, 2, 3, 4, 5 or 6 carbon atoms; or R(35) and R(36) together are 4–7 methylene groups, of which one $CH_2$ group can be replaced by oxygen, —S—, —NH—, —$NCH_3$ or —N-benzyl;

the other radical R(3) in each case is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, $CF_3$, $CH_3$, methoxy, hydroxyl, amino, methylamino and dimethylamino; or R(25) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

one of the radicals R(6), R(7), R(8), R(9) and R(10) is —CO—N═$C(NH_2)_2$;

the other radicals R(6) and R(10) in each case independently of one another are hydrogen, alkyl having 1, 2, 3 or 4 carbon atoms, F, Cl, —OR(132), —NR(133)R(134) or $CF_3$;

R(132), R(133) and R(134) independently of one another are hydrogen or alkyl having 1, 2, 3 or 4 carbon atoms;

the other radicals R(7) and R(9) in each case independently of one another are hydrogen, F, Cl, Br, I, OH, —CN, $CF_3$, —CO—N═$C(NH_2)_2$, alkyl having 1, 2, 3, 4, 5, 6, 7 or 8 carbon atoms, alkenyl having 2, 3, 4, 5, 6, 7 or 8 carbon atoms or —$(CH_2)_{mm}$R(114);

mm is zero, 1 or 2;

R(114) is —($C_3$–$C_8$)-cycloalkyl or phenyl, which is not substituted or is substituted by 1–3 substituents selected from the group consisting of F and Cl, —$CF_3$, methyl, methoxy and —NR(115)R(116);

R(115) and R(116) are hydrogen or —$CH_3$; or the other radicals R(7) and R(9) in each case independently of one another are pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl and methoxy; or the other radicals R(7) and R(9) in each case are R(122)—$SO_2$—, R(123)R(124)N—CO—, R(128)—CO— or R(129)R(130)N—$SO_2$;

R(122) and R(128) independently of one another are methyl or —$CF_3$;

R(123), R(124), R(129) and R(130) independently of one another are hydrogen or methyl; or the other radicals R(7) and R(9) in each case independently of one another are —OR(35) or —NR(135)R(136);

R(135) and R(136) independently of one another are hydrogen or alkyl having 1, 2, 3, 4, 5 or 6 carbon atoms; or R(135) and R(136) together are 4–7 methylene groups, of which one $CH_2$ group can be replaced by oxygen, —S—, —NH—, —$NCH_3$ or —N-benzyl;

the other radical R(8) in each case is hydrogen, —SR(125), —OR(125), —NR(125)R(126) or —CR(125)R(126)R(127);

R(125) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino; or R(125) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

R(126) and R(127) independently of one another are defined as R(125) or are hydrogen or alkyl having 1, 2, 3, 4, 5, 6, 7 or 8 carbon atoms;

A is absent or is —NR(11)—CO—, —NR(12)—CO—NR(13)—, —NR(17)—CO—NR(18)—$SO_2$—, —NR(19)—$SO_2$—, —$SO_2$—NR(19)—$SO_2$—, —$SO_2$—NR(19)—CO—, —O—CO—NR(19)—$SO_2$— or —CR(20)═CR(21)—;

R(11), R(12), R(13), R(17), R(18), R(19), R(20) and R(21) independently of one another are hydrogen or alkyl having 1, 2, 3, 4, 5, 6, 7 or 8 carbon atoms or a pharmaceutically tolerable salt thereof;

at) a substituted thiophenylalkenylcarboxylic acid guanidide of the formula in which:

at least one of the substituents R(1), R(2) and R(3) is —$O_p$—$(CH_2)_s$—$C_qF_{2q+1}$, R(40)CO— or R(31)$SO_k$—;

p is zero or 1;
s is zero, 1, 2, 3 or 4;
q is 1, 2, 3, 4, 5, 6, 7 or 8;
k is zero, 1 or 2;
R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl and methoxy;
R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl or methoxy; or
R(31) is NR(41)R(42);
R(41) and R(42) independently of one another are hydrogen, alkyl having 1, 2, 3 or 4 carbon atoms, perfluoroalkyl having 1, 2, 3 or 4 carbon atoms, or
R(41) and R(42) together are 4 or 5 methylene groups, of which one $CH_2$ group can be replaced by oxygen, S, NH, N—$CH_3$ or N-benzyl;
and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}R(10)$;
na is zero or 1;
ma is zero, 1, 2, 3, 4, 5, 6, 7 or 8;
ga is zero or 1;
ra is zero, 1, 2, 3 or 4;
R(10) is cycloalkyl having 3, 4, 5, 6, 7 or 8 carbon atoms or phenyl, where the phenyl is not substituted or is substituted by 1–3 substituents selected from the group consisting of F, Cl, $CF_3$, methyl and methoxy;
R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;
or a pharmaceutically tolerable salt thereof;
au) an ortho-substituted benzoylguanidine of the formula

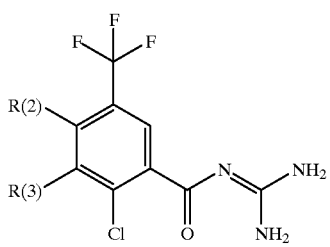

in which:
R(2) and R(3) independently of one another are hydrogen, Cl, Br, I, ($C_1$-$C_8$)-alkyl, ($C_3$-$C_8$)-cycloalkyl or —OR(5);
R(5) is ($C_1$-$C_8$)-alkyl or —$C_dH_2d$—($C_3$-$C_8$)-cycloalkyl;
d is zero, 1 or 2;
where one of the two substituents R(2) and R(3) is always hydrogen but both substituents R(2) and R(3) are not simultaneously hydrogen,
or a pharmaceutically tolerable salt thereof;
av) a benzoylguanidine of the formula

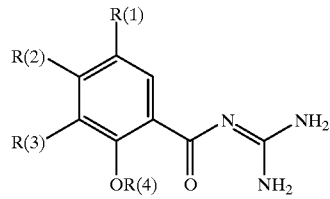

in which:
R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S, NR(5),
a is zero or 1;
b is zero, 1 or 2;
c is zero, 1, 2 or 3;
R(5) is H, alkyl having 1, 2, 3 or 4 carbon atoms or —$C_dH_{2d}R(6)$;
d is zero, 1, 2 or 3 or 4;
R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);
R(7) and R(8) independently are H or alkyl having 1, 2, 3 or 4 carbon atoms; or
R(1) is —SR(10), —OR(10) or —CR(10)R(11)R(12);
R(10) is —$C_fH_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, $CF_3$, $CH_3$, methoxy, hydroxyl, amino, methylamino and dimethylamino;
f is zero, 1 or 2;
R(11) and R(12) independently of one another are defined as R(10) or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
R(13) and R(14) identically or differently are —$(CH_2)_g$—$(CHOH)_h$—$(CH_2)_i$—$(CHOH)_j$—R(17) or —$(CH_2)_g$—O—$(CH_2$—$CH_2O)_h$—R(24); R(17) is hydrogen or methyl,
g, h and i identically or differently are zero, 1, 2, 3 or 4;

j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18) is phenyl, which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms; or
R(18) is heteroaryl having 1, 2, 3, 4, 5, 6, 7, 8 or 9 carbon atoms, which is unsubstituted or substituted as phenyl; or
R(18) is alkyl having 1, 2, 3, 4, 5 or 6 carbon atoms, which is unsubstituted or substituted by 1–3 OH; or
R(18) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
m is 1, 2, 3 or 4;
R(2) and R(3) are defined as R(1);
R(4) is alkyl having 1, 2, 3 or 4 carbon atoms;
or a pharmaceutically tolerable salt thereof;
aw) an ortho-substituted benzoylguanidine of the formula

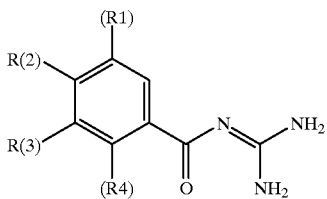

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S, NR(5),
a is zero or 1;
b is zero, 1 or 2;
c is zero, 1, 2 or 3;
R(5) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);
R(7) and R(8) independently are H or alkyl having 1, 2, 3 or 4 carbon atoms; or
R(1) is —SR(10), —OR(10) or —CR(10)R(11)R(12);
R(10) is —C$_f$H$_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;

f is zero, 1 or 2;
R(11) and R(12) independently of one another are defined as R(10), or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$-CH$_2$O)$_h$—R(24);
R(17) is hydrogen or methyl,
g, h and i identically or differently are zero, 1, 2, 3 or 4;
j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18) is phenyl, which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms; or
R(18) is heteroaryl having 1, 2, 3, 4, 5, 6, 7, 8 or 9 carbon atoms, which is unsubstituted or substituted as phenyl; or
R(18) is alkyl having 1, 2, 3, 4, 5 or 6 carbon atoms, which is unsubstituted or substituted by 1–3 OH; or
R(18) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
m is 1, 2, 3 or 4;
one of the two substituents R(2) and R(3) is hydroxyl; and
the other of the substituents R(2) and R(3) in each case is defined as R(1);
R(4) is alkyl having 1, 2, 3 or 4 carbon atoms; alkoxy having 1, 2, 3 or 4 carbon atoms, F, Cl, Br, I, or —(CH$_2$)$_n$—(CF$_2$)$_o$—CF$_3$;
n is zero or 1;
o is zero or 1;
or a pharmaceutically tolerable salt thereof;

ax) a bis-ortho-substituted benzoylguanidine of the formula

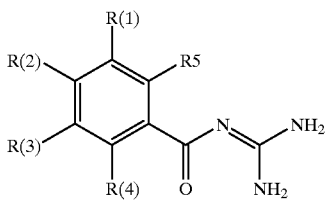

in which:
R(1), R(2) and R(3) independently of one another are R(10)—SO$_a$— or R(14)R(15)N—SO$_2$—;
a is zero, 1 or 2,
R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —C$_{ab}$H$_{2ab}$—R(16);
ab is zero, 1, 2, 3 or 4;
R(16) is cycloalkyl having 3, 4, 5, 6 or 7 carbon atoms, or phenyl, which is not substituted or is substituted by 1–3 substituents selected from the group consisting of F, Cl, CF$_3$, methyl, methoxy and NR(17)R(18);
R(17) and R(18) independently of one another are hydrogen, CF$_3$ or alkyl having 1, 2, 3 or 4 carbon atoms; or
R(14) and R(15) together are 4 or 5 methylene groups, of which one CH$_2$ group can be replaced by oxygen, sulfur, NH, N—CH$_3$ or N-benzyl; or
R(14) and R(15) are hydrogen; or
R(1), R(2) and R(3) independently of one another are SR(21), —OR(22), —NR(23)R(24) or —CR(25)R(26) R(27);
R(21), R(22), R(23) and R(25) independently of one another are —C$_b$H$_{2b}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
b is zero, 1 or 2;
R(24), R(26) and R(27) independently of one another are hydrogen, alkyl having 1, 2, 3 or 4 carbon atoms or perfluoroalkyl having 1, 2, 3 or 4 carbon atoms; or
R(1), R(2) and R(3) independently of one another are hydrogen, F, Cl, Br, I, CN, —(Xa)$_{dg}$—C$_{da}$H$_{2da+i}$, —(Xb)$_{dh}$—(CH$_2$)$_{db}$—C$_{de}$F$_{2de+1}$, alkenyl having 3, 4, 5, 6, 7 or 8 carbon atoms or —C$_{df}$H$_{2df}$R(30);
(Xa) is oxygen, sulfur or NR(33);
R(33) is hydrogen, alkyl having 1, 2, 3 or 4 carbon atoms or perfluoroalkyl having 1, 2, 3 or 4 carbon atoms;
dg is zero or 1;
(Xb) is oxygen, sulfur or NR(34);
R(34) is hydrogen, alkyl having 1, 2, 3 or 4 carbon atoms or perfluoroalkyl having 1, 2, 3 or 4 carbon atoms;
dh is zero or 1;
da is zero, 1, 2, 3, 4, 5, 6, 7 or 8;
db is zero, 1, 2, 3 or 4;
de is zero, 1, 2, 3, 4, 5, 6 or 7;
df is zero, 1, 2, 3 or 4;
R(30) is cycloalkyl having 3, 4, 5, 6, 7 or 8 carbon atoms, phenyl, biphenylyl or naphthyl, where the aromatics phenyl, biphenylyl and naphthyl are not substituted or are substituted by 1–3 substituents selected from the group consisting of F, Cl, CF$_3$, methyl, methoxy and NR(31)R(32);
R(31) and R(32) are hydrogen, alkyl having 1, 2, 3 or 4 carbon atoms or perfluoroalkyl having 1, 2, 3 or 4 carbon atoms; or
R(1), R(2) and R(3) independently of one another are NR(40)R(41) or —(Xe)—(CH$_2$)$_{eb}$R(45);
R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or (CH$_2$)$_e$—R(42);
e is zero, 1, 2, 3 or 4;
R(42) is cycloalkyl having 3, 4, 5, 6 or 7 carbon atoms or phenyl, which is not substituted or is substituted by 1–3 substituents selected from the group consisting of F, Cl, CF$_3$, methyl, methoxy and NR(43)R(44);
R(43) and R(44) independently of one another are hydrogen, CF$_3$ or alkyl having 1, 2, 3 or 4 carbon atoms; or
R(40) and R(41) together are 4 or 5 methylene groups, of which one CH$_2$ group can be replaced by oxygen, sulfur, NH, N—CH$_3$ or N-benzyl;
(Xe) is oxygen, sulfur or NR(47);
R(47) is hydrogen, alkyl having 1, 2, 3 or 4 carbon atoms or perfluoroalkyl having 1, 2, 3 or 4 carbon atoms;
eb is zero, 1, 2, 3 or 4;
R(45) is cycloalkyl having 3, 4, 5, 6 or 7 carbon atoms, or phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);
Xfa is CH$_2$, oxygen, sulfur or NR(48);
Xfb is oxygen, sulfur or NR(49);
R(48), R(49), R(50) and R(51) independently of one another are hydrogen, alkyl having 1, 2, 3 or 4 carbon atoms or perfluoroalkyl having 1, 2, 3 or 4 carbon atoms;
ed is 1, 2, 3 or 4;
R(46) is hydrogen, alkyl having 1, 2, 3 or 4 carbon atoms or perfluoroalkyl having 1, 2, 3 or 4 carbon atoms; or
R(1), R(2) and R(3) independently of one another are —CHR(52)R(53);
R(52) is —(CH$_2$)$_g$—(CHOH)$_h$—(CH)$_i$—(CHOH)$_k$—R(54) or —(CH$_2$)$_g$—O—(CH$_2$—CH$_2$O)$_h$—R(54);
R(54) is hydrogen or methyl;
g, h, i identically or differently are zero, 1, 2, 3 or 4;
k is 1, 2, 3 or 4;
R(53) is hydrogen or alkyl having 1, 2, 3 or 4 carbon atoms; or
R(1), R(2) and R(3) independently of one another are —C(OH)R(55)R(56);
R(55) and R(56) identically or differently are hydrogen or alkyl having 1, 2, 3 or 4 carbon atoms; or
R(55) and R(56) together are cycloalkyl having 3, 4, 5 or 6 carbon atoms; or
R(55) is —CH$_{20}$H; and
R(4) and R(5) independently of one another are alkyl having 1, 2, 3 or 4 carbon atoms, alkoxy having 1, 2, 3 or 4 carbon atoms, OH, F, Cl, Br, l, CN, —O$_n$—(CH$_2$)$_o$—(CF$_2$)$_p$—CF$_3$;
n is zero or 1;
o is zero, 1 or 2;
p is zero, 1 or 2;

or a pharmaceutically tolerable salt thereof;
ay) a substituted 1-naphthoylguanidine of the formula

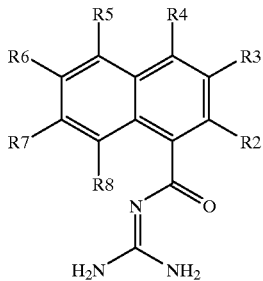

in which:
R2, R3, R4, R5, R6, R7 and R8 independently of one another are H, F, Cl, Br, I, CN, $NO_2$, $CF_3$, $C_2F_5$ or $X_aY_bZ$;
  X is O, S, NR(10), CR(11)R(12), C=O, C(=O)NR(10), C(=O)O, SO, $SO_2$, $SO_2$NR(10), OC=O, NR(10)C=O or NR(10)$SO_2$, where the linkage with the naphthalene ring in each case takes place via the left atom;
    R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
  a is zero or 1;
  Y is alkylene having 1, 2, 3, 4, 5, 6, 7 or 8 $CH_2$ groups, where one of these $CH_2$ groups can be replaced by O, S, NR(13) or o-, p- or m-phenylene;
    R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
  b is zero or 1;
  z is H, alkyl having 1, 2, 3, 4, 5, 6 or 7 carbon atoms, cycloalkyl having 3, 4, 5, 6 or 7 carbon atoms, C(=O)R(15), $SO_2$R(15), NR(16)R(17) or phenyl, which is not substituted or is substituted by 1–3 substituents selected from the group consisting of F, Cl, Br, $CF_3$, methyl, methoxy and NR(21)R(22);
    R(21) and R(22) independently of one another are H or alkyl having 1, 2, 3 or 4 carbon atoms or perfluoroalkyl having 1, 2, 3 or 4 carbon atoms;
    R(15) is $N=C(NH_2)_2$, NR(18)R(19), $N(CH_2)_c$NR(18)R(19) or OR(20);
      c is 2 or 3;
      R(18) and R(19) independently of one another are H, alkyl having 1, 2, 3, 4, 5, 6, 7 or 8 carbon atoms or perfluoroalkyl having 1, 2, 3 or 4 carbon atoms; or
      R(18) and R(19) together are 4 or 5 methylene groups, of which one $CH_2$ group can be replaced by oxygen, S, NH, N—$CH_3$, N-benzyl or N-(p-chlorophenyl);
    R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
    R(16) and R(17) independently of one another are H, alkyl having 1, 2, 3, 4, 5, 6, 7 or 8 carbon atoms or perfluoroalkyl having 1, 2, 3 or 4 carbon atoms; or
    R(16) and R(17) together are 4 or 5 methylene groups, of which one $CH_2$ group can be replaced by oxygen, S, NH, N—$CH_3$, N-benzyl or N-(p-chlorophenyl); or
  Z is an N-containing heterocycle having 1, 2, 3, 4, 5, 6, 7, 8 or 9 carbon atoms, where the N-containing heterocycle is linked via N or C and is not substituted or is substituted by 1–3 substiuents selected from the group consisting of F, Cl, Br, $CF_3$, methyl, methoxy and NR(21)R(22);
but where, in the case where R(4) is an alkoxy radical, at least one of the substituents R(2), R(3), R(5), R(6), R(7) and R(8) is not hydrogen;
or a pharmaceutically tolerable salt thereof;
az) a substituted 2-naphthoylguanidine of the formula

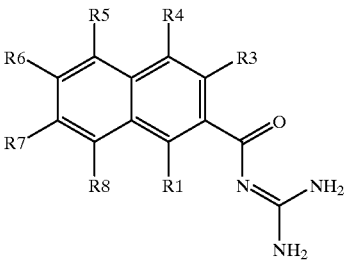

in which:
at least one of the substituents R1, R3, R4, R5, R6, R7 and R8 is $XY_aWZ$ or $X'Y_aWZ'$;
  X is O, S, NR(10) or CR(11)R(12);
    R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
  Y is alkylene having 1, 2, 3, 4, 5, 6, 7 or 8 $CH_2$ groups, where one of these $CH_2$ groups can be replaced by O, S, N R(3) or o-, p- or m-phenylene;
    R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
  a is zero or 1;
  W is $CH_2$, $SO_2$, S(=O)(=NH) or — if W does not immediately follow a heteroatom of the group $XY_a$— alternatively O or NR(14);
    R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
  z is C(=O)R(15), $SO_2$R(15) or— if W is not O or NR(14)— alternatively NR(16)R(17);
    R(15) is $N=C(NH_2)_2$, NR(18)R(19), $N(CH_2)_b$NR(18)R(19) or OR(20);
      b is 2 or 3;
      R(18) and R(19) independently of one another are H, alkyl having 1, 2, 3, 4, 5, 6, 7 or 8 carbon atoms or perfluoroalkyl having 1, 2, 3 or 4 carbon atoms; or
      R(18) and R(19) together are 4 or 5 methylene groups, of which one $CH_2$ group can be replaced by oxygen, S, NH, N—$CH_3$, N-benzyl or N-(p-chlorophenyl);
    R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one $CH_2$ group can be replaced by oxygen, S, NH, N—$CH_3$, N-benzyl or N-(p-chlorophenyl);

X' is C=O, C(=O)NR(30), C(=O)O, SO, $SO_2$, $SO_2$NR(30), OC=O, NR(30)C=O or NR(30)$SO_2$, where the linkage with the naphthalene ring in each case takes place via the left atom;

R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

Z' is C(=O)R(15), $SO_2$R(15), an N-containing heterocycle having 1, 2, 3, 4, 5, 6, 7,8 or 9 carbon atoms, where the N-containing heterocycle is linked via N or C and is not substituted or is substituted by 1–3 substituents selected from the group consisting of F, Cl, Br, $CF_3$, methyl, methoxy and NR(21)R(22);

R(21) and R(22) independently of one another are H, alkyl having 1, 2, 3 or 4 carbon atoms or perfluoroalkyl having 1, 2, 3 or 4 carbon atoms;

R(15) is N=C($NH_2$)$_2$, NR(18)R(19), N($CH_2$)$_b$NR(18)R(19) or OR(20);

R(18) and R(19) independently of one another are H, alkyl having 1, 2, 3, 4, 5, 6, 7 or 8 carbon atoms or perfluoroalkyl having 1, 2, 3 or 4 carbon atoms; or R(18) and R(19) together are 4 or 5 methylene groups, of which one $CH_2$ group can be replaced by oxygen, S, NH, N—$CH_3$, N-benzyl or N-(p-chlorophenyl);

b is 2 or 3;

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms; or Z'— if W is not O or NR(14)—is NR(16)R(17);

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one $CH_2$ group can be replaced by oxygen, S, NH, N—$CH_3$, N-benzyl or N-(p-chloro-phenyl);

and the other substituents R1, R3, R4, R5, R6, R7 and R8 in each case, which are still not allocated by the definitions given above, independently of one another are H, F, Cl, Br, I, CN, $NO_2$, $CF_3$, $C_2F_5$ or $V_pQ_qU$;

V is O, S, SO, $SO_2$, NR(60), OC=O, C=O, C(=O)NR(60), C(=O)O or CR(66)R(67);

R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

p is zero or 1;

Q is alkylene having 1, 2, 3, 4, 5, 6, 7 or 8 $CH_2$ groups, where one of these $CH_2$ groups can be replaced by O, S, NR(68) or o-, p- or m-phenylene;

R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

q is zero or 1;

U is H, alkyl having 1, 2, 3, 4, 5, 6 or 7 carbon atoms, cycloalkyl having 3, 4, 5, 6 or 7 carbon atoms, C(=O)R(65), $SO_2$R(65), NR(61)R(62) or phenyl, which is not substituted or is substituted by 1–3 substituents selected from the group consisting of F, Cl, Br, $CF_3$, methyl, methoxy and NR(63)R(64);

R(63) and R(64) independently of one another are H, alkyl having 1, 2, 3 or 4 carbon atoms or perfluoroalkyl having 1, 2, 3 or 4 carbon atoms;

R(65) is N=C($NH_2$)$_2$, NR(61)R(62) or OR(60);

R(61) and R(62) independently of one another are H, alkyl having 1, 2, 3, 4, 5, 6, 7 or 8 carbon atoms or perfluoroalkyl having 1, 2, 3 or 4 carbon atoms; or R(61) and R(62) together are 4 or 5 methylene groups, of which one $CH_2$ group can be replaced by oxygen, S, NH, N—$CH_3$, N-benzyl or N-(p-chlorophenyl); or U is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, $CF_3$, methyl, methoxy and NR(63)R(64);

but where at least one of the substituents R5, R6, R7 and R8 is not hydrogen; or a pharmaceutically tolerable salt thereof;

ba) an ortho-substituted benzoylguanidine of the formula

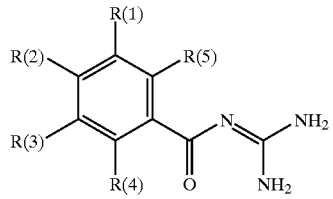

in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—($CH_2$)$_b$—($CF_2$)$_c$—$CF_3$;

X is oxygen, sulfur or NR(9);

a is zero or 1;

b is zero, 1 or 2;

c is zero, 1, 2 or 3;

R(9) is H, alkyl having 1, 2, 3 or 4 carbon atoms or —$C_dH_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);

R(7) and R(8) are independently, H or alkyl having 1, 2, 3 or 4 carbon atoms; or R(1) is —SR(10), —OR(10) or —CR(10)R(11)R(12);

R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, $CF_3$, $CH_3$, methoxy, hydroxyl, amino, methylamino and dimethylamino;

f is zero, 1 or 2;

R(11) and (R12), independently of one another, are defined as R(10) or are hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, the latter linked via a carbon or nitrogen atom of the ring, each of which is unsubstituted or is substituted by 1–3 substituents selected from the group consisting of F, Cl, $CF_3$, $CH_3$, methoxy, hydroxyl, amino, methylamino and dimethylamino, or (R1) is —SR(13), —OR(13), —NHR(13), —NR(13)R(14), —CHR(13)R(15), —C[R(15)R(16)]OH, —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14), identically or differently, are —(CH$_2$)$_g$—(CHOH)$_h$—(CH$_2$)$_i$—(CHOH)$_{kk}$—R(17) or —(CH$_2$)$_g$—O—(CH$_2$—CH$_{2O}$)$_h$—R(24);

R(17) is hydrogen or methyl, g, h and i, identically or differently, are zero, 1, 2, 3 or 4;

kk is 1, 2, 3 or 4;

R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;

R(18) is phenyl, which is unsubstituted or is substituted by 1–3 substituents selected from the group consisting of F, Cl, $CF_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms, which is unsubstituted or is substituted as phenyl; or R(18) is alkyl having 1, 2, 3, 4, 5 or 6 carbon atoms, which is unsubstituted or is substituted by 1–3 OH; or R(18) is cycloalkyl having 3, 4, 5, 6, 7 or 8 carbon atoms;

R(19), R(20), R(21), R(22) and R(23), identically or differently, are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18); m is 1, 2, 3 or 4;

one of the two substituents R(2) and R(3) is —O—CO—R(27);

R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolinyl are unsubstituted or substituted by 1–3 substituents selected from the group consisting of F, Cl, $CF_3$, methyl, methoxy and NR(7)R(8);

R(7) and R(8) independently of one another are hydrogen or alkyl having 1, 2, 3 or 4 carbon atoms;

where one of the substituents R(2) and R(3) is always defined as R(1);

R(4) and R(5) independently of one another are hydrogen, alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$, n is zero or 1, o is zero or 1, or a pharmaceutically tolerable salt thereof;

bb) a benzoylguanidine of the formula

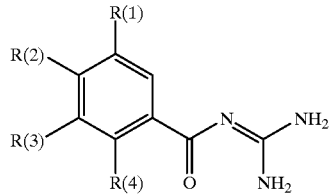

in which:

R(1) is R(13)—SO$_m$ or R(14)R(15)N—SO$_2$—;

m is 1 or 2;

R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(16), n is zero, 1, 2, 3 or 4;

R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(25)R(26);

R(25) and R(26), independently of one another, are hydrogen, alkyl having 1, 2, 3 or 4 carbon atoms or perfluoroalkyl having 1, 2, 3 or 4 carbon atoms;

R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(27), n is zero, 1, 2, 3 or 4;

R(27) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(28)R(29);

R(28) and R(29), independently of one another, are hydrogen, alkyl having 1, 2, 3 or 4 carbon atoms or perfluoroalkyl having 1, 2, 3 or 4 carbon atoms;

R(15) is hydrogen, alkyl having 1, 2, 3 or 4 carbon atoms or perfluoroalkyl having 1, 2, 3 or 4 carbon atoms; or R(14) and R(15), together, are 4 or 5 methylene groups of which one CH$_2$ group can be replaced by oxygen, S, NH, N—CH$_3$ or N-benzyl;

one of the substituents R(2) and R(3) is hydrogen;

and the other of the substituents R(2) and R(3) in each case is —CHR(30)R(31);

R(30) is —(CH$_2$)$_g$—(CHOH)$_h$—(CH$_2$)$_i$—(CHOH)$_k$—R(32) or —(CH$_2$)$_g$—O—(CH$_2$—CH$_{2O}$)$_h$—R(24);

R(24) and R(32), independently of one another, are hydrogen or methyl;

g, h and i, identically or differently, are zero, 1, 2, 3 or 4;

k is 1, 2, 3 or 4;

or the other of the substituents R(2) and R(3) in each case is —C(OH)R(33)R(34);

R(31), R(33) and R(34), identically or differently, are hydrogen or alkyl having 1, 2, 3 or 4 carbon atoms, or R(33) and R(34), together, are cycloalkyl having 3, 4, 5 or 6 carbon atoms; or R(33) is —CH$_2$OH;

R(4) is alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;

n is zero or 1;

o is zero, 1 or 2;

or a pharmaceutically tolerable salt thereof;

bc) an indanylideneacetylguanidine of the formula

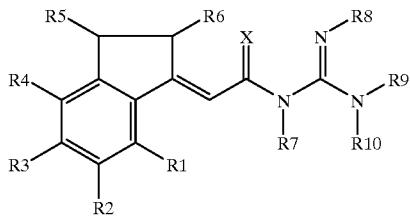

in which:

R1, R2, R3, R4, R5 and R6 independently of one another are H, C$_1$-C$_{10}$-alkyl; haloalkyl having 1–6 carbon atoms, O—C$_1$-C$_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O—C(=O)—C$_1$-C$_4$-alkylaryl, O—C(=O)—NH—C$_1$-C$_4$-alkyl, O—C(=O)—N(C$_1$-C$_4$-alkyl)$_2$, NO$_2$, CN, CF$_3$, NH$_2$, NH—C(=O)—C$_1$-C$_4$-alkyl, NH—C(=O)—NH$_2$, COOH, C(=O)—O—C$_1$-C$_4$-alkyl, C(=O)—NH$_2$, C(=O)—NH—C$_1$-C$_4$-alkyl, C(=O)—N(C$_1$-C$_4$-alkyl)$_2$, C$_1$-C$_4$—COOH, C$_1$-C$_4$-alkyl-C(=O)—O—C$_1$-C$_4$-alkyl, SO$_3$H, SO$_2$-alkyl; SO$_2$-alkylaryl, SO$_2$—N—(alkyl)$_2$, SO$_2$—N(alkyl)(alkylaryl), C(=O)—R11, C$_1$-C$_{10}$-alkyl-C(=O)—R11, C$_2$-C$_{10}$-alkenyl-C(=O)—R11, C$_2$-C$_{10}$-alkynyl-C(=O)—R11, NH—C(=O)—C$_1$-C$_{10}$-alkyl-C(=O)—R11 or O—C$_1$-C$_{11}$-alkyl-C(=O)—R11;

R11 is C$_1$-C$_4$-alkyl, C$_1$-C$_4$-alkynyl, aryl, substituted aryl, NH$_2$, NH—C$_1$-C$_4$-alkyl, N—(C$_1$-C$_4$-alkyl)$_2$, SO$_3$H, SO$_2$-alkyl, SO$_2$-alkylaryl, SO$_2$—N—(alkyl)$_2$ or SO$_2$—N(alkyl)(alkylaryl);

X is O, S or NH;

R7, R8, R9 and R10 independently of one another are H, alkyl, cycloalkyl, aryl, alkylaryl, or R8 and R9 together are part of a 5-, 6- or 7-membered heterocyclic ring;

or a pharmaceutically tolerable salt thereof;

bd) a phenyl-substituted alkenylcarboxylic acid guanidide of the formula

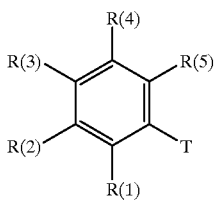

in which is

T:

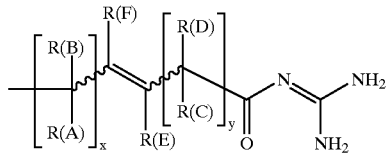

R(A) is hydrogen, F, Cl, Br, I, CN, OH, OR(6), (C$_1$-C$_4$)-alkyl, O$_r$(CH$_2$)$_a$C$_b$F$_{2b+1}$, (C$_3$-C$_8$)-cycloalkyl or NR(7)R(8)

r is zero or 1;

a is zero, 1, 2, 3 or 4;

b is 1, 2, 3 or 4;

R(6) is (C$_1$-C$_4$)-alkyl, (C$_1$-C$_4$)-perfluoroalkyl, (C$_3$-C$_6$)-alkenyl, (C$_{3–C8}$)-cycloalkyl, phenyl or benzyl, where the phenyl nucleus is unsubstituted or is substituted by 1–3 substituents selected from the group consisting of F, Cl, CF$_3$, methyl, methoxy and NR(9)R(10);

R(9) and R(10) are H, (C$_1$-C$_4$)-alkyl or (C$_1$-C$_4$)-perfluoroalkyl;

R(7) and R(8) independently of one another are defined as R(6); or

R(7) and R(8) together are 4 or 5 methylene groups, of which one CH$_2$ group can be replaced by oxygen, sulfur, NH, N—CH$_3$ or N-benzyl;

R(B), R(C) and R(D) independently are defined as R(A);

x is zero, 1 or 2;

y is zero, 1 or 2;

R(F) is hydrogen, F, Cl, Br, I, CN, OR(12), (C$_1$-C$_8$)-alkyl, O$_p$(CH$_2$)$_f$C$_g$F$_{2g+1}$, (C$_3$-C$_8$)-cycloalkyl or (C$_1$-C$_9$)-heteroaryl;

p is zero or 1;

f is zero, 1, 2, 3 or 4;

g is 1, 2, 3, 4, 5, 6, 7 or 8;

R(12) is (C$_1$-C$_8$)-alkyl, (C$_1$-C$_4$)-perfluoroalkyl, (C$_3$-C$_8$)-alkenyl, (C$_3$-C$_8$)-cycloalkyl, phenyl or benzyl, where the phenyl nucleus is unsubstituted or is substituted by 1–3 substituents selected from the group consisting of F, Cl, CF$_3$, methyl, methoxy and NR(13)R(14);

R(13) and R(14) are H, (C$_1$-C$_4$)-alkyl or (C$_1$-C$_4$)-perfluoroalkyl;

R(E) is defined independently as R(F);

R(1) is defined independently as T; or

R(1) is hydrogen, —O$_k$C$_m$H$_{2m+1}$, —O$_n$(CH$_2$)$_p$C$_q$F$_{2q+1}$, F, Cl, Br, I, CN, —(C=O)—N=C(NH$_2$)$_2$, —SO$_r$R(17), —SO$_{r2}$NR(31)R(32), —O$_u$(CH$_2$)$_v$C$_6$H$_5$, —O$_{u2}$—(C$_1$-C$_9$)-heteroaryl or —S$_{u2}$—(C$_1$-C$_9$)-heteroaryl;

k is zero or 1;

m is zero, 1, 2, 3, 4, 5, 6, 7 or 8;

n is zero or 1;

p is zero, 1, 2, 3 or 4;

q is 1, 2, 3, 4, 5, 6, 7 or 8;

r is zero, 1 or 2;

r2 is zero, 1 or 2;

R(31) and R(32) independently of one another are hydrogen, (C$_1$-C$_8$)-alkyl or (C$_1$-C$_8$)-perfluoroalkyl; or R(31) and R(32) together are 4 or 5 methylene groups of which one CH$_2$ group can be replaced by oxygen, S, NH, N—CH$_3$ or N-benzyl;

R(17) is $(C_1-C_8)$-alkyl;

u is zero or 1;

u2 is zero or 1;

v is zero, 1, 2, 3 or 4; where the phenyl nucleus is unsubstituted or is substituted by 1–3 substituents selected from the group consisting of F, Cl, $CF_3$, methyl, methoxy, —$(CH_2)_w$NR(21)R(22), NR(18)R(19) and $(C_1-C_9)$-heteroaryl;

R(18), R(19), R(21) and R(22) independently of one another are $(C_1-C_4)$-alkyl or $(C_1-C_4)$-perfluoroalkyl;

w is 1, 2, 3 or 4;

where the heterocycle of the $(C_1-C_9)$-heteroaryl is unsubstituted or is substituted by 1–3 substituents selected from the group consisting of F, Cl, $CF_3$, methyl or methoxy;

R(2), R(3), R(4) and R(5) independently of one another are defined as R(1), or

R(1) and R(2) or R(2) and R(3) in each case together are —CH—CH=CH—CH—, which is not substituted or is substituted by 1–3 substituents selected from the group consisting of F, Cl, $CF_3$, methyl, methoxy, —$(CH_2)_{w2}$NR(24)R(25) and NR(26)R(27);

R(24), R(25), R(26) and R(27) are H, $(C_1-C_4)$-alkyl or $(C_1-C_4)$-perfluoroalkyl;

w2 is 1, 2, 3 or 4;

where the radical T is present in the molecule at least twice, but only three times at most;

or a pharmaceutically tolerable salt thereof; and be) a benzoylguanidine of the formula

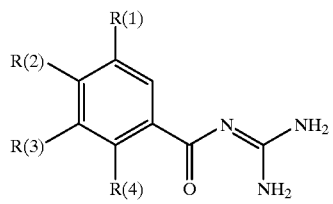

which:

R(1) is $CF_3$;

one of the substituents R(2) and R(3) is hydrogen;

and the other substituent R(2) or R(3) in each case is —$C(OH)(CH_3)$—$CH_2OH$, —$CH(CH_3)$—$CH_2OH$ or —$C(OH)(CH_3)_2$;

R(4) is methyl, methoxy, Cl or $CF_3$;

or a pharmaceutically tolerable salt thereof.

10. A method as claimed in claim 1, wherein the $Na^+/H^+$ inhibitor is selected from (4-isopropyl-3-methanesulfonylbenzoyl)guanidine, 2-methyl-4-pyrrolyl-5-methanesulfonylbenzoylguanidine, and pharmaceutically tolerable salts thereof.

11. A method as claimed in claim 10, wherein the pharmaceutically tolerable salt is selected from (4-isopropyl-3-methanesulfonylbenzoyl)guanidine methanesulfonate and 2-methyl-4-pyrrolyl-5-methanesulfonylbenzoylguanidine methanesulfonate.

* * * * *

UNITED STATES PATENT AND TRADEMARK OFFICE
CERTIFICATE OF CORRECTION

PATENT NO. : 6,420,430 B1 Page 1 of 7
APPLICATION NO. : 09/469299
DATED : July 16, 2002
INVENTOR(S) : Wolfgang Linz et al.

It is certified that error appears in the above-identified patent and that said Letters Patent is hereby corrected as shown below:

Claim 7, column 175, line 37, "C-CH$_3$" should read --N-CH$_3$--, and "R(2) isHhydrogen" should read --R(2) is hydrogen--.

Claim 7, column 176, line 42, "formula 1" should read --formula I--.

Claim 7, column 177, line 48, "R($^4$)" should read --R(4)--.

Claim 7, column 178, line 6, "(C$_3$-C$_9$)-cycloalkyl" should read --(C$_3$-C$_8$)-cycloalkyl--.

Claim 7, column 180, line 64, "$_{or\,R(}$5)R(6)N-SO$_2$-" should read --or R(5)R(6)N-SO$_2$- --.

Claim 7, column 181, line 60, "is zero 1, 2, 3, or 4" should read --n is zero 1, 2, 3, or 4--.

Claim 7, column 188, line 27, "x" should read --X--.

Claim 7, column 188, line 45, "benzofused" should read --benzo-fused--.

Claim 7, column 199, line 57, "is zero 1 or 2" should read --a is zero, 1 or 2--.

Claim 7, column 201, line 11, "+C≡ CR(56)" should read -- -C≡ CR(56)--.

Claim 7, column 202, line 38, insert --is-- after "q".

Claim 7, column 210, line 19, "R($^5$)-SO$_m$" should read --R(5)-SO$_m$--.

Claim 7, column 210, line 49, "lafter" should read --latter--.

Claim 7, column 216, line 29, "x" should read --X--.

Claim 7, column 219, line 40, "(C$_1$-C$_8$)" should read --(C$_1$-C$_9$)--.

Claim 7, column 223, line 56, "NR(1)" should read --NR(11)--.

UNITED STATES PATENT AND TRADEMARK OFFICE
CERTIFICATE OF CORRECTION

PATENT NO.       : 6,420,430 B1
APPLICATION NO. : 09/469299
DATED            : July 16, 2002
INVENTOR(S)      : Wolfgang Linz et al.

It is certified that error appears in the above-identified patent and that said Letters Patent is hereby corrected as shown below:

Claim 7, column 235, line 40, after "m is 1,2,3, or 4;" insert

--R(2) and R(3)

are defined as R(1);

R(4) is alkyl having 1, 2, 3 or 4 carbon atoms;

or a pharmaceutically tolerable salt thereof;

aw) an orthosubstituted benzoylguanidine of the formula

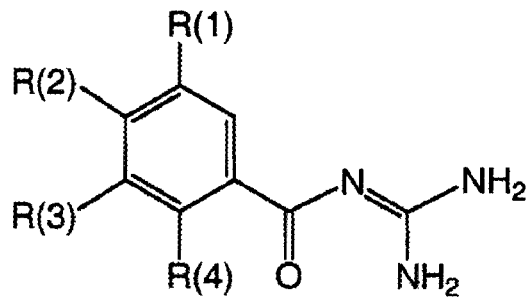

in which:

R(1)    is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a\text{-}(CH_2)_b\text{-}(CF_2)_c\text{-}CF_3$;

X       is oxygen, S, NR(5), a       is zero or 1;

b       is zero, 1 or 2;

c       is zero, 1, 2 or 3;

UNITED STATES PATENT AND TRADEMARK OFFICE
CERTIFICATE OF CORRECTION

| | |
|---|---|
| PATENT NO. | : 6,420,430 B1 |
| APPLICATION NO. | : 09/469299 |
| DATED | : July 16, 2002 |
| INVENTOR(S) | : Wolfgang Linz et al. |

It is certified that error appears in the above-identified patent and that said Letters Patent is hereby corrected as shown below:

R (5) is H, alkyl having 1, 2, 3 or 4 carbon atoms or $-C_dH_{2d}R(6)$;

d      is zero, 1, 2, 3 or 4;

R(6)      is cycloalkyl having 3, 4, 5, 6, 7 or 8 carbon atoms, phenyl, biphenylyl or naphthyl, where the aromatics phenyl, biphenylyl or naphthyl are not substituted or are substituted by 1 - 3 substituents selected from the group consisting of F, Cl, $CF_3$, methyl, methoxy and NR(7)R(8);
       R(7) and R(8)

independently are H or alkyl having 1, 2, 3 or 4 carbon atoms;

or

R(1)      is -SR(10), -OR(10) or -CR(10)R(11)R(12);

R(10)      is $-C_fH_{2f}$-cycloalkyl having 3, 4, 5, 6, 7 or 8 carbon atoms in the cycloalkyl ring, or phenyl, where phenyl is unsubstituted or substituted by 1 - 3 substituents selected from the group consisting of F, Cl, $CF_3$, $CH_3$, methoxy, hydroxyl, amino, methylamino and dimethylamino;

f      is zero, 1 or 2;

R(11) and R(12)

independently of one another are defined as R(10), or are hydrogen or alkyl having 1, 2, 3 or 4 carbon atoms;

or

UNITED STATES PATENT AND TRADEMARK OFFICE
CERTIFICATE OF CORRECTION

| | |
|---|---|
| PATENT NO. | : 6,420,430 B1 |
| APPLICATION NO. | : 09/469299 |
| DATED | : July 16, 2002 |
| INVENTOR(S) | : Wolfgang Linz et al. |

It is certified that error appears in the above-identified patent and that said Letters Patent is hereby corrected as shown below:

R(1)  is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1 - 3 substituents selected from the group consisting of F, Cl, $CF_3$, $CH_3$, methoxy, hydroxyl, amino, methylamino and dimethylamino, or R(1)  is -SR(13), -OR(13), -NHR(13), -NR(13)R(14), -CHR(13)R(15), -C[R(15)R(16)OH], -C≡CR(18), -C[R(19)]=CHR(18), -C[R(20)R(21)]$_k$-(CO)-[CR(22)R(23)]$_l$-R(24), k  is zero, 1, 2, 3 or 4;

l  is zero, 1, 2, 3 or 4;

R(13) and R(14)

identically or differently are -(CH$_2$)$_g$-(CHOH)$_h$-(CH$_2$)$_i$-(CHOH)$_j$-R(17) or -(CH2)$_g$-O-(CH$_2$-CH$_2$O)$_h$-R(24);

R(17) is hydrogen or methyl, g, h and i identically or differently are zero, 1, 2, 3 or 4;

j  is 1, 2, 3 or 4;

R(15) and R(16)

identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

UNITED STATES PATENT AND TRADEMARK OFFICE
CERTIFICATE OF CORRECTION

| | | |
|---|---|---|
| PATENT NO. | : 6,420,430 B1 | |
| APPLICATION NO. | : 09/469299 | |
| DATED | : July 16, 2002 | |
| INVENTOR(S) | : Wolfgang Linz et al. | |

It is certified that error appears in the above-identified patent and that said Letters Patent is hereby corrected as shown below:

R(18)

is phenyl, which is unsubstituted or substituted by 1 - 3 substituents selected from the group consisting of F, Cl, $CF_3$, methyl, methoxy and NR(25) and R(26);

R(25) and R(26)

are H or alkyl having 1, 2, 3 or 4 carbon atoms;

or

R(18)    is heteroaryl having 1, 2, 3, 4, 5, 6, 7, 8 or 9 carbon atoms, which is unsubstituted or substituted as phenyl;

or

R(18)    is alkyl having 1, 2, 3, 4, 5 or 6 carbon atoms, which is unsubstituted or substituted by 1 - 3 OH;

or

R(18)

is cycloalkyl having 3, 4, 5, 6, 7 or 8 carbon atoms;

R(19), R(20), R(21), R(22) and R(23)

identically or differently are hydrogen or methyl;

R(24) is H, alkyl having 1, 2, 3, 4, 5 or 6 carbon atoms, cycloalkyl having 3, 4, 5, 6, 7 or 8 carbon atoms or -$C_mH_{2m}$-R(18)--.

\* Claim 7, column 244, line 66, "oder" should read --or--.

UNITED STATES PATENT AND TRADEMARK OFFICE
CERTIFICATE OF CORRECTION

PATENT NO. : 6,420,430 B1
APPLICATION NO. : 09/469299
DATED : July 16, 2002
INVENTOR(S) : Wolfgang Linz et al.

It is certified that error appears in the above-identified patent and that said Letters Patent is hereby corrected as shown below:

Claim 7, column 255, line 30, "R1 H or Alkyl" should read --R1 is H or alkyl--.

Claim 7, column 255, lines 36-41, delete the formula and replace with

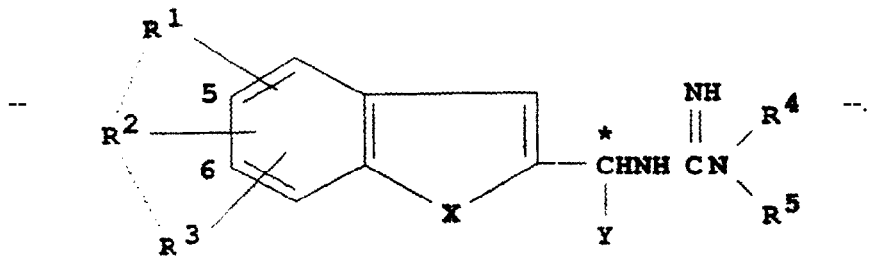

Claim 7, column 258, line 64, delete "Q1(R5)-P2(R4)--.

Claim 7, column 259, line 25, "$CONH_2z$" should read --$CONH_2$,--.

* Claim 9, column 267, line 60, "und" should read --and--.

Claim 9, column 281, line 20, "z" should read --Z--.

Claim 9, column 281, line 22, "z" should read --Z--.

Claim 9, column 281, line 24, "z" should read --Z--.

Claim 9, column 284, line 1, "orbenzyl" should read --or benzyl--.

Claim 9, column 289, line 13, "R(8)" should read --R(B)--.

UNITED STATES PATENT AND TRADEMARK OFFICE
CERTIFICATE OF CORRECTION

PATENT NO. : 6,420,430 B1
APPLICATION NO. : 09/469299
DATED : July 16, 2002
INVENTOR(S) : Wolfgang Linz et al.

It is certified that error appears in the above-identified patent and that said Letters Patent is hereby corrected as shown below:

Claim 9, column 297, line 62, "R(8)" should read --R(B)--.

Signed and Sealed this

Twelfth Day of August, 2008

JON W. DUDAS
*Director of the United States Patent and Trademark Office*